US009650378B2

(12) United States Patent
Guzzo et al.

(10) Patent No.: US 9,650,378 B2
(45) Date of Patent: May 16, 2017

(54) (1-AZINONE)-SUBSTITUTED PYRIDOINDOLES

(71) Applicant: Albany Molecular Research, Inc., Albany, NY (US)

(72) Inventors: Peter Guzzo, Niskayuna, NY (US); Matthew David Surman, Albany, NY (US); Alan John Henderson, Albany, NY (US); May Xiaowu Jiang, Guilderland, NY (US); Mark Hadden, Albany, NY (US); James Grabowski, Castleton on Hudson, NY (US); Alexander Usyatinsky, Troy, NY (US)

(73) Assignee: Albany Molecular Research, Inc., Albany, NY (US)

( * ) Notice: Subject to any disclaimer, the term of this patent is extended or adjusted under 35 U.S.C. 154(b) by 0 days.

(21) Appl. No.: 15/045,652

(22) Filed: Feb. 17, 2016

(65) Prior Publication Data

US 2016/0159798 A1     Jun. 9, 2016

Related U.S. Application Data

(62) Division of application No. 14/223,151, filed on Mar. 24, 2014, now Pat. No. 9,296,743, which is a division of application No. 12/351,561, filed on Jan. 9, 2009, now Pat. No. 8,716,308.

(60) Provisional application No. 61/020,530, filed on Jan. 11, 2008, provisional application No. 61/048,677, filed on Apr. 29, 2008.

(51) Int. Cl.
| C07D 471/04 | (2006.01) |
| C07D 521/00 | (2006.01) |
| C07D 519/00 | (2006.01) |

(52) U.S. Cl.
CPC .......... *C07D 471/04* (2013.01); *C07D 519/00* (2013.01); *C07D 521/00* (2013.01)

(58) Field of Classification Search
CPC .................................................... C07D 471/04
See application file for complete search history.

(56) References Cited

U.S. PATENT DOCUMENTS

| 3,514,462 A | 5/1970 | Hester |
| 4,978,669 A | 12/1990 | Barchas et al. |
| 4,985,422 A | 1/1991 | North et al. |
| 5,013,733 A | 5/1991 | Coates et al. |
| 5,162,336 A | 11/1992 | Molino et al. |
| 5,169,852 A | 12/1992 | Barchas et al. |
| 5,183,820 A | 2/1993 | Coates et al. |
| 5,187,180 A | 2/1993 | Gillard |
| 5,223,625 A | 6/1993 | Van Wijngaarden et al. |
| 5,225,407 A | 7/1993 | Oakley et al. |
| 5,424,314 A | 6/1995 | Clemence et al. |
| 5,466,688 A | 11/1995 | Commons et al. |
| 5,506,234 A | 4/1996 | Huth et al. |
| 5,527,794 A | 6/1996 | Commons et al. |
| 5,563,147 A | 10/1996 | Gilmore et al. |
| 5,569,661 A | 10/1996 | Haffer et al. |
| 5,767,131 A | 6/1998 | Gluchowski et al. |
| 5,811,551 A | 9/1998 | Chen et al. |

(Continued)

FOREIGN PATENT DOCUMENTS

| CA | 2 597 193 A1 | 2/2009 |
| CN | 101074207 A | 11/2007 |

(Continued)

OTHER PUBLICATIONS

U.S. Appl. No. 13/330,989, Surman et al.
U.S. Appl. No. 13/331,814, Surman et al.
International Search Report for International Patent Application No. PCT/US2009/030646 (Apr. 2, 2009).
Written Opinion of the International Searching Authority for International Patent Application No. PCT/US2009/030646 (Apr. 2, 2009).
International Search Report for International Patent Application No. PCT/US10/40800 (Aug. 30, 2010).
Written Opinion of the International Searching Authority for International Patent Application No. PCT/US10/40800 (Aug. 30, 2010).
International Search Report for International Patent Application No. PCT/US10/40803 (Aug. 30, 2010).

(Continued)

*Primary Examiner* — Paul V Ward
(74) *Attorney, Agent, or Firm* — LeClairRyan

(57) ABSTRACT

Substituted pyridoindoles for incorporation in pharmaceutical compositions employed in the treatment of various diseases correspond to formula (I)

(I)

wherein $R^1$ is H or optionally substituted alkyl; $R^2$, $R^3$, $R^4$ are each independently selected from H, —O-alkyl, —S-alkyl, alkyl, halo, —$CF_3$, and —CN; G is —$CR^{12}R^{13}$—$NR^5$— or —$NR^5$—$CR^{12}R^{13}$; $R^5$ is H, optionally substituted alkyl, optionally substituted heterocycle, —C(=O)—$R^6$, —C(=O)—O—$R^7$, or —C(=O)—$NR^{19}R^{20}$; $R^6$ and $R^7$ are each optionally substituted alkyl or optionally substituted heterocycle; $R^8$, $R^9$, $R^{10}$, $R^{11}$, $R^{12}$, $R^{13}$, $R^{19}$ and $R^{20}$ are each independently selected from H or optionally substituted alkyl; $R^{14}$ and $R^{15}$ are each independently H or halogen; L is —$CH_2$—O—, —$CH_2CH_2$—, —CH=CH— or a bond; and B is aryl or heteroaryl or cycloalkyl; with the proviso that, when L is a direct bond, B cannot be unsubstituted heteroaryl or heteroaryl monosubstituted with fluorine.

41 Claims, No Drawings

(56) References Cited

U.S. PATENT DOCUMENTS

| | | |
|---|---|---|
| 5,854,245 A | 12/1998 | Duggan et al. |
| 5,932,582 A | 8/1999 | Young et al. |
| 5,972,980 A | 10/1999 | Cornicelli et al. |
| 6,001,866 A | 12/1999 | Cornicelli et al. |
| 6,177,440 B1 | 1/2001 | Bach et al. |
| 6,255,306 B1 | 7/2001 | Macor |
| 6,407,092 B1 | 6/2002 | Hester et al. |
| 6,548,493 B1 | 4/2003 | Robichaud et al. |
| 6,552,017 B1 | 4/2003 | Robichaud et al. |
| 6,605,639 B1 | 8/2003 | Tamura et al. |
| 6,610,684 B2 | 8/2003 | Zaharevitz et al. |
| 6,653,304 B2 | 11/2003 | Leftheris et al. |
| 6,699,852 B2 | 3/2004 | Robichaud et al. |
| 6,713,471 B1 | 3/2004 | Robichaud et al. |
| 6,713,645 B1 | 3/2004 | Bach et al. |
| 6,727,264 B1 | 4/2004 | Marzabadi et al. |
| 6,838,456 B2 | 1/2005 | Orme et al. |
| 6,849,619 B2 | 2/2005 | Robichaud et al. |
| 6,849,640 B2 | 2/2005 | Ennis et al. |
| 6,872,721 B2 | 3/2005 | Orme et al. |
| 6,872,743 B2 | 3/2005 | Beight et al. |
| 6,875,762 B2 | 4/2005 | Hester et al. |
| 6,890,933 B1 | 5/2005 | Feng et al. |
| 6,906,095 B2 | 6/2005 | Cole et al. |
| 6,927,222 B2 | 8/2005 | Hansen et al. |
| 6,927,223 B1 | 8/2005 | Meadows et al. |
| 6,943,188 B2 | 9/2005 | Eriksson et al. |
| 6,951,874 B2 | 10/2005 | Hansen et al. |
| 6,951,881 B2 | 10/2005 | Cole et al. |
| 6,992,192 B2 | 1/2006 | Sawyer et al. |
| 7,022,856 B2 | 4/2006 | Orme et al. |
| 7,115,621 B2 | 10/2006 | Sawyer et al. |
| 7,122,554 B2 | 10/2006 | Sawyer et al. |
| 7,193,079 B1 | 3/2007 | Tepe |
| 7,196,103 B2 | 3/2007 | Nazare et al. |
| 7,250,514 B1 | 7/2007 | Xiao |
| 7,332,519 B2 | 2/2008 | Hinze et al. |
| 7,335,769 B2 | 2/2008 | Tepe |
| 7,385,055 B2 | 6/2008 | Tepe |
| 7,482,360 B2 | 1/2009 | Burnett et al. |
| 7,485,634 B2 | 2/2009 | Martin et al. |
| 7,872,017 B2 | 1/2011 | Ji et al. |
| 8,067,590 B2 | 11/2011 | Stenkamp et al. |
| 8,101,632 B2 | 1/2012 | Guzzo et al. |
| 8,158,643 B2 | 4/2012 | Andres-Gil et al. |
| 8,268,868 B2 | 9/2012 | Guzzo et al. |
| 8,273,770 B2 | 9/2012 | Guzzo et al. |
| 8,697,700 B2 | 4/2014 | Surman et al. |
| 8,716,308 B2 * | 5/2014 | Guzzo ............... C07D 471/04 514/290 |
| 2002/0013333 A1 | 1/2002 | Batty et al. |
| 2002/0099068 A1 | 7/2002 | Ritzeler et al. |
| 2002/0173503 A1 | 11/2002 | Robichaud et al. |
| 2003/0022819 A1 | 1/2003 | Ling et al. |
| 2003/0095958 A1 | 5/2003 | Bhisetti et al. |
| 2003/0130293 A1 | 7/2003 | Bamdad |
| 2003/0144267 A1 | 7/2003 | Hansen et al. |
| 2003/0149047 A1 | 8/2003 | Eriksson et al. |
| 2003/0158225 A1 | 8/2003 | Hansen et al. |
| 2003/0225058 A1 | 12/2003 | Frank et al. |
| 2003/0232843 A1 | 12/2003 | Cole et al. |
| 2004/0002527 A1 | 1/2004 | Cole et al. |
| 2004/0023947 A1 | 2/2004 | Martin et al. |
| 2004/0116458 A1 | 6/2004 | Sawyer et al. |
| 2004/0122035 A1 | 6/2004 | Orme et al. |
| 2004/0186094 A1 | 9/2004 | Robichaud et al. |
| 2004/0235820 A1 | 11/2004 | Tepe |
| 2005/0004156 A1 | 1/2005 | Feng et al. |
| 2005/0026941 A1 | 2/2005 | Sawyer et al. |
| 2005/0033049 A1 | 2/2005 | Nazare et al. |
| 2005/0054634 A1 | 3/2005 | Busch et al. |
| 2005/0176775 A1 | 8/2005 | Devadas et al. |
| 2005/0187387 A1 | 8/2005 | Lynch et al. |
| 2005/0192333 A1 | 9/2005 | Hinze et al. |
| 2005/0215580 A1 | 9/2005 | Wang et al. |
| 2006/0004041 A1 | 1/2006 | Cummings et al. |
| 2006/0019952 A1 | 1/2006 | Distefano et al. |
| 2006/0128711 A1 | 6/2006 | Gallego et al. |
| 2006/0167259 A1 | 7/2006 | Chao et al. |
| 2006/0189639 A1 | 8/2006 | Stewart et al. |
| 2006/0235012 A1 | 10/2006 | Davidson et al. |
| 2006/0247228 A1 | 11/2006 | Umeda et al. |
| 2006/0276451 A1 | 12/2006 | Tepe |
| 2006/0281786 A1 | 12/2006 | Hamprecht et al. |
| 2006/0281796 A1 | 12/2006 | Edmondson et al. |
| 2006/0287296 A1 | 12/2006 | Tepe |
| 2006/0293305 A1 | 12/2006 | Tepe |
| 2007/0004765 A1 | 1/2007 | Graffner-Nordberg et al. |
| 2007/0027178 A1 | 2/2007 | Lee |
| 2007/0037791 A1 | 2/2007 | Rawson et al. |
| 2007/0049575 A1 | 3/2007 | Tepe |
| 2007/0049593 A1 | 3/2007 | Oka et al. |
| 2007/0149557 A1 | 6/2007 | Collins et al. |
| 2007/0173537 A1 | 7/2007 | Takemiya et al. |
| 2007/0185184 A1 | 8/2007 | Hanson et al. |
| 2007/0213351 A1 | 9/2007 | Sundermann et al. |
| 2007/0254877 A1 | 11/2007 | Nishikimi et al. |
| 2007/0293491 A1 | 12/2007 | Shafer et al. |
| 2008/0045539 A1 | 2/2008 | Ji et al. |
| 2008/0103164 A1 | 5/2008 | Gudmundsson et al. |
| 2008/0124319 A1 | 5/2008 | Pothoulakis et al. |
| 2008/0125475 A1 | 5/2008 | Linz et al. |
| 2008/0194803 A1 | 8/2008 | Sinclair et al. |
| 2008/0207594 A1 | 8/2008 | Mussmann et al. |
| 2008/0221141 A1 | 9/2008 | Friderichs et al. |
| 2008/0269055 A1 | 10/2008 | Bastiaans et al. |
| 2008/0287423 A1 | 11/2008 | Mussmann et al. |
| 2008/0292626 A1 | 11/2008 | Wang et al. |
| 2008/0312218 A1 | 12/2008 | Burnett et al. |
| 2009/0012062 A1 | 1/2009 | Andres-Gill et al. |
| 2009/0012077 A1 | 1/2009 | Dessetter et al. |
| 2009/0069367 A1 | 3/2009 | Bamdad |
| 2009/0075996 A1 | 3/2009 | Alper et al. |
| 2009/0232879 A1 | 9/2009 | Cable et al. |
| 2009/0264426 A1 | 10/2009 | Sakuraba et al. |
| 2010/0105679 A1 | 4/2010 | Guzzo et al. |
| 2010/0249105 A1 | 9/2010 | Schrimpf et al. |
| 2011/0003737 A1 | 1/2011 | Guzzo et al. |
| 2011/0003738 A1 | 1/2011 | Guzzo et al. |
| 2011/0003739 A1 | 1/2011 | Guzzo et al. |
| 2011/0003793 A1 | 1/2011 | Guzzo et al. |
| 2012/0035102 A9 | 2/2012 | Guzzo et al. |
| 2012/0058939 A9 | 3/2012 | Guzzo et al. |
| 2012/0058940 A9 | 3/2012 | Guzzo et al. |
| 2012/0157460 A1 | 6/2012 | Surman et al. |

FOREIGN PATENT DOCUMENTS

| | | |
|---|---|---|
| EP | 0 950 661 A1 | 10/1999 |
| EP | 1 462 103 A1 | 9/2004 |
| EP | 1 757 607 A1 | 2/2007 |
| EP | 2 003 129 A1 | 12/2008 |
| EP | 2062895 A1 | 5/2009 |
| GB | 2 120 662 A | 12/1983 |
| IN | 2000CH01126 | 3/2005 |
| WO | WO 92/00295 A1 | 1/1992 |
| WO | WO 94/22829 A2 | 10/1994 |
| WO | WO 96/11197 A1 | 4/1996 |
| WO | WO 96/12721 A1 | 5/1996 |
| WO | WO 96/33211 A1 | 10/1996 |
| WO | WO 97/12613 A1 | 4/1997 |
| WO | WO 97/23458 A1 | 7/1997 |
| WO | WO 97/31910 A1 | 9/1997 |
| WO | WO 98/00134 A1 | 1/1998 |
| WO | WO 98/00401 A1 | 1/1998 |
| WO | WO 99/47521 A1 | 9/1999 |
| WO | WO 00/64899 A1 | 11/2000 |
| WO | WO 00/77002 A1 | 12/2000 |
| WO | WO 01/05793 A1 | 1/2001 |
| WO | WO 01/58869 A2 | 8/2001 |
| WO | WO 01/64680 A1 | 9/2001 |
| WO | WO 01/68648 A1 | 9/2001 |
| WO | WO 01/87038 A2 | 11/2001 |
| WO | WO 01/87883 A1 | 11/2001 |

(56) References Cited

FOREIGN PATENT DOCUMENTS

| | | |
|---|---|---|
| WO | WO 01/94345 A2 | 12/2001 |
| WO | WO 02/04456 A1 | 1/2002 |
| WO | WO 02/04457 A1 | 1/2002 |
| WO | WO 02/24701 A2 | 3/2002 |
| WO | WO 02/28859 A2 | 4/2002 |
| WO | WO 02/28865 A2 | 4/2002 |
| WO | WO 02/50034 A2 | 6/2002 |
| WO | WO 02/059082 A2 | 8/2002 |
| WO | WO 02/059129 A2 | 8/2002 |
| WO | WO 02/064590 A2 | 8/2002 |
| WO | WO 02/064591 A2 | 8/2002 |
| WO | WO 02/088101 A2 | 11/2002 |
| WO | WO 02/088123 A1 | 11/2002 |
| WO | WO 02/098875 A1 | 12/2002 |
| WO | WO 03/014118 A1 | 2/2003 |
| WO | WO 03/099821 A1 | 12/2003 |
| WO | WO 2004/030629 A2 | 4/2004 |
| WO | WO 2004/081010 A1 | 9/2004 |
| WO | 2951434 B2 | 11/2004 |
| WO | WO 2005/070930 A2 | 8/2005 |
| WO | WO 2005/107471 A1 | 11/2005 |
| WO | WO 2005/118587 A1 | 12/2005 |
| WO | WO 2006/015035 A1 | 2/2006 |
| WO | WO 2006/018184 A2 | 2/2006 |
| WO | WO 2006/064355 A2 | 6/2006 |
| WO | WO 2006/064757 A1 | 6/2006 |
| WO | WO 2006/089874 A1 | 8/2006 |
| WO | WO 2005/108367 A1 | 11/2006 |
| WO | WO 2006/117548 A1 | 11/2006 |
| WO | WO 2006/122931 A1 | 11/2006 |
| WO | WO 2007/002051 A1 | 1/2007 |
| WO | WO 2007/009120 A2 | 1/2007 |
| WO | WO 2007/024004 A1 | 3/2007 |
| WO | WO 2007/035620 A2 | 3/2007 |
| WO | WO 2007/062175 A2 | 5/2007 |
| WO | WO 2007/070796 A1 | 6/2007 |
| WO | WO 2007/120333 A2 | 10/2007 |
| WO | WO 2007/124903 A1 | 11/2007 |
| WO | WO 2007/141200 A1 | 12/2007 |
| WO | WO 2007/142217 A1 | 12/2007 |
| WO | WO 2008/011805 A1 | 1/2008 |
| WO | WO 2008/024029 A1 | 2/2008 |
| WO | WO 2008/046155 A1 | 4/2008 |
| WO | WO 2008/060190 A2 | 5/2008 |
| WO | WO 2008/081282 A2 | 7/2008 |
| WO | WO 2008/101659 A1 | 8/2008 |
| WO | WO 2008/101660 A1 | 8/2008 |
| WO | WO 2008/103470 A2 | 8/2008 |
| WO | WO 2008/106594 A2 | 9/2008 |
| WO | WO 2008/112280 A1 | 9/2008 |
| WO | WO 2009/003003 A2 | 12/2008 |
| WO | WO 2009/022104 A1 | 2/2009 |
| WO | WO 2009/032123 A2 | 3/2009 |
| WO | WO 2011/003005 A1 | 1/2011 |
| WO | WO 2011/003007 A1 | 1/2011 |
| WO | WO 2011/003012 A1 | 1/2011 |
| WO | WO 2011/003021 A1 | 1/2011 |

OTHER PUBLICATIONS

Written Opinion of the International Searching Authority for International Patent Application No. PCT/US10/40803 (Aug. 30, 2010).
International Search Report for International Patent Application No. PCT/US10/40809 (Aug. 30, 2010).
Written Opinion of the International Searching Authority for International Patent Application No. PCT/US10/40809 (Aug. 30, 2010).
International Search Report for International Patent Application No. PCT/US10/40820 (Aug. 30, 2010).
Written Opinion of the International Searching Authority for International Patent Application No. PCT/US10/40820 (Aug. 30, 2010).
BE 896590 to Gadient (Oct. 28, 1983) (abstract only).
CN 101074207 to Deng et al. (Nov. 21, 2007) (abstract only).
IN 2000CH01126 to Bipul et al. (Mar. 4, 2005) (abstract only).
JP 04319958 to Ito, A. (Nov. 10, 1992) (abstract only).
JP 2951434 to Ito, A. (Sep. 20, 1999) (abstract only).
Kokkotou et al., "Melanin-Concentrating Hormone as a Mediator of Intestinal Inflammation," PNAS 105(30):10613-10618 (2008).
First Office Action for China Patent Application No. 200980105529.7 (issued Mar. 7, 2012).
Lakaye et al., "Melanin-Concentrating Hormone and Immune Function," Peptides 30:2076-2080 (2009).
Kokkotou et al., "Melanin-Concentrating Hormone (MCH) Modulates C Difficile Toxin A-Mediated Enteritis in Mice," Gut. 58(1):34-40 (2009).
Hadden et al., "Synthesis and SAR of 4-aryl-l-(indazol-5-yl)pyridin-2(1H)ones as MCH-1 Antagonists for the Treatment of Obesity," Bioorg. Med. Chem. Lett. 20:7020-7023 (2010).
Sargent et al., "New Central Targets for the Treatment of Obesity," Br. J. Clin. Pharmacol. 68(6):852-860 (2009).
Office Action dated Jul. 2, 2012 for U.S. Appl. No. 12/828,807.
Henderson et al., "Tetrahydrocarboline Analogs as MCH-1 Antagonists," Bioorg. Med. Chem. Lett. 20:7024-7028 (2010).
Office Action dated Jan. 30, 2013 for U.S. Appl. No. 12/828,890.
Office Action dated Feb. 20, 2013 for U.S. Appl. No. 12/828,955.
Patent Examination Report dated Oct. 22, 2012 for Australian Application No. 2009204048.
Office Action dated Jan. 5, 2013 for Chinese Application No. 200980105529.7.
Translation of Office Action dated Oct. 30, 2012 for Israeli Application No. 206594.
Office Action dated Feb. 17, 2011 for New Zealand Application No. 586120.
Office Action dated May 30, 2012 for New Zealand Application No. 586120.
Extended Search Report dated Jun. 7, 2012 for European Application No. 12163813.4.
Office Action dated Jan. 17, 2013 for U.S. Appl. No. 12/828,855.
Jantzen and Robinson, Modern Pharmaceutics, 596 (1996).
STN Registry Database, RN 1260582-72-6, available online Jan. 27, 2011.
Surman et al., "5-(Pyridinon-1-yl)indazoles and 5-(furopyridinon-5-yl)indazoles as MCH-1 Antagonists," Bioorg. Med. Chem. Lett. 20:7015-7019 (2010).
Viggers et al., "Development and Validation of a Radioligand Receptor Binding Assay for MCH-1 Receptors Using [3H] AMR-MCH-1 In Vitro and Ex Vivo," Abstract 584.27/SS8, Society for Neuroscience Annual Meeting (2008).
Office Action for U.S. Appl. No. 13/330,989 (Jul. 19, 2013).
"Burger's Medicinal Chemistry and Drug Discovery" edited by Manfred E. Wolff, 5th Ed. Part 1, pp. 975-977 (1995).
Banker et al., "Modern Pharmaceutics," 3rd Ed., p. 451, 596 (1996).
Carpenter et al., "Melanin-Concentrating Hormone Receptor Antagonists as Potential Antiobesity Agents," Expert Opin. Ther. Patents 12(11):1639-1646 (2002).
Dyke et al., "Recent Developments in the Discovery of MCH-1R Antagonists for the Treatment of Obesity—An Update," Expert Opin. Ther. Patents 15(10):1303-1313 (2005).
Johansson, "Recent Progress in the Discovery of Melanin-Concentrating Hormone 1-Receptor Antagonists," Expert Opin. Ther. Patents 21(6):905-925 (2011).
Vippagunta et al., "Crystalline Solids," Adv. Drug Del. Rev. 48:3-26 (2001).
International Search Report and Written Opinion for PCT/US2011/066027 (Aug. 14, 2012).
International Search Report and Written Opinion for PCT/US2011/066177 (Jun. 28, 2012).
Translation of Office Action dated Oct. 3, 2013 for Japanese Application No. 2010-542381.
Extended European Search Report for EP Application No. 10794771.5 (mailed Oct. 16, 2012).
Nahon, "The Melanocortins and Melanin-concentrating Hormone in the Central Regulation of Feeding Behavior and Energy Homeostasis," C.R. Biologies 329:623-638 (2006).
Kowalski et al., "Therapeutic Potential of Melanin-concentrating Hormone-I Receptor Antagonists for the Treatment of Obesity," Expert Opin. Investig. Drugs 13(9):1113-1122 (2004).

(56) References Cited

OTHER PUBLICATIONS

Méndez-Andino et al., "MCH-R1 Antagonists: What is Keeping Most Research Programs Away from the Clinic?," Drug Discovery Today 12(21/22):972-979 (2007).
Office Action for U.S. Appl. No. 13/331,814 dated Dec. 31, 2013.
Translation of Notice Prior to Notice of Allowance dated Jan. 23, 2014 for Israeli Application No. 206594.
Translation of Notice of Reasons for Rejection for Japanese Patent Application No. 2012-518609 (Jul. 7, 2014).
Office Action for U.S. Appl. No. 13/331,814 dated Aug. 12, 2014.
Office Action for Canadian Patent Application No. 2,727,055 (Jan. 15, 2015).
Translation of Notice of Reasons for Rejection for Japanese Patent Application No. 2014-047896 (Mar. 11, 2015).
Translation of Office Action dated Apr. 22, 2015 for Korean Patent Application No. 10-2010-7017685.
Translation of Office Action dated Nov. 4, 2015 for Korean Patent Application No. 10-2010-7017685.

\* cited by examiner

(1-AZINONE)-SUBSTITUTED PYRIDOINDOLES

This application is a divisional of U.S. patent application Ser. No. 14/223,151, filed Mar. 24, 2014, which is a divisional of U.S. patent application Ser. No. 12/351,561, filed Jan. 9, 2009, which claims priority of U.S. Provisional Patent Application Ser. No. 61/020,530, filed Jan. 11, 2008, and U.S. Provisional Patent Application Ser. No. 61/048,677, filed Apr. 29, 2008, which are hereby incorporated by reference in their entirety.

FIELD OF THE INVENTION

The invention relates to human melanin-concentrating hormone ($MCH_1$) receptor-selective antagonists substituted pyridoindoles that are useful for treating obesity, to pharmaceutical compositions comprising these compounds, and to methods for the treatment of obesity, anxiety, depression, and psychiatric disorders in a mammal.

BACKGROUND OF THE INVENTION

Obesity and the multitude of co-morbidities associated with obesity such as diabetes, dyslipidemia, coronary heart disease, and certain cancers are a major concern for public health. The currently available pharmaceutical therapies for the treatment of obesity have limited efficacy and side effects that limit their use. Thus, there is a significant medical need for better pharmacotherapy for obesity.

Melanin-concentrating hormone (MCH) has been identified as an orexigenic peptide that exerts an effect on food intake and body weight regulation. MCH is a cyclic 19 amino acid neuropeptide expressed in the zona incerta and lateral hypothalamus in response to both energy restriction and leptin deficiency. MCH is known to stimulate feeding when injected into the lateral ventricle of rats and the mRNA for MCH is upregulated in the hypothalamus of genetically obese mice (ob/ob) and in fasted control and ob/ob animals. In addition, animals treated with MCH show increases in glucose, insulin and leptin levels, mimicking human metabolic syndrome (Gomori, A. Chronic infusion of MCH causes obesity in mice Am. J. Physiol. Endocrinol. Metab. 284, E583, 2002). Mice lacking MCH are hypophagic and lean with increased metabolic rate, whereas animals overexpressing MCH gain excess weight on both standard and high fat diets. MCH is thought to have effects on other nervous system functions as well (Rocksz, L. L. Biological Examination of Melanin Concentrating Hormone 1: Multitasking from the hypothalamus Drug News Perspect 19(5), 273, 2006). An orphan G-protein coupled receptor (GPCR) was recently identified as a receptor for MCH. Disruption of the binding between MCH and the MCH receptor, i.e. MCH antagonism, may thus be used to counteract the effects of MCH (McBriar, M. D. Recent advances in the discovery of melanin-concentrating hormone receptor antagonists Curr. Opin. Drug Disc. & Dev. 9(4), 496, 2006).

SUMMARY OF THE INVENTION

In accordance the present invention, there is provided a compound of formula (I)

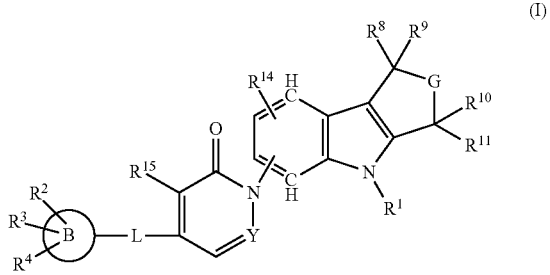

wherein
$R^1$ is H or optionally substituted alkyl;
$R^2$, $R^3$, $R^4$ are each independently selected from H, —O-alkyl, —S-alkyl, alkyl, halo, —$CF_3$, and —CN;
G is —$CR^{12}R^{13}$—$NR^5$— or —$NR^5$—$CR^{12}R^{13}$—;
$R^5$ is H, optionally substituted alkyl, optionally substituted heterocycle, —C(=O)—$R^6$, —C(=O)—O—$R^7$, or —C(=O)—$NR^{19}R^{20}$;
$R^6$ and $R^7$ are each optionally substituted alkyl or optionally substituted heterocycle; $R^8$, $R^9$, $R^{10}$, $R^{11}$, $R^{12}$, $R^{13}$, $R^{19}$ and $R^{20}$ are each independently selected from H or optionally substituted alkyl;
$R^{14}$ and $R^{15}$ are each independently H or halogen;
Y is CH or N;
L is —$CH_2$—O—, —$CH_2CH_2$—, —CH=CH— or a bond; and
B is aryl or heteroaryl or cycloalkyl;
with the proviso that, when L is a direct bond, B cannot be unsubstituted heteroaryl or heteroaryl monosubstituted with fluorine.

DETAILED DESCRIPTION OF THE INVENTION

In accordance with the present invention, compounds represented by formula (I) above may be substituted derivatives either of tetrahydro-β-carboline, where G is —$CR^{12}R^{13}$—$NR^5$—, or of tetrahydro-γ-carboline, where G is —$NR^5$—$CR^{12}R^{13}$—. In some embodiments of the invention, G is —$CH_2$—$NR^5$—; in other embodiments, G is —$NR^5$—$CH_2$—.

In accordance with some embodiments of the invention, $R^1$ is H.

In accordance with other embodiments of the invention, $R^1$ is alkyl, for example, methyl or ethyl.

In accordance with some embodiments of the invention, $R^5$ is H. In other embodiments, $R^5$ is optionally substituted alkyl. In some embodiments, $R^5$ is selected from methyl, ethyl, 2-propyl, 2-hydroxyethyl, 2,2,2-trifluoroethyl, 3,3,3-trifluoropropyl, 2-oxo-2-(pyrrolidin-1-yl)ethyl, 2-(pyrrolidin-1-yl)ethyl and (S)-pyrrolidin-2-ylmethyl. In other embodiments, $R^5$ is optionally substituted heterocycle. In some embodiments, $R^5$ is selected from piperidin-4-yl and 1-methylpiperidin-4-yl. In other embodiments, $R^5$ is —C(=O)—$R^6$. In other embodiments, $R^5$ is —C(=O)—O—$R^7$.

In some embodiments, $R^6$ and $R^7$ are each optionally substituted alkyl, for example, methyl, 2-propyl, 2-(pyrrolidin-1-yl)-ethyl, pyrrolidin-1-ylmethyl, and dimethylaminomethyl. In some embodiments, $R^6$ is optionally substituted heterocycle, for example, pyrrolidin-3-yl, (R)-pyrrolidin-2-yl, (S)-pyrrolidin-2-yl, 1-methylpyrrolidin-3-yl, (R)-1-methylpyrrolidin-2-yl and (S)-1-methylpyrrolidin-2-yl.

In accordance with some embodiments of the invention, the compound has the structure

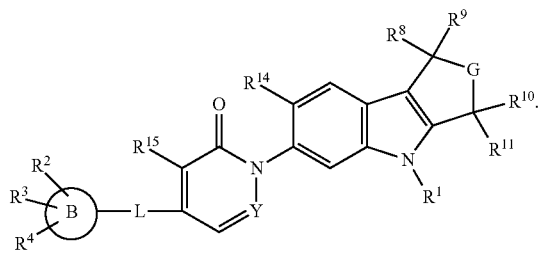

In accordance with other embodiments of the invention, the compound has the structure

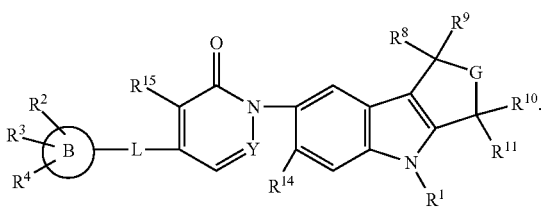

In accordance with some embodiments of the invention, the L is a bond. In accordance with other embodiments of the invention, L is —$CH_2$—O—. In accordance with some embodiments of the invention, L is —$CH_2CH_2$—. In accordance with other embodiments of the invention, L is —CH=CH—.

In accordance with some embodiments of the invention, B is aryl, for example, phenyl. In accordance with other embodiments of the invention, B is heteroaryl, for example, pyridinyl. In some embodiments, B is pyridin-2-yl or pyridin-3-yl. In other embodiments, B is pyridazinyl, for example, pyridazin-3-yl. In some other embodiments, B is pyrimidinyl, for example, pyrimidin-5-yl or pyrimidin-2-yl. In accordance with other embodiments of the invention, B is cycloalkyl, for example, cyclohexyl.

In accordance with some embodiments of the invention, $R^2$, $R^3$ and $R^4$ are each H. In accordance with other embodiments of the invention, two of $R^2$, $R^3$ and $R^4$ are H, and the other of $R^2$, $R^3$ and $R^4$ is selected from trifluoromethyl, chloro, fluoro, methyl, methoxy and methanethio.

In accordance with other embodiments of the invention, one of $R^2$, $R^3$ and $R^4$ is H, another of $R^2$, $R^3$ and $R^4$ is Cl, and the third of $R^2$, $R^3$ and $R^4$ is F, Cl or methoxy. In accordance with other embodiments of the invention, one of $R^2$, $R^3$ and $R^4$ is H, another of $R^2$, $R^3$ and $R^4$ is F, and the third of $R^2$, $R^3$ and $R^4$ is methoxy. In accordance with other embodiments of the invention, one of $R^2$, $R^3$ and $R^4$ is H, another of $R^2$, $R^3$ and $R^4$ is methoxy, and the third of $R^2$, $R^3$ and $R^4$ is methyl.

In accordance with some embodiments of the invention, B, together with $R^2$, $R^3$ and $R^4$, is selected from phenyl, 4-trifluoromethylphenyl, 4-chlorophenyl, 2,4-dichlorophenyl, 4-fluorophenyl, 4-chloro-2-fluorophenyl, 2-fluoro-4-methoxyphenyl, pyridin-2-yl, 5-chloropyridin-2-yl, 5-(trifluoromethyl)pyridin-2-yl, 5-fluoropyridin-2-yl, 6-(trifluoromethyl)pyridazin-3-yl, 6-methylpyridazin-3-yl, 4-fluoro-2-methoxyphenyl, 6-(trifluoromethyl)pyridin-3-yl, 2-(trifluoromethyl)pyrimidin-5-yl, 5-(trifluoromethyl)pyrimidin-2-yl, 5-methylpyridin-2-yl, 6-methylpyridin-3-yl, cyclohexyl, 4-chloro-2-methoxyphenyl, pyrimidin-2-yl, imidazo[1,2-a]pyridin-6-yl, imidazo[1,2-a]pyridin-2-yl, 4-methoxyphenyl, 4-methanethiophenyl and 4-methoxy-2-methylphenyl.

In accordance with some embodiments of the invention, at least one of $R^8$, $R^9$, $R^{10}$, $R^{11}$, $R^{12}$, $R^{13}$, $R^{19}$ and $R^{20}$ is H. In other embodiments, at least one of $R^8$, $R^9$, $R^{10}$, $R^{11}$, $R^{12}$, $R^{13}$, $R^{19}$ and $R^{20}$ is optionally substituted alkyl, for example, methyl, ethyl, or hydroxymethyl.

In accordance with some embodiments of the invention, the compound is selected from

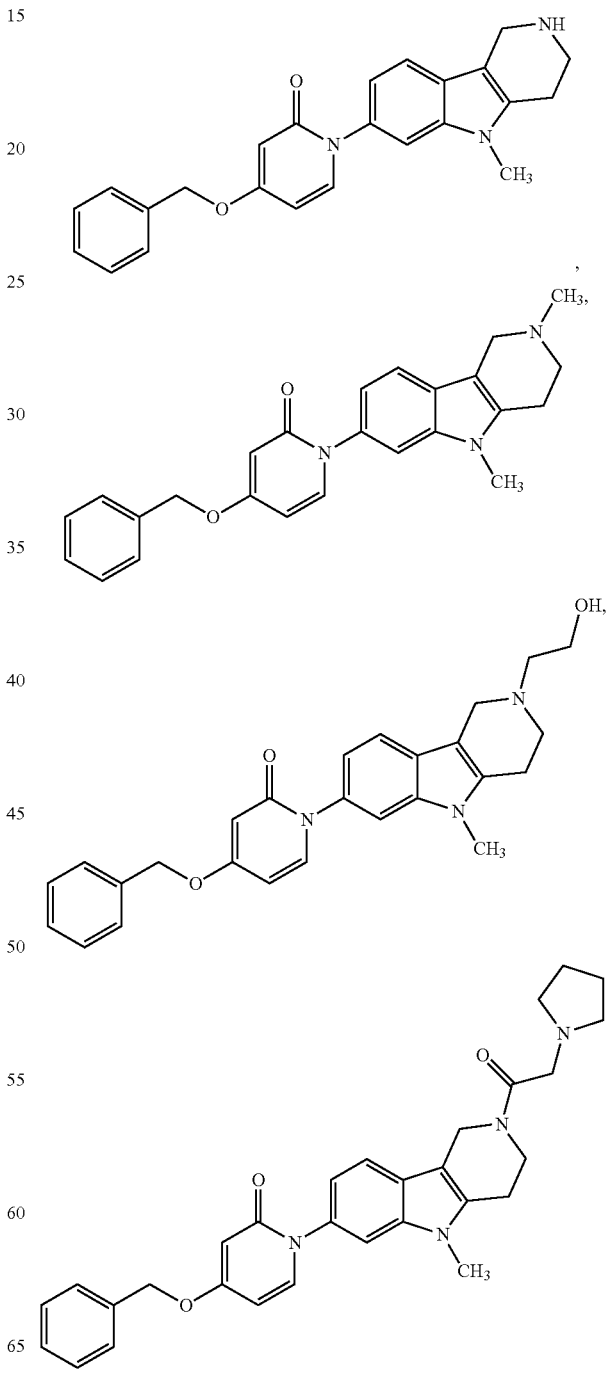

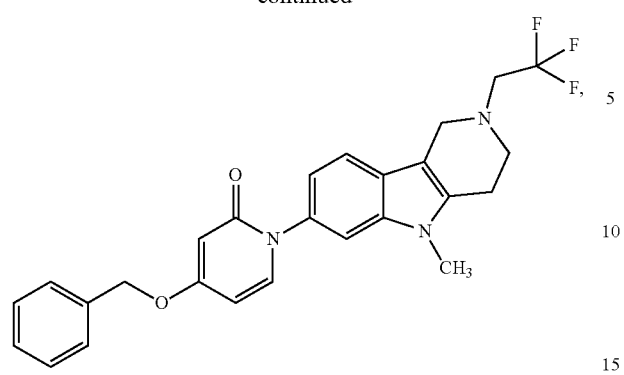
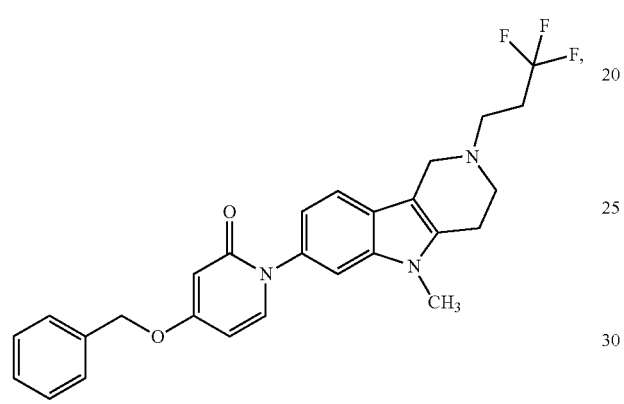
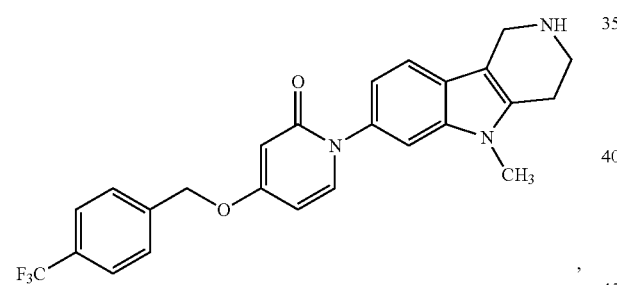
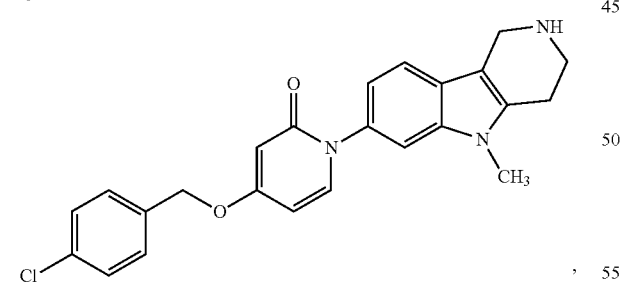
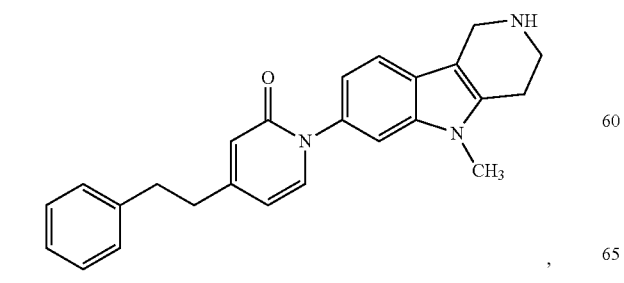
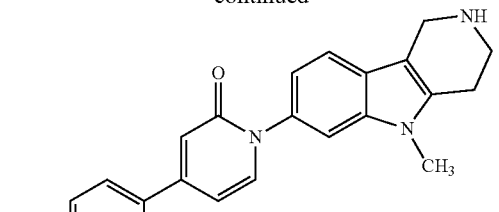
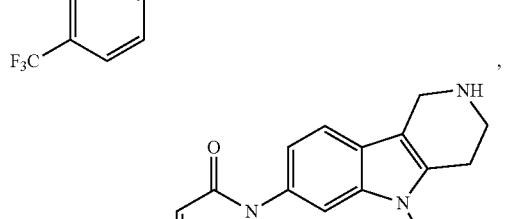
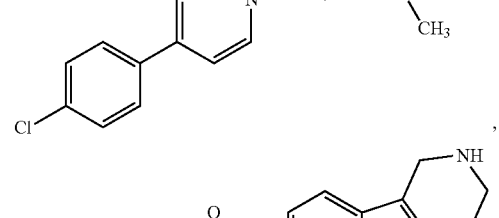
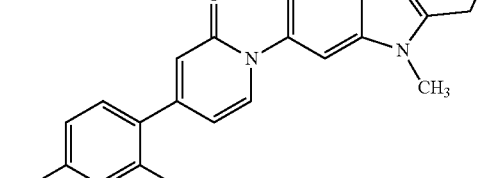
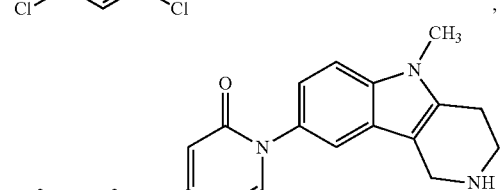
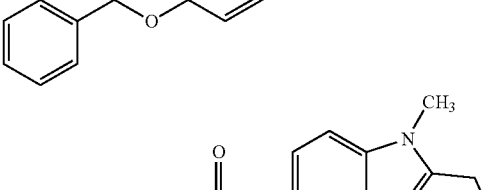

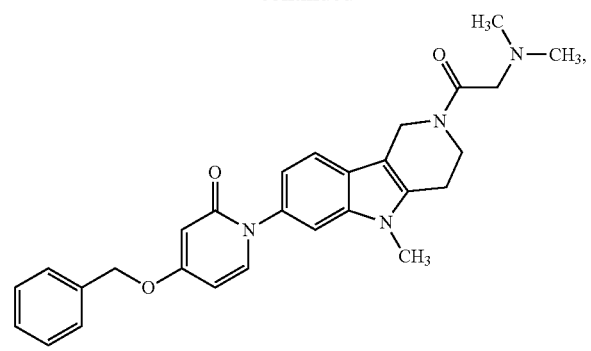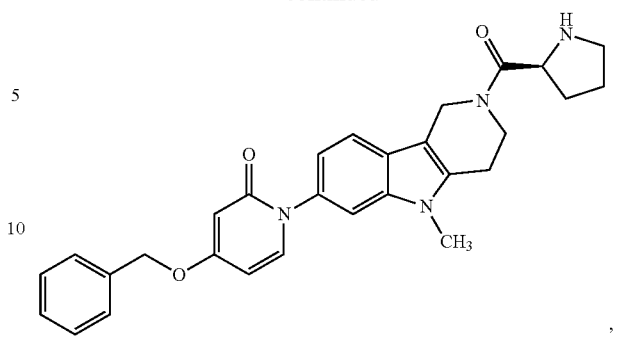
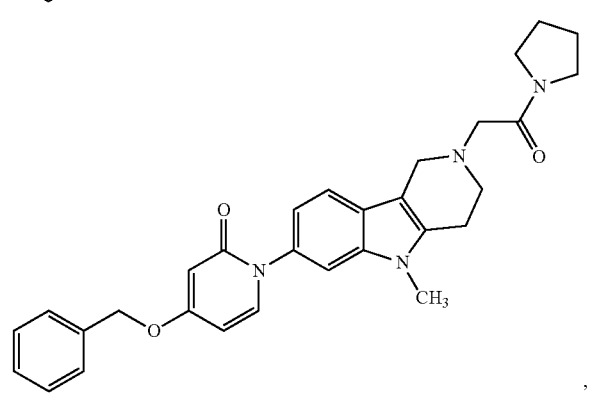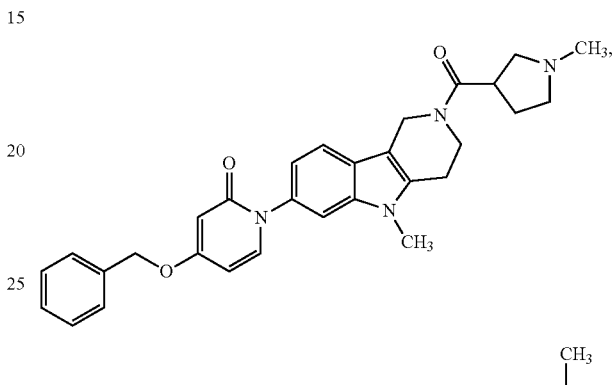
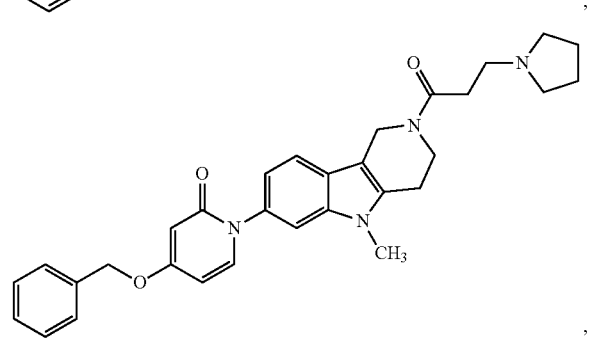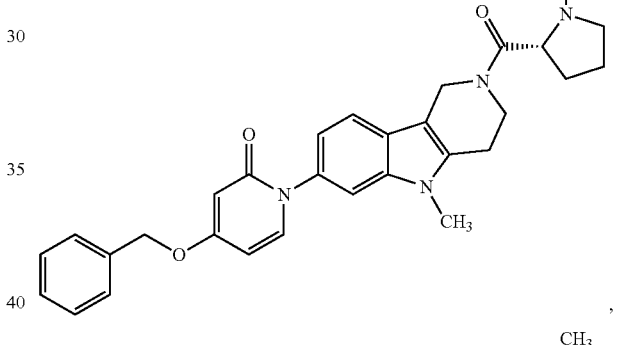
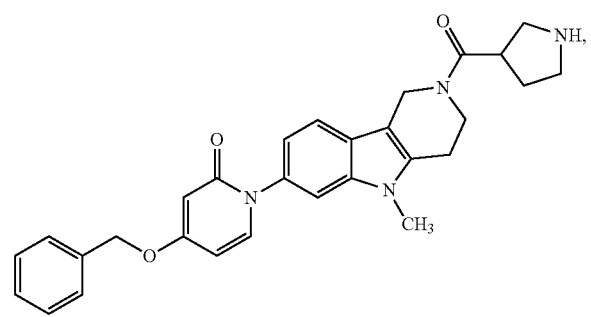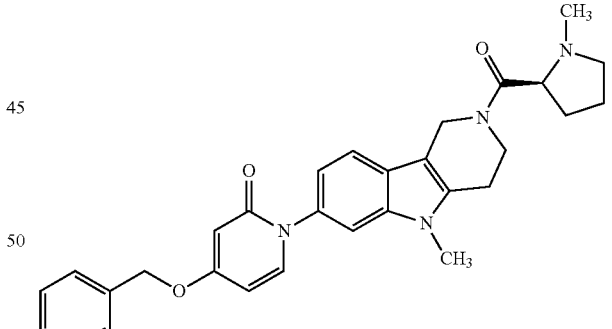

-continued
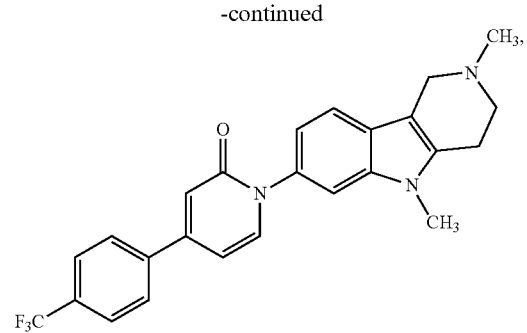
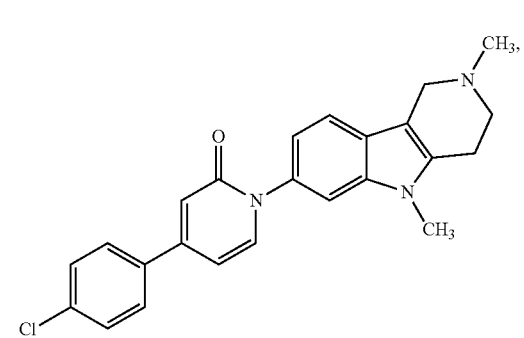
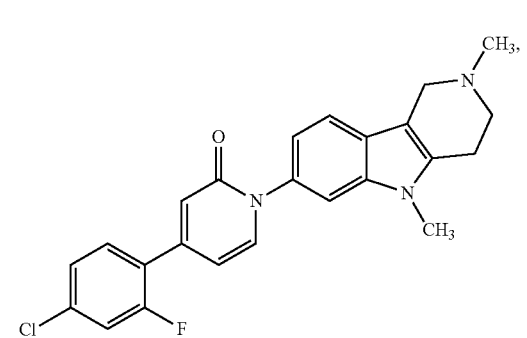
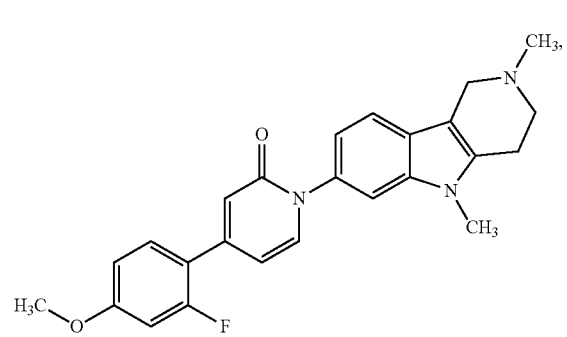
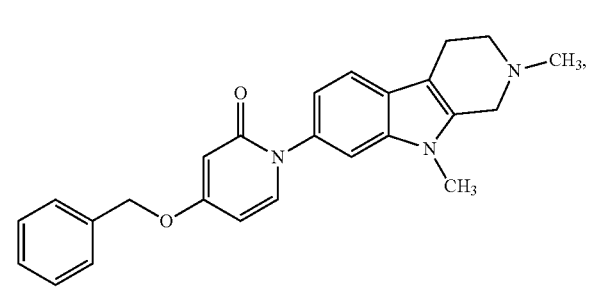
-continued
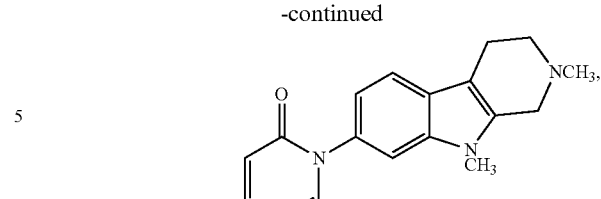
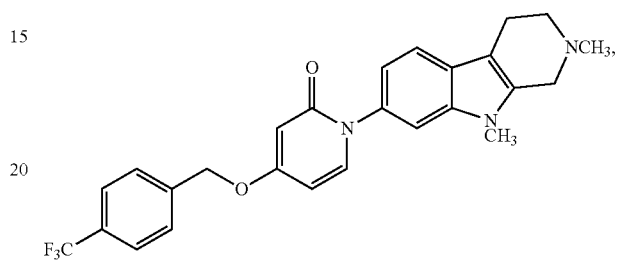
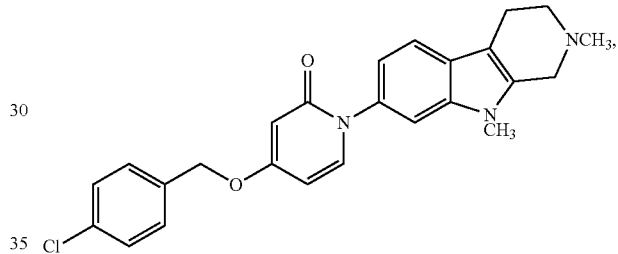
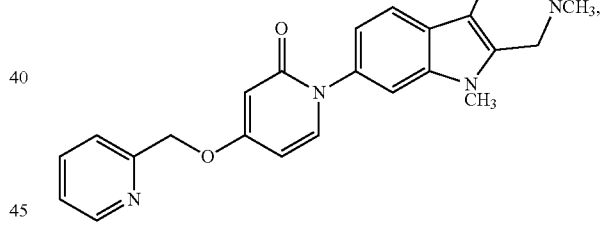
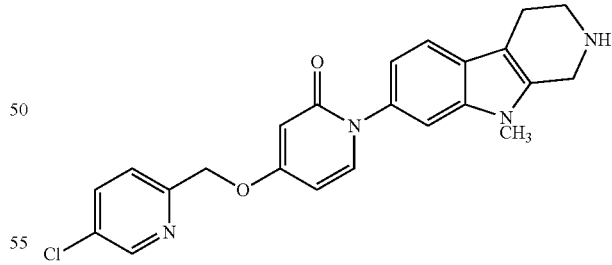
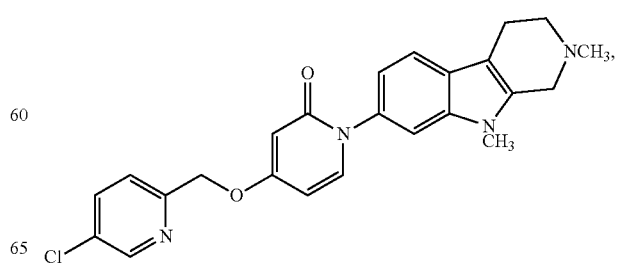

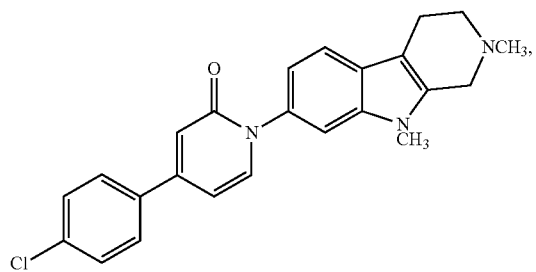
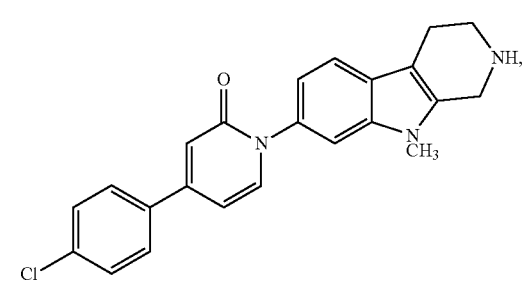
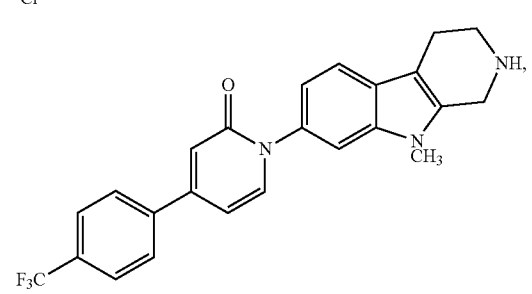
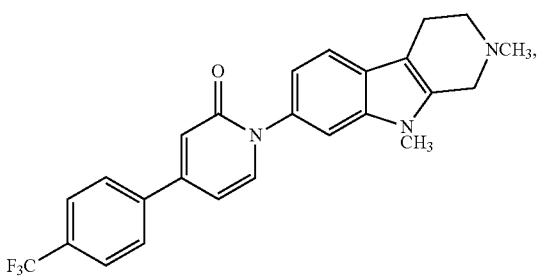
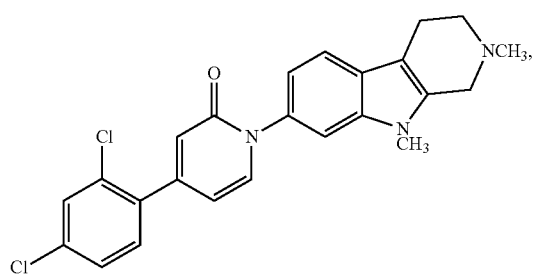
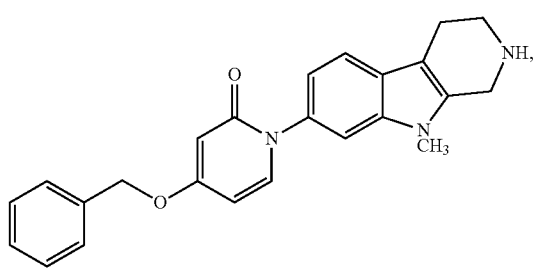
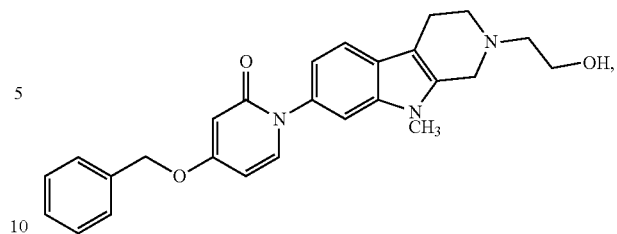
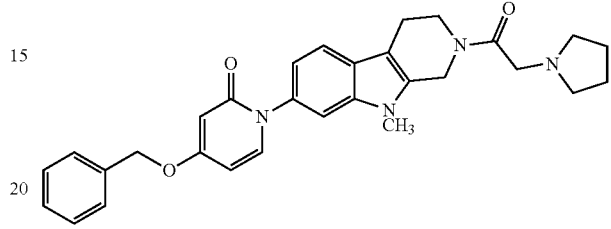
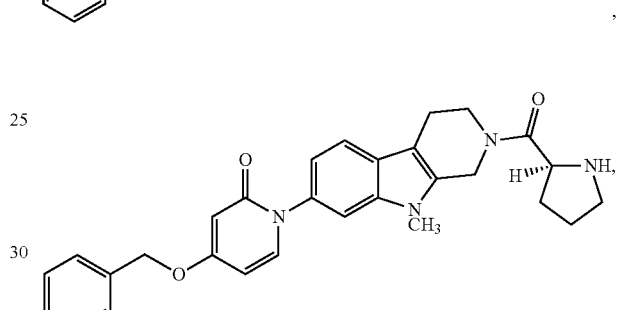
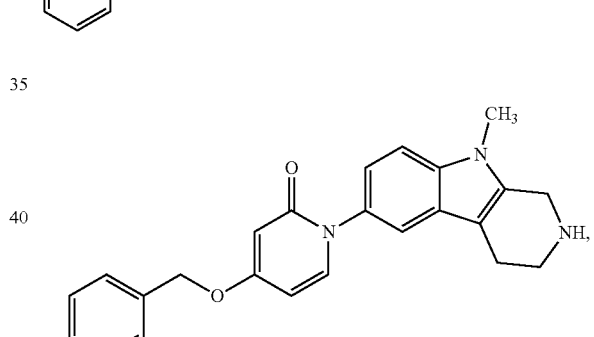
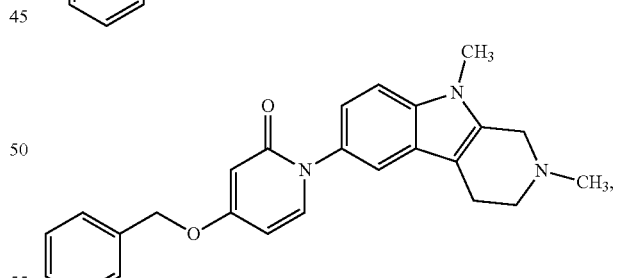
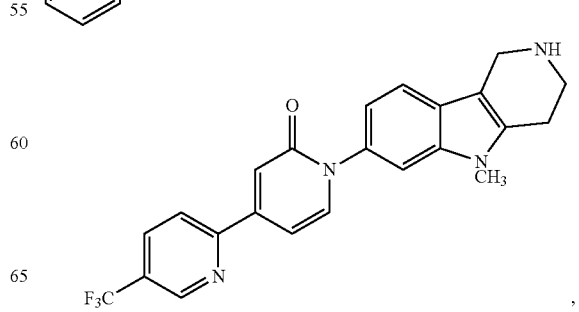

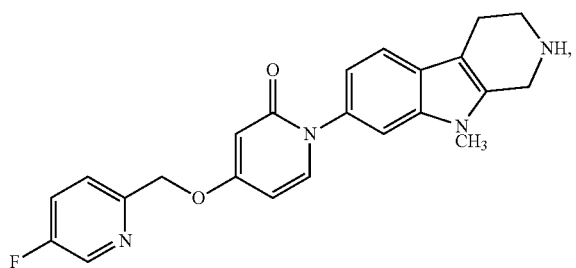
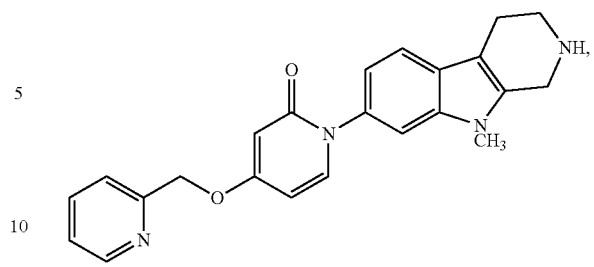
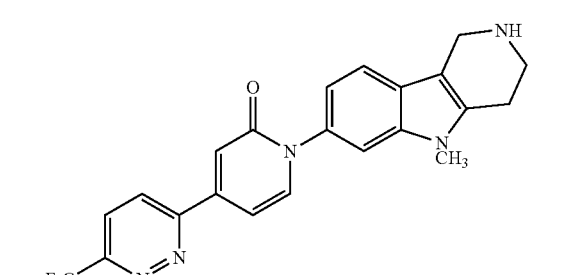
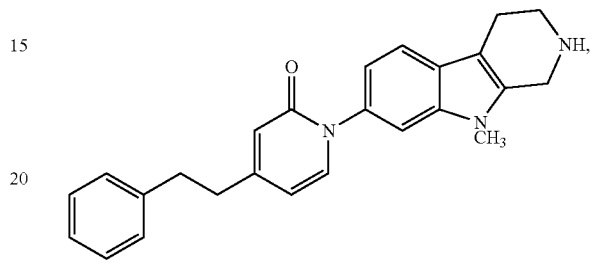
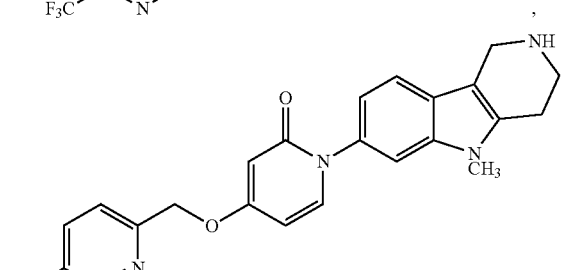
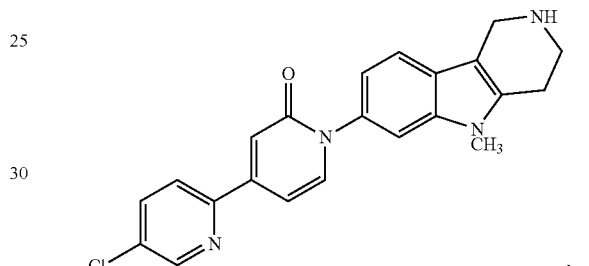
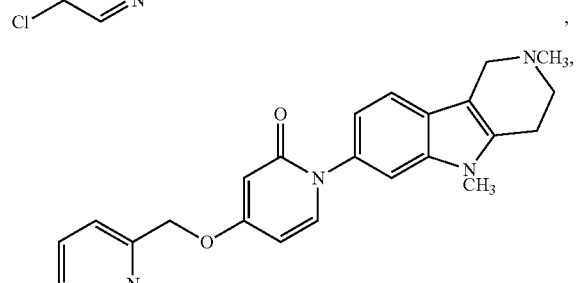
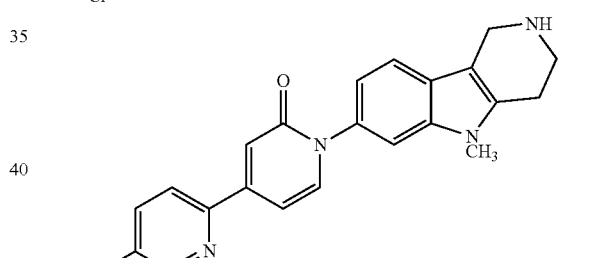
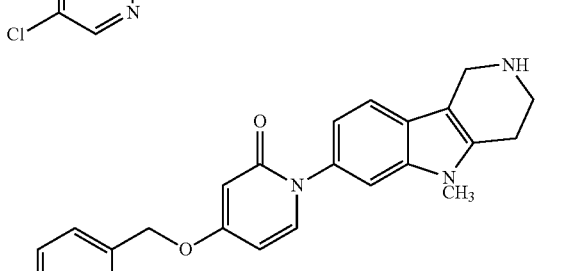
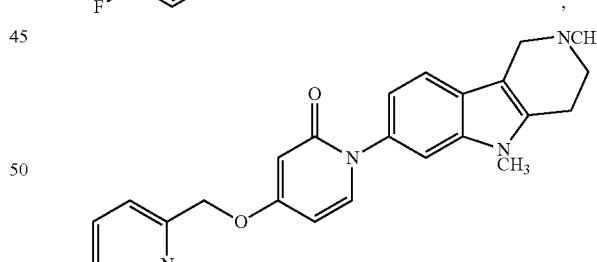
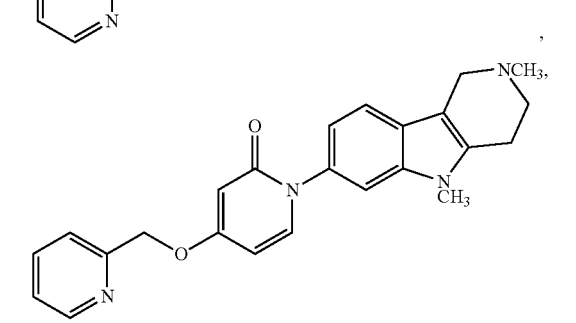
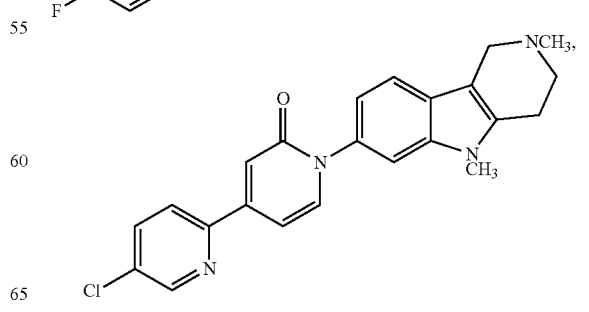

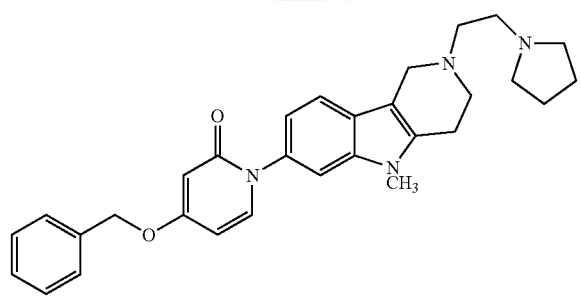,
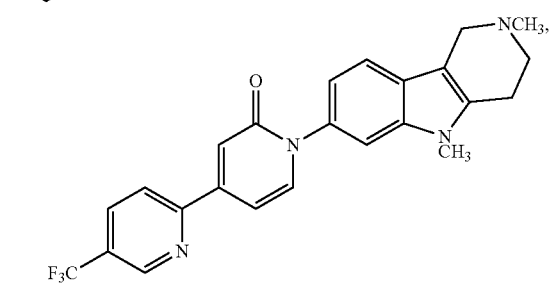,
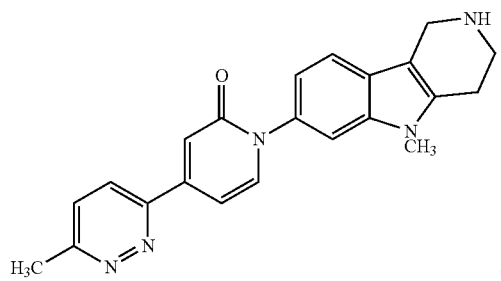,
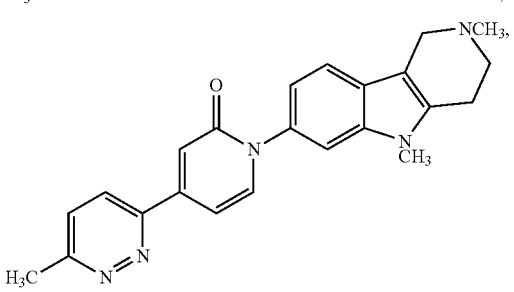,
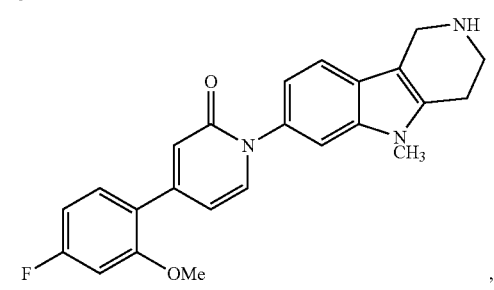,
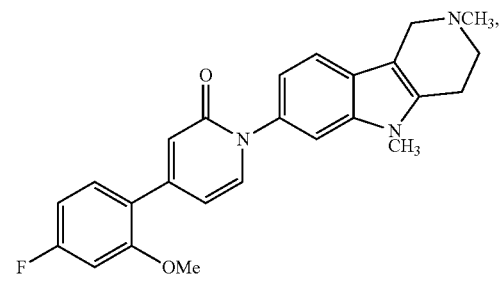,
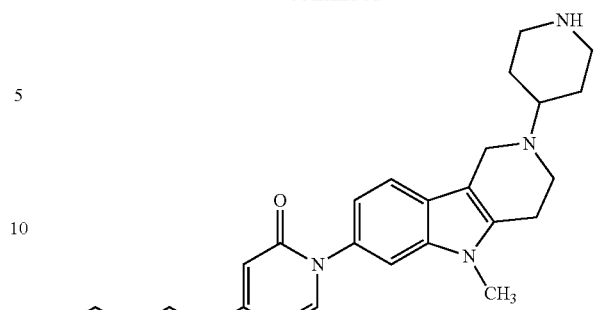,
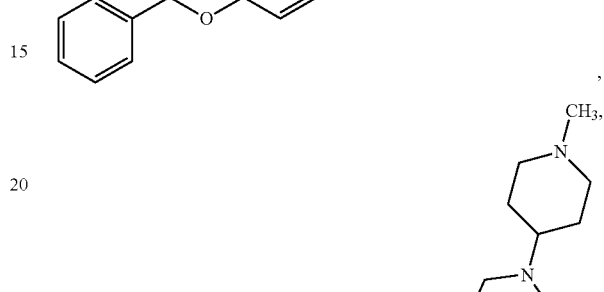,
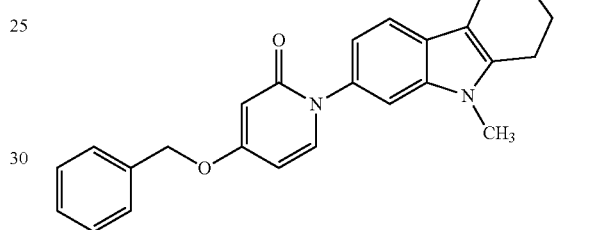,
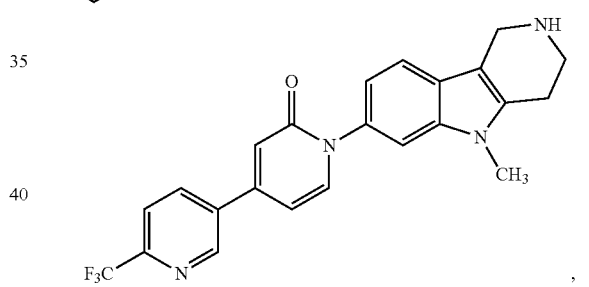,
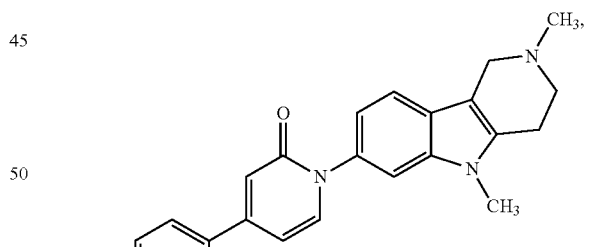,
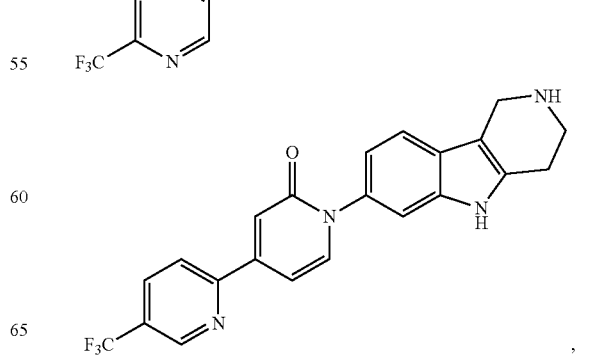,

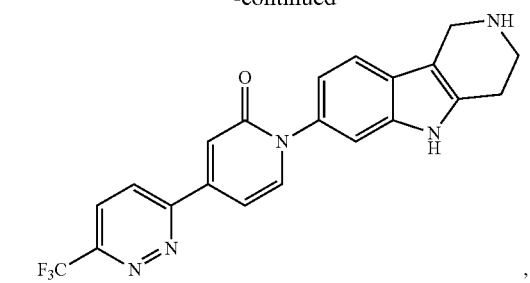
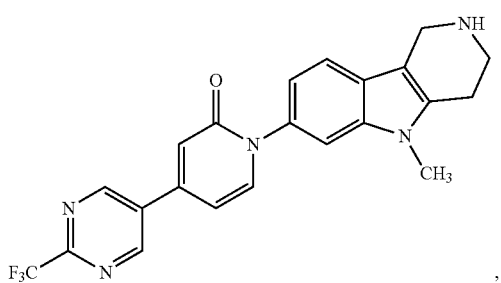
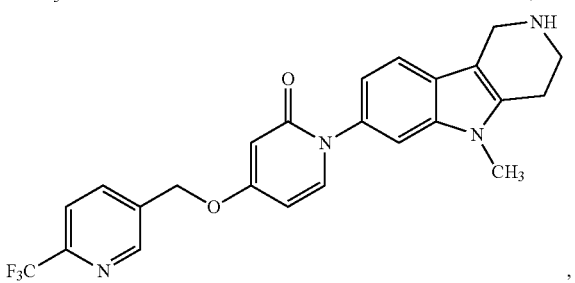
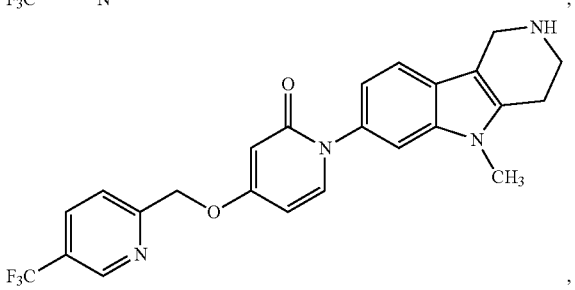
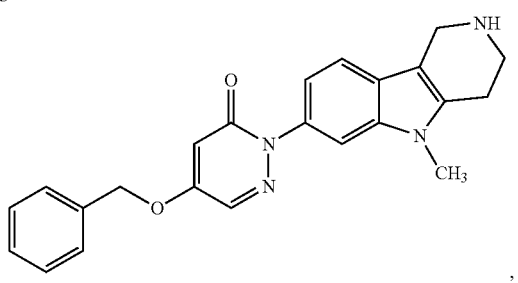
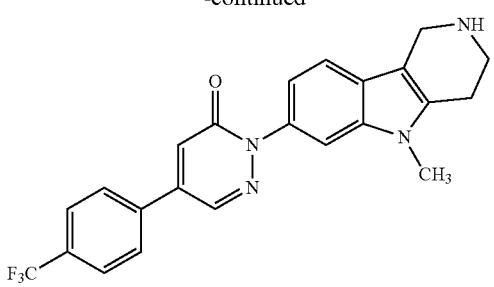
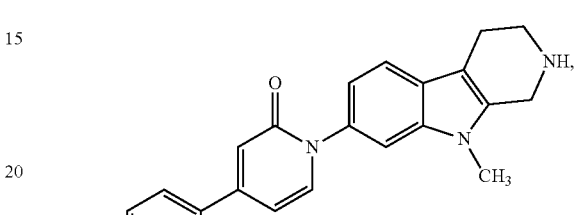
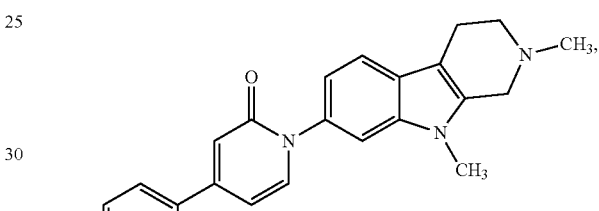
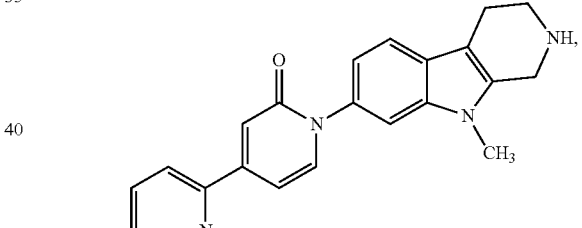
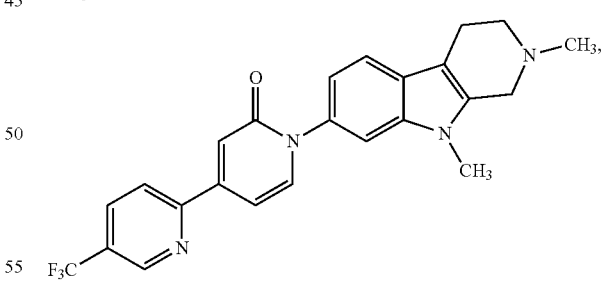
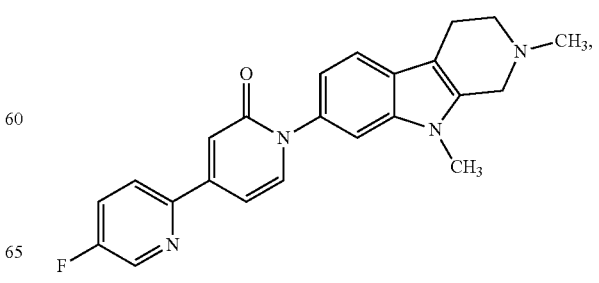

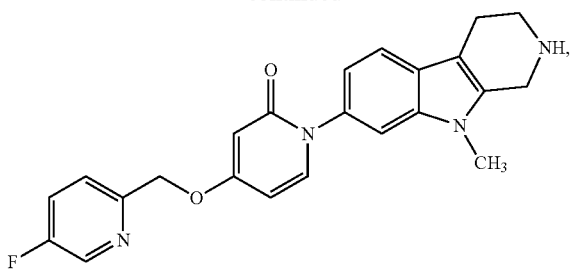
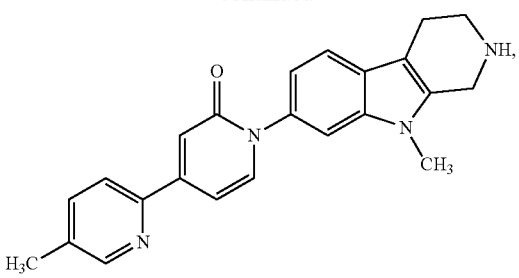
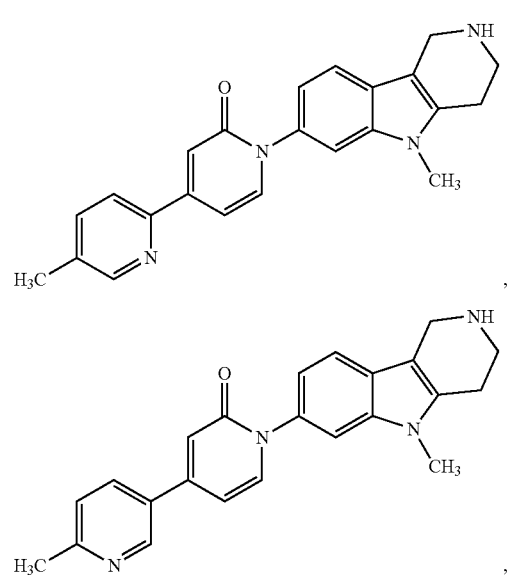
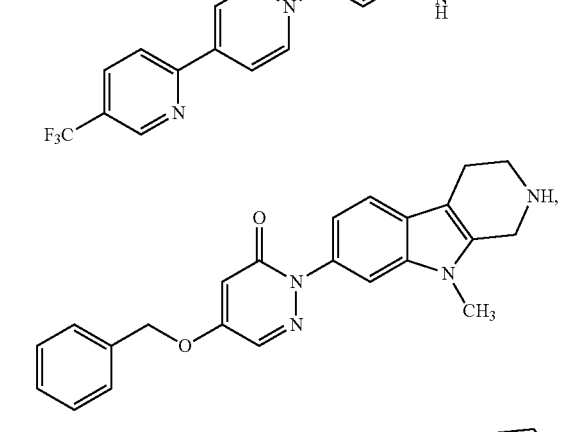
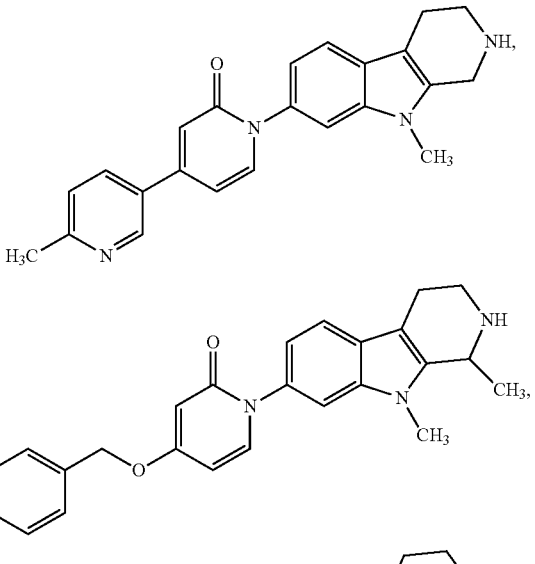
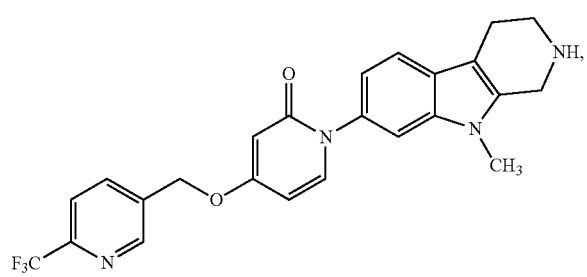

21
-continued
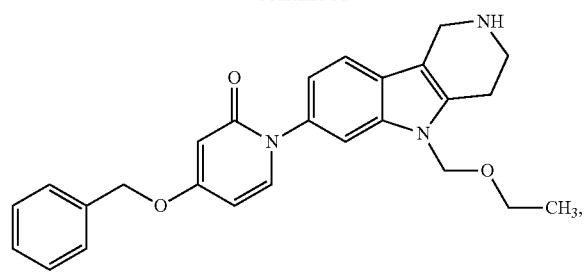
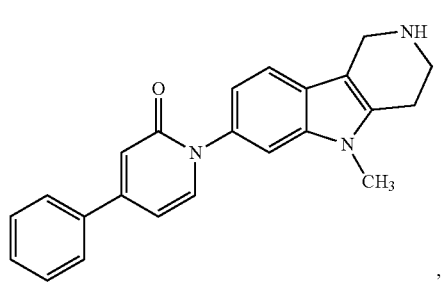
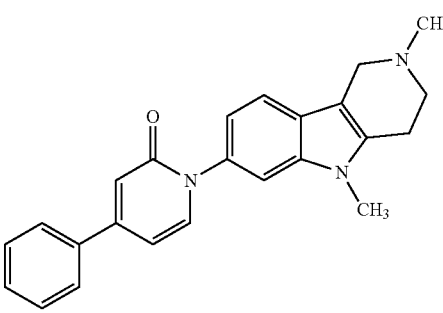
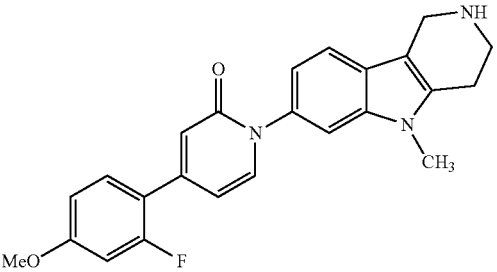
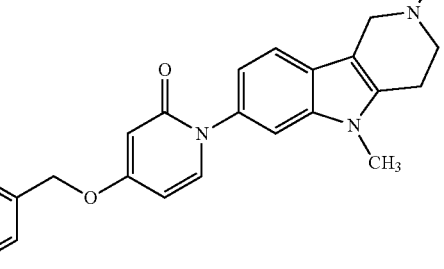
22
-continued 23
-continued
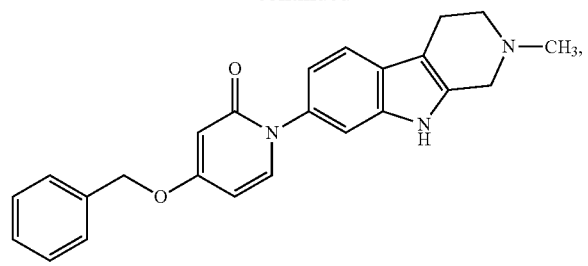
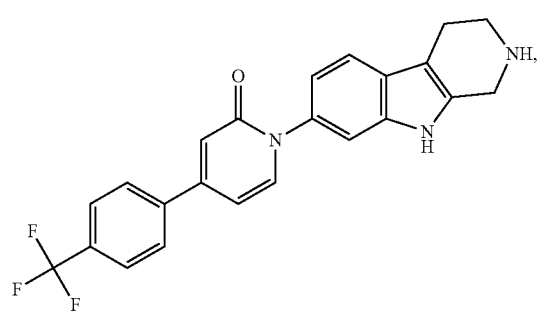
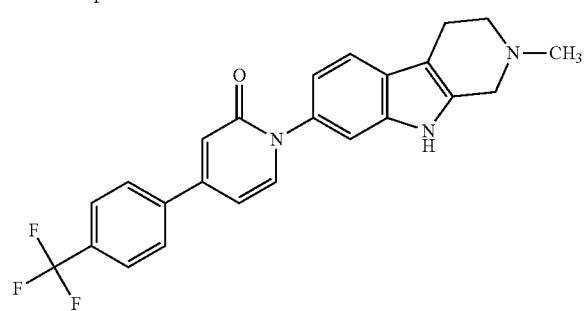
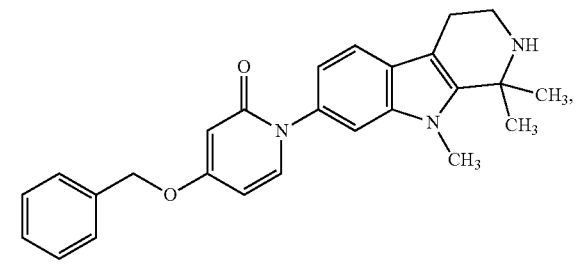
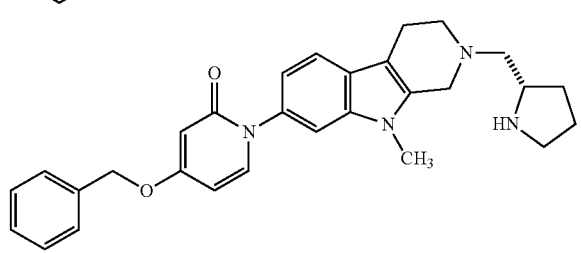
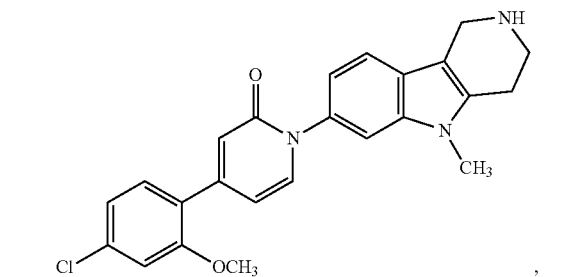
24
-continued 25
-continued
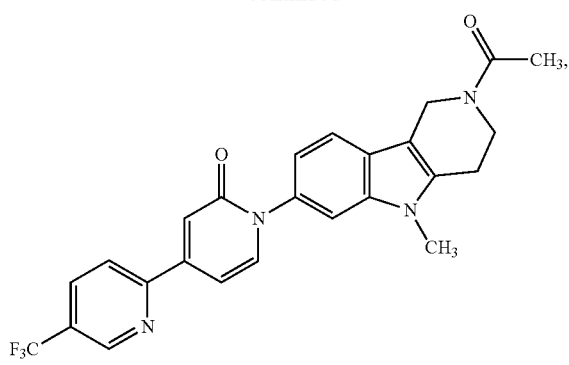
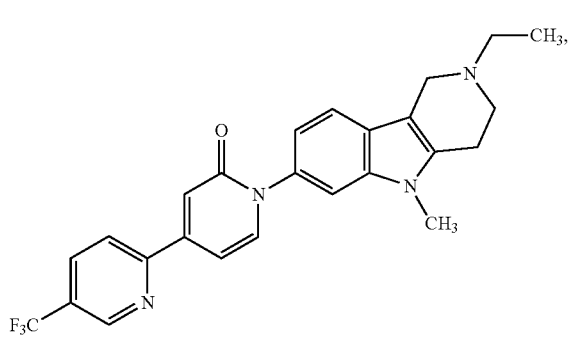
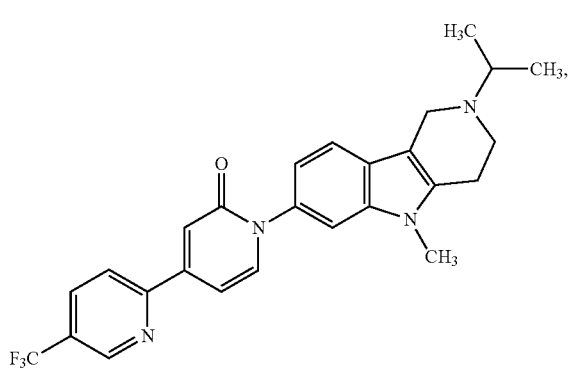
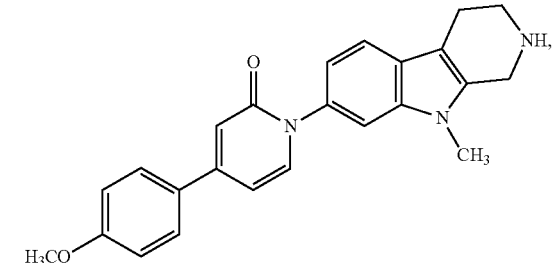
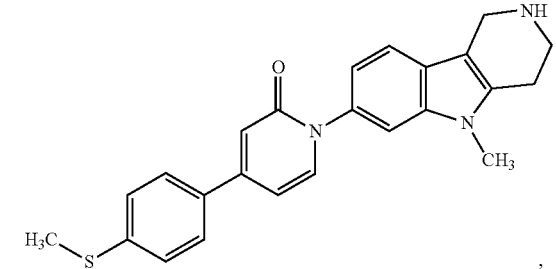
26
-continued
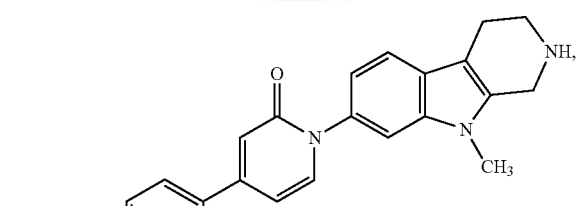
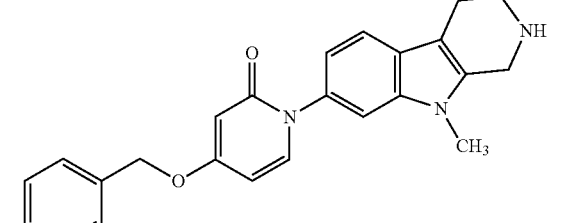
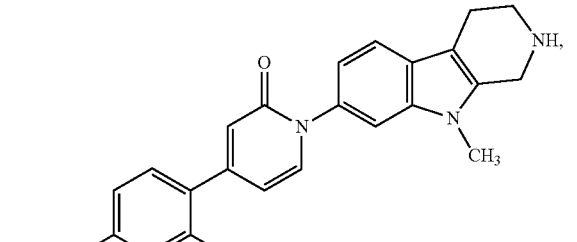
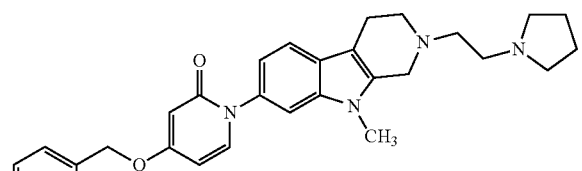
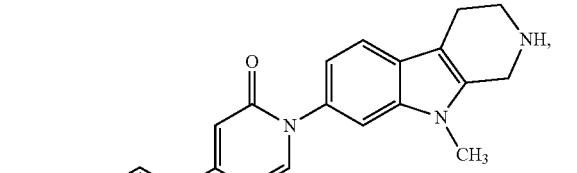
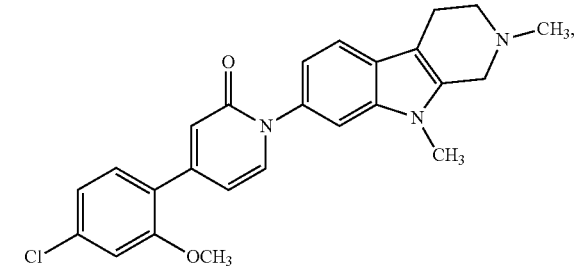

27
-continued
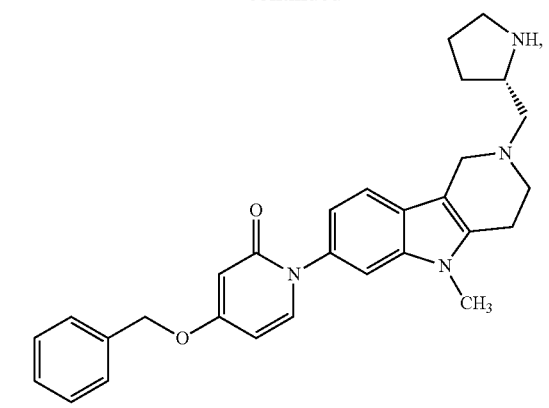
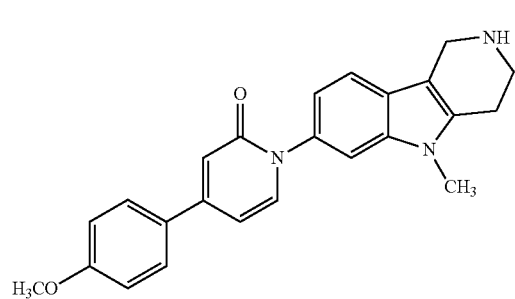
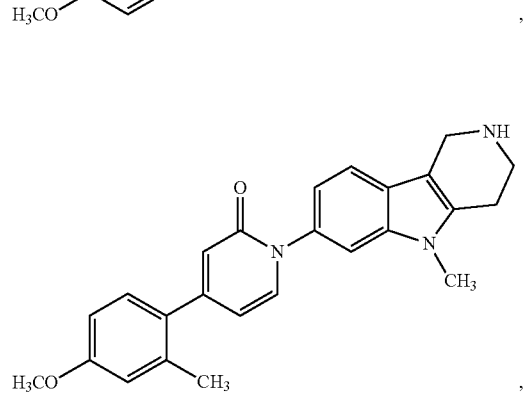
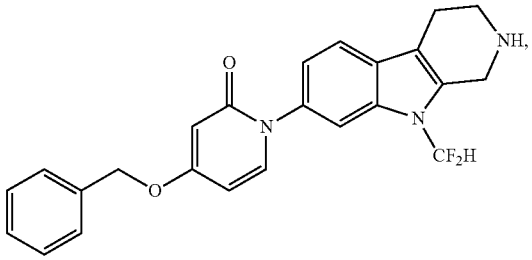
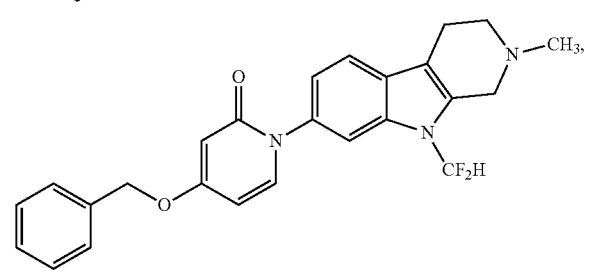
28
-continued
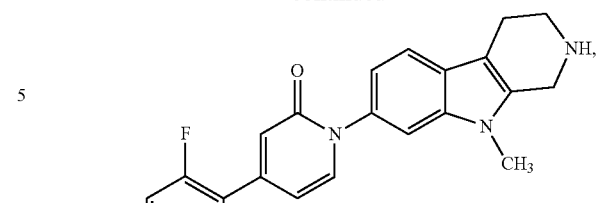
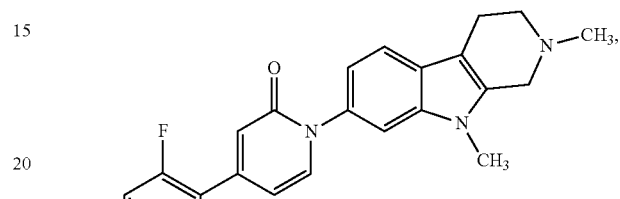
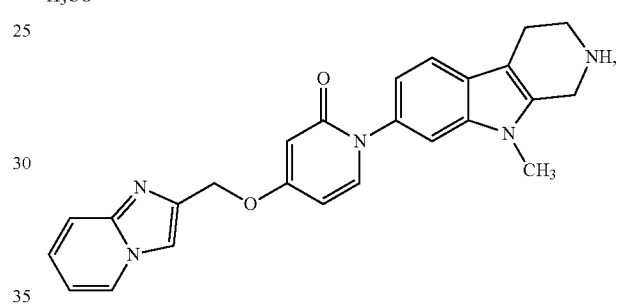
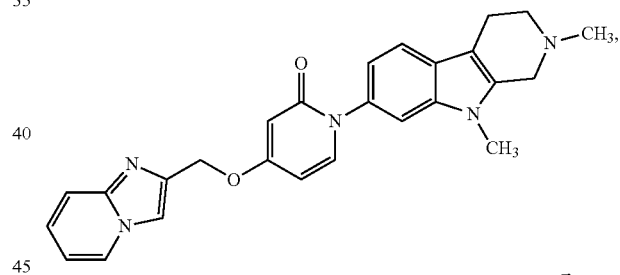
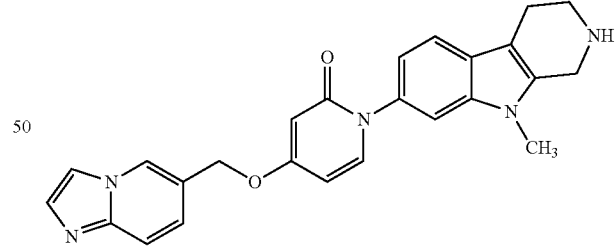
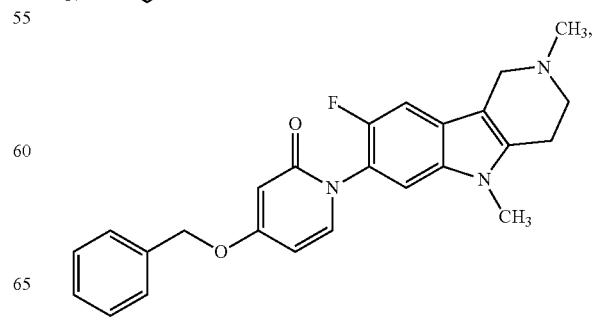

-continued

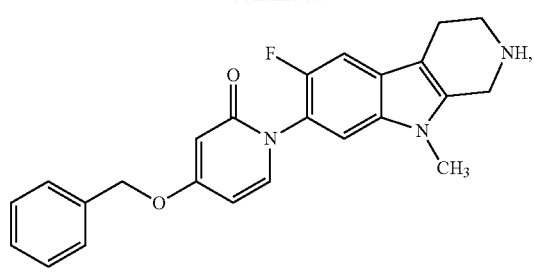

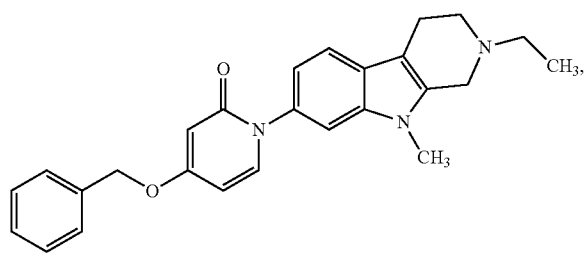

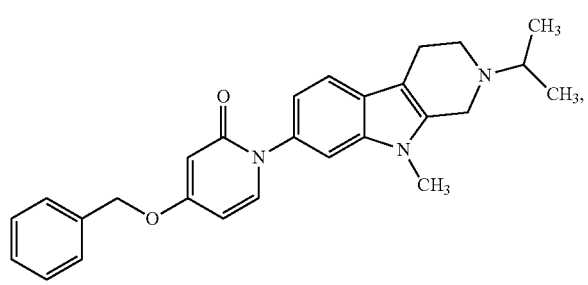

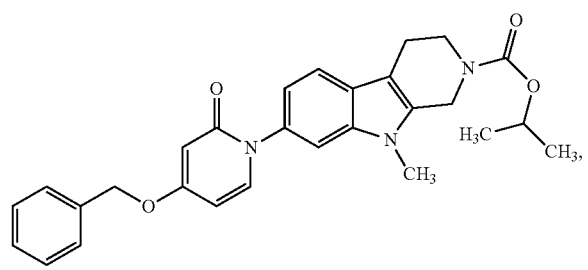

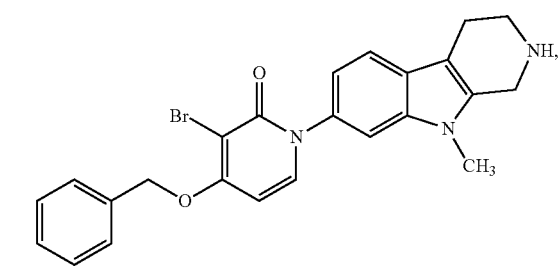

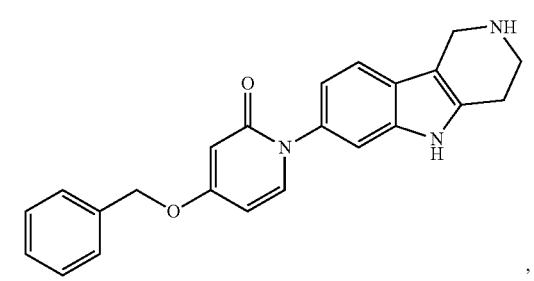

, and

-continued

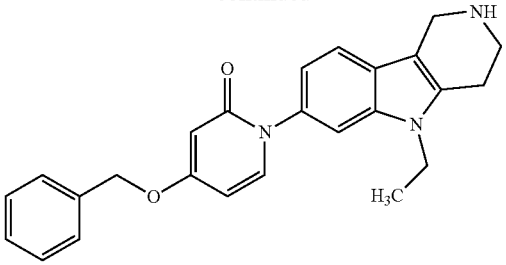

In accordance with some embodiments of the invention, the compound is a pharmaceutically acceptable salt thereof. In some embodiments, the salt is an HCl salt.

There is also provided, in accordance with embodiments of the invention, a pharmaceutical composition comprising a compound as described herein, and a pharmaceutically acceptable carrier, excipient or diluent therefore.

There is also provided, in accordance with embodiments of the invention, a method of treating obesity, comprising administering to a patient in need of obesity reduction an obesity-reducing effective amount of a compound as described herein.

There is also provided, in accordance with embodiments of the invention, a method of treating anxiety, comprising administering to a patient in need of such treatment a therapeutically effective amount of a compound as described herein.

There is also provided, in accordance with embodiments of the invention, a method of treating depression, comprising administering to a patient in need of such treatment a therapeutically effective amount of a compound as described herein.

There is also provided, in accordance with embodiments of the invention, a method of treating non-alcoholic fatty liver disease, comprising administering to a patient in need of such treatment a therapeutically effective amount of a compound as described herein.

There is also provided, in accordance with embodiments of the invention, a method of treating a disease or condition which is susceptible to treatment with an $MCH_1$ receptor modulator, comprising administering to a patient in need thereof a therapeutically effective amount of a compound as described herein.

DEFINITIONS

Throughout this specification the terms and substituents retain their definitions.

Alkyl is intended to include linear, branched, or cyclic hydrocarbon structures and combinations thereof. When not otherwise restricted, the term refers to alkyl of 20 or fewer carbons. Lower alkyl refers to alkyl groups of 1, 2, 3, 4, 5 and 6 carbon atoms. Examples of lower alkyl groups include methyl, ethyl, propyl, isopropyl, butyl, s- and t-butyl and the like. Cycloalkyl is a subset of alkyl and includes cyclic hydrocarbon groups of 3, 4, 5, 6, 7, and 8 carbon atoms. Examples of cycloalkyl groups include c-propyl, c-butyl, c-pentyl, norbornyl, adamantyl and the like.

$C_1$ to $C_{20}$ Hydrocarbon (e.g. $C_1$, $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, $C_{20}$) includes alkyl, cycloalkyl, alkenyl, alkynyl, aryl and combinations thereof. Examples include benzyl, phenethyl, cyclohexylmethyl, camphoryl and naphthylethyl. The term "phenylene" refers to ortho, meta or para residues of the formulae:

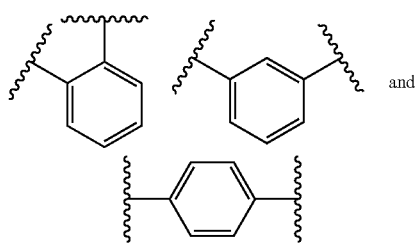

Alkoxy or alkoxyl refers to groups of 1, 2, 3, 4, 5, 6, 7 or 8 carbon atoms of a straight, branched, cyclic configuration and combinations thereof attached to the parent structure through an oxygen. Examples include methoxy, ethoxy, propoxy, isopropoxy, cyclopropyloxy, cyclohexyloxy and the like. Lower-alkoxy refers to groups containing one to four carbons. For the purposes of the present patent application alkoxy also includes methylenedioxy and ethylenedioxy in which each oxygen atom is bonded to the atom, chain or ring from which the methylenedioxy or ethylenedioxy group is pendant so as to form a ring. Thus, for example, phenyl substituted by alkoxy may be, for example,

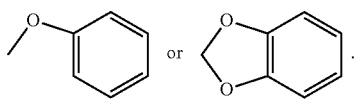

Oxaalkyl refers to alkyl residues in which one or more carbons (and their associated hydrogens) have been replaced by oxygen. Examples include methoxypropoxy, 3,6,9-trioxadecyl and the like. The term oxaalkyl is intended as it is understood in the art [see Naming and Indexing of Chemical Substances for Chemical Abstracts, published by the American Chemical Society, ¶196, but without the restriction of ¶127(a)], i.e. it refers to compounds in which the oxygen is bonded via a single bond to its adjacent atoms (forming ether bonds). Similarly, thiaalkyl and azaalkyl refer to alkyl residues in which one or more carbons have been replaced by sulfur or nitrogen, respectively. Examples include ethylaminoethyl and methylthiopropyl.

Acyl refers to groups of 1, 2, 3, 4, 5, 6, 7 and 8 carbon atoms of a straight, branched, cyclic configuration, saturated, unsaturated and aromatic and combinations thereof, attached to the parent structure through a carbonyl functionality. One or more carbons in the acyl residue may be replaced by nitrogen, oxygen or sulfur as long as the point of attachment to the parent remains at the carbonyl. Examples include formyl, acetyl, propionyl, isobutyryl, t-butoxycarbonyl, benzoyl, benzyloxycarbonyl and the like. Lower-acyl refers to groups containing one to four carbons.

Aryl and heteroaryl refer to aromatic or heteroaromatic rings, respectively, as substituents. Heteroaryl contains one, two or three heteroatoms selected from O, N, or S. Both refer to monocyclic 5- or 6-membered aromatic or heteroaromatic rings, bicyclic 9- or 10-membered aromatic or heteroaromatic rings and tricyclic 13- or 14-membered aromatic or heteroaromatic rings. Aromatic 6, 7, 8, 9, 10, 11, 12, 13 and 14-membered carbocyclic rings include, e.g., benzene, naphthalene, indane, tetralin, and fluorene and the 5, 6, 7, 8, 9 and 10-membered aromatic heterocyclic rings include, e.g., imidazole, pyridine, indole, thiophene, benzopyranone, thiazole, furan, benzimidazole, quinoline, isoquinoline, quinoxaline, pyrimidine, pyrazine, tetrazole and pyrazole.

Arylalkyl means an alkyl residue attached to an aryl ring. Examples are benzyl, phenethyl and the like.

Substituted alkyl, aryl, cycloalkyl, heterocyclyl etc. refer to alkyl, aryl, cycloalkyl, or heterocyclyl wherein up to three H atoms in each residue are replaced with alkyl, halogen, haloalkyl, hydroxy, lower alkoxy, carboxy, carboalkoxy (also referred to as alkoxycarbonyl), carboxamido (also referred to as alkylaminocarbonyl), cyano, carbonyl, nitro, amino, alkylamino, dialkylamino, mercapto, alkylthio, sulfoxide, sulfone, acylamino, amidino, phenyl, benzyl, heteroaryl, phenoxy, benzyloxy, or heteroaryloxy.

The term "halogen" means fluorine, chlorine, bromine or iodine.

The term "prodrug" refers to a compound that is made more active in vivo. Commonly the conversion of prodrug to drug occurs by enzymatic processes in the liver or blood of the mammal. Many of the compounds of the invention may be chemically modified without absorption into the systemic circulation, and in those cases, activation in vivo may come about by chemical action (as in the acid-catalyzed cleavage in the stomach) or through the intermediacy of enzymes and microflora in the gastrointestinal GI tract.

In the characterization of some of the substituents, it is recited that certain substituents may combine to form rings. Unless stated otherwise, it is intended that such rings may exhibit various degrees of unsaturation (from fully saturated to fully unsaturated), may include heteroatoms and may be substituted with lower alkyl or alkoxy.

It will be recognized that the compounds of this invention can exist in radiolabeled form, i.e., the compounds may contain one or more atoms containing an atomic mass or mass number different from the atomic mass or mass number usually found in nature. Radioisotopes of hydrogen, carbon, phosphorous, fluorine, iodine and chlorine include $^3$H, $^{14}$C, $^{35}$S, $^{18}$F, $^{32}$P, $^{33}$P, $^{125}$I, and $^{36}$Cl, respectively. Compounds that contain those radioisotopes and/or other radioisotopes of other atoms are within the scope of this invention. Radiolabeled compounds described herein and prodrugs thereof can generally be prepared by methods well known to those skilled in the art. Conveniently, such radiolabeled compounds can be prepared by carrying out the procedures disclosed in the Examples and Schemes by substituting a readily available radiolabeled reagent for a non-radiolabeled reagent.

The terms "methods of treating or preventing" mean amelioration, prevention or relief from the symptoms and/or effects associated with lipid disorders. The term "preventing" as used herein refers to administering a medicament beforehand to forestall or obtund an acute episode or, in the case of a chronic condition to diminish the likelihood or seriousness of the condition. The person of ordinary skill in the medical art (to which the present method claims are directed) recognizes that the term "prevent" is not an absolute term. In the medical art it is understood to refer to the prophylactic administration of a drug to substantially diminish the likelihood or seriousness of a condition, and this is the sense intended in applicants' claims. As used herein, reference to "treatment" of a patient is intended to include prophylaxis.

Throughout this application, various references are referred to. Each of the patents, patent applications, patent publications, and references mentioned herein is hereby incorporated by reference in its entirety.

The term "mammal" is used in its dictionary sense. The term "mammal" includes, for example, mice, hamsters, rats, cows, sheep, pigs, goats, and horses, monkeys, dogs (e.g., *Canis familiaris*), cats, rabbits, guinea pigs, and primates, including humans.

Compounds described herein may contain one or more asymmetric centers and may thus give rise to enantiomers, diastereomers, and other stereoisomeric forms. Each chiral center may be defined, in terms of absolute stereochemistry, as (R)- or (S)-. The present invention is meant to include all such possible isomers, as well as mixtures thereof, including racemic and optically pure forms. Optically active (R)- and (S)-, (−)- and (+)-, or (D)- and (L)-isomers may be prepared using chiral synthons or chiral reagents, or resolved using conventional techniques. When the compounds described herein contain olefinic double bonds or other centers of geometric asymmetry, and unless specified otherwise, it is intended that the compounds include both E and Z geometric isomers. The configuration of any carbon-carbon double bond appearing herein is selected for convenience only and is not intended to designate a particular configuration; thus a carbon-carbon double bond depicted arbitrarily herein as E may be Z, E, or a mixture of the two in any proportion. Likewise, all tautomeric forms are also intended to be included.

As used herein, and as would be understood by the person of skill in the art, the recitation of "a compound" is intended to include salts, solvates and inclusion complexes of that compound as well as any stereoisomeric form, or a mixture of any such forms of that compound in any ratio. Thus, in accordance with some embodiments of the invention, a compound as described herein, including in the contexts of pharmaceutical compositions, methods of treatment, and compounds per se, is provided as the salt form. In accordance with some embodiments of the invention, the salt is a hydrochloride salt.

The term "enantiomeric excess" is well known in the art and is defined for a resolution of ab into a+b as $$ee_a = \left(\frac{\text{conc. of } a - \text{conc. of } b}{\text{conc. of } a + \text{conc. of } b}\right) \times 100$$

The term "enantiomeric excess" is related to the older term "optical purity" in that both are measures of the same phenomenon. The value of ee will be a number from 0 to 100, zero being racemic and 100 being pure, single enantiomer. A compound which in the past might have been called 98% optically pure is now more precisely described as 96% ee; in other words, a 90% ee reflects the presence of 95% of one enantiomer and 5% of the other in the material in question.

Terminology related to "protecting", "deprotecting" and "protected" functionalities occurs throughout this application. Such terminology is well understood by persons of skill in the art and is used in the context of processes which involve sequential treatment with a series of reagents. In that context, a protecting group refers to a group which is used to mask a functionality during a process step in which it would otherwise react, but in which reaction is undesirable. The protecting group prevents reaction at that step, but may be subsequently removed to expose the original functionality. The removal or "deprotection" occurs after the completion of the reaction or reactions in which the functionality would interfere. Thus, when a sequence of reagents is specified, as it is in the processes of the invention, the person of ordinary skill can readily envision those groups that would be suitable as "protecting groups". Suitable groups for that purpose are discussed in standard textbooks in the field of chemistry, such as Protective Groups in Organic Synthesis by T. W. Greene [John Wiley & Sons, New York, 1991], which is incorporated herein by reference. Particular attention is drawn to the chapters entitled "Protection for the Hydroxyl Group, Including 1,2- and 1,3-Diols" (pages 10-86).

The following abbreviations and terms have the indicated meanings throughout: Ac=acetyl; Bu=butyl; c-=cyclo; DIEA=N,N-diisopropylethyl amine; TEA=triethylamine; HOAc=acetic acid; mesyl=methanesulfonyl; rt=room temperature; sat'd=saturated; s-=secondary; t-=tertiary; TMS=trimethylsilyl; tosyl=p-toluenesulfonyl; TFA=trifluoroacetic acid; HATU=O-(7-azabenzotriazol-1-yl)-N,N,N'N'-tetramethyluronium hexafluorophosphate. The abbreviations HPLC, THF, DCM and DMSO represent high performance liquid chromatography, tetrahydrofuran, dichloromethane and dimethylsulfoxide, respectively. The abbreviations Me, Et, Ph, Tf, Ts, Boc and Ms represent methyl, ethyl, phenyl, trifluoromethanesulfonyl, toluenesulfonyl, butyloxycarbonyl and methanesulfonyl respectively. The term dppf refers to 1,1'-Bis-(diphosphenylphosphino) ferrocene. A comprehensive list of abbreviations utilized by organic chemists (i.e. persons of ordinary skill in the art) appears in the first issue of each volume of the Journal of Organic Chemistry. The list, which is typically presented in a table entitled "Standard List of Abbreviations" is incorporated herein by reference.

While it may be possible for the compounds of the invention to be administered as the raw chemical, it is preferable to present them as a pharmaceutical composition. In accordance with an embodiment of the present invention there is provided a pharmaceutical composition comprising a compound of formula I or a pharmaceutically acceptable salt or solvate thereof, together with one or more pharmaceutically carriers thereof and optionally one or more other therapeutic ingredients. The carrier(s) must be "acceptable" in the sense of being compatible with the other ingredients of the formulation and not deleterious to the recipient thereof. Furthermore, notwithstanding the statement above regarding the term "compound" including salts thereof as well, so that independent claims reciting "a compound" will be understood as referring to salts thereof as well, if in an independent claim reference is made to a compound or a pharmaceutically acceptable salt thereof, it will be understood that claims which depend from that independent claim which refer to such a compound also include pharmaceutically acceptable salts of the compound, even if explicit reference is not made to the salts in the dependent claim.

The formulations include those suitable for oral, parenteral (including subcutaneous, intradermal, intramuscular, intravenous and intraarticular), rectal and topical (including dermal, buccal, sublingual and intraocular) administration. The most suitable route may depend upon the condition and disorder of the recipient. The formulations may conveniently be presented in unit dosage form and may be prepared by any of the methods well known in the art of pharmacy. Such methods include the step of bringing into association a compound of formula I or a pharmaceutically acceptable salt or solvate thereof ("active ingredient") with the carrier, which constitutes one or more accessory ingredients. In general, the formulations are prepared by uniformly and intimately bringing into association the active ingredient with liquid carriers or finely divided solid carriers or both and then, if necessary, shaping the product into the desired formulation.

Formulations suitable for oral administration may be presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion. The active ingredient may also be presented as a bolus, electuary or paste.

A tablet may be made by compression or molding, optionally with one or more accessory ingredients. Compressed tablets may be prepared by compressing in a suitable machine the active ingredient in a free-flowing form such as a powder or granules, optionally mixed with a binder, lubricant, inert diluent, lubricating, surface active or dispersing agent. Molded tablets may be made by molding in a suitable machine a mixture of the powdered compound moistened with an inert liquid diluent. The tablets may optionally be coated or scored and may be formulated so as to provide sustained, delayed or controlled release of the active ingredient therein.

The pharmaceutical compositions may include a "pharmaceutically acceptable inert carrier", and this expression is intended to include one or more inert excipients, which include starches, polyols, granulating agents, microcrystalline cellulose, diluents, lubricants, binders, disintegrating agents, and the like. If desired, tablet dosages of the disclosed compositions may be coated by standard aqueous or nonaqueous techniques, "Pharmaceutically acceptable carrier" also encompasses controlled release means.

Pharmaceutical compositions may also optionally include other therapeutic ingredients, anti-caking agents, preservatives, sweetening agents, colorants, flavors, desiccants, plasticizers, dyes, and the like. Any such optional ingredient must be compatible with the compound of formula I to insure the stability of the formulation. The composition may contain other additives as needed, including for example lactose, glucose, fructose, galactose, trehalose, sucrose, maltose, raffinose, maltitol, melezitose, stachyose, lactitol, palatinate, starch, xylitol, mannitol, myoinositol, and the like, and hydrates thereof, and amino acids, for example alanine, glycine and betaine, and peptides and proteins, for example albumen.

Examples of excipients for use as the pharmaceutically acceptable carriers and the pharmaceutically acceptable inert carriers and the aforementioned additional ingredients include, but are not limited to binders, fillers, disintegrants, lubricants, anti-microbial agents, and coating agents.

The dose range for adult humans is generally from 0.005 mg to 10 g/day orally. Tablets or other forms of presentation provided in discrete units may conveniently contain an amount of compound of formula I which is effective at such dosage or as a multiple of the same, for instance, units containing 5 mg to 500 mg, usually around 10 mg to 200 mg. The precise amount of compound administered to a patient will be the responsibility of the attendant physician. However, the dose employed will depend on a number of factors, including the age and sex of the patient, the precise disorder being treated, and its severity.

A dosage unit (e.g. an oral dosage unit) can include from, for example, 1 to 30 mg, 1 to 40 mg, 1 to 100 mg, 1 to 300 mg, 1 to 500 mg, 2 to 500 mg, 3 to 100 mg, 5 to 20 mg, 5 to 100 mg (e.g. 1 mg, 2 mg, 3 mg, 4 mg, 5 mg, 6 mg, 7 mg, 8 mg, 9 mg, 10 mg, 11 mg, 12 mg, 13 mg, 14 mg, 15 mg, 16 mg, 17 mg, 18 mg, 19 mg, 20 mg, 25 mg, 30 mg, 35 mg, 40 mg, 45 mg, 50 mg, 55 mg, 60 mg, 65 mg, 70 mg, 75 mg, 80 mg, 85 mg, 90 mg, 95 mg, 100 mg, 150 mg, 200 mg, 250 mg, 300 mg, 350 mg, 400 mg, 450 mg, 500 mg) of a compound described herein.

For additional information about pharmaceutical compositions and their formulation, see, for example, Remington: The Science and Practice of Pharmacy, 20$^{th}$ Edition, 2000.

The agents can be administered, e.g., by intravenous injection, intramuscular injection, subcutaneous injection, intraperitoneal injection, topical, sublingual, intraarticular (in the joints), intradermal, buccal, ophthalmic (including intraocular), intranasaly (including using a cannula), or by other routes. The agents can be administered orally, e.g., as a tablet or cachet containing a predetermined amount of the active ingredient, gel, pellet, paste, syrup, bolus, electuary, slurry, capsule, powder, granules, as a solution or a suspension in an aqueous liquid or a non-aqueous liquid, as an oil-in-water liquid emulsion or a water-in-oil liquid emulsion, via a micellar formulation (see, e.g. WO 97/11682) via a liposomal formulation (see, e.g., EP 736299, WO 99/59550 and WO 97/13500), via formulations described in WO 03/094886 or in some other form. The agents can also be administered transdermally (i.e. via reservoir-type or matrix-type patches, microneedles, thermal poration, hypodermic needles, iontophoresis, electroporation, ultrasound or other forms of sonophoresis, jet injection, or a combination of any of the preceding methods (Prausnitz et al. 2004, Nature Reviews Drug Discovery 3:115)). The agents can be administered locally, for example, at the site of injury to an injured blood vessel. The agents can be coated on a stent. The agents can be administered using high-velocity transdermal particle injection techniques using the hydrogel particle formulation described in U.S. 20020061336. Additional particle formulations are described in WO 00/45792, WO 00/53160, and WO 02/19989. An example of a transdermal formulation containing plaster and the absorption promoter dimethylisosorbide can be found in WO 89/04179. WO 96/11705 provides formulations suitable for transdermal administration.

The agents can be administered in the form a suppository or by other vaginal or rectal means. The agents can be administered in a transmembrane formulation as described in WO 90/07923. The agents can be administered non-invasively via the dehydrated particles described in U.S. Pat. No. 6,485,706. The agent can be administered in an enteric-coated drug formulation as described in WO 02/49621. The agents can be administered intranasaly using the formulation described in U.S. Pat. No. 5,179,079. Formulations suitable for parenteral injection are described in WO 00/62759. The agents can be administered using the casein formulation described in U.S. 20030206939 and WO 00/06108. The agents can be administered using the particulate formulations described in U.S. 20020034536.

The agents, alone or in combination with other suitable components, can be administered by pulmonary route utilizing several techniques including but not limited to intratracheal instillation (delivery of solution into the lungs by syringe), intratracheal delivery of liposomes, insufflation (administration of powder formulation by syringe or any other similar device into the lungs) and aerosol inhalation. Aerosols (e.g., jet or ultrasonic nebulizers, metered-dose inhalers (MDIs), and dry-Powder inhalers (DPIs)) can also be used in intranasal applications. Aerosol formulations are stable dispersions or suspensions of solid material and liquid droplets in a gaseous medium and can be placed into pressurized acceptable propellants, such as hydrofluoroalkanes (HFAs, i.e. HFA-134a and HFA-227, or a mixture thereof), dichlorodifluoromethane (or other chlorofluorocarbon propellants such as a mixture of Propellants 11, 12, and/or 114), propane, nitrogen, and the like. Pulmonary formulations may include permeation enhancers such as fatty acids, and saccharides, chelating agents, enzyme inhibitors (e.g., protease inhibitors), adjuvants (e.g., glycocholate, surfactin, span 85, and nafamostat), preservatives (e.g., benzalkonium chloride or chlorobutanol), and ethanol (normally up to 5% but possibly up to 20%, by weight). Ethanol is commonly included in aerosol compositions as it can improve the function of the metering valve and in some cases also improve the stability of the dispersion.

Pulmonary formulations may also include surfactants which include but are not limited to bile salts and those described in U.S. Pat. No. 6,524,557 and references therein. The surfactants described in U.S. Pat. No. 6,524,557, e.g., a $C_8$-$C_{16}$ fatty acid salt, a bile salt, a phospholipid, or alkyl saccharide are advantageous in that some of them also reportedly enhance absorption of the compound in the formulation.

Also suitable in the invention are dry powder formulations comprising a therapeutically effective amount of active compound blended with an appropriate carrier and adapted for use in connection with a dry-powder inhaler. Absorption enhancers that can be added to dry powder formulations of the present invention include those described in U.S. Pat. No. 6,632,456. WO 02/080884 describes new methods for the surface modification of powders. Aerosol formulations may include U.S. Pat. Nos. 5,230,884, 5,292,499, WO 017/8694, WO 01/78696, U.S. 2003019437, U. S. 20030165436, and WO 96/40089 (which includes vegetable oil). Sustained release formulations suitable for inhalation are described in U.S. 20010036481A1, 20030232019A1, and U.S. 20040018243A1 as well as in WO 01/13891, WO 02/067902, WO 03/072080, and WO 03/079885.

Pulmonary formulations containing microparticles are described in WO 03/015750, U.S. 20030008013, and WO 00/00176. Pulmonary formulations containing stable glassy state powder are described in U.S. 20020141945 and U.S. Pat. No. 6,309,671. Other aerosol formulations are described in EP 1338272A1 WO 90/09781, U.S. Pat. Nos. 5,348,730, 6,436,367, WO 91/04011, and U.S. Pat. Nos. 6,294,153 and 6,290,987 describes a liposomal based formulation that can be administered via aerosol or other means.

Powder formulations for inhalation are described in U.S. 20030053960 and WO 01/60341. The agents can be administered intranasally as described in U.S. 20010038824.

Solutions of medicament in buffered saline and similar vehicles are commonly employed to generate an aerosol in a nebulizer. Simple nebulizers operate on Bernoulli's principle and employ a stream of air or oxygen to generate the spray particles. More complex nebulizers employ ultrasound to create the spray particles. Both types are well known in the art and are described in standard textbooks of pharmacy such as Sprowls' American Pharmacy and Remington's The Science and Practice of Pharmacy.

Other devices for generating aerosols employ compressed gases, usually hydrofluorocarbons and chlorofluorocarbons, which are mixed with the medicament and any necessary excipients in a pressurized container, these devices are likewise described in standard textbooks such as Sprowls and Remington.

The agent can be incorporated into a liposome to improve half-life. The agent can also be conjugated to polyethylene glycol (PEG) chains. Methods for pegylation and additional formulations containing PEG-conjugates (i.e. PEG-based hydrogels, PEG modified liposomes) can be found in Harris and Chess, Nature Reviews Drug Discovery 2:214-221 and the references therein. The agent can be administered via a nanocochleate or cochleate delivery vehicle (BioDelivery Sciences International). The agents can be delivered transmucosally (i.e. across a mucosal surface such as the vagina, eye or nose) using formulations such as that described in U.S. Pat. No. 5,204,108. The agents can be formulated in microcapsules as described in WO 88/01165. The agent can be administered intra-orally using the formulations described in U.S. 20020055496, WO 00/47203, and U.S. Pat. No. 6,495,120. The agent can be delivered using nanoemulsion formulations described in WO 01/91728A2.

TABLE 1 lists compounds representative of embodiments of the invention.

In general, the compounds of the present invention may be prepared by the methods illustrated in the general reaction schemes as, for example, described below, or by modifications thereof, using readily available starting materials, reagents and conventional synthesis procedures. In these reactions, it is also possible to make use of variants that are in themselves known, but are not mentioned here.

Processes for obtaining the compounds of the invention are presented below. Other compounds of the invention may be prepared in analogous fashion to those whose synthesis is exemplified herein. The procedures below illustrate such methods. Furthermore, although the syntheses depicted herein may result in the preparation of enantiomers having a particular stereochemistry, included within the scope of the present invention are compounds of formula I in any stereoisomeric form, and preparation of compounds of formula I in stereoisomeric forms other than those depicted herein would be obvious to one of ordinary skill in the chemical arts based on the procedures presented herein.

Synthetic Methods

Scheme 1

Compounds of formula 3 (wherein $R^{14}$ is H or halogen; $R^1$ is H; $R^5$ is a protecting group such as tert-butoxycarbonyl or benzyloxycarbonyl; $R^8$, $R^9$, $R^{10}$, $R^{11}$, $R^{12}$ and $R^{13}$ are each independently selected from H or optionally substituted alkyl) can be prepared from 3- or 4-bromo phenylhydrazine 1 (or a salt thereof) and piperidinone 2 under heated acidic conditions. Optional N5-alkylation or N5-protection of compound 3 can provide compounds of formula 3 wherein $R^1$ is alkyl or a protecting group such as tert-butoxycarbonyl, benzyloxycarbonyl or p-toluenesulfonyl. Optional removal of N2-protecting group $R^5$ and reductive amination, alkylation or acylation can provide compounds of formula 3 wherein $R^5$ is alkyl or acyl.

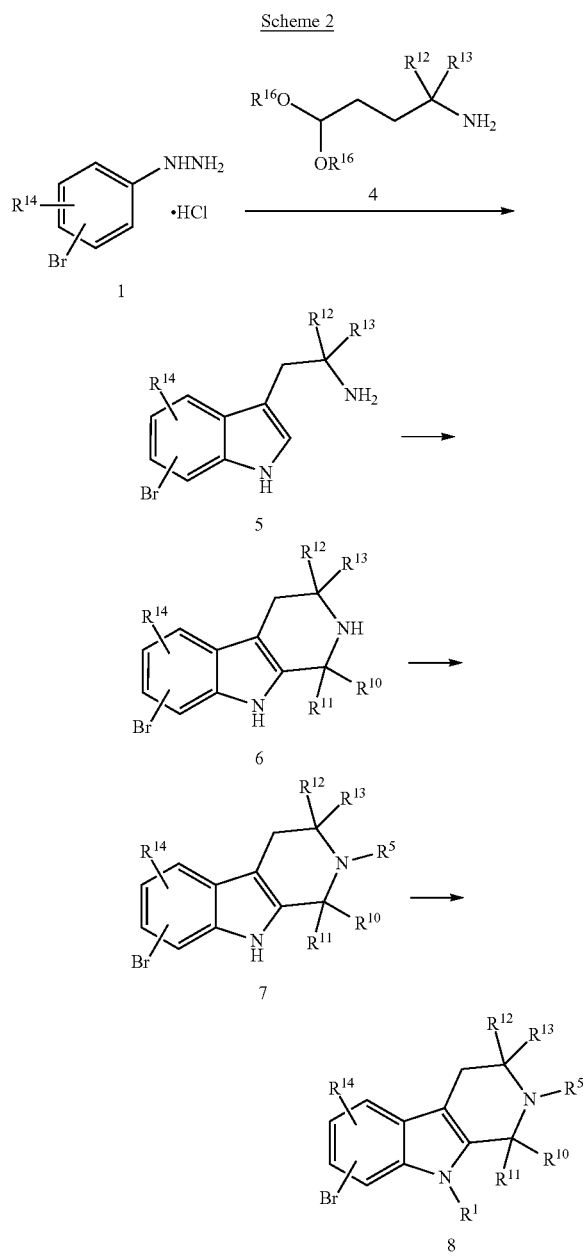

Scheme 2

Compounds of formula 1 (wherein $R^{14}$ is H or halogen) can be treated with compounds of formula 4 (wherein $R^{12}$ and $R^{13}$ are each independently selected from H or optionally substituted alkyl and $R^{16}$ is alkyl) and a Lewis acid such as $ZnCl_2$ under heated conditions to give compounds of formula 5. Treatment of compounds of formula 5 with ethyl glyoxylate under heated acidic conditions can provide compounds of formula 6 wherein $R^{10}$ and $R^{11}$ are H. Alternatively, compounds of formula 5 can be treated with a ketone under heated acidic conditions to provide compounds of formula 6 wherein $R^{10}$ and $R^{11}$ are optionally substituted alkyl. Compounds of formula 5 also can be treated with an acid chloride under basic conditions, followed by heating with $POCl_3$ and finally by treatment with a reducing agent such as $NaBH_4$ to provide compounds of formula 6 wherein $R^{10}$ is H and $R^{11}$ is optionally substituted alkyl. Protection of the N2-position on the tetrahydrocarboline ring can provide compounds of formula 7 (wherein $R^5$ is a protecting group such as tert-butoxycarbonyl or benzyloxycarbonyl). Protection of the N9-position on the tetrahydrocarboline ring can provide compounds of formula 8 (wherein $R^1$ is a protecting group such as tert-butoxycarbonyl, benzyloxycarbonyl or p-toluenesulfonyl). Alternatively, treatment of compound 7 with a base such as sodium hydride and an alkylating agent can provide compounds of formula 8 wherein $R^1$ is optionally substituted alkyl. Optional removal of N2-protecting group $R^5$ and reductive amination, alkylation or acylation can provide compounds of formula 8 wherein $R^5$ is alkyl or acyl.

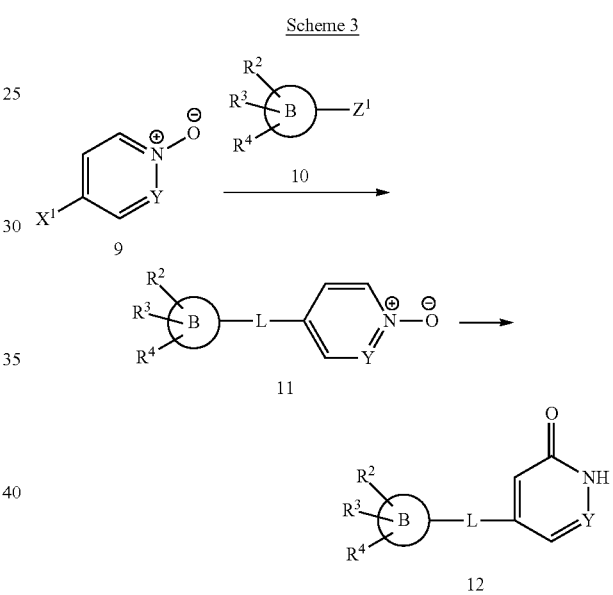

Scheme 3

Compounds of formula 12 (wherein B is aryl or heteroaryl; $R^2$, $R^3$, $R^4$ are each independently selected from H, —O-alkyl, S-alkyl, alkyl, halo, —$CF_3$, and —CN; and Y is CH) can be prepared by treating compounds of formula 9 (wherein $X^1$ is chlorine, bromine or iodine and Y is CH) with compounds of formula 10 (wherein B is aryl or heteroaryl; $R^2$, $R^3$, $R^4$ are each independently selected from H, —O-alkyl, alkyl, halo, —$CF_3$, and —CN; $Z^1$ is $B(OH)_2$, $B(OR^{17})_2$, $SnR^{17}_3$ or the like and $R^{17}$ is alkyl), a catalyst such as palladium(0), and a base such as potassium carbonate to give compounds of formula 11, wherein L is a direct bond. Alternatively, in the case where $Z^1$ is —$CH_2OH$ and B is aryl, heteroaryl or cycloalkyl, compounds of formula 10 can be treated with a base such as sodium hydride and compounds of formula 9 under heated conditions to give compounds of formula 11, wherein L is —$CH_2O$—. In turn, compounds of formula 11 can be treated with acetic anhydride under heated conditions followed by methanol and water or methanol and sodium hydroxide under ambient to heated conditions to provide compounds of formula 12, wherein L is —$CH_2O$— or a direct bond.

Scheme 4

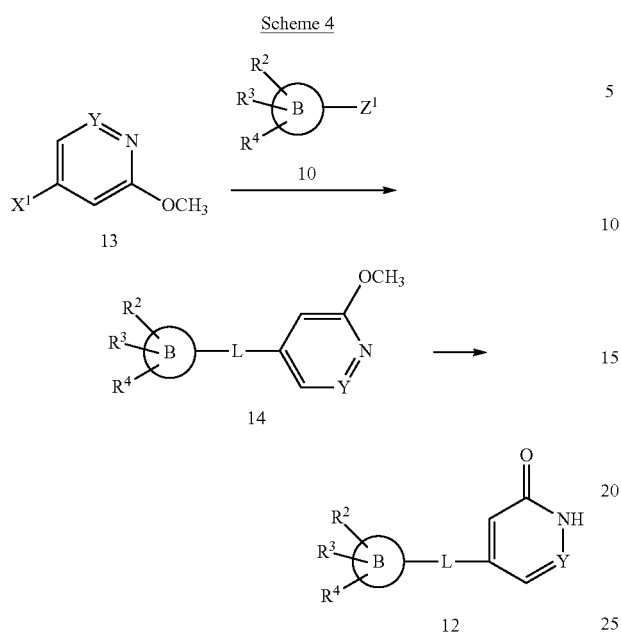

Alternatively, compounds of formula 12 (wherein B is aryl or heteroaryl; $R^2$, $R^3$, $R^4$ are each independently selected from H, —O-alkyl, S-alkyl, alkyl, halo, —$CF_3$, and —CN; and Y is CH) can be prepared by treating compounds of formula 13 (wherein X is chlorine, bromine or iodine and Y is CH) with compounds of formula 10 (wherein $Z^1$ is —CH=CH—B(OR$^{17}$)$_2$, B(OR$^{17}$)$_2$, SnR$^{17}$$_3$ or the like and $R^{17}$ is H or alkyl), a catalyst such as palladium(0), and a base such as potassium carbonate to give compounds of formula 14, wherein L is —CH=CH— or a direct bond, in accordance with $Z^1$. In the case where L is —CH=CH—, compounds of formula 14 can be treated with palladium on carbon under an atmosphere of hydrogen to give compounds of formula 14, wherein L is —$CH_2CH_2$—. Alternatively, in the case where $Z^1$ is —$CH_2$OH, compounds of formula 10 can be treated with compounds of formula 13, a catalyst such as copper iodide, a ligand such as 3,4,7,8-tetramethylphenanthroline and a base such as cesium carbonate under heated conditions to give compounds of formula 14, wherein L is —$CH_2$O—. In turn, when L is —CH=CH—, —$CH_2CH_2$—, —$CH_2$O— or a direct bond, compounds of formula 14 can be heated under acid conditions to provide compounds of formula 12, wherein L is —CH=CH—, —$CH_2CH_2$—, —$CH_2$O— or a direct bond, respectively.

Scheme 5

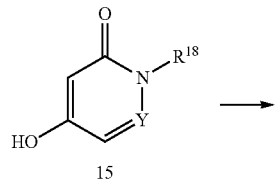

Alternatively, compounds of formula 12 (wherein B is aryl or heteroaryl; $R^2$, $R^3$, $R^4$ are each independently selected from H, —O-alkyl, S-alkyl, alkyl, halo, —$CF_3$, and —CN; and Y is N) can be prepared from compounds of formula 15 (wherein Y is N and $R^{18}$ is a protecting group such as tetrahydropyran-2-yl). The hydroxyl group on compound 15 can be converted to an appropriate activating group to give compounds of formula 16. In the case where $Z^2$ is triflate, compounds of formula 15 can be treated with trifluoromethylsulfonic anhydride or N-phenyl trifluoromethanesulfonamide and a base such as triethylamine, pyridine or lithium bis(trimethylsilyl)amide under cooled conditions to give compounds of formula 16. Treatment of compounds of formula 16 with compounds of formula 10 (wherein B is aryl or heteroaryl; $R^2$, $R^3$, $R^4$ are each independently selected from H, —O-alkyl, S-alkyl, alkyl, halo, —$CF_3$, and —CN; $Z^1$=—CH=CH—B(OR$^{17}$)$_2$, B(OH)$_2$, B(OR$^{17}$)$_2$, SnR$^{17}$$_3$ or the like, and $R^{17}$=alkyl), a catalyst such as palladium(0), and a base such as potassium carbonate under heated conditions can provide compounds of formula 17, wherein L is —CH=CH— or a direct bond. Removal of the protecting group $R^{18}$ on compound 17 can provide compounds of formula 12.

Scheme 6

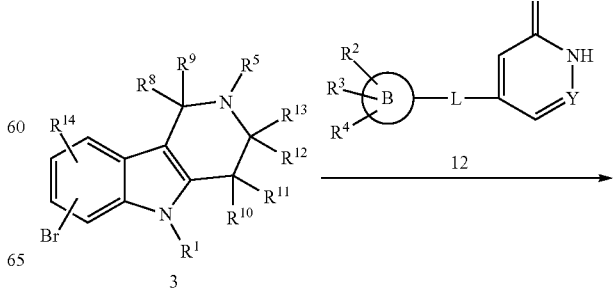

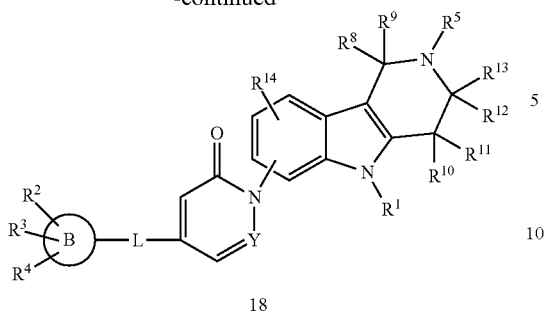

18

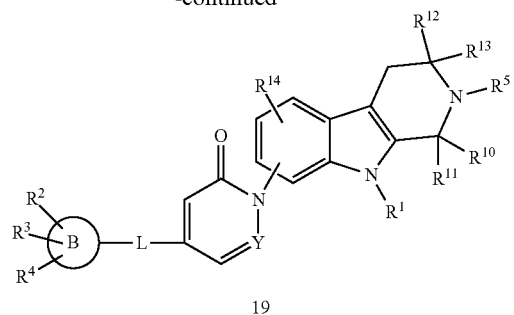

19

Compounds of formula 18 (wherein B is aryl, heteroaryl or cycloalkyl; $R^2$, $R^3$, $R^4$ are each independently selected from H, —O-alkyl, —S-alkyl, alkyl, halo, —$CF_3$, and —CN; L is —$CH_2$—O—, —CH=CH—, —$CH_2CH_2$—, or a bond; Y is CH or N; $R^{14}$ is H or halogen; $R^5$ is alkyl, acyl or a protecting group such as tert-butoxycarbonyl or benzyloxycarbonyl; $R^1$ is alkyl or a protecting group such as tert-butoxycarbonyl, benzyloxycarbonyl or p-toluenesulfonyl; and $R^8$, $R^9$, $R^{10}$, $R^{11}$, $R^{12}$ and $R^{13}$ are each independently selected from H or optionally substituted alkyl) can be prepared by treating compounds of formula 3 (wherein $R^5$ is alkyl, acyl or a protecting group such as tert-butoxycarbonyl or benzyloxycarbonyl and $R^1$ is alkyl or a protecting group such as tert-butoxycarbonyl, benzyloxycarbonyl or p-toluenesulfonyl) under heated conditions with a catalyst such as copper iodide, a ligand such as trans-1,2-diaminocyclohexane or 8-hydroxyquinoline, a base such as potassium carbonate, cesium carbonate or potassium phosphate and compounds of formula 12 (wherein B is aryl, heteroaryl or cycloalkyl; $R^2$, $R^3$, $R^4$ are each independently selected from H, —O-alkyl, —S-alkyl, alkyl, halo, —$CF_3$, and —CN; L is —$CH_2$—O—, —CH=CH—, —$CH_2CH_2$—, or a bond; and Y is CH or N). Removal of the N2-protecting group $R^5$ followed by reductive amination or alkylation can provide compounds of formula 18, wherein $R^5$ is an optionally substituted alkyl group.

Alternatively, following deprotection, N2 can be acylated to give compounds of formula 18 wherein $R^5$ is —C(=O)—$R^6$ or —C(=O)—O—$R^7$, and $R^6$ and $R^7$ are each optionally substituted alkyl or optionally substituted heterocycle. Additionally, in the case where $R^1$ is a protecting group, the protecting group can be removed to give compounds of formula 18 wherein $R^1$ is H.

Alternatively, following removal of the $R^1$ protecting group, N5 can be alkylated to give compounds of formula 18 wherein $R^5$ is an optionally substituted alkyl.

Compounds of formula 19 (wherein B is aryl, heteroaryl or cycloalkyl; $R^2$, $R^3$, $R^4$ are each independently selected from H, —O-alkyl, —S-alkyl, alkyl, halo, —$CF_3$, and —CN; L is —$CH_2$—O—, —CH=CH—, —$CH_2CH_2$—, or a bond; Y is CH or N; $R^{14}$ is H or halogen; $R^5$ is alkyl, acyl or a protecting group such as tert-butoxycarbonyl or benzyloxycarbonyl; $R^1$ is alkyl or a protecting group such as tert-butoxycarbonyl, benzyloxycarbonyl or p-toluenesulfonyl; and $R^8$, $R^9$, $R^{10}$, $R^{11}$, $R^{12}$ and $R^{13}$ are each independently selected from H or optionally substituted alkyl) can be prepared by treating compounds of formula 3 (wherein $R^5$ is alkyl, acyl or a protecting group such as tert-butoxycarbonyl or benzyloxycarbonyl and $R^1$ is alkyl or a protecting group such as tert-butoxycarbonyl, benzyloxycarbonyl or p-toluenesulfonyl) under heated conditions with a catalyst such as copper iodide, a ligand such as trans-1,2-diaminocyclohexane or 8-hydroxyquinoline, a base such as potassium carbonate, cesium carbonate or potassium phosphate and compounds of formula 12 (wherein B is aryl, heteroaryl or cycloalkyl; $R^2$, $R^3$, $R^4$ are each independently selected from H, —O-alkyl, —S-alkyl, alkyl, halo, —$CF_3$, and —CN; L is —$CH_2$—O—, —CH=CH—, —$CH_2CH_2$—, or a bond; and Y is CH or N). Removal of the N2-protecting group $R^5$ followed by reductive amination or alkylation can provide compounds of formula 18, wherein $R^5$ is an optionally substituted alkyl group.

Alternatively, following deprotection, N2 can be acylated to give compounds of formula 18 wherein $R^5$ is —C(=O)—$R^6$ or —C(=O)—O—$R^7$, and $R^6$ and $R^7$ are each optionally substituted alkyl or optionally substituted heterocycle. Additionally, in the case where $R^1$ is a protecting group, the protecting group can be removed to give compounds of formula 18 wherein $R^1$ is H.

Alternatively, following removal of the $R^1$ protecting group, N5 can be alkylated to give compounds of formula 18 wherein $R^5$ is an optionally substituted alkyl.

Scheme 7

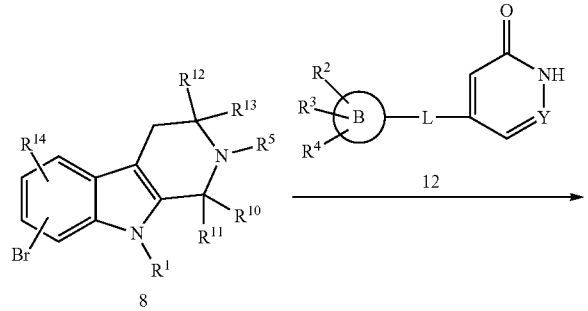

Scheme 8

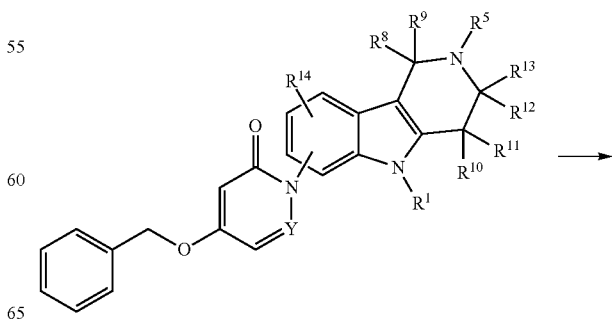

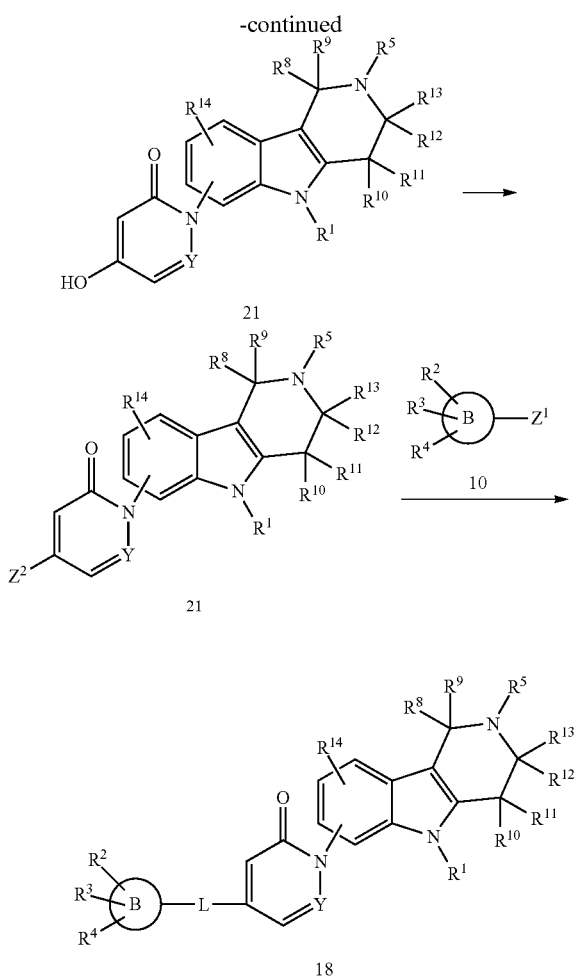

21

18

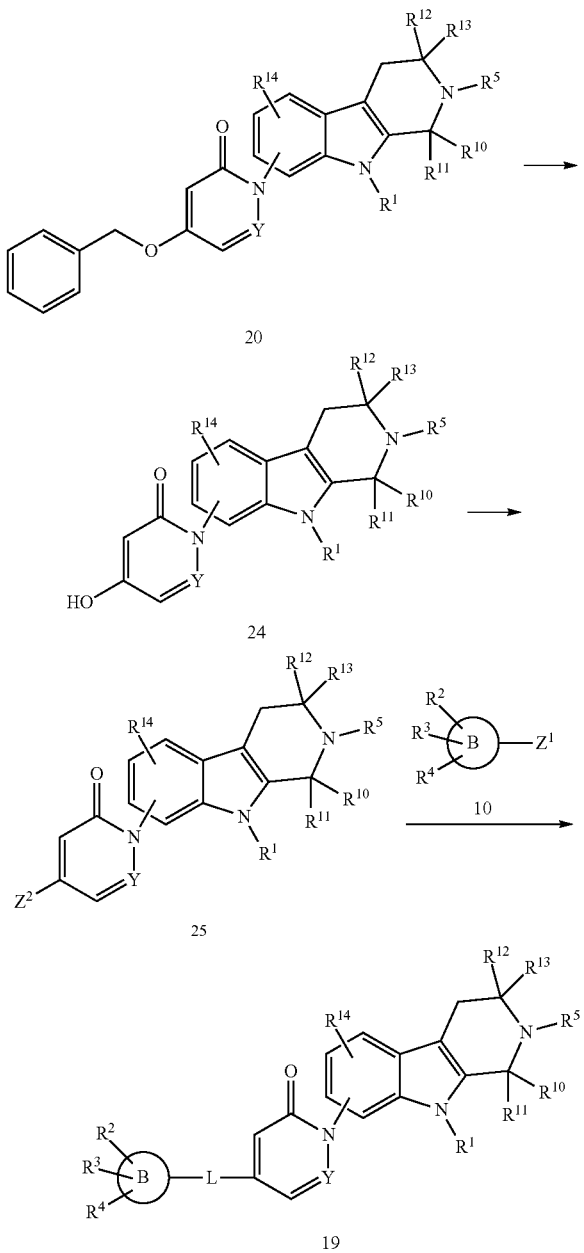

Scheme 9

20

24

25

19 treated with palladium on carbon under an atmosphere of hydrogen to give compounds of formula 18, where L is —$CH_2CH_2$—.

Compounds of formula 20 (wherein Y is CH or N; $R^{14}$ is H or halogen; $R^5$ is alkyl, acyl or a protecting group such as tert-butoxycarbonyl or benzyloxycarbonyl; $R^1$ is alkyl or a protecting group such as tert-butoxycarbonyl, benzyloxycarbonyl or p-toluenesulfonyl; and $R^8$, $R^9$, $R^{10}$, $R^{11}$, $R^{12}$ and $R^{13}$ are each independently selected from H or optionally substituted alkyl) can be treated with hydrogen and a catalyst such as palladium on carbon to provide compounds of formula 21. The hydroxyl group on compounds of formula 21 can be converted to an appropriate activating group to give compounds of formula 22. In the case where $Z^2$ is triflate, compounds of formula 21 can be treated with trifluoromethylsulfonic anhydride or N-phenyl trifluoromethanesulfonamide and a base such as pyridine or lithium bis(trimethylsilyl)amide under cooled conditions to give compounds of formula 22. Treatment of compounds of formula 22 with compounds of formula 10 (wherein B is aryl or heteroaryl; $R^2$, $R^3$, $R^4$ are each independently selected from H, —O-alkyl, —S-alkyl, alkyl, halo, —$CF_3$, and —CN; $Z^1$=—CH=CH—$B(OR^{17})_2$, $B(OH)_2$, $B(OR^{17})_2$, $SnR^{17}_3$ or the like and $R^{17}$=alkyl), a catalyst such as palladium(0), and a base such as potassium carbonate under heated conditions can provide compounds of formula 18, wherein L is —CH=CH— or a direct bond. In the case where L is —CH=CH—, compounds of formula 18 can be Compounds of formula 23 (wherein Y is CH or N; $R^{14}$ is H or halogen; $R^5$ is alkyl, acyl or a protecting group such as tert-butoxycarbonyl or benzyloxycarbonyl; $R^1$ is alkyl or a protecting group such as tert-butoxycarbonyl, benzyloxycarbonyl or p-toluenesulfonyl; and $R^8$, $R^9$, $R^{10}$, $R^{11}$, $R^{12}$ and $R^{13}$ are each independently selected from H or optionally substituted alkyl) can be treated with hydrogen and a catalyst such as palladium on carbon to provide compounds of formula 24. The hydroxyl group on compounds of formula 24 can be converted to an appropriate activating group to give compounds of formula 25. In the case where $Z^2$ is triflate, compounds of formula 24 can be treated with trifluoromethylsulfonic anhydride or N-phenyl trifluoromethanesulfonamide and a base such as pyridine or lithium bis(trimethylsilyl)amide under cooled conditions to give compounds of formula 25.

Treatment of compounds of formula 25 with compounds of formula 10 (wherein B is aryl or heteroaryl; $R^2$, $R^3$, $R^4$ are each independently selected from H, —O— alkyl, —S-alkyl, alkyl, halo, —$CF_3$, and —CN; $Z^1$=—CH=CH—B$(OR^{17})_2$, $B(OH)_2$, $B(OR^{17})_2$, $SnR^{17}_3$ or the like and $R^{17}$=alkyl), a catalyst such as palladium(0), and a base such as potassium carbonate under heated conditions can provide compounds of formula 19, wherein L is —CH=CH— or a direct bond.

In the case where L is —CH=CH—, compounds of formula 18 can be treated with palladium on carbon under an atmosphere of hydrogen to give compounds of formula 18, where L is —$CH_2CH_2$—.

Scheme 10

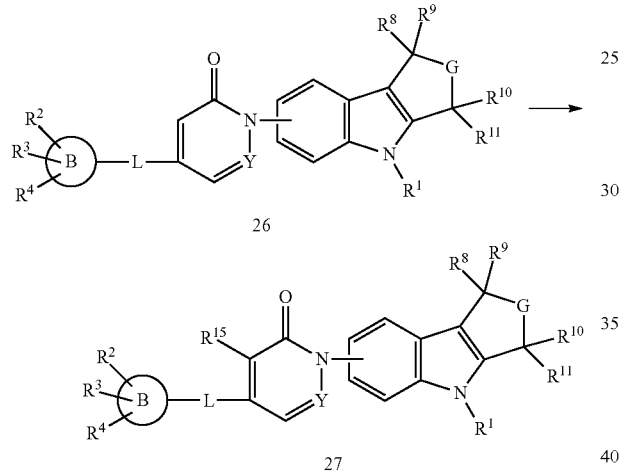

26

27

Compounds of formula 26 (wherein B is aryl or heteroaryl; $R^2$, $R^3$, $R^4$ are each independently selected from H, —O-alkyl, —S-alkyl, alkyl, halo, —$CF_3$, and —CN; L is —$CH_2$—O—, —CH=CH—, —$CH_2CH_2$—, or a bond; G is —$CR^{12}R^{13}$—NH— or —NH—$CR^{12}R^{13}$—; $R^1$ is alkyl; and $R^8$, $R^9$, $R^{10}$, $R^{11}$, $R^{12}$ and $R^{13}$ are each independently selected from H or optionally substituted alkyl) can be treated under halogenation conditions such as 2-bromopropane under heated conditions to provide compounds of formula 27 wherein $R^{15}$ is a halogen such as bromine.

EXAMPLES

Unless otherwise noted, reagents and solvents were used as received from commercial suppliers. Proton nuclear magnetic resonance (NMR) spectra were obtained on Bruker spectrometers at 300, 400 or 500 MHz. Spectra are given in ppm (δ) and coupling constants, J, are reported in Hertz. Tetramethylsilane (TMS) was used as an internal standard. Mass spectra were collected using either a Finnigan LCQ Duo LCMS ion trap electrospray ionization (ESI) or a mass Varian 1200L single quadrapole mass spectrometer (ESI). High performance liquid chromatograph (HPLC) analyses were obtained using a Luna C18(2) column (250×4.6 mm, Phenomenex) or a Gemini C18 column (250×4.6 mm, Phenomenex) with UV detection at 254 nm or 223 nm using a standard solvent gradient program (Method A or Method B).

Method A:

| Time (min) | Flow (mL/min) | % A | % B |
|---|---|---|---|
| 0.0 | 1.0 | 90.0 | 10.0 |
| 20 | 1.0 | 10.0 | 90.0 |
| 25 | 1.0 | 10.0 | 90.0 |

A = Water with 0.025% Trifluoroacetic Acid
B = Acetonitrile with 0.025% Trifluoroacetic Acid Method B:

| Time (min) | Flow (mL/min) | % A | % B |
|---|---|---|---|
| 0.0 | 1.0 | 98.0 | 2.0 |
| 25 | 1.0 | 10.0 | 90.0 |
| 30 | 1.0 | 10.0 | 90.0 |

A = Water with 0.025% Trifluoroacetic Acid
B = Acetonitrile with 0.025% Trifluoroacetic Acid Example 1

Preparation of 4-(Benzyloxy)-1-(5-methyl-2,3,4,5-tetrahydro-1H-pyrido[4,3-b]indol-7-yl)pyridin-2(1H)-one hydrochloride a) tert-Butyl 7-bromo-3,4-dihydro-1H-pyrido[4,3-b]indole-2(5H)-carboxylate

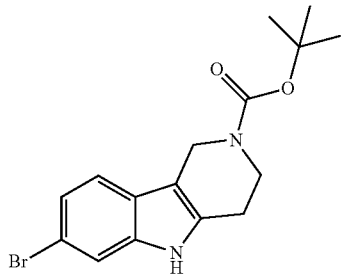

Chemical Formula: $C_{16}H_{19}BrN_2O_2$
Exact Mass: 350.06
Molecular Weight: 351.24

3-Bromophenylhydrazine (40.0 g, 0.179 mol) and N-Boc-4-oxo-piperidine (35.4 g, 0.179 mol) were dissolved in ethanol (368 mL), and conc. HCl (72 mL) was added. The reaction mixture was then heated to reflux for 18 h, concentrated and basified using 10% $NH_4OH$ in methanol (10%, 100 mL). The solvent was removed, and the residue was suspended in $CH_2Cl_2$ (1.2 L). $Boc_2O$ (39.2 g, 0.179 mol) followed by DMAP (195 mg, 1.6 mmol) and triethylamine (46.4 mL, 0.358 mol) were then added, and the reaction progressed at room temperature for 18 h. The mixture was washed with 0.5 N HCl, and the organic phase was removed, dried over $Na_2SO_4$, filtered and concentrated to dryness. The resulting mixture of regioisomers was purified by flash column chromatography (silica gel, hexanes/EtOAc, 100:0 to 80:20 to 50:50 then 25:75) to give the more polar title compound (26.2 g, 42%) as a yellow solid: $^1$H NMR (300 MHz, CDCl$_3$) δ 8.16 (br s, 1H), 7.42 (s, 1H), 7.28 (d, J=8.1 Hz, 1H, partially masked by solvent), 7.18 (d, J=8.1 Hz, 1H), 4.60 (s, 2H), 3.80 (t, J=5.5 Hz, 2H), 2.79 (t, J=5.6 Hz, 2H), 1.51 (s, 9H).

b) tert-Butyl 7-bromo-5-methyl-3,4-dihydro-1H-pyrido[4,3-b]indole-2(5H)-carboxylate

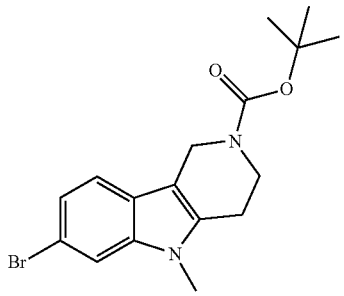

Chemical Formula: C$_{17}$H$_{21}$BrN$_2$O$_2$
Exact Mass: 364.08
Molecular Weight: 365.26

Sodium hydride (60% weight dispersion in mineral oil, 4.19 g, 0.105 mol) was added portionwise to a solution of tert-butyl 7-bromo-3,4-dihydro-1H-pyrido[4,3-b]indole-2(5H)-carboxylate (23.6 g, 0.07 mol) in DMF (300 mL) at room temperature under N$_2$. After 1 h, methyl iodide (14.8 g, 6.47 mL, 0.105 mol) was added, and the reaction was allowed to proceed for an additional 2 h. The mixture was quenched with H$_2$O, upon which a solid precipitated out of solution. The suspension was therefore diluted to 2 L with H$_2$O and filtered. The solids were washed thoroughly with water, then dissolved in CH$_2$Cl$_2$, dried over Na$_2$SO$_4$, filtered and concentrated to dryness. This provided the title compound (22.4 g, 91%) as a yellow solid: $^1$H NMR (300 MHz, CDCl$_3$) δ 7.41 (s, 1H), 7.30 (d, J=8.3 Hz, 1H), 7.17 (d, J=8.4 Hz, 1H), 4.60 (s, 2H), 3.81 (br t, 2H), 3.58 (s, 3H), 2.77 (t, J=5.4 Hz, 2H), 1.50 (s, 9H).

c) tert-Butyl 7-(4-(benzyloxy)-2-oxopyridin-1(2H)-yl)-5-methyl-3,4-dihydro-1H-pyrido[4,3-b]indole-2(5H)-carboxylate

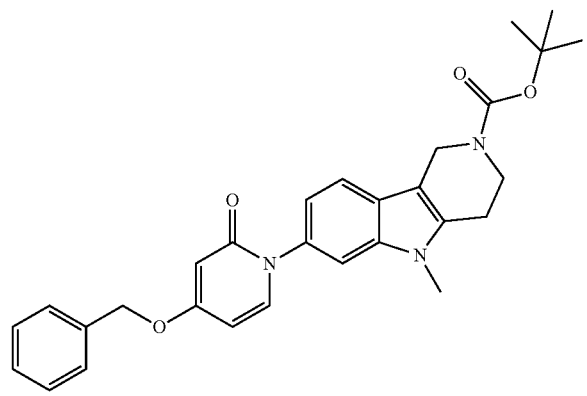

Chemical Formula: C$_{29}$H$_{31}$N$_3$O$_4$
Exact Mass: 485.23
Molecular Weight: 485.57 tert-Butyl 7-bromo-5-methyl-3,4-dihydro-1H-pyrido[4,3-b]indole-2(5H)-carbox-ylate (7.0 g, 19 mmol), 4-benzyloxy-pyridone (3.85 g, 19.2 mmol), K$_2$CO$_3$ (2.91 g, 21.1 mmol) and 8-hydroxyquinoline (418 mg, 2.88 mmol) were suspended in DMSO (50 mL) and the air removed under vacuum for 15 min. The system was then flushed with N$_2$. This process was repeated and then copper iodide (547 mg, 2.88 mmol) was added. The evacuation/N$_2$ flushing process was repeated twice more, and the reaction mixture was heated to 100-120° C. for 18 h. The mixture was cooled, partitioned between EtOAc and sat. NH$_4$Cl and the organic phase removed, dried over Na$_2$SO$_4$, filtered and concentrated to dryness. Purification by flash column chromatography (silica gel, CH$_2$Cl$_2$/MeOH, 100:0 to 98:2 to 95:5 to 92:8 then 90:10) gave the title compound (4.71 g, 51%) as a yellow solid: $^1$H NMR (300 MHz, CDCl$_3$) δ 7.50 (d, J=8.2 Hz, 1H), 7.43-7.35 (m, 5H), 7.32-7.29 (m, 2H), 7.01 (d, J=7.9 Hz, 1H), 6.10-6.03 (m, 2H), 5.06 (s, 2H), 4.64 (s, 2H), 3.89 (br t, 2H), 3.63 (s, 3H), 2.82 (br t, 2H), 1.50 (s, 9H).

d) 4-(Benzyloxy)-1-(5-methyl-2,3,4,5-tetrahydro-1H-pyrido[4,3-b]indol-7-yl)pyridin-2(1H)-one hydrochloride

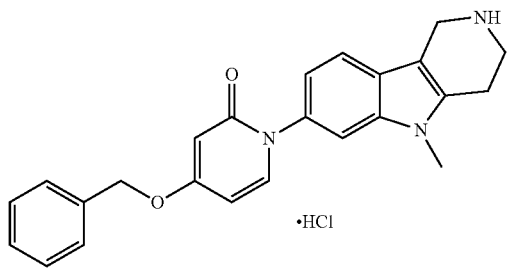

Chemical Formula: C$_{24}$H$_{24}$ClN$_3$O$_2$
Exact Mass: 421.16
Molecular Weight: 421.92 tert-Butyl 7-(4-(benzyloxy)-2-oxopyridin-1(2H)-yl)-5-methyl-3,4-dihydro-1H-pyrido[4,3-b]indole-2(5H)-carboxylate (12.0 g, 24.7 mmol) was dissolved in MeOH (100 mL), and 2 N HCl in Et$_2$O (300 mL) was added. The reaction was allowed to proceed for 18 h. The mixture was concentrated, and the residue was partitioned between CH$_2$Cl$_2$ and sat. Na$_2$CO$_3$ solution. The organic phase was removed, and the aqueous phase was back extracted with CH$_2$Cl$_2$. The combined organic extracts were dried over Na$_2$SO$_4$, filtered and concentrated to dryness providing the free base of the title compound (8.1 g, 85%) as a yellow solid. A portion of the free base was converted to the HCl salt for biological testing. Free base: $^1$H NMR (500 MHz, CDCl$_3$) δ 7.47-7.34 (m, 6H), 7.32-7.28 (m, 2H), 6.98 (d, J=7.1 Hz, 1H), 6.07 (d, J=2.6 Hz, 1H), 6.04 (dd, J=7.5, 2.6 Hz, 1H), 5.05 (s, 2H), 4.15 (s, 2H), 3.61 (s, 3H), 3.34 (br s, 2H), 2.78 (br s, 2H). HCl salt: melting point (mp) 296-302° C.; $^1$H NMR (500 MHz, CD$_3$OD) δ 7.61-7.57 (2×d, 2H), 7.47-7.46 (m, 3H), 7.43-7.40 (m, 2H), 7.37-7.34 (m, 1H), 7.05 (dd, J=8.3, 1.7 Hz, 1H), 6.33 (dd, J=7.5, 2.7 Hz, 1H), 6.16 (d, J=2.6 Hz, 1H), 5.19 (s, 2H), 4.57 (s, 2H), 3.73 (s, 3H), 3.67 (t, J=6.2 Hz, 2H), 3.20 (t, J=6.1 Hz, 2H); ESI MS m/z 386 [M+H]$^+$; HPLC (Method A) 95.7% (AUC), $t_R$=13.6 min.

Example 2

Preparation of 4-(Benzyloxy)-1-(2,5-dimethyl-2,3,4, 5-tetrahydro-1H-pyrido[4,3-b]indol-7-yl)pyridin-2 (1H)-one hydrochloride

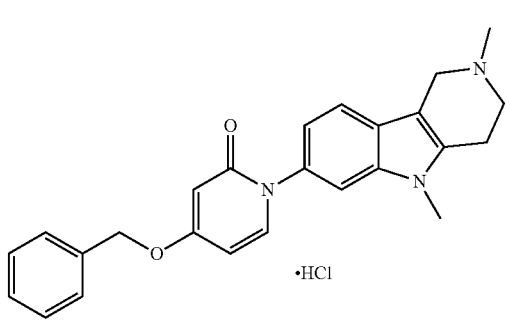

Chemical Formula: C$_{25}$H$_{26}$ClN$_3$O$_2$
Exact Mass: 435.17
Molecular Weight: 435.95

4-(Benzyloxy)-1-(5-methyl-2,3,4,5-tetrahydro-1H-pyrido [4,3-b]indol-7-yl)pyridin-2(1H)-one (8.1 g, 21.0 mmol) and 37% aqueous formaldehyde (2.56 mL, 31.5 mmol) were dissolved in MeOH (200 mL) and stirred at room temperature for 2 h. Sodium triacetoxyborohydride (8.9 g, 42.0 mmol) was then added, and the reaction was stirred at room temperature for an additional 1 h. The mixture was concentrated, and the residue was partitioned between CH$_2$Cl$_2$ and sat. Na$_2$CO$_3$ solution. The organic phase was removed and the aqueous phase was back extracted with CH$_2$Cl$_2$. The combined organics were dried over Na$_2$SO$_4$, filtered and concentrated to dryness. Purification by column chromatography (120 g ISCO column eluting with methylene chloride and a methanol/ammonia mixture (10:1); gradient 100% methylene chloride to 85% methylene chloride over 60 min) provided the free base of the title compound. This was converted to the HCl salt using 2 N HCl in Et$_2$O providing the title compound (5.57 g, 61%) as a yellow solid: mp 268-274° C.; $^1$H NMR (500 MHz, CD$_3$OD) δ 7.57 (dd, J=7.6, 1.7 Hz, 2H), 7.47-7.46 (m, 3H) 7.43-7.34 (m, 3H), 7.06 (dd, J=8.4, 1.9 Hz, 1H), 6.29 (dd, J=7.6, 2.7 Hz, 1H), 6.13 (d, J=2.6 Hz, 1H), 5.18 (s, 2H), 4.75 (d, J=14.3 Hz, 1H), 4.38 (d, J=14.2 Hz, 1H), 3.90 (m, 1H), 3.73 (s, 3H), 3.64-3.58 (m, 1H), 3.29-3.26 (m, 2H, partially masked by solvent), 3.13 (s, 3H); ESI MS m/z 400 [M+H]$^+$; HPLC (Method B) 97.4% (AUC), $t_R$=14.7 min.

Example 3

Preparation of 4-(Benzyloxy)-1-(2-(2-hydroxy-ethyl)-5-methyl-2,3,4,5-tetrahydro-1H-pyrido[4,3-b] indol-7-yl)pyridin-2(1H)-one dihydrochloride

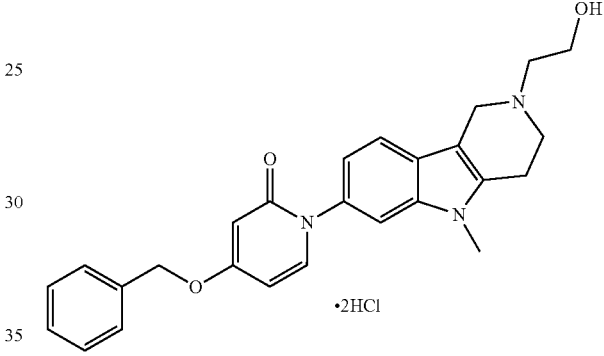

Chemical Formula: C$_{26}$H$_{29}$Cl$_2$N$_3$O$_3$
Exact Mass: 501.16
Molecular Weight: 502.43

4-(Benzyloxy)-1-(5-methyl-2,3,4,5-tetrahydro-1H-pyrido [4,3-b]indol-7-yl)pyridin-2(1H)-one (75 mg, 0.16 mmol), 2-iodoethanol (17 μL, 36 mg, 0.21 mmol) and triethylamine (105 μL, 0.82 mmol) were dissolved in MeCN (2 mL) and heated to reflux for 3 h. The mixture was then concentrated and purified by flash column chromatography (4 g ISCO column eluting with methylene chloride and a methanol/ammonia mixture (10:1); gradient 100% methylene chloride to 85% methylene chloride over 30 min) providing the free base. This was converted to the HCl salt (2 N HCl/Et$_2$O) providing the title compound (22 mg, 27%) as a yellow solid: mp 162-168° C.; $^1$H NMR (500 MHz, CD$_3$OD) δ 7.63 (dd, J=7.6, 2.0 Hz, 2H), 7.51-7.50 (m, 3H) 7.46-7.43 (m, 2H), 7.41-7.38 (m, 1H), 7.09 (dd, J=8.3, 1.7 Hz, 1H), 6.36 (dd, J=7.6, 2.7 Hz, 1H), 6.18 (d, J=2.7 Hz, 1H), 5.23 (s, 2H), 4.82 (d, 1H, partially masked by solvent), 4.520 (d, J=14.3 Hz, 1H), 4.06-4.02 (m, 3H), 3.77 (s, 3H), 3.70-3.68 (m, 1H), 3.55-3.51 (m, 2H), 3.33-3.31 (m, 2H, partially masked by solvent); ESI MS m/z 430 [M+H]$^+$; HPLC (Method B) 95.1% (AUC), $t_R$=12.4 min.

Example 4

Preparation of 4-(Benzyloxy)-1-(5-methyl-2-(2-(pyrrolidin-1-yl)acetyl)-2,3,4,5-tetrahydro-1H-pyrido[4,3-b]indol-7-yl)pyridin-2(1H)-one dihydrochloride a) 4-(Benzyloxy)-1-(2-(2-chloroacetyl)-5-methyl-2,3,4,5-tetrahydro-1H-pyrido[4,3-b]indol-7-yl)pyridin-2(1H)-one

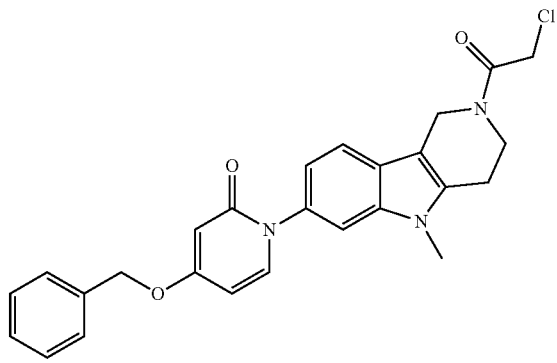

Chemical Formula: $C_{26}H_{24}ClN_3O_3$
Exact Mass: 461.15
Molecular Weight: 461.94

4-(Benzyloxy)-1-(5-methyl-2,3,4,5-tetrahydro-1H-pyrido[4,3-b]indol-7-yl)pyridin-2(1H)-one (75 mg, 0.16 mmol) was dissolved in a mixture of $CH_2Cl_2$ (1 mL) and sat. $NaHCO_3$ solution (1 mL) and chloroacetyl chloride (28 mg, 0.25 mmol) was added. The reaction mixture was vigorously stirred for 1 h then the phases were separated. The aqueous phase was extracted with $CH_2Cl_2$ and the combined organic extracts were dried over $Na_2SO_4$, filtered and concentrated to dryness providing the title compound (74 mg, 97%) as a beige solid which was a mixture of rotamers: ESI MS m/z 462 [M+H]$^+$.

b) 4-(Benzyloxy)-1-(5-methyl-2-(2-(pyrrolidin-1-yl)acetyl)-2,3,4,5-tetrahydro-1H-pyrido[4,3-b]indol-7-yl)pyridin-2(1H)-one dihydrochloride

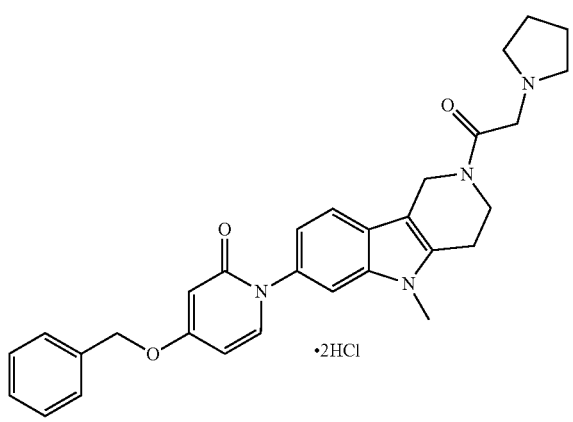

Chemical Formula: $C_{30}H_{34}Cl_2N_4O_3$
Exact Mass: 568.20
Molecular Weight: 569.52

4-(Benzyloxy)-1-(2-(2-chloroacetyl)-5-methyl-2,3,4,5-tetrahydro-1H-pyrido[4,3-b]indol-7-yl)pyridin-2(1H)-one (70 mg, 0.15 mmol) was dissolved in MeCN (0.5 mL) and pyrrolidine (54 mg, 0.76 mmol) was added. The reaction mixture was refluxed for 2 h, concentrated and the residue purified by preparative HPLC. The fractions were concentrated, and the residue was converted to the free base by partitioning between $CH_2Cl_2$ and sat. $Na_2CO_3$ solution. The organic phase was removed, and the aqueous layer was extracted with $CH_2Cl_2$. The combined organic extracts were dried over $Na_2SO_4$, filtered and concentrated to dryness. Conversion to the HCl salt (2 N HCl/$Et_2O$) provided the title compound (74 mg, 97%) as a beige solid: $^1$H NMR (500 MHz, $CD_3OD$) δ 7.62 (dd, J=7.7, 1.9 Hz, 1H), 7.53 (d, J=8.0 Hz, 1H) 7.46-7.44 (m, 2H), 7.41-7.35 (m, 4H), 7.06 (dd, J=8.0, 1.7 Hz, 1H), 6.36 (d, J=7.6 Hz, 1H), 6.18 (s, 1H), 5.25 (s, 2H), 4.90 (m, 1H, masked by solvent), 4.82 (s, 1H), 4.53 (d, J=14.2 Hz, 2H), 4.09 (t, J=6.5 Hz, 1H), 3.91 (t, J=6.4 Hz, 1H), 3.89-3.86 (m, 2H), 3.77 (s, 3H), 3.20-3.18 (m, 2H), 3.05-3.03 (m, 1H), 2.99-2.97 (m, 1H), 2.12-2.10 (m, 2H), 2.08-2.05 (m, 2H); ESI MS m/z 497 [M+H]$^+$; HPLC (Method B) 95.0% (AUC), $t_R$=13.1 min.

Example 5

Preparation of 4-(Benzyloxy)-1-(5-methyl-2-(2,2,2-trifluoroethyl)-2,3,4,5-tetrahydro-1H-pyrido[4,3-b]indol-7-yl)pyridin-2(1H)-one dihydrochloride

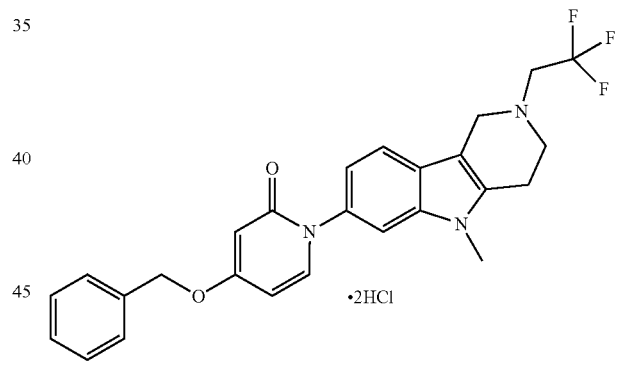

Chemical Formula: $C_{26}H_{26}Cl_2F_3N_3O_2$
Exact Mass: 539.14
Molecular Weight: 540.40

4-(Benzyloxy)-1-(5-methyl-2,3,4,5-tetrahydro-1H-pyrido[4,3-b]indol-7-yl)pyridin-2(1H)-one (75 mg, 0.16 mmol) and triethylamine (105 µL, 0.753 mmol) were dissolved in MeCN (2 mL) and 1,1,1-trifluoro-2-bromoethane (32 mg, 0.20 mmol) was added. The reaction mixture was heated to reflux for 4 h, but no reaction occurred. The mixture was concentrated, DMF (2 mL) and NaI (5 mg) were added, and the reaction mixture was heated to reflux. Again, no reaction occurred. 1,1,1-trifluoroethyl triflate (76 mg, 0.328 mmol) was then added, and the mixture was heated to reflux. After 1.5 h, the mixture was concentrated and purified by flash column chromatography (4 g ISCO column eluting with methylene chloride and a methanol/ammonia mixture (10:

1); gradient 100% methylene chloride to 85% methylene chloride over 30 min). Further purification by preparative HPLC, followed by conversion to the HCl salt (2 N HCl/ Et$_2$O) provided the title compound (6 mg, 7%) as a white solid: $^1$H NMR (300 MHz, CD$_3$OD) δ 7.48 (d, J=7.5 Hz, 1H), 7.40-7.24 (m, 7H), 6.87 (dd, J=8.3, 1.9 Hz, 1H), 6.19 (dd, J=7.6, 2.7 Hz, 1H), 6.03 (d, J=2.7 Hz, 1H), 5.08 (s, 2H), 3.96 (s, 2H), 3.58 (s, 3H), 3.37 (q, J=9.7 Hz, 2H), 3.15-3.14 (m, 2H, partially masked by solvent), 2.87 (t, J=5.5 Hz, 2H); ESI MS m/z 468 [M+H]$^+$; HPLC (Method B) 98.9% (AUC), t$_R$=17.3 min.

Example 6

Preparation of 4-(Benzyloxy)-1-(5-methyl-2-(3,3,3-trifluoropropyl)-2,3,4,5-tetrahydro-1H-pyrido[4,3-b]indol-7-yl)pyridin-2(1H)-one dihydrochloride

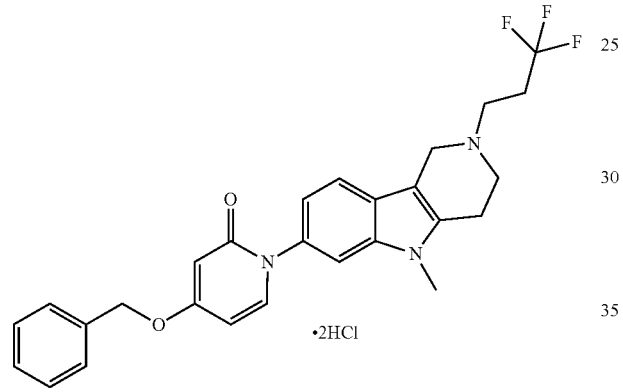

Chemical Formula: C$_{27}$H$_{28}$Cl$_2$F$_3$N$_3$O$_2$
Exact Mass: 553.15
Molecular Weight: 554.43

4-(Benzyloxy)-1-(5-methyl-2,3,4,5-tetrahydro-1H-pyrido [4,3-b]indol-7-yl)pyridin-2(1H)-one (63 mg, 0.14 mmol) and K$_2$CO$_3$ (97 mg, 0.70 mmol) were suspended in DMF (1 mL) and 1,1,1-trifluoro-3-bromopropane (50 mg, 0.28 mmol) was added. The reaction mixture was heated to 80° C. for 18 h, cooled and partitioned between ethyl acetate and water. The aqueous phase was removed and the organic phase washed with 5% LiCl (5×), dried over Na$_2$SO$_4$, filtered and concentrated to dryness. Purification by flash column chromatography (4 g ISCO column eluting with methylene chloride and a methanol/ammonia mixture (10: 1); gradient 100% methylene chloride to 85% methylene chloride over 30 min) followed by conversion to the HCl salt (2 N HCl/Et$_2$O) provided the title compound (12 mg, 16%) as a yellow solid: $^1$H NMR (500 MHz, CD$_3$OD) δ 7.66 (d, J=8.3 Hz, 1H), 7.63 (d, J=7.6 Hz, 1H), 7.52-7.51 (m, 3H), 7.48-7.45 (m, 2H), 7.43 (d, J=7.2 Hz, 1H), 7.11 (dd, J=8.3, 1.7 Hz, 1H), 6.36 (dd, J=7.6, 2.7 Hz, 1H), 6.19 (d, J=2.7 Hz, 1H), 5.24 (s, 2H), 4.96 (m, 6H, masked by solvent), 3.79- 3.74 (m, 5H), 3.03-3.02 (m, 2H); ESI MS m/z 482 [M+H]$^+$; HPLC (Method B) 95.6% (AUC), t$_R$=14.3 min.

Example 7

Preparation of 1-(5-Methyl-2,3,4,5-tetrahydro-1H-pyrido[4,3-b]indol-7-yl)-4-(4-(trifluoromethyl)benzyloxy)pyridin-2(1H)-one dihydrochloride a) tert-Butyl 5-methyl-7-(2-oxo-4-(4-(trifluoromethyl)benzyloxy)pyridin-1(2H)-yl)-3,4-dihydro-1H-pyrido[4,3-b]indole-2(5H)-carboxylate

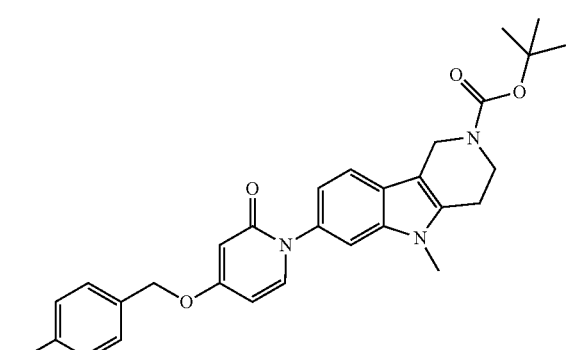

Chemical Formula: C$_{30}$H$_{30}$F$_3$N$_3$O$_4$
Exact Mass: 553.22
Molecular Weight: 553.57

The compound was prepared from tert-butyl 7-bromo-5-methyl-3,4-dihydro-1H-pyrido[4,3-b]indole-2(5H)-carboxylate (250 mg, 0.701 mmol) and 4-(4-(trifluoromethyl) benzyloxy)pyridin-2(1H)-one (142 mg, 0.526 mmol) according to the procedure in Example 1 (step c). Purification by flash column chromatography (silica gel, hexanes/ EtOAc, 100:0 to 80:20 to 50:50 to 25:75 then 0:100) provided the title compound (73 mg, 19%) as a solid, that contained an impurity: ESI MS m/z 554 [M+H]$^+$.

b) 1-(5-Methyl-2,3,4,5-tetrahydro-1H-pyrido[4,3-b]indol-7-yl)-4-(4-(trifluoromethyl)benzyloxy)pyridin-2(1H)-one dihydrochloride

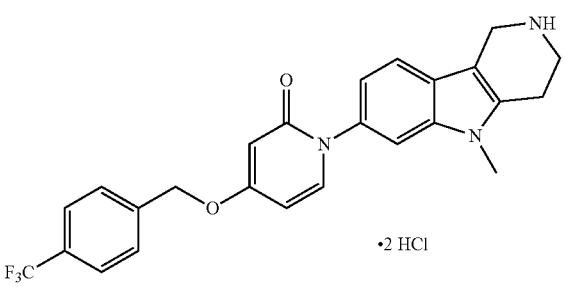

Chemical Formula: C$_{25}$H$_{24}$Cl$_2$F$_3$N$_3$O$_2$
Exact Mass: 525.12
Molecular Weight: 526.38 tert-Butyl 5-methyl-7-(2-oxo-4-(4-(trifluoromethyl)benzyloxy)pyridin-1(2H)-yl)-3,4-dihydro-1H-pyrido[4,3-b]indole-2(5H)-carboxylate (73 mg, 0.13 mmol) was dissolved in MeOH (0.5 mL) and 2 N HCl in Et$_2$O (3 mL) was added. The reaction was allowed to proceed for 3 h. The mixture was concentrated and purified by preparative HPLC. Conversion to the HCl salt (2 N HCl/Et$_2$O) provided the title compound (26 mg, 38%) as a yellow solid: mp 311-315° C.; $^1$H NMR (500 MHz, CD$_3$OD) δ 7.77 (d, J=8.3 Hz, 2H), 7.71 (d, J=8.2 Hz, 2H), 7.65 (d, J=7.6 Hz, 1H), 7.62 (d, J=8.3 Hz, 1H), 7.50 (s, 1H), 7.09 (dd, J=8.3, 1.8 Hz, 1H), 6.38 (dd, J=7.6, 2.7 Hz, 1H), 6.17 (d, J=2.7 Hz, 1H), 5.33 (s, 2H), 4.51 (s, 2H), 3.77 (s, 3H), 3.71 (t, J=6.2 Hz, 2H), 3.24 (t, J=6.1 Hz, 2H); ESI MS m/z 454 [M+H]$^+$; HPLC (Method B)>99% (AUC), t$_R$=14.2 min.

Example 8

Preparation of 4-(4-Chlorobenzyloxy)-1-(5-methyl-2,3,4,5-tetrahydro-1H-pyrido[4,3-b]indol-7-yl)pyridin-2(5H)-one dihydrochloride a) tert-Butyl 7-(4-(4-chlorobenzyloxy)-2-oxopyridin-1(2H)-yl)-5-methyl-3,4-dihydro-1H-pyrido[4,3-b]indole-2(5H)-carboxylate

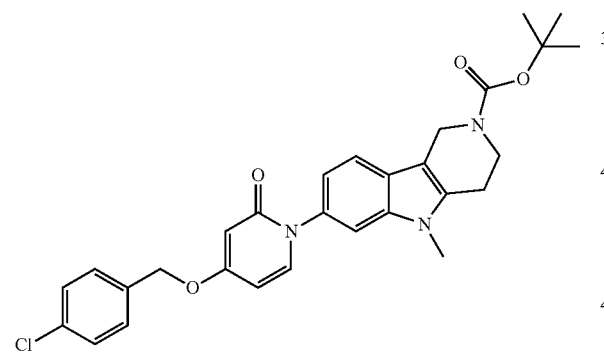

Chemical Formula: C$_{29}$H$_{30}$ClN$_3$O$_4$
Exact Mass: 519.19
Molecular Weight: 520.02

The compound was prepared from tert-butyl 7-bromo-5-methyl-3,4-dihydro-1H-pyrido[4,3-b]indole-2(5H)-carboxylate (200 mg, 0.548 mmol) and 4-(4-chlorobenzyloxy)pyridin-2(1H)-one (129 mg, 0.548 mmol) according to the procedure in Example 1 (step c). Purification by flash column chromatography (silica gel, hexanes/EtOAc, 100:0 to 80:20 to 50:50 to 25:75 then 0:100) provided the title compound (143 mg, 50%) as a yellow solid: $^1$H NMR (300 MHz, CDCl$_3$) δ 7.51 (d, J=8.0 Hz, 1H), 7.43-7.29 (m, 6H), 7.01 (d, J=7.9 Hz, 1H), 6.05-6.02 (m, 2H), 5.02 (s, 2H), 4.64 (br s, 2H), 3.84 (br s, 2H), 3.63 (s, 3H), 2.82 (br s, 2H), 1.50 (s, 9H).

b) 4-(4-Chlorobenzyloxy)-1-(5-methyl-2,3,4,5-tetrahydro-1H-pyrido[4,3-b]indol-7-yl)pyridin-2(1H)-one dihydrochloride

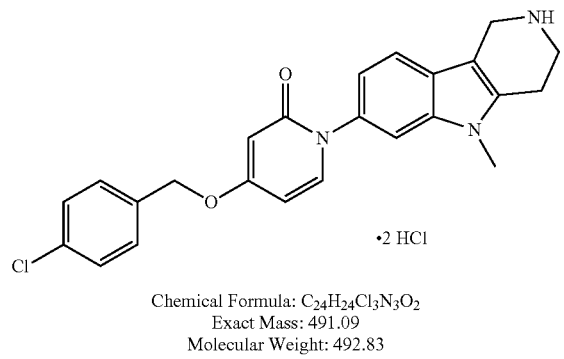 [SMILES: Cn1c2c(c3ccc(-n4ccc(OCc5ccc(Cl)cc5)cc4=O)cc31)CNCC2]

Chemical Formula: C$_{24}$H$_{24}$Cl$_3$N$_3$O$_2$
Exact Mass: 491.09
Molecular Weight: 492.83 tert-Butyl-7-(4-(4-chlorobenzyloxy)-2-oxopyridin-1(2H)-yl)-5-methyl-3,4-dihydro-1H-pyrido[4,3-b]indole-2(5H)-carboxylate (143 mg, 0.275 mmol) was dissolved in MeOH (1 mL) and 2 N HCl in Et$_2$O (5 mL) was added. The reaction was allowed to proceed for 3 h. The resulting precipitate was collected by filtration and washed with Et$_2$O to provide the title compound (95 mg, 71%) as a yellow solid: mp 305-310° C. dec; $^1$H NMR (500 MHz, DMSO-d$_6$) δ 9.54 (br s, 2H), 7.57 (m, 2H), 7.51 (s, 5H), 6.99 (d, J=7.8 Hz, 1H), 6.12 (dd, J=7.8, 2.7 Hz, 1H), 5.99 (d, J=2.7 Hz, 1H), 5.16 (s, 2H), 4.33 (br s, 2H), 3.68 (s, 3H), 3.52-3.48 (m, 2H), 3.12-3.08 (m, 2H); ESI MS m/z 420 [M+H]$^+$; HPLC (Method B) 97% (AUC), t$_R$=13.99 min.

Example 9

Preparation of 1-(5-Methyl-2,3,4,5-tetrahydro-1H-pyrido[4,3-b]indol-7-yl)-4-phenethylpyridin-2(1H)-one dihydrochloride a) tert-Butyl 5-methyl-7-(2-oxo-4-phenethylpyridin-1(2H)-yl)-3,4-dihydro-1H-pyrido[4,3-b]indole-2(5H)-carboxylate

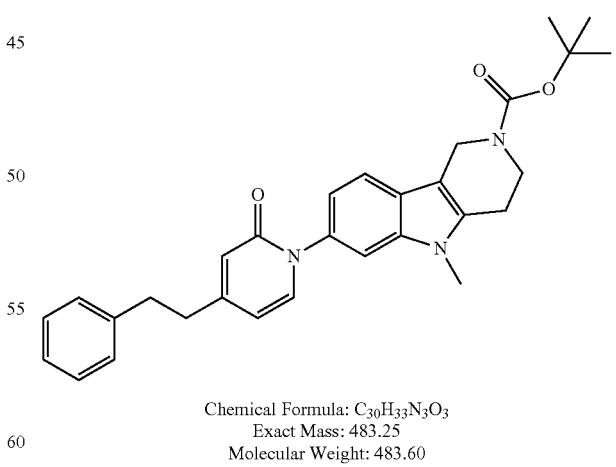

Chemical Formula: C$_{30}$H$_{33}$N$_3$O$_3$
Exact Mass: 483.25
Molecular Weight: 483.60

The compound was prepared from tert-butyl 7-bromo-5-methyl-3,4-dihydro-1H-pyrido[4,3-b]indole-2(5H)-carboxylate (200 mg, 0.548 mmol) and 4-phenethylpyridin-2(1H)-one (109 mg, 0.548 mmol) according to the procedure in Example 1 (step c). Purification by flash column chromatography (silica gel, hexanes/EtOAc, 100:0 to 80:20 to 50:50 to 25:75 then 0:100) provided the title compound (126 mg, 48%) as a yellow solid: $^1$H NMR (300 MHz, CDCl$_3$) δ 7.52 (d, J=8.2 Hz, 1H), 7.34-7.30 (m, 4H), 7.24-7.20 (m, 3H, partially masked by solvent), 7.03 (d, J=7.8 Hz, 1H), 6.52 (s, 1H), 6.10 (dd, J=7.9, 1.7 Hz, 1H), 4.65 (br s, 2H), 3.84 (br s, 2H), 3.63 (s, 3H), 2.98-2.93 (m, 2H), 2.84-2.81 (m, 4H), 1.51 (s, 9H).

b) 1-(5-Methyl-2,3,4,5-tetrahydro-1H-pyrido[4,3-b]indol-7-yl)-4-phenethylpyridin-2(1H)-one dihydrochloride

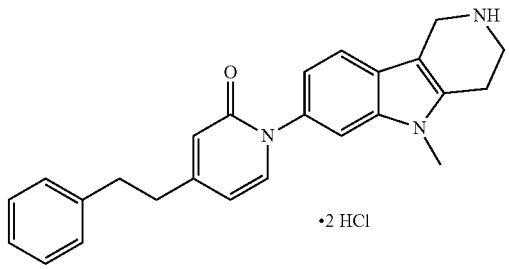

Chemical Formula: C$_{25}$H$_{27}$Cl$_2$N$_3$O
Exact Mass: 455.15
Molecular Weight: 456.41 tert-Butyl 5-methyl-7-(2-oxo-4-phenethylpyridin-1(2H)-yl)-3,4-dihydro-1H-pyrido[4,3-b]indole-2(5H)-carboxylate (120 mg, 0.248 mmol) was dissolved in MeOH (1.5 mL) and 2 N HCl in Et$_2$O (5 mL) was added. The reaction was allowed to proceed for 3 h. The resulting precipitate was collected by filtration and washed with Et$_2$O to provide the title compound (90 mg, 80%) as a yellow solid: mp 282-286° C.; $^1$H NMR (500 MHz, CD$_3$OD) δ 7.70 (d, J=6.9 Hz, 1H), 7.62 (d, J=8.3 Hz, 1H), 7.52 (s, 1H), 7.33-7.26 (m, 4H), 7.22 (t, J=7.2 Hz, 1H), 7.09 (dd, J=8.3, 1.6 Hz, 1H), 6.59-6.56 (m, 2H), 4.50 (s, 2H), 3.76 (s, 3H), 3.70 (t, J=6.2 Hz, 2H), 3.24 (t, J=6.0 Hz, 2H), 3.04-3.01 (m, 2H), 2.98-2.95 (m, 2H); ESI MS m/z 384 [M+H]$^+$; HPLC (Method B)>99% (AUC), t$_R$=13.3 min.

Example 10

Preparation of 1-(5-Methyl-2,3,4,5-tetrahydro-1H-pyrido[4,3-b]indol-7-yl)-4-(4-(trifluoromethyl)phenyl)pyridin-2(1H)-one dihydrochloride a) tert-Butyl 5-methyl-7-(2-oxo-4-(4-(trifluoromethyl)phenyl)pyridin-1(2H)-yl)-3,4-dihydro-1H-pyrido[4,3-b]indole-2(5H)-carboxylate

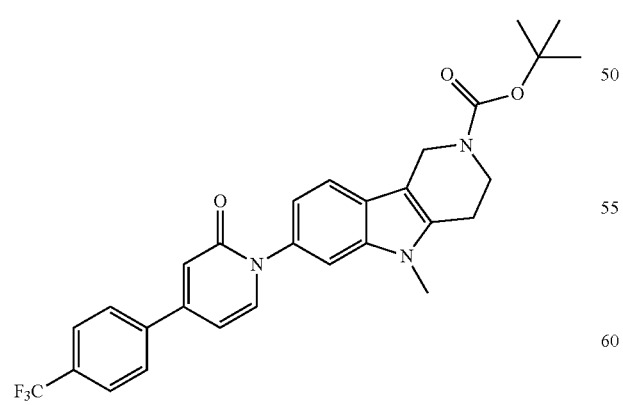

Chemical Formula: C$_{29}$H$_{28}$F$_3$N$_3$O$_3$
Exact Mass: 523.21
Molecular Weight: 523.55

The compound was prepared from tert-butyl 7-bromo-5-methyl-3,4-dihydro-1H-pyrido[4,3-b]indole-2(5H)-carboxylate (153 mg, 0.418 mmol) and 4-(4-(trifluoromethyl)phenyl)pyridine-2(1H)-one (100 mg g, 0.418 mmol) according to the procedure in Example 1 (step c). Purification by flash column chromatography (silica gel, hexanes/EtOAc, 100:0 to 80:20 to 50:50 to 25:75 then 0:100) provided the title compound (98 mg, 45%) as a yellow/green solid: $^1$H NMR (500 MHz, CDCl$_3$) δ 7.75 (s, 4H), 7.57-7.53 (m, 2H), 7.37 (s, 1H), 7.09 (d, J=8.0 Hz, 1H), 6.92 (s, 1H), 6.50 (d, J=6.7 Hz, 1H), 4.67 (s, 2H), 3.86 (br s, 2H), 3.60 (s, 3H), 2.84 (br s, 2H), 1.51 (s, 9H).

b) 1-(5-Methyl-2,3,4,5-tetrahydro-1H-pyrido[4,3-b]indol-7-yl)-4-(4-(trifluoromethyl)phenyl)pyridin-2(1H)-one dihydrochloride

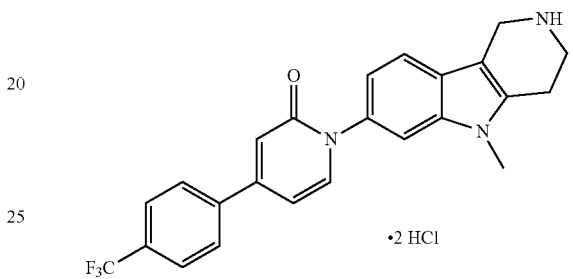

Chemical Formula: C$_{24}$H$_{22}$Cl$_2$F$_3$N$_3$O
Exact Mass: 495.11
Molecular Weight: 496.35 tert-Butyl 5-methyl-7-(2-oxo-4-(4-(trifluoromethyl)phenyl)pyridin-1(2H)-yl)-3,4-dihydro-1H-pyrido[4,3-b]indole-2(5H)-carboxylate (95 mg, 0.18 mmol) was dissolved in MeOH (2 mL) and 2 N HCl in Et$_2$O (10 mL) was added. The reaction was allowed to proceed for 3 h. The resulting precipitate was collected by filtration and washed with Et$_2$O to provide the title compound (45 mg, 50%) as a pale yellow solid: mp 318-323° C.; $^1$H NMR (500 MHz, CD$_3$OD) δ 7.95 (d, J=8.2 Hz, 2H), 7.84 (d, J=8.2 Hz, 2H), 7.81 (d, J=7.1 Hz, 1H), 7.63 (d, J=8.3 Hz, 1H), 7.57 (s, 1H), 7.14 (dd, J=8.3, 1.3 Hz, 1H), 6.96 (d, J=1.6 Hz, 1H), 6.87 (dd, J=7.1, 1.7 Hz, 1H), 4.50 (s, 2H), 3.76 (s, 3H), 3.68 (t, J=6.1 Hz, 2H), 3.22 (t, J=6.1 Hz, 2H); ESI MS m/z 424 [M+H]$^+$; HPLC (Method B) 97.6% (AUC), t$_R$=13.9 min.

Example 11

Preparation of 4-(4-Chlorophenyl)-1-(5-methyl-2,3,4,5-tetrahydro-1H-pyrido[4,3-b]indol-7-yl)pyridin-2(1H)-one dihydrochloride a) 4-(4-Chlorophenyl)pyridine 1-oxide Beilstein Registry Number 5510914

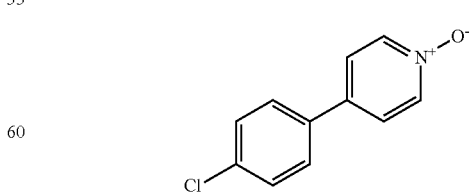

Chemical Formula: C$_{11}$H$_8$ClNO
Exact Mass: 205.03
Molecular Weight: 205.64

4-Chloropyridine-N-oxide (1.5 g, 12 mmol), 4-chlorophenylboronic acid (2.7 g, 17 mmol) and K₂CO₃ (4.78 g, 34.6 mmol) were suspended in DMSO (15 mL) and [1,1'-bis(diphenylphosphino)ferrocene]dichloropalladium(II) (PdCl₂(dppf)) (225 mg, 0.276 mmol) was added. The reaction mixture was placed under vacuum for 20 min and then flushed with N₂. This process was repeated, and the reaction mixture was heated to 120° C. for 3 h, cooled and partitioned between ethyl acetate and brine. The aqueous phase was removed, and the organic phase was washed with brine, dried over Na₂SO₄, filtered and concentrated to dryness. Purification by flash column chromatography (silica gel, hexanes/EtOAc, 100:0 to 80:20 to 50:50 then 25:75 followed by methylene chloride/MeOH 100:0 to 95:5 then 90:10) provided the title compound (1.05 g, 44%) as a grey solid: ¹H NMR (300 MHz, CDCl₃) δ 8.26 (d, J=7.1 Hz, 2H), 7.58-7.43 (m, 6H).

b) 4-(4-Chlorophenyl)pyridin-2(1H)-one

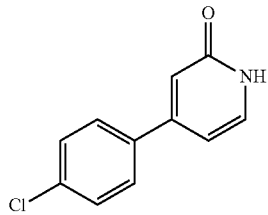

Chemical Formula: C₁₁H₈ClNO
Exact Mass: 205.03
Molecular Weight: 205.64

4-(4-Chlorophenyl)pyridine 1-oxide (1.04 g, 5.07 mmol) and acetic anhydride (25 mL) were heated to reflux for 24 h. The mixture was then concentrated, and 1 N NaOH (10 mL) in MeOH (10 mL) was added. The reaction mixture was heated to reflux for 1 h, then cooled, concentrated, and purified by flash column chromatography (silica gel, methylene chloride/MeOH 100:0 to 98:2 to 95:5 then 90:10) providing the title compound (500 mg, 48%) as an off-white solid: ¹H NMR (300 MHz, CDCl₃) δ 11.64 (s, 1H), 7.73 (d, J=8.6 Hz, 2H), 7.54 (d, J=8.6 Hz, 2H), 7.46 (d, J=6.8 Hz, 1H), 6.60 (d, J=1.4 Hz, 1H), 6.50 (dd, J=6.9, 1.8 Hz, 1H).

c) tert-Butyl 7-(4-(4-chlorophenyl)-2-oxopyridin-1(2H)-yl)-5-methyl-3,4-dihydro-1H-pyrido[4,3-b]indole-2(5H)-carboxylate The compound was prepared from tert-Butyl 7-bromo-5-methyl-3,4-dihydro-1H-pyrido[4,3-b]indole-2(5H)-carboxylate (250 mg, 0.685 mmol) and 4-(4-chlorophenyl)pyridine-2(1H)-one (100 mg, 0.418 mmol) according to the procedure in Example 1 (step c). Purification by flash column chromatography (silica gel, hexanes/EtOAc, 100:0 to 80:20 to 50:50 to 25:75 then 0:100) provided the title compound (59 mg, 18%) as a solid, that contained an impurity: ESI MS m/z 490 [M+H]⁺.

d) 4-(4-Chlorophenyl)-1-(5-methyl-2,3,4,5-tetrahydro-1H-pyrido[4,3-b]indol-7-yl)pyridin-2(1H)-one dihydrochloride

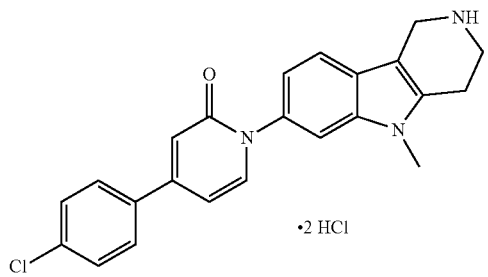

Chemical Formula: C₂₃H₂₂Cl₃N₃O
Exact Mass: 461.08
Molecular Weight: 462.80 tert-Butyl 7-(4-(4-chlorophenyl)-2-oxopyridin-1(2H)-yl)-5-methyl-3,4-dihydro-1H-pyrido[4,3-b]indole-2(5H)-carboxylate (59 mg, 0.12 mmol) was dissolved in MeOH (0.5 mL) and 2 N HCl in Et₂O (3 mL) was added. The reaction was allowed to proceed for 3 h. The mixture was concentrated and purified by preparative HPLC. Conversion to the HCl salt (2 N HCl in Et₂O) provided the title compound (22 mg, 40%) as a pale yellow solid: ¹H NMR (500 MHz, CD₃OD) δ 7.80-7.78 (m, 3H), 7.66 (d, J=8.5 Hz, 1H), 7.58-7.57 (m, 3H), 7.16 (dd, J=8.3, 1.7 Hz, 1H), 6.94 (d, J=1.8 Hz, 1H), 6.87 (dd, J=7.1, 1.9 Hz, 1H), 6.17 (d, J=2.7 Hz, 1H), 4.53 (s, 2H), 3.79 (s, 3H), 3.72 (t, J=5.9 Hz, 2H), 3.25 (t, J=5.9 Hz, 2H); ESI MS m/z 390 [M+H]⁺; HPLC (Method B) 98.2% (AUC), t_R=16.3 min.

Example 12

Preparation of 4-(2,4-Dichlorophenyl)-1-(5-methyl-2,3,4,5-tetrahydro-1H-pyrido[4,3-b]indol-7-yl)pyridin-2(1H)-one dihydrochloride a) tert-Butyl 7-(4-(2,4-dichlorophenyl)-2-oxopyridin-1(2H)-yl)-5-methyl-3,4-dihydro-1H-pyrido[4,3-b]indole-2(5H)-carboxylate

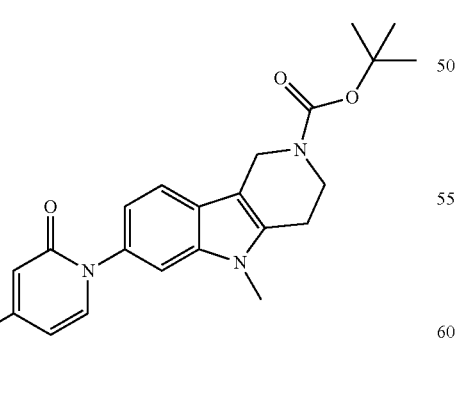

Chemical Formula: C₂₈H₂₈ClN₃O₃
Exact Mass: 489.18
Molecular Weight: 489.99

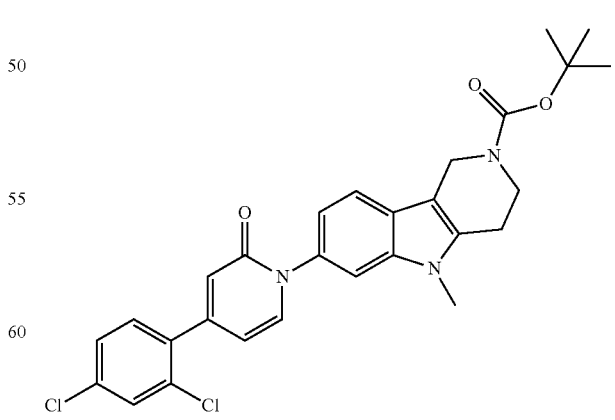

Chemical Formula: C₂₈H₂₇Cl₂N₃O₃
Exact Mass: 523.14
Molecular Weight: 524.44

The compound was prepared from tert-butyl 7-bromo-5-methyl-3,4-dihydro-1H-pyrido[4,3-b]indole-2(5H)-carboxylate (200 mg, 0.548 mmol) and 4-(2,4-dichlorophenyl)pyridine-2(1H)-one (132 mg, 0.548 mmol) according to the procedure in Example 1 (step c). Purification by flash column chromatography (silica gel, hexanes/EtOAc, 100:0 to 80:20 to 50:50 then 25:75) provided the title compound (56 mg, 20%) as a yellow solid: $^1$H NMR (500 MHz, CDCl$_3$) δ 7.56-7.52 (m, 2H), 7.47 (d, J=7.0 Hz, 1H), 7.39-7.32 (m, 3H), 7.10 (br s, 1H), 6.69 (s, 1H), 6.35 (d, J=5.7 Hz, 1H), 4.66 (s, 2H), 3.85 (br s, 2H), 3.65 (s, 3H), 2.84 (br s, 2H), 1.51 (s, 9H).

b) 4-(2,4-Dichlorophenyl)-1-(5-methyl-2,3,4,5-tetrahydro-1H-pyrido[4,3-b]indol-7-yl)pyridin-2(1H)-one dihydrochloride

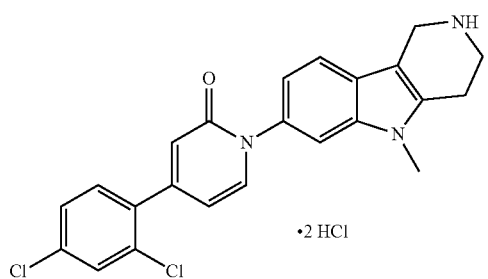

Chemical Formula: C$_{23}$H$_{21}$Cl$_4$N$_3$O
Exact Mass: 495.04
Molecular Weight: 497.24 tert-Butyl 7-(4-(2,4-dichlorophenyl)-2-oxopyridin-1(2H)-yl)-5-methyl-3,4-dihydro-1H-pyrido[4,3-b]indole-2(5H)-carboxylate (56 mg, 0.11 mmol) was dissolved in MeOH (1 mL) and 2 N HCl in Et$_2$O (5 mL) was added. The reaction was allowed to proceed for 3 h. The mixture was concentrated and purified by preparative HPLC. Conversion to the HCl salt (2 N HCl in Et$_2$O) provided the title compound (22 mg, 42%) as a yellow solid: mp 321-324° C.; $^1$H NMR (500 MHz, CD$_3$OD) δ 7.80 (d, J=7.0 Hz, 1H), 7.70 (s, 1H), 7.68 (d, J=7.9 Hz, 1H), 7.62 (s, 1H), 7.54 (s, 2H), 7.13 (d, J=7.0 Hz, 1H), 6.73 (s, 1H), 6.61 (d, J=7.2 Hz, 1H), 4.54 (s, 2H), 3.80 (s, 3H), 3.72 (t, J=6.0 Hz, 2H), 3.26 (t, J=5.9 Hz, 2H); ESI MS m/z 424 [M+H]$^+$; HPLC (Method B)>99% (AUC), $t_R$=14.1 min.

Example 13

Preparation of 4-(Benzyloxy)-1-(5-methyl-2,3,4,5-tetrahydro-1H-pyrido[4,3-b]indol-8-yl)pyridin-2(1H)-one hydrochloride a) tert-Butyl 8-bromo-3,4-dihydro-1H-pyrido[4,3-b]indole-2(5H)-carboxylate

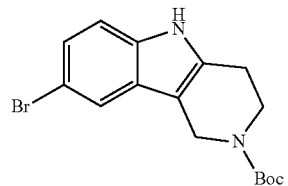

Chemical Formula: C$_{16}$H$_{19}$BrN$_2$O$_2$
Exact Mass: 350.0630
Molecular Weight: 351.2383

To a mixture of 4-bromophenylhydryzine hydrochloride (1.00 g, 4.47 mmol) and tert-butyl 4-oxopiperidine-1-carboxylate (0.89 g, 4.5 mmol) were added EtOH (10 mL) and conc. HCl (3 mL). The reaction mixture was heated to 90° C. and stirred at 90° C. until the reaction was complete. Then the mixture was concentrated and the residue was dissolved in CH$_2$Cl$_2$ (10 mL) and CH$_3$OH (5 mL). To the above solution were added Boc$_2$O (1.46 g, 6.69 mmol), TEA (0.94 mL, 6.7 mmol) and DMAP (55 mg, 0.45 mmol). The reaction mixture was stirred at room temperature until it was complete. The mixture was concentrated and the residue was dissolved in CH$_2$Cl$_2$, washed with H$_2$O and brine, dried with Na$_2$SO$_4$, filtered and concentrated. Purification by flash column chromatography (silica gel, hexanes/EtOAc, 1:1) gave the title compound (1.12 g, 72%) as a yellow foam: $^1$H NMR (500 MHz, CDCl$_3$) δ 7.89 (br s, 1H), 7.57 (s, 1H), 7.17-7.24 (m, 2H), 4.58 (s, 2H), 3.81 (m, 2H), 2.83 (m, 2H), 1.5 (s, 9H); ESI MS m/z 351 [M+H]$^+$.

b) tert-Butyl 8-4-(benzyloxy)-2-oxopyridin-1(2H)-yl)-5-methyl-3,4-dihydro-1H-pyrido[4,3-b]indole-2-(5H)-carboxylate

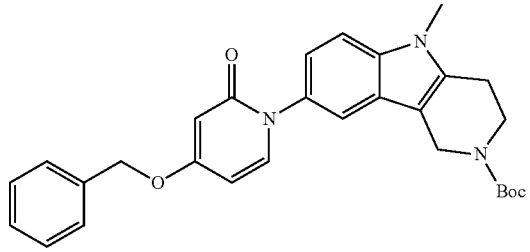

Chemical Formula: C$_{29}$H$_{31}$N$_3$O$_4$
Exact Mass: 485.2315
Molecular Weight: 485.5741

To a solution of tert-butyl 8-bromo-3,4-dihydro-1H-pyrido[4,3-b]indole-2(5H)-carboxylate (0.53 g, 1.5 mmol) in DMF (6 mL) was added NaH (60% weight dispersion in mineral oil, 91 mg, 2.3 mmol) and CH$_3$I (0.14 mL, 2.3 mmol). The reaction mixture was stirred at room temperature until the reaction was complete. Then the reaction was quenched with H$_2$O and extracted with CH$_2$Cl$_2$. The organic layer was washed with H$_2$O and 5% LiCl, dried with Na$_2$SO$_4$, filtered and concentrated to give tert-butyl 8-bromo-5-methyl-3,4-dihydro-1H-pyrido[4,3-b]indole-2(5H)-carboxylate, which was used directly without purification.

To a mixture of tert-butyl 8-bromo-5-methyl-3,4-dihydro-1H-pyrido[4,3-b]indole-2(5H)-carboxylate (0.48 g, 1.3 mmol), 4-(benzyloxy)pyridin-2(1H)-one (264 mg, 1.31 mmol), 8-hydroxyquinoline (29 mg, 0.20 mmol), K$_2$CO$_3$ (217 mg, 1.57 mmol) and CuI (38 mg, 0.20 mmol) was added DMSO (5 mL). The reaction mixture was degassed and back-filled with N$_2$. The reaction mixture was heated to 130° C. and stirred at 130° C. overnight. After it was cooled, the mixture was filtered through a layer of Celite. The filtrate was diluted with CH$_2$Cl$_2$, washed with H$_2$O and 5% LiCl, dried with Na$_2$SO$_4$, filtered, and concentrated. Purification by flash column chromatography (silica gel, 5% CH$_3$OH in CH$_2$Cl$_2$) gave the title compound (0.28 g, 44%) as a yellow solid: $^1$H NMR (500 MHz, CDCl$_3$) δ 7.36-7.29 (m, 8H), 7.13 (d, J=8.0 Hz, 1H), 6.09 (d, J=2.0 Hz, 1H), 6.03 (dd, J=7.5, 2.0 Hz, 1H), 5.05 (s, 2H), 4.61 (s, 2H), 3.84 (m, 2H), 3.66 (s, 3H), 2.82 (m, 2H), 1.49 (s, 9H); ESI MS m/z 486 [M+H]$^+$.

c) 4-(Benzyloxy)-1-(5-methyl-2,3,4,5-tetrahydro-1H-pyrido[4,3-b]indol-8-yl)pyridin-2(1H)-one hydrochloride

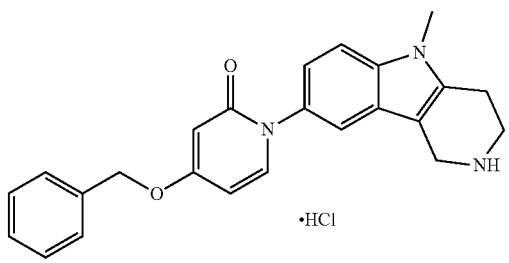

Chemical Formula: C$_{24}$H$_{24}$ClN$_3$O$_2$
Exact Mass: 421.16
Molecular Weight: 421.92

To a solution of tert-butyl 8-4-(benzyloxy)-2-oxopyridin-1(2H)-yl)-5-methyl-3,4-dihydro-1H-pyrido[4,3-b]indole-2-(5H)-carboxylate (180 mg, 0.37 mmol) in CH$_3$OH (2 mL) was added 1 N HCl in Et$_2$O (2 mL). The reaction mixture was stirred at room temperature until the reaction was complete. The resulting solid was dried under vacuum to give the title compound (142 mg, 91%) as a yellow solid: mp 280-285° C. (decompose); $^1$H NMR (500 MHz, CD$_3$OD) δ 7.59 (d, J=7.5 Hz, 1H), 7.54 (d, J=9.0 Hz, 1H), 7.48-7.40 (m, 5H), 7.38-7.36 (m, 1H), 7.17 (dd, J=8.5, 1.5 Hz, 1H), 6.33 (dd, J=7.5, 2.5 Hz, 1H), 6.16 (d, J=2.5 Hz, 1H), 5.20 (s, 2H), 4.45 (s, 2H), 3.77 (s, 3H), 3.67 (t, J=6.0 Hz, 2H), 3.21 (t, J=6.0 Hz, 2H); ESI MS m/z 386 [M+H]$^+$; HPLC (Method B) 98.8% (AUC), t$_R$=12.9 min.

Example 14

Preparation of 4-(Benzyloxy)-1-(2,5-dimethyl-2,3,4,5-tetrahydro-1H-pyrido[4,3-b]indol-8-yl)pyridin-2(1H)-one hydrochloride

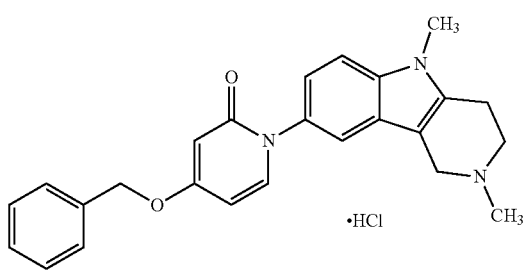

Chemical Formula: C$_{25}$H$_{26}$ClN$_3$O$_2$
Exact Mass: 435.17
Molecular Weight: 435.95

To a solution of 4-(benzyloxy)-1-(5-methyl-2,3,4,5-tetrahydro-1H-pyrido[4,3-b]indol-8-yl)pyridin-2(1H)-one (100 mg, 0.26 mmol) in CH$_3$OH (3 mL) was added formaldehyde (30 μL, 0.29 mmol) and NaBH(OAc)$_3$ (110 mg, 0.52 mmol). The reaction mixture was stirred at room temperature until the reaction was complete. Then the mixture was concentrated and the residue was dissolved in CH$_2$Cl$_2$. The organic layer was washed with H$_2$O and 5% LiCl, dried with Na$_2$SO$_4$, filtered and concentrated. Purification by flash column chromatography (silica gel, 10% CH$_3$OH in CH$_2$Cl$_2$) gave 4-(benzyloxy)-1-(2,5-dimethyl-2,3,4,5-tetrahydro-1H-pyrido[4,3-b]indol-8-yl)pyridin-2(1H)-one (102 mg, 98%) as a yellow solid. The free base was converted to the HCl salt to give the title compound (100 mg, 90%) as a yellow solid: mp 264-268° C. (decompose); $^1$H NMR (500 MHz, DMSO-d$_6$) δ 10.26 (s, 1H), 7.56-7.36 (m, 8H), 7.10 (dd, J=8.5, 1.5 Hz, 1H), 6.10 (dd, J=7.5, 3.0 Hz, 1H), 5.97 (d, J=3.0 Hz, 1H), 5.15 (s, 2H), 4.58 (m, 1H), 4.27 (m, 1H), 3.78 (m, 1H), 3.72 (s, 3H), 3.50 (m, 1H), 3.18 (m, 2H), 2.97 (s, 3H); ESI MS m/z 400 [M+H]$^+$; HPLC (Method B)>99% (AUC), t$_R$=12.9 min.

Example 15

Preparation of 2-(Pyrrolidin-1-yl)ethyl-7-4-(benzyloxy)-2-oxopyridin-1(2H)-5-methyl-3,4-dihydro-1H-pyrido[4,3-b]indole-2(5H)-carboxylate hydrochloride Chemical Formula: C$_{31}$H$_{35}$ClN$_4$O$_4$
Exact Mass: 562.23
Molecular Weight: 563.09

To a solution of 4-benzyloxy-1-(5-methyl-2,3,4,5-tetrahydro-1H-pyrido[4,3-b]indol-7-yl)pyridin-2(1H)-one hydrochloride (100 mg, 0.24 mmol) in DMSO (2 mL) was added 1-(2-chloroethyl)pyrrolidine hydrochloride (53 mg, 0.29 mmol) and Cs$_2$CO$_3$ (313 mg, 1.06 mmol). The reaction mixture was stirred at room temperature under Ar until the reaction was complete. The reaction was quenched with water and extracted with CH$_2$Cl$_2$. The organic layer was washed with H$_2$O and 5% LiCl, dried with Na$_2$SO$_4$, filtered, and concentrated. Purification by flash column chromatography (silica gel, 5% CH$_3$OH in CH$_2$Cl$_2$) gave 2-(pyrrolidin-1-yl)ethyl-7-4-(benzyloxy)-2-oxopyridin-1(2H)-5-methyl-3,4-dihydro-1H-pyrido[4,3-b]indole-2(5H)-carboxylate (56 mg, 44%) as a yellow foam. The free base was converted to the HCl salt to give the title compound (44 mg, 73%) as a yellow solid: mp 95-97° C.; $^1$H NMR (500 MHz, CD$_3$OD) δ 7.78-7.75 (m, 1H), 7.57-7.54 (m, 1H), 7.49-7.37 (m, 6H), 7.04-7.01 (m, 1H), 6.55-6.52 (m, 1H), 6.33-6.31 (m, 1H), 5.26 (s, 2H), 4.80-4.73 (m, 2H), 4.49-4.48 (m, 2H), 3.94-3.93 (m, 2H), 3.82-3.72 (m, 2H), 3.69 (s, 3H), 3.58-3.57 (m, 2H), 3.20-3.14 (m, 2H), 2.98-2.94 (m, 2H), 2.15-1.99 (m, 4H); ESI MS m/z 527 [M+H]$^+$; HPLC (Method B)>99% (AUC), $t_R$=13.8 min.

Example 16

Preparation of 4-(Benzyloxy)-1-(2-(2-(dimethylamino)acetyl)-5-methyl-2,3,4,5-tetrahydro-1H-pyrido[4,3-b]indol-7-yl)pyridin-2(1H)-one hydrochloride

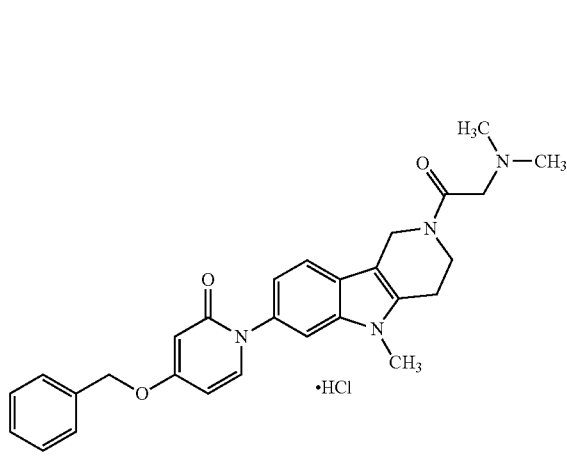

Chemical Formula: C$_{28}$H$_{31}$ClN$_4$O$_3$
Exact Mass: 506.21
Molecular Weight: 507.02

To a solution of 4-benzyloxy-1-(5-methyl-2,3,4,5-tetrahydro-1H-pyrido[4,3-b]indol-7-yl)pyridin-2(1H)-one (100 mg, 0.26 mmol) in CH$_2$Cl$_2$ (2 mL) was added 2-chloroacetyl chloride (29 µL, 0.36 mmol) and Et$_3$N (0.1 mL, 0.7 mmol). The reaction mixture was stirred at room temperature until the reaction was complete. After the solvent was removed, the residue was dissolved in DMF. To the DMF solution was added (CH$_3$)$_2$NH (64 µL, 1.2 mmol) and K$_2$CO$_3$ (166 mg, 1.2 mmol). The reaction mixture was heated to 70° C. and stirred at 70° C. until the reaction was complete. After it was cooled, the reaction was quenched with water and extracted with CH$_2$Cl$_2$. The organic layer was washed with H$_2$O and 5% LiCl, dried with Na$_2$SO$_4$, filtered, and concentrated. Purification by flash column chromatography (silica gel, 10% CH$_3$OH in CH$_2$Cl$_2$) gave 4-(benzyloxy)-1-(2-(2-(dimethylamino)acetyl)-5-methyl-2,3,4,5-tetrahydro-1H-pyrido[4,3-b]indol-7-yl)pyridin-2(1H)-one (58 mg, 51%) as a yellow foam. The free base was converted to the HCl salt to give the title compound (31 mg, 50%) as a yellow solid and as a mixture of rotamers: mp 135-140° C.; $^1$H NMR (500 MHz, CD$_3$OD) δ 7.75-7.71 (m, 1H), 7.59-7.55 (m, 1H), 7.49-7.37 (m, 6H), 7.05-7.01 (m, 1H), 6.49-6.45 (m, 1H), 6.28-6.26 (m, 1H), 5.24 (s, 2H), 4.87 (br s, 1H), 4.69 (br s, 1H), 4.44-4.41 (m, 2H), 4.11-4.07 (m, 1H), 3.85-3.82 (m, 1H), 3.70 (2×s, 3H), 3.06-2.92 (m, 2H), 2.97-2.94 (2×s, 6H); ESI MS m/z 471 [M+H]$^+$; HPLC (Method B) 97.0% (AUC), $t_R$=13.2 min.

Example 17

Preparation of 4-(Benzyloxy)-1-(5-methyl-2-(2-oxo-2-(pyrrolidin-1-yl)ethyl)-2,3,4,5-tetrahydro-1H-pyrido[4,3-b]indol-7-yl)pyridine-2(1H)-one hydrochloride Chemical Formula: C$_{30}$H$_{33}$ClN$_4$O$_3$
Exact Mass: 532.22
Molecular Weight: 533.06

To a solution of 4-benzyloxy-1-(5-methyl-2,3,4,5-tetrahydro-1H-pyrido[4,3-b]indol-7-yl)pyridin-2(1H)-one (100 mg, 0.26 mmol) in DMF (3 mL) was added 2-chloro-1-(pyrrolidin-1-yl)ethanone (77 mg, 0.52 mmol) and K$_2$CO$_3$ (72 mg, 0.52 mmol). The reaction mixture was heated to 70° C. and stirred at 70° C. until the reaction was complete. After it was cooled, the reaction was quenched with water and extracted with CH$_2$Cl$_2$. The organic layer was washed with H$_2$O and 5% LiCl, dried with Na$_2$SO$_4$, filtered, and concentrated. Purification by flash column chromatography (silica gel, 5% CH$_3$OH in CH$_2$Cl$_2$) gave 4-(benzyloxy)-1-(5-methyl-2-(2-oxo-2-(pyrrolidin-1-yl)ethyl)-2,3,4,5-tetrahydro-1H-pyrido[4,3-b]indol-7-yl)pyridine-2(1H)-one (35 mg, 27%) as a yellow foam. The free base was converted to the HCl salt to the give title compound (30 mg, 80%) as a yellow solid: mp 162-166° C.; $^1$H NMR (500 MHz, CD$_3$OD) δ 7.60 (d, J=7.5 Hz, 1H), 7.56 (d, J=8.0 Hz, 1H), 7.49-7.35 (m, 6H), 7.06 (dd, J=8.5, 1.5 Hz, 1H), 6.33 (dd, J=7.5, 3.0 Hz, 1H), 6.16 (d, J=3.0 Hz, 1H), 5.20 (s, 2H), 4.80 (d, J=14.5 Hz, 1H), 4.54 (d, J=14.5 Hz, 1H), 4.36 (s, 2H), 4.00-3.98 (m, 1H), 3.75 (s, 3H), 3.68-3.65 (m, 1H), 3.54 (t, J=7.0 Hz, 2H), 3.49-3.45 (m, 2H), 3.35-3.33 (m, 2H), 2.05-1.92 (m, 4H); ESI MS m/z 497 [M+H]$^+$; HPLC (Method B) 97.9% (AUC), $t_R$=13.4 min.

Example 18

Preparation of 4-(Benzyloxy)-1-(5-methyl-2-(3-(pyrrolidin-1-yl)propanoyl)-2,3,4,5-tetrahydro-1H-pyrido[4,3-b]indol-7-yl)pyridine-2(1H)-one hydrochloride

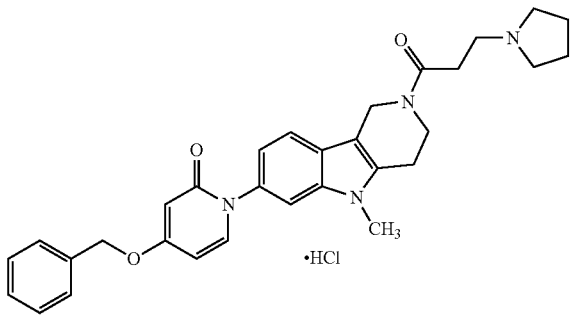

Chemical Formula: C$_{31}$H$_{35}$ClN$_4$O$_3$
Exact Mass: 546.24
Molecular Weight: 547.09

To a solution of 4-benzyloxy-1-(5-methyl-2,3,4,5-tetrahydro-1H-pyrido[4,3-b]indol-7-yl)pyridin-2(1H)-one (100 mg, 0.26 mmol) in DMF (3 mL) was added O-(7-azabenzotriazol-1-yl)-N,N,N'N'-tetramethyluronium hexafluorophosphate (HATU) (148 mg, 0.389 mmol), 3-(pyrrolidin-1-yl)propanoic acid hydrochloride (56 mg, 0.31 mmol), and Et$_3$N (73 μL, 0.52 mmol). The reaction mixture was stirred at room temperature under Ar until the reaction was complete. The reaction was quenched with water and extracted with CH$_2$Cl$_2$. The organic layer was washed with H$_2$O and 5% LiCl, dried with Na$_2$SO$_4$, filtered and concentrated. Purification by flash column chromatography (silica gel, 5% CH$_3$OH in CH$_2$Cl$_2$) gave 4-(benzyloxy)-1-(5-methyl-2-(3-(pyrrolidin-1-yl)propanoyl)-2,3,4,5-tetrahydro-1H-pyrido[4,3-b]indol-7-yl)pyridine-2(1H)-one as a yellow foam. The free base was converted to the HCl salt to give the title compound (75 mg, 86%) as a yellow solid: mp 110-115° C.; $^1$H NMR (500 MHz, CD$_3$OD) δ 7.79-7.76 (m, 1H), 7.61-7.55 (m, 1H), 7.49-7.36 (m, 6H), 7.05-7.02 (m, 1H), 6.55-6.52 (m, 1H), 6.33-6.32 (m, 1H), 5.26 (s, 2H), 4.06 (t, J=5.5 Hz, 1H), 3.94 (t, J=5.5 Hz, 1H), 3.70-3.69 (m, 5H), 3.54-3.50 (m, 2H), 3.18-2.89 (m, 8H), 2.18-2.04 (m, 4H); ESI MS m/z 511 [M+H]$^+$; HPLC (Method B) 97.7% (AUC), $t_R$=13.6 min.

Example 19

Preparation of 4-(Benzyloxy)-1-(5-methyl-2-(pyrrolidine-3-carbonyl)-2,3,4,5-tetrahydro-1H-pyrido[4,3-b]indol-7-yl)pyridin-2(1H)-one hydrochloride

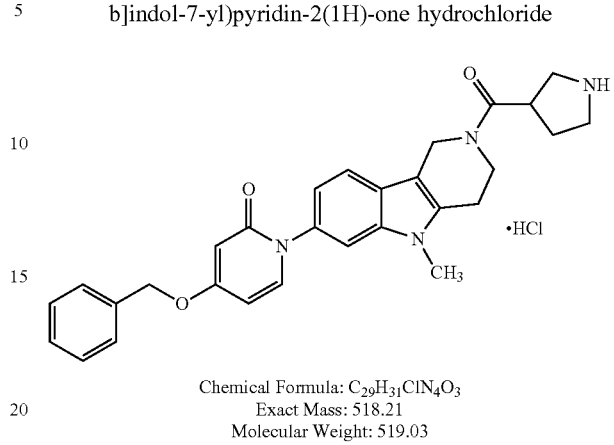

Chemical Formula: C$_{29}$H$_{31}$ClN$_4$O$_3$
Exact Mass: 518.21
Molecular Weight: 519.03

Following the procedure of Example 18, but substituting 1-(tert-butoxycarbonyl)pyrrolidine-3-carboxylic acid for 3-(pyrrolidin-1-yl)propanoic acid hydrochloride, a yellow solid was obtained in 78% yield (118 mg). The yellow solid was dissolved in CH$_3$OH (3 mL) and was treated with 1 N HCl in Et$_2$O (2 mL). The resulting solid was isolated by filtration and dried under vacuum to give the title compound (90 mg, 90%) as a green-yellow powder: $^1$H NMR (500 MHz, CD$_3$OD) δ 7.75-7.72 (m, 1H), 7.63-7.55 (m, 1H), 7.49-7.36 (m, 6H), 7.05-7.02 (m, 1H), 6.51-6.46 (m, 1H), 6.29-6.27 (m, 1H), 5.25 (s, 2H), 4.79-4.76 (m, 2H), 4.14-3.97 (m, 2H), 3.87-3.82 (m, 1H), 3.71-3.69 (m, 4H), 3.60-3.50 (m, 1H), 3.45-3.36 (m, 3H), 3.04-3.03 (m, 1H), 2.94-2.92 (m, 1H), 2.52-2.36 (m, 1H), 2.18-2.00 (m, 1H); ESI MS m/z 483 [M+H]$^+$; HPLC (Method B) 98.1% (AUC), $t_R$=13.2 min.

Example 20

Preparation of (R)-4-(Benzyloxy)-1-(5-methyl-2-(pyrrolidine-2-carbonyl)-2,3,4,5-tetrahydro-1H-pyrido[4,3-b]indol-7-yl)pyridin-2(1H)-one hydrochloride

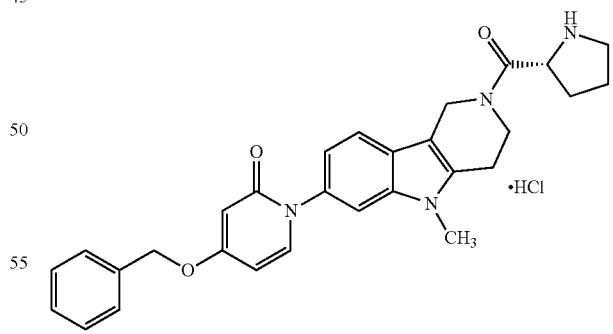

Chemical Formula: C$_{29}$H$_{31}$ClN$_4$O$_3$
Exact Mass: 518.21
Molecular Weight: 519.03

Following the procedure of Example 19, but substituting (R)-1-(tert-butoxycarbonyl)pyrrolidine-2-carboxylic acid for 1-(tert-butoxycarbonyl)pyrrolidine-3-carboxylic acid, the title compound (67 mg, 50%) was obtained as a yellow solid and as a mixture of rotamers: $^1$H NMR (500 MHz, CD$_3$OD) δ 7.82-7.79 (m, 1H), 7.66-7.56 (m, 1H), 7.49-7.36

(m, 6H), 7.07-7.03 (m, 1H), 6.59-6.56 (m, 1H), 6.36 (dd, J=5.0, 2.5 Hz, 1H), 5.28 (s, 2H), 4.82-4.81 (m, 2H), 4.14-4.05 (m, 1H), 3.97-3.95 (m, 1H), 3.71-3.69 (2×s, 3H), 3.58-3.34 (m, 3H), 3.07-2.94 (m, 2H), 2.70-2.57 (m, 1H), 2.17-1.85 (m, 3H); ESI MS m/z 483 [M+H]+; HPLC (Method B)>99% (AUC), $t_R$=13.3 min.

Example 21

Preparation of (S)-4-(Benzyloxy)-1-(5-methyl-2-(pyrrolidine-2-carbonyl)-2,3,4,5-tetrahydro-1H-pyrido[4,3-b]indol-7-yl)pyridin-2(1H)-one hydrochloride

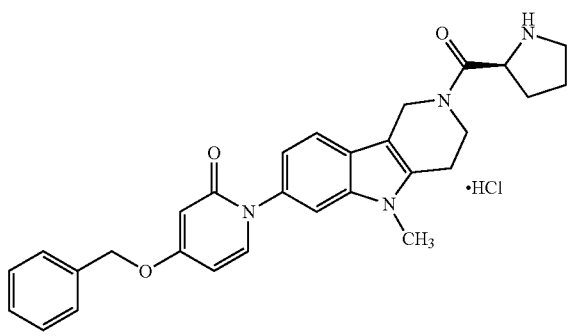

Chemical Formula: $C_{29}H_{31}ClN_4O_3$
Exact Mass: 518.21
Molecular Weight: 519.03

Following the procedure of Example 20, but substituting (S)-1-(tert-butoxycarbonyl)pyrrolidine-2-carboxylic acid for (R)-1-(tert-butoxycarbonyl)pyrrolidine-2-carboxylic acid, the title compound (47 mg, 72%) was obtained as a yellow solid and as a mixture of rotamers: 1H NMR (500 MHz, CD3OD) δ 7.82-7.79 (m, 1H), 7.66-7.56 (m, 1H), 7.49-7.36 (m, 6H), 7.07-7.03 (m, 1H), 6.59-6.56 (m, 1H), 6.36 (dd, J=5.0, 2.5 Hz, 1H), 5.28 (s, 2H), 4.82-4.81 (m, 2H), 4.14-4.05 (m, 1H), 3.97-3.95 (m, 1H), 3.71-3.69 (2×s, 3H), 3.58-3.34 (m, 3H), 3.07-2.94 (m, 2H), 2.70-2.57 (m, 1H), 2.17-1.85 (m, 3H); ESI MS m/z 483 [M+H]+; HPLC (Method B)>99% (AUC), $t_R$=13.3 min.

Example 22

Preparation of 4-(Benzyloxy)-1-(5-methyl-2-(1-methylpyrrolidine-3-carbonyl)-2,3,4,5-tetrahydro-1H-pyrido[4,3-b]indol-7-yl)pyridin-2(1H)-one hydrochloride

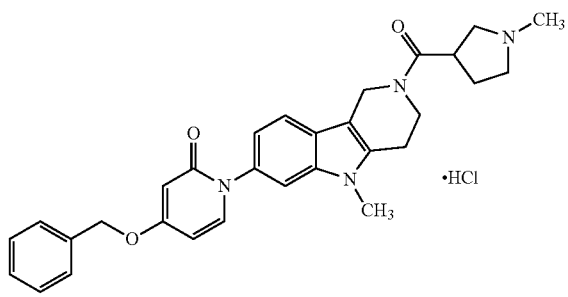

Chemical Formula: $C_{30}H_{33}ClN_4O_3$
Exact Mass: 532.22
Molecular Weight: 533.06

To a solution of 4-(benzyloxy)-1-(5-methyl-2-(pyrrolidine-3-carbonyl)-2,3,4,5-tetrahydro-1H-pyrido[4,3-b]indol-7-yl)pyridin-2(1H)-one hydrochloride (105 mg, 0.197 mmol) in CH3OH (3 mL) was added Et3N (40 μL, 0.29 mmol), formaldehyde (23 μL, 0.29 mmol), and NaBH(OAc)3 (86 mg, 0.41 mmol). The reaction mixture was stirred at room temperature until the reaction was complete. Then the mixture was concentrated and the residue was dissolved in CH2Cl2. The organic layer was washed with H2O and 5% LiCl, dried with Na2SO4, filtered and concentrated. Purification by flash column chromatography (silica gel, 10% CH3OH in CH2Cl2) gave 4-(benzyloxy)-1-(5-methyl-2-(1-methylpyrrolidine-3-carbonyl)-2,3,4,5-tetrahydro-1H-pyrido[4,3-b]indol-7-yl)pyridin-2(1H)-one (60 mg, 60%) as a yellow solid. The free base was converted to the HCl salt to give the title compound (43 mg, 80%) as a yellow solid and as a mixture of rotamers: mp 132-136° C.; 1H NMR (500 MHz, CD3OD) δ 7.61-7.33 (m, 8H), 7.02-6.98 (m, 1H), 6.29-6.27 (m, 1H), 6.12-6.11 (m, 1H), 5.17 (s, 2H), 4.79-4.76 (m, 2H), 4.09-3.97 (m, 2H), 3.81-3.79 (m, 1H), 3.69-3.67 (m, 4H), 3.49-3.42 (m, 1H), 3.22-3.16 (m, 2H), 3.00 (m, 1H), 2.92-2.91 (m, 1H), 2.81-2.78 (2×s, 3H), 2.52-2.36 (m, 1H), 2.18-2.00 (m, 1H); ESI MS m/z 497 [M+H]+; HPLC (Method B) 98.7% (AUC), $t_R$=13.6 min.

Example 23

Preparation of (R)-4-(Benzyloxy)-1-(5-methyl-2-(1-methylpyrrolidine-2-carbonyl)-2,3,4,5-tetrahydro-1H-pyrido[4,3-b]indol-7-yl)pyridin-2(1H)-one hydrochloride Chemical Formula: $C_{30}H_{33}ClN_4O_3$
Exact Mass: 532.22
Molecular Weight: 533.06

Following the procedure of Example 22, but substituting (R)-4-(benzyloxy)-1-(5-methyl-2-(pyrrolidine-2-carbonyl)-2,3,4,5-tetrahydro-1H-pyrido[4,3-b]indol-7-yl)pyridin-2 (1H)-one hydrochloride for 4-(benzyloxy)-1-(5-methyl-2-(pyrrolidine-3-carbonyl)-2,3,4,5-tetrahydro-1H-pyrido[4,3-b]indol-7-yl)pyridin-2(1H)-one hydrochloride, the title compound (80 mg, 67%) was obtained as a yellow solid and as a mixture of rotamers: mp 158-162° C.; 1H NMR (500 MHz, CD3OD) δ 7.61-7.33 (m, 8H), 7.03-6.99 (m, 1H), 6.30 (dd, J=7.5, 2.5 Hz, 1H), 6.13 (d, J=2.5 Hz, 1H), 5.18 (s, 2H), 4.80-4.70 (m, 2H), 4.12-4.09 (m, 1H), 3.92-3.90 (m, 1H), 3.78-3.72 (m, 1H), 3.69-3.68 (2s, 3H), 3.49-3.42 (m, 1H), 3.28-3.20 (m, 1H), 3.07-3.00 (m, 2H), 2.96-2.94 (2s, 3H), 2.79-2.65 (m, 1H), 2.21-2.09 (m, 1H), 2.09-1.86 (m, 2H); ESI MS m/z 497 [M+H]+; HPLC (Method B)>99% (AUC), $t_R$=13.4 min.

Example 24

Preparation of (S)-4-(Benzyloxy)-1-(5-methyl-2-(1-methylpyrrolidine-2-carbonyl)-2,3,4,5-tetrahydro-1H-pyrido[4,3-b]indol-7-yl)pyridin-2(1H)-one hydrochloride

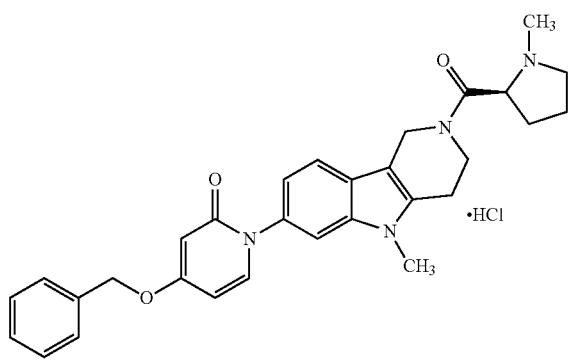

Chemical Formula: C₃₀H₃₃ClN₄O₃
Exact Mass: 532.22
Molecular Weight: 533.06

Following the procedure of Example 22, but substituting (S)-4-(benzyloxy)-1-(5-methyl-2-(pyrrolidine-2-carbonyl)-2,3,4,5-tetrahydro-1H-pyrido[4,3-b]indol-7-yl)pyridin-2(1H)-one hydrochloride for 4-(benzyloxy)-1-(5-methyl-2-(pyrrolidine-3-carbonyl)-2,3,4,5-tetrahydro-1H-pyrido[4,3-b]indol-7-yl)pyridin-2(1H)-one hydrochloride, the title compound (40 mg, 61%) was obtained as a yellow solid and as a mixture of rotamers: mp 154-160° C.; $^1$H NMR (500 MHz, CD₃OD) δ 7.61-7.33 (m, 8H), 7.03-6.99 (m, 1H), 6.30 (dd, J=7.5, 2.5 Hz, 1H), 6.13 (d, J=2.5 Hz, 1H), 5.18 (s, 2H), 4.80-4.70 (m, 2H), 4.12-4.09 (m, 1H), 3.92-3.90 (m, 1H), 3.78-3.72 (m, 1H), 3.69-3.68 (2s, 3H), 3.49-3.42 (m, 1H), 3.28-3.20 (m, 1H), 3.07-3.00 (m, 2H), 2.96-2.94 (2×s, 3H), 2.79-2.65 (m, 1H), 2.21-2.09 (m, 1H), 2.09-1.86 (m, 2H); ESI MS m/z 497 [M+H]⁺; HPLC (Method B) 98.9% (AUC), $t_R$=13.3 min.

Example 25

Preparation of 1-(2,5-Dimethyl-2,3,4,5-tetrahydro-1H-pyrido[4,3-b]indol-7-yl)-4-(4-fluorophenyl)pyridine-2(1H)-one hydrochloride a) tert-Butyl 5-methyl-7-(2-oxo-4-(trifluoromethylsulfonyloxy)pyridine-1(2H)-yl)3,4-dihydro-1H-pyrido[4,3-b]indole-2(5H)-carboxylate

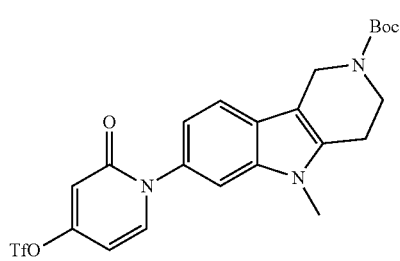

Chemical Formula: C₂₃H₂₄F₃N₃O₆S
Exact Mass: 527.13
Molecular Weight: 527.51

To a solution of tert-butyl 7-(4-(benzyloxy)-2-oxopyridin-1(2H)-yl)-5-methyl-3,4-dihydro-1H-pyrido[4,3-b]indole-2(5H)-carboxylate (0.98 g, 2.0 mmol) in CH₃OH (30 mL) was added 5% Pd/C (0.3 g) and ammonium formate (0.32 g, 5 mmol) under Ar atmosphere. The reaction mixture was heated to 90° C. and stirred at 90° C. until the reaction was complete. After it was cooled, the reaction mixture was filtered through a layer of Celite. The solvent was concentrated to give tert-butyl 7-(4-hydroxy-2-oxopyridin-1(2H)-yl)-5-methyl-3,4-dihydro-1H-pyrido[4,3-b]indole-2(5H)-carboxylate, which was used directly without purification.

To a solution of tert-butyl 7-(4-hydroxy-2-oxopyridin-1(2H)-yl)-5-methyl-3,4-dihydro-1H-pyrido[4,3-b]indole-2(5H)-carboxylate (800 mg, 2.02 mmol) in THF (10 mL) was added LiN(SiMe₃)₂ (2.6 mL, 2.6 mmol) followed by PhN(Tf)₂ (0.94 g, 2.6 mmol) under Ar atmosphere. The reaction mixture was stirred at room temperature until the reaction was complete. Then the mixture was concentrated and the residue was purified by flash column chromatography (silica gel, hexanes/EtOAc, 1:1) to give the title compound (0.42 g, 40%) as a white solid: $^1$H NMR (300 MHz, CDCl₃) δ 7.57-7.53 (m, 2H), 7.30 (d, J=1.5 Hz, 1H), 7.02-6.99 (m, 1H), 6.60 (d, J=2.7 Hz, 1H), 6.27 (dd, J=7.8, 2.7 Hz, 1H), 4.65 (s, 2H), 3.85 (m, 2H), 3.65 (s, 3H), 2.84 (m, 2H), 1.51 (s, 9H); ESI MS m/z 528 [M+H]⁺.

b) 1-(2,5-Dimethyl-2,3,4,5-tetrahydro-1H-pyrido[4,3-b]indol-7-yl)-4-(4-fluorophenyl)pyridine-2(1H)-one hydrochloride

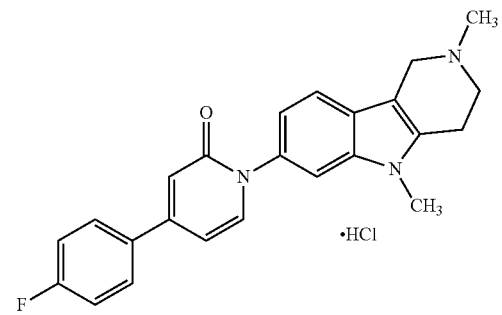

Chemical Formula: C₂₄H₂₃ClFN₃O
Exact Mass: 423.15
Molecular Weight: 423.91

To a solution of tert-butyl 5-methyl-7-(2-oxo-4-(trifluoromethylsulfonyloxy)pyridine-1(2H)-yl)3,4-dihydro-1H-pyrido[4,3-b]indole-2(5H)-carboxylate (100 mg, 0.19 mmol) in DMSO (2 mL) was added 4-fluorophenylboronic acid (66 mg, 0.48 mmol), K₂CO₃ (66 mg, 0.48 mmol), and PdCl₂(dppf) (14 mg, 0.019 mmol). The reaction mixture was degassed, then back-filled with N₂. The reaction mixture was stirred at 80° C. in a pre-heated oil bath for 2 hours. After cooling, the reaction was quenched with water and extracted with CH₂Cl₂. The organic layer was washed with H₂O and 5% LiCl, dried with Na₂SO₄, filtered and concentrated. Purification by flash column chromatography (silica gel, 5% CH₃OH in CH₂Cl₂) gave a yellow solid (120 mg, >100%). The solid was dissolved in CH₃OH (2 mL) and treated with 1 N HCl in Et₂O (1.9 mL). The reaction mixture was stirred at room temperature until the reaction was complete. After the solvent was removed, the resulting solid was dissolved in CH₃OH (3 mL). Et₃N (40 μL), formaldehyde (22 μL, 0.29 mmol), and NaBH(OAc)₃ were added sequentially. The reaction mixture was stirred at room temperature until the reaction was complete. The solvent was removed and the residue was dissolved in $CH_2Cl_2$. The organic layer was washed with $H_2O$ and 5% LiCl, dried with $Na_2SO_4$, filtered and concentrated. Purification by flash column chromatography (silica gel, 5% $CH_3OH$ in $CH_2Cl_2$) gave 1-(2,5-dimethyl-2,3,4,5-tetrahydro-1H-pyrido[4,3-b]indol-7-yl)-4-(4-fluorophenyl)pyridine-2(1H)-one (37 mg 50% yield over three steps) as a yellow solid. The free base was converted to the HCl salt to give the title compound (36.5 mg, 91%) as a yellow solid: mp 276-280° C. (decompose); $^1H$ NMR (500 MHz, $CD_3OD$) δ 7.82-7.79 (m, 2H), 7.75 (d, J=7.0 Hz, 1H), 7.61 (d, J=8.5 Hz, 1H), 7.56 (d, J=1.5 Hz, 1H), 7.29-7.25 (m, 2H), 7.14 (dd, J=8.5, 1.5 Hz, 1H), 6.88 (d, J=2.0 Hz, 1H), 6.82 (dd, J=7.0, 2.0 Hz, 1H), 4.77 (d, J=14.0 Hz, 1H), 4.41 (d, J=14.0 Hz, 1H), 3.93-3.90 (m, 1H), 3.76 (s, 3H), 3.66-3.60 (m, 1H), 3.27 (m, 2H), 3.15 (s, 3H); ESI MS m/z 388 [M+H]$^+$; HPLC (Method B) 98.1% (AUC), $t_R$=12.8 min.

Example 26

Preparation of 1-(2,5-Dimethyl-2,3,4,5-tetrahydro-1H-pyrido[4,3-b]indol-7-yl)-4-(4-(trifluoromethylphenyl)pyridin-2(1H)-one hydrochloride

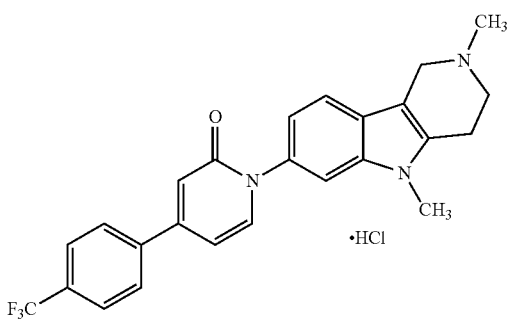

Chemical Formula: $C_{25}H_{23}ClF_3N_3O$
Exact Mass: 475.15
Molecular Weight: 473.92

Following the procedure of Example 25 (step b), but substituting 4-trifluoromethylphenylboronic acid for 4-fluorophenylboronic acid, the title compound (47 mg, 53%) was obtained as a yellow solid: mp 270-274° C.; $^1H$ NMR (500 MHz, $CD_3OD$) δ 7.95 (d, J=8.5 Hz, 2H), 7.84 (d, J=8.5 Hz, 2H), 7.80 (d, J=7.5 Hz, 1H), 7.62 (d, J=8.0 Hz, 1H), 7.57 (d, J=1.5 Hz, 1H), 7.15 (dd, J=8.5, 2.0 Hz, 1H), 6.96 (d, J=1.5 Hz, 1H), 6.87 (dd, J=7.5, 2.0 Hz, 1H), 4.78 (d, J=14.0 Hz, 1H), 4.41 (d, J=14.0 Hz, 1H), 3.93-3.90 (m, 1H), 3.77 (s, 3H), 3.66-3.60 (m, 1H), 3.27 (m, 2H), 3.15 (s, 3H); ESI MS m/z 438 [M+H]$^+$; HPLC (Method B)>99% (AUC), $t_R$=13.8 min.

Example 27

Preparation of 4-(4-Chlorophenyl)-1-(2,5-dimethyl-2,3,4,5-tetrahydro-1H-pyrido[4,3-b]indol-7-yl)-pyridin-2(1H)-one hydrochloride

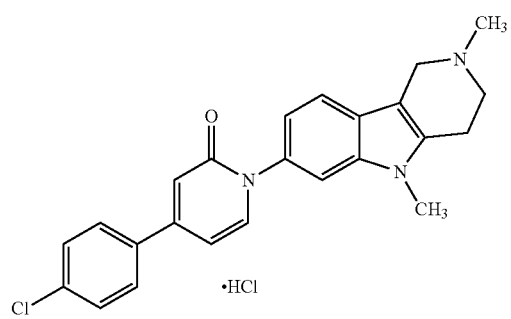

Chemical Formula: $C_{24}H_{23}Cl_2N_3O$
Exact Mass: 439.12
Molecular Weight: 440.36

Following the procedure of Example 25 (step b), but substituting 4-chlorophenylboronic acid for 4-fluorophenylboronic acid, the title compound (55 mg, 65%) was obtained as a yellow solid: mp 276-280° C.; $^1H$ NMR (500 MHz, $CD_3OD$) δ 7.77-7.75 (m, 3H), 7.62 (d, J=8.5 Hz, 1H), 7.57 (d, J=2.0 Hz, 1H), 7.56-7.54 (m, 2H), 7.15 (dd, J=8.5, 2.0 Hz, 1H), 6.91 (d, J=2.0 Hz, 1H), 6.84 (dd, J=7.0, 2.0 Hz, 1H), 4.78 (d, J=14.0 Hz, 1H), 4.41 (d, J=14.0 Hz, 1H), 3.93-3.90 (m, 1H), 3.77 (s, 3H), 3.66-3.60 (m, 1H), 3.27 (m, 2H), 3.15 (s, 3H); ESI MS m/z 404 [M+H]$^+$; HPLC (Method B) 98% (AUC), $t_R$=13.4 min.

Example 28

Preparation of 4-(4-Chloro-2-fluorophenyl)-1-(2,5-dimethyl-2,3,4,5-tetrahydro-1H-pyrido[4,3-b]indol-7-yl)-pyridin-2(1H)-one hydrochloride

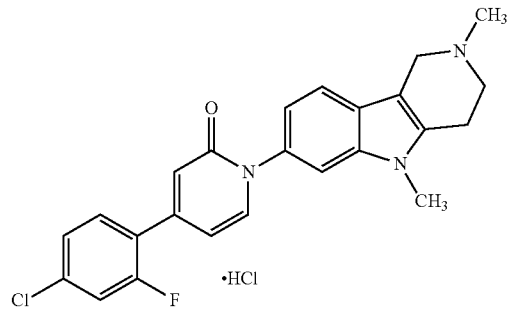

Chemical Formula: $C_{24}H_{22}Cl_2FN_3O$
Exact Mass: 457.11
Molecular Weight: 458.36

Following the procedure of Example 25 (step b), but substituting 4-chloro-2-fluorophenylboronic acid for 4-fluorophenylboronic acid, the title compound (20 mg, 32%) was obtained as a yellow solid: mp 270-274° C.; $^1H$ NMR (500 MHz, $CD_3OD$) δ 7.76 (d, J=7.0 Hz, 1H), 7.66-7.57 (m, 2H), 7.57 (d, J=2.0 Hz, 1H), 7.42-7.39 (m, 2H), 7.15 (dd, J=8.5, 2.0 Hz, 1H), 6.84 (s, 1H), 6.73-6.71 (m, 1H), 4.77 (d, J=14.0 Hz, 1H), 4.41 (d, J=14.0 Hz, 1H), 3.93-3.90 (m, 1H), 3.76 (s, 3H), 3.64-3.61 (m, 1H), 3.27 (m, 2H), 3.15 (s, 3H); ESI MS m/z 422 [M+H]$^+$; HPLC (Method B)>99% (AUC), $t_R$=12.9 min.

Example 29

Preparation of 1-(2,5-Dimethyl-2,3,4,5-tetrahydro-1H-pyrido[4,3-b]indol-7-yl)-4-(2-fluoro-4-methoxy-phenyl)pyridin-2(1H)-one hydrochloride

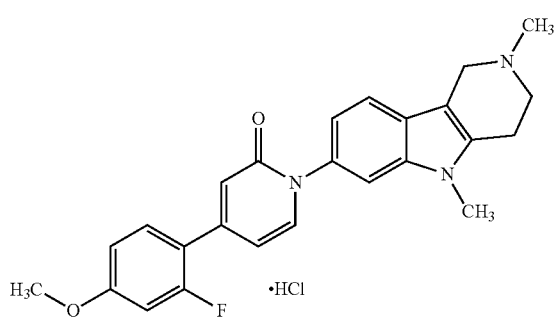

Chemical Formula: C$_{25}$H$_{25}$ClFN$_3$O$_2$
Exact Mass: 453.16
Molecular Weight: 453.94

Following the procedure of Example 25 (step b), but substituting 2-fluoro-4-methoxyphenylboronic acid for 4-fluorophenylboronic acid, the title compound (46 mg, 53%) was obtained as a yellow solid: mp 280-282° C.; $^1$H NMR (500 MHz, CD$_3$OD) δ 7.72 (d, J=7.0 Hz, 1H), 7.63-7.56 (m, 3H), 7.15 (dd, J=8.5, 1.5 Hz, 1H), 6.92 (dd, J=8.5, 2.5 Hz, 1H), 6.87 (dd, J=13.0, 2.0 Hz, 1H), 6.83 (s, 1H), 6.76 (d, J=7.0 Hz, 1H), 4.77 (d, J=14.0 Hz, 1H), 4.41 (d, J=14.0 Hz, 1H), 3.94-3.90 (m, 1H), 3.88 (s, 3H), 3.76 (s, 3H), 3.66-3.60 (m, 1H), 3.27 (m, 2H), 3.15 (s, 3H); ESI MS m/z 418 [M+H]$^+$; HPLC (Method B)>99% (AUC), $t_R$=12.9 min.

Example 30

Preparation of 4-(Benzyloxy)-1-(2,9-dimethyl-2,3,4,9-tetrahydro-1H-pyrido[3,4-b]indol-7-yl)pyridin-2(1H)-one hydrochloride a) 2-(6-Bromo-1H-indol-3-yl)ethanamine Beilstein Registry Number 6056308

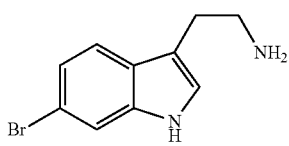

Chemical Formula: C$_{10}$H$_{11}$BrN$_2$
Exact Mass: 238.01
Molecular Weight: 239.11

3-Bromophenylhydrazine hydrochloride (20.0 g, 85.8 mmol) was reacted according to the procedure of Mascal et al. (Rinehart, Kenneth L.; Kobayashi, Jun'ichi; Harbour, Gary C.; Gilmore, Jeremy; Mascal, Mark; et al. *J. Am. Chem. Soc.* 1987, 109, 3378-3387) to provide the title compound as a 1:1 mixture of the 6-bromo and 7-bromo-regioisomers (13.2 g, 65%), obtained as an orange solid: ESI MS m/z 239 [M+H]$^+$.

b) 7-Bromo-2,3,4,9-tetrahydro-1H-pyrido[3,4-b]indole

Beilstein Registry Number 5935540

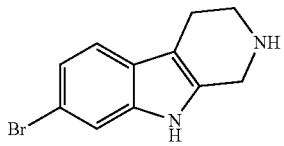

Chemical Formula: C$_{11}$H$_{11}$BrN$_2$
Exact Mass: 250.01
Molecular Weight: 251.12

2-(6-Bromo-1H-indol-3-yl)ethanamine (13.2 g, 55.2 mmol) was reacted according to the procedure of Mascal et al. (Rinehart, Kenneth L.; Kobayashi, Jun'ichi; Harbour, Gary C.; Gilmore, Jeremy; Mascal, Mark; et al. *J. Am. Chem. Soc.* 1987, 109, 3378-3387) to provide the title compound as a 1:1 mixture of the 7-bromo and 8-bromo-regioisomers (8.8 g, 63%), obtained as an orange solid: ESI MS m/z 251 [M+H]$^+$.

c) tert-Butyl 7-bromo-3,4-dihydro-1H-pyrido[3,4-b]indole-2(9H)-carboxylate

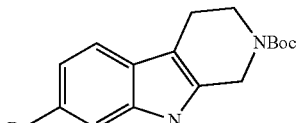

Chemical Formula: C$_{16}$H$_{19}$BrN$_2$O$_2$
Exact Mass: 350.06
Molecular Weight: 351.24

7-Bromo-2,3,4,9-tetrahydro-1H-pyrido[3,4-b]indole (8.81 g, 35.1 mmol, present as a mixture with the 8-bromo regioisomer) was suspended in CH$_2$Cl$_2$ (100 mL) and THF (10 mL). Boc anhydride (7.83 g, 38.6 mmol) and a catalytic amount of 4-(dimethylamino)pyridine (DMAP) were added. After 24 h, the mixture was concentrated. Purification by flash column chromatography (silica gel, hexanes/ethyl acetate, 97:3 to 70:30) separated the 7- and 8-regioisomers and gave the title compound (3.37 g, 27%) as a white powder: $^1$H NMR (500 MHz, CDCl$_3$) δ 7.94 (br s, 1H), 7.45 (d, J=1.6 Hz, 1H), 7.32 (d, J=8.3 Hz, 1H), 7.19 (dd, J=8.3, 1.3 Hz, 1H), 4.61 (br s, 2H), 3.75 (br s, 2H), 2.76 (br s, 2H), 1.50 (s, 9H).

d) tert-Butyl 7-bromo-9-methyl-3,4-dihydro-1H-pyrido[3,4-b]indole-2(9H)-carboxylate

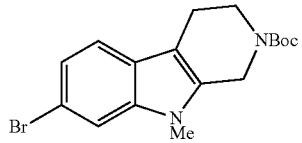

Chemical Formula: $C_{17}H_{21}BrN_2O_2$
Exact Mass: 364.08
Molecular Weight: 365.26 tert-Butyl 7-bromo-3,4-dihydro-1H-pyrido[3,4-b]indole-2(9H)-carboxylate (1.96 g, 5.58 mmol) was dissolved in DMF (20 mL), and sodium hydride (60% weight dispersion in mineral oil, 330 mg, 8.37 mmol) was added. After 30 minutes, methyl iodide (0.52 mL, 8.4 mmol) was added, and the reaction stirred for a further 2 h. The mixture was diluted with methylene chloride and washed with 5% lithium chloride solution (5×), dried and concentrated. Purification by flash column chromatography (silica gel, hexanes/ethyl acetate, 97:3 to 75:25) gave the title compound (1.75 g, 86%) as a white powder: $^1$H NMR (500 MHz, CD$_3$OD) δ 7.41 (d, J=1.5 Hz, 1H), 7.32 (d, J=8.3 Hz, 1H), 7.18 (dd, J=8.4, 1.6 Hz, 1H), 4.60 (br s, 2H), 3.73 (br s, 2H), 3.59 (s, 3H), 2.76 (br s, 2H), 1.50 (s, 9H).

e) 7-Bromo-9-methyl-2,3,4,9-tetrahydro-1H-pyrido[3,4-b]indole

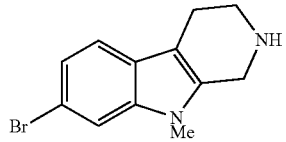

Chemical Formula: $C_{12}H_{13}BrN_2$
Exact Mass: 264.03
Molecular Weight: 265.15 tert-Butyl-7-bromo-9-methyl-3,4-dihydro-1H-pyrido[3,4-b]indole-2(9H)-carboxylate (1.75 g, 4.79 mmol) was dissolved in CH$_2$Cl$_2$ (10 mL) and trifluoroacetic acid (TFA) (10 mL) was added. After stirring for 1 h, the mixture was diluted with methylene chloride (50 mL), washed with saturated Na$_2$CO$_3$ solution, dried over sodium sulfate and concentrated to provide the title compound (1.24 g, 97%) as a yellow oil: $^1$H NMR (300 MHz, CDCl$_3$) δ 7.41 (d, J=1.4 Hz, 1H), 7.32 (d, J=8.3 Hz, 1H), 7.17 (dd, J=8.3, 1.4 Hz, 1H), 4.01 (s, 2H), 3.55 (s, 3H), 3.15 (t, J=6.0 Hz, 2H), 2.72 (t, J=5.7 Hz, 2H).

f) 7-Bromo-2,9-dimethyl-2,3,4,9-tetrahydro-1H-pyrido[3,4-b]indole

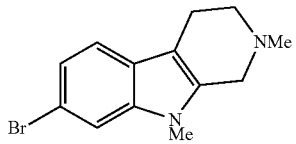

Chemical Formula: $C_{13}H_{15}BrN_2$
Exact Mass: 278.04
Molecular Weight: 279.18

7-Bromo-9-methyl-2,3,4,9-tetrahydro-1H-pyrido[3,4-b]indole (1.24 g, 4.68 mmol) was dissolved in a mixture of MeOH (20 mL) and CH$_2$Cl$_2$ (5 mL) and formaldehyde (0.56 mL, 37% aqueous solution) was added. After stirring for 1 h, NaBH(OAc)$_3$ (1.98 g, 9.34 mmol) was added and the mixture stirred for a further 10 minutes. The mixture was diluted with methylene chloride (50 mL), washed with saturated Na$_2$CO$_3$ solution, concentrated and purified by flash column chromatography (40 g ISCO column eluting with methylene chloride and a methanol/ammonia mixture (10:1); gradient 100% methylene chloride to 90% methylene chloride over 30 min at 40 mL/min) to provide the title compound (1.15 g, 88%) as a white powder: $^1$H NMR (500 MHz, CDCl$_3$) δ 7.40 (d, J=1.6 Hz, 1H), 7.32 (d, J=8.4 Hz, 1H), 7.16 (dd, J=8.3, 1.7 Hz, 1H), 3.61 (s, 2H), 3.55 (s, 3H), 2.86-2.76 (m, 4H), 2.56 (s, 3H).

g) 4-(Benzyloxy)-1-(2,9-dimethyl-2,3,4,9-tetrahydro-1H-pyrido[3,4-b]indol-7-yl)pyridin-2(1H)-one hydrochloride

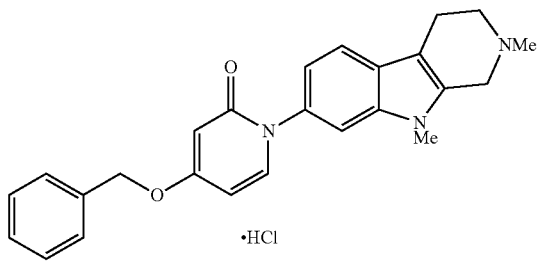

Chemical Formula: $C_{25}H_{26}ClN_3O_2$
Exact Mass: 435.17
Molecular Weight: 435.95

A stirred solution of 7-bromo-2,9-dimethyl-2,3,4,9-tetrahydro-1H-pyrido[3,4-b]indole (250 mg, 0.895 mmol) in DMSO (4 mL) under nitrogen was treated sequentially with 4-(benzyloxy)pyridin-2(1H)-one (180 mg, 0.895 mmol), 8-hydroxyquinoline (20 mg, 0.14 mmol), CuI (196 mg, 1.04 mmol) and K$_2$CO$_3$ (142 mg, 1.04 mmol). The mixture was placed under vacuum for 30 minutes and then flushed with nitrogen. After stirring overnight at 130° C., the mixture was allowed to cool to room temperature, diluted with CH$_2$Cl$_2$, washed with brine, dried over Na$_2$SO$_4$ and concentrated. Purification by flash column chromatography (12 g ISCO column eluting with methylene chloride and a methanol/ammonia mixture (10:1); gradient 100% methylene chloride to 80% methylene chloride over 30 min at 25 mL/min)

provided the free-base. This was dissolved in methylene chloride (2 mL) and treated with 2 N HCl in Et$_2$O (1 equivalent) and the mixture was concentrated to provide the title compound (131 mg, 33%) as a yellow solid: mp 270-274° C.; $^1$H NMR (500 MHz, CD$_3$OD) δ 7.67-7.63 (m, 2H), 7.50-7.40 (m, 3H), 7.43-7.35 (m, 3H), 7.08 (dd, J=8.3, 1.6 Hz, 1H), 6.40 (dd, J=7.5, 2.6 Hz, 1H), 6.21 (d, J=2.6 Hz, 1H), 5.22 (s, 2H), 4.81-4.80 (m, 1H), 4.58 (d, J=15.3 Hz, 1H), 3.88-3.84 (m, 1H), 3.72 (s, 3H), 3.55-3.49 (m, 1H), 3.21-3.16 (m, 5H); ESI MS m/z 400 [M+H]$^+$; HPLC (Method B)>98.9% (AUC), t$_R$=13.0 min.

Example 31

Preparation of 1-(2,9-Dimethyl-2,3,4,9-tetrahydro-1H-pyrido[3,4-b]indol-7-yl)-4-phenethylpyridin-2(1H)-one hydrochloride a) (E)-2-Methoxy-4-styrylpyridine

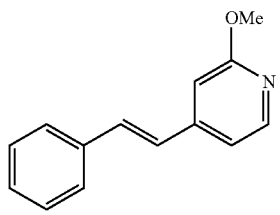

Chemical Formula: C$_{14}$H$_{13}$NO
Exact Mass: 211.10
Molecular Weight: 211.26

4-Bromo-2-methoxypyridine (1.85 g, 9.84 mmol), (E)-phenylvinylboronic acid (4.3 g, 30 mmol), K$_2$CO$_3$ (4.0 g, 30 mmol) and PdCl$_2$(dppf) (400 mg, 0.5 mmol) were stirred in DMSO (15 mL) under vacuum for 30 min. The flask was flushed with nitrogen and the mixture was heated to 90° C. for 30 min. Upon cooling, the mixture was diluted with methylene chloride and washed with 5% lithium chloride solution (5×), dried, concentrated, and the residue was purified by flash column chromatography (silica gel, hexanes/ethyl acetate, 97:3 to 75:25) to provide the title compound (1.93 g, 93%) as an orange oil: $^1$H NMR (300 MHz, CDCl$_3$) δ 8.12 (d, J=5.2 Hz, 1H), 7.51 (m, 2H), 7.40-7.22 (m, 4H), 7.02-6.94 (m, 2H), 6.78 (s, 1H), 3.95 (s, 3H).

b) 2-Methoxy-4-phenethylpyridine

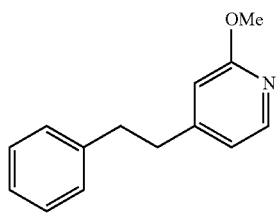

Chemical Formula: C$_{14}$H$_{15}$NO
Exact Mass: 213.12
Molecular Weight: 213.28

(E)-2-Methoxy-4-styrylpyridine (22.15 g, 104.8 mmol) was dissolved in MeOH (400 mL) and degassed with a nitrogen stream for 10 minutes. Palladium on charcoal (10%, wet, 5 g) was added and the reaction mixture was stirred under an atmosphere of hydrogen for 24 h. The reaction mixture was degassed again, and the catalyst was removed by filtration. Concentration of the filtrate provided the title compound (22 g, 98%) as a green oil: $^1$H NMR (500 MHz, CDCl$_3$) δ 8.04 (d, J=5.3 Hz, 1H), 7.29-7.24 (m, 2H), 7.21-7.15 (m, 3H), 6.69-6.67 (m, 1H), 6.54 (s, 1H), 3.91 (s, 3H), 2.91-2.89 (m, 2H), 2.87-2.84 (m, 2H).

c) 4-Phenethylpyridin-2(1H)-one

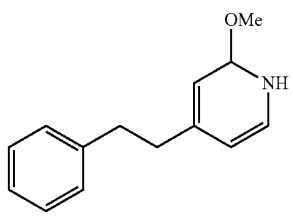

Chemical Formula: C$_{13}$H$_{13}$NO
Exact Mass: 199.10
Molecular Weight: 199.25

2-Methoxy-4-phenethylpyridine (22.0 g, 102 mmol) was stirred in concentrated hydrochloric acid (200 mL) at 120° C. for 18 h and then concentrated. The residue was dissolved in MeOH (100 mL) and made basic with aqueous 6 N NaOH and re-concentrated until most of the solvent had been removed. The solids were filtered off, washed with water and dried under vacuum to provide the title compound (21.3 g, 95%) as a beige solid: $^1$H NMR (500 MHz, DMSO-d$_6$) δ 11.31 (br s, 1H), 7.28-7.21 (m, 5H), 7.17 (t, J=7.1 Hz, 1H), 6.10-6.08 (m, 2H), 2.85-2.82 (m, 2H), 2.70-2.67 (m, 2H).

d) 1-(2,9-Dimethyl-2,3,4,9-tetrahydro-1H-pyrido[3,4-b]indol-7-yl)-4-phenethylpyridin-2(1H)-one hydrochloride

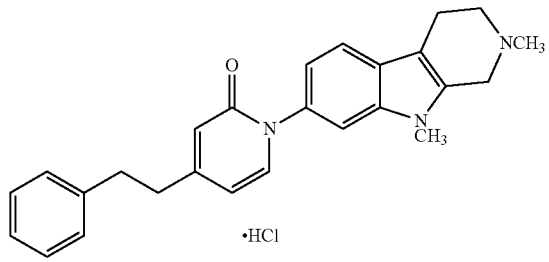

Chemical Formula: C$_{26}$H$_{28}$ClN$_3$O
Exact Mass: 433.19
Molecular Weight: 433.97

4-Phenethylpyridin-2(1H)-one (82 mg, 0.41 mmol) and 7-bromo-2,9-dimethyl-2,3,4,9-tetrahydro-1H-pyrido[3,4-b]indole (115 mg, 0.412 mmol) were reacted following the procedure for Example 30 (step g) to provide the title compound (54 mg, 30%) as a yellow solid: mp 299-304° C.; $^1$H NMR (500 MHz, CD$_3$OD) δ 7.67-7.64 (m, 2H), 7.51 (d, J=1.8 Hz, 1H), 7.30-7.24 (m, 4H), 7.20-7.17 (m, 1H), 7.08 (dd, J=8.4, 1.9 Hz, 1H), 6.56 (dd, J=6.9, 1.9 Hz, 1H), 6.53 (s, 1H), 4.85 (m, 1H), 4.49 (d, J=15.3 Hz, 1H), 3.89-3.84 (m, 1H), 3.72 (s, 3H), 3.55-3.50 (m, 1H), 3.21-3.19 (m, 2H), 3.16 (s, 3H), 3.02-2.99 (m, 2H), 2.96-2.93 (m, 2H); ESI MS m/z 398 [M+H]$^+$; HPLC (Method B) 98.1% (AUC), $t_R$=13.5 min.

Example 32

Preparation of 1-(2,9-Dimethyl-2,3,4,9-tetrahydro-1H-pyrido[3,4-b]indol-7-yl)-4-(4-(trifluoromethyl)benzyloxy)pyridin-2(1H)-one hydrochloride a) 4-(4-(Trifluoromethyl)benzyloxy)pyridine 1-oxide

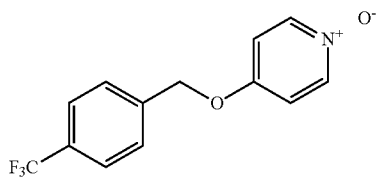

Chemical Formula: C$_{13}$H$_{10}$F$_3$NO$_2$
Exact Mass: 269.07
Molecular Weight: 269.22

4-Trifluoromethylbenzylalcohol (4.2 g, 23 mmol) was dissolved in DMF (20 mL) and NaH (60% weight dispersion in mineral oil, 0.92 g, 23 mmol) was added. After stirring for 30 minutes, 4-chloropyridine-N-oxide (1.5 g, 11.5 mmol) was added and the reaction mixture was heated for 1 h at 120° C. Upon cooling the mixture was diluted with methylene chloride and washed with 5% lithium chloride solution (5×), dried and concentrated. Purification by flash column chromatography (40 g ISCO column eluting with methylene chloride and a methanol/ammonia mixture (10:1); gradient 100% methylene chloride to 90% methylene chloride over 30 min at 40 mL/min) provided the title compound (0.6 g, 19%) as a yellow solid: $^1$H NMR (300 MHz, CDCl$_3$) δ 8.14 (d, J=7.8 Hz, 2H), 7.68 (d, J=8.1 Hz, 2H), 7.52 (d, J=8.1 Hz, 2H), 6.86 (d, J=7.8 Hz, 2H), 5.15 (s, 2H).

b) 4-(4-(Trifluoromethyl)benzyloxy)pyridin-2(1H)-one

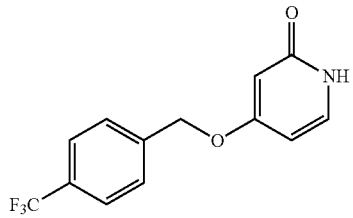

Chemical Formula: C$_{13}$H$_{10}$F$_3$NO$_2$
Exact Mass: 269.07
Molecular Weight: 269.22

4-(4-(Trifluoromethyl)benzyloxy)pyridine 1-oxide (600 mg, 2.22 mmol) was heated to 140° C. in acetic anhydride (20 mL) for 2 h. The mixture was concentrated and then heated at 80° C. for 1 h in a mixture of MeOH (10 mL) and aqueous 1 N NaOH (10 mL). The resultant black solution was concentrated to a volume of 10 mL and extracted with CHCl$_3$/EtOH (3:1). The organic layer was removed and concentrated to provide the title compound (550 mg, 91%) as a tan solid: $^1$H NMR (300 MHz, CD$_3$OD) δ 7.70-7.60 (m, 4H), 7.41 (d, J=7.0 Hz, 1H), 6.17 (dd, J=7.0, 2.5 Hz, 1H), 5.96 (d, J=2.4 Hz, 1H), 5.18 (s, 2H).

c) 1-(2,9-Dimethyl-2,3,4,9-tetrahydro-1H-pyrido[3,4-b]indol-7-yl)-4-(4-(trifluoromethyl)benzyloxy)pyridin-2(1H)-one hydrochloride

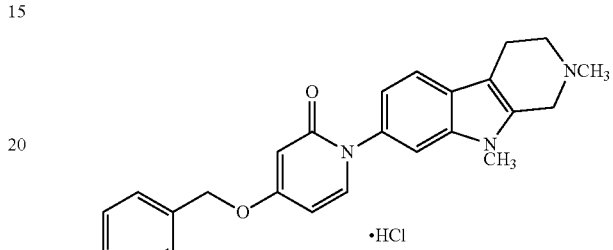

Chemical Formula: C$_{26}$H$_{25}$ClF$_3$N$_3$O$_2$
Exact Mass: 503.16
Molecular Weight: 503.94

4-(4-(Trifluoromethyl)benzyloxy)pyridin-2(1H)-one (100 mg, 0.37 mmol) and 7-bromo-2,9-dimethyl-2,3,4,9-tetrahydro-1H-pyrido[3,4-b]indole (103 mg, 0.47 mmol) were reacted following the procedure for Example 30 (step g) to provide the title compound (67 mg, 36%) as a light-brown solid: mp 280-285° C.; $^1$H NMR (500 MHz, CD$_3$OD) δ 7.78-7.73 (m, 3H), 7.69-7.64 (m, 3H), 7.52 (d, J=1.8 Hz, 1H), 7.18-7.08 (m, 1H), 6.55-6.52 (m, 1H), 6.28 (d, J=2.6 Hz, 1H), 5.35 (s, 2H), 4.82-4.80 (m, 1H), 4.50 (d, J=15.4 Hz, 1H), 3.89-3.85 (m, 1H), 3.73 (s, 3H), 3.55-3.50 (m, 1H), 3.22-3.16 (m, 5H); ESI MS m/z 468 [M+H]$^+$; HPLC (Method B)>99% (AUC), $t_R$=14.4 min.

Example 33

Preparation of 4-(4-Chlorobenzyloxy)-1-(2,9-dimethyl-2,3,4,9-tetrahydro-1H-pyrido[3,4-b]indol-7-yl)pyridin-2(1H)-one hydrochloride a) 4-(4-Chlorobenzyloxy)pyridine 1-oxide Beilstein Registry Number 7707045

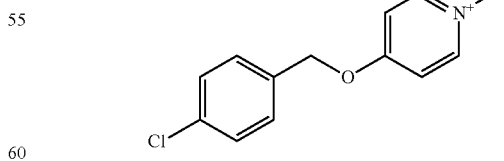

Chemical Formula: C$_{12}$H$_{10}$ClNO$_2$
Exact Mass: 235.04
Molecular Weight: 235.67

4-Chlorobenzylalcohol (5.0 g, 35 mmol) was dissolved in DMF (25 mL) and NaH (60% weight dispersion in mineral oil, 0.92 g, 23 mmol) was added. After stirring for 30 minutes, 4-chloropyridine-N-oxide (2.27 g, 17.5 mmol) was added and the reaction mixture was heated for 1 h at 120° C. Upon cooling, the mixture was diluted with methylene chloride and washed with 5% lithium chloride solution (5×), dried and concentrated. Purification by flash column chromatography (12 g ISCO column eluting with methylene chloride and a methanol/ammonia mixture (10:1); gradient 100% methylene chloride to 90% methylene chloride over 30 min at 25 mL/min) provided the title compound (1.9 g, 47%) as an orange solid: $^1$H NMR (300 MHz, CDCl$_3$) δ 8.11 (d, J=7.7 Hz, 2H), 7.40 (d, J=8.6 Hz, 2H), 7.34 (d, J=8.6 Hz, 2H), 6.86 (d, J=7.7 Hz, 2H), 5.06 (s, 2H).

b) 4-(4-Chlorobenzyloxy)pyridin-2(1H)-one

Beilstein Registry Number 7707762

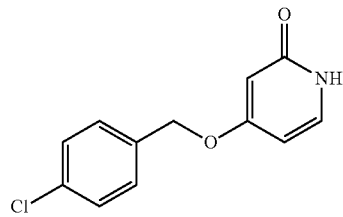

Chemical Formula: C$_{12}$H$_{10}$ClNO$_2$
Exact Mass: 235.04
Molecular Weight: 235.67

4-(4-Chlorobenzyloxy)pyridine 1-oxide (1.95 g, 8.24 mmol) was reacted according to the procedure of Example 32 (step b), and the crude product was purified by flash column chromatography (40 g ISCO column eluting with methylene chloride and a methanol/ammonia mixture (10:1); gradient 100% methylene chloride to 90% methylene chloride over 30 min at 40 mL/min) to provide the title compound (1.0 g, 51%) as a yellow solid: $^1$H NMR (500 MHz, CDCl$_3$) δ 12.70 (br s, 1H), 7.37 (d, J=8.5 Hz, 2H), 7.33 (d, J=8.5 Hz, 2H), 7.22 (d, J=7.3 Hz, 1H), 6.02 (dd, J=7.3, 2.5 Hz, 1H), 5.93 (d, J=2.5 Hz, 1H), 4.98 (s, 2H).

c) 4-(4-Chlorobenzyloxy)-1-(2,9-dimethyl-2,3,4,9-tetrahydro-1H-pyrido[3,4-b]indol-7-yl)pyridin-2(1H)-one hydrochloride

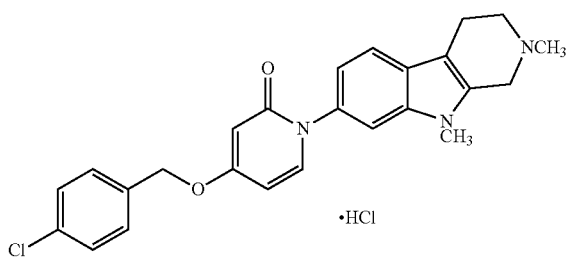

Chemical Formula: C$_{25}$H$_{25}$Cl$_2$N$_3$O$_2$
Exact Mass: 469.13
Molecular Weight: 470.39

4-(4-Chlorobenzyloxy)pyridin-2(1H)-one (82 mg, 0.34 mmol) and 7-bromo-2,9-dimethyl-2,3,4,9-tetrahydro-1H-pyrido[3,4-b]indole (97 mg, 0.34 mmol) were reacted following the procedure for Example 30 (step g) to provide the title compound (28 mg, 17%) as a yellow solid: mp 290-296° C.; $^1$H NMR (500 MHz, CD$_3$OD) δ 7.83 (d, J=7.6 Hz, 1H), 7.68 (d, J=8.3 Hz, 1H), 7.50-7.46 (m, 3H), 7.44-7.42 (m, 2H), 7.08 (dd, J=8.3, 1.8 Hz, 1H), 6.41 (dd, J=7.6, 2.6 Hz, 1H), 6.21 (d, J=2.6 Hz, 1H), 5.21 (s, 2H), 4.86-4.84 (m, 1H), 4.49 (d, J=15.4 Hz, 1H), 3.88-3.84 (m, 1H), 3.72 (s, 3H), 3.55-3.50 (m, 1H), 3.21-3.16 (m, 5H); ESI MS m/z 434 [M+H]$^+$; HPLC (Method B) 98.6% (AUC), t$_R$=14.0 min.

Example 34

Preparation of 1-(2,9-Dimethyl-2,3,4,9-tetrahydro-1H-pyrido[3,4-b]indol-7-yl)-4-(pyridin-2-ylmethoxy)pyridin-2(1H)-one dihydrochloride a) 4-(Pyridin-2-ylmethoxy)pyridine 1-oxide

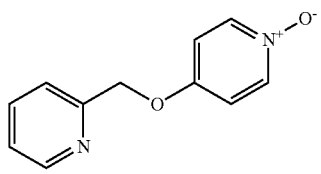

Chemical Formula: C$_{11}$H$_{10}$N$_2$O$_2$
Exact Mass: 202.07
Molecular Weight: 202.21

2-Pyridylbenzylalcohol (1.67 g, 15.3 mmol) was dissolved in 1,4-dioxane (25 mL) and NaH (60% weight dispersion in mineral oil, 0.92 g, 23 mmol) was added. After stirring for 30 minutes, 4-chloropyridine-N-oxide (2.27 g, 17.5 mmol) was added and the reaction mixture was heated for 1 h at 120° C. Upon cooling, the mixture was purified by flash column chromatography (40 g ISCO column eluting with methylene chloride and a methanol/ammonia mixture (10:1); gradient 100% methylene chloride to 90% methylene chloride over 30 min at 40 mL/min) to provide the title compound (600 mg, 38%) as a brown solid: $^1$H NMR (500 MHz, CDCl$_3$) δ 8.62-8.61 (m, 1H), 8.13-8.10 (m, 2H), 7.74 (overlapping ddd, J=7.8, 1.4 Hz, 1H), 7.44 (d, J=7.8 Hz, 1H), 7.30 (d, J=4.8 Hz, 1H), 6.92-6.89 (m, 2H), 5.23 (s, 2H).

b) 4-(Pyridin-2-ylmethoxy)pyridin-2(1H)-one

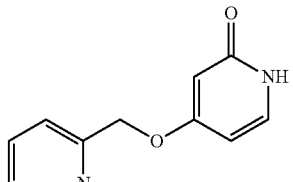

Chemical Formula: C$_{11}$H$_{10}$N$_2$O$_2$
Exact Mass: 202.07
Molecular Weight: 202.21

4-(Pyridin-2-ylmethoxy)pyridine 1-oxide (9.0 g, 45 mmol) was heated to 140° C. in acetic anhydride (100 mL) for 2 h. The solution was concentrated and then heated at 80° C. for 1 h in a mixture of MeOH (50 mL) and H$_2$O (50 mL). The resultant black solution was concentrated and the residue was dissolved in hot i-PrOH (40 ml). Et$_2$O (250 mL)

was added and the mixture was placed in the freezer for 16 h. The solid was filtered off to provide the title compound (1.9 g, 21%) as a brown solid: ¹H NMR (300 MHz, DMSO-d₆) δ 11.13 (br s, 1H), 8.58 (d, J=4.7 Hz, 1H), 7.85 (overlapping ddd, J=7.9, 1.6 Hz, 1H), 7.49 (d, J=7.9 Hz, 1H), 7.38-7.34 (m, 1H), 7.26 (d, J=7.3 Hz, 1H), 5.96 (dd, J=7.3, 2.5 Hz, 1H), 5.76 (d, J=3.4 Hz, 1H), 5.12 (s, 2H).

c) 1-(2,9-Dimethyl-2,3,4,9-tetrahydro-1H-pyrido[3,4-b]indol-7-yl)-4-(pyridin-2-ylmethoxy)pyridin-2(1H)-one dihydrochloride

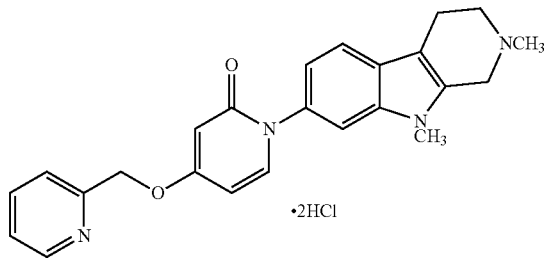

Chemical Formula: C₂₄H₂₆Cl₂N₄O₂
Exact Mass: 472.14
Molecular Weight: 473.39

4-(Pyridin-2-ylmethoxy)pyridin-2(1H)-one (109 mg, 0.539 mmol) and 7-bromo-2,9-dimethyl-2,3,4,9-tetrahydro-1H-pyrido[3,4-b]indole (97 mg, 0.34 mmol) were reacted following the procedure for Example 30 (step g) to provide the title compound (28 mg, 11%) as a yellow solid: mp 160-175° C.; ¹H NMR (500 MHz, CD₃OD) δ 8.90 (dd, J=5.8, 1.8 Hz, 1H), 8.65 (overlapping ddd, J=7.9, 1.6 Hz, 1H), 8.20 (d, J=8.0 Hz, 1H), 8.07 (overlapping dd, J=6.4 Hz, 1H), 7.70 (d, J=7.6 Hz, 1H), 7.65 (d, J=6.4 Hz, 1H), 7.49 (d, J=1.7 Hz, 1H), 7.07 (dd, J=6.8, 1.8 Hz, 1H), 6.63 (dd, J=7.6, 2.7 Hz, 1H), 6.21 (d, J=2.7 Hz, 1H), 5.59 (s, 2H), 4.80 (m, 1H), 4.50 (d, J=15.3 Hz, 1H), 3.88-3.85 (m, 1H), 3.73 (s, 3H), 3.55-3.50 (m, 1H), 3.21-3.16 (m, 5H); ESI MS m/z 401 [M+H]⁺; HPLC (Method B)>99% (AUC), t_R=9.3 min.

Example 35

Preparation of 4-((5-Chloropyridin-2-yl)methoxy)-1-(2,9-dimethyl-2,3,4,9-tetrahydro-1H-pyrido[3,4-b]indol-7-yl)pyridin-2(1H)-one dihydrochloride a) 4-((5-Chloropyridin-2-yl)methoxy)pyridine 1-oxide

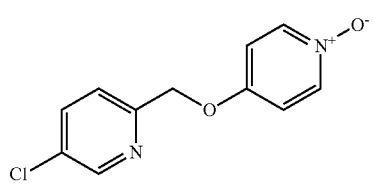

Chemical Formula: C₁₁H₉ClN₂O₂
Exact Mass: 236.04
Molecular Weight: 236.65

5-Chloro-2-pyridylbenzylalcohol (4.9 g, 34 mmol) and 4-chloropyridine-N-oxide (2.94 g, 22.7 mmol) were reacted according to Example 34 (step a) to provide the title compound (2.2 g, 40%) as a tan solid: ¹H NMR (300 MHz, CDCl₃) δ 8.58 (d, J=2.2 Hz, 1H), 8.13 (d, J=7.7 Hz, 2H), 7.74 (dd, J=8.4, 2.5 Hz, 1H), 7.43 (d, J=8.4 Hz, 1H), 6.90 (d, J=7.7 Hz, 2H), 5.20 (s, 2H).

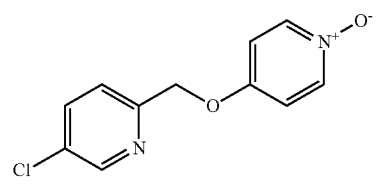

Chemical Formula: C₁₁H₉ClN₂O₂
Exact Mass: 236.04
Molecular Weight: 236.65

5-Chloro-2-pyridylbenzylalcohol (4.9 g, 34 mmol) and 4-chloropyridine-N-oxide (2.94 g, 22.7 mmol) were reacted according to Example 34 (step a) to provide the title compound (2.2 g, 40%) as a tan solid: ¹H NMR (300 MHz, CDCl₃) δ 8.58 (d, J=2.2 Hz, 1H), 8.13 (d, J=7.7 Hz, 2H), 7.76-7.72 (dd, J=8.4, 2.5 Hz, 1H), 7.43 (d, J=8.4 Hz, 1H), 6.90 (d, J=7.7 Hz, 2H), 5.20 (s, 2H).

b) 4-((5-Chloropyridin-2-yl)methoxy)pyridin-2(1H)-one

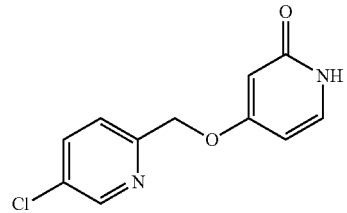

Chemical Formula: C₁₁H₉ClN₂O₂
Exact Mass: 236.04
Molecular Weight: 236.65

4-((5-Chloropyridin-2-yl)methoxy)pyridine 1-oxide (2.2 g, 9.2 mmol) was reacted according to Example 34 (step b) to provide the title compound (1.52 g, 69%) as a tan solid: ¹H NMR (500 MHz, CD₃OD) δ 8.56 (d, J=2.3 Hz, 1H), 7.91-7.89 (dd, J=8.4, 2.5 Hz, 1H), 7.56 (d, J=8.4 Hz, 1H), 7.34 (d, J=8.3 Hz, 1H), 6.21-6.19 (dd, J=7.2, 2.5 Hz, 1H), 5.97 (d, J=2.4 Hz, 1H), 5.18 (s, 2H).

c) tert-Butyl 7-(4-((5-chloropyridin-2-yl)methoxy)-2-oxopyridin-1(2H)-yl)-9-methyl-3,4-dihydro-1H-pyrido[3,4-b]indole-2(9H)-carboxylate

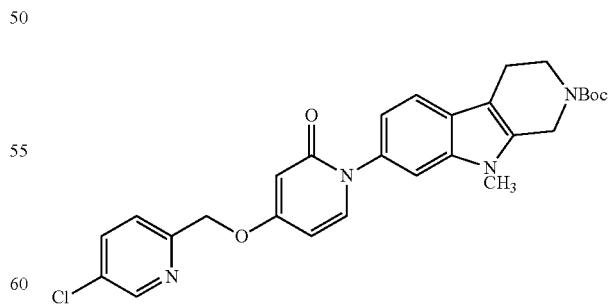

Chemical Formula: C₂₈H₂₉ClN₄O₄
Exact Mass: 520.19
Molecular Weight: 521.01

4-((5-Chloropyridin-2-yl)methoxy)pyridin-2(1H)-one (259 mg, 1.09 mmol) and tert-butyl 7-bromo-9-methyl-3,4- dihydro-1H-pyrido[3,4-b]indole-2(9H)-carboxylate (400 mg, 1.1 mmol) were reacted following the procedure of Example 30 (step g) to provide the title compound (145 mg, 25%) as a yellow solid: ESI MS m/z 521 [M+H]⁺.

d) 4-((5-Chloropyridin-2-yl)methoxy)-1-(9-methyl-2,3,4,9-tetrahydro-1H-pyrido[3,4-b]indol-7-yl)pyridin-2(1H)-one dihydrochloride

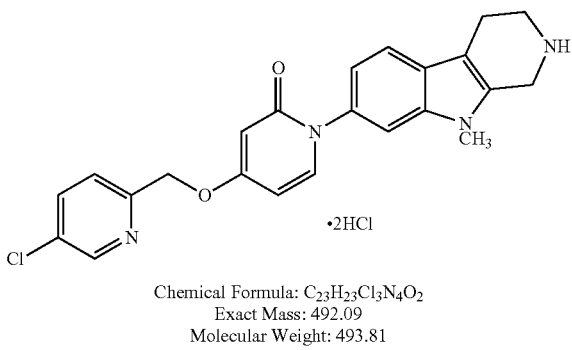 [SMILES: Cn1c2c(c3ccc(-n4ccc(OCc5ccc(Cl)cn5)cc4=O)cc31)CCNC2]

Chemical Formula: C₂₃H₂₃Cl₃N₄O₂
Exact Mass: 492.09
Molecular Weight: 493.81 tert-Butyl 7-(4-((5-chloropyridin-2-yl)methoxy)-2-oxopyridin-1(2H)-yl)-9-methyl-3,4-dihydro-1H-pyrido[3,4-b]indole-2(9H)-carboxylate (145 mg, 0.278 mmol) was deprotected and converted to the dihydrochloride salt according to the procedure of Example 30 (steps e and g) to provide the title compound (114 mg, 94%) as a yellow solid: mp 275-280° C.; ¹H NMR (500 MHz, CD₃OD) δ 8.61 (s, 1H), 7.77 (dd, J=8.3, 3.8 Hz, 1H), 7.64-7.62 (m, 3H), 7.47 (d, J=1.6 Hz, 1H), 7.03 (dd, J=8.4, 1.8 Hz, 1H), 6.37 (dd, J=7.6, 3.8 Hz, 1H), 6.15 (d, J=2.7 Hz, 1H), 5.28 (s, 2H), 4.54 (s, 2H), 3.71 (s, 3H), 3.60 (t, J=6.1 Hz, 2H), 3.12 (t, J=6.0 Hz, 2H); ESI MS m/z 421 [M+H]⁺; HPLC (Method B) 98.5% (AUC), $t_R$=12.1 min Example 36

Preparation of 4-((5-Chloropyridin-2-yl)methoxy)-1-(2,9-dimethyl-2,3,4,9-tetrahydro-1H-pyrido[3,4-b]indol-7-yl)pyridin-2(1H)-one dihydrochloride

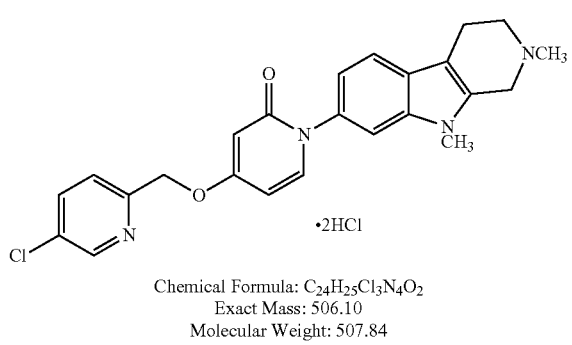 [SMILES: CN1CCc2c(n(C)c3cc(-n4ccc(OCc5ccc(Cl)cn5)cc4=O)ccc23)C1]

Chemical Formula: C₂₄H₂₅Cl₃N₄O₂
Exact Mass: 506.10
Molecular Weight: 507.84

4-((5-Chloropyridin-2-yl)methoxy)-1-(9-methyl-2,3,4,9-tetrahydro-1H-pyrido[3,4-b]indol-7-yl)pyridin-2(1H)-one (80 mg, 0.19 mmol) was dissolved a mixture of MeOH (3 mL) and CH₂Cl₂ (1 mL) and formaldehyde (9.0 mg, 0.29 mmol, 37% aqueous solution) was added. After stirring for 45 minutes, NaBH(OAc)₃ (80 mg, 0.38 mmol) was added and the reaction mixture was stirred for a further 10 minutes. The mixture was diluted with CH₂Cl₂, washed with saturated Na₂CO₃ solution and concentrated to provide the free base. Conversion to the dihydrochloride salt using the procedure of Example 30 (step g) provided the title compound (83 mg, 86%) as an orange solid: mp 202-210° C.; ¹H NMR (500 MHz, CD₃OD) δ 8.68 (br s, 1H), 8.05 (dd, J=8.0, 2.4 Hz, 1H), 7.76 (d, J=8.4 Hz, 1H), 7.71 (d, J=8.4 Hz, 1H), 7.65 (d, J=8.3 Hz, 1H), 7.51 (d, J=1.6 Hz, 1H), 7.09 (dd, J=8.3, 1.8 Hz, 1H), 6.53 (dd, J=7.6, 1.7 Hz, 1H), 6.28 (d, J=1.6 Hz, 1H), 5.36 (s, 2H), 4.85-4.80 (m, 1H), 4.49 (d, J=15.3 Hz, 1H), 3.89-3.84 (m, 1H), 3.72 (s, 3H), 3.53-3.47 (m, 1H), 3.22-3.19 (m, 2H), 3.16 (s, 3H); ESI MS m/z 435 [M+H]⁺; HPLC (Method B) 97.8% (AUC), $t_R$=12.2 min.

Example 37

Preparation of 4-(4-Chlorophenyl)-1-(2,9-dimethyl-2,3,4,9-tetrahydro-1H-pyrido[3,4-b]indol-7-yl)pyridin-2(1H)-one hydrochloride

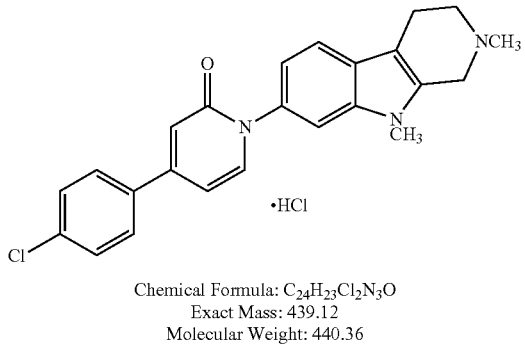 [SMILES: CN1CCc2c(n(C)c3cc(-n4ccc(-c5ccc(Cl)cc5)cc4=O)ccc23)C1 ; Cl]

Chemical Formula: C₂₄H₂₃Cl₂N₃O
Exact Mass: 439.12
Molecular Weight: 440.36

4-(4-Chlorophenyl)pyridin-2(1H)-one (80 mg, 0.33 mmol) and 7-bromo-2,9-dimethyl-2,3,4,9-tetrahydro-1H-pyrido[3,4-b]indole (49 mg, 0.33 mmol) were reacted following the procedure of Example 30 (step g) to provide the title compound (28 mg, 19%) as a yellow-green solid: mp 316-323° C.; ¹H NMR (500 MHz, DMSO-d₆) δ 11.0 (br s, 1H), 7.83 (dd, J=6.8, 1.9 Hz, 2H), 7.76 (d, J=7.1 Hz, 1H), 7.62-7.57 (m, 4H), 7.07 (dd, J=8.3, 1.8 Hz, 1H), 6.81 (d, J=2.0 Hz, 1H), 6.69 (dd, J=7.2, 2.1 Hz, 1H), 4.79 (d, J=15.2 Hz, 1H), 4.44 (dd, J=15.2, 6.0 Hz, 1H), 3.74-3.68 (m, 4H), 3.48-3.38 (m, 1H), 3.10-2.99 (m, 5H); ESI MS m/z 404 [M+H]⁺; HPLC (Method B)>99% (AUC), $t_R$=13.5 min.

Example 38

Preparation of 4-(4-Chlorophenyl)-1-(9-methyl-2,3,4,9-tetrahydro-1H-pyrido[3,4-b]indol-7-yl)pyridin-2(1H)-one hydrochloride a) tert-Butyl 7-(4-(4-chlorophenyl)-2-oxopyridin-1(2H)-yl)-9-methyl-3,4-dihydro-1H-pyrido[3,4-b]indole-2(9H)-carboxylate

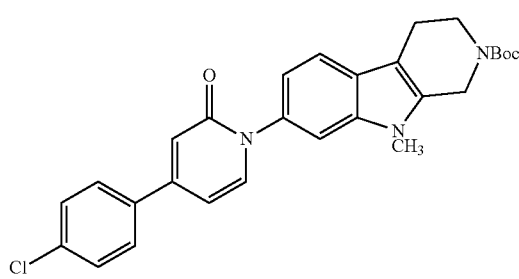

Chemical Formula: C₂₈H₂₈ClN₃O₃
Exact Mass: 489.18
Molecular Weight: 489.99

4-(4-Chlorophenyl)pyridin-2(1H)-one (74 mg, 0.32 mmol) and tert-butyl 7-bromo-9-methyl-3,4-dihydro-1H-pyrido[3,4-b]indole-2(9H)-carboxylate (74 mg, 0.36 mmol) were coupled following the procedure of Example 30 (step g) to provide the title compound (85 mg, 54%) as a yellow solid: $^1$H NMR (300 MHz, CD$_3$OD) δ 7.58-7.55 (m, 3H), 7.51-7.44 (m, 3H), 7.35 (s, 1H), 7.07 (dd, J=8.2, 1.6 Hz, 1H), 6.87 (d, J=1.8 Hz, 1H), 6.47 (dd, J=7.1, 1.8 Hz, 1H), 4.65 (br m, 2H), 3.75 (br m, 2H), 3.64 (s, 3H), 2.81 (br m, 2H), 1.52 (s, 9H).

b) 4-(4-Chlorophenyl)-1-(9-methyl-2,3,4,9-tetrahydro-1H-pyrido[3,4-b]indol-7-yl)pyridin-2(1H)-one hydrochloride

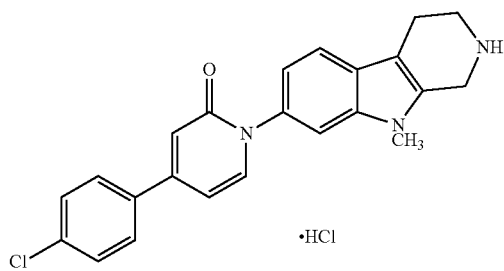

Chemical Formula: C$_{23}$H$_{21}$Cl$_2$N$_3$O
Exact Mass: 425.11
Molecular Weight: 426.34 tert-Butyl 7-(4-(4-chlorophenyl)-2-oxopyridin-1(2H)-yl)-9-methyl-3,4-dihydro-1H-pyrido[3,4-b]indole-2(9H)-carboxylate (85 mg, 0.17 mmol) was deprotected and converted to the hydrochloride salt according to the procedure of Example 30 (steps e and g) to provide the title compound (38 mg, 52%) as a yellow solid: mp 310-315° C.; $^1$H NMR (500 MHz, CD$_3$OD) δ 7.78-7.75 (m, 3H), 7.67 (d, J=8.3 Hz, 1H), 7.55-7.53 (m, 3H), 7.13 (dd, J=8.3, 1.8 Hz, 1H), 6.91 (d, J=1.9 Hz, 1H), 6.84 (dd, J=7.1, 2.0 Hz, 1H), 4.56 (s, 2H), 3.74 (s, 3H), 3.61 (t, J=6.0 Hz, 2H), 3.14 (t, J=6.0 Hz, 2H); ESI MS m/z 390 [M+H]$^+$; HPLC (Method B)>99% (AUC), t$_R$=13.6 min.

Example 39

Preparation of 1-(9-Methyl-2,3,4,9-tetrahydro-1H-pyrido[3,4-b]indol-7-yl)-4-(4-(trifluoromethyl)phenyl)pyridin-2(1H)-one hydrochloride hydrochloride a) 4-(4-(Trifluoromethyl)phenyl)pyridine 1-oxide

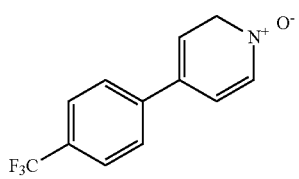

Chemical Formula: C$_{12}$H$_8$F$_3$NO
Exact Mass: 239.06
Molecular Weight: 239.19

4-Chloropyridine-N-oxide (3.0 g, 23 mmol), 4-trifluoromethylphenylboronic acid (6.57 g, 34.6 mmol), K$_2$CO$_3$ (4.8 g, 35 mmol) and PdCl$_2$(dppf) (470 mg, 0.57 mmol) were stirred in DMSO (40 mL) under vacuum for 30 min. The flask was flushed with nitrogen and the mixture was heated to 80° C. for 10 min. Upon cooling, the mixture was diluted with methylene chloride and washed with 5% lithium chloride solution (5×), dried, concentrated and the residue was purified by flash column chromatography (40 g ISCO column eluting with methylene chloride and a methanol/ammonia mixture (10:1); gradient 100% methylene chloride to 80% methylene chloride over 30 min at 40 mL/min) to provide the title compound (1.90 g, 34%) as a tan solid: ESI MS m/z 240 [M+H]$^+$.

b) 4-(4-(Trifluoromethyl)phenyl)pyridin-2(1H)-one

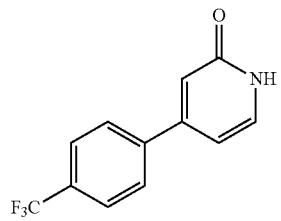

Chemical Formula: C$_{12}$H$_8$F$_3$NO
Exact Mass: 239.06
Molecular Weight: 239.19

4-(4-(Trifluoromethyl)phenyl)pyridine-1-oxide (1.9 g, 7.9 mmol) was reacted according to the procedure of Example 32 (step b) to provide the title compound (1.26 g, 66%) as a brown solid: $^1$H NMR (300 MHz, CD$_3$OD) δ 7.80-7.74 (br m, 5H), 6.85-6.66 (br m, 2H).

c) tert-Butyl 9-methyl-7-(2-oxo-4-(4-(trifluoromethyl)phenyl)pyridin-1(2H)-yl)-3,4-dihydro-1H-pyrido[3,4-b]indole-2(9H)-carboxylate

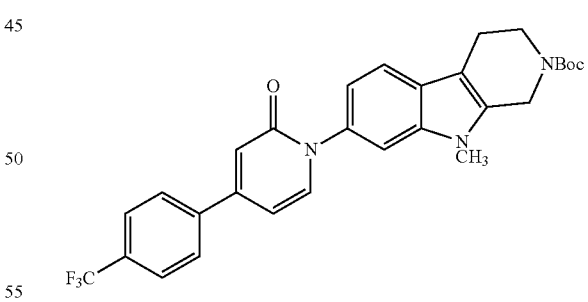

Chemical Formula: C$_{29}$H$_{28}$F$_3$N$_3$O$_3$
Exact Mass: 523.21
Molecular Weight: 523.55

4-(4-(Trifluoromethyl)phenyl)pyridin-2(1H)-one (86 mg, 0.36 mmol) and tert-butyl 7-bromo-9-methyl-3,4-dihydro-1H-pyrido[3,4-b]indole-2(9H)-carboxylate (120 mg, 0.32 mmol) were reacted following the procedure of Example 30 (step g) to provide the title compound (97 mg, 58%) as a yellow solid: $^1$H NMR (300 MHz, CDCl$_3$) δ 7.74 (s, 4H), 7.58-7.52 (m, 2H), 7.36 (s, 1H), 7.08 (dd, J=8.2, 1.8 Hz, 1H), 6.92 (d, J=1.9 Hz, 1H), 6.50 (dd, J=7.2, 2.0 Hz, 1H), 4.65 (br m, 2H), 3.76 (br m, 2H), 3.65 (s, 3H), 2.81 (br m, 2H), 1.52 (s, 9H).

d) 1-(9-Methyl-2,3,4,9-tetrahydro-1H-pyrido[3,4-b]indol-7-yl)-4-(4-(trifluoromethyl)phenyl)pyridin-2(1H)-one hydrochloride

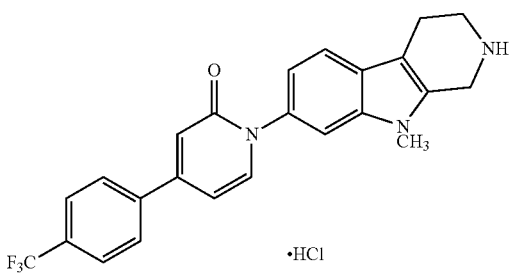

Chemical Formula: C$_{24}$H$_{21}$ClF$_3$N$_3$O
Exact Mass: 459.13
Molecular Weight: 459.89 tert-Butyl 9-methyl-7-(2-oxo-4-(4-(trifluoromethyl)phenyl)pyridin-1(2H)-yl)-3,4-dihydro-1H-pyrido[3,4-b]indole-2(9H)-carboxylate (97 mg, 0.19 mmol) was deprotected and converted to the hydrochloride salt according to the procedure of Example 30 (steps e and g) to provide the title compound (53 mg, 62%) as a yellow solid: mp 316-321° C.; $^1$H NMR (300 MHz, CD$_3$OD) δ 7.97 (d, J=8.1 Hz, 2H), 7.87-7.80 (m, 3H), 7.68 (d, J=8.2 Hz, 1H), 7.57 (d, J=1.5 Hz, 1H), 7.14 (dd, J=8.3, 1.8 Hz, 1H), 6.96 (d, J=1.8 Hz, 1H), 6.87 (dd, J=7.2, 1.8 Hz, 1H), 4.56 (s, 2H), 3.74 (s, 3H), 3.61 (t, J=6.0 Hz, 2H), 3.14 (t, J=6.0 Hz, 2H); ESI MS m/z 424 [M+H]$^+$; HPLC (Method B) 96.3% (AUC), t$_R$=14.0 min.

Example 40

Preparation of 1-(2,9-Dimethyl-2,3,4,9-tetrahydro-1H-pyrido[3,4-b]indol-7-yl)-4-(4-(trifluoromethyl)phenyl)pyridin-2(1H)-one hydrochloride

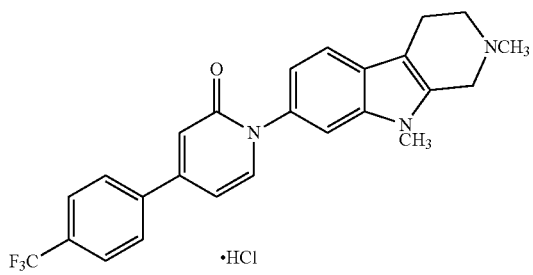

Chemical Formula: C$_{25}$H$_{23}$ClF$_3$N$_3$O
Exact Mass: 473.15
Molecular Weight: 473.92

4-(4-(Trifluoromethyl)phenyl)pyridin-2(1H)-one (100 mg, 0.42 mmol) and 7-bromo-2,9-dimethyl-2,3,4,9-tetrahydro-1H-pyrido[3,4-b]indole (117 mg, 0.419 mmol) were reacted following the procedure of Example 30 (step g) to provide the title compound (70 mg, 35%) as a yellow-brown solid: mp 294-299° C.; $^1$H NMR (500 MHz, CD$_3$OD) δ 7.96 (d, J=8.2 Hz, 2H), 7.85-7.83 (m, 3H), 7.68 (d, J=8.3 Hz, 1H), 7.58 (d, J=1.6 Hz, 1H), 7.16 (dd, J=8.3, 1.7 Hz, 1H), 6.98 (d, J=1.8 Hz, 1H), 6.90 (dd, J=7.1, 1.9 Hz, 1H), 4.87-4.86 (m, 1H), 4.51 (d, J=15.3 Hz, 1H), 3.90-3.86 (m, 1H), 3.74 (s, 3H), 3.57-3.51 (m, 1H), 3.23-3.20 (m, 2H), 3.17 (s, 3H); ESI MS m/z 438 [M+H]$^+$; HPLC (Method B) 95.6% (AUC), t$_R$=14.1 min.

Example 41

Preparation of 4-(2,4-Dichlorophenyl)-1-(2,9-dimethyl-2,3,4,9-tetrahydro-1H-pyrido[3,4-b]indol-7-yl)pyridin-2(1H)-one hydrochloride a) 4-(2,4-Dichlorophenyl)pyridine 1-oxide

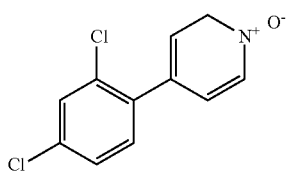

Chemical Formula: C$_{11}$H$_7$Cl$_2$NO
Exact Mass: 238.99
Molecular Weight: 240.09

4-Chloropyridine-N-oxide (1.5 g, 12 mmol), 2,4-dichlorophenylboronic acid (5.4 g, 29 mmol) were reacted according to the procedure of Example 39 (step a) to provide the title compound (1.40 g, 50%) as a grey solid: $^1$H NMR (500 MHz, CD$_3$OD) δ 8.26 (d, J=6.9 Hz, 2H), 7.53 (d, J=2.0 Hz, 1H), 7.37-7.35 (m, 3H), 7.29 (d, J=8.3 Hz, 1H).

b) 4-(2,4-Dichlorophenyl)pyridin-2(1H)-one

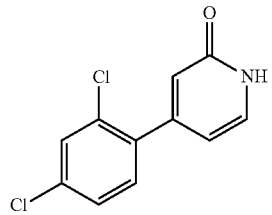

Chemical Formula: C$_{11}$H$_7$Cl$_2$NO
Exact Mass: 238.99
Molecular Weight: 240.09

4-(2,4-Dichlorophenyl)pyridine 1-oxide (1.4 g, 5.8 mmol) was reacted according to the procedure of Example 32 (step b) to provide the title compound (0.95 g, 67%) as a brown solid: $^1$H NMR (300 MHz, DMSO-d$_6$) δ 11.75 (br m, 1H), 7.75 (s, 1H), 7.51-7.46 (m, 3H), 6.31-6.22 (m, 2H).

c) 4-(2,4-Dichlorophenyl)-1-(2,9-dimethyl-2,3,4,9-tetrahydro-1H-pyrido[3,4-b]indol-7-yl)pyridin-2(1H)-one hydrochloride

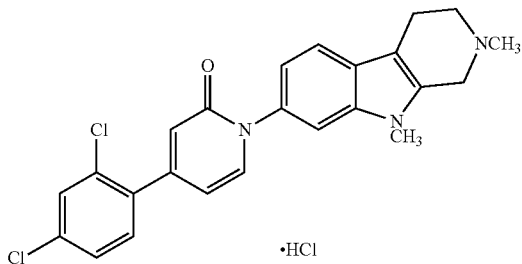

Chemical Formula: C₂₄H₂₂Cl₃N₃O
Exact Mass: 473.08
Molecular Weight: 474.81

4-(2,4-Dichlorophenyl)pyridin-2(1H)-one (103 mg, 0.429 mmol) and 7-bromo-2,9-dimethyl-2,3,4,9-tetrahydro-1H-pyrido[3,4-b]indole (120 mg, 0.43 mmol) were reacted following the procedure of Example 30 (step g) to provide the title compound (44 mg, 21%) as a yellow solid: mp 308-313° C.; ¹H NMR (500 MHz, CD₃OD) δ 7.77 (d, J=7.0 Hz, 1H), 7.68 (d, J=8.4 Hz, 1H), 7.65 (overlapping dd, J=1.1 Hz, 1H), 7.58 (d, J=1.7 Hz, 1H), 7.49 (s, 2H), 7.16 (dd, J=8.3, 1.8 Hz, 1H), 6.70 (d, J=1.5 Hz, 1H), 6.62 (dd, J=7.0, 1.9 Hz, 1H), 4.86 (m, 1H), 4.50 (d, J=15.3 Hz, 1H), 3.89-3.85 (m, 1H), 3.74 (s, 3H), 3.56-3.55 (m, 1H), 3.23-3.20 (m, 2H), 3.16 (s, 3H); ESI MS m/z 438 [M+H]⁺; HPLC (Method B) 98.5% (AUC), t_R=14.3 min.

Example 42

Preparation of 4-(Benzyloxy)-1-(9-methyl-2,3,4,9-tetrahydro-1H-pyrido[3,4-b]indol-7-yl)pyridin-2(1H)-one hydrochloride a) tert-Butyl 7-(4-(benzyloxy)-2-oxopyridin-1(2H)-yl)-9-methyl-3,4-dihydro-1H-pyrido[3,4-b]indole-2(9H)-carboxylate

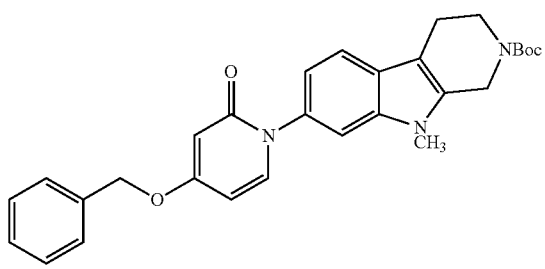

Chemical Formula: C₂₉H₃₁N₃O₄
Exact Mass: 485.23
Molecular Weight: 485.57

4-(Benzyloxy)pyridin-2(1H)-one (580 mg, 0.28 mmol) and tert-butyl 7-bromo-9-methyl-3,4-dihydro-1H-pyrido[3,4-b]indole-2(9H)-carboxylate (850 mg, 0.23 mmol) were reacted following the procedure of Example 30 (step g) to provide the title compound (700 mg, 62%) as a green solid: ¹H NMR (500 MHz, CDCl₃) δ 7.52 (d, J=8.2 Hz, 1H), 7.44-7.39 (m, 4H), 7.38-7.35 (m, 1H), 7.31-7.28 (m, 2H), 7.01 (dd, J=8.3, 1.8 Hz, 1H), 6.09 (d, J=2.6 Hz, 1H), 6.04 (dd, J=7.6, 2.6 Hz, 1H), 5.05 (s, 2H), 4.64 (br m, 2H), 3.74 (br m, 2H), 3.62 (s, 3H), 2.79 (br m, 2H), 1.47 (s, 9H).

b) 4-(Benzyloxy)-1-(9-methyl-2,3,4,9-tetrahydro-1H-pyrido[3,4-b]indol-7-yl)pyridin-2(1H)-one hydrochloride

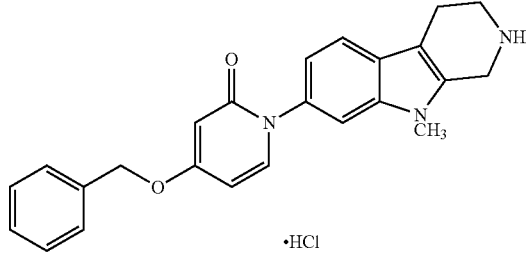

Chemical Formula: C₂₄H₂₄ClN₃O₂
Exact Mass: 421.16
Molecular Weight: 421.92 tert-Butyl 7-(4-(benzyloxy)-2-oxopyridin-1(2H)-yl)-9-methyl-3,4-dihydro-1H-pyrido[3,4-b]indole-2(9H)-carboxylate (700 mg, 1.44 mmol) was deprotected and converted to the hydrochloride salt according to the procedure of Example 30 (steps e and g) to provide the title compound (530 mg, 83%) as a yellow solid: mp 251-257° C.; ¹H NMR (500 MHz, DMSO-d₆) δ 9.71 (br s, 2H), 7.56 (d, J=7.6 Hz, 1H), 7.54 (d, J=8.3 Hz, 1H), 7.50-7.47 (m, 3H), 7.44-7.41 (m, 2H), 7.38-7.37 (m, 1H), 6.99 (dd, J=8.3, 1.8 Hz, 1H), 6.11 (dd, J=7.6, 2.8 Hz, 1H), 5.97 (d, J=2.6 Hz, 1H), 5.15 (s, 2H), 4.45 (s, 2H), 3.81 (s, 3H), 3.42-3.41 (m, 2H), 2.98-2.97 (m, 2H); ESI MS m/z 386 [M+H]⁺; HPLC (Method B)>99% (AUC), t_R=12.9 min.

Example 43

Preparation of 4-(Benzyloxy)-1-(2-(2-hydroxyethyl)-9-methyl-2,3,4,9-tetrahydro-1H-pyrido[3,4-b]indol-7-yl)pyridin-2(1H)-one hydrochloride

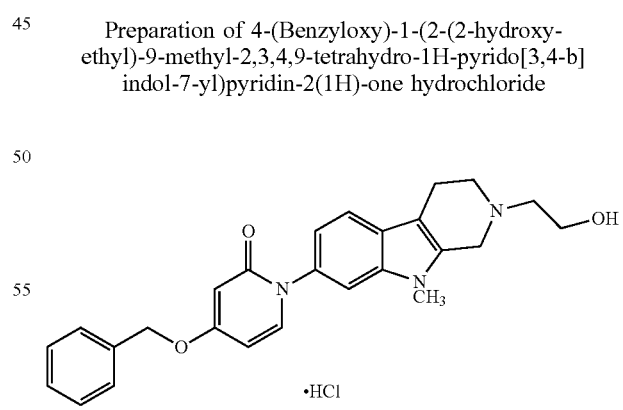

Chemical Formula: C₂₆H₂₈ClN₃O₃
Exact Mass: 465.18
Molecular Weight: 465.97

4-(Benzyloxy)-1-(9-methyl-2,3,4,9-tetrahydro-1H-pyrido[3,4-b]indol-7-yl)pyridin-2(1H)-one (70 mg, 0.18 mmol), 2-iodoethanol (156 mg, 0.907 mmol) and K₂CO₃ (250 mg, 1.8 mmol) were combined in DMF (3 mL) and heated to 80° C. for 1 h. Upon cooling, the product was purified by preparative HPLC and then flash column chromatography (12 g ISCO column eluting with methylene chloride and a methanol/ammonia mixture (10:1); gradient 100% methylene chloride to 90% methylene chloride over 30 min at 25 mL/min) to provide the free-base. This was converted to the hydrochloride salt as of Example 30 (step g) to provide the title compound (14.8 mg, 18%) as a yellow solid: ¹H NMR (500 MHz, CD₃OD) δ 7.63 (d, J=8.4 Hz, 1H), 7.61 (d, J=7.5 Hz, 1H), 7.47-7.46 (m, 3H), 7.42-7.39 (m, 2H), 7.36 (d, J=7.1 Hz, 1H), 7.06 (dd, J=8.3, 1.8 Hz, 1H), 6.33 (dd, J=7.6, 2.6 Hz, 1H), 6.15 (d, J=2.6 Hz, 1H), 5.19 (s, 2H), 4.81-4.79 (m, 1H), 4.59 (d, J=15.3 Hz, 1H), 4.01 (t, J=5.1 Hz, 2H), 3.97-3.94 (m, 1H), 3.73 (s, 3H), 3.58-3.50 (m, 3H), 3.21-3.16 (m, 2H); ESI MS m/z 430 [M+H]⁺; HPLC (Method B) 97.2% (AUC), t_R=12.8 min.

Example 44

Preparation of 4-(Benzyloxy)-1-(9-methyl-2-(2-(pyrrolidin-1-yl)acetyl)-2,3,4,9-tetrahydro-1H-pyrido[3,4-b]indol-7-yl)pyridin-2(1H)-one hydrochloride a) 4-(Benzyloxy)-1-(2-(2-chloroacetyl)-9-methyl-2,3,4,9-tetrahydro-1H-pyrido[3,4-b]indol-7-yl)pyridin-2(1H)-one

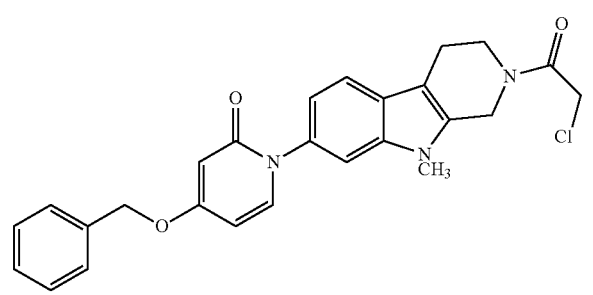

Chemical Formula: C₂₆H₂₄ClN₃O₃
Exact Mass: 461.15
Molecular Weight: 461.94

4-(Benzyloxy)-1-(2-(2-hydroxyethyl)-9-methyl-2,3,4,9-tetrahydro-1H-pyrido[3,4-b]indol-7-yl)pyridin-2(1H)-one hydrochloride (100 mg, 0.23 mmol) was stirred in a mixture of CH₂Cl₂ (2 mL) and saturated NaHCO₃ solution (2 mL) and chloroacetyl chloride (32 mg, 0.28 mmol) was added. After 1.5 h, the organic layer was removed and concentrated to provide the title compound (120 mg, 100%) as a yellow oil: ESI MS m/z 462 [M+H]⁺.

b) 4-(Benzyloxy)-1-(9-methyl-2-(2-(pyrrolidin-1-yl)acetyl)-2,3,4,9-tetrahydro-1H-pyrido[3,4-b]indol-7-yl)pyridin-2(1H)-one hydrochloride

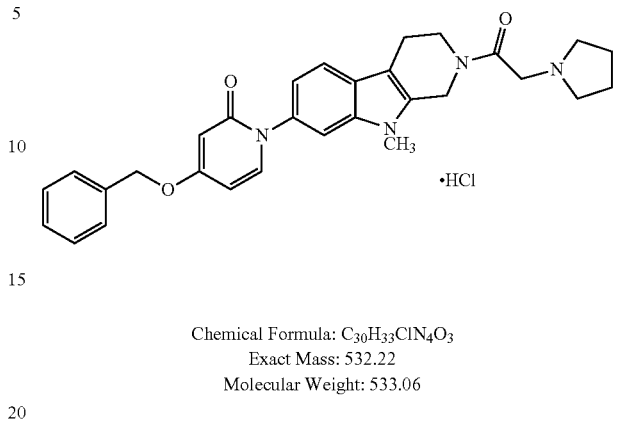

Chemical Formula: C₃₀H₃₃ClN₄O₃
Exact Mass: 532.22
Molecular Weight: 533.06

4-(Benzyloxy)-1-(2-(2-chloroacetyl)-9-methyl-2,3,4,9-tetrahydro-1H-pyrido[3,4-b]indol-7-yl)pyridin-2(1H)-one (120 mg. 0.23 mmol), pyrrolidine (85 mg, 1.2 mmol) and K₂CO₃ (331 mg, 2.39 mmol) were combined in DMF (3 mL) and heated to 80° C. for 1 h. Upon cooling, the mixture was diluted with methylene chloride and washed with 5% lithium chloride solution (5×), dried over Na₂SO₄ and concentrated. The residue was converted to the hydrochloride salt as of Example 30 (step g) to provide the title compound (110 mg, 60%) as a yellow solid: mp 190-200° C.; ¹H NMR (500 MHz, CD₃OD) δ 7.86 (d, J=7.5 Hz, 1H), 7.62 (dd, J=8.2, 2.7 Hz, 1H), 7.51-7.50 (m, 3H), 7.46-7.43 (m, 2H), 7.41-7.40 (m, 1H), 7.08-7.06 (m, 1H), 6.63 (dd, J=7.8, 2.6 Hz, 1H), 6.40 (d, J=1.4 Hz, 1H), 5.31 (s, 2H), 4.93 (s, 1.3H), 4.77 (s, 0.7H), 4.56-4.55 (m, 2H), 4.04-4.02 (m, 0.6H), 3.81-3.78 (m, 3.4H), 3.76 (s, 3H), 3.24-3.19 (m, 2H), 2.79-2.97 (m, 1.3H), 2.92-2.85 (m, 0.7H), 2.22-2.19 (m, 2H), 2.11-2.19 (m, 2H); ESI MS m/z 497 [M+H]⁺; HPLC (Method B)>99% (AUC), t_R=13.7 min.

Example 45

Preparation of (S)-4-(Benzyloxy)-1-(9-methyl-2-(pyrrolidine-2-carbonyl)-2,3,4,9-tetrahydro-1H-pyrido[3,4-b]indol-7-yl)pyridin-2(1H)-one hydrochloride a) (S)-tert-Butyl 2-(7-(4-(benzyloxy)-2-oxopyridin-1(2H)-yl)-9-methyl-2,3,4,9-tetrahydro-1H-pyrido[3,4-b]indole-2-carbonyl)pyrrolidine-1-carboxylate

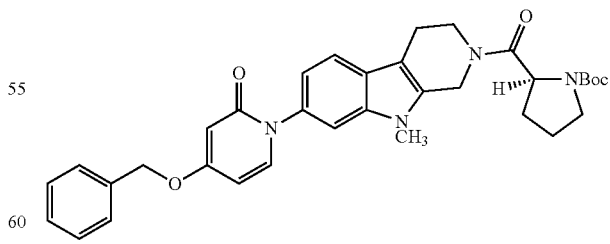

Chemical Formula: C₃₄H₃₈N₄O₅
Exact Mass: 582.28
Molecular Weight: 582.69

4-(Benzyloxy)-1-(9-methyl-2,3,4,9-tetrahydro-1H-pyrido[3,4-b]indol-7-yl)pyridin-2(1H)-one hydrochloride (50 mg, 0.12 mmol) was stirred in DMF (1 mL) and saturated Boc-L-proline (30 mg, 0.14 mmol), HATU (68 mg, 0.18 mmol) and Et₃N (36 mg, 0.36 mmol) were added. After 16 h, the mixture was diluted with methylene chloride and washed with 5% lithium chloride solution (5×), dried over Na₂SO₄ and concentrated. The residue was purified by flash column chromatography (12 g ISCO column eluting with methylene chloride and a methanol/ammonia mixture (10:1); gradient 100% methylene chloride to 90% methylene chloride over 30 min at 25 mL/min) to provide the title compound (55 mg, 78%) as a colorless oil: ESI MS m/z 583 [M+H]⁺.

b) (S)-4-(Benzyloxy)-1-(9-methyl-2-(pyrrolidine-2-carbonyl)-2,3,4,9-tetrahydro-1H-pyrido[3,4-b]indol-7-yl)pyridin-2(1H)-one hydrochloride

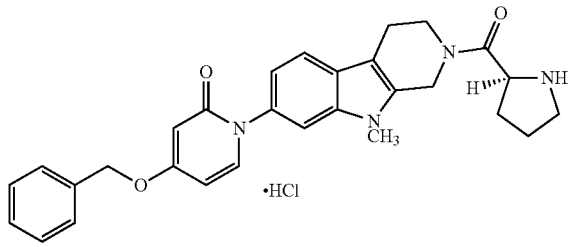

Chemical Formula: C₂₉H₃₁ClN₄O₃
Exact Mass: 518.21
Molecular Weight: 519.03

(S)-tert-Butyl 2-(7-(4-(benzyloxy)-2-oxopyridin-1(2H)-yl)-9-methyl-2,3,4,9-tetrahydro-1H-pyrido[3,4-b]indole-2-carbonyl)pyrrolidine-1-carboxylate (55 mg, 0.094 mmol) was stirred in a mixture of MeOH (2 mL) and 2 N HCl in Et₂O (8 mL) for 5 h. The reaction mixture was concentrated to provide the title compound (42 mg, 85%) as a yellow-green solid: mp 220-226° C.; ¹H NMR (500 MHz, CD₃OD) δ 7.79 (dd, J=7.5, 1.4 Hz, 1H), 7.47 (d, J=8.3 Hz, 1H), 7.49-7.46 (m, 3H), 7.44-7.46 (m, 2H), 7.39-7.36 (m, 1H), 7.04 (dd, J=8.3, 1.6 Hz, 1H), 6.57-6.55 (m, 1H), 6.34 (d, J=2.5 Hz, 1H), 5.27 (s, 2H), 4.96-4.87 (m, 2H), 3.90-8.86 (m, 2H), 3.77 (s, 3H), 3.48-3.34 (m, 3H), 3.00-2.86 (m, 2H), 2.67-2.61 (m, 1H), 2.17-2.02 (m, 3H); ESI MS m/z 483 [M+H]⁺; HPLC (Method B) 95.5% (AUC), t_R=13.5 min.

Example 46

Preparation of 4-(Benzyloxy)-1-(9-methyl-2,3,4,9-tetrahydro-1H-pyrido[3,4-b]indol-6-yl)pyridin-2(1H)-one hydrochloride a) 2-(5-Bromo-1H-indol-3-yl)ethanamine Beilstein Registry Number 143491

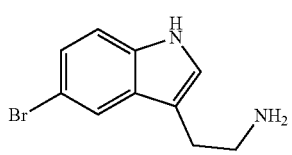

Chemical Formula: C₁₀H₁₁BrN₂
Exact Mass: 238.01
Molecular Weight: 239.11

4-Bromophenylhydrazine hydrochloride (20.0 g, 85.8 mmol) was reacted according to the procedure of Mascal et al. (Rinehart, Kenneth L.; Kobayashi, Jun'ichi; Harbour, Gary C.; Gilmore, Jeremy; Mascal, Mark; et al. *J. Am. Chem. Soc.* 1987, 109, 3378-3387) to provide the title compound (5.2 g, 25%) as an orange solid: ESI MS m/z 239 [M+H]⁺.

b) 6-Bromo-2,3,4,9-tetrahydro-1H-pyrido[3,4-b]indole

Beilstein Registry Number 911238

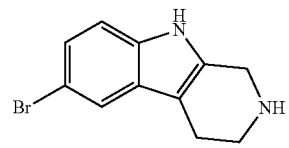

Chemical Formula: C₁₁H₁₁BrN₂
Exact Mass: 250.01
Molecular Weight: 251.12

2-(5-Bromo-1H-indol-3-yl)ethanamine (5.2 g, 22 mmol) was reacted according to the procedure of Mascal et al. (Rinehart, Kenneth L.; Kobayashi, Jun'ichi; Harbour, Gary C.; Gilmore, Jeremy; Mascal, Mark; et al. *J. Am. Chem. Soc.* 1987, 109, 3378-3387) to provide the title compound (2.6 g, 48%) as an orange solid: ESI MS m/z 251 [M+H]⁺.

c) tert-Butyl 6-bromo-3,4-dihydro-1H-pyrido[3,4-b]indole-2(9H)-carboxylate

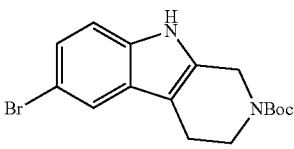

Chemical Formula: C₁₆H₁₉N₂O₂
Exact Mass: 350.06
Molecular Weight: 351.24

6-Bromo-2,3,4,9-tetrahydro-1H-pyrido[3,4-b]indole (2.6 g, 10 mmol) was suspended in CH₂Cl₂ (50 mL) and THF (7.5 mL) and Boc₂O (2.3 g, 11 mmol) was added. After 2.5 h, the mixture was concentrated. Purification by flash column chromatography (silica gel, hexanes/ethyl acetate, 97:3 to 70:30) gave the title compound (1.15 g, 30%) as an orange powder: ¹H NMR (300 MHz, CDCl₃) δ 7.59 (s, 1H), 7.23 (d, J=8.5 Hz, 1H), 7.18 (d, J=8.5 Hz, 1H), 4.68-4.59 (br m, 2H), 3.80-3.70 (br m, 2H), 2.78-2.71 (br m, 2H), 1.50 (s, 9H).

d) tert-Butyl 6-bromo-9-methyl-3,4-dihydro-1H-pyrido[3,4-b]indole-2(9H)-carboxylate

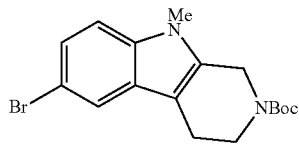

Chemical Formula: C₁₇H₂₁BrN₂O₂
Exact Mass: 364.08
Molecular Weight: 365.26 tert-Butyl 6-bromo-3,4-dihydro-1H-pyrido[3,4-b]indole-2(9H)-carboxylate (1.15 g, 3.26 mmol) was dissolved in DMF (20 mL) and sodium hydride (60% weight dispersion in mineral oil, 196 mg, 4.89 mmol) was added. After 1 h, methyl iodide (0.30 mL, 4.9 mmol) was added and the reaction mixture was stirred for a further 30 min. The mixture was diluted with methylene chloride and washed with 5% lithium chloride solution (5×), dried over Na₂SO₄ and concentrated. Purification by flash column chromatography (silica gel, hexanes/ethyl acetate, 97:3 to 75:25) gave the title compound (740 mg, 36%) as a yellow solid: ¹H NMR (500 MHz, CDCl₃) δ 7.58 (s, 1H), 7.24 (d overlapped by solvent, J=8.5, 1H), 7.14 (d, J=8.5, 1H), 4.67-4.53 (br m, 2H), 3.79-3.67 (br m, 2H), 3.60 (s, 3H), 2.78-2.66 (br m, 2H), 1.51 (s, 9H).

e) tert-Butyl 6-(4-(benzyloxy)-2-oxopyridin-1(2H)-yl)-9-methyl-3,4-dihydro-1H-pyrido[3,4-b]indole-2(9H)-carboxylate

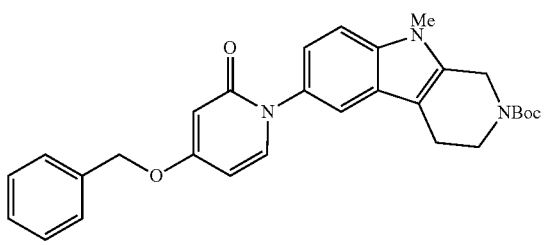

Chemical Formula: C₂₉H₃₁N₃O₄
Exact Mass: 485.23
Molecular Weight: 485.57

A solution of tert-Butyl-6-bromo-9-methyl-3,4-dihydro-1H-pyrido[3,4-b]indole-2(9H)-carboxylate (750 mg, 2.03 mmol) in DMSO (10 mL) was stirred under nitrogen and treated sequentially with 4-(benzyloxy)pyridin-2(1H)-one (448 mg, 2.23 mmol), 8-hydroxyquinoline (44 mg, 0.305 mmol), CuI (58 mg, 0.305 mmol) and K₂CO₃ (308 mg, 2.23 mmol). After stirring overnight at 130° C., the mixture was allowed to cool to room temperature and a mixture of MeOH and NH₄OH (10:1, 10 mL) was added. After stirring for 15 min, the mixture was diluted with CH₂Cl₂, washed with brine, dried over Na₂SO₄, filtered and concentrated to dryness. Purification by flash column chromatography (40 g ISCO column eluting with a 1:1 ethylacetate/hexanes and a methanol/ammonia mixture (10:1); gradient 100% 1:1 ethylacetate/hexanes to 90% 1:1 ethylacetate/hexanes/10% methanol/ammonia mixture (10:1) over 30 min at 25 mL/min) provided the title compound (340 mg, 33%) as a yellow solid; ¹H NMR (500 MHz, CDCl₃) δ 7.50-7.36 (m, 8H), 7.13 (d, J=7.8, Hz, 1H), 6.09 (d, J=2.6 Hz, 1H), 6.03 (dd, J=7.5, 2.7 Hz, 1H), 5.05 (s, 2H), 4.65 (br s, 2H), 3.73 (br s, 2H), 3.66 (s, 3H), 2.77 (br s, 2H), 1.51 (s, 9H).

f) 4-(Benzyloxy)-1-(9-methyl-2,3,4,9-tetrahydro-1H-pyrido[3,4-b]indol-6-yl)pyridin-2(1H)-one hydrochloride

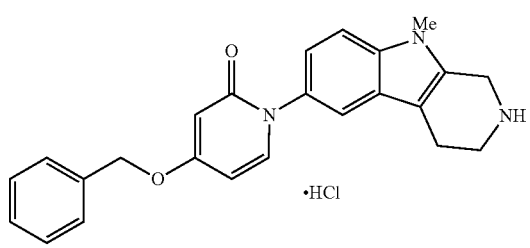

Chemical Formula: C₂₄H₂₄ClN₃O₂
Exact Mass: 421.16
Molecular Weight: 421.92 tert-Butyl 6-(4-(benzyloxy)-2-oxopyridin-1(2H)-yl)-9-methyl-3,4-dihydro-1H-pyrido[3,4-b]indole-2(9H)-carboxylate (0.340 g, 0.70 mmol) was dissolved in MeOH (5 mL) and 2 N HCl in ether (15 mL) was added. After stirring for 1 h, the liquid was decanted off and the resultant solid was filtered and washed with ether (3×). This provided the title compound (267 mg, 98%) as a light yellow solid: mp 290-300° C.; ¹H NMR (500 MHz, CD₃OD) δ 7.66 (d, J=7.5 Hz, 1H), 7.57-7.52 (m, 2H), 7.46 (d, J=7.7 Hz, 2H), 7.41 (overlapping dd, J=7.3 Hz, 2H), 7.36 (d, J=7.5 Hz, 1H), 7.19 (dd, J=8.6, 2.0 Hz, 1H), 6.42 (dd, J=7.5, 2.7 Hz, 1H), 6.22 (d, J=2.6 Hz, 1H), 5.22 (s, 2H), 4.55 (s, 2H), 3.75 (s, 3H), 3.58 (t, J=6.0 Hz, 2H), 3.10 (t, J=6.0 Hz, 2H); ESI MS m/z 386 [M+H]⁺; HPLC (Method B) 98.8% (AUC), t_R=12.8 min.

Example 47

Preparation of 4-(Benzyloxy)-1-(2,9-dimethyl-2,3,4,9-tetrahydro-1H-pyrido[3,4-b]indol-7-yl)pyridin-2(1H)-one hydrochloride

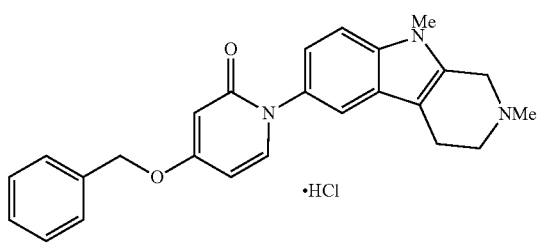

Chemical Formula: C₂₅H₂₆ClN₃O₂
Exact Mass: 435.17
Molecular Weight: 435.95

4-(Benzyloxy)-1-(9-methyl-2,3,4,9-tetrahydro-1H-pyrido[3,4-b]indol-6-yl)pyridine-2(1H)-one hydrochloride (126 mg, 0.325 mmol) was dissolved in MeOH (2 mL) and CH₂Cl₂ (0.5 mL) and formaldehyde (0.036 mL, 37% aqueous solution) was added. After stirring for 1 h, NaBH(OAc)₃

(138 mg, 0.651 mmol) was added and the mixture was stirred for a further 40 min. The mixture was diluted with methylene chloride (50 mL), washed with saturated $Na_2CO_3$ solution, concentrated and purified by flash column chromatography (12 g ISCO column eluting with methylene chloride and a methanol/ammonia mixture (10:1); gradient 100% methylene chloride to 85% methylene chloride over 30 min at 40 mL/min), and further purified by preparative HPLC to provide the title compound (55.5 mg, 43%) as a white powder: mp 260-270° C.; $^1$H NMR (500 MHz, $CD_3OD$) δ 7.56-7.53 (m, 2H), 7.51 (d, J=1.8, 1H), 7.46 (d, J=7.3 Hz, 2H), 7.41 (overlapping dd, J=7.4 Hz, 2H), 7.36 (d, J=7.2 Hz, 1H), 7.19 (dd, J=8.6, 2.0 Hz, 1H), 6.27 (dd, J=7.6, 2.7 Hz, 1H), 6.11 (d, J=2.6 Hz, 1H), 5.18 (s, 2H), 4.64 (br s, 2H), 3.75 (s, 3H), 3.67 (br s, 2H), 3.18-3.13 (m, 5H); ESI MS m/z 400 [M+H]$^+$; HPLC (Method B)>99% (AUC), $t_R$=12.9 min.

Example 48

Preparation of 1-(5-Methyl-2,3,4,5-tetrahydro-1H-pyrido[4,3-b]indol-7-yl)-4-(5-(trifluoromethyl)pyridin-2-yl)pyridin-2(1H)-one dihydrochloride a) 2'-Methoxy-5-(trifluoromethyl)-2,4'-bipyridine

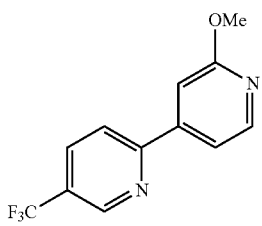

Chemical Formula: $C_{12}H_9F_3N_2O$
Exact Mass: 254.07
Molecular Weight: 254.21

2-Bromo-5-trifluoromethylpyridine (410 mg, 2.13 mmol) and 2-methoxy-4-(4,4,5,5-tetramethyl-1,3,2-dioxaborolan-2-yl)pyridine (500 mg, 1.81 mmol) were reacted according to Example 31 (step a) to provide the title compound (337 mg, 62%) as a white solid: $^1$H NMR (300 MHz, CDCl$_3$) δ 8.96 (s, 1H), 8.31 (d, J=5.4 Hz, 1H), 8.04 (dd, J=8.3, 2.1 Hz, 1H), 7.87 (d, J=8.3 Hz, 1H), 7.51 (dd, J=5.4, 1.4 Hz, 1H), 7.36 (s, 1H), 3.52 (s, 3H).

b) 4-(5-(Trifluoromethyl)pyridin-2-yl)pyridin-2(1H)-one

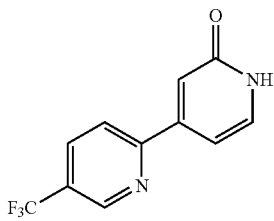

Chemical Formula: $C_{11}H_7F_3N_2O$
Exact Mass: 240.05
Molecular Weight: 240.18

2'-Methoxy-5-(trifluoromethyl)-2,4'-bipyridine (337 mg, 1.32 mmol) was reacted according to Example 31 (step c) to provide the title compound (289 mg, 89%) as a white solid: $^1$H NMR (300 MHz, DMSO-d$_6$) δ 11.08 (s, 1H) 9.10 (s, 1H), 8.35 (dd, J=8.4, 2.1 Hz, 1H), 8.25 (d, J=8.3 Hz, 1H), 7.53 (d, J=6.8, 1H), 7.09 (d, J=1.3 Hz, 1H), 6.90 (dd, J=6.8, 1.6 Hz, 1H).

c) tert-Butyl 5-methyl-7-(2-oxo-4-(5-(trifluoromethyl)pyridin-2-yl)pyridin-1(2H)-yl)-3,4-dihydro-1H-pyrido[4,3-b]indole-2(5H)-carboxylate

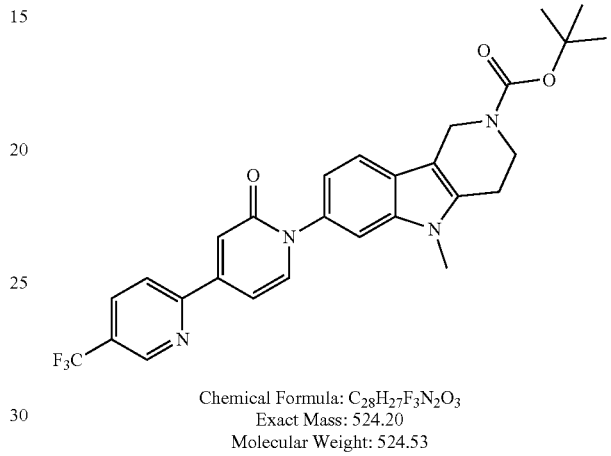

Chemical Formula: $C_{28}H_{27}F_3N_2O_3$
Exact Mass: 524.20
Molecular Weight: 524.53

4-(5-(Trifluoromethyl)pyridin-2-yl)pyridin-2(1H)-one (100 mg, 0.41 mmol) and tert-butyl 7-bromo-5-methyl-3,4-dihydro-1H-pyrido[4,3-b]indole-2(5H)-carboxylate (152 mg, 0.416 mmol) were reacted following the procedure of Example 30 (step g) to provide the title compound (83 mg, 38%) as a green solid: $^1$H NMR (500 MHz, CDCl$_3$) δ 9.00 (s, 1H), 8.06 (dd, J=8.3, 2.1 Hz, 1H), 7.91 (d, J=8.3 Hz, 1H), 7.58 (d, J=7.2 Hz, 1H), 7.55 (d, J=8.2 Hz, 1H), 7.37 (d, J=1.6 Hz, 1H), 7.25 (d, J=1.6 Hz, 1H), 7.08 (d, J=7.5 Hz, 1H), 7.03 (dd, J=7.1, 1.8 Hz, 1H), 4.66 (s, 2H), 3.85 (br m, 2H), 3.66 (s, 3H), 2.84 (br m, 2H), 1.51 (s, 9H).

d) 1-(5-Methyl-2,3,4,5-tetrahydro-1H-pyrido[4,3-b]indol-7-yl)-4-(5-(trifluoromethyl)pyridin-2-yl)pyridin-2(1H)-one dihydrochloride

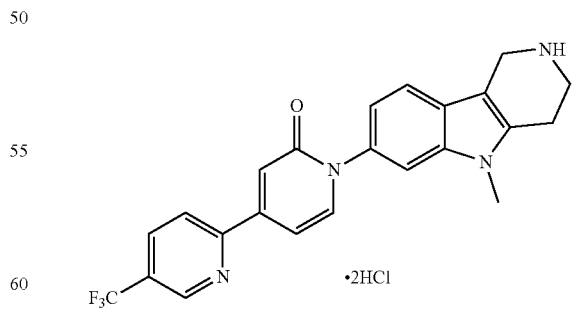

Chemical Formula: $C_{23}H_{21}Cl_2F_3N_4O$
Exact Mass: 496.10
Molecular Weight: 497.34 tert-Butyl 5-methyl-7-(2-oxo-4-(5-(trifluoromethyl)pyridin-2-yl)pyridin-1(2H)-yl)-3,4-dihydro-1H-pyrido[4,3-b]indole-2(5H)-carboxylate (83 mg, 0.16 mmol) was deprotected and converted to the dihydrochloride salt according to the procedure of Example 30 (steps e and g) to provide the title compound (51 mg, 78%) as a yellow solid: mp 320-330° C.; $^1$H NMR (500 MHz, CD$_3$OD) δ 9.06 (s, 1H), 8.28 (dd, J=8.4, 2.1 Hz, 1H), 8.23 (d, J=8.2 Hz, 1H), 7.87 (d, J=7.1 Hz, 1H), 7.64 (d, J=8.3 Hz, 1H), 7.58 (d, J=1.6 Hz, 1H), 7.43 (d, J=1.6 Hz, 1H), 7.29 (dd, J=Hz, 1H), 7.17 (dd, J=8.3, 1.8 Hz, 1H), 4.50 (s, 2H), 3.76 (s, 3H), 3.69 (t, J=6.0 Hz, 2H), 3.22 (t, J=Hz, 2H); ESI MS m/z 425 [M+H]$^+$; HPLC (Method B)>99% (AUC), $t_R$=12.5 min.

Example 49

Preparation of 4-((5-Fluoropyridin-2-yl)methoxy)-1-(9-methyl-2,3,4,9-tetrahydro-1H-pyrido[3,4-b]indol-7-yl)pyridin-2(1H)-one dihydrochloride a) 4-((5-Fluoropyridin-2-yl)methoxy)pyridine 1-oxide

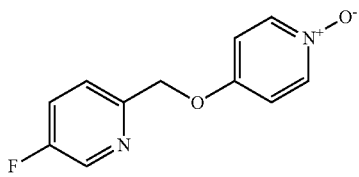

Chemical Formula: C$_{11}$H$_9$FN$_2$O$_2$
Exact Mass: 220.06
Molecular Weight: 220.20

5-Fluoro-2-pyridylbenzylalcohol (3.00 g, 23.6 mmol) and 4-chloropyridine-N-oxide (2.03 g, 15.7 mmol) were reacted according to Example 34 (step a) to provide the title compound (1.76 g, 50%) as a tan solid: $^1$H NMR (300 MHz, CDCl$_3$) δ 8.48 (s, 1H), 8.12 (d, J=7.7 Hz, 2H), 7.48-7.46 (m, 2H), 6.90 (d, J=7.7 Hz, 2H), 5.20 (s, 2H).

b) 4-((5-Fluoropyridin-2-yl)methoxy)pyridin-2(1H)-one

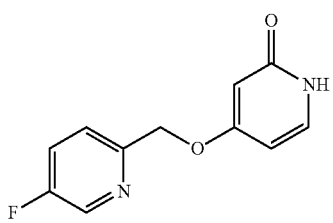

Chemical Formula: C$_{11}$H$_9$FN$_2$O$_2$
Exact Mass: 220.06
Molecular Weight: 220.20

4-((5-Fluoropyridin-2-yl)methoxy)pyridine 1-oxide (1.76 g, 7.99 mmol) was reacted according to Example 34 (step b) to provide the title compound (1.29 g, 73%) as a yellow solid: $^1$H NMR (500 MHz, DMSO-d$_6$) δ 11.12 (s, 1H), 8.59 (d, J=2.9 Hz, 1H), 7.79 (dt, J=8.7, 2.9 Hz, 1H), 7.60 (dd, J=8.7, 4.5 Hz, 1H), 7.26 (d, J=7.3 Hz, 1H), 5.95 (dd, J=7.4, 2.6 Hz, 1H), 5.78 (d, J=2.5 Hz, 1H), 5.12 (s, 2H).

c) tert-Butyl 7-(4-((5-fluoropyridin-2-yl)methoxy)-2-oxopyridin-1(2H)-yl)-5-methyl-3,4-dihydro-1H-pyrido[4,3-b]indole-2(5H)-carboxylate

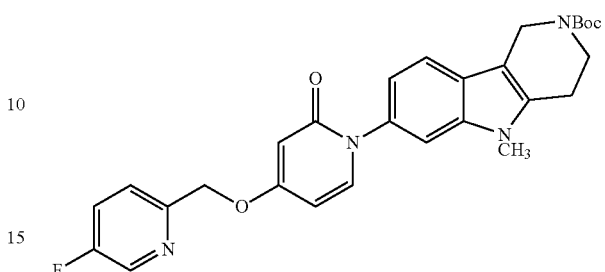

Chemical Formula: C$_{28}$H$_{29}$FN$_4$O$_4$
Exact Mass: 504.22
Molecular Weight: 504.55

4-((5-Fluoropyridin-2-yl)methoxy)pyridin-2(1H)-one (275 mg, 1.25 mmol) and tert-butyl 7-bromo-5-methyl-3,4-dihydro-1H-pyrido[4,3-b]indole-2(5H)-carboxylate (456 mg, 1.25 mmol) were reacted following the procedure of Example 30 (step g) to provide the title compound (420 mg, 66%) as a yellow solid: $^1$H NMR (500 MHz, CDCl$_3$) δ 8.15 (d, J=2.1 Hz, 1H), 7.50 (m, 3H), 7.36 (d, J=7.8 Hz, 1H), 7.31 (d, J=1.6 Hz, 1H), 7.01 (d, J=8.9 Hz, 1H), 6.11-6.08 (m, 2H), 5.18 (s, 2H), 4.65 (s, 2H), 3.87 (t, J=5.3 Hz, 2H), 3.65 (s, 3H), 2.84 (t, J=4.2 Hz, 2H), 1.60 (s, 9H).

d) 4-((5-Fluoropyridin-2-yl)methoxy)-1-(5-methyl-2,3,4,5-tetrahydro-1H-pyrido[4,3-b]indol-7-yl)pyridin-2(1H)-one dihydrochloride

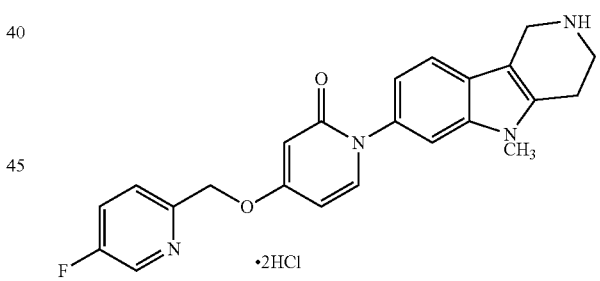

Chemical Formula: C$_{23}$H$_{23}$Cl$_2$FN$_4$O$_2$
Exact Mass: 476.12
Molecular Weight: 477.36 tert-Butyl 7-(4-((5-fluoropyridin-2-yl)methoxy)-2-oxopyridin-1(2H)-yl)-5-methyl-3,4-dihydro-1H-pyrido[4,3-b]indole-2(5H)-carboxylate (415 mg, 0.823 mmol) was deprotected and converted to the dihydrochloride according to procedure of Example 30 (steps e and g) to provide the title compound (328 mg, 84%) as a white solid: mp 174-180° C.; $^1$H NMR (500 MHz, CD$_3$OD) δ 8.70 (s, 1H), 8.00 (dt, J=8.4, 2.8 Hz, 1H), 7.91-7.88 (m, 2H), 7.63 (d, J=8.4 Hz, 1H), 7.55 (s, 1H), 7.11 (dd, J=8.3, 1.7 Hz, 1H), 6.69 (dd, J=7.5, 2.7 Hz, 1H), 6.45 (d, J=2.6 Hz, 1H), 5.46 (s, 2H), 4.49 (s, 2H), 3.75 (s, 3H), 3.68 (t, J=6.1 Hz, 2H), 3.22 (t, J=6.1 Hz, 2H); ESI MS m/z 405 [M+H]$^+$; HPLC (Method B) 95.5% (AUC), $t_R$=10.9 min.

Example 50

Preparation of 1-(5-Methyl-2,3,4,5-tetrahydro-1H-pyrido[4,3-b]indol-7-yl)-4-(6-(trifluoromethyl)pyridazin-3-yl)pyridin-2(1H)-one hydrochloride a) 3-(2-Methoxypyridin-4-yl)-6-(trifluoromethyl)pyridazine

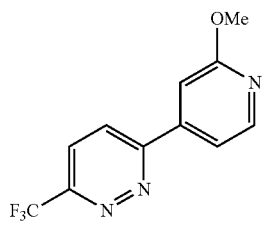

Chemical Formula: C$_{11}$H$_8$F$_3$N$_3$O
Exact Mass: 255.06
Molecular Weight: 255.20

3-Chloro-6-(trifluoromethyl)pyridazine (137 mg, 0.751 mmol) and 2-methoxy-4-(4,4,5,5-tetramethyl-1,3,2-dioxaborolan-2-yl)pyridine (176 mg, 0.749 mmol) were reacted according to Example 31 (step a) to provide the title compound (115 mg, 60%) as a white solid: $^1$H NMR (500 MHz, CDCl$_3$) δ 8.39 (d, J=5.8 Hz, 1H), 8.05 (d, J=8.8 Hz, 1H), 7.94 (d, J=8.8 Hz, 1H), 7.62 (dd, J=5.4, 1.5 Hz, 1H), 7.45 (s, 1H), 4.03 (s, 3H).

b) 4-(6-(Trifluoromethyl)pyridazin-3-yl)pyridin-2(1H)-one

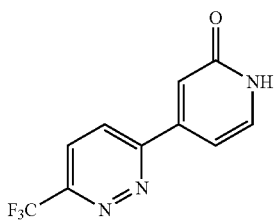

Chemical Formula: C$_{10}$H$_6$F$_3$N$_3$O
Exact Mass: 241.05
Molecular Weight: 241.17

3-(2-Methoxypyridin-4-yl)-6-(trifluoromethyl)pyridazine (115 mg, 0.451 mmol) was reacted according to Example 31 (step c) to provide the title compound (120 mg, quant) as a white solid: $^1$H NMR (500 MHz, DMSO-d$_6$) δ 11.87 (s, 1H), 8.61 (d, J=8.9 Hz, 1H), 8.42 (d, J=8.9 Hz, 1H), 7.62 (d, J=6.8 Hz, 1H), 7.19 (s, 1H), 7.01 (dd, J=6.8, 1.6 Hz, 1H).

c) tert-Butyl 5-methyl-7-(2-oxo-4-(6-(trifluoromethyl)pyridazin-3-yl)pyridin-1(2H)-yl)-3,4-dihydro-1H-pyrido[4,3-b]indole-2(5H)-carboxylate

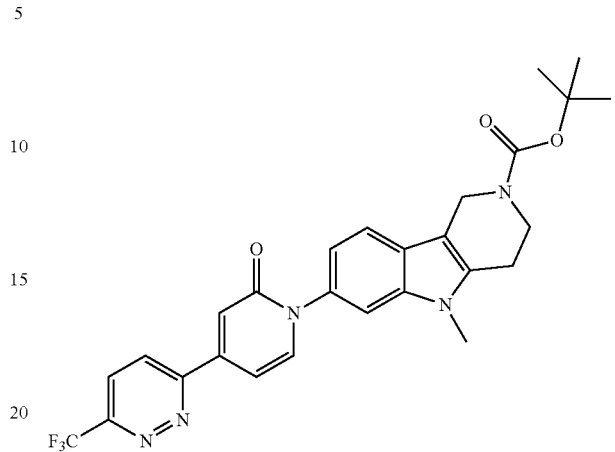

Chemical Formula: C$_{27}$H$_{26}$F$_3$N$_5$O$_3$
Exact Mass: 525.20
Molecular Weight: 525.52

4-(6-(Trifluoromethyl)pyridazin-3-yl)pyridin-2(1H)-one (60 mg, 0.25 mmol) and tert-butyl 7-bromo-5-methyl-3,4-dihydro-1H-pyrido[4,3-b]indole-2(5H)-carboxylate (90 mg, 0.25 mmol) were reacted following the procedure of Example 30 (step g) to provide the title compound (60 mg, 46%) as a yellow solid: $^1$H NMR (500 MHz, CDCl$_3$) δ 8.10 (d, J=8.8 Hz, 1H), 7.79 (d, J=8.8 Hz, 1H), 7.66 (d, J=7.0 Hz, 1H), 7.56 (d, J=8.2 Hz, 1H), 7.38 (d, J=1.3 Hz, 1H), 7.26-7.24 (m, 2H), 7.10 (d, J=7.8 Hz, 1H), 4.66 (s, 2H), 3.66 (t, J=3.3 Hz, 2H), 3.86 (s, 3H), 2.84 (t, J=3.3 Hz, 2H), 1.51 (s, 9H).

d) 1-(5-Methyl-2,3,4,5-tetrahydro-1H-pyrido[4,3-b]indol-7-yl)-4-(6-(trifluoromethyl)pyridazin-3-yl)pyridin-2(1H)-one hydrochloride

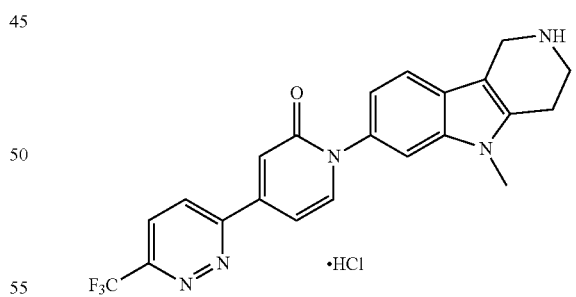

Chemical Formula: C$_{22}$H$_{19}$ClF$_3$N$_5$O
Exact Mass: 461.12
Molecular Weight: 461.87 tert-Butyl 5-methyl-7-(2-oxo-4-(6-(trifluoromethyl)pyridazin-3-yl)pyridin-1(2H)-yl)-3,4-dihydro-1H-pyrido[4,3-b]indole-2(5H)-carboxylate (60 mg, 0.11 mmol) was deprotected and converted to the hydrochloride salt according to the procedure of Example 30 (steps e and g) to provide the title compound (44 mg, 88%) as a yellow solid: mp 315-320° C.; $^1$H NMR (500 MHz, CD$_3$OD) δ 8.54 (d, J=8.8

Hz, 1H), 8.28 (d, J=8.9 Hz, 1H), 7.91 (d, J=7.0 Hz, 1H), 7.64 (d, J=8.4 Hz, 1H), 7.60 (d, J=1.5 Hz, 1H), 7.44 (d, J=1.5 Hz, 1H), 7.35 (dd, J=7.2, 1.9 Hz, 1H), 7.16 (dd, J=8.3, 1.8 Hz, 1H), 4.50 (s, 2H), 3.77 (s, 3H), 3.69 (t, J=6.1 Hz, 2H), 3.22 (t, J=6.0 Hz, 2H); ESI MS m/z 426 [M+H]$^+$; HPLC (Method B) 95.9% (AUC), $t_R$=11.7 min.

Example 51

Preparation of 4-((5-Chloropyridin-2-yl)methoxy)-1-(5-methyl-2,3,4,5-tetrahydro-1H-pyrido[4,3-b]indol-7-yl)pyridin-2(1H)-one dihydrochloride a) tert-Butyl 7-(4-((5-chloropyridin-2-yl)methoxy)-2-oxopyridin-1(2H)-yl)-5-methyl-3,4-dihydro-1H-pyrido[4,3-b]indole-2(5H)-carboxylate

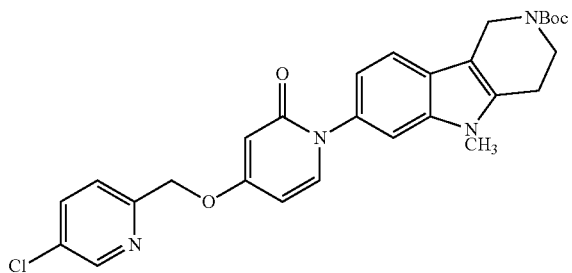

Chemical Formula: C$_{28}$H$_{29}$ClN$_4$O$_4$
Exact Mass: 520.19
Molecular Weight: 521.02

4-((5-Chloropyridin-2-yl)methoxy)pyridin-2(1H)-one (127 mg, 0.537 mmol) and tert-butyl 7-bromo-5-methyl-3,4-dihydro-1H-pyrido[4,3-b]indole-2(5H)-carboxylate (200 mg, 1.1 mmol) were reacted following the procedure of Example 30 (step g) to provide the title compound (113 mg, 40%) as a white solid: $^1$H NMR (300 MHz, CDCl$_3$) δ 8.59 (d, J=2.4 Hz, 1H), 7.73 (dd, J=8.4, 2.4 Hz, 1H), 7.51 (d, J=8.3 Hz, 1H), 7.45 (d, J=8.3 Hz, 1H), 7.33 (d, J=7.5 Hz, 1H), 7.29 (d, J=1.5 Hz, 1H), 7.01 (d, J=7.9 Hz, 1H), 6.09 (dd, J=7.5, 2.7 Hz, 1H), 6.05 (d, J=2.5 Hz, 1H), 5.17 (s, 2H), 4.64 (s, 2H), 3.84 (t, J=5.4 Hz, 2H), 3.63 (s, 3H), 2.82 (t, J=5.4 Hz, 2H), 1.50 (s, 9H).

b) 4-((5-Chloropyridin-2-yl)methoxy)-1-(5-methyl-2,3,4,5-tetrahydro-1H-pyrido[4,3-b]indol-7-yl)pyridin-2(1H)-one dihydrochloride

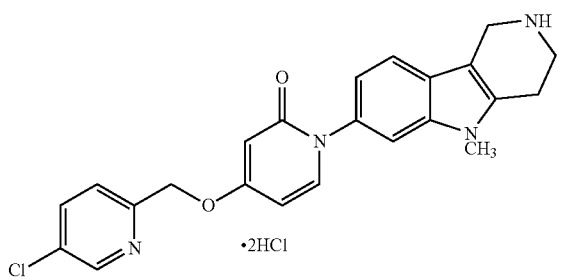

Chemical Formula: C$_{23}$H$_{23}$Cl$_3$N$_4$O$_2$
Exact Mass: 492.09
Molecular Weight: 493.81 tert-Butyl 7-(4-((5-chloropyridin-2-yl)methoxy)-2-oxopyridin-1(2H)-yl)-5-methyl-3,4-dihydro-1H-pyrido[4,3-b]indole-2(5H)-carboxylate (108 mg, 0.207 mmol) was deprotected and converted to the dihydrochloride salt according to the procedure of Example 30 (steps e and g) to provide the title compound (99 mg, 97%) as a white solid: mp 290-320° C. dec; $^1$H NMR (300 MHz, CD$_3$OD) δ 8.61 (d, J=2.1 Hz, 1H), 7.95 (dd, J=8.4, 2.4 Hz, 1H), 7.62 (d, J=7.6 Hz, 2H), 7.58 (d, J=8.4 Hz, 1H), 7.47 (d, J=1.6 Hz, 1H), 7.05 (dd, J=8.3, 1.8 Hz, 1H), 6.36 (dd, J=7.6, 2.2 Hz, 1H), 6.13 (d, J=2.6 Hz, 1H), 5.28 (s, 2H), 4.48 (s, 2H), 3.73 (s, 3H), 3.67 (t, J=6.2 Hz, 2H), 3.02 (t, J=6.2 Hz, 2H); ESI MS m/z 421 [M+H]$^+$; HPLC (Method B) 98.2% (AUC), $t_R$=12.0 min.

Example 52

Preparation of 4-((5-Chloropyridin-2-yl)methoxy)-1-(2,5-dimethyl-2,3,4,5-tetrahydro-1H-pyrido[4,3-b]indol-7-yl)pyridin-2(1H)-one dihydrochloride

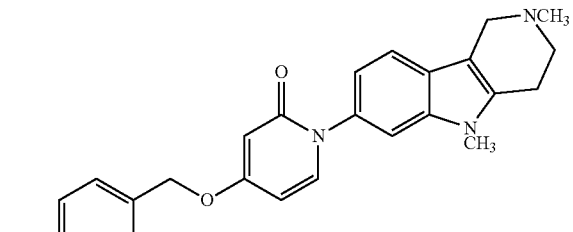

Chemical Formula: C$_{24}$H$_{25}$Cl$_3$N$_4$O$_2$
Exact Mass: 506.10
Molecular Weight: 507.84

4-((5-Chloropyridin-2-yl)methoxy)-1-(5-methyl-2,3,4,5-tetrahydro-1H-pyrido[4,3-b]indol-7-yl)pyridin-2(1H)-one (50 mg, 0.12 mmol) was reacted according to the procedure of Example 47 to provide the free-base. Conversion to the dihydrochloride salt using the procedure of Example 30 (step g) provided the title compound (39 mg, 64%) as a white solid: mp 278-282° C.; 1H NMR (300 MHz, CD$_3$OD) δ 8.60 (d, J=2.0 Hz, 1H), 7.96-7.92 (m, 1H), 7.61 (d, J=7.7 Hz, 2H), 7.57 (d, J=8.3 Hz, 1H), 7.47 (d, J=1.4 Hz, 1H), 7.06 (dd, J=8.4, 1.7 Hz, 1H), 6.34 (dd, J=7.6, 2.6 Hz, 1H), 6.12 (d, J=2.6 Hz, 1H), 5.27 (s, 2H), 4.75 (d, J=14.2 Hz, 1H), 4.38 (d, J=14.1 Hz, 1H), 3.95-3.85 (m, 1H), 3.73 (s, 3H), 3.63 (m, 1H), 3.31 (m overlapping with solvent, 2H), 3.13 (s, 3H); ESI MS m/z 435 [M+H]$^+$; HPLC (Method B) 98.9% (AUC), $t_R$=12.1 min.

Example 53

Preparation of 1-(5-Methyl-2,3,4,5-tetrahydro-1H-pyrido[4,3-b]indol-7-yl)-4-(pyridin-2-ylmethoxy)pyridin-2(1H)-one dihydrochloride a) tert-Butyl 5-methyl-7-(2-oxo-4-(pyridin-2-ylmethoxy)pyridin-1(2H)-yl)-3,4-dihydro-1H-pyrido[4,3-b]indole-2(5H)-carboxylate

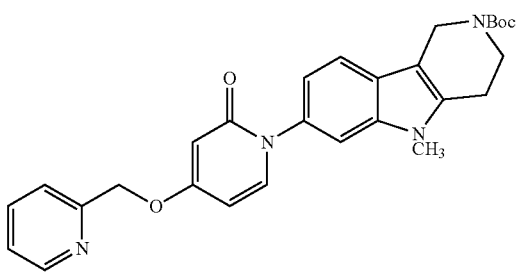

Chemical Formula: $C_{28}H_{30}N_4O_4$
Exact Mass: 486.23
Molecular Weight: 486.56

4-(Pyridin-2-ylmethoxy)pyridin-2(1H)-one (110 mg, 0.54 mmol) and tert-butyl 7-bromo-5-methyl-3,4-dihydro-1H-pyrido[4,3-b]indole-2(5H)-carboxylate (200 mg, 0.54 mmol) were reacted following the procedure of Example 30 (step g) to provide the title compound (113 mg, 43%) as a yellow oil: $^1$H NMR (300 MHz, CDCl$_3$) δ 8.63 (ddd, J=4.9, 1.6, 0.9 Hz, 1H), 7.75 (overlapping ddd, J=7.6, 1.8 Hz, 1H), 7.49 (t, J=7.3 Hz, 2H), 7.33 (d, J=7.5 Hz, 1H), 7.29 (d, J=1.4 Hz, 1H), 7.26 (m overlapping with solvent, 1H), 7.01 (d, J=7.9 Hz, 1H), 6.12-6.07 (m, 2H), 5.19 (s, 2H), 4.64 (s, 2H), 3.84 (t, J=5.4 Hz, 2H), 3.62 (s, 3H), 2.82 (t, J=5.4 Hz, 2H), 1.52 (s, 9H).

b) 1-(5-Methyl-2,3,4,5-tetrahydro-1H-pyrido[4,3-b]indol-7-yl)-4-(pyridin-2-ylmethoxy)pyridin-2(1H)-one dihydrochloride

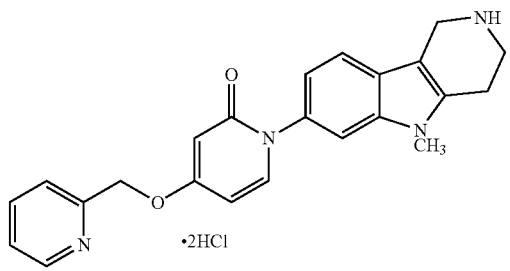

Chemical Formula: $C_{23}H_{24}Cl_2N_4O_2$
Exact Mass: 458.13
Molecular Weight: 459.37 tert-Butyl 5-methyl-7-(2-oxo-4-(pyridin-2-ylmethoxy)pyridin-1(2H)-yl)-3,4-dihydro-1H-pyrido[4,3-b]indole-2(5H)-carboxylate (113 mg, 0.23 mmol) was deprotected and converted to the dihydrochloride salt according to the procedure of Example 30 (steps e and g) to provide the title compound (81 mg, 77%) as a white solid: mp 206-211° C.; $^1$H NMR (300 MHz, CDCl$_3$) δ 8.88 (d, J=5.2 Hz, 1H), 8.59 (dd, J=7.9, 1.5 Hz, 1H), 8.15 (d, J=8.0 Hz, 1H), 8.01 (overlapping dd, J=6.6 Hz, 1H), 7.69 (d, J=7.6 Hz, 1H), 7.60 (d, J=8.4 Hz, 1H), 7.48 (d, J=1.6 Hz, 1H), 7.06 (dd, J=8.4, 1.8 Hz, 1H), 6.44 (dd, J=7.6, 2.7 Hz, 1H), 6.21 (d, J=2.7 Hz, 1H), 5.57 (s, 2H), 4.48 (s, 2H), 3.74 (s, 3H), 3.68 (t, J=6.2 Hz, 2H), 3.21 (t, J=6.2 Hz, 2H); ESI MS m/z 387 [M+H]$^+$; HPLC (Method B) 98% (AUC), $t_R$=9.3 min.

Example 54

Preparation of 1-(2,5-Dimethyl-2,3,4,5-tetrahydro-1H-pyrido[4,3-b]indol-7-yl)-4-(pyridin-2-ylmethoxy)pyridin-2(1H)-one dihydrochloride

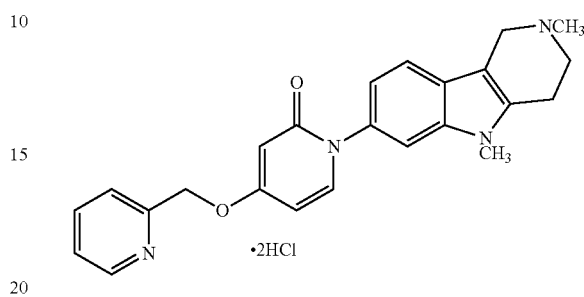

Chemical Formula: $C_{24}H_{26}Cl_2N_4O_2$
Exact Mass: 472.14
Molecular Weight: 473.39

1-(5-Methyl-2,3,4,5-tetrahydro-1H-pyrido[4,3-b]indol-7-yl)-4-(pyridin-2-ylmethoxy)pyridin-2(1H)-one (45 mg, 0.116 mmol) was reacted according to the procedure of Example 47 to provide the free-base. Conversion to the dihydrochloride salt using the procedure of Example 30 (step g) provided the title compound (54 mg, 98%) as a white solid: mp 260-265° C.; $^1$H NMR (500 MHz, CD$_3$OD) δ 8.87 (d, J=5.7 Hz, 1H), 8.58 (overlapping dd, J=8.2 Hz, 1H), 8.14 (d, J=7.9 Hz, 1H), 8.00 (overlapping dd, J=6.6 Hz, 1H), 7.69 (d, J=7.6 Hz, 1H), 7.59 (d, J=8.3 Hz, 1H), 7.49 (s, 1H), 7.07 (dd, J=8.3, 1.7 Hz, 1H), 6.44 (dd, J=7.5, 2.6 Hz, 1H), 6.20 (d, J=2.0 Hz, 1H), 5.56 (s, 2H), 4.76 (d, J=14.2 Hz, 1H), 4.40 (d, J=14.2 Hz, 1H), 3.91 (m, 1H), 3.74 (s, 3H), 3.61 (m, 1H), 3.29-3.17 (m overlapping with solvent, 2H), 3.13 (s, 3H); ESI MS m/z 401 [M+H]$^+$; HPLC (Method B)>99% (AUC), $t_R$=9.2 min.

Example 55

Preparation of 1-(9-Methyl-2,3,4,9-tetrahydro-1H-pyrido[3,4-b]indol-7-yl)-4-(pyridin-2-ylmethoxy)pyridin-2(1H)-one dihydrochloride a) tert-Butyl 9-methyl-7-(2-oxo-4-(pyridin-2-ylmethoxy)pyridin-1(2H)-yl)-3,4-dihydro-1H-pyrido[3,4-b]indole-2(9H)-carboxylate

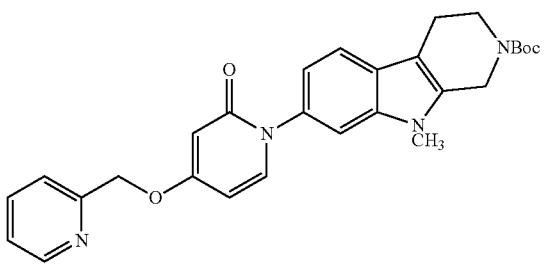

Chemical Formula: $C_{28}H_{30}N_4O_4$
Exact Mass: 486.23
Molecular Weight: 486.56

4-(Pyridin-2-ylmethoxy)pyridin-2(1H)-one (138 mg, 0.682 mmol) and tert-butyl 7-bromo-9-methyl-3,4-dihydro-1H-pyrido[3,4-b]indole-2(9H)-carboxylate (250 mg, 0.68 mmol) were reacted following the procedure of Example 30 (step g) to provide the title compound (170 mg, 51%) as a white foam: $^1$H NMR (300 MHz, CDCl$_3$) δ 8.63 (d, J=4.1 Hz, 1H), 7.76 (overlapping ddd, J=7.7, 1.7 Hz, 1H), 7.53 (d, J=8.3 Hz, 1H), 7.48 (d, J=7.8 Hz, 1H), 7.33 (d, J=7.4 Hz, 1H), 7.29-7.26 (m overlapping with solvent, 2H), 7.01 (dd, J=8.2, 1.8 Hz, 1H), 6.12-6.07 (m, 2H), 5.19 (s, 2H), 4.63 (s, 2H), 3.74 (br s, 2H), 3.62 (s, 3H), 2.79 (s, 2H), 1.51 (s, 9H).

b) 1-(9-Methyl-2,3,4,9-tetrahydro-1H-pyrido[3,4-b]indol-7-yl)-4-(pyridin-2-ylmethoxy)pyridin-2(1H)-one dihydrochloride

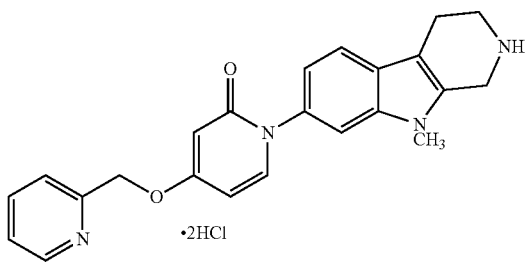

Chemical Formula: C$_{23}$H$_{24}$Cl$_2$N$_4$O$_2$
Exact Mass: 458.13
Molecular Weight: 459.37 tert-Butyl 9-methyl-7-(2-oxo-4-(pyridin-2-ylmethoxy)pyridin-1(2H)-yl)-3,4-dihydro-1H-pyrido[3,4-b]indole-2(9H)-carboxylate (167 mg, 0.34 mmol) was deprotected and converted to the dihydrochloride salt according to the procedure of Example 30 (steps e and g) to provide the title compound (124 mg, 79%) as a yellow solid: mp 226-231° C.; $^1$H NMR (500 MHz, CD$_3$OD) δ 8.89 (d, J=5.4 Hz, 1H), 8.61 (overlapping ddd, J=8.0, 1.6 Hz, 1H), 8.16 (d, J=8.0 Hz, 1H), 8.02 (overlapping dd, J=6.6 Hz, 1H), 7.70 (d, J=7.6 Hz, 1H), 7.63 (d, J=8.4 Hz, 1H), 7.47 (d, J=1.6 Hz, 1H), 7.06 (dd, J=8.4, 1.8 Hz, 1H), 6.44 (dd, J=7.6, 2.7 Hz, 1H), 6.21 (d, J=2.6 Hz, 1H), 5.57 (s, 2H), 4.56 (s, 2H), 3.73 (s, 3H), 3.60 (t, J=6.0, 2H), 3.13 (t, J=6.0, 2H); ESI MS m/z 387 [M+H]$^+$; HPLC (Method B) 98.6% (AUC), t$_R$=9.2 min.

Example 56

Preparation of 1-(9-Methyl-2,3,4,9-tetrahydro-1H-pyrido[3,4-b]indol-7-yl)-4-phenethylpyridin-2(1H)-one dihydrochloride a) tert-Butyl 9-methyl-7-(2-oxo-4-phenethylpyridin-1(2H)-yl)-3,4-dihydro-1H-pyrido[3,4-b]indole-2(9H)-carboxylate

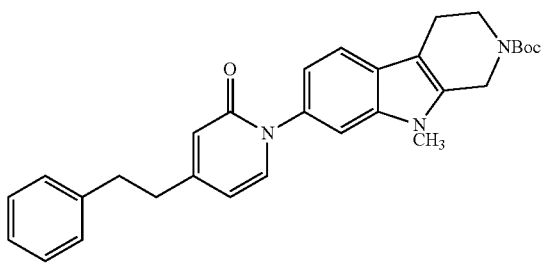

Chemical Formula: C$_{30}$H$_{33}$N$_3$O$_3$
Exact Mass: 483.25
Molecular Weight: 483.60

4-Phenethylpyridin-2(1H)-one (817 mg, 4.10 mmol) and tert-butyl 7-bromo-9-methyl-3,4-dihydro-1H-pyrido[3,4-b]indole-2(9H)-carboxylate (1.5 g, 4.1 mmol) were reacted following the procedure of Example 30 (step g) to provide the title compound (1.2 g, 60%) as a yellow solid: $^1$H NMR (300 MHz, CDCl$_3$) δ 7.53 (d, J=8.1 Hz, 1H), 7.34-7.29 (m, 4H), 7.26-7.20 (m, 3H), 7.03 (dd, J=8.2, 1.5 Hz, 1H), 6.50 (s, 1H), 6.09 (dd, J=6.9, 1.6 Hz, 1H), 4.63 (br s, 2H), 3.74 (br s, 2H), 3.63 (s, 3H), 2.98-2.91 (m, 2H), 2.84-2.79 (m, 4H), 1.51 (s, 9H).

b) 1-(9-Methyl-2,3,4,9-tetrahydro-1H-pyrido[3,4-b]indol-7-yl)-4-phenethylpyridin-2(1H)-one dihydrochloride

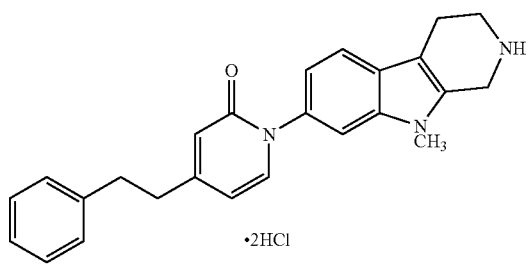

Chemical Formula: C$_{25}$H$_{27}$Cl$_2$N$_3$O
Exact Mass: 455.15
Molecular Weight: 456.41 tert-Butyl 9-methyl-7-(2-oxo-4-phenethylpyridin-1(2H)-yl)-3,4-dihydro-1H-pyrido[3,4-b]indole-2(9H)-carboxylate (1.2 g, 2.4 mmol) was deprotected and converted to the dihydrochloride salt according to the procedure of Example 30 (steps e and g) to provide the title compound (550 mg, 51%) as a yellow solid: mp 280-295° C.; $^1$H NMR (300 MHz, DMSO-d$_6$) δ 9.67 (s, 2H), 7.59-7.52 (m, 3H), 7.35-7.27 (m, 4H), 7.24-7.17 (m, 1H), 7.01 (dd, J=7.4, 2.0 Hz, 1H), 6.38-6.27 (m, 2H), 4.45 (s, 2H), 3.67 (s, 3H), 3.42 (t, J=6.4 Hz, 2H), 2.97-2.89 (m, 4H), 2.81-2.76 (m, 2H); ESI MS m/z 384 [M+H]$^+$; HPLC (Method B)>99% (AUC), t$_R$=13.3 min.

Example 57

Preparation of 4-(5-Chloropyridin-2-yl)-1-(5-methyl-2,3,4,5-tetrahydro-1H-pyrido[4,3-b]indol-7-yl)pyridin-2(1H)-one dihydrochloride a) tert-Butyl 7-(4-(5-chloropyridin-2-yl)-2-oxopyridin-1(2H)-yl)-5-methyl-3,4-dihydro-1H-pyrido[4,3-b]indole-2(5H)-carboxylate

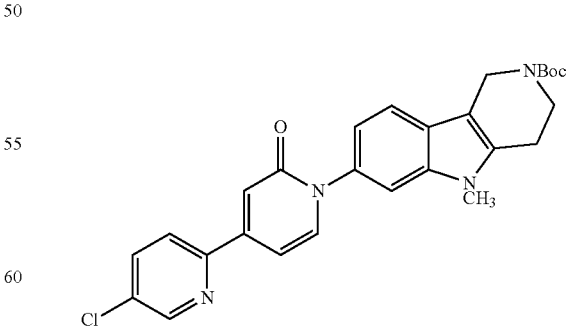

Chemical Formula: C$_{27}$H$_{27}$ClN$_4$O$_3$
Exact Mass: 490.18
Molecular Weight: 490.98

4-(5-Chloropyridin-2-yl)pyridin-2(1H)-one (111 mg, 0.537 mmol) and tert-butyl 7-bromo-5-methyl-3,4-dihydro-1H-pyrido[4,3-b]indole-2(5H)-carboxylate (200 mg, 0.54 mmol) were reacted following the procedure of Example 30 (step g) to provide the title compound (80 mg, 30%) as a green solid: ¹H NMR (500 MHz, CDCl₃) δ 8.69 (d, J=2.2 Hz, 1H), 7.79 (dd, J=8.5, 2.4 Hz, 1H), 7.74 (d, J=8.5 Hz, 1H), 7.53 (d, J=7.2 Hz, 2H), 7.36 (d, J=1.5 Hz, 1H), 7.17 (d, J=1.5 Hz, 1H), 7.07 (d, J=7.4 Hz, 1H), 6.98 (dd, J=7.1, 1.8 Hz, 1H), 4.65 (br s, 2H), 3.85 (br s, 2H), 3.65 (s, 3H), 2.83 (br s, 2H), 1.50 (s, 9H).

b) 4-(5-Chloropyridin-2-yl)-1-(5-methyl-2,3,4,5-tetrahydro-1H-pyrido[4,3-b]indol-7-yl)pyridin-2(1H)-one dihydrochloride

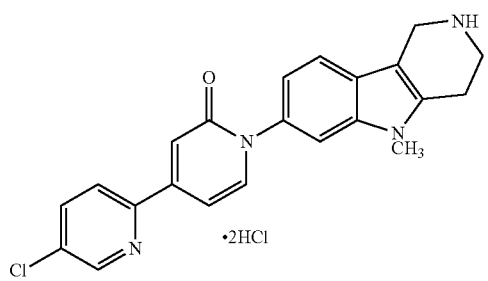

Chemical Formula: C₂₂H₂₁Cl₃N₄O
Exact Mass: 462.08
Molecular Weight: 463.79 tert-Butyl 7-(4-(5-chloropyridin-2-yl)-2-oxopyridin-1(2H)-yl)-5-methyl-3,4-dihydro-1H-pyrido[4,3-b]indole-2(5H)-carboxylate (80 mg, 0.16 mmol) was deprotected and converted to the dihydrochloride salt according to the procedure of Example 30 (steps e and g) to provide the title compound (40 mg, 54%) as a white solid: ¹H NMR (500 MHz, CD₃OD) δ 8.74 (d, J=2.4 Hz, 1H), 8.06 (d, J=8.5 Hz, 1H), 8.02 (dd, J=8.7, 2.4 Hz, 1H), 7.86 (d, J=7.2 Hz, 1H), 7.64 (d, J=8.3 Hz, 1H), 7.58 (d, J=1.9 Hz, 1H), 7.37 (d, J=1.5 Hz, 1H), 7.27 (dd, J=8.5, 1.8 Hz, 1H), 7.15 (dd, J=8.4, 1.8 Hz, 1H), 4.50 (s, 2H), 3.75 (s, 3H), 3.68 (t, J=6.5 Hz, 2H), 3.22 (t, J=6.5 Hz, 2H); ESI MS m/z 391 [M+H]⁺; HPLC (Method B)>99% (AUC), t_R=12.2 min.

Example 59

Preparation of 1-(2,5-Dimethyl-2,3,4,5-tetrahydro-1H-pyrido[4,3-b]indol-7-yl)-4-((5-fluoropyridin-2-yl)methoxy)pyridin-2(1H)-one dihydrochloride

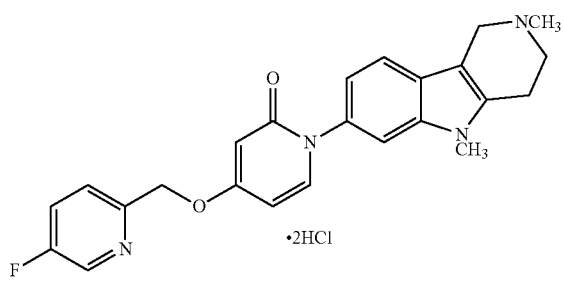

Chemical Formula: C₂₄H₂₅Cl₃FN₄O₂
Exact Mass: 490.13
Molecular Weight: 491.39

4-((5-Fluoropyridin-2-yl)methoxy)-1-(5-methyl-2,3,4,5-tetrahydro-1H-pyrido[4,3-b]indol-7-yl)pyridin-2(1H)-one (75 mg, 0.19 mmol) was reacted according to the procedure of Example 47 to provide the free-base. Conversion to the dihydrochloride salt using the procedure of Example 30 (step g) provided the title compound (71 mg, 78%) as a white solid: mp 215-230° C.; ¹H NMR (500 MHz, CD₃OD) δ 8.65 (d, J=2.6 Hz, 1H), 7.91 (overlapping ddd, J=9.6, 2.1 Hz, 1H), 7.83-7.20 (m, 2H), 7.61 (d, J=8.4 Hz, 1H), 7.53 (d, J=1.8 Hz, 1H), 7.09 (dd, J=8.4, 1.8 Hz, 1H), 6.59 (dd, J=7.5, 2.6 Hz, 1H), 6.36 (d, J=2.6 Hz, 1H), 5.41 (s, 2H), 4.76 (d, J=14.2 Hz, 1H), 4.39 (d, J=14.2 Hz, 1H), 3.94-3.82 (m, 2H), 3.74 (s, 3H), 3.65-3.58 (m, 2H), 3.13 (s, 3H); ESI MS m/z 419 [M+H]⁺; HPLC (Method B) 95.8% (AUC), t_R=11.0 min.

Example 60

Preparation of 4-(5-Chloropyridin-2-yl)-1-(2,5-dimethyl-2,3,4,5-tetrahydro-1H-pyrido[4,3-b]indol-7-yl)pyridin-2(1H)-one dihydrochloride

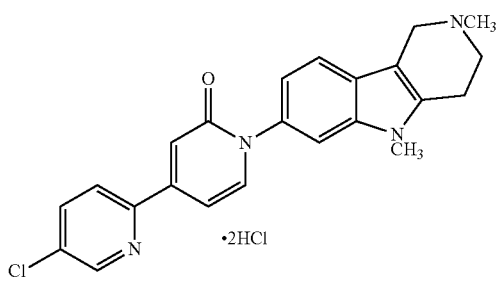

Chemical Formula: C₂₃H₂₃Cl₃N₄O
Exact Mass: 476.09
Molecular Weight: 477.81

4-(5-Chloropyridin-2-yl)-1-(5-methyl-2,3,4,5-tetrahydro-1H-pyrido[4,3-b]indol-7-yl)pyridin-2(1H)-one (57 mg, 0.14 mmol) was reacted according to the procedure of Example 47 to provide the free-base. Conversion to the dihydrochloride salt using the procedure of Example 30 (step g) provided the title compound (54.5 mg, 81%) as a yellow solid: ¹H NMR (500 MHz, CD₃OD) δ 8.72 (d, J=1.7 Hz, 1H), 8.03 (d, J=7.9 Hz, 1H), 7.99 (dd, J=8.2, 2.2 Hz, 1H), 7.79 (d, J=7.1 Hz, 1H), 7.61 (d, J=8.3 Hz, 1H), 7.56 (d, J=1.3 Hz, 1H), 7.34 (d, J=1.5 Hz, 1H), 7.19 (dd, J=7.2, 1.8 Hz, 1H), 7.14 (dd, J=8.3, 1.8 Hz, 1H), 4.80-4.72 (br m, 1H), 4.46-4.34 (m, 1H), 3.96-3.86 (m, 1H), 3.75 (s, 3H), 3.65-3.55 (br m, 1H), 3.28 (s, 2H), 3.14 (s, 3H); ESI MS m/z 405 [M+H]⁺; HPLC (Method B)>99% (AUC), t_R=12.0 min.

Example 61

Preparation of 4-(Benzyloxy)-1-(5-methyl-2-(2-(pyrrolidin-1-yl)ethyl)-2,3,4,5-tetrahydro-1H-pyrido[4,3-b]indol-7-yl)pyridin-2(1H)-one dihydrochloride

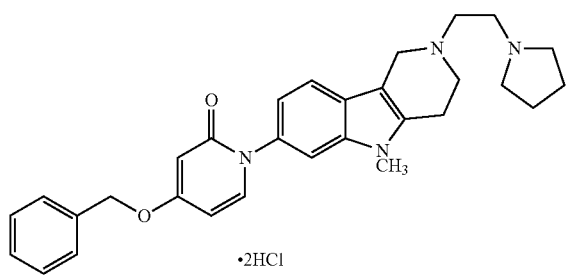

Chemical Formula: $C_{30}H_{36}Cl_2N_4O_2$
Exact Mass: 554.22
Molecular Weight: 555.54

4-(Benzyloxy)-1-(5-methyl-2,3,4,5-tetrahydro-1H-pyrido[4,3-b]indol-7-yl)pyridin-2(1H)-one (180 mg, 0.46 mmol), 1-(2-chloroethyl)pyrrolidine hydrochloride (95 mg, 0.56 mmol), (i-Pr)$_2$EtN (0.25 mL, 1.4 mmol) were combined in ethanol (2 mL) and heated at 60° C. for 2 h. Purification by preparative HPLC and conversion to the dihydrochloride salt using the procedure of Example 30 (step g) provided the title compound as a white solid: mp 285-289° C.; $^1$H NMR (300 MHz, D$_2$O) δ 7.50 (d, J=8.3 Hz, 1H), 7.46 (d, J=7.7 Hz, 1H), 7.42-7.31 (m, 6H), 6.96 (dd, J=8.3, 1.6 Hz, 1H), 6.27 (dd, J=7.7, 2.6 Hz, 1H), 6.10 (d, J=2.6 Hz, 1H), 5.90 (s, 2H), 4.59 (br s, 2H), 3.81-3.59 (m, 8H), 3.55 (s, 3H), 3.20 (t, J=5.7 Hz, 2H), 3.18-3.05 (br m, 2H), 2.15-1.90 (m, 4H); ESI MS m/z 483 [M+H]$^+$; HPLC (Method B) 98.8% (AUC), $t_R$=11.3 min.

Example 62

Preparation of 1-(2,5-Dimethyl-2,3,4,5-tetrahydro-1H-pyrido[4,3-b]indol-7-yl)-4-(5-(trifluoromethyl)pyridin-2-yl)pyridin-2(1H)-one dihydrochloride

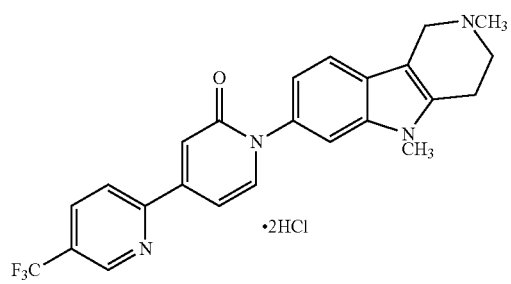

Chemical Formula: $C_{24}H_{23}Cl_2F_3N_4O$
Exact Mass: 510.12
Molecular Weight: 511.37

1-(5-Methyl-2,3,4,5-tetrahydro-1H-pyrido[4,3-b]indol-7-yl)-4-(5-(trifluoromethyl)pyridin-2-yl)pyridin-2(1H)-one (68 mg, 0.16 mmol) was reacted according to the procedure of Example 47 to provide the free-base. Conversion to the dihydrochloride salt using the procedure of Example 30 (step g) provided the title compound (39.6 mg, 48%) as a brown solid: mp 274-280° C.; $^1$H NMR (500 MHz, CD$_3$OD) δ 9.04 (s, 1H), 8.28 (dd, J=8.7, 1.9 Hz, 1H), 8.21 (d, J=2.1 Hz, 1H), 7.83 (d, J=7.1 Hz, 1H), 7.62 (d, J=8.3 Hz, 1H), 7.58 (d, J=1.3 Hz, 1H), 7.39 (d, J=1.6 Hz, 1H), 7.24 (dd, J=7.1, 1.9 Hz, 1H), 7.15 (dd, J=8.3, 1.7 Hz, 1H), 4.80-4.71 (br m, 1H), 4.44-4.35 (br m, 1H), 3.96-3.86 (br m, 1H), 3.75 (s, 3H), 3.67-3.57 (br m, 1H), 3.28 (s, 2H), 3.14 (s, 3H); ESI MS m/z 439 [M+H]$^+$; HPLC (Method B) 96.4% (AUC), $t_R$=12.6 min.

Example 63

Preparation of 1-(5-Methyl-2,3,4,5-tetrahydro-1H-pyrido[4,3-b]indol-7-yl)-4-(6-methylpyridazin-3-yl)pyridin-2(1H)-one dihydrochloride a) 3-(2-Methoxypyridin-4-yl)-6-methylpyridazine

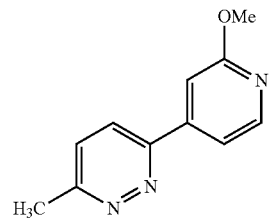

Chemical Formula: $C_{11}H_{11}N_3O$
Exact Mass: 201.09
Molecular Weight: 201.22

3-Chloro-6-methylpyridazine (343 mg, 2.67 mmol) and 2-methoxy-4-(4,4,5,5-tetramethyl-1,3,2-dioxaborolan-2-yl)pyridine (470 mg, 2.0 mmol) were reacted according to Example 31 (step a) to provide the title compound (183 mg, 45%) as a cream solid: $^1$H NMR (500 MHz, CDCl$_3$) δ 8.31 (d, J=5.3 Hz, 1H), 7.62 (d, J=8.7 Hz, 1H), 7.59 (dd, J=5.3, 1.5 Hz, 1H), 7.43 (d, J=8.6 Hz, 1H), 7.38 (s, 1H), 4.00 (s, 3H), 2.79 (s, 3H).

b) 4-(6-Methylpyridazin-3-yl)pyridin-2(1H)-one

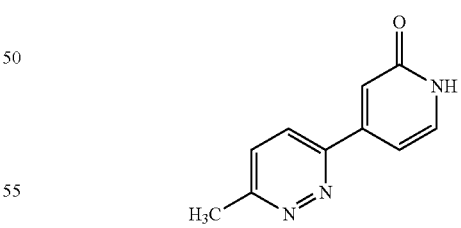

Chemical Formula: $C_{10}H_9N_3O$
Exact Mass: 187.07
Molecular Weight: 187.20

3-(2-Methoxypyridin-4-yl)-6-methylpyridazine (183 mg, 0.909 mmol) was reacted according to Example 31 (step c) to provide the title compound (133 mg, 75%) as a white solid: $^1$H NMR (300 MHz, CD$_3$OD) δ 8.12 (d, J=8.8 Hz, 1H), 7.73 (d, J=8.8 Hz, 1H), 7.59 (d, J=6.6 Hz, 1H), 7.17-7.14 (m, 2H), 2.75 (s, 3H).

c) tert-Butyl 5-methyl-7-(4-(6-methylpyridazin-3-yl)-2-oxopyridin-1(2H)-yl)-3,4-dihydro-1H-pyrido[4,3-b]indole-2(5H)-carboxylate

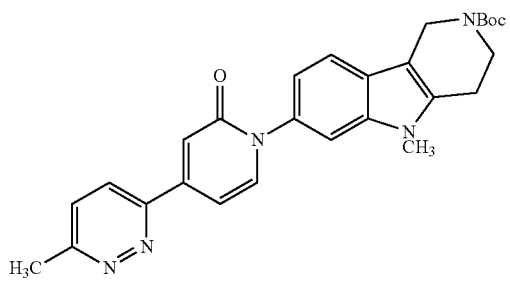

Chemical Formula: C₂₇H₂₉N₅O₃
Exact Mass: 471.23
Molecular Weight: 471.55

3-(2-Methoxypyridin-4-yl)-6-methylpyridazine (133 mg, 0.710 mmol) and tert-butyl 7-bromo-5-methyl-3,4-dihydro-1H-pyrido[4,3-b]indole-2(5H)-carboxylate (259 mg, 0.71 mmol) were reacted following the procedure of Example 30 (step g) to provide the title compound (200 mg, 59%) as a yellow solid: ¹H NMR (300 MHz, CDCl₃) δ 7.83 (d, J=8.7 Hz, 1H), 7.60 (d, J=7.2 Hz, 1H), 7.56 (d, J=8.3 Hz, 1H), 7.48 (d, J=8.8 Hz, 1H), 7.39 (d, J=1.6 Hz, 1H), 7.29 (overlapping ddd, J=7.3, 1.8 Hz, 1H), 7.17 (d, J=1.8 Hz, 1H), 7.11 (d, J=7.6 Hz, 1H), 4.67 (br s, 2H), 3.91-3.83 (br m, 2H), 3.67 (s, 3H), 2.89-2.83 (br m, 2H), 2.53 (s, 3H), 1.52 (s, 9H).

d) 1-(5-Methyl-2,3,4,5-tetrahydro-1H-pyrido[4,3-b]indol-7-yl)-4-(6-methylpyridazin-3-yl)pyridin-2(1H)-one dihydrochloride

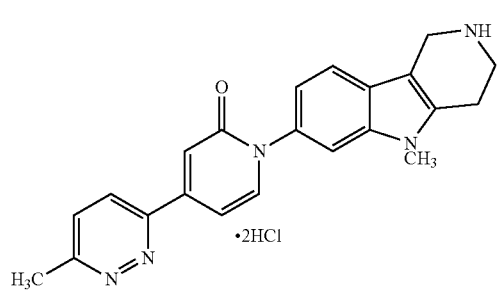

Chemical Formula: C₂₂H₂₂Cl₂N₅O
Exact Mass: 443.13
Molecular Weight: 444.36 tert-Butyl 5-methyl-7-(4-(6-methylpyridazin-3-yl)-2-oxopyridin-1(2H)-yl)-3,4-dihydro-1H-pyrido[4,3-b]indole-2(5H)-carboxylate (200 mg, 0.42 mmol) was deprotected and converted to the dihydrochloride salt according to the procedure of Example 30 (steps e and g) to provide the title compound (57 mg, 33%) as an orange solid: mp 310-315° C.; ¹H NMR (500 MHz, CD₃OD) δ 8.47 (d, J=8.8 Hz, 1H), 8.03 (d, J=8.8 Hz, 1H), 7.89 (d, J=7.4 Hz, 1H), 7.64 (d, J=8.4 Hz, 1H), 7.58 (d, J=1.6 Hz, 1H), 7.35 (d, J=1.6 Hz, 1H), 7.25 (dd, J=7.1, 1.9 Hz, 1H), 7.15 (dd, J=8.3, 1.9 Hz, 1H), 4.49 (s, 2H), 3.75 (s, 3H), 3.68 (t, J=6.2 Hz, 2H), 3.24 (t, J=6.2 Hz, 2H), 2.85 (s, 3H); ESI MS m/z 372 [M+H]⁺; HPLC (Method B) 98% (AUC), $t_R$=9.3 min.

Example 64

Preparation of 1-(2,5-Dimethyl-2,3,4,5-tetrahydro-1H-pyrido[4,3-b]indol-7-yl)-4-(6-methylpyridazin-3-yl)pyridin-2(1H)-one dihydrochloride

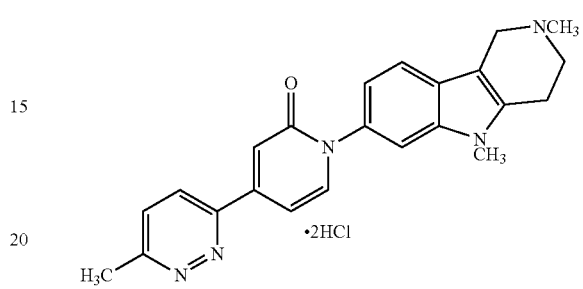

Chemical Formula: C₂₃H₂₅Cl₂N₅O
Exact Mass: 457.14
Molecular Weight: 458.38

1-(5-Methyl-2,3,4,5-tetrahydro-1H-pyrido[4,3-b]indol-7-yl)-4-(6-methylpyridazin-3-yl)pyridin-2(1H)-one (77 mg, 0.21 mmol) was reacted according to the procedure of Example 47 to provide the free-base. Conversion to the dihydrochloride salt using the procedure of Example 30 (step g) provided the title compound (60 mg, 74%) as a yellow solid: mp 285-288° C.; ¹H NMR (300 MHz, DMSO-d₆) δ 10.9 (s, 1H), 8.32 (d, J=8.8 Hz, 1H), 7.85 (d, J=7.2 Hz, 1H), 7.79 (d, J=8.8 Hz, 1H), 7.64 (d, J=1.5 Hz, 1H), 7.56 (d, J=8.3 Hz, 1H), 7.25 (d, J=1.7 Hz, 1H), 7.14-7.11 (m, 2H), 4.65 (d, J=12.1 Hz, 1H), 4.31 (dd, J=14.2, 7.5 Hz, 1H), 3.81-3.74 (m, 1H), 3.71 (s, 3H), 3.55-3.45 (m, 1H), 3.26-3.15 (m, 2H), 2.98 (s, 3H), 2.72 (s, 3H); ESI MS m/z 386 [M+H]⁺; HPLC (Method B)>99% (AUC), $t_R$=9.4 min.

Example 65

Preparation of 4-(4-Fluoro-2-methoxyphenyl)-1-(5-methyl-2,3,4,5-tetrahydro-1H-pyrido[4,3-b]indol-7-yl)pyridin-2(1H)-one hydrochloride a) 4-(4-Fluoro-2-methoxyphenyl)pyridine 1-oxide

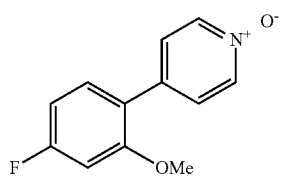

Chemical Formula: C₁₂H₁₀FNO₂
Exact Mass: 219.07
Molecular Weight: 219.21

4-Chloropyridine-N-oxide (305 mg, 2.35 mmol), 4-fluoro-2-methoxyphenylboronic acid (1.0 g, 8.8 mmol) were reacted according to the procedure of Example 39 (step a) to provide the title compound (450 mg, 87%) as a purple solid: ¹H NMR (300 MHz, CDCl₃) δ 8.21 (d, J=7.2 Hz, 2H), 7.45 (d, J=7.2 Hz, 2H), 7.31 (d, J=6.5 Hz, 1H), 6.80-6.71 (m, 2H), 3.85 (s, 3H).

b) 4-(4-Fluoro-2-methoxyphenyl)pyridin-2(1H)-one

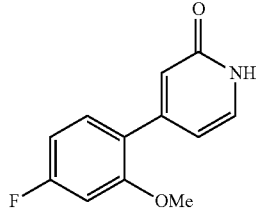

Chemical Formula: C₁₂H₁₀FNO₂
Exact Mass: 219.07
Molecular Weight: 219.21

4-(4-Fluoro-2-methoxyphenyl)pyridine 1-oxide (450 mg, 2.05 mmol) was reacted according to the procedure of Example 32 (step b) to provide the title compound (291 mg, 66%) as a brown solid: ¹H NMR (300 MHz, DMSO-d₆) δ 11.4 (br s, 1H), 7.39-7.31 (m, 2H), 7.03 (d, J=10.2 Hz, 1H), 6.85 (overlapping dd, J=7.4 Hz, 1H), 6.35 (s, 1H), 6.27 (d, J=6.1 Hz, 1H), 3.80 (s, 3H).

c) tert-Butyl 7-(4-(4-fluoro-2-methoxyphenyl)-2-oxopyridin-1(2H)-yl)-5-methyl-3,4-dihydro-1H-pyrido[4,3-b]indole-2(5H)-carboxylate

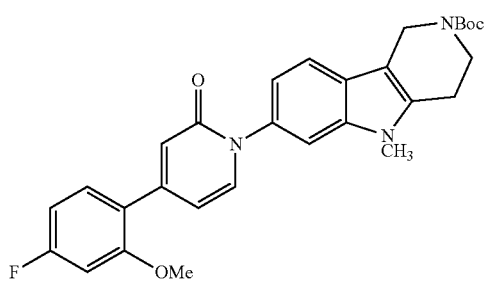

Chemical Formula: C₂₉H₃₀FN₃O₄
Exact Mass: 503.22
Molecular Weight: 503.56

4-(4-Fluoro-2-methoxyphenyl)pyridin-2(1H)-one (100 mg, 0.45 mmol) and tert-butyl 7-bromo-5-methyl-3,4-dihydro-1H-pyrido[4,3-b]indole-2(5H)-carboxylate (166 mg, 0.454 mmol) were reacted following the procedure of Example 30 (step g) to provide the title compound (106 mg, 46%) as a yellow oil: ¹H NMR (300 MHz, CDCl₃) δ 7.53 (d, J=8.2 Hz, 1H), 7.41 (d, J=7.1 Hz, 1H), 7.39-7.32 (m, 2H), 7.08 (d, J=8.0 Hz, 1H), 6.80-6.70 (m, 3H), 6.46 (dd, J=7.1, 1.9 Hz, 1H), 4.66 (br s, 2H), 3.87 (s, 3H), 3.86-3.78 (m, 2H), 3.64 (s, 3H), 2.83 (t, J=6.1 Hz, 2H), 1.50 (s, 9H).

d) 4-(4-Fluoro-2-methoxyphenyl)-1-(5-methyl-2,3,4,5-tetrahydro-1H-pyrido[4,3-b]indol-7-yl)pyridin-2(1H)-one hydrochloride

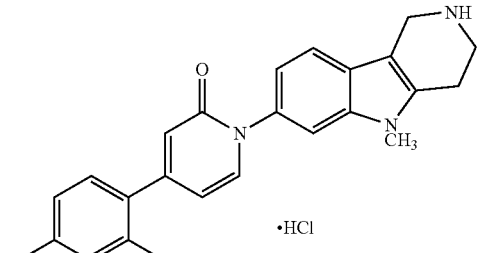

Chemical Formula: C₂₄H₂₃ClFN₃O₂
Exact Mass: 439.15
Molecular Weight: 439.91 tert-Butyl 7-(4-(4-fluoro-2-methoxyphenyl)-2-oxopyridin-1(2H)-yl)-5-methyl-3,4-dihydro-1H-pyrido[4,3-b]indole-2(5H)-carboxylate (106 mg, 0.211 mmol) was deprotected according to the procedure of Example 30 (step e) to provide the free base (74 mg, 88%). The free-base (37 mg, 0.092 mmol) was converted to the hydrochloride salt according to the procedure of Example 30 (steps g) to provide the title compound (35 mg, 89%) as a yellow solid: mp 296-300° C.; ¹H NMR (300 MHz, DMSO-d₆) δ 9.56 (br s, 2H), 7.64 (d, J=7.1 Hz, 1H), 7.62-7.55 (m, 2H), 7.47 (dd, J=8.4, 6.9 Hz, 1H), 7.12-7.06 (m, 2H), 6.90 (overlapping ddd, J=8.4, 2.4 Hz, 1H), 6.55 (d, J=1.6 Hz, 1H), 6.47 (dd, J=7.1, 1.8 Hz, 1H), 4.37-4.30 (br m, 2H), 3.81 (s, 3H), 3.69 (s, 3H), 3.56-3.45 (br m, 2H), 3.10 (t, J=5.5 Hz, 2H); ESI MS m/z 404 [M+H]⁺; HPLC (Method B)>99% (AUC), t_R=12.5 min.

Example 66

Preparation of 1-(2,5-Dimethyl-2,3,4,5-tetrahydro-1H-pyrido[4,3-b]indol-7-yl)-4-(4-fluoro-2-methoxyphenyl)pyridin-2(1H)-one hydrochloride

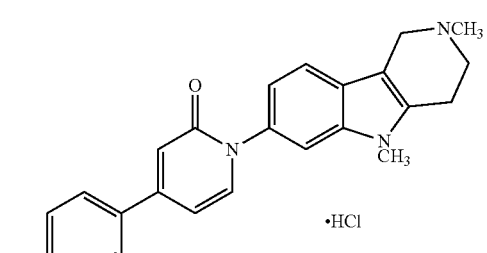

Chemical Formula: C₂₅H₂₅ClFN₃O₂
Exact Mass: 453.16
Molecular Weight: 453.94

4-(4-Fluoro-2-methoxyphenyl)-1-(5-methyl-2,3,4,5-tetrahydro-1H-pyrido[4,3-b]indol-7-yl)pyridin-2(1H)-one (37 mg, 0.092 mmol) was reacted according to the procedure of Example 47 to provide the free-base. Conversion to the dihydrochloride salt using the procedure of Example 30 (step g) provided the title compound (21 mg, 52%) as a yellow solid: mp 294-298° C.; ¹H NMR (300 MHz, DMSO-d₆) δ 10.83 (br s, 1H), 7.65 (d, J=7.1 Hz, 1H), 7.61 (d, J=1.4 Hz, 1H), 7.54 (d, J=8.3 Hz, 1H), 7.46 (dd, J=8.4, 6.9 Hz, 1H), 7.12-7.10 (m, 1H), 7.08 (d, J=1.4 Hz, 1H), 6.91 (overlapping ddd, J=8.4, 2.4 Hz, 1H), 6.55 (d, J=1.6 Hz, 1H), 6.48 (dd, J=7.1, 1.6 Hz, 1H), 4.62 (d, J=12.2 Hz, 1H), 4.30 (dd, J=14.2, 7.5 Hz, 1H), 3.86 (s, 3H), 3.80-3.76 (m, 1H), 3.75 (s, 3H), 3.52-3.42 (m, 1H), 3.24-3.15 (m, 2H), 2.79 (d, J=4.6 Hz, 3H); ESI MS m/z 418 [M+H]⁺; HPLC (Method B)>99% (AUC), $t_R$=12.6 min.

Example 67

Preparation of 4-(Benzyloxy)-1-(5-methyl-2-(piperidin-4-yl)-2,3,4,5-tetrahydro-1H-pyrido[4,3-b]indol-7-yl)pyridin-2(1H)-one dihydrochloride a) tert-Butyl 4-(7-(4-(benzyloxy)-2-oxopyridin-1(2H)-yl)-5-methyl-3,4-dihydro-1H-pyrido[4,3-b]indol-2(5H)-yl)piperidine-1-carboxylate

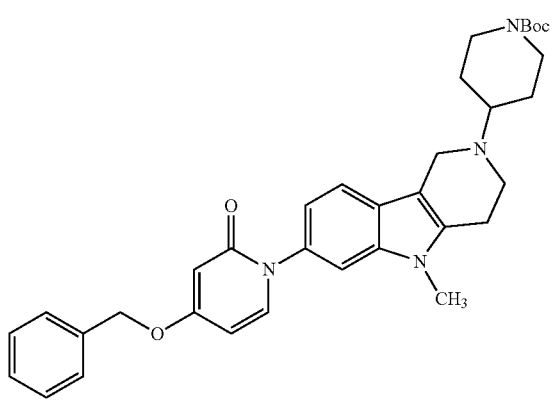

Chemical Formula: C₃₄H₄₀N₄O₄
Exact Mass: 568.30
Molecular Weight: 568.71

4-(Benzyloxy)-1-(5-methyl-2,3,4,5-tetrahydro-1H-pyrido[4,3-b]indol-7-yl)pyridin-2(1H)-one (100 mg, 0.26 mmol) and tert-butyl 4-oxopiperidine-1-carboxylate (27 mg, 0.26 mmol) were stirred in methylene chloride (1 mL) and AcOH (0.1 mL), and picoline borane complex (27 mg, 0.26 mmol) was added. After stirring for 16 h, the mixture was diluted with methylene chloride, washed with sodium carbonate solution and concentrated. The obtained residue was purified by flash column chromatography (silica gel, (1:1 EtOAc/hexanes)/(10:1 methanol/ammonia), 10:0 to 9:1) to provide the title compound (90 mg, 61%) as a white solid: ¹H NMR (300 MHz, CDCl₃) δ 7.45-7.36 (m, 5H), 7.32-7.30 (m, 1H), 7.32-7.27 (m, 2H), 6.99 (dd, J=8.2, 1.6 Hz, 1H), 6.05-6.01 (m, 2H), 5.05 (s, 2H), 4.20 (s, 2H), 3.85 (s, 2H), 3.60 (s, 3H), 3.04-2.93 (m, 2H), 2.88-2.66 (m, 5H), 1.98-1.87 (m, 2H), 1.60-1.54 (m, 2H), 1.47 (s, 9H).

b) 4-(Benzyloxy)-1-(5-methyl-2-(piperidin-4-yl)-2,3,4,5-tetrahydro-1H-pyrido[4,3-b]indol-7-yl)pyridin-2(1H)-one dihydrochloride

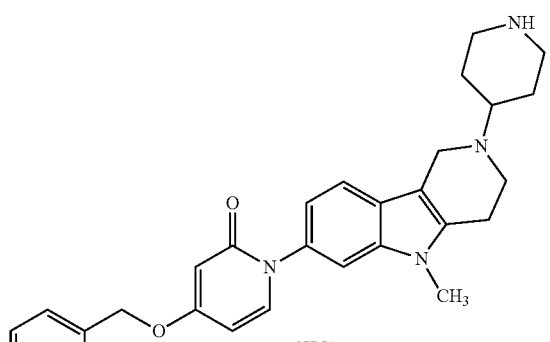

Chemical Formula: C₂₉H₃₄Cl₂N₄O₄
Exact Mass: 540.21
Molecular Weight: 541.51 tert-Butyl 4-(7-(4-(benzyloxy)-2-oxopyridin-1(2H)-yl)-5-methyl-3,4-dihydro-1H-pyrido[4,3-b]indol-2(5H)-yl)piperidine-1-carboxylate (90 mg, 0.16 mmol) was deprotected and converted to the dihydrochloride salt according to the procedure of Example 30 (steps e and g) to provide the title compound (85 mg, 100%) as an orange solid: ¹H NMR (500 MHz, D₂O) δ 7.56-7.53 (m, 2H), 7.48-7.40 (m, 6H), 7.02 (dd, J=8.4, 1.4 Hz, 1H), 6.33 (dd, J=7.5, 2.4 Hz, 1H), 6.17 (d, J=2.4 Hz, 1H), 5.16 (s, 2H), 4.63 (br s, 2H), 4.09-3.79 (br m, 2H), 3.69-3.53 (m, 6H), 3.26-3.23 (m, 2H), 3.14 (t, J=12.8 Hz, 2H), 2.49 (d, J=1.3 Hz, 2H), 2.16-2.04 (m, 2H); ESI MS m/z 469 [M+H]⁺; HPLC (Method B) 98.1% (AUC), $t_R$=11.4 min.

Example 68

Preparation of 4-(Benzyloxy)-1-(5-methyl-2-(1-methylpiperidin-4-yl)-2,3,4,5-tetrahydro-1H-pyrido[4,3-b]indol-7-yl)pyridin-2(1H)-one dihydrochloride

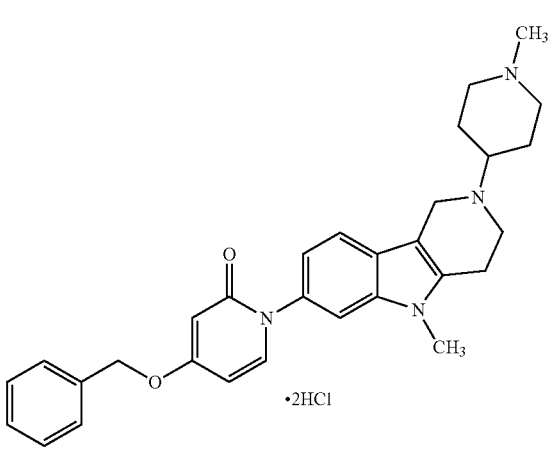

Chemical Formula: C₃₀H₃₆Cl₂N₄O₂
Exact Mass: 554.22
Molecular Weight: 555.54

4-(Benzyloxy)-1-(5-methyl-2-(piperidin-4-yl)-2,3,4,5-tetrahydro-1H-pyrido[4,3-b]indol-7-yl)pyridin-2(1H)-one (50 mg, 0.11 mmol) was methylated according to the procedure of Example 47 to provide the title compound (30 mg, 51%) as a white solid: $^1$H NMR (500 MHz, D$_2$O) δ 7.56-7.52 (m, 2H), 7.48-7.38 (m, 6H), 7.02 (dd, J=8.3, 1.6 Hz, 1H), 6.33 (dd, J=7.5, 2.6 Hz, 1H), 6.16 (d, J=2.5 Hz, 1H), 5.16 (s, 2H), 4.63 (s, 2H), 3.85-3.83 (m, 2H), 3.74-3.71 (m, 2H), 3.62 (s, 3H), 3.26-3.14 (m, 5H), 2.89 (s, 3H), 2.55-2.50 (m, 2H), 2.19-2.12 (m, 2H); ESI MS m/z 483 [M+H]$^+$; HPLC (Method B)>99% (AUC), $t_R$=11.4 min.

Example 69

Preparation of 1-(5-Methyl-2,3,4,5-tetrahydro-1H-pyrido[4,3-b]indol-7-yl)-4-(6-(trifluoromethyl)pyridin-3-yl)pyridin-2(1H)-one dihydrochloride a) 2'-Methoxy-6-(trifluoromethyl)-3,4'-bipyridine

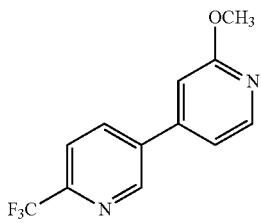

Chemical Formula: C$_{12}$H$_9$F$_3$N$_2$O
Exact Mass: 254.07
Molecular Weight: 254.21

2-Methoxy-4-(4,4,5,5-tetramethyl-1,3,2-dioxaborolan-2-yl)pyridine (1.24 g, 0.53 mmol) and 5-bromo-2-(trifluoromethyl)pyridine (2.4 g, 11 mmol) were reacted according to the procedure of Example 31 (step a) to provide the title compound (1.1 g, 81%) as a white solid: ESI MS m/z 255 [M+H].

b) 4-(6-(Trifluoromethyl)pyridin-3-yl)pyridin-2 (1H)-one

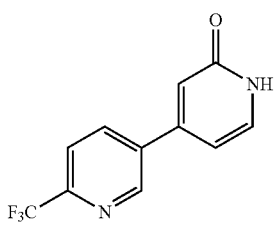

Chemical Formula: C$_{11}$H$_7$F$_3$N$_2$O
Exact Mass: 240.05
Molecular Weight: 240.18

2'-Methoxy-6-(trifluoromethyl)-3,4'-bipyridine (1.1 g, 4.3 mmol) was reacted according to the procedure of Example 31 (step c) to provide the title compound (522 mg, 50%) as a white solid: $^1$H NMR (500 MHz, DMSO-d$_6$) δ 11.8 (br s, 1H), 9.10 (s, 1H), 8.40 (dd, J=8.1, 1.2 Hz, 1H), 8.00 (d, J=8.2 Hz, 1H), 7.56 (d, J=6.7 Hz, 1H), 6.81 (s, 1H), 6.63 (dd, J=6.7, 1.3 Hz, 1H).

c) tert-Butyl 5-methyl-7-(2-oxo-4-(6-(trifluoromethyl)pyridin-3-yl)pyridin-1(2H)-yl)-3,4-dihydro-1H-pyrido[4,3-b]indole-2(5H)-carboxylate

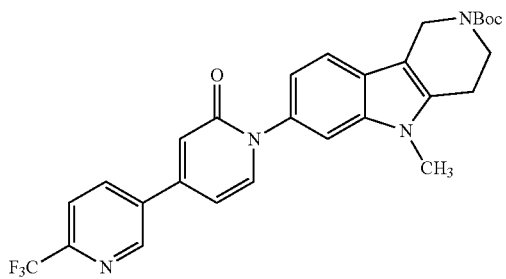

Chemical Formula: C$_{28}$H$_{27}$F$_3$N$_4$O$_3$
Exact Mass: 524.20
Molecular Weight: 524.53

4-(6-(Trifluoromethyl)pyridin-3-yl)pyridin-2(1H)-one (131 mg, 0.54 mmol) and tert-butyl 7-bromo-5-methyl-3,4-dihydro-1H-pyrido[4,3-b]indole-2(5H)-carboxylate (200 mg, 0.54 mmol) were reacted following the procedure of Example 30 (step g) to provide the title compound (167 mg, 59%) as a green solid: $^1$H NMR (300 MHz, CDCl$_3$) δ 8.99 (d, J=2.0 Hz, 1H), 8.10 (dd, J=8.1, 1.8 Hz, 1H), 7.84 (d, J=8.2 Hz, 1H), 7.60-7.54 (m, 2H), 7.32 (d, J=1.9 Hz, 1H), 7.07 (d, J=8.0 Hz, 1H), 6.93 (d, J=1.8 Hz, 1H), 6.49 (dd, J=7.1, 2.0 Hz, 1H), 4.66 (s, 2H), 3.85 (br m, 2H), 3.65 (s, 3H), 2.84 (s, 2H), 1.50 (s, 9H).

d) 1-(5-Methyl-2,3,4,5-tetrahydro-1H-pyrido[4,3-b]indol-7-yl)-4-(6-(trifluoromethyl)pyridin-3-yl)pyridin-2(1H)-one dihydrochloride

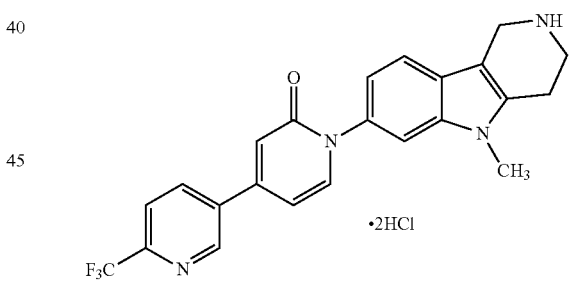

Chemical Formula: C$_{23}$H$_{21}$Cl$_2$F$_3$N$_4$O
Exact Mass: 496.10
Molecular Weight: 497.34 tert-Butyl 5-methyl-7-(2-oxo-4-(6-(trifluoromethyl)pyridin-3-yl)pyridin-1(2H)-yl)-3,4-dihydro-1H-pyrido[4,3-b]indole-2(5H)-carboxylate (165 mg, 0.315 mmol) was deprotected and converted to the dihydrochloride salt according to the procedure of Example 30 (steps e and g) to provide the title compound (40 mg, 26%) as a yellow solid: $^1$H NMR (300 MHz, CD$_3$OD) δ 9.10 (d, J=2.0 Hz, 1H), 8.41 (dd, J=8.2, 1.7 Hz, 1H), 7.98 (d, J=8.2 Hz, 1H), 7.85 (d, J=7.2 Hz, 1H), 7.61 (d, J=8.2 Hz, 1H), 7.57 (d, J=1.6 Hz, 1H), 7.14 (dd, J=8.3, 1.9 Hz, 1H), 7.02 (d, J=1.6 Hz, 1H), 6.89 (dd, J=7.1, 2.0 Hz, 1H), 4.49 (s, 2H), 3.76 (s, 3H), 3.68 (t, J=6.2 Hz, 2H), 3.22 (t, J=6.2 Hz, 2H); ESI MS m/z 425 [M+H]$^+$; HPLC (Method B)>99% (AUC), $t_R$=12.3 min.

Example 70

Preparation of 1-(2,5-Dimethyl-2,3,4,5-tetrahydro-1H-pyrido[4,3-b]indol-7-yl)-4-(6-(trifluoromethyl)pyridin-3-yl)pyridin-2(1H)-one

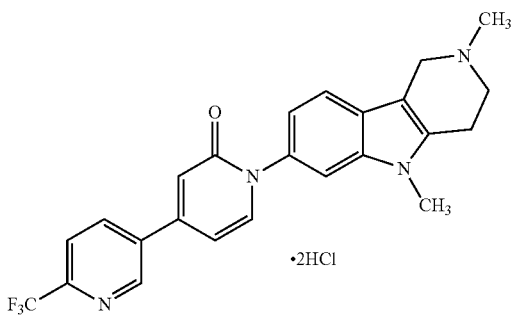

Chemical Formula: $C_{24}H_{23}Cl_2F_3N_4O$
Exact Mass: 510.12
Molecular Weight: 511.37

1-(5-Methyl-2,3,4,5-tetrahydro-1H-pyrido[4,3-b]indol-7-yl)-4-(6-(trifluoromethyl)pyridin-3-yl)pyridin-2(1H)-one (77 mg, 0.18 mmol) was reacted according to the procedure of Example 47 and converted to the dihydrochloride to provide the title compound (27 mg, 29%) as a yellow solid: mp 295-300° C.; $^1$H NMR (500 MHz, CD$_3$OD) δ 9.09 (d, J=1.7 Hz, 1H), 8.42 (dd, J=8.1, 2.0 Hz, 1H), 7.97 (d, J=8.2 Hz, 1H), 7.85 (d, J=7.1 Hz, 1H), 7.62 (d, J=8.3 Hz, 1H), 7.58 (d, J=1.5 Hz, 1H), 7.15 (dd, J=8.3, 1.8 Hz, 1H), 7.02 (d, J=1.8 Hz, 1H), 6.89 (dd, J=7.1, 2.0 Hz, 1H), 4.79-4.37 (br m, 2H), 3.90-3.60 (br m, 5H), 3.30 (br m, 2H), 3.14 (s, 3H); ESI MS m/z 439 [M+H]$^+$; HPLC (Method B)>99% (AUC), $t_R$=12.4 min.

Example 71

Preparation of 1-(2,3,4,5-Tetrahydro-1H-pyrido[4,3-b]indol-7-yl)-4-(5-(trifluoromethyl)pyridin-2-yl)pyridin-2(1H)-one dihydrochloride a) tert-Butyl 7-bromo-5-tosyl-3,4-dihydro-1H-pyrido[4,3-b]indole-2(5H)-carboxylate

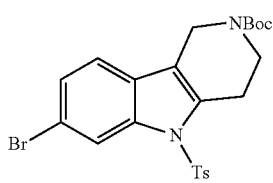

Chemical Formula: $C_{23}H_{25}BrN_2O_4S$
Exact Mass: 504.07
Molecular Weight: 505.42 tert-Butyl 7-bromo-3,4-dihydro-1H-pyrido[4,3-b]indole-2(5H)-carboxylate (1.07 g, 3.04 mmol) was reacted according to the procedure of Example 87 (step a) to provide the title compound (1.39 g, 91%) as a white solid: $^1$H NMR (300 MHz, CDCl$_3$) δ 8.35 (s, 1H), 7.66 (d, J=6.6 Hz, 2H), 7.35 (d, J=8.2 Hz, 1H), 7.28-7.21 (m, 2H), 7.18 (d, J=8.1 Hz, 1H), 4.47 (s, 2H), 3.77-3.65 (br m, 2H), 3.11-3.03 (br m, 2H), 2.36 (s, 3H), 1.48 (s, 9H).

b) tert-Butyl 7-(2-oxo-4-(5-(trifluoromethyl)pyridin-2-yl)pyridin-1(2H)-yl)-5-tosyl-3,4-dihydro-1H-pyrido[4,3-b]indole-2(5H)-carboxylate

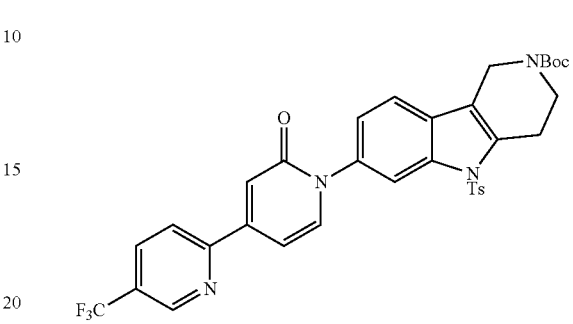

Chemical Formula: $C_{34}H_{31}F_3N_4O_5S$
Exact Mass: 664.20
Molecular Weight: 664.69

4-(5-(Trifluoromethyl)pyridin-2-yl)pyridin-2(1H)-one (131 mg, 0.545 mmol) and tert-butyl 7-bromo-5-tosyl-3,4-dihydro-1H-pyrido[4,3-b]indole-2(5H)-carboxylate (255 mg, 0.505 mmol) were reacted following the procedure of Example 30 (step g) to provide the title compound (125 mg, 34%) as a yellow oil: $^1$H NMR (300 MHz, CDCl$_3$) δ 9.01 (s, 1H), 8.29 (d, J=1.6 Hz, 1H), 8.08 (dd, J=8.3, 1.9 Hz, 1H), 7.92 (d, J=8.3 Hz, 1H), 7.74 (d, J=8.3 Hz, 1H), 7.57 (d, J=7.2 Hz, 1H), 7.46 (d, J=8.2 Hz, 1H), 7.33 (dd, J=8.2, 1.6 Hz, 1H), 7.29-7.23 (m, 4H), 7.09 (dd, J=7.2, 1.8 Hz, 1H), 4.52 (s, 2H), 3.80-3.73 (br m, 2H), 3.18-3.09 (br m, 2H), 2.35 (s, 3H), 1.50 (s, 9H).

b) 1-(5-Tosyl-2,3,4,5-tetrahydro-1H-pyrido[4,3-b]indol-7-yl)-4-(5-(trifluoromethyl)pyridin-2-yl)pyridin-2(1H)-one trifluoroacetic acid salt

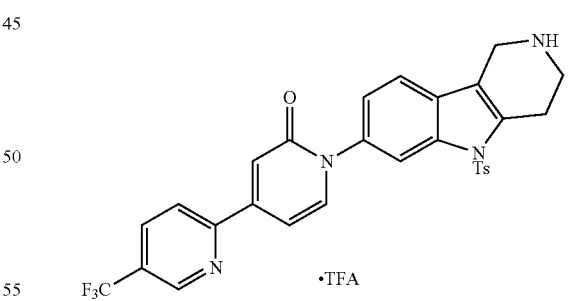

Chemical Formula: $C_{31}H_{23}F_6N_4O_4S$
Exact Mass: 661.13
Molecular Weight: 661.59 tert-Butyl 7-(2-oxo-4-(5-(trifluoromethyl)pyridin-2-yl)pyridin-1(2H)-yl)-5-tosyl-3,4-dihydro-1H-pyrido[4,3-b]indole-2(5H)-carboxylate (165 mg, 0.248 mmol) was stirred in TFA (3 mL) and methylene chloride (1 mL) for 3 h. Concentration of the solution under reduced pressure provided the title compound (164 mg, 100%) as a yellow oil; ESI MS m/z 565 [M+H]$^+$.

c) 1-(2,3,4,5-Tetrahydro-1H-pyrido[4,3-b]indol-7-yl)-4-(5-(trifluoromethyl)pyridin-2-yl)pyridin-2(1H)-one dihydrochloride

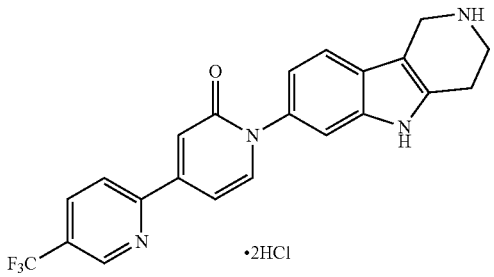

Chemical Formula: $C_{22}H_{19}Cl_2F_3N_4O$
Exact Mass: 482.09
Molecular Weight: 483.31

1-(5-Tosyl-2,3,4,5-tetrahydro-1H-pyrido[4,3-b]indol-7-yl)-4-(5-(trifluoromethyl)pyridin-2-yl)pyridin-2(1H)-one trifluoroacetic acid salt (163 mg, 0.248 mmol) was deprotected and converted to the dihydrochloride salt according to the procedure of Example 106 (step b) to provide the title compound (30 mg, 25%) as an orange solid: mp 308-313° C.; $^1$H NMR (500 MHz, CD$_3$OD) δ 9.04 (s, 1H), 8.28 (dd, J=8.3, 2.2 Hz, 1H), 8.22 (d, J=8.2 Hz, 1H), 7.81 (d, J=7.0 Hz, 1H), 7.62 (d, J=8.3 Hz, 1H), 7.46 (d, J=1.8 Hz, 1H), 7.38 (d, J=1.8 Hz, 1H), 7.24 (dd, J=7.1, 2.0 Hz, 1H), 7.11 (dd, J=8.3, 2.0 Hz, 1H), 4.49 (s, 2H), 3.65 (t, J=6.2 Hz, 2H), 3.21 (t, J=6.2 Hz, 2H); ESI MS m/z 411 [M+H]$^+$; HPLC (Method B) 97.6% (AUC), $t_R$=12.4 min.

Example 72

Preparation of 1-(2,3,4,5-Tetrahydro-1H-pyrido[4,3-b]indol-7-yl)-4-(6-(trifluoromethyl)pyridazin-3-yl)pyridin-2(1H)-one hydrochloride a) tert-Butyl 7-bromo-5-(triisopropylsilyl)-3,4-dihydro-1H-pyrido[4,3-b]indole-2(5H)-carboxylate

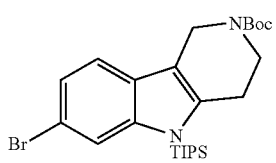

Chemical Formula: $C_{25}H_{39}BrN_2O_2Si$
Exact Mass: 506.20
Molecular Weight: 507.58 tert-Butyl 7-bromo-3,4-dihydro-1H-pyrido[4,3-b]indole-2(5H)-carboxylate (300 mg, 0.85 mmol) was dissolved in DMF (3 mL), and NaH (60% weight dispersion in mineral oil, 40 mg, 1.02 mmol) and TIPSCl (164 mg, 1.02 mmol) were added. After stirring for 1 h, the mixture was poured into water and extracted with EtOAc. Concentration of the organic extracts and purification of the residue by flash column chromatography (silica gel, EtOAc/hexanes) provided the title compound (262 mg, 61%) as a clear oil: $^1$H NMR (300 MHz, CDCl$_3$) δ 7.70 (s, 1H), 7.25 (d, J=8.2 Hz, 1H), 7.19 (dd, J=8.2, 1.4 Hz, 1H), 4.59 (s, 2H), 3.76-3.71 (br m, 2H), 2.96-2.90 (br m, 2H), 1.81-1.71 (m, 3H), 1.51 (s, 9H), 1.15 (d, J=7.5 Hz, 18H).

b) tert-Butyl 7-(2-oxo-4-(6-(trifluoromethyl)pyridazin-3-yl)pyridin-1(2H)-yl)-3,4-dihydro-1H-pyrido[4,3-b]indole-2(5H)-carboxylate

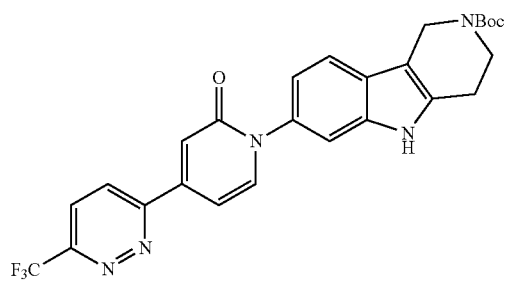

Chemical Formula: $C_{26}H_{24}F_3N_5O_3$
Exact Mass: 511.18
Molecular Weight: 511.50 tert-Butyl 7-bromo-5-(triisopropylsilyl)-3,4-dihydro-1H-pyrido[4,3-b]indole-2(5H)-carboxylate (260 mg, 0.51 mmol) and 4-(6-(trifluoromethyl)pyridazin-3-yl)pyridin-2(1H)-one (123 mg, 0.510 mmol) were reacted according to the procedure of Example 30 (step g) to provide the title compound (80 mg, 30%) as a yellow solid: ESI MS m/z 512 [M+H]$^+$.

c) 1-(2,3,4,5-Tetrahydro-1H-pyrido[4,3-b]indol-7-yl)-4-(6-(trifluoromethyl)pyridazin-3-yl)pyridin-2(1H)-one hydrochloride

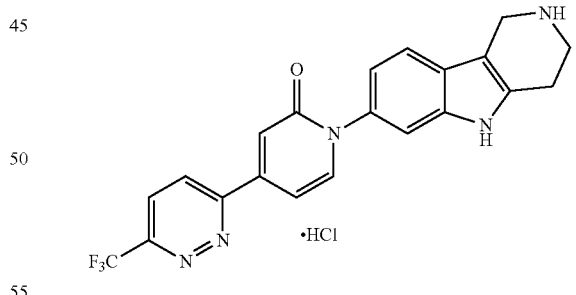

Chemical Formula: $C_{21}H_{17}ClF_3N_5O$
Exact Mass: 447.11
Molecular Weight: 447.84 tert-Butyl 7-(2-oxo-4-(6-(trifluoromethyl)pyridazin-3-yl)pyridin-1(2H)-yl)-3,4-dihydro-1H-pyrido[4,3-b]indole-2(5H)-carboxylate (80 mg, 0.15 mmol) was deprotected and converted to the hydrochloride salt according to the procedure of Example 30 (steps e and g) to provide the title compound (30 mg, 44%) as an orange solid: mp 314-318° C.; $^1$H NMR (300 MHz, CD$_3$OD) δ 8.52 (d, J=8.9 Hz, 1H), 8.28 (d, J=8.9 Hz, 1H), 7.89 (d, J=7.2 Hz, 1H), 7.62 (d, J=8.3

Hz, 1H), 7.48 (d, J=1.5 Hz, 1H), 7.43 (d, J=1.5 Hz, 1H), 7.33 (dd, J=7.2, 2.0 Hz, 1H), 7.14 (dd, J=7.4, 2.0 Hz, 1H), 4.49 (s, 2H), 3.65 (t, J=6.2 Hz, 2H), 3.21 (t, J=6.2 Hz, 2H); ESI MS m/z 412 [M+H]$^+$; HPLC (Method B) 96.0% (AUC), $t_R$=11.6 min.

Example 73

Preparation of 1-(5-Methyl-2,3,4,5-tetrahydro-1H-pyrido[4,3-b]indol-7-yl)-4-(2-(trifluoromethyl)pyrimidin-5-yl)pyridin-2(1H)-one hydrochloride a) 5-(2-Methoxypyridin-4-yl)-2-(trifluoromethyl)pyrimidine

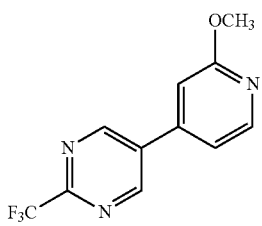

Chemical Formula: C$_{11}$H$_8$F$_3$N$_3$O
Exact Mass: 255.06
Molecular Weight: 255.20

2-Methoxy-4-(4,4,5,5-tetramethyl-1,3,2-dioxaborolan-2-yl)pyridine (2.0 g, 8.5 mmol) and 5-chloro-2-(trifluoromethyl)pyrimidine (2.3 g, 13 mmol) were reacted according to the procedure of Example 31 (step a) to provide the title compound (1.0 g, 46%) as a white solid: $^1$H NMR (300 MHz, CDCl$_3$) δ 9.10 (s, 2H), 8.35 (d, J=5.5 Hz, 1H), 7.11 (dd, J=5.5, 1.6 Hz, 1H), 6.98 (d, J=1.6 Hz, 1H), 4.02 (s, 3H).

b) 4-(2-(Trifluoromethyl)pyrimidin-5-yl)pyridin-2(1H)-one

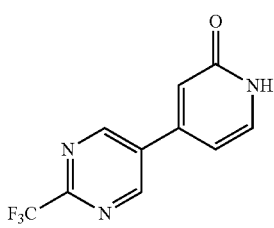

Chemical Formula: C$_{10}$H$_6$F$_3$N$_3$O
Exact Mass: 241.05
Molecular Weight: 241.17

5-(2-Methoxypyridin-4-yl)-2-(trifluoromethyl)pyrimidine (900 mg, 3.5 mmol) was reacted according to the procedure of Example 31 (step c) to provide the title compound (470 mg, 56%) as an orange solid: $^1$H NMR (300 MHz, DMSO-d$_6$) δ 11.6 (br s, 1H), 9.41 (s, 2H), 7.61 (d, J=6.8 Hz, 1H), 6.91 (s, 1H), 6.68 (dd, J=6.8, 1.6 Hz, 1H).

c) tert-Butyl 5-methyl-7-(2-oxo-4-(2-(trifluoromethyl)pyrimidin-5-yl)pyridin-1(2H)-yl)-3,4-dihydro-1H-pyrido[4,3-b]indole-2(5H)-carboxylate

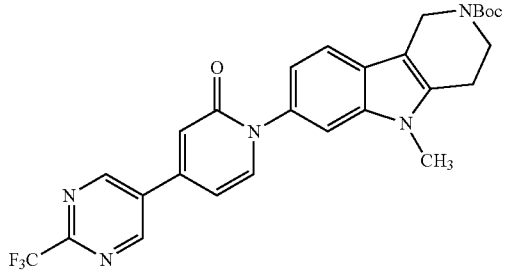

Chemical Formula: C$_{27}$H$_{26}$F$_3$N$_5$O$_3$
Exact Mass: 525.20
Molecular Weight: 525.52

4-(2-(Trifluoromethyl)pyrimidin-5-yl)pyridin-2(1H)-one (100 mg, 0.42 mmol) and tert-butyl 7-bromo-5-methyl-3,4-dihydro-1H-pyrido[4,3-b]indole-2(5H)-carboxylate (116 mg, 0.32 mmol) were reacted following the procedure of Example 30 (step g) to provide the title compound (41 mg, 24%) as a yellow oil: ESI MS m/z 526 [M+H]$^+$.

d) 1-(5-Methyl-2,3,4,5-tetrahydro-1H-pyrido[4,3-b]indol-7-yl)-4-(2-(trifluoromethyl)pyrimidin-5-yl)pyridin-2(1H)-one hydrochloride

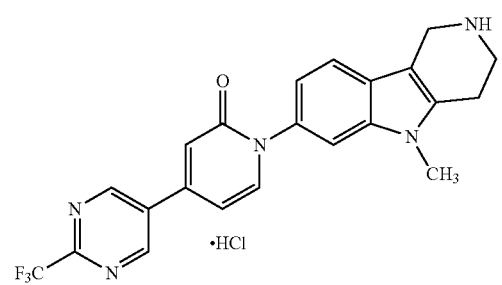

Chemical Formula: C$_{22}$H$_{19}$ClF$_3$N$_5$O
Exact Mass: 461.12
Molecular Weight: 461.87 tert-Butyl 5-methyl-7-(2-oxo-4-(2-(trifluoromethyl)pyrimidin-5-yl)pyridin-1(2H)-yl)-3,4-dihydro-1H-pyrido[4,3-b]indole-2(5H)-carboxylate (41 mg, 0.078 mmol) was deprotected and converted to the hydrochloride salt according to the procedure of Example 30 (steps e and g) to provide the title compound (29 mg, 80%) as a yellow solid: $^1$H NMR (500 MHz, DMSO-d$_6$) δ 9.51 (s, 2H), 9.37 (br s, 2H), 7.90 (d, J=7.2 Hz, 1H), 7.62-7.60 (m, 2H), 7.13 (d, J=1.9 Hz, 1H), 7.10 (dd, J=8.3, 1.7 Hz, 1H), 6.88 (dd, J=7.1, 2.0 Hz, 1H), 4.38-4.34 (br m, 2H), 3.70 (s, 3H), 3.56-3.50 (br m, 2H), 3.11 (t, J=5.8 Hz, 2H); ESI MS m/z 426 [M+H]$^+$; HPLC (Method B)>100% (AUC), $t_R$=12.2 min.

Example 74

Preparation of 1-(5-Methyl-2,3,4,5-tetrahydro-1H-pyrido[4,3-b]indol-7-yl)-4-(5-(trifluoromethyl)pyrimidin-2-yl)pyridin-2(1H)-one hydrochloride a) 2-(2-Methoxypyridin-4-yl)-5-(trifluoromethyl)pyrimidine

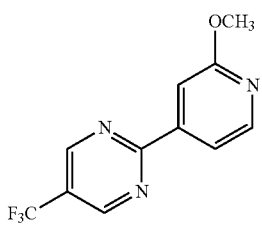

Chemical Formula: $C_{11}H_8F_3N_3O$
Exact Mass: 255.06
Molecular Weight: 255.20

2-Methoxy-4-(4,4,5,5-tetramethyl-1,3,2-dioxaborolan-2-yl)pyridine (1.66 g, 7.06 mmol) and 2-chloro-5-(trifluoromethyl)pyrimidine (1.3 g, 7.1 mmol) were reacted according to the procedure of Example 31 (step a) to provide the title compound (307 mg, 16%) as a white solid: $^1$H NMR (300 MHz, CDCl$_3$) δ 9.08 (s, 2H), 8.34 (d, J=5.3 Hz, 1H), 7.89 (dd, J=5.3, 1.4 Hz, 1H), 7.81 (s, 1H), 4.01 (s, 3H).

b) 4-(5-(Trifluoromethyl)pyrimidin-2-yl)pyridin-2(1H)-one

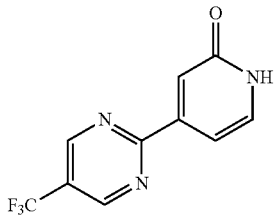

Chemical Formula: $C_{10}H_6F_3N_3O$
Exact Mass: 241.05
Molecular Weight: 241.17

2-(2-Methoxypyridin-4-yl)-5-(trifluoromethyl)pyrimidine (400 mg, 1.56 mmol) was reacted according to the procedure of Example 31 (step c) to provide the title compound (200 mg, 63%) as a white solid: $^1$H NMR (300 MHz, DMSO-d$_6$) δ 11.9 (br s, 1H), 9.43 (s, 2H), 7.58 (d, J=6.8 Hz, 1H), 7.34 (s, 1H), 7.06 (dd, J=6.8, 1.7 Hz, 1H).

c) tert-Butyl 5-methyl-7-(2-oxo-4-(5-(trifluoromethyl)pyrimidin-2-yl)pyridin-1(2H)-yl)-3,4-dihydro-1H-pyrido[4,3-b]indole-2(5H)-carboxylate

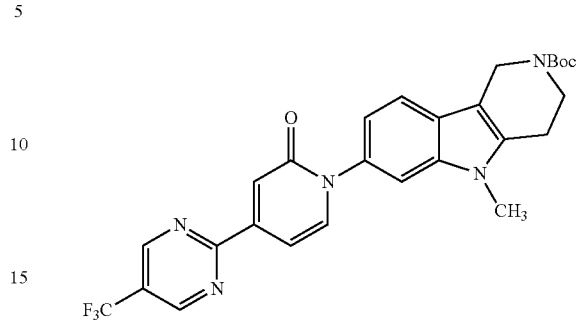

Chemical Formula: $C_{27}H_{26}F_3N_5O_3$
Exact Mass: 525.20
Molecular Weight: 525.52

4-(5-(Trifluoromethyl)pyrimidin-2-yl)pyridin-2(1H)-one (100 mg, 0.34 mmol) and tert-butyl 7-bromo-5-methyl-3,4-dihydro-1H-pyrido[4,3-b]indole-2(5H)-carboxylate (124 mg, 0.339 mmol) were reacted following the procedure of Example 30 (step g) to provide the title compound (70 mg, 39%) as a yellow solid: $^1$H NMR (300 MHz, CDCl$_3$) δ 9.11 (s, 2H), 7.86 (s, 1H), 7.59-7.53 (m, 2H), 7.38 (s, 1H), 7.28-7.26 (m, 1H), 7.08 (d, J=8.4 Hz, 1H), 4.89-4.63 (br m, 2H), 3.90-3.80 (br m, 2H), 3.65 (s, 3H), 2.88-2.79 (br m, 2H), 1.50 (s, 9H).

d) 1-(5-Methyl-2,3,4,5-tetrahydro-1H-pyrido[4,3-b]indol-7-yl)-4-(5-(trifluoromethyl)pyrimidin-2-yl)pyridin-2(1H)-one hydrochloride

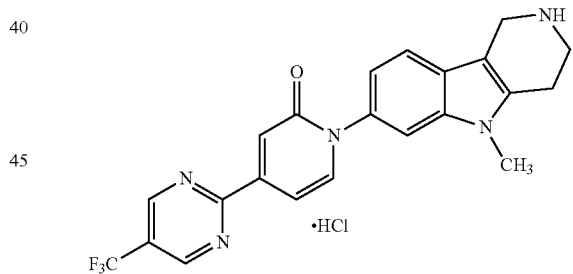

Chemical Formula: $C_{22}H_{19}ClF_3N_5O$
Exact Mass: 461.12
Molecular Weight: 461.87 tert-Butyl 5-methyl-7-(2-oxo-4-(5-(trifluoromethyl)pyrimidin-2-yl)pyridin-1(2H)-yl)-3,4-dihydro-1H-pyrido[4,3-b]indole-2(5H)-carboxylate (70 mg, 0.13 mmol) was deprotected and converted to the hydrochloride salt according to the procedure of Example 30 (steps e and g) to provide the title compound (51 mg, 87%) as a yellow solid: mp 301-309° C.; $^1$H NMR (500 MHz, DMSO-d$_6$) δ 9.48 (s, 2H), 9.37 (br s, 2H), 7.89 (d, J=7.2 Hz, 1H), 7.65 (d, J=1.6 Hz, 1H), 7.61 (d, J=8.3 Hz, 1H), 7.50 (d, J=1.6 Hz, 1H), 7.21 (dd, J=7.6, 1.9 Hz, 1H), 7.12 (dd, J=8.3, 1.8 Hz, 1H), 4.41-4.31 (br m, 2H), 3.71 (s, 3H), 3.51-3.48 (br m, 2H), 3.10 (t, J=5.6 Hz, 2H); ESI MS m/z 426 [M+H]$^+$; HPLC (Method B) 97.9% (AUC), $t_R$=12.6 min.

Example 75

Preparation of 1-(5-Methyl-2,3,4,5-tetrahydro-1H-pyrido[4,3-b]indol-7-yl)-4-((6-(trifluoromethyl)pyridin-3-yl)methoxy)pyridin-2(1H)-one hydrochloride a) 2-Methoxy-4-((6-(trifluoromethyl)pyridin-3-yl)methoxy)pyridine

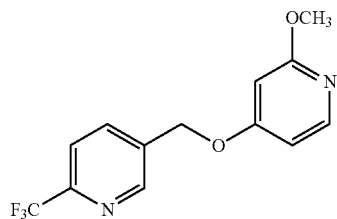

Chemical Formula: $C_{13}H_{11}F_3N_2O_2$
Exact Mass: 284.08
Molecular Weight: 284.23

4-BromoBromo-2-methoxypyridine (3.06 g, 16.2 mmol), (6-(trifluoromethyl)pyridin-3-yl)methanol (2.74 g, 15.5 mmol), 3,4,7,8-tetramethylphenanthroline (0.36 g, 0.15 mmol), CuI (0.14 g, 0.74 mmol) and $Cs_2CO_3$ (7.57 g, 23.2 mmol) were combined in toluene (15 mL) and heated to reflux under a nitrogen atmosphere for 16 h. Upon cooling the mixture was purified by flash column chromatography (silica gel, hexanes/EtOAc, 1:0 to 1:1) to provide the title compound (3.19 g, 72%) as a red oil: $^1$H NMR (300 MHz, $CDCl_3$) δ 8.78 (s, 1H), 8.02 (d, J=5.9 Hz, 1H), 7.95 (d, J=8.1 Hz, 1H), 7.32 (d, J=8.0 Hz, 1H), 6.55 (dd, J=5.9, 2.2 Hz, 1H), 6.26 (d, J=2.2 Hz, 1H), 5.16 (s, 2H), 3.93 (s, 3H).

b) 4-((6-(Trifluoromethyl)pyridin-3-yl)methoxy)pyridin-2(1H)-one

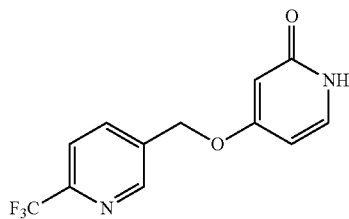

Chemical Formula: $C_{12}H_9F_3N_2O_2$
Exact Mass: 270.06
Molecular Weight: 270.21

2-Methoxy-4-((6-(trifluoromethyl)pyridin-3-yl)methoxy)pyridine (3.19 g, 11.2 mmol) was reacted according to the procedure of Example 31 (step c) to provide the title compound (2.04 g, 67%) as a white solid: $^1$H NMR (300 MHz, DMSO-$d_6$) δ 11.2 (br s, 1H), 8.84 (s, 1H), 8.14 (d, J=8.5 Hz, 1H), 7.96 (d, J=8.0 Hz, 1H), 7.28 (d, J=7.3 Hz, 1H), 5.95 (dd, J=7.3, 2.5 Hz, 1H), 5.82 (d, J=2.4 Hz, 1H), 5.25 (s, 2H).

c) tert-Butyl 5-methyl-7-(2-oxo-4-((6-(trifluoromethyl)pyridin-3-yl)methoxy)pyridin-1(2H)-yl)-3,4-dihydro-1H-pyrido[4,3-b]indole-2(5H)-carboxylate

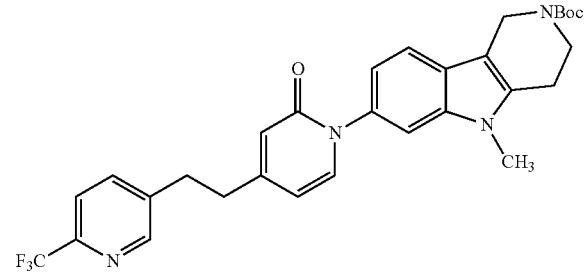

Chemical Formula: $C_{29}H_{29}F_3N_4O_4$
Exact Mass: 554.21
Molecular Weight: 554.56

4-((6-(Trifluoromethyl)pyridin-3-yl)methoxy)pyridin-2(1H)-one (177 mg, 0.655 mmol) and tert-butyl 7-bromo-5-methyl-3,4-dihydro-1H-pyrido[4,3-b]indole-2(5H)-carboxylate (200 mg, 0.54 mmol) were reacted following the procedure of Example 30 (step g) to provide the title compound (120 mg, 40%) as a yellow oil: $^1$H NMR (300 MHz, $CDCl_3$) δ 8.80 (s, 1H), 7.95 (d, J=8.1 Hz, 1H), 7.76 (d, J=8.0 Hz, 1H), 7.51 (d, J=7.9 Hz, 1H), 7.35 (d, J=8.0 Hz, 1H), 7.28 (m, 1H), 7.01 (d, J=8.1 Hz, 1H), 6.06-6.04 (m, 2H), 5.16 (s, 2H), 4.65-4.60 (br m, 2H), 3.89-3.79 (br m, 2H), 3.63 (s, 3H), 2.87-2.78 (br m, 2H), 1.50 (s, 9H).

d) 1-(5-Methyl-2,3,4,5-tetrahydro-1H-pyrido[4,3-b]indol-7-yl)-4-((6-(trifluoromethyl)pyridin-3-yl)methoxy)pyridin-2(1H)-one dihydrochloride

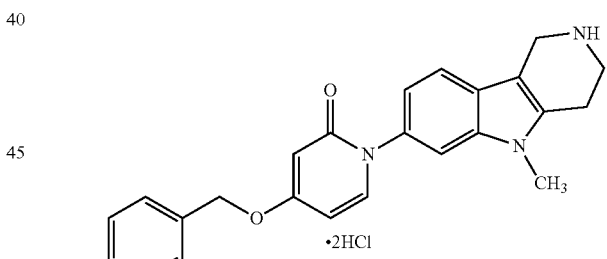

Chemical Formula: $C_{24}H_{23}Cl_2F_3N_4O_2$
Exact Mass: 526.12
Molecular Weight: 527.37 tert-Butyl 5-methyl-7-(2-oxo-4-((6-(trifluoromethyl)pyridin-3-yl)methoxy)pyridin-1(2H)-yl)-3,4-dihydro-1H-pyrido[4,3-b]indole-2(5H)-carboxylate (120 mg, 0.21 mmol) was deprotected and converted to the dihydrochloride salt according to the procedure of Example 30 (steps e and g) to provide the title compound (90 mg, 81%) as a white solid: mp 286-291° C.; $^1$H NMR (500 MHz, DMSO-$d_6$) δ 9.54 (br s, 2H), 8.89 (s, 1H), 8.19 (dd, J=7.9, 1.4 Hz, 1H), 8.00 (d, J=8.0 Hz, 1H), 7.60 (d, J=7.6 Hz, 1H), 7.55 (d, J=8.3 Hz, 1H), 7.50 (d, J=1.7 Hz, 1H), 6.98 (dd, J=8.3, 1.8 Hz, 1H), 6.15 (dd, J=7.5, 2.7 Hz, 1H), 6.02 (d, J=2.7 Hz, 1H), 5.35 (s, 2H), 4.35-4.30 (br m, 2H), 3.67 (s, 3H), 3.53-3.47 (br m, 2H), 3.09 (t, J=5.8 Hz, 2H); ESI MS m/z 455 [M+H]⁺; HPLC (Method B)>99% (AUC), $t_R$=12.7 min.

Example 76

Preparation of 1-(5-Methyl-2,3,4,5-tetrahydro-1H-pyrido[4,3-b]indol-7-yl)-4-((5-(trifluoromethyl)pyridin-2-yl)methoxy)pyridin-2(1H)-one a) tert-Butyl 5-methyl-7-(2-oxo-4-((5-(trifluoromethyl)pyridin-2-yl)methoxy)pyridin-1(2H)-yl)-3,4-dihydro-1H-pyrido[4,3-b]indole-2(5H)-carboxylate

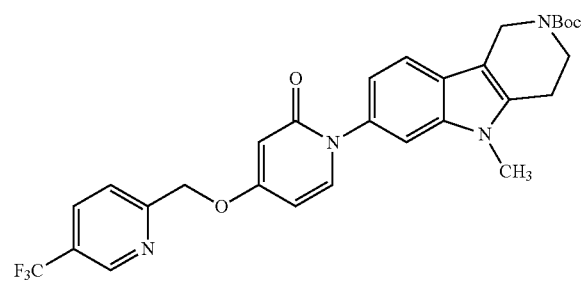

Chemical Formula: C₂₉H₂₉F₃N₄O₄
Exact Mass: 554.21
Molecular Weight: 554.56

2-(Bromomethyl)-5-(trifluoromethyl)pyridine (140 mg, 0.58 mmol), tert-butyl 7-(4-hydroxy-2-oxopyridin-1(2H)-yl)-5-methyl-3,4-dihydro-1H-pyrido[4,3-b]indole-2(5H)-carboxylate (230 mg, 0.58 mmol) and K₂CO₃ (160 mg, 1.16 mmol) were stirred in acetonitrile/DMF (3 mL/0.5 mL) for 72 h. The mixture was diluted with methylene chloride, washed with water and concentrated to provide the title compound (96 mg, 29%) as a yellow solid: ¹H NMR (300 MHz, CDCl₃) δ 8.88 (s, 1H), 8.00 (dd, J=8.2, 2.0 Hz, 1H), 7.63 (d, J=8.2 Hz, 1H), 7.51 (d, J=8.2 Hz, 1H), 7.36 (d, J=7.6 Hz, 1H), 7.28-7.26 (m, 1H), 7.00 (d, J=7.7 Hz, 1H), 6.12 (dd, J=7.6, 2.7 Hz, 1H), 6.04 (d, J=2.7 Hz, 1H), 5.26 (s, 2H), 4.63-4.58 (br m, 2H), 3.87-3.76 (br m, 2H), 3.63 (s, 3H), 2.86-2.76 (br m, 2H), 1.50 (s, 9H).

b) 1-(5-Methyl-2,3,4,5-tetrahydro-1H-pyrido[4,3-b]indol-7-yl)-4-((5-(trifluoromethyl)pyridin-2-yl)methoxy)pyridin-2(1H)-one dihydrochloride

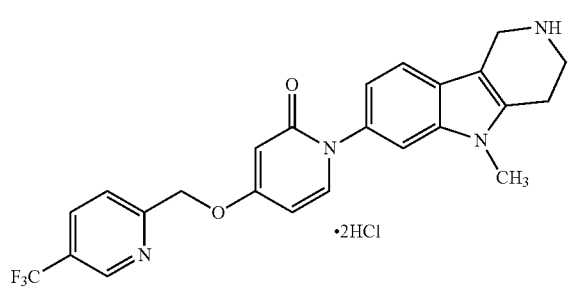

Chemical Formula: C₂₄H₂₃Cl₂F₃N₄O₂
Exact Mass: 526.12
Molecular Weight: 527.37 tert-Butyl 5-methyl-7-(2-oxo-4-((5-(trifluoromethyl)pyridin-2-yl)methoxy)pyridin-1(2H)-yl)-3,4-dihydro-1H-pyrido[4,3-b]indole-2(5H)-carboxylate (90 mg, 0.16 mmol) was deprotected and converted to the dihydrochloride salt according to the procedure of Example 30 (steps e and g) to provide the title compound (76 mg, 90%) as a white solid: mp 296-300° C.; ¹H NMR (300 MHz, CD₃OD) δ 8.93 (s, 1H), 8.23 (dd, J=8.2, 2.1 Hz, 1H), 7.82 (d, J=8.2 Hz, 1H), 7.70 (d, J=7.5 Hz, 1H), 7.59 (d, J=8.3 Hz, 1H), 7.49 (d, J=1.7 Hz, 1H), 7.06 (dd, J=8.3, 1.8 Hz, 1H), 6.47 (dd, J=7.5, 2.7 Hz, 1H), 6.20 (d, J=2.6 Hz, 1H), 5.42 (s, 2H), 4.48 (s, 2H), 3.73 (s, 3H), 3.67 (t, J=6.1 Hz, 2H), 3.20 (t, J=6.1 Hz, 2H); ESI MS m/z 455 [M+H]⁺; HPLC (Method B) 97.6% (AUC), $t_R$=12.6 min.

Example 77

Preparation of 5-(Benzyloxy)-2-(5-methyl-2,3,4,5-tetrahydro-1H-pyrido[4,3-b]indol-7-yl)pyridazin-3(2H)-one hydrochloride a) 5-(Benzyloxy)pyridazin-3(2H)-one CAS Registry Number 1008517-73-4

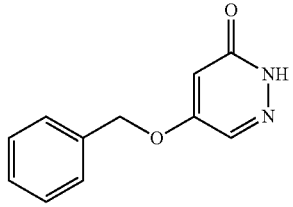

Chemical Formula: C₁₁H₁₀N₂O₂
Exact Mass: 202.07
Molecular Weight: 202.21

This compound was prepared in accordance with the procedure of Stenkamp et al., WO 2008/022979.

b) tert-Butyl 7-(4-(benzyloxy)-6-oxopyridazin-1(6H)-yl)-5-methyl-3,4-dihydro-1H-pyrido[4,3-b]indole-2(5H)-carboxylate

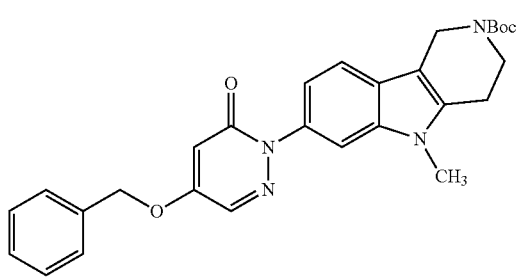

Chemical Formula: C₂₈H₃₀N₄O₄
Exact Mass: 486.23
Molecular Weight: 486.56

5-(Benzyloxy)pyridazin-3(2H)-one (100 mg, 0.5 mmol) and tert-butyl 7-bromo-5-methyl-3,4-dihydro-1H-pyrido[4,3-b]indole-2(5H)-carboxylate (180 mg, 0.5 mmol) were reacted following the procedure of Example 30 (step g) to provide the title compound (106 mg, 43%) as a solid: ESI MS m/z 487 [M+H]+.

c) 5-(Benzyloxy)-2-(5-methyl-2,3,4,5-tetrahydro-1H-pyrido[4,3-b]indol-7-yl)pyridazin-3(2H)-one hydrochloride

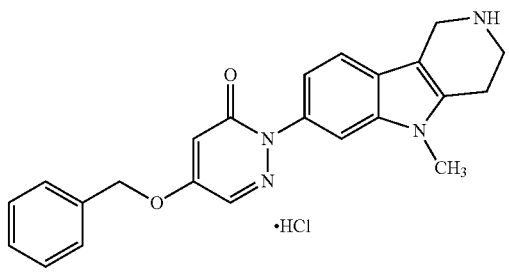

Chemical Formula: $C_{23}H_{23}ClN_4O_2$
Exact Mass: 422.15
Molecular Weight: 422.91 tert-Butyl 7-(4-(benzyloxy)-6-oxopyridazin-1(6H)-yl)-5-methyl-3,4-dihydro-1H-pyrido[4,3-b]indole-2(5H)-carboxylate (100 mg, 0.2 mmol) was deprotected and converted to the hydrochloride salt according to the procedure of Example 30 (steps e and g) to provide the title compound (30 mg, 35%) as a white solid: mp 261-265° C.; $^1$H NMR (500 MHz, DMSO-$d_6$) δ 9.23 (s, 2H), 7.96 (d, J=2.8 Hz, 1H), 7.59 (d, J=1.6 Hz, 1H), 7.54 (d, J=8.4 Hz, 1H), 7.51-7.48 (m, 2H), 7.46-7.42 (m, 2H), 7.40 (d, J=7.5 Hz, 1H), 7.13 (dd, J=8.4, 1.7 Hz, 1H), 6.51 (d, J=2.8 Hz, 1H), 5.22 (s, 2H), 4.34 (s, 2H), 3.69 (s, 3H), 3.52 (t, J=5.8 Hz, 2H), 3.09 (t, J=5.8 Hz, 2H); ESI MS m/z 387 [M+H]+; HPLC (Method B) 97.7% (AUC), $t_R$=12.8 min.

Example 78

Preparation of 2-(5-Methyl-2,3,4,5-tetrahydro-1H-pyrido[4,3-b]indol-7-yl)-5-(4-(trifluoromethyl)phenyl)pyridazin-3(2H)-one hydrochloride a) 5-Hydroxy-2-(tetrahydro-2H-pyran-2-yl)pyridazin-3(2H)-one CAS Registry Number 1008517-74-5

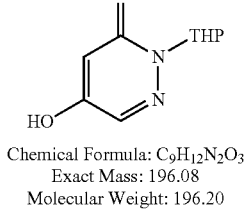

Chemical Formula: $C_9H_{12}N_2O_3$
Exact Mass: 196.08
Molecular Weight: 196.20

This compound was prepared in accordance with the procedure of Stenkamp et al., WO 2008/022979.

b) 6-Oxo-1-(tetrahydro-2H-pyran-2-yl)-1,6-dihydropyridazin-4-yl trifluoromethanesulfonate

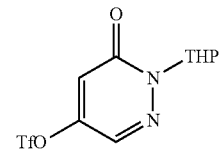

Chemical Formula: $C_{10}H_{11}F_3N_2O_5S$
Exact Mass: 328.03
Molecular Weight: 328.26

5-Hydroxy-2-(tetrahydro-2H-pyran-2-yl)pyridazin-3 (2H)-one (2.4 g, 13 mmol) dissolved in methylene chloride (75 mL) and cooled to 0° C. Triethylamine (3.5 mL, 25 mmol) and Tf$_2$O (2.3 mL, 14 mmol) were added and the mixture stirred for a further 2.5 h. Saturated NaHCO$_3$ solution was added and the organic phase removed, dried over Na$_2$SO$_4$ and concentrated. Purification by flash column chromatography (silica gel, EtOAc/hexanes) provided the title compound (2.47 g, 60%) as a yellow oil: $^1$H NMR (500 MHz, CDCl$_3$) δ 7.85 (d, J=2.8 Hz, 1H), 6.86 (d, J=2.7 Hz, 1H), 6.01 (dd, J=10.2, 2.2 Hz, 1H), 4.15-4.12 (m, 1H), 3.75 (dt, J=11.6, 2.5 Hz, 1H), 2.18-2.02 (m, 2H), 1.78-1.66 (m, 3H), 1.62-1.55 (m, 1H).

c) 2-(Tetrahydro-2H-pyran-2-yl)-5-(4-(trifluoromethyl)phenyl)pyridazin-3(2H)-one

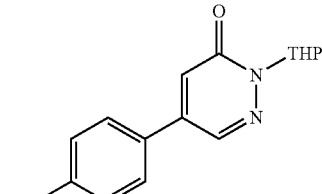

Chemical Formula: $C_{16}H_{15}F_3N_2O_2$
Exact Mass: 324.11
Molecular Weight: 324.30

6-Oxo-1-(tetrahydro-2H-pyran-2-yl)-1,6-dihydropyridazin-4-yl trifluoromethanesulfonate (2.47 g, 7.5 mmol) and 4-trifluoromethylphenylboronic acid (2.56 g, 15 mmol) were reacted according to the procedure of Example 31 (step a) to provide the title compound (500 mg, 20%) as a white solid: ESI MS m/z 325 [M+H]+.

d) 5-(4-(Trifluoromethyl)phenyl)pyridazin-3(2H)-one

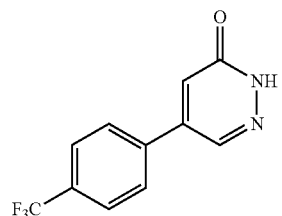

Chemical Formula: $C_{11}H_7F_3N_2O$
Exact Mass: 240.05
Molecular Weight: 240.18

2-(Tetrahydro-2H-pyran-2-yl)-5-(4-(trifluoromethyl)phenyl)pyridazin-3(2H)-one (500 mg, 1.54 mmol) was reacted according to the procedure of Example 31 (step c) to provide the title compound (100 mg, 27%) as a solid: ESI MS m/z 241 [M+H]⁺.

e) tert-Butyl 5-methyl-7-(6-oxo-4-(4-(trifluoromethyl)phenyl)pyridazin-1(6H)-yl)-3,4-dihydro-1H-pyrido[4,3-b]indole-2(5H)-carboxylate

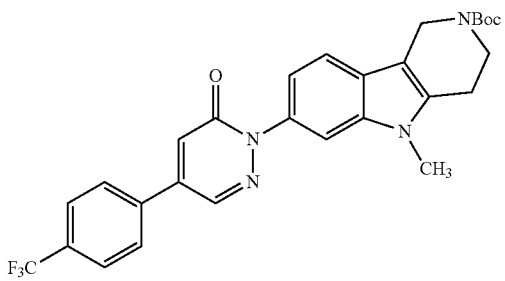

Chemical Formula: C₂₈H₂₇F₃N₄O₃
Exact Mass: 524.20
Molecular Weight: 524.53

5-(4-(Trifluoromethyl)phenyl)pyridazin-3(2H)-one (100 mg, 0.41 mmol) and tert-butyl 7-bromo-5-methyl-3,4-dihydro-1H-pyrido[4,3-b]indole-2(5H)-carboxylate (151 mg, 0.41 mmol) were reacted following the procedure of Example 30 (step g) to provide the title compound (65 mg, 30%) as a yellow solid: ¹H NMR (300 MHz, CDCl₃) δ 8.20 (s, 1H), 7.81 (d, J=8.4 Hz, 2H), 7.76 (d, J=8.4 Hz, 2H), 7.59 (d, J=1.6 Hz, 1H), 7.54 (d, J=8.4 Hz, 1H), 7.31 (d, J=6.9 Hz, 1H), 7.26-7.24 (m, 1H), 4.62 (s, 2H), 3.89-3.80 (br m, 2H), 3.66 (s, 3H), 2.84 (br m, 2H), 1.51 (s, 9H).

f) 2-(5-Methyl-2,3,4,5-tetrahydro-1H-pyrido[4,3-b]indol-7-yl)-5-(4-(trifluoromethyl)phenyl)pyridazin-3(2H)-one hydrochloride

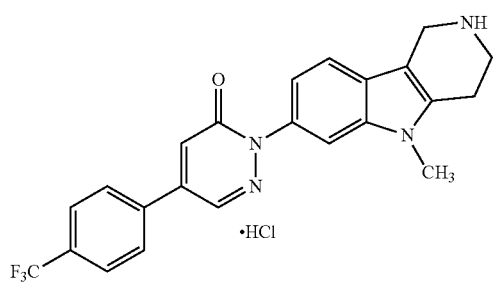

Chemical Formula: C₂₃H₂₀ClF₃N₄O
Exact Mass: 460.13
Molecular Weight: 460.88 tert-Butyl 5-methyl-7-(6-oxo-4-(4-(trifluoromethyl)phenyl)pyridazin-1(6H)-yl)-3,4-dihydro-1H-pyrido[4,3-b]indole-2(5H)-carboxylate (65 mg, 0.12 mmol) was deprotected and converted to the hydrochloride salt according to the procedure of Example 30 (steps e and g) to provide the title compound (47 mg, 80%) as an orange solid: mp 315-320° C.; ¹H NMR (300 MHz, DMSO-d₆) δ 9.37 (s, 2H), 8.56 (d, J=2.2 Hz, 1H), 8.13 (d, J=Hz, 2H), 7.93 (d, J=8.2 Hz, 2H), 7.72 (d, J=1.6 Hz, 1H), 7.61 (d, J=8.4 Hz, 1H), 7.48 (d, J=2.2 Hz, 1H), 7.25 (dd, J=8.4, 1.8 Hz, 1H), 4.36 (s, 2H), 3.70 (s, 3H), 3.58-3.48 (br m, 2H), 3.11 (t, J=5.7 Hz, 2H); ESI MS m/z 425 [M+H]⁺; HPLC (Method A) 96.6% (AUC), t_R=15.7 min.

Example 79

Preparation of 4-(5-Chloropyridin-2-yl)-1-(9-methyl-2,3,4,5-tetrahydro-1H-pyrido[3,4-b]indol-7-yl)pyridin-2(1H)-one hydrochloride a) tert-Butyl 7-(4-(5-chloropyridin-2-yl)-2-oxopyridin-1(2H)-yl)-9-methyl-3,4-dihydro-1H-pyrido[3,4-b]indole-2(9H)-carboxylate

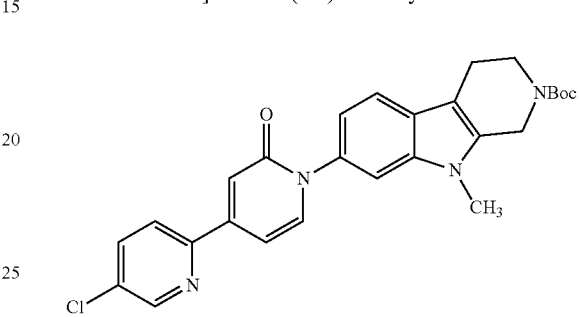

Chemical Formula: C₂₇H₂₇ClN₄O₃
Exact Mass: 490.18
Molecular Weight: 490.98 tert-Butyl 7-bromo-9-methyl-3,4-dihydro-1H-pyrido[3,4-b]indole-2(9H)-carboxylate (200 mg, 0.549 mmol) and 4-(5-chloropyridin-2-yl)pyridin-2(1H)-one (87 mg, 0.42 mmol) were reacted following the procedure of Example 30 (step g) to provide the title compound (97 mg, 47%) as a yellow solid: ¹H NMR (300 MHz, CDCl₃) δ 8.69 (d, J=2.0 Hz, 1H), 7.80 (dd, J=8.5, 2.3 Hz, 1H), 7.75 (d, J=8.4 Hz, 1H), 7.55 (overlapping dd, J=7.4 Hz, 2H), 7.36 (s, 1H), 7.18 (d, J=1.7 Hz, 1H), 7.08 (dd, J=8.3, 1.6 Hz, 1H), 7.00 (dd, J=7.1, 1.8 Hz, 1H), 4.65 (s, 2H), 3.76 (br m, 2H), 3.65 (s, 3H), 2.82 (br m, 2H), 1.52 (s, 9H).

b) 4-(5-Chloropyridin-2-yl)-1-(9-methyl-2,3,4,5-tetrahydro-1H-pyrido[3,4-b]indol-7-yl)pyridin-2(1H)-one hydrochloride

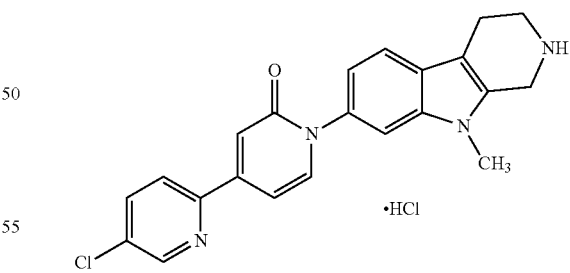

Chemical Formula: C₂₂H₂₀Cl₂N₄O
Exact Mass: 426.10
Molecular Weight: 427.33 tert-Butyl 7-(4-(5-chloropyridin-2-yl)-2-oxopyridin-1(2H)-yl)-5-methyl-3,4-dihydro-1H-pyrido[4,3-b]indole-2(5H)-carboxylate (97 mg, 0.20 mmol) was deprotected and converted to the hydrochloride salt according to the procedure of Example 30 (steps e and g) to provide the title compound as a orange solid (68 mg, 88%): mp 310-320° C.; ¹H NMR (500 MHz, CD₃OD) δ 8.73 (dd, J=2.4, 0.6 Hz, 1H), 8.03 (dd, J=8.5, 0.5 Hz, 1H), 8.00 (dd, J=8.5, 2.4 Hz, 1H), 7.80 (d, J=7.1 Hz, 1H), 7.67 (d, J=8.3 Hz, 1H), 7.56 (d, J=1.7 Hz, 1H), 7.31 (d, J=1.7 Hz, 1H), 7.19 (dd, J=7.1, 2.0 Hz, 1H), 7.14 (dd, J=8.4, 1.8 Hz, 1H), 4.56 (s, 2H), 3.74 (s, 3H), 3.61 (t, J=6.1 Hz, 2H), 3.14 (t, J=6.1 Hz, 2H); ESI MS m/z 391 [M+H]$^+$; HPLC (Method A)>99% (AUC), $t_R$=11.9 min.

Example 80

Preparation of 1-(2,9-Dimethyl-2,3,4,9-tetrahydro-1H-pyrido[3,4-b]indol-7-yl)-4-(5-chloropyridin-2-yl)pyridin-2(1H)-one hydrochloride

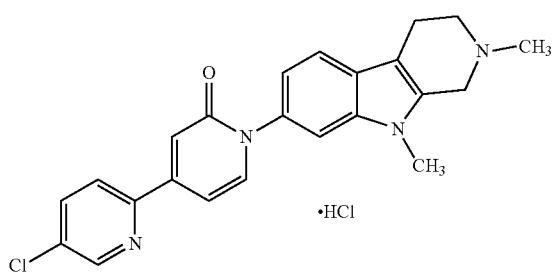

Chemical Formula: C$_{23}$H$_{22}$Cl$_2$N$_4$O
Exact Mass: 440.12
Molecular Weight: 441.35

4-(5-Chloropyridin-2-yl)-1-(5-methyl-2,3,4,5-tetrahydro-1H-pyrido[3,4-b]indol-7-yl)pyridin-2(1H)-one (104 mg, 0.266 mmol) was reacted following the procedure of Example 47 to provide the title compound (75 mg, 70%) as a yellow solid: mp 283-295° C.; $^1$H NMR (500 MHz, CD$_3$OD) δ 8.73 (d, J=2.3 Hz, 1H), 8.03 (d, J=8.5 Hz, 1H) 7.99 (dd, J=8.5, 2.3 Hz, 1H), 7.79 (d, J=7.2 Hz, 1H), 7.67 (d, J=8.3 Hz, 1H), 7.57 (s, 1H), 7.31 (d, J=1.6 Hz, 1H), 7.19 (dd, J=7.1, 1.8 Hz, 1H), 7.15 (dd, J=8.3, 1.7 Hz, 1H), 4.65 (br s, 2H), 3.74 (m, 5H), 3.21 (t, J=5.7 Hz, 2H), 3.17 (s, 3H); ESI MS m/z 405 [M+H]$^+$; HPLC (Method B) 98.7% (AUC), $t_R$=12.1 min.

Example 81

Preparation of 4-(5-(Trifluoromethyl)pyridin-2-yl)-1-(9-methyl-2,3,4,5-tetrahydro-1H-pyrido[3,4-b]indol-7-yl)pyridin-2(1H)-one hydrochloride a) tert-Butyl 9-methyl-7-(2-oxo-4-(5-(trifluoromethyl)pyridin-2-yl)pyridin-1(2H)-yl)-3,4-dihydro-1H-pyrido[3,4-b]indole-2(9H)-carboxylate

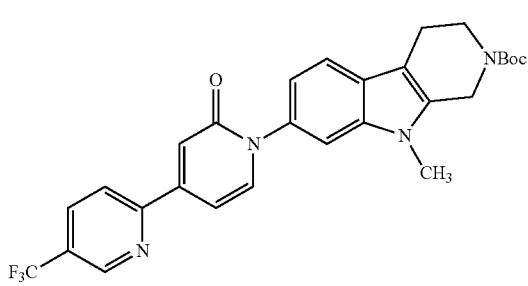

Chemical Formula: C$_{28}$H$_{27}$F$_3$N$_4$O$_3$
Exact Mass: 524.20
Molecular Weight: 524.53 tert-Butyl 7-bromo-9-methyl-3,4-dihydro-1H-pyrido[3,4-b]indole-2(9H)-carboxylate (100 mg, 0.417 mmol) and 4-(5-(trifluoromethyl)pyridin-2-yl)pyridin-2(1H)-one (197 mg, 0.542 mmol), were reacted following the procedure of Example 30 (step g) to provide the title compound (168 mg, 66%) as a yellow solid: $^1$H NMR (300 MHz, CDCl$_3$) δ 9.00 (s, 1H), 8.07 (dd, J=8.3, 1.9 Hz, 1H), 7.90 (d, J=8.3 Hz, 1H), 7.58 (overlapping dd, J=7.1 Hz, 2H), 7.37 (s, 1H), 7.26 (d, 1H under solvent), 7.08 (dd, J=8.3, 1.7 Hz, 1H), 7.03 (dd, J=7.1, 1.9 Hz, 1H), 4.66 (s, 2H), 3.76 (br m, 2H), 3.65 (s, 3H), 2.82 (br m, 2H), 1.52 (s, 9H).

b) 4-(5-(Trifluoromethyl)pyridin-2-yl)-1-(9-methyl-2,3,4,5-tetrahydro-1H-pyrido[3,4-b]indol-7-yl)pyridin-2(1H)-one hydrochloride

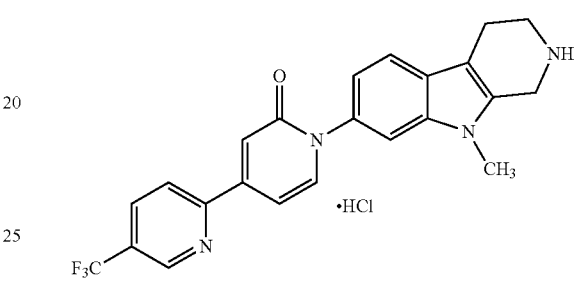

Chemical Formula: C$_{23}$H$_{20}$ClF$_3$N$_4$O
Exact Mass: 460.13
Molecular Weight: 460.88 tert-Butyl 9-methyl-7-(2-oxo-4-(5-(trifluoromethyl)pyridin-2-yl)pyridin-1(2H)-yl)-3,4-dihydro-1H-pyrido[3,4-b]indole-2(9H)-carboxylate (168 mg, 0.321 mmol) was deprotected and converted to the hydrochloride salt according to the procedure of Example 30 (steps e and g) to provide the title compound as an orange solid (73 mg, 54%): mp 305-315° C.; $^1$H NMR (500 MHz, CD$_3$OD) δ 9.05 (s, 1H), 8.28 (dd, J=8.3, 2.2 Hz, 1H), 8.22 (d, J=8.3, Hz, 1H), 7.84 (d, J=7.1 Hz, 1H), 7.67 (d, J=8.4 Hz, 1H), 7.58 (d, J=1.8 Hz, 1H), 7.40 (d, J=1.8 Hz, 1H), 7.25 (dd, J=7.2, 2.0 Hz, 1H), 7.15 (dd, J=8.4, 1.8 Hz, 1H), 4.57 (s, 2H), 3.74 (s, 3H), 3.62 (t, J=6.1 Hz, 2H), 3.15 (t, J=5.9 Hz, 2H); ESI MS m/z 425 [M+H]$^+$; HPLC (Method A) 96.4% (AUC), $t_R$=12.6 min.

Example 82

Preparation of 1-(2,9-Dimethyl-2,3,4,9-tetrahydro-1H-pyrido[3,4-b]indol-7-yl)-4-(5-(trifluoromethyl)pyridin-2-yl)pyridin-2(1H)-one hydrochloride

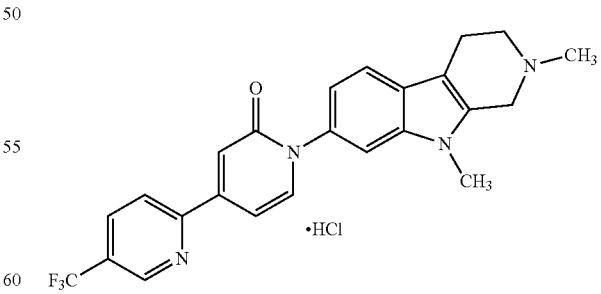

Chemical Formula: C$_{24}$H$_{22}$ClF$_3$N$_4$O
Exact Mass: 474.14
Molecular Weight: 474.91

4-(5-(Trifluoromethyl)pyridin-2-yl)-1-(9-methyl-2,3,4,5-tetrahydro-1H-pyrido[3,4-b]indol-7-yl)pyridin-2(1H)-one (125 mg, 0.294 mmol) was reacted following the procedure of Example 47 to provide the title compound (97.9 g, 78%) as a yellow solid: mp 280-290° C.; ¹H NMR (500 MHz, CD₃OD) δ 9.05 (s, 1H), 8.28 (dd, J=8.3, 2.1 Hz, 1H) 8.22 (d, J=8.4, Hz, 1H), 7.84 (d, J=7.1 Hz, 1H), 7.68 (d, J=8.3 Hz, 1H), 7.59 (d, J=1.6, 1H), 7.40 (d, J=1.7 Hz, 1H), 7.25 (dd, J=7.2, 1.9 Hz, 1H), 7.16 (dd, J=8.3, 1.8 Hz, 1H), 4.87 (s, 1H), 4.51 (s, 1H), 3.87 (s, 1H), 3.75 (br s, 3H), 3.55 (br s, 1H), 3.21-3.17 (m, 5H); ESI MS m/z 439 [M+H]⁺; HPLC (Method B) 98.3% (AUC), $t_R$=12.8 min.

Example 84

Preparation of 4-((5-Fluoropyridin-2-yl)methoxy)-1-(9-methyl-2,3,4,9-tetrahydro-1H-pyrido[3,4-b]indol-7-yl)pyridin-2(1H)-one hydrochloride a) tert-Butyl 7-(4-((5-fluoropyridin-2-yl)methoxy)-2-oxopyridin-1(2H)-yl)-9-methyl-3,4-dihydro-1H-pyrido[3,4-b]indole-2(9H)-carboxylate

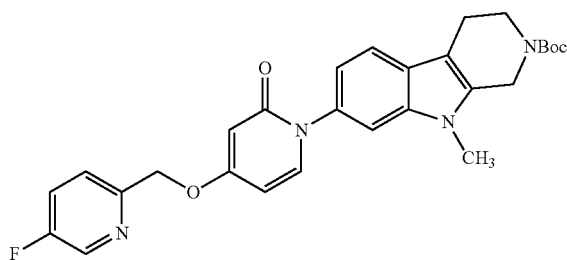

Chemical Formula: C₂₈H₂₉FN₄O₄
Exact Mass: 504.22
Molecular Weight: 504.55 tert-Butyl 7-bromo-9-methyl-3,4-dihydro-1H-pyrido[3,4-b]indole-2(9H)-carboxylate (306 mg, 0.840 mmol) and 4-(4-fluorobenzyloxy)pyridin-2(1H)-one (142 mg, 0.640 mmol) were reacted following the procedure of Example 30 (step g) to provide the title compound (157 mg, 49%) as a yellow/green solid: ¹H NMR (300 MHz, CDCl₃) δ 8.49 (d, J=2.0 Hz, 1H), 7.54-7.46 (m, 3H), 7.34-7.28 (m, 2H), 7.01 (dd, J=8.2, 1.8 Hz, 1H), 6.10 (d, J=2.7 Hz, 1H), 6.07 (s, 1H), 5.17 (s, 2H), 4.63 (br m, 2H), 3.74 (br m, 2H), 3.62 (s, 3H), 2.80 (br m, 2H), 1.51 (s, 9H).

b) 4-((5-Fluoropyridin-2-yl)methoxy)-1-(9-methyl-2,3,4,9-tetrahydro-1H-pyrido[3,4-b]indol-7-yl)pyridin-2(1H)-one hydrochloride

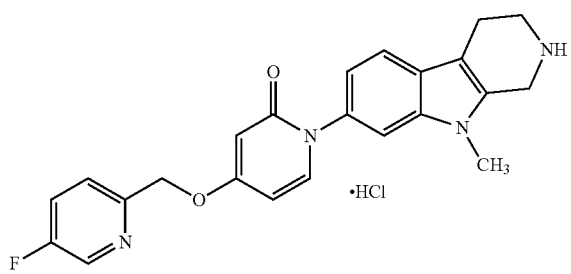

Chemical Formula: C₂₃H₂₂ClFN₄O₂
Exact Mass: 440.14
Molecular Weight: 440.90 tert-Butyl 7-(4-((5-fluoropyridin-2-yl)methoxy)-2-oxopyridin-1(2H)-yl)-9-methyl-3,4-dihydro-1H-pyrido[3,4-b]indole-2(9H)-carboxylate (157 mg, 0.312 mmol) was deprotected and converted to the hydrochloride salt according to the procedure of Example 30 (steps e and g) to provide the title compound as a yellow solid (72.7 mg, 54%): mp 285-295° C.; ¹H NMR (500 MHz, CD₃OD) δ 8.51 (s, 1H), 7.72-7.59 (m, 4H), 7.46 (d, J=1.0 Hz, 1H), 7.05 (dd, J=8.3, 1.5 Hz, 1H), 6.32 (dd, J=7.6, 2.6 Hz, 1H), 7.05 (d, J=2.6 Hz, 1H), 5.26 (s, 2H), 4.54 (s, 2H), 3.71 (s, 3H), 3.60 (t, J=6.0 Hz, 2H), 3.12 (t, J=5.8 Hz, 2H); ESI MS m/z 405 [M+H]⁺; HPLC (Method B) 98.3% (AUC), $t_R$=12.0 min.

Example 85

Preparation of 1-(2,9-Dimethyl-2,3,4,9-tetrahydro-1H-pyrido[3,4-b]indol-7-yl)-4-((5-fluoropyridin-2-yl)methoxy)pyridin-2(1H)-one hydrochloride

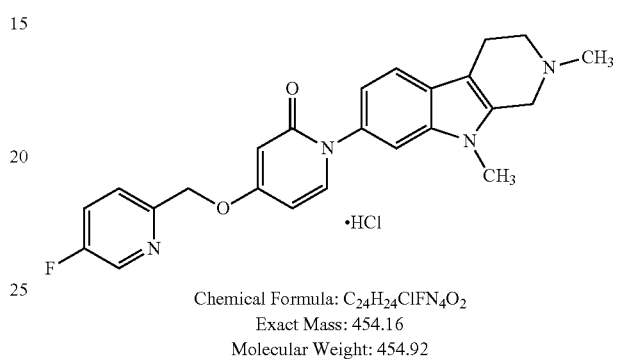

Chemical Formula: C₂₄H₂₄ClFN₄O₂
Exact Mass: 454.16
Molecular Weight: 454.92

4-((5-Fluoropyridin-2-yl)methoxy)-1-(9-methyl-2,3,4,9-tetrahydro-1H-pyrido[3,4-b]indol-7-yl)pyridin-2(1H)-one (76 mg, 0.19 mmol) was reacted following the procedure of Example 47 to provide the title compound (61 mg, 79%) as a yellow solid: mp 287-300° C.; ¹H NMR (500 MHz, CD₃OD) δ 8.51 (d, J=2.6 Hz, 1H), 7.72-7.59 (m, 4H), 7.47 (s, 1H), 7.06 (dd, J=8.3, 1.7 Hz, 1H), 6.32 (dd, J=7.6, 2.6 Hz, 1H), 6.13 (d, J=2.6 Hz, 1H), 5.26 (s, 2H), 4.68 (m, 2H), 3.71 (m, 5H), 3.18 (t, J=5.9 Hz, 2H), 3.15 (s, 3H); ESI MS m/z 419 [M+H]⁺; HPLC (Method B) 98.4% (AUC), $t_R$=11.1 min.

Example 86

Preparation of 1-(9-Methyl-2,3,4,9-tetrahydro-1H-pyrido[3,4-b]indol-7-yl)-4-(6-(trifluoromethyl)pyridin-3-yl)pyridin-2(1H)-one hydrochloride a) tert-Butyl 9-methyl-7-(2-oxo-4-(6-(trifluoromethyl)pyridin-3-yl)pyridin-1(2H)-yl)-3,4-dihydro-1H-pyrido[3,4-b]indole-2(9H)-carboxylate

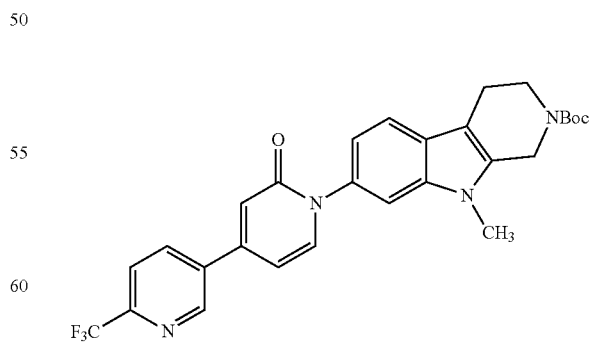

Chemical Formula: C₂₈H₂₇F₃N₄O₃
Exact Mass: 524.20
Molecular Weight: 524.53

4-(6-(Trifluoromethyl)pyridin-3-yl)pyridin-2(1H)-one (145 mg, 0.604 mmol) and tert-butyl 7-bromo-9-methyl-3,4-dihydro-1H-pyrido[3,4-b]indole-2(9H)-carboxylate (200 mg, 0.549 mmol) were coupled following the procedure of Example 30 (step g) to provide the title compound (129 mg, 45%) as a yellow/green solid: $^1$H NMR (500 MHz, CDCl$_3$) δ 9.00 (s, 1H), 8.10 (dd, J=8.1, 2.0 Hz, 1H), 7.82 (d, J=8.2 Hz, 1H), 7.60-7.57 (m, 2H), 7.36 (s, 1H), 7.08 (dd, J=8.3, 1.8 Hz, 1H), 6.93 (d, J=1.8 Hz, 1H), 6.49 (dd, J=7.1, 2.0 Hz, 1H), 4.66 (br m, 2H), 3.76 (br m, 2H), 3.66 (s, 3H), 2.82 (br m, 2H), 1.52 (s, 9H).

b) 1-(9-Methyl-2,3,4,9-tetrahydro-1H-pyrido[3,4-b]indol-7-yl)-4-(6-(trifluoromethyl)pyridin-3-yl)pyridin-2(1H)-one hydrochloride

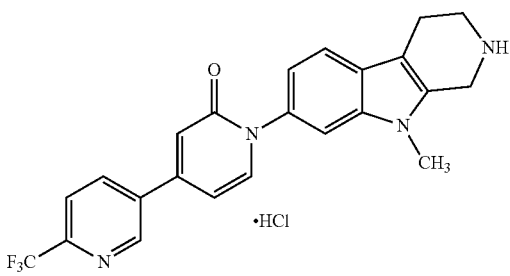

Chemical Formula: C$_{23}$H$_{20}$ClF$_3$N$_4$O
Exact Mass: 460.13
Molecular Weight: 460.88 tert-Butyl 9-methyl-7-(2-oxo-4-(6-(trifluoromethyl)pyridin-3-yl)pyridin-1(2H)-yl)-3,4-dihydro-1H-pyrido[3,4-b]indole-2(9H)-carboxylate (129 mg, 0.25 mmol) was deprotected and converted to the hydrochloride salt according to the procedure of Example 30 (steps e and g) to provide the title compound (67 mg, 58%) as a yellow/brown solid: mp 315-320° C.; $^1$H NMR (500 MHz, CD$_3$OD) δ 9.10 (d, J=1.9 Hz, 1H), 8.41 (dd, J=8.2, 2.2 Hz, 1H), 7.97 (d, J=8.3 Hz, 1H), 7.85 (d, J=7.0 Hz, 1H), 7.68 (d, J=8.3 Hz, 1H), 7.57 (d, J=1.7 Hz, 1H), 7.15 (dd, J=8.3, 1.8 Hz, 1H), 7.03 (d, J=1.8 Hz, 1H), 6.89 (dd, J=7.1, 2.0 Hz, 1H), 4.57 (br m, 2H), 3.75 (s, 3H), 3.62 (br m, 2H), 3.15 (br m, 2H); ESI MS m/z 425 [M+H]$^+$; HPLC (Method B) 97.4% (AUC), t$_R$=12.3 min.

Example 87

Preparation of 1-(2,3,4,9-Tetrahydro-1H-pyrido[3,4-b]indol-7-yl)-4-(5-(trifluoromethyl)pyridin-2-yl)pyridin-2(1H)-one hydrochloride a) tert-Butyl 7-bromo-9-tosyl-3,4-dihydro-1H-pyrido[3,4-b]indole-2(9H)-carboxylate

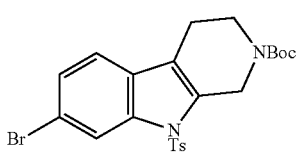

Chemical Formula: C$_{23}$H$_{25}$BrN$_2$O$_4$S
Exact Mass: 504.07
Molecular Weight: 505.42

6 N NaOH solution (6 mL), (Bu$_4$N)$_2$SO$_4$ (50% wt. solution in H$_2$O, 0.20 mL), and TsCl (646 mg, 3.39 mmol) were added to a suspension of tert-butyl 7-bromo-3,4-dihydro-1H-pyrido[3,4-b]indole-2(9H)-carboxylate (991 mg, 2.82 mmol) in toluene (20 mL) and the resulting suspension was stirred at 25° C. for 1.5 h. H$_2$O and EtOAc were added to the suspension and the phases were separated. The organic phase was washed with H$_2$O, dried over Na$_2$SO$_4$ and concentrated under reduced pressure to afford the title compound (1.285 g, 90%) as a white foam: $^1$H NMR (300 MHz, CDCl$_3$) δ 8.32 (d, J=1.5 Hz, 1H), 7.78-7.66 (m, 2H), 7.36 (dd, J=8.4, 1.5 Hz, 1H), 7.25-7.21 (m, 2H), 7.21-7.13 (m, 1H), 4.92-4.81 (m, 2H), 3.74-3.63 (m, 2H), 2.70-2.61 (m, 2H), 2.37 (s, 3H), 1.50 (s, 9H).

b) tert-Butyl 7-(2-oxo-4-(5-(trifluoromethyl)pyridin-2-yl)pyridin-1(2H)-yl)-9-tosyl-3,4-dihydro-1H-pyrido[3,4-b]indole-2(9H)-carboxylate

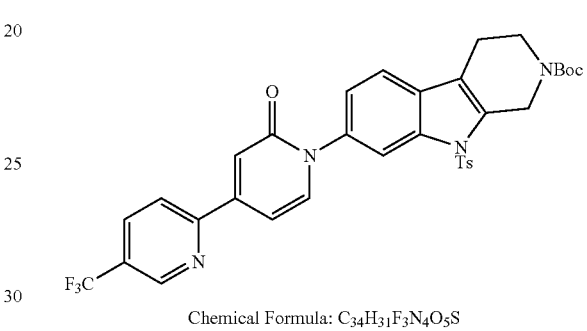

Chemical Formula: C$_{34}$H$_{31}$F$_3$N$_4$O$_5$S
Exact Mass: 664.20
Molecular Weight: 664.69

4-(5-(Trifluoromethyl)pyridin-2-yl)pyridin-2(1H)-one (200 mg, 0.830 mmol) and tert-butyl 7-bromo-9-tosyl-3,4-dihydro-1H-pyrido[3,4-b]indole-2(9H)-carboxylate (419 mg, 0.830 mmol) were coupled following the procedure of Example 30 (step g) to provide the title compound (222 mg, 40%) as a yellow solid: $^1$H NMR (500 MHz, CDCl$_3$) δ 9.02 (s, 1H), 8.26 (s, 1H), 8.08 (d, J=7.6 Hz, 1H), 7.80 (br s, 2H), 7.57 (d, J=7.2 Hz, 1H), 7.47 (d, J=7.2 Hz, 1H), 7.47 (d, J=8.0 Hz, 1H), 7.32 (d, J=7.9 Hz, 1H), 7.27 (3H, under solvent peak), 7.07 (d, J=6.8 Hz, 1H), 4.91 (br m, 2H), 3.71 (br m, 2H), 2.71 (br m, 2H), 2.36 (s, 3H), 1.52 (s, 9H).

c) 1-(9-Tosyl-2,3,4,9-tetrahydro-1H-pyrido[3,4-b]indol-7-yl)-4-(5-(trifluoromethyl)pyridin-2-yl)pyridin-2(1H)-one

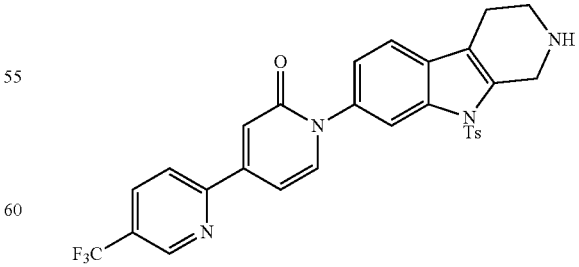

Chemical Formula: C$_{29}$H$_{23}$F$_3$N$_4$O$_3$S
Exact Mass: 564.14
Molecular Weight: 564.58 tert-Butyl 7-(2-oxo-4-(5-(trifluoromethyl)pyridin-2-yl)pyridin-1(2H)-yl)-9-tosyl-3,4-dihydro-1H-pyrido[3,4-b]indole-2(9H)-carboxylate (222 mg, 0.334 mmol) was deprotected according to the procedure of Example 30 (step e) to provide the title compound (131 mg, 58%) as a yellow solid: $^1$H NMR (300 MHz, CDCl$_3$) δ 9.02 (s, 1H), 8.25 (d, J=1.6 Hz, 1H), 8.08 (dd, J=8.3, 1.9 Hz, 1H), 7.93 (d, J=8.3 Hz, 1H), 7.75 (d, J=8.4 Hz, 2H), 7.58 (d, J=7.2 Hz, 1H), 7.48 (d, J=8.3 Hz, 1H), 7.32 (dd, J=8.3, 1.8 Hz, 1H), 7.28-7.24 (3H, under solvent peak), 7.08 (dd, J=7.2, 2.0 Hz, 1H), 4.30 (br s, 2H), 3.13 (t, J=5.6 Hz, 2H), 3.61 (br m, 2H), 2.36 (s, 3H).

d) 1-(2,3,4,9-Tetrahydro-1H-pyrido[3,4-b]indol-7-yl)-4-(5-(trifluoromethyl)pyridin-2-yl)pyridin-2(1H)-one dihydrochloride

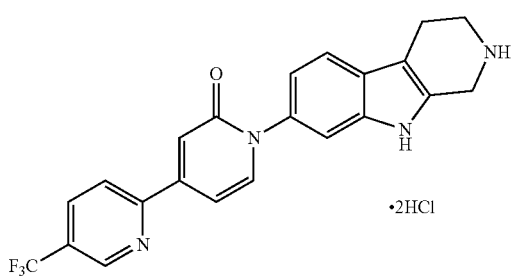

Chemical Formula: C$_{22}$H$_{19}$Cl$_2$F$_3$N$_4$O
Exact Mass: 482.09
Molecular Weight: 483.31

1-(9-Tosyl-2,3,4,9-tetrahydro-1H-pyrido[3,4-b]indol-7-yl)-4-(5-(trifluoromethyl)pyridin-2-yl)pyridin-2(1H)-one (130 mg, 0.23 mmol) was deprotected according to the procedure of Example 106 (step b) to provide the title compound (39.5 mg, 36%) as a yellow solid: mp 320-330° C.; $^1$H NMR (500 MHz, CD$_3$OD) δ 9.05 (s, 1H), 8.28 (dd, J=8.4, 2.1 Hz, 1H), 8.22 (d, J=8.4 Hz, 1H), 7.82 (d, J=7.2 Hz, 1H), 7.66 (d, J=8.4 Hz, 1H), 7.48 (d, J=7.1 Hz, 1H), 7.39 (d, J=1.7 Hz, 1H), 7.24 (dd, J=7.2, 1.9 Hz, 1H), 7.13 (dd, J=8.4, 1.8 Hz, 1H), 4.50 (s, 2H), 3.63 (t, J=6.1 Hz, 2H), 3.14 (t, J=6.1 Hz, 2H); ESI MS m/z 411 [M+H]$^+$; HPLC (Method B) 98.4% (AUC), t$_R$=12.6 min.

Example 88

Preparation of 5-(Benzyloxy)-2-(9-methyl-2,3,4,9-tetrahydro-1H-pyrido[3,4-b]indol-7-yl)pyridazin-3(2H)-one hydrochloride a) tert-Butyl 7-(4-(benzyloxy)-6-oxopyridazin-1(6H)-yl)-9-methyl-3,4-dihydro-1H-pyrido[3,4-b]indole-2(9H)-carboxylate

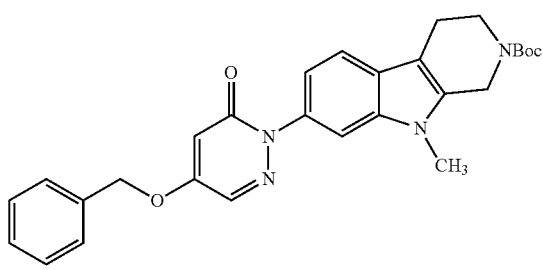

Chemical Formula: C$_{28}$H$_{30}$N$_4$O$_4$
Exact Mass: 486.23
Molecular Weight: 486.56

5-(Benzyloxy)pyridazin-3(2H)-one (197 mg, 0.974 mmol) and tert-butyl 7-bromo-9-methyl-3,4-dihydro-1H-pyrido[3,4-b]indole-2(9H)-carboxylate (353 mg, 0.966 mmol) were coupled following the procedure of Example 30 (step g) to provide the title compound (130 mg, 28%) as a yellow/green solid: $^1$H NMR (300 MHz, CDCl$_3$) δ 7.77 (d, J=2.7 Hz, 1H), 7.52 (d, J=8.2 Hz, 1H), 7.45-7.40 (m, 7H), 7.21 (dd, J=8.4, 1.5 Hz, 1H), 5.08 (s, 2H), 4.64 (br m, 2H), 3.75 (br m, 2H), 3.63 (s, 3H), 2.80 (br m, 2H), 1.52 (s, 9H).

b) 5-(Benzyloxy)-2-(9-methyl-2,3,4,9-tetrahydro-1H-pyrido[3,4-b]indol-7-yl)pyridazin-3(2H)-one hydrochloride

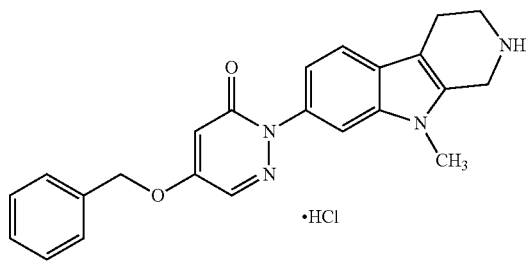

Chemical Formula: C$_{23}$H$_{23}$ClN$_4$O$_2$
Exact Mass: 422.15
Molecular Weight: 422.91 tert-Butyl 7-(4-(benzyloxy)-6-oxopyridazin-1(6H)-yl)-9-methyl-3,4-dihydro-1H-pyrido[3,4-b]indole-2(9H)-carboxylate (130 mg, 0.27 mmol) was deprotected and converted to the hydrochloride salt according to the procedure of Example 30 (steps e and g) to provide the title compound (55.7, 48%) as a yellow solid: mp 235-245° C.; $^1$H NMR (500 MHz, CD$_3$OD) δ 7.93 (d, J=2.7 Hz, 1H), 7.59 (d, J=8.4 Hz, 1H), 7.56 (d, J=1.5 Hz, 1H), 7.50-7.48 (m, 2H), 7.43 (overlapping dd, J=7.8 Hz, 2H), 7.39 (d, J=1.7 Hz, 1H), 7.18 (dd, J=8.4, 1.7 Hz, 1H), 6.48 (d, J=2.7 Hz, 1H), 5.22 (s, 2H), 4.54 (s, 2H), 3.71 (s, 3H), 3.59 (t, J=5.6 Hz, 2H), 3.12 (t, J=5.9 Hz, 2H); ESI MS m/z 387 [M+H]$^+$; HPLC (Method B)>99% (AUC), t$_R$=11.7 min.

Example 89

Preparation of 1-(9-Methyl-2,3,4,9-tetrahydro-1H-pyrido[3,4-b]indol-7-yl)-4-((6-(trifluoromethyl)pyridin-3-yl)methoxy)pyridin-2(1H)-one hydrochloride a) tert-Butyl 9-methyl-7-(2-oxo-4-((6-(trifluoromethyl)pyridin-3-yl)methoxy)pyridin-1(2H)-yl)-3,4-dihydro-1H-pyrido[3,4-b]indole-2(9H)-carboxylate

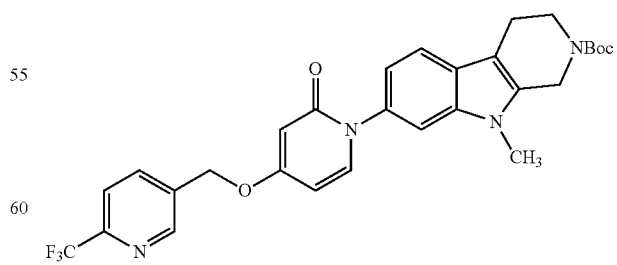

Chemical Formula: C$_{29}$H$_{29}$F$_3$N$_4$O$_4$
Exact Mass: 554.21
Molecular Weight: 554.56

4-((6-(Trifluoromethyl)pyridin-3-yl)methoxy)pyridin-2(1H)-one (100 mg, 0.37 mmol) and tert-butyl 7-bromo-9-methyl-3,4-dihydro-1H-pyrido[3,4-b]indole-2(9H)-carboxylate (135 mg, 0.370 mmol) were coupled following the procedure of Example 30 (step g) to provide the title compound (44 mg, 21%) as a yellow/brown solid: $^1$H NMR (300 MHz, CDCl$_3$) δ 8.81 (s, 1H), 7.96 (d, J=8.6 Hz, 1H), 7.75 (d, J=8.0 Hz, 1H), 7.54 (d, J=8.3 Hz, 1H), 7.37-7.34 (m, 1H), 7.27 (1H, under solvent peak), 7.02 (dd, J=8.3, 1.7 Hz, 1H), 6.07-6.04 (m, 2H), 5.16 (s, 2H), 4.64 (br m, 2H), 3.75 (br m, 2H), 3.63 (s, 3H), 2.80 (br m, 2H), 1.52 (s, 9H).

b) 1-(9-Methyl-2,3,4,9-tetrahydro-1H-pyrido[3,4-b]indol-7-yl)-4-((6-(trifluoromethyl)pyridin-3-yl)methoxy)pyridin-2(1H)-one hydrochloride

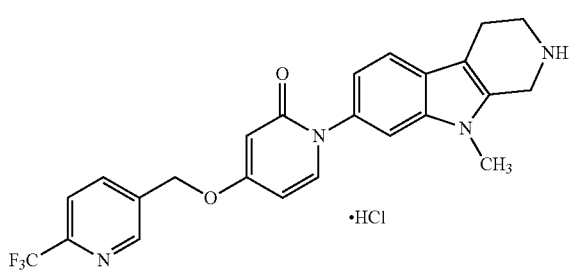

Chemical Formula: C$_{24}$H$_{22}$ClF$_3$N$_4$O$_2$
Exact Mass: 490.14
Molecular Weight: 490.91 tert-Butyl 9-methyl-7-(2-oxo-4-((6-(trifluoromethyl)pyridin-3-yl)methoxy)pyridin-1(2H)-yl)-3,4-dihydro-1H-pyrido[3,4-b]indole-2(9H)-carboxylate (44 mg, 0.079 mmol) was deprotected and converted to the hydrochloride salt according to the procedure of Example 30 (steps e and g) to provide the title compound (28 mg, 65%) as a yellow solid: mp 285-295° C.; $^1$H NMR (500 MHz, CD$_3$OD) δ 8.75 (s, 1H), 8.08 (d, J=7.9 Hz, 1H), 7.79 (d, J=8.1 Hz, 1H), 7.53 (dd, J=7.9, 2.0 Hz, 2H), 7.38 (d, J=1.7 Hz, 1H), 6.97 (dd, J=8.4, 1.8 Hz, 1H), 6.25 (dd, J=7.6, 2.7 Hz, 1H), 6.08 (d, J=2.6 Hz, 1H), 5.26 (s, 2H), 4.46 (s, 2H), 3.63 (s, 3H), 3.51 (t, J=6.1 Hz, 2H), 3.03 (t, J=6.1 Hz, 2H); ESI MS m/z 455 [M+H]$^+$; HPLC (Method B)>99% (AUC), t$_R$=12.8 min.

Example 90

Preparation of 1-(9-Methyl-2,3,4,9-tetrahydro-1H-pyrido[3,4-b]indol-7-yl)-4-(5-methylpyridin-2-yl)pyridin-2(1H)-one dihydrochloride a) 2'-Methoxy-5-methyl-2,4'-bipyridine

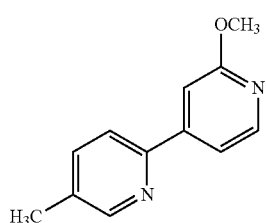

Chemical Formula: C$_{12}$H$_{12}$N$_2$O
Exact Mass: 200.09
Molecular Weight: 200.24

2-Bromo-5-methylpyridine (2.93 g, 17.0 mmol) and 2-methoxy-4-(4,4,5,5-tetramethyl-1,3,2-dioxaborolan-2-yl)pyridine (3.34 g, 14.2 mmol) were reacted according to Example 31 (step a) to provide the title compound (1.2 g, 42%) as a brown solid: ESI MS m/z 201 [M+H]$^+$.

b) 4-(5-Methylpyridin-2-yl)pyridin-2(1H)-one

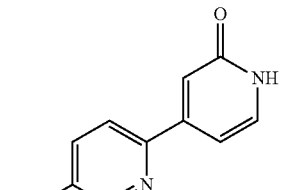

Chemical Formula: C$_{11}$H$_{10}$N$_2$O
Exact Mass: 186.08
Molecular Weight: 186.21

2'-Methoxy-5-methyl-2,4'-bipyridine (1.2 g, 6.0 mmol) was reacted according to Example 31 (step c) to provide the title compound (301 mg, 27%) as a white solid: $^1$H NMR (500 MHz, DMSO-d$_6$) δ 11.58 (s, 1H) 8.53 (s, 1H), 7.88 (overlapping dd, J=8.2 Hz, 1H), 7.71 (d, J=6.0 Hz, 1H), 7.43 (d, J=7.7, 1H), 6.95 (d, J=1.5 Hz, 1H), 6.84 (dd, J=6.9, 1.7 Hz, 1H), 2.34 (s, 3H).

c) tert-Butyl 9-methyl-7-(4-(5-methylpyridin-2-yl)-2-oxopyridin-1(2H)-yl)-3,4-dihydro-1H-pyrido[3,4-b]indole-2(9H)-carboxylate

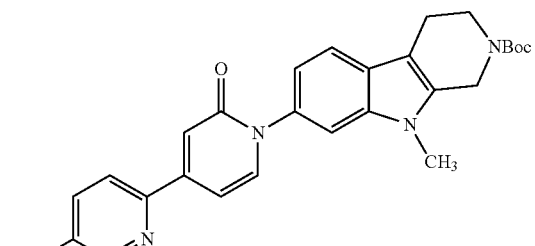

Chemical Formula: C$_{28}$H$_{30}$N$_4$O$_3$
Exact Mass: 470.23
Molecular Weight: 470.56

4-(5-methylpyridin-2-yl)pyridin-2(1H)-one (150 mg, 0.81 mmol) and tert-butyl 7-bromo-9-methyl-3,4-dihydro-1H-pyrido[3,4-b]indole-2(9H)-carboxylate (294 mg, 0.805 mmol) were reacted following the procedure of Example 30 (step g) to provide the title compound (138 mg, 36%) as a yellow/green solid: $^1$H NMR (500 MHz, CDCl$_3$) δ 8.56 (s, 1H), 7.71 (d, J=8.2 Hz, 1H), 7.63-7.61 (m, 1H), 7.56 (d, J=8.3 Hz, 1H), 7.52 (d, J=7.2 Hz, 1H), 7.37 (s, 1H), 7.17 (d, J=1.6 Hz, 1H), 7.09 (dd, J=8.3, 1.7 Hz, 1H), 7.04 (dd, J=7.2, 1.9 Hz, 1H), 4.65 (br m, 2H), 3.76 (br m, 2H), 3.65 (s, 3H), 2.82 (br m, 2H), 2.42 (s, 3H), 1.51 (s, 9H).

d) 1-(9-Methyl-2,3,4,9-tetrahydro-1H-pyrido[3,4-b]indol-7-yl)-4-(5-methylpyridin-2-yl)pyridin-2(1H)-one dihydrochloride

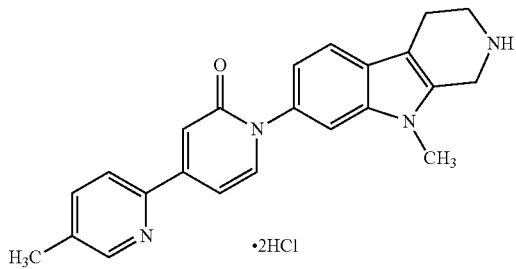

Chemical Formula: $C_{23}H_{24}Cl_2N_4O$
Exact Mass: 442.13
Molecular Weight: 443.37 tert-Butyl 9-methyl-7-(4-(5-methylpyridin-2-yl)-2-oxopyridin-1(2H)-yl)-3,4-dihydro-1H-pyrido[3,4-b]indole-2(9H)-carboxylate (138 mg, 0.27 mmol) was deprotected and converted to the dihydrochloride salt according to the procedure of Example 30 (steps e and g) to provide the title compound (18 mg, 15%) as a yellow solid: mp 303-310° C.; $^1$H NMR (500 MHz, CD$_3$OD) δ 8.59 (s, 1H), 7.95 (d, J=8.1 Hz, 1H), 7.87 (d, J=6.5 Hz, 1H), 7.80 (d, J=7.0 Hz, 1H), 7.67 (d, J=8.4 Hz, 1H), 7.56 (d, J=1.4 Hz, 1H), 7.24 (d, J=1.6 Hz, 1H), 7.15-7.12 (m, 2H), 4.57 (s, 2H), 3.74 (s, 3H), 3.61 (t, J=6.0 Hz, 2H), 3.14 (t, J=6.1 Hz, 2H), 2.46 (s, 3H); ESI MS m/z 371 [M+H]$^+$; HPLC (Method B)>99% (AUC), $t_R$=11.0 min.

Example 91

Preparation of 1-(5-Methyl-2,3,4,5-tetrahydro-1H-pyrido[4,3-b]indol-7-yl)-4-(5-methylpyridin-2-yl)pyridin-2(1H)-one dihydrochloride a) tert-Butyl 5-methyl-7-(4-(5-methylpyridin-2-yl)-2-oxopyridin-1(2H)-yl)-3,4-dihydro-1H-pyrido[4,3-b]indole-2(5H)-carboxylate

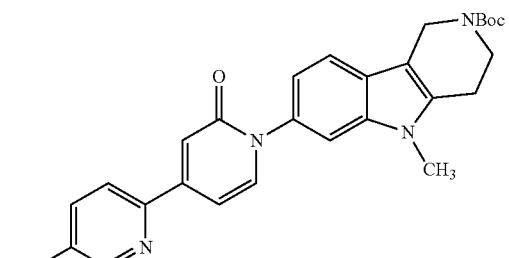

Chemical Formula: $C_{28}H_{30}N_4O_3$
Exact Mass: 470.23
Molecular Weight: 470.56

4-(5-Methylpyridin-2-yl)pyridin-2(1H)-one (150 mg, 0.81 mmol) and tert-butyl 7-bromo-5-methyl-3,4-dihydro-1H-pyrido[4,3-b]indole-2(5H)-carboxylate (294 mg, 0.805 mmol) were reacted following the procedure of Example 30 (step g) to provide the title compound (245 mg, 64%) as a yellow/green solid: $^1$H NMR (300 MHz, CDCl$_3$) δ 8.57 (d, J=2.0 Hz, 1H), 7.71 (d, J=8.0 Hz, 1H), 7.64-7.60 (m, 1H), 7.55-7.51 (m, 2H), 7.37 (d, J=1.6 Hz, 1H), 7.17 (d, J=1.6 Hz, 1H), 7.10-7.03 (m, 2H), 4.66 (br m, 2H), 3.85 (br m, 2H), 3.65 (s, 3H), 2.84 (br m, 2H), 2.42 (s, 3H), 1.51 (s, 9H).

b) 1-(5-Methyl-2,3,4,5-tetrahydro-1H-pyrido[4,3-b]indol-7-yl)-4-(5-methylpyridin-2-yl)pyridin-2(1H)-one dihydrochloride

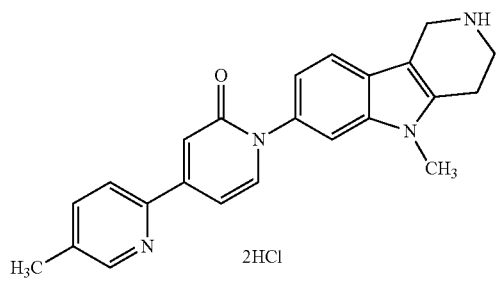

Chemical Formula: $C_{23}H_{24}Cl_2N_4O$
Exact Mass: 442.13
Molecular Weight: 443.37 tert-Butyl 5-methyl-7-(4-(5-methylpyridin-2-yl)-2-oxopyridin-1(2H)-yl)-3,4-dihydro-1H-pyrido[4,3-b]indole-2(5H)-carboxylate (245 mg, 0.520 mmol) was deprotected and converted to the dihydrochloride salt according to the procedure of Example 30 (steps e and g) to provide the title compound (57 mg, 30%) as a yellow solid: mp 295-305° C.; $^1$H NMR (500 MHz, CD$_3$OD) δ 8.76 (d, J=1.8 Hz, 1H), 8.34 (d, J=6.9 Hz, 1H), 8.24 (d, J=8.2 Hz, 1H), 7.94 (d, J=7.2 Hz, 1H), 7.67 (d, J=8.3 Hz, 1H), 7.61 (d, J=1.7 Hz, 1H), 7.23 (d, J=1.8 Hz, 1H), 7.17 (dd, J=8.3, 1.8 Hz, 1H), 7.04 (dd, J=7.1, 2.1 Hz, 1H), 4.53 (s, 2H), 3.79 (s, 3H), 3.71 (t, J=6.2 Hz, 2H), 3.25 (t, J=6.2 Hz, 2H), 2.61 (s, 3H); ESI MS m/z 371 [M+H]$^+$; HPLC (Method B) 97.3% (AUC), $t_R$=10.9 min.

Example 92

Preparation of 1-(5-Methyl-2,3,4,9-tetrahydro-1H-pyrido[4,3-b]indol-7-yl)-4-(6-methylpyridin-3-yl)pyridin-2(1H)-one dihydrochloride a) 2'-Methoxy-6-methyl-3,4'-bipyridine

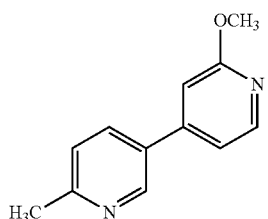

Chemical Formula: $C_{12}H_{12}N_2O$
Exact Mass: 200.09
Molecular Weight: 200.24

2-Methyl-5-(4,4,5,5-tetramethyl-1,3,2-dioxaborolan-2-yl)pyridine (3.5 g, 16 mmol) and 4-bromo-2-methoxypyridine (2.0 g, 11 mmol) were reacted according to Example 31

(step a) to provide the title compound (2.1 g, 98%) as a brown solid: ¹H NMR (300 MHz, CDCl₃) δ 8.75 (d, J=2.1 Hz, 1H), 8.23 (d, J=5.4 Hz, 1H), 7.78 (dd, J=8.0, 2.4 Hz, 1H), 7.24 (d, J=8.1, 1H), 7.08 (dd, J=5.4, 1.5 Hz, 1H), 6.84 (d, J=1.0, 1H), 3.98 (s, 3H), 2.61 (s, 3H).

b) 4-(6-Methylpyridin-3-yl)pyridin-2(1H)-one

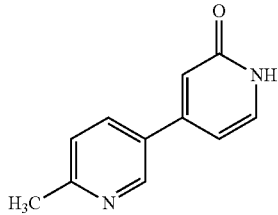

Chemical Formula: C₁₁H₁₀N₂O
Exact Mass: 186.08
Molecular Weight: 186.21

2'-Methoxy-6-methyl-3,4'-bipyridine (2.1 g, 10.4 mmol) was reacted according to Example 31 (step c) to provide the title compound (1.36 mg, 68%) as a white solid: ¹H NMR (300 MHz, DMSO-d₆) δ 11.65 (s, 1H) 8.78 (d, J=2.1 Hz, 1H), 8.01 (dd, J=8.1, 2.5 Hz, 1H), 7.47 (d, J=6.9 Hz, 1H), 7.36 (d, J=8.1, 1H), 6.66 (d, J=1.4 Hz, 1H), 6.55 (dd, J=6.9, 1.8 Hz, 1H), 2.51 (s, 3H).

c) tert-Butyl 5-methyl-7-(4-(6-methylpyridin-3-yl)-2-oxopyridin-1(2H)-yl)-3,4-dihydro-1H-pyrido[4,3-b]indole-2(5H)-carboxylate

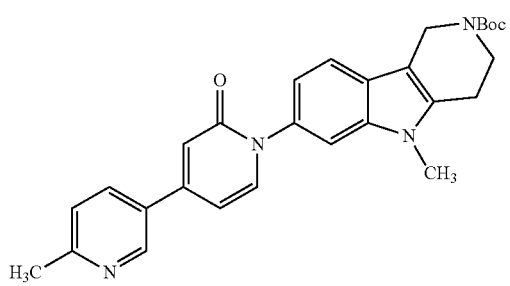

Chemical Formula: C₂₈H₃₀N₄O₃
Exact Mass: 470.23
Molecular Weight: 470.56

4-(6-Methylpyridin-3-yl)pyridin-2(1H)-one (150 mg, 0.81 mmol) and tert-butyl 7-bromo-5-methyl-3,4-dihydro-1H-pyrido[4,3-b]indole-2(5H)-carboxylate (294 mg, 0.805 mmol) were reacted following the procedure of Example 30 (step g) to provide the title compound (220 mg, 58%) as a yellow/green solid: ¹H NMR (500 MHz, CDCl₃) δ 8.79 (d, J=8.2 Hz, 1H), 7.83 (dd, J=8.1, 2.4 Hz, 1H), 7.56-7.51 (m, 2H), 7.37 (d, J=1.4 Hz, 1H), 7.30 (1H, partially under solvent), 7.08 (d, J=8.7 Hz, 1H), 6.90 (d, J=1.6 Hz, 1H), 6.50 (dd, J=7.1, 1.9 Hz, 1H), 4.66 (br s, 2H), 3.85 (br m, 2H), 3.65 (s, 3H), 2.84 (br m, 2H), 2.64 (s, 3H), 1.51 (s, 9H).

d) 1-(5-Methyl-2,3,4,5-tetrahydro-1H-pyrido[4,3-b]indol-7-yl)-4-(6-methylpyridin-3-yl)pyridin-2(1H)-one dihydrochloride

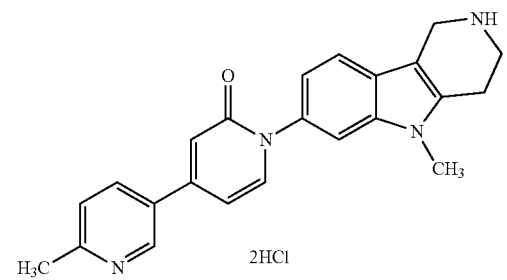

Chemical Formula: C₂₃H₂₄Cl₂N₄O
Exact Mass: 442.13
Molecular Weight: 443.37 tert-Butyl 5-methyl-7-(4-(6-methylpyridin-3-yl)-2-oxopyridin-1(2H)-yl)-3,4-dihydro-1H-pyrido[4,3-b]indole-2(5H)-carboxylate (220 mg, 0.47 mmol) was deprotected and converted to the dihydrochloride salt according to the procedure of Example 30 (steps e and g) to provide the title compound (50.2 mg, 29%) as a yellow solid: mp 295-305° C.; ¹H NMR (500 MHz, CD₃OD) δ 8.80 (d, J=2.2 Hz, 1H), 8.12 (dd, J=8.1, 2.5 Hz, 1H), 7.79 (d, J=7.0 Hz, 1H), 7.59 (d, J=8.3 Hz, 1H), 7.52 (d, J=1.7 Hz, 1H), 7.47 (d, J=8.2 Hz, 1H), 7.10 (dd, J=8.3, 1.9 Hz, 1H), 6.93 (d, J=1.8 Hz, 1H), 6.85 (dd, J=7.1, 2.0 Hz, 1H), 4.34 (s, 2H), 3.73 (s, 3H), 3.52 (t, J=6.1 Hz, 2H), 3.10 (t, J=6.1 Hz, 2H), 2.62 (s, 3H); ESI MS m/z 371 [M+H]⁺; HPLC (Method B)>99% (AUC), t_R=8.7 min.

Example 93

Preparation of 1-(9-Methyl-2,3,4,9-tetrahydro-1H-pyrido[3,4-b]indol-7-yl)-4-(6-methylpyridin-3-yl)pyridin-2(1H)-one dihydrochloride a) tert-Butyl 9-methyl-7-(4-(6-methylpyridin-3-yl)-2-oxopyridin-1(2H)-yl)-3,4-dihydro-1H-pyrido[3,4-b]indole-2(9H)-carboxylate

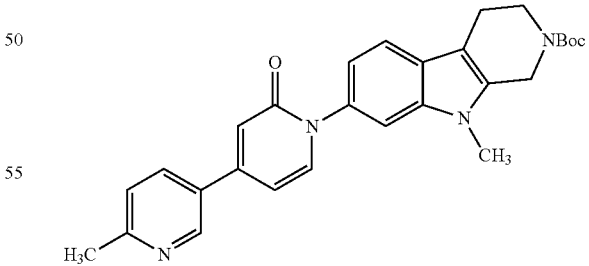

Chemical Formula: C₂₈H₃₀N₄O₃
Exact Mass: 470.23
Molecular Weight: 470.56

4-(6-Methylpyridin-3-yl)pyridin-2(1H)-one (150 mg, 0.81 mmol) and tert-butyl 7-bromo-9-methyl-3,4-dihydro-1H-pyrido[3,4-b]indole-2(9H)-carboxylate (294 mg, 0.805 mmol) were reacted following the procedure of Example 30

(step g) to provide the title compound (208 mg, 55%) as a yellow/green solid: $^1$H NMR (300 MHz, CDCl$_3$) δ 8.79 (d, J=8.2 Hz, 1H), 7.83 (dd, J=8.0, 2.3 Hz, 1H), 7.58-7.51 (m, 2H), 7.36 (s, 1H), 7.30 (1H, partially under solvent), 7.08 (dd, J=8.3, 1.8 Hz, 1H), 6.90 (d, J=1.7 Hz, 1H), 6.50 (dd, J=7.1, 2.0 Hz, 1H), 4.65 (br s, 2H), 3.76 (br m, 2H), 3.65 (s, 3H), 2.82 (br m, 2H), 2.64 (s, 3H), 1.52 (s, 9H).

b) 1-(9-Methyl-2,3,4,9-tetrahydro-1H-pyrido[3,4-b]indol-7-yl)-4-(6-methylpyridin-3-yl)pyridin-2(1H)-one dihydrochloride

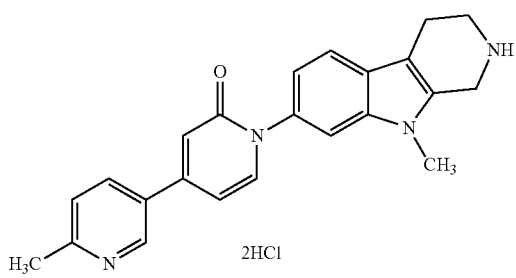

Chemical Formula: C$_{23}$H$_{24}$Cl$_2$N$_4$O
Exact Mass: 442.13
Molecular Weight: 443.37 tert-Butyl 9-methyl-7-(4-(6-methylpyridin-3-yl)-2-oxopyridin-1(2H)-yl)-3,4-dihydro-1H-pyrido[3,4-b]indole-2(9H)-carboxylate (208 mg, 0.442 mmol) was deprotected and converted to the dihydrochloride salt according to the procedure of Example 30 (steps e and g) to provide the title compound (40.6 mg, 23%) as a yellow solid: mp 305-313° C.; $^1$H NMR (500 MHz, CD$_3$OD) δ 8.80 (d, J=8.1 Hz, 1H), 8.11 (dd, J=8.2, 2.5 Hz, 1H), 7.79 (d, J=7.0 Hz, 1H), 7.64 (d, J=8.3 Hz, 1H), 7.52 (d, J=1.7 Hz, 1H), 7.47 (d, J=8.2 Hz, 1H), 7.11 (dd, J=8.3, 1.8 Hz, 1H), 6.93 (d, J=1.9 Hz, 1H), 6.85 (dd, J=7.1, 2.0 Hz, 1H), 4.40 (s, 2H), 3.71 (s, 3H), 3.46 (t, J=5.9 Hz, 2H), 3.04 (t, J=5.9 Hz, 2H), 2.62 (s, 3H); ESI MS m/z 371 [M+H]$^+$; HPLC (Method B)>99% (AUC), t$_R$=8.9 min.

Example 94

Preparation of 4-(Benzyloxy)-1-(1,9-dimethyl-2,3,4,9-tetrahydro-1H-pyrido[3,4-b]indol-7-yl)pyridin-2(1H)-one hydrochloride a) tert-Butyl 7-bromo-1,9-dimethyl-3,4-dihydro-1H-pyrido[4,3-b]indole-2(9H)-carboxylate

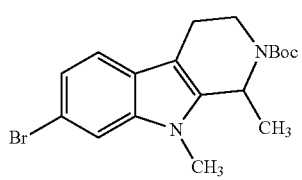

Chemical Formula: C$_{18}$H$_{23}$BrN$_2$O$_2$
Exact Mass: 378.0943
Molecular Weight: 379.2914

To a solution of 2-(6-bromo-1H-indol-3-yl)ethanamine (1.9 g, 8.0 mmol) in THF (30 mL) at 0° C. was added saturated aqueous NaHCO$_3$ (30 mL) and acetyl chloride (0.56 mL, 7.95 mmol). The reaction was warmed up to room temperature and stirred at room temperature until complete. The solution was concentrated, and the residue was dissolved in CH$_2$Cl$_2$, washed with H$_2$O and brine and dried with Na$_2$SO$_4$. The organic solution was filtered and concentrated to give a pale yellow foam. The foam was suspended in benzene (70 mL) and treated with POCl$_3$ (3.52 mL, 38.4 mmol). The reaction was heated and stirred at 85° C. for one hour. After the solution was concentrated, the residue was purified by flash column chromatography (silica gel, 10% CH$_3$OH in CH$_2$Cl$_2$) to give a brown solid (1.83 g 91%). The solid was suspended in EtOH (20 mL) and CHCl$_3$ (20 mL) and cooled to 0° C. NaBH$_4$ (0.26 g, 6.95 mmol) was added, and the reaction was stirred from 0° C. to room temperature for one hour. The reaction was quenched with H$_2$O, extracted with CH$_2$Cl$_2$, washed with H$_2$O and brine and dried over Na$_2$SO$_4$. The organic solution was filtered and concentrated to give a yellow foam (1.44 g, 78%). The foam was dissolved in i-PrOH (15 mL) and H$_2$O (10 mL) and treated with Boc$_2$O (1.36 g, 6.24 mmol) and K$_2$CO$_3$ (0.86 g, 6.2 mmol). The reaction was stirred at room temperature for one hour and then concentrated under reduced pressure. The resulting residue was dissolved in CH$_2$Cl$_2$, washed with H$_2$O and brine and dried over Na$_2$SO$_4$. After filtration and concentration, the residue was purified by flash column chromatography (silica gel, hexanes/EtOAc, 4:1) to give a yellow foam (0.92 g, 46%). The foam was dissolved in DMF (6 mL) and cooled to 0° C. The solution was treated with NaH (60% weight dispersion in mineral oil, 108 mg, 2.68 mmol) followed by CH$_3$I (0.17 mL, 0.69 mmol). The reaction was stirred at 0° C. until complete. The reaction was quenched with H$_2$O, extracted with CH$_2$Cl$_2$ washed with H$_2$O and brine and dried over Na$_2$SO$_4$. The organic solution was filtered and concentrated, and the residue was purified by flash column chromatography (silica gel, hexanes/EtOAc, 4:1) to give the title compound as a white foam (0.82 g, 89%). $^1$H NMR (300 MHz, CDCl$_3$) δ 7.42 (s, 1H), 7.31 (d, J=8.0 Hz, 1H), 7.18 (d, J=8.0 Hz, 1H), 5.43-5.20 (m, 1H), 4.48-4.26 (m, 1H), 3.62 (s, 3H), 3.24-3.13 (m, 1H), 2.78-2.66 (m, 2H), 1.49 (s, 9H), 1.47 (d, J=6.5 Hz, 3H); MS (ESI) m/z 380 [M+H]$^+$.

b) 4-(Benzyloxy)-1-(1,9-dimethyl-2,3,4,9-tetrahydro-1H-pyrido[3,4-b]indol-7-yl)pyridin-2(1H)-one hydrochloride

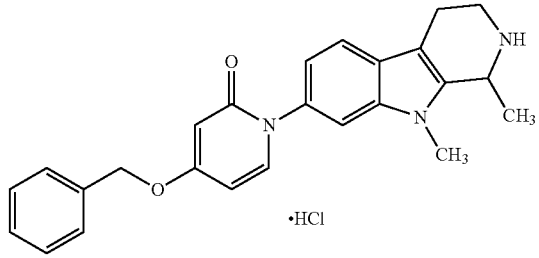

Chemical Formula: C$_{25}$H$_{26}$ClN$_3$O$_2$
Exact Mass: 435.17
Molecular Weight: 435.95

To a mixture of tert-butyl 7-bromo-1,9-dimethyl-3,4-dihydro-1H-pyrido[4,3-b]indole-2(9H)-carboxylate (0.57 g, 1.6 mmol), 4-(benzyloxy)pyridin-2(1H)-one (0.32 g, 1.6 mmol), 8-hydroxyquilinine (46 mg, 0.32 mmol), $K_2CO_3$ (0.26 g, 1.9 mmol) and CuI (0.15 g, 0.79 mmol) was added DMSO (4 mL). The reaction mixture was degassed and back-filled with $N_2$. The reaction was stirred at 130° C. overnight. The mixture was cooled and filtered through a layer of Celite. The filtrate was diluted with $CH_2Cl_2$, washed with $H_2O$ and 5% aqueous LiCl and dried over $Na_2SO_4$. The organic solution was filtered and concentrated. The residue was purified by flash column chromatography (silica gel, 5% $CH_3OH$ in $CH_2Cl_2$) to give a yellow solid (0.5 g, 64%). The solid was dissolved in $CH_3OH$ (8 mL) and treated with 1 N HCl in $Et_2O$ (5 mL). The reaction was stirred at room temperature until complete. The solvent was removed under reduced pressure and the resulting solid was dried under vacuum to give the title compound (0.44 g, 100%) as a yellow powder: $^1$H NMR (500 MHz, $CD_3OD$) δ 7.79 (d, J=7.0 Hz, 1H), 7.66 (d, J=8.0 Hz, 1H), 7.53 (s, 1H), 7.48-7.36 (m, 5H), 7.10 (d, J=8.5 Hz, 1H), 6.55 (d, J=6.5 Hz, 1H), 6.33 (s, 1H), 5.27 (s, 2H), 4.98 (q, J=6.5 Hz, 1H), 3.76 (s, 3H), 3.67-3.59 (m, 2H), 3.13-3.08 (m, 2H), 1.76 (d, J=7.0 Hz, 3H); ESI MS m/z 400 [M+H]$^+$; HPLC (Method A)>99% (AUC), $t_R$=12.9 min.

Example 95

Preparation of 4-(Benzyloxy)-1-(1,2,9-trimethyl-2,3,4,9-tetrahydro-1H-pyrido[3,4-b]indol-7-yl)pyridin-2(1H)-one hydrochloride

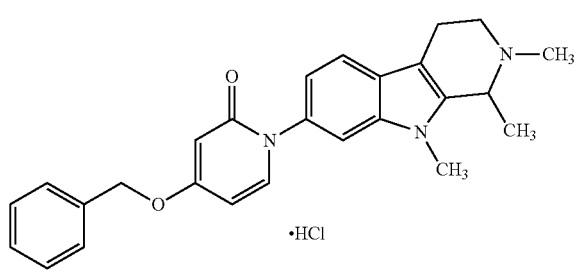

Chemical Formula: $C_{26}H_{28}ClN_3O_2$
Exact Mass: 449.19
Molecular Weight: 449.97

To a solution of 4-(benzyloxy)-1-(1,9-dimethyl-2,3,4,9-tetrahydro-1H-pyrido[3,4-b]indol-7-yl)pyridin-2(1H)-one hydrochloride (205 mg, 0.470 mmol) in $CH_3OH$ (8 mL) was added formaldehyde (53 µL, 0.71 mmol) and NaBH(OAc)$_3$ (200 mg, 0.94 mmol). The reaction was stirred at room temperature until complete and then concentrated under reduced pressure. The residue was dissolved in $CH_2Cl_2$ and washed with $H_2O$ and 5% aqueous LiCl and dried over $Na_2SO_4$. The organic solution was filtered and concentrated. The residue was purified by flash column chromatography (silica gel, 10% $CH_3OH$ in $CH_2Cl_2$) to give 4-(benzyloxy)-1-(1,2,9-trimethyl-2,3,4,9-tetrahydro-1H-pyrido[3,4-b]indol-7-yl)pyridin-2(1H)-one as a white solid (0.15 g, 77%). The free base was converted to the HCl salt to give the title compound (147 mg, 90%) as an off-white powder: $^1$H NMR (500 MHz, $CD_3OD$) δ 7.58-7.55 (m, 2H), 7.47-7.34 (m, 6H), 6.99 (d, J=8.5, 1.0 Hz, 1H), 6.28 (dd, J=7.5, 2.5 Hz, 1H), 6.11 (d, J=2.5 Hz, 1H), 5.18 (s, 2H), 4.27 (q, J=6.5 Hz, 1H), 3.69 (s, 3H), 3.36-3.33 (m, 1H), 3.10-2.96 (m, 2H), 2.84-2.80 (m, 1H), 2.65 (s, 3H), 1.51 (d, J=6.5 Hz, 3H); ESI MS m/z 414 [M+H]$^+$; HPLC (Method A)>99% (AUC), $t_R$=13.0 min.

Example 96

Preparation of 4-(Benzyloxy)-1-(5-(ethoxymethyl)-2,3,4,5-tetrahydro-1H-pyrido[4,3-b]indol-7-yl)pyridin-2(1H)-one hydrochloride a) tert-Butyl 7-(4-(benzyloxy)-2-oxopyridin-1(2H)-yl)-5-(ethoxymethyl)-3,4-dihydro-1H-pyrido[4,3-b]indole-2(5H)-carboxylate

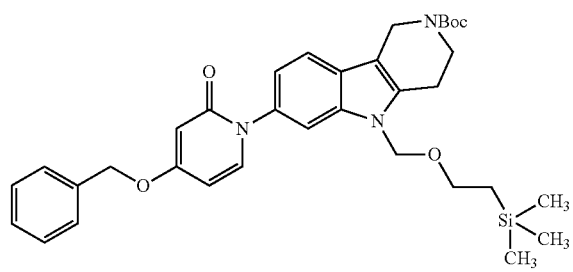

Chemical Formula: $C_{34}H_{43}N_3O_5Si$
Exact Mass: 601.30
Molecular Weight: 601.81

To a solution of tert-butyl 7-bromo-3,4-dihydro-1H-pyrido[4,3-b]indole-2(5H)-carboxylate (0.66 g, 1.9 mmol) in DMF (8 mL) was added NaH (60% weight dispersion in mineral oil, 113 mg, 2.82 mmol) followed by SEMCl (0.50 mL, 2.8 mmol). The reaction was stirred at room temperature until complete. The reaction was quenched with $H_2O$, and the aqueous mixture was extracted with $CH_2Cl_2$. The organic phase was washed with $H_2O$ and brine and dried over $Na_2SO_4$. After filtration and concentration, the residue was dried under vacuum to give tert-butyl 7-bromo-5-((2-(trimethylsilyl)ethoxy)methyl)-3,4-dihydro-1H-pyrido[4,3-b]indole-2(5H)-carboxylate, which and used directly in the next step. To a mixture of tert-butyl 7-bromo-5-((2-(trimethylsilyl)ethoxy)methyl)-3,4-dihydro-1H-pyrido[4,3-b]indole-2(5H)-carboxylate (0.75 g, 1.6 mmol), 4-benzyloxy-pyridine (0.31 g, 1.6 mmol), 8-hydroxyquilinine (34 mg, 0.23 mmol), $K_2CO_3$ (0.26 g, 1.9 mmol) and CuI (45 mg, 0.23 mmol) was added DMSO (6 mL). The reaction mixture was degassed and back-filled with $N_2$. The reaction was stirred at 130° C. overnight. The mixture was cooled and filtered through a layer of Celite. The filtrate was diluted with $CH_2Cl_2$, washed with $H_2O$ and 5% aqueous LiCl and dried over $Na_2SO_4$. The organic solution was filtered and concentrated, and the residue was purified by flash column chromatography (silica gel, 5% $CH_3OH$ in $CH_2Cl_2$) to give the title compound as a yellow oil (0.12 g, 13%): $^1$H NMR (500 MHz, $CDCl_3$) δ 7.60 (d, J=8.5 Hz, 1H), 7.44-7.37 (m, 6H), 7.31 (d, J=7.5 Hz, 1H), 7.09 (m, 1H), 6.12 (s, 1H), 6.07 (d, J=6.5 Hz, 1H), 5.40 (s, 2H), 5.07 (s, 2H), 4.65 (m, 2H), 3.86 (m, 2H), 3.51 (t, J=8.0 Hz, 2H), 2.73 (m, 2H), 1.53 (s, 9H), 0.89 (t, J=8.0 Hz, 2H), −0.04 (s, 9H); ESI MS m/z 602 [M+H]$^+$.

b) 4-(Benzyloxy)-1-(5-(ethoxymethyl)-2,3,4,5-tetrahydro-1H-pyrido[4,3-b]indol-7-yl)pyridin-2(1H)-one hydrochloride

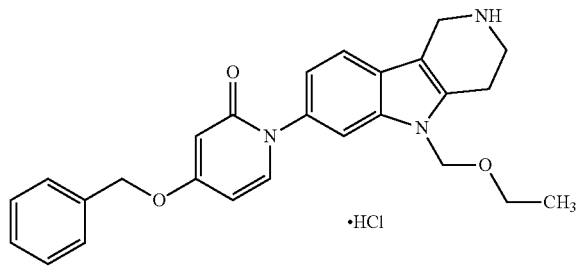

Chemical Formula: $C_{26}H_{28}ClN_3O_3$
Exact Mass: 465.18
Molecular Weight: 465.97

To a solution of tert-butyl 7-(4-(benzyloxy)-2-oxopyridin-1(2H)-yl)-5-(ethoxymethyl)-3,4-dihydro-1H-pyrido[4,3-b]indole-2(5H)-carboxylate (120 mg, 0.20 mmol) in EtOH (2 mL) was added 1 N HCl in Et$_2$O (1 mL). The reaction was stirred at 60° C. until complete. The solvent was concentrated and the residue was purified by preparative HPLC (Phenomenex Luna C18 (2), 250×50 mm, 15 micron, H$_2$O with 0.05% TFA and CH$_3$CN with 0.05% TFA) to give 4-(benzyloxy)-1-(5-(ethoxymethyl)-2,3,4,5-tetrahydro-1H-pyrido[4,3-b]indol-7-yl)pyridin-2(1H)-one as a white solid (54 mg, 73%). The free base was converted to the HCl salt to give the title compound (35 mg, 65%) as a white powder: mp 148-149° C.; $^1$H NMR (500 MHz, DMSO-d$_6$) δ 9.12 (s, 2H), 7.66 (d, J=2.0 Hz, 1H), 7.59-7.56 (m, 2H), 7.49-7.37 (m, 5H), 7.08-7.05 (m, 1H), 6.14-6.12 (m, 1H), 5.99 (d, J=2.5 Hz, 1H), 5.57 (s, 2H), 5.17 (s, 2H), 4.38 (m, 2H), 3.55 (m, 2H), 3.45-3.40 (m, 2H), 3.13 (m, 2H), 1.08-1.05 (m, 3H); ESI MS m/z 430 [M+H]$^+$; HPLC (Method A)>99% (AUC), $t_R$=12.8 min.

Example 97

Preparation of 1-(5-Methyl-2,3,4,5-tetrahydro-1H-pyrido[4,3-b]indol-7-yl)-4-phenylpyridin-2(1H)-one hydrochloride a) tert-Butyl 5-methyl-7-(2-oxo-4-(trifluoromethylsulfonyloxy)pyridine-1(2H)-yl)3,4-dihydro-1H-pyrido[4,3-b]indole-2(5H)-carboxylate

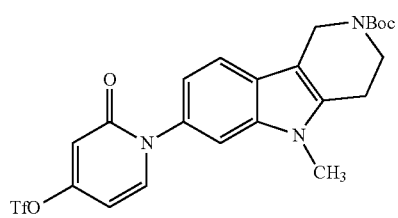

Chemical Formula: $C_{23}H_{24}F_3N_3O_6S$
Exact Mass: 527.13
Molecular Weight: 527.51

To a solution of tert-butyl 7-(4-(benzyloxy)-2-oxopyridin-1(2H)-yl)-5-methyl-3,4-dihydro-1H-pyrido[4,3-b]indole-2(5H)-carboxylate (0.98 g, 2.0 mmol) in CH$_3$OH (30 mL) was added 5% Pd/C (0.3 g) and ammonium formate (0.32 g, 5.1 mmol) under an atmosphere of argon. The reaction was stirred at 90° C. until complete. The reaction mixture was cooled and filtered through a layer of Celite. The solvent was removed under reduced pressure to give tert-butyl 7-(4-hydroxy-2-oxopyridin-1(2H)-yl)-5-methyl-3,4-dihydro-1H-pyrido[4,3-b]indole-2(5H)-carboxylate, which was used directly in the next step. To a solution of tert-butyl 7-(4-hydroxy-2-oxopyridin-1(2H)-yl)-5-methyl-3,4-dihydro-1H-pyrido[4,3-b]indole-2(5H)-carboxylate (800 mg, 2.02 mmol) in THF (10 mL) was added LiN(SiMe$_3$)$_2$ (1.0 M in THF, 2.6 mL, 2.6 mmol) followed by PhN(Tf)$_2$ (0.94 g, 2.6 mmol) under an atmosphere of argon. The reaction was stirred at room temperature until complete. The solvent was removed under reduced pressure, and the residue was purified by flash column chromatography (silica gel, hexanes/EtOAc, 1:1) to give the title compound (0.42 g, 40% yield) as a white solid: $^1$H NMR (300 MHz, CDCl$_3$) δ 7.57-7.53 (m, 2H), 7.30 (d, J=1.5 Hz, 1H), 7.02-6.99 (m, 1H), 6.60 (d, J=2.7 Hz, 1H), 6.27 (dd, J=7.8, 2.7 Hz, 1H), 4.65 (s, 2H), 3.85 (m, 2H), 3.65 (s, 3H), 2.84 (m, 2H), 1.51 (s, 9H); ESI MS m/z 528 [M+H]$^+$.

b) 1-(5-Methyl-2,3,4,5-tetrahydro-1H-pyrido[4,3-b]indol-7-yl)-4-phenylpyridin-2(1H)-one hydrochloride

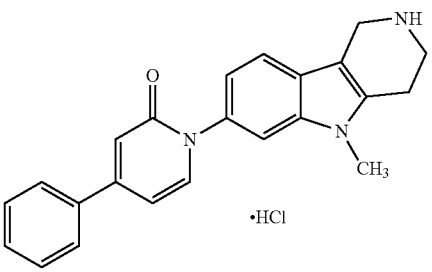

Chemical Formula: $C_{23}H_{22}ClN_3O$
Exact Mass: 391.15
Molecular Weight: 391.89

Following the procedure of Example 25 (step b), but substituting phenylboronic acid for 4-fluorophenylboronic acid and eliminating the methylation step, the title compound (37 mg, 46%) was obtained as a yellow solid: mp 275-280° C. (decompose); $^1$H NMR (500 MHz, DMSO-d$_6$) δ 9.26 (s, 2H), 7.79 (dd, J=8.0, 1.5 Hz, 2H), 7.75 (d, J=7.5 Hz, 1H), 7.62 (d, J=1.5 Hz, 1H), 7.59 (d, J=8.5 Hz, 1H), 7.55-7.50 (m, 3H), 7.10 (dd, J=8.5, 2.0 Hz, 1H), 6.78 (d, J=1.5 Hz, 1H), 6.70 (dd, J=7.0, 2.0 Hz, 1H), 4.37 (m, 2H), 3.71 (s, 3H), 3.54-3.53 (m, 2H), 3.10 (t, J=6.0 Hz, 2H); ESI MS m/z 356 [M+H]$^+$; HPLC (Method A)>99% (AUC), $t_R$=12.3 min.

Example 98

Preparation of 1-(2,5-Dimethyl-2,3,4,5-tetrahydro-1H-pyrido[4,3-b]indol-7-yl)-4-phenylpyridin-2(1H)-one hydrochloride

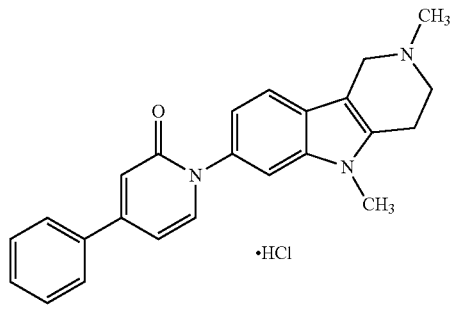

•HCl

Chemical Formula: $C_{24}H_{24}ClN_3O$
Exact Mass: 405.16
Molecular Weight: 405.92

Following the procedure of Example 25 (step b), but substituting phenylboronic acid for 4-fluorophenylboronic acid, the title compound (56 mg, 83%) was obtained as an off-white solid: mp 290-295° C. (decompose); $^1$H NMR (500 MHz, DMSO-$d_6$) δ 10.46 (s, 1H), 7.80-7.74 (m, 3H), 7.63 (s, 1H), 7.56-7.52 (m, 4H), 7.11 (d, J=8.0 Hz, 1H), 6.78 (s, 1H), 6.70 (d, J=7.0 Hz, 1H), 4.68-4.65 (m, 1H), 4.34-4.30 (m, 1H), 3.82-3.79 (m, 1H), 3.71 (s, 3H), 3.53-3.51 (m, 1H), 3.20 (m, 2H), 3.00 (d, J=4.0 Hz, 3H); ESI MS m/z 370 [M+H]$^+$; HPLC (Method A) 98% (AUC), $t_R$=12.5 min.

Example 99

Preparation of 4-(2-Fluoro-4-methoxyphenyl)-1-(5-methyl-2,3,4,5-tetrahydro-1H-pyrido[4,3-b]indol-7-yl)pyridin-2(1H)-one hydrochloride

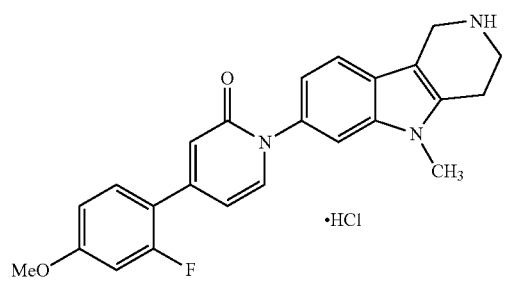

•HCl

Chemical Formula: $C_{24}H_{23}ClFN_3O_2$
Exact Mass: 439.15
Molecular Weight: 439.91

Following the procedure of Example 25 (step b), but substituting 2-fluoro-4-methoxyphenylboronic acid for 4-fluorophenylboronic acid and eliminating the methylation step, the title compound (34 mg, 19%) was obtained as a green powder: mp 270-274° C.; $^1$H NMR (500 MHz, CD$_3$OD) δ 7.72 (d, J=7.0 Hz, 1H), 7.63-7.56 (m, 3H), 7.14 (dd, J=8.5, 1.5 Hz, 1H), 6.92 (dd, J=8.5, 2.5 Hz, 1H), 6.87 (dd, J=13.0, 2.5 Hz, 1H), 6.84 (s, 1H), 6.77-6.75 (m, 1H), 4.50 (s, 2H), 3.88 (s, 3H), 3.76 (s, 3H), 3.68 (t, J=6.0 Hz, 2H), 3.22 (t, J=6.0 Hz, 2H); ESI MS m/z 404 [M+H]$^+$; HPLC (Method A)>99% (AUC), $t_R$=12.3 min

Example 100

Preparation of 1-(2-Acetyl-5-methyl-2,3,4,5-tetrahydro-1H-pyrido[4,3-b]indol-7-yl)-4-(benzyloxy)pyridin-2(1H)-one

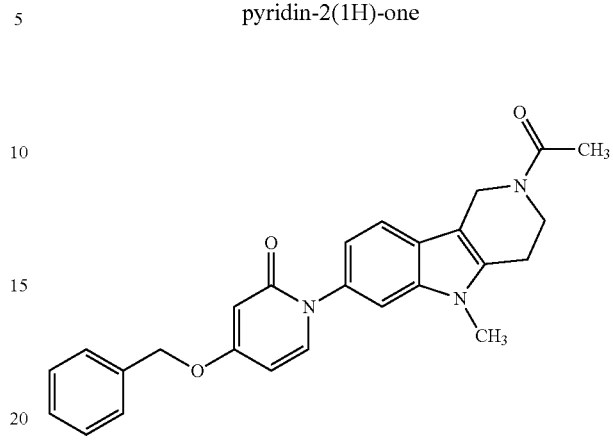

Chemical Formula: $C_{26}H_{25}N_3O_3$
Exact Mass: 427.19
Molecular Weight: 427.50

To a solution of 4-(benzyloxy)-1-(5-methyl-2,3,4,5-tetrahydro-1H-pyrido[4,3-b]indol-7-yl)pyridin-2(1H)-one (0.2 g, 0.5 mmol) in CH$_2$Cl$_2$ (6 mL) was added triethylamine (0.20 mL, 1.4 mmol) followed by acetyl chloride (50 μL, 0.71 mmol). The reaction was stirred at room temperature until complete. After the solvent was removed under reduced pressure, the residue was purified by flash column chromatography (silica gel, 5% CH$_3$OH in CH$_2$Cl$_2$) to give the title compound (72.2 mg, 36%) as a yellow solid and as a mixture of rotamers: mp 225-230° C.; $^1$H NMR (500 MHz, CDCl$_3$) δ 7.53-7.36 (m, 6H), 7.32-7.30 (m, 2H), 7.06-7.00 (m, 1H), 6.09 (d, J=3.0 Hz, 1H), 6.07-6.04 (m, 1H), 5.06 (s, 2H), 4.82 (s, 1H), 4.67 (s, 1H), 4.03 (t, J=5.5 Hz, 1H), 3.84 (t, J=5.5 Hz, 1H), 3.64 (s, 3H), 2.90 (t, J=5.5 Hz, 1H), 2.84 (t, J=5.5 Hz, 1H), 2.24, 2.22 (2×s, 3H); ESI MS m/z 428 [M+H]$^+$; HPLC (Method A) 95.7% (AUC), $t_R$=16.8 min.

Example 101

Preparation of 1-(2-Acetyl-5-methyl-2,3,4,5-tetrahydro-1H-pyrido[4,3-b]indol-7-yl)-4-((5-fluoropyridin-2-yl)methoxy)pyridin-2(1H)-one

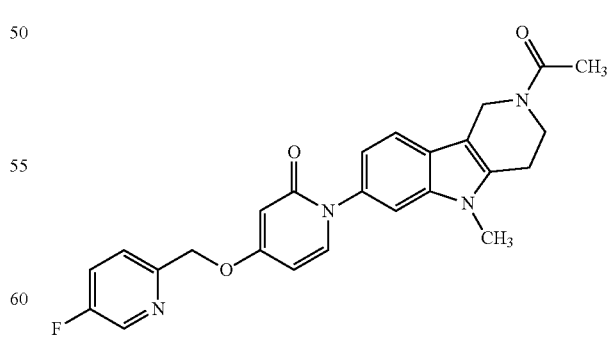

Chemical Formula: $C_{25}H_{23}FN_4O_3$
Exact Mass: 446.18
Molecular Weight: 446.47

Following the procedure of Example 100, but substituting 4-((5-fluoropyridin-2-yl)methoxy)-1-(5-methyl-2,3,4,5-tetrahydro-1H-pyrido[4,3-b]indol-7-yl)-pyridin-2(1H)-one for 4-(benzyloxy)-1-(5-methyl-2,3,4,5-tetrahydro-1H-pyrido[4,3-b]indol-7-yl)pyridin-2(1H)-one, the title compound (71 mg, 61%) was obtained as a yellow solid and as a mixture of rotamers: mp 220-224° C.; $^1$H NMR (500 MHz, CDCl$_3$) δ 8.50 (d, J=1.5 Hz, 1H), 7.54-7.46 (m, 3H), 7.35 (d, J=7.5 Hz, 1H), 7.32 (d, J=2.0 Hz, 1H), 7.03 (ddd, J=20, 8.0, 1.5 Hz, 1H), 6.15-6.08 (m, 2H), 5.18 (s, 2H), 4.83, 4.70 (2×s, 2H), 4.04 (t, J=5.5 Hz, 1H), 3.85 (t, J=5.5 Hz, 1H), 3.65, 3.64 (2×s, 3H), 2.91 (t, J=5.5 Hz, 1H), 2.85 (t, J=5.5 Hz, 1H), 2.23, 2.25 (2×s, 3H); ESI MS m/z 447 [M+H]$^+$; HPLC (Method A) 96.4% (AUC), $t_R$=14.5 min.

Example 102

Preparation of 4-(Cyclohexylmethoxy)-1-(9-methyl-2,3,4,9-tetrahydro-1H-pyrido[3,4-b]indol-7-yl)pyridin-2(1H)-one hydrochloride a) 4-(Cyclohexylmethoxy)pyridin-2(1H)-one

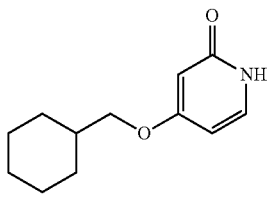

Chemical Formula: C$_{12}$H$_{17}$NO$_2$
Exact Mass: 207.1259
Molecular Weight: 207.2689

To a solution of cyclohexylmethanol (1.1 mL, 9.3 mmol) in DMF (8 mL) was added NaH (60% weight dispersion in mineral oil, 0.37 g, 9.3 mmol) in one portion. After the bubbles disappeared, 4-chloropyridine N-oxide (1.0 g, 7.7 mmol) was added. The reaction was stirred at room temperature under Ar until complete. The reaction was quenched with water and the aqueous mixture was extracted with CH$_2$Cl$_2$. The combined organic extracts were washed with H$_2$O and 5% aqueous LiCl and dried over Na$_2$SO$_4$. After filtration and concentration, the residue was purified by flash column chromatography (silica gel, 10% CH$_3$OH in CH$_2$Cl$_2$) to give a yellow solid. The yellow solid was suspended in Ac$_2$O (5 mL) and heated at 140° C. for 4 h. The reaction mixture was cooled, diluted with CH$_3$OH/H$_2$O (10 mL, 1:1) and stirred at room temperature for 1 h. The mixture was concentrated, and the residue was purified by flash column chromatography (silica gel, 10% CH$_3$OH in CH$_2$Cl$_2$) to give the title compound (0.92 g, 58%) as a brown solid: $^1$H NMR (300 MHz, DMSO-d$_6$) δ 11.03 (s, 1H), 7.21 (d, J=7.2 Hz, 1H), 5.83 (dd, J=7.2, 2.4 Hz, 1H), 5.64 (d, J=2.4 Hz, 1H), 3.72 (d, J=6.0 Hz, 2H), 1.84-1.68 (m, 6H), 1.30-1.01 (m, 5H).

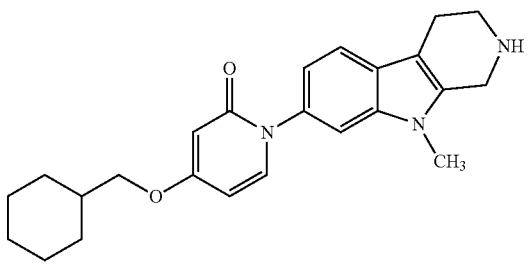

Chemical Formula: C$_{24}$H$_{30}$ClN$_3$O$_2$
Exact Mass: 427.20
Molecular Weight: 427.97

Following the procedure of Example 1 (steps c and d), but substituting 4-(cyclohexylmethoxy)pyridin-2(1H)-one for 4-benzyloxypyridone, the title compound (56 mg, 81%) was obtained as a yellow solid: mp 256-260° C.; $^1$H NMR (500 MHz, CD$_3$OD) δ 7.67-7.65 (m, 2H), 7.50 (s, 1H), 7.09 (d, J=8.5 Hz, 1H), 6.35 (d, J=6.0 Hz, 1H), 6.10 (s, 1H), 4.58 (s, 2H), 3.92 (d, J=5.5 Hz, 2H), 3.75 (s, 3H), 3.63 (t, J=6.0 Hz, 2H), 3.15 (d, J=6.0 Hz, 2H), 1.92-1.74 (m, 6H), 1.39-1.19 (m, 5H); ESI MS m/z 392 [M+H]$^+$; HPLC (Method A) 97.8% (AUC), $t_R$=14.4 min.

Example 103

Preparation of 4-(Cyclohexylmethoxy)-1-(5-methyl-2,3,4,5-tetrahydro-1H-pyrido[4,3-b]indol-7-yl)pyridin-2(1H)-one hydrochloride

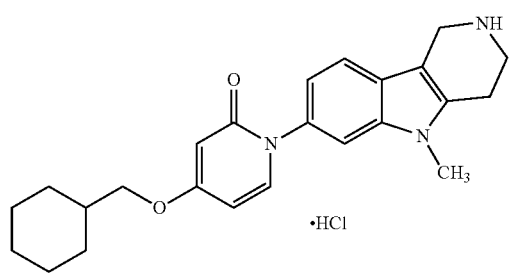

Chemical Formula: C$_{24}$H$_{30}$ClN$_3$O$_2$
Exact Mass: 427.20
Molecular Weight: 427.97

Following the procedure of Example 102, but substituting tert-butyl 7-bromo-5-methyl-3,4-dihydro-1H-pyrido[4,3-b]indole-2(5H)-carboxylate for tert-butyl 7-bromo-9-methyl-3,4-dihydro-1H-pyrido[4,3-b]indole-2(9H)-carboxylate, the title compound (197 mg, 100%) was obtained as a pale green solid: mp 245-250° C. (decompose); $^1$H NMR (500 MHz, DMSO-d$_6$) δ 9.21 (s, 2H), 7.55 (d, J=8.5 Hz, 1H), 7.52 (d, J=7.5 Hz, 1H), 7.50 (s, 1H), 6.99 (dd, J=8.5, 1.5 Hz, 1H), 6.04 (dd, J=7.5, 2.5 Hz, 1H), 5.85 (d, J=2.5 Hz, 1H), 4.35 (s, 2H), 3.82 (d, J=6.0 Hz, 2H), 3.68 (s, 3H), 3.54-3.53 (m, 2H), 3.09 (t, J=5.5 Hz, 2H), 1.80-1.65 (m, 6H), 1.30-1.01 (m, 5H); ESI MS m/z 392 [M+H]$^+$; HPLC (Method A)>99% (AUC), $t_R$=14.3 min.

Example 104

Preparation of 4-(Cyclohexylmethoxy)-1-(2,5-dimethyl-2,3,4,5-tetrahydro-1H-pyrido[4,3-b]indol-7-yl)pyridin-2(1H)-one hydrochloride

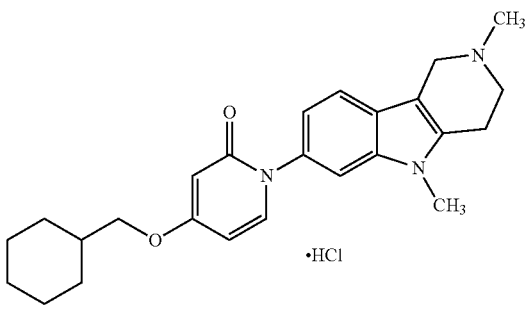

Chemical Formula: C$_{25}$H$_{32}$ClN$_3$O$_2$
Exact Mass: 441.22
Molecular Weight: 441.99

To a solution of 4-(cyclohexylmethoxy)-1-(5-methyl-2,3,4,5-tetrahydro-1H-pyrido[4,3-b]indol-7-yl)pyridin-2(1H)-one hydrochloride (110 mg, 0.26 mmol) in CH$_3$OH (5 mL) was added triethylamine (90 µL, 2.5 mmol), formaldehyde (30 µL, 0.39 mmol) and NaBH(OAc)$_3$ (110 mg, 0.52 mmol). The reaction was stirred at room temperature until complete. The solvent was removed under reduced pressure, and the residue was dissolved in CH$_2$Cl$_2$. The organic solution was washed with H$_2$O and 5% aqueous LiCl and dried over Na$_2$SO$_4$. After filtration and concentration, the residue was purified by flash column chromatography (silica gel, 10% CH$_3$OH in CH$_2$Cl$_2$) to give 4-(cyclohexylmethoxy)-1-(2,5-dimethyl-2,3,4,5-tetrahydro-1H-pyrido[4,3-b]indol-7-yl)pyridin-2(1H)-one as a white solid (73 mg, 69%). The free base was converted to the HCl salt to give the title compound (84 mg, 100%) as a white powder: mp 270-272° C.; $^1$H NMR (500 MHz, DMSO-d$_6$) δ 10.53 (s, 1H), 7.53 (d, J=7.5 Hz, 1H), 7.51 (d, J=8.0 Hz, 1H), 7.50 (d, J=1.5 Hz, 1H), 7.00 (dd, J=8.5, 1.5 Hz, 1H), 6.04 (dd, J=7.5, 2.5 Hz, 1H), 5.85 (d, J=3.0 Hz, 1H), 4.64 (d, J=13 Hz, 1H), 4.30 (dd, J=14, 7.5 Hz, 1H), 3.82 (d, J=6.0 Hz, 2H), 3.80-3.78 (m, 1H), 3.69 (s, 3H), 3.51-3.47 (m, 1H), 3.18 (t, J=5.5 Hz, 2H), 2.98 (d, J=4.5 Hz, 3H), 1.80-1.65 (m, 6H), 1.30-1.01 (m, 5H); ESI MS m/z 406 [M+H]$^+$; HPLC (Method A)>99% (AUC), t$_R$=14.4 min.

Example 105

Preparation of 4-(Benzyloxy)-1-(1-(hydroxymethyl)-9-methyl-2,3,4,9-tetrahydro-1H-pyrido[3,4-b]indol-7-yl)pyridin-2(1H)-one hydrochloride a) 7-Bromo-2,3,4,9-tetrahydro-1H-pyrido[3,4-b]indole-1-carboxylic acid

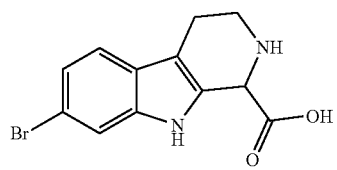

Chemical Formula: C$_{12}$H$_{11}$BrN$_2$O$_2$
Exact Mass: 294.00
Molecular Weight: 295.13

Glyoxylic acid monohydrate (3.69 g, 40.1 mmol) was added to a solution of a 2:1 mixture of 2-(6-bromo-1H-indol-3-yl)ethanamine and 2-(4-bromo-1H-indol-3-yl)ethanamine (7.38 g, 30.9 mmol) in 0.4 N HCl (50 mL), and the resulting solution was stirred at 25° C. for 30 min. The solution was adjusted to pH 3.5 with 6 N NaOH solution, and the resulting tan suspension was stirred at 25° C. for 22 h. The suspension was adjusted to pH 5 with 6 N NaOH solution, and the resulting suspension was filtered. The filtered solid was dried under reduced pressure to afford 3.85 g (42%) of a 2:1 mixture of the title compound and an undesired regioisomer as a tan solid: $^1$H NMR (300 MHz, DMSO-d$_6$) δ 10.90 (s, 1H), 9.00 (br s, 1H), 7.63 (s, 1H), 7.33 (d, J=8.4 Hz, 1H), 7.12-7.04 (m, 1H), 4.66 (s, 1H), 3.50-2.70 (m, 4H).

Undesired regioisomer: $^1$H NMR (300 MHz, DMSO-d$_6$) δ 11.09 (s, 1H), 9.00 (br s, 1H), 7.47 (d, J=8.0 Hz, 1H), 7.12-7.04 (m, 1H), 6.91 (overlapping dd, J=8.0 Hz, 1H), 4.66 (s, 1H), 3.50-2.70 (m, 4H).

b) 7-Bromo-1-(((tert-butyldimethylsilyloxy)methyl)-2,3,4,9-tetrahydro-1H-pyrido[3,4-b]indole

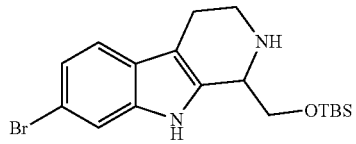

Chemical Formula: C$_{18}$H$_{27}$BrN$_2$OSi
Exact Mass: 394.11
Molecular Weight: 395.41

A 1.0 M solution of LiAlH$_4$ in THF (26 mL, 26.1 mmol) was added to a solution of a 2:1 mixture of 7-bromo-2,3,4,9-tetrahydro-1H-pyrido[3,4-b]indole-1-carboxylic acid and the undesired regioisomer (3.85 g, 13.1 mmol) in THF (50 mL) under N$_2$, and the resulting solution was heated at reflux for 1 h. The solution was cooled to 0° C. and H$_2$O, 6 N NaOH in H$_2$O and H$_2$O were added carefully in succession. The resulting suspension was filtered through celite. The filtrate was dried over Na$_2$SO$_4$ and concentrated under reduced pressure. Flash chromatography (silica gel, (1:1 EtOAc/hexanes)/(9:0.9:0.1 CH$_2$Cl$_2$/MeOH/NH$_4$OH), 100:0 to 0:100) afforded 2.48 g of a tan foam. Et$_3$N (6.2 mL, 44.3 mmol) was added to a suspension of TBSCl (6.68 g, 44.3 mmol) and the above tan foam in CH$_2$Cl$_2$ (50 mL) under N$_2$, and the resulting suspension was stirred at 25° C. overnight. H$_2$O was added to the suspension, and the phases were separated. The organic phase was dried over Na$_2$SO$_4$ and concentrated under reduced pressure. Flash chromatography (silica gel, (1:1 EtOAc/hexanes)/(9:0.9:0.1 Et$_2$O/MeOH/NH$_4$OH), 100:0 to 75:25) yielded the title compound (1.186 g, 32%) as a clear oil: $^1$H NMR (300 MHz, CDCl$_3$) δ 8.50 (s, 1H), 7.45 (d, J=1.7 Hz, 1H), 7.35 (d, J=8.4 Hz, 1H), 7.18

(dd, J=8.4, 1.7 Hz, 1H), 4.19-4.10 (m, 1H), 3.92 (dd, J=9.2, 5.0 Hz, 1H), 3.69 (dd, J=9.2, 9.2 Hz, 1H), 3.32 (ddd, J=12.6, 4.2, 4.2 Hz, 1H), 3.11-3.01 (m, 1H), 2.75-2.62 (m, 2H), 0.97 (s, 9H), 0.13 (s, 6H).

c) tert-Butyl 7-bromo-1-((tert-butyldimethylsilyloxy)methyl)-9-methyl-3,4-dihydro-1H-pyrido[3,4-b]indole-2(9H)-carboxylate

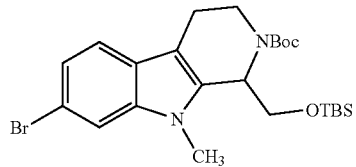

Chemical Formula: C$_{24}$H$_{37}$BrN$_2$O$_3$Si
Exact Mass: 508.18
Molecular Weight: 509.55

Boc$_2$O (752 mg, 3.45 mmol) was added to a suspension of 7-Bromo-1-((tert-butyldimethyl-silyloxy)methyl)-2,3,4,9-tetrahydro-1H-pyrido[3,4-b]indole (1.239 g, 3.14 mmol) and K$_2$CO$_3$ (476 mg, 3.45 mmol) in a 1:1 mixture of H$_2$O/i-PrOH (80 mL), and the resulting suspension was stirred at 25° C. for 2 h. The suspension was filtered, and the solid was concentrated under reduced pressure. MeI (0.19 mL, 3.1 mmol) was added to a suspension of the above solid and Cs$_2$CO$_3$ (1.34 g, 4.12 mmol) in DMSO (20 mL) under N$_2$, and the resulting suspension was stirred at 25° C. for 4 h. H$_2$O was added to the suspension, and the resulting suspension was filtered. The solid was dried under reduced pressure to afford the title compound (728 mg, 46%) as a white solid: $^1$H NMR (500 MHz, CDCl$_3$) δ 7.44 (br s, 1H), 7.37-7.28 (m, 1H), 7.23-7.15 (m, 1H), 5.49-5.43 (m, 0.6H), 5.37-5.32 (m, 0.4H), 4.56-4.48 (m, 0.4H), 4.35-4.24 (m, 0.6H), 3.98-3.84 (m, 2H), 3.68 (s, 3H), 3.43-3.35 (m, 0.6H), 3.30-3.21 (m, 0.4H), 2.90-2.75 (m, 1H), 2.72-2.63 (m, 1H), 1.50 (s, 9H), 0.90-0.82 (m, 9H), 0.14-0.02 (m, 6H).

d) 4-(Benzyloxy)-1-(1-(hydroxymethyl)-9-methyl-2,3,4,9-tetrahydro-1H-pyrido[3,4-b]indol-7-yl)pyridin-2(1H)-one A suspension of tert-butyl 7-bromo-1-((tert-butyldimethylsilyloxy)methyl)-9-methyl-3,4-dihydro-1H-pyrido[3,4-b]indole-2(9H)-carboxylate (727 mg, 1.47 mmol), 4-(benzyloxy)pyridin-2(1H)-one (591 mg, 2.94 mmol), CuI (110 mg, 0.576 mmol), 8-hydroxyquinoline (84 mg, 0.58 mmol) and Cs$_2$CO$_3$ (720 mg, 2.21 mmol) in DMSO (10 mL) was degassed under reduced pressure for 45 min. The suspension was put under Ar and heated at 135° C. with stirring for 14 h. The suspension was cooled, 1:1 MeOH/NH$_4$OH (40 mL) was added, and the resulting suspension was stirred for 30 min. CH$_2$Cl$_2$ was added and the phases were separated. The aqueous phase was extracted with CH$_2$Cl$_2$, and the combined organic extracts were washed with brine, dried over Na$_2$SO$_4$ and concentrated under reduced pressure. Flash chromatography (silica gel, (1:1 EtOAc/hexanes)/(9:0.9:0.1 Et$_2$O/MeOH/NH$_4$OH) 100:0 to 0:100) afforded the amine as a yellow amorphous solid. A 1.0 M solution of TBAF in THF (0.57 mL, 0.57 mmol) was added to a solution of the above yellow semi-solid in THF (10 mL) under N$_2$, and the resulting solution was stirred at 25° C. for 1.5 h. H$_2$O and CH$_2$Cl$_2$ were added to the solution and the phases were separated. The aqueous phase was extracted with CH$_2$Cl$_2$, and the combined organic phases were dried over Na$_2$SO$_4$ and concentrated under reduced pressure. Flash chromatography (silica gel, (1:1 EtOAc/hexanes)/(9:0.9:0.1 Et$_2$O/MeOH/NH$_4$OH) 100:0 to 0:100) yielded a yellow amorphous solid. TFA (2 mL) was added to a solution of the above amorphous solid in CH$_2$Cl$_2$ (10 mL) under N$_2$, and the resulting solution was stirred at 25° C. for 1 h. The solution was concentrated under reduced pressure. The resulting residue was diluted with CH$_2$Cl$_2$ and neutralized with a saturated aqueous NaHCO$_3$ solution. The phases were separated. The organic phase was dried over Na$_2$SO$_4$ and concentrated under reduced pressure. Flash chromatography (silica gel, (1:1 EtOAc/hexanes)/(9:0.9:0.1 CH$_2$Cl$_2$/MeOH/NH$_4$OH) 100:0 to 0:100) yielded the title compound (56 mg, 9%) as a viscous oil: $^1$H NMR (500 MHz, CDCl$_3$) δ 7.56 (d, J=8.0 Hz, 1H), 7.46-7.37 (m, 5H), 7.32 (d, J=7.5 Hz, 1H), 7.30 (d, J=1.5 Hz, 1H), 7.03 (dd, J=8.0, 1.5 Hz, 1H), 6.11 (d, J=2.5 Hz, 1H), 6.06 (dd, J=7.5, 2.5 Hz, 1H), 5.08 (s, 2H), 4.14 (dd, J=10.0, 4.5 Hz, 1H), 3.80 (dd, J=10.0, 4.5 Hz, 1H), 3.69-3.62 (m, 4H), 3.23 (ddd, J=14.0, 4.5, 4.5 Hz, 1H), 3.12-3.05 (m, 1H), 2.78-2.73 (m, 2H); ESI MS m/z 416 [M+H]$^+$.

e) 4-(Benzyloxy)-1-(1-(hydroxymethyl)-9-methyl-2,3,4,9-tetrahydro-1H-pyrido[3,4-b]indol-7-yl)pyridin-2(1H)-one hydrochloride

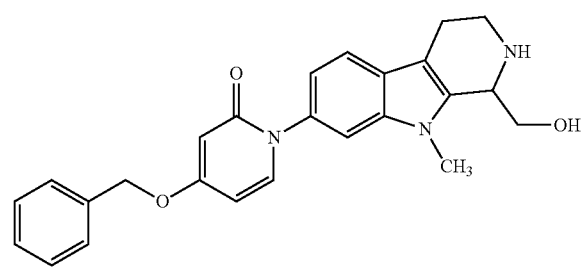

Chemical Formula: C$_{25}$H$_{25}$N$_3$O$_3$
Exact Mass: 415.19
Molecular Weight: 415.48

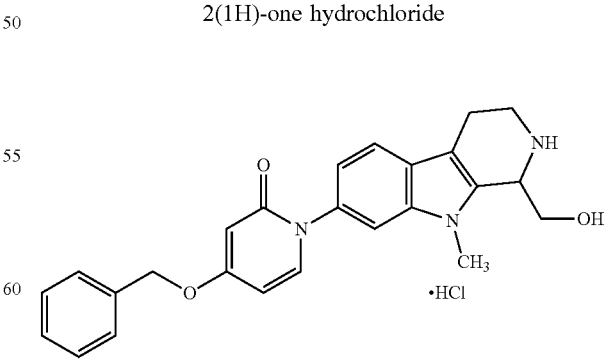

Chemical Formula: C$_{25}$H$_{26}$ClN$_3$O$_3$
Exact Mass: 451.17
Molecular Weight: 451.95

A 1.0 M solution of HCl in Et$_2$O (0.13 mL, 0.13 mmol) was added to a solution of 4-(benzyloxy)-1-(1-(hydroxymethyl)-9-methyl-2,3,4,9-tetrahydro-1H-pyrido[3,4-b]indol-7-yl)pyridin-2(1H)-one (55 mg, 0.13 mmol) in CH$_2$Cl$_2$ (10 mL) under N$_2$ and stirred at 25° C. for 1 h. The solution was concentrated to afford the title compound (32 mg, 54%) as an off-white powder: mp 168-170° C.; $^1$H NMR (500 MHz, DMSO-d$_6$) δ 9.48 (br s, 1H), 9.10 (br s, 1H), 7.56 (overlapping dd, J=8.5 Hz, 2H), 7.52 (s, 1H), 7.49-7.41 (m, 4H), 7.40-7.36 (m, 1H), 7.01 (dd, J=7.0, 1.5 Hz, 1H), 6.12 (dd, J=7.5, 1.5 Hz, 1H), 5.98 (d, J=1.5 Hz, 1H), 5.72 (t, J=3.3 Hz, 1H), 5.16 (s, 2H), 4.89-4.82 (m, 1H), 4.07-4.01 (m, 1H), 3.80-3.71 (m, 1H), 3.72 (s, 3H), 3.61-3.50 (m, 1H), 3.49-3.43 (m, 1H), 3.02-2.94 (m, 2H); ESI MS m/z 416 [M+H]$^+$.

Example 106

Preparation of 4-(Benzyloxy)-1-(2,3,4,9-tetrahydro-1H-pyrido[3,4-b]indol-7-yl)pyridin-2(1H)-one hydrochloride a) tert-Butyl 7-(4-(benzyloxy)-2-oxopyridin-1(2H)-yl)-9-tosyl-3,4-dihydro-1H-pyrido[3,4-b]indole-2(9H)-carboxylate

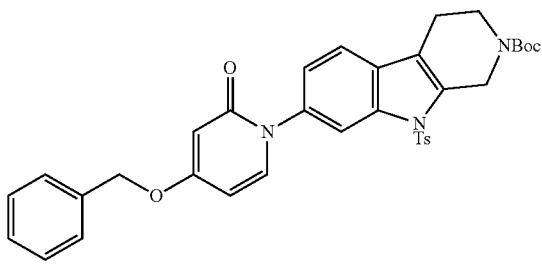

Chemical Formula: C$_{35}$H$_{35}$N$_3$O$_6$S
Exact Mass: 625.22
Molecular Weight: 625.73

A suspension of 4-(benzyloxy)pyridin-2(1H)-one (426 mg, 2.12 mmol), tert-butyl 7-bromo-9-tosyl-3,4-dihydro-1H-pyrido[3,4-b]indole-2(9H)-carboxylate (1.28 g, 2.54 mmol), CuI (484 mg, 2.54 mmol), 8-hydroxyquinoline (369 mg, 2.54 mmol) and Cs$_2$CO$_3$ (760 mg, 2.33 mmol) in DMSO (10 mL) was degassed under reduced pressure for 45 min. The suspension was put under Ar and heated at 135° C. with stirring for 1.5 h. The suspension was cooled, 4:1 CH$_2$Cl$_2$/(9:1 MeOH/NH$_4$OH) (50 mL) was added and the resulting suspension was stirred at 25° C. for 10 min. The suspension was passed through a plug of silica gel and the filtrate was washed with brine. The solution was dried over Na$_2$SO$_4$ and concentrated under reduced pressure to afford an amorphous solid. Flash chromatography (silica gel, (1:1 EtOAc/hexanes)/(9:0.9:0.1 CH$_2$Cl$_2$/MeOH/NH$_4$OH) 100:0 to 0:100) yielded the title compound (715 mg, 54%) as an off-white solid: $^1$H NMR (300 MHz, CDCl$_3$) δ 8.18 (br s, 1H), 7.82-7.73 (m, 2H), 7.48-7.35 (m, 6H), 7.33-7.23 (m, 4H), 6.12-5.97 (m, 2H) 5.07 (s, 2H), 4.90 (br s, 2H), 3.72-3.64 (m, 2H), 2.73-2.63 (m, 2H), 2.34 (s, 3H), 1.51 (s, 9H).

b) 4-(Benzyloxy)-1-(2,3,4,9-tetrahydro-1H-pyrido[3,4-b]indol-7-yl)pyridin-2(1H)-one hydrochloride

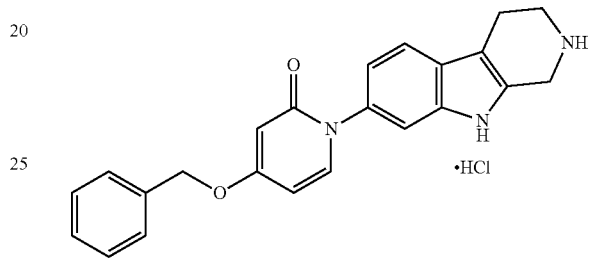

Chemical Formula: C$_{23}$H$_{22}$ClN$_3$O$_2$
Exact Mass: 407.14
Molecular Weight: 407.89

TFA (2 mL) was added to a solution of tert-butyl 7-(4-(benzyloxy)-2-oxopyridin-1(2H)-yl)-9-tosyl-3,4-dihydro-1H-pyrido[3,4-b]indole-2(9H)-carboxylate (678 mg, 1.09 mmol) in CH$_2$Cl$_2$ (10 mL) under N$_2$, and the resulting solution was stirred at 25° C. for 1 h. Saturated NaHCO$_3$ solution and EtOAc were added, and the phases were separated. The aqueous phase was extracted with CH$_2$Cl$_2$, and the combined organic phases were dried over Na$_2$SO$_4$. The organic solution was concentrated under reduced pressure to afford 510 mg of an off-white solid. NaOH (469 mg, 11.7 mmol) was added to a solution of the off-white solid (123 mg) in CH$_2$Cl$_2$/MeOH (10 mL) that had been degassed with N$_2$. The resulting solution was heated at 40° C. with stirring for 5 h under N$_2$. The solution was allowed to cool, saturated NH$_4$Cl solution and CH$_2$Cl$_2$ were added, and the phases were separated. The organic phase was washed with saturated NaHCO$_3$ solution, dried over Na$_2$SO$_4$ and concentrated under reduced pressure to yield an off-white solid. Flash chromatography (silica gel, (1:1 EtOAc/hexanes)/(9:0.9:0.1 CH$_2$Cl$_2$/MeOH/NH$_4$OH) 100:0 to 0:100) afforded a white solid. 1 M HCl in Et$_2$O (0.28 ml, 0.28 mmol) was added to a solution of the white solid in CH$_2$Cl$_2$ (10 mL) under N$_2$, and the resulting solution was stirred at 25° C. for 30 min. The resulting suspension was filtered. The solid was washed with CH$_2$Cl$_2$ and dried under reduced pressure to afford the title compound (26 mg, 24%) as a white solid: mp 246-248° C.; $^1$H NMR (500 MHz, DMSO-d$_6$) δ 11.22 (s, 1H), 9.29 (br s, 2H), 7.54 (dd, J=12.0, 8.0 Hz, 2H), 7.50-7.41

(m, 4H), 7.40-7.33 (m, 2H), 6.96 (dd, J=8.0, 1.5 Hz, 1H), 6.09 (dd, J=7.5, 2.5 Hz, 1H), 5.97 (d, J=2.5 Hz, 1H), 5.15 (s, 2H), 4.38 (s, 2H), 3.50-3.42 (m, 2H) 3.00-2.92 (m, 2H); ESI MS m/z 372 [M+H]$^+$.

Example 107

Preparation of 4-(Benzyloxy)-1-(2-methyl-2,3,4,9-tetrahydro-1H-pyrido[3,4-b]indol-7-yl)pyridin-2(1H)-one hydrochloride a) 4-(Benzyloxy)-1-(2-methyl-9-tosyl-2,3,4,9-tetrahydro-1H-pyrido[3,4-b]indol-7-yl)pyridin-2(1H)-one

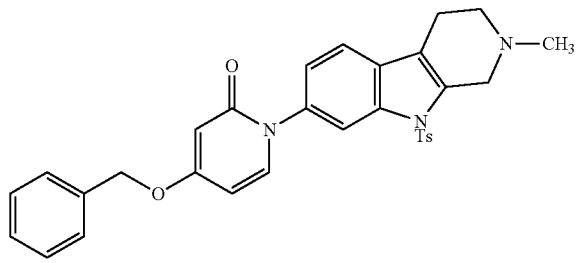

Chemical Formula: C$_{31}$H$_{29}$N$_3$O$_4$S
Exact Mass: 539.19
Molecular Weight: 539.64

TFA (2 mL) was added to a solution of tert-butyl 7-(4-(benzyloxy)-2-oxopyridin-1(2H)-yl)-9-tosyl-3,4-dihydro-1H-pyrido[3,4-b]indole-2(9H)-carboxylate (678 mg, 1.09 mmol) in CH$_2$Cl$_2$ (10 mL) under N$_2$ and the resulting solution was stirred at 25° C. for 1 h. Saturated NaHCO$_3$ solution and EtOAc were added to the solution and the phases were separated. The aqueous phase was extracted with CH$_2$Cl$_2$ and the combined organic phases were dried over Na$_2$SO$_4$. The organic solution was concentrated under reduced pressure to afford 510 mg of an off-white solid. Formaldehyde (37% in H$_2$O, 0.04 mL, 0.49 mmol) was added to a solution of the off-white solid (170 mg) in 1:1 MeOH/CH$_2$Cl$_2$ (10 mL) and the resulting solution was stirred at 25° C. for 45 min. NaBH(OAc)$_3$ (137 mg, 0.648 mmol) was added to the solution and the resulting suspension was stirred at 25° C. for 30 min. The suspension was concentrated under reduced pressure and the resulting residue was diluted with CH$_2$Cl$_2$ and saturated NaHCO$_3$ solution. The phases were separated. The organic phase was dried over Na$_2$SO$_4$ and concentrated under reduced pressure to yield the title compound (174 mg, 89%) as a viscous oil: $^1$H NMR (300 MHz, CDCl$_3$) δ 8.14 (d, J=1.5 Hz, 1H), 7.72 (d, J=8.4 Hz, 2H), 7.47-7.35 (m, 6H), 7.33-7.28 (m, 1H), 7.26-7.21 (m, 3H), 6.12-6.05 (m, 2H), 5.07 (s, 2H), 3.92 (br s, 2H), 2.79-2.70 (m, 4H), 2.56 (s, 3H), 2.33 (s, 3H).

b) 4-(Benzyloxy)-1-(2-methyl-2,3,4,9-tetrahydro-1H-pyrido[3,4-b]indol-7-yl)pyridin-2(1H)-one hydrochloride

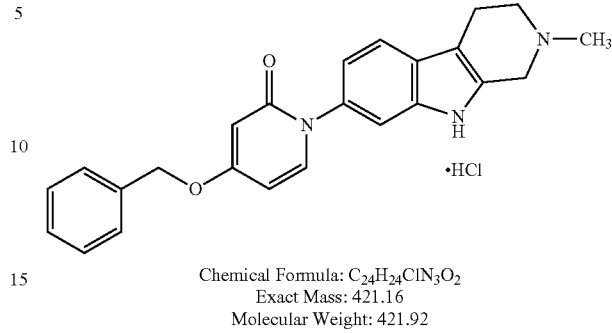

Chemical Formula: C$_{24}$H$_{24}$ClN$_3$O$_2$
Exact Mass: 421.16
Molecular Weight: 421.92

NaOH (644 mg, 16.1 mmol) was added to a solution of the 4-(benzyloxy)-1-(2-methyl-9-tosyl-2,3,4,9-tetrahydro-1H-pyrido[3,4-b]indol-7-yl)pyridin-2(1H)-one (174 mg, 0.322 mmol) in CH$_2$Cl$_2$/MeOH (10 mL) that had been degassed with N$_2$. The resulting solution was heated at reflux with stirring for 2 h under N$_2$. The solution was allowed to cool, saturated NH$_4$Cl solution and CH$_2$Cl$_2$ were added, and the phases were separated. The organic phase was washed with saturated NaHCO$_3$ solution, dried over Na$_2$SO$_4$ and concentrated under reduced pressure to yield a white solid. 1 M HCl in Et$_2$O (0.38 ml, 0.38 mmol) was added to a solution of the white solid in 9:1 CH$_2$Cl$_2$/MeOH (10 mL) under N$_2$, and the resulting solution was stirred at 25° C. for 30 min. The solution was concentrated, and the residue was diluted with a small amount of CH$_2$Cl$_2$/CH$_3$CN. The resulting suspension was filtered, and the solid was dried under reduced pressure to yield the title compound (46 mg, 34%) as a white solid: mp 168-170° C.; $^1$H NMR (500 MHz, DMSO-d$_6$) δ 11.30 (s, 1H), 10.50-10.41 (m, 1H), 7.58-7.52 (m, 2H), 7.49-7.40 (m, 4H), 7.39-7.35 (m, 2H), 6.96 (br d, J=8.0 Hz, 1H), 6.09 (br d, J=7.5 Hz, 1H), 5.97 (br s, 1H), 5.15 (s, 2H), 4.60 (br d, J=15.0 Hz, 1H), 4.41 (dd, J=15.0, 7.5 Hz, 1H), 3.78-3.71 (m, 1H), 3.45-3.38 (m, 1H), 3.09-2.98 (m, 5H); ESI MS m/z 386 [M+H]$^+$.

Example 108

Preparation of 1-(2,3,4,9-Tetrahydro-1H-pyrido[3,4-b]indol-7-yl)-4-(4-(trifluoro-methyl)phenyl)pyridin-2(1H)-one hydrochloride a) tert-Butyl 7-(2-oxo-4-(4-(trifluoromethyl)phenyl)pyridin-1(2H)-yl)-9-tosyl-3,4-dihydro-1H-pyrido[3,4-b]indole-2(9H)-carboxylate

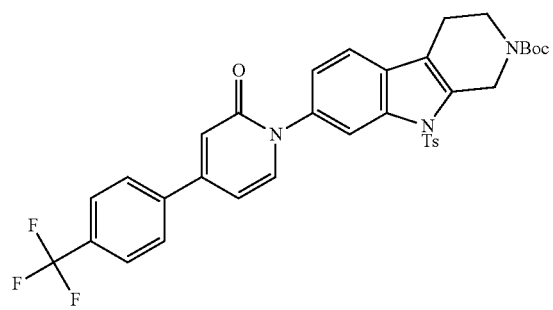

Chemical Formula: C$_{35}$H$_{32}$F$_3$N$_3$O$_5$S
Exact Mass: 663.20
Molecular Weight: 663.71

A suspension of 4-(4-(trifluoromethyl)phenyl)pyridin-2(1H)-one (121 mg, 0.504 mmol), tert-butyl 7-bromo-9-tosyl-3,4-dihydro-1H-pyrido[3,4-b]indole-2(9H)-carboxylate (305 mg, 0.605 mmol), CuI (115 mg, 0.605 mmol), 8-hydroxyquinoline (88 mg, 0.605 mmol) and $Cs_2CO_3$ (181 mg, 0.605 mmol) in DMSO (5 mL) was degassed under reduced pressure for 45 min. The suspension was put under Ar and heated at 135° C. with stirring for 2.5 h. The suspension was cooled, 4:1 $CH_2Cl_2$/(9:1 $MeOH/NH_4OH$) (25 mL) was added and the resulting suspension was stirred at 25° C. for 10 min. The suspension was passed through a plug of silica gel and the filtrate was washed with brine. The solution was dried over $Na_2SO_4$ and concentrated under reduced pressure to afford an amorphous solid. Flash chromatography (silica gel, (1:1 EtOAc/hexanes)/(9:0.9:0.1 $CH_2Cl_2$/MeOH/$NH_4OH$) 100:0 to 0:100) gave the title compound (170 mg, 51%) as a pink foam: $^1$H NMR (300 MHz, $CDCl_3$) δ 8.26 (br s, 1H), 7.83-7.74 (m, 6H), 7.53 (d, J=7.2 Hz, 1H), 7.51-7.45 (m, 1H), 7.35-7.23 (m, 3H), 6.93 (d, J=1.8 Hz, 1H), 6.54 (dd, J=7.2, 1.8 Hz, 1H), 4.91 (br s, 2H), 3.75-3.65 (m, 2H), 2.73-2.68 (m, 2H), 2.36 (s, 3H), 1.52 (s, 9H).

b) 1-(2,3,4,9-Tetrahydro-1H-pyrido[3,4-b]indol-7-yl)-4-(4-(trifluoromethyl)phenyl)pyridin-2(1H)-one hydrochloride

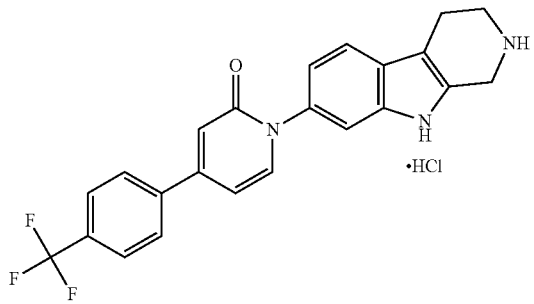

Chemical Formula: $C_{23}H_{19}ClF_3N_3O$
Exact Mass: 445.12
Molecular Weight: 445.86

TFA (1 mL) was added to a solution of tert-butyl 7-(2-oxo-4-(4-(trifluoro-methyl)phenyl)pyridin-1(2H)-yl)-9-tosyl-3,4-dihydro-1H-pyrido[3,4-b]indole-2(9H)-carboxylate (170 mg, 0.256 mmol) in $CH_2Cl_2$ (5 mL) under $N_2$, and the resulting solution was stirred at 25° C. for 30 min. Saturated $NaHCO_3$ solution and $CH_2Cl_2$ were added to the solution, and the phases were separated. The organic phase was dried over $Na_2SO_4$ and concentrated under reduced pressure to afford 145 mg of a pink solid. NaOH (227 mg, 5.67 mmol) was added to a solution of the pink solid (64 mg) in $CH_2Cl_2$/MeOH (10 mL) that had been degassed with $N_2$. The resulting solution was heated at reflux with stirring for 7 h under $N_2$. The solution was allowed to cool, saturated $NH_4Cl$ solution and $CH_2Cl_2$ were added, and the phases were separated. The organic phase was washed with saturated $NaHCO_3$ solution, dried over $Na_2SO_4$ and concentrated under reduced pressure to yield a yellow powder. Flash chromatography (silica gel, (1:1 EtOAc/hexanes)/(9:0.9:0.1 $CH_2Cl_2$/MeOH/$NH_4OH$) 100:0 to 0:100) afforded a yellow solid. 1 M HCl in $Et_2O$ (0.07 ml, 0.06 mmol) was added to a solution of the yellow solid in 9:1 $CH_2Cl_2$/MeOH (10 mL) under $N_2$ and the resulting solution was stirred at 25° C. for 30 min. The solution was concentrated under reduced pressure to yield the title compound (27 mg, 54%) as a yellow solid: $^1$H NMR (500 MHz, DMSO-$d_6$) δ 11.28 (s, 1H), 9.21 (br s, 2H), 8.01 (d J=8.3 Hz, 2H), 7.88 (d, J=8.3 Hz, 2H), 7.80 (d, J=7.0 Hz, 1H), 7.58 (d, J=8.0 Hz, 1H), 7.49 (d, J=1.5 Hz, 1H), 7.07 (dd, J=8.0, 1.5 Hz, 1H), 6.87 (d, J=2.0 Hz, 1H), 6.72 (dd, J=7.0, 2.0 Hz, 1H), 4.40 (s, 2H), 3.52-3.48 (m, 2H), 2.99 (t, J=6.0 Hz, 2H); ESI MS m/z 410 $[M+H]^+$.

Example 109

Preparation of 1-(2-Methyl-2,3,4,9-tetrahydro-1H-pyrido[3,4-b]indol-7-yl)-4-(4-(trifluoro-methyl)phenyl)pyridin-2(1H)-one hydrochloride a) 1-(2-Methyl-9-tosyl-2,3,4,9-tetrahydro-1H-pyrido[3,4-b]indol-7-yl)-4-(4-(trifluoromethyl)phenyl)pyridin-2(1H)-one

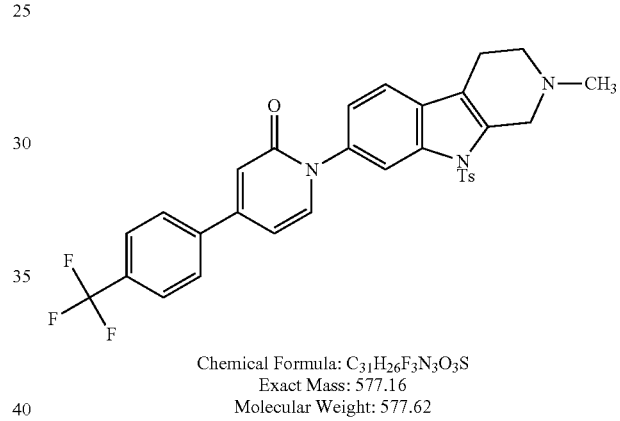

Chemical Formula: $C_{31}H_{26}F_3N_3O_3S$
Exact Mass: 577.16
Molecular Weight: 577.62

TFA (1 mL) was added to a solution of tert-butyl 7-(2-oxo-4-(4-(trifluoro-methyl)phenyl)pyridin-1(2H)-yl)-9-tosyl-3,4-dihydro-1H-pyrido[3,4-b]indole-2(9H)-carboxylate (170 mg, 0.256 mmol) in $CH_2Cl_2$ (5 mL) under $N_2$, and the resulting solution was stirred at 25° C. for 30 min. Saturated $NaHCO_3$ solution and $CH_2Cl_2$ were added to the solution, and the phases were separated. The organic phase was dried over $Na_2SO_4$ and concentrated under reduced pressure to afford 145 mg of a pink solid. Formaldehyde (37% in $H_2O$, 0.02 mL, 0.2 mmol) was added to a solution of the pink solid (80 mg) in 1:1 MeOH/$CH_2Cl_2$ (4 mL) and the resulting solution was stirred at 25° C. for 45 min. $NaBH(OAc)_3$ (60 mg, 0.28 mmol) was added to the solution and the resulting suspension was stirred at 25° C. for 30 min. The suspension was concentrated under reduced pressure. The residue was diluted with $CH_2Cl_2$ and saturated $NaHCO_3$ solution. The phases were separated. The organic phase was dried over $Na_2SO_4$ and concentrated under reduced pressure to yield the title compound (61 mg, 74%) as a pink foam: $^1$H NMR (300 MHz, $CDCl_3$) δ 8.23 (d, J=1.8 Hz, 1H), 7.79-7.71 (m, 6H), 7.53 (d, J=7.2 Hz, 1H), 7.47 (d, J=8.4 Hz, 1H), 7.32 (dd, J=8.4, 1.8 Hz, 1H), 7.27-7.22 (m, 2H), 6.93 (d, J=1.8 Hz, 1H), 6.53 (dd, J=7.2, 1.8 Hz, 1H), 3.93 (br s, 2H), 2.80-2.60 (m, 4H), 2.57 (s, 3H), 2.34 (s, 3H).

b) 1-(2-Methyl-2,3,4,9-tetrahydro-1H-pyrido[3,4-b]indol-7-yl)-4-(4-(trifluoro-methyl)phenyl)pyridin-2(1H)-one hydrochloride

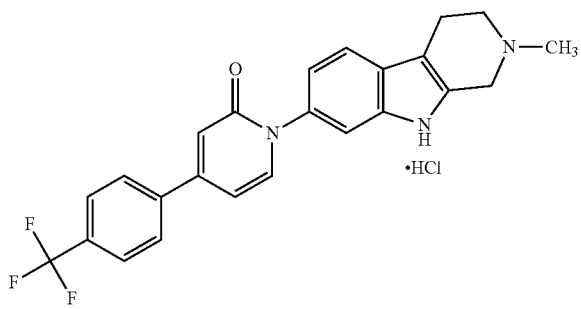

Chemical Formula: $C_{24}H_{21}ClF_3N_3O$
Exact Mass: 459.13
Molecular Weight: 459.89

NaOH (211 mg, 5.28 mmol) was added to a solution of 1-(2-methyl-9-tosyl-2,3,4,9-tetrahydro-1H-pyrido[3,4-b]indol-7-yl)-4-(4-(trifluoromethyl)phenyl)pyridin-2(1H)-one (61 mg, 0.11 mmol) in $CH_2Cl_2$/MeOH (10 mL) that had been degassed with $N_2$. The resulting solution was heated at reflux with stirring for 7 h under $N_2$. The solution was allowed to cool, saturated $NH_4Cl$ solution and $CH_2Cl_2$ were added, and the phases were separated. The organic phase was washed with saturated $NaHCO_3$ solution, dried over $Na_2SO_4$ and concentrated under reduced pressure to yield a yellow solid. Flash chromatography (silica gel, (1:1 EtOAc/hexanes)/(9:0.9:0.1 $CH_2Cl_2$/MeOH/$NH_4OH$) 100:0 to 0:100) afforded a yellow solid. 1 M HCl in $Et_2O$ (0.06 ml, 0.06 mmol) was added to a solution of the yellow solid in 9:1 $CH_2Cl_2$/MeOH (10 mL) under $N_2$ and the resulting solution was stirred at 25° C. for 30 min. The solution was concentrated under reduced pressure to yield the title compound (28 mg, 58%) as a yellow solid: mp 200-204° C.; $^1$H NMR (500 MHz, DMSO-$d_6$) δ 11.36 (s, 1H), 10.35 (br s, 1H), 8.02 (d, J=8.3 Hz, 2H), 7.88 (d, J=8.3 Hz, 2H), 7.80 (d, J=7.0 Hz, 1H), 7.59 (d, J=8.0 Hz, 1H), 7.49 (br s, 1H), 7.07 (dd, J=8.0, 1.5 Hz, 1H), 6.87 (d, J=1.5 Hz, 1H), 6.72 (d, J=7.0, 1.5 Hz, 1H), 4.62 (br d, J=16.0 Hz, 1H), 4.49-4.40 (m, 1H), 3.81-3.73 (m, 1H), 3.49-3.39 (m, 1H), 3.12-3.00 (m, 5H); ESI MS m/z 424 [M+H]$^+$.

Example 110

Preparation of 4-(Benzyloxy)-1-(1,1,9-trimethyl-2,3,4,9-tetrahydro-1H-pyrido[3,4-b]indol-7-yl)pyridin-2(1H)-one hydrochloride a) 7-Bromo-1,1-dimethyl-2,3,4,9-tetrahydro-1H-pyrido[3,4-b]indole

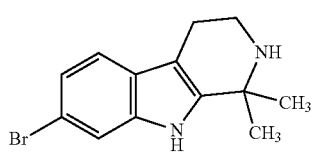

Chemical Formula: $C_{13}H_{15}BrN_2$
Exact Mass: 278.04
Molecular Weight: 279.18

Concentrated HCl (10 mL) was added to a suspension of a 2:1 mixture of 2-(6-bromo-1H-indol-3-yl)ethanamine and 2-(4-bromo-1H-indol-3-yl)ethanamine (9.90 g, 41.4 mmol) and $Na_2SO_4$ (30 g) in 1:1 acetone/n-butanol (100 mL). The resulting suspension was heated at 60° C. with stirring for 4 d. The suspension was cooled and concentrated under reduced pressure. The residue was diluted with EtOAc, and the suspension was filtered. The filtrate was washed with saturate $NaHCO_3$ solution, dried over $Na_2SO_4$ and concentrated under reduced pressure. Flash chromatography (silica gel, (1:1 EtOAc/hexanes)/(9:0.9:0.1 $CH_2Cl_2$/MeOH/$NH_4OH$) 100:0 to 0:100) yielded the title compound (1.68 g, 15%) as a red foam: $^1$H NMR (500 MHz, CDCl$_3$) δ 7.66 (br s, 1H), 7.45 (d, J=1.5 Hz, 1H), 7.32 (d, J=8.5 Hz, 1H), 7.19 (dd, J=8.5, 1.5 Hz, 1H), 3.20 (t, J=5.5 Hz, 2H), 2.68 (t, J=5.5 Hz, 2H), 1.47 (s, 6H).

b) tert-Butyl 7-bromo-1,1,9-trimethyl-3,4-dihydro-1H-pyrido[3,4-b]indole-2(9H)-carboxylate

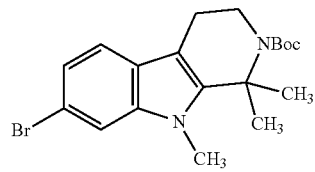

Chemical Formula: $C_{19}H_{25}BrN_2O_2$
Exact Mass: 392.11
Molecular Weight: 393.32

Boc$_2$O (7.88 g, 36.1 mmol) was added to a suspension of 7-bromo-1,1-dimethyl-2,3,4,9-tetrahydro-1H-pyrido[3,4-b]indole (1.68 g, 6.02 mmol) and K$_2$CO$_3$ (1.66 g, 12.0 mmol) in 1:1 H$_2$O/i-PrOH (80 mL), and the resulting suspension was stirred at 25° C. for 2 h. The suspension was filtered. The solid was washed with H$_2$O and dried under reduced pressure to afford 1.285 g of a white solid. NaH (60% dispersion in oil, 152 mg, 3.80 mmol) was added to a solution of the white solid (720 mg) in DMF (10 mL) under N$_2$ and the resulting suspension was stirred at 25° C. for 30 min. MeI (0.18 mL, 2.9 mmol) was added to the suspension, and the resulting suspension was stirred at 25° C. for 30 min. The suspension was cooled to 0° C., and H$_2$O was added slowly. Hexanes was added and the phases were separated. The organic phase was dried over Na$_2$SO$_4$ and concentrated under reduced pressure. Flash chromatography (silica gel, hexanes/(1:1 EtOAc/hexanes) 100:0 to 60:40) yielded the title compound (471 mg, 36%) as a white solid: $^1$H NMR (300 MHz, CDCl$_3$) δ 7.43 (d, J=1.5 Hz, 1H), 7.33 (d, J=8.4 Hz, 1H), 7.20 (dd, J=8.4, 1.5 Hz, 1H), 3.79-3.72 (m, 5H), 2.73 (t, J=5.4 Hz, 2H), 1.88 (s, 6H), 1.53 (s, 9H).

c) tert-Butyl 7-(4-(benzyloxy)-2-oxopyridin-1(2H)-yl)-1,1,9-trimethyl-3,4-dihydro-1H-pyrido[3,4-b]indole-2(9H)-carboxylate

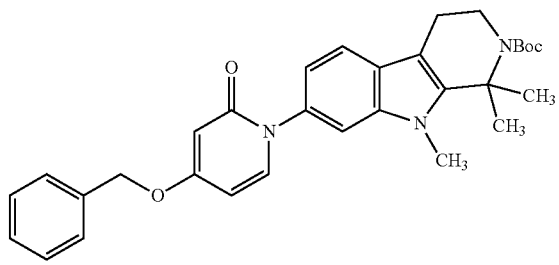

Chemical Formula: C₃₁H₃₅N₃O₄
Exact Mass: 513.26
Molecular Weight: 513.63

A suspension of 4-(benzyloxy)pyridin-2(1H)-one (107 mg, 0.532 mmol), tert-butyl 7-bromo-1,1,9-trimethyl-3,4-dihydro-1H-pyrido[3,4-b]indole-2(9H)-carboxylate (251 mg, 0.639 mmol), CuI (122 mg, 0.639 mmol), 8-hydroxyquinoline (93 mg, 0.639 mmol) and Cs₂CO₃ (190 mg, 0.585 mmol) in DMSO (10 mL) was degassed under reduced pressure for 45 min. The suspension was put under Ar and heated at 135° C. with stirring overnight. The suspension was cooled, 40:9:1 CH₂Cl₂/MeOH/NH₄OH was added and the resulting suspension was stirred at 25° C. for 30 min. The suspension was passed through a plug of silica gel, and the filtrate was washed with brine. The solution was dried over Na₂SO₄ and concentrated under reduced pressure to afford an amorphous solid. Flash chromatography (silica gel, (1:1 EtOAc/hexanes)/(9:0.9:0.1 CH₂Cl₂/MeOH/NH₄OH) 100:0 to 1:1) yielded the title compound (74 mg, 27%) as a white powder: ¹H NMR (300 MHz, CDCl₃) δ 7.54 (d, J=8.1 Hz, 1H), 7.46-7.35 (m, 4H), 7.33-7.25 (m, 3H), 7.12 (dd, J=8.1, 2.1 Hz, 1H), 6.09 (d, J=2.6 Hz, 1H), 6.04 (dd, J=7.5, 2.6 Hz, 1H), 5.06 (s, 2H), 3.80 (s, 3H), 3.77 (t, J=4.8 Hz, 2H), 2.77 (t, J=4.8 Hz, 2H), 1.89 (s, 6H), 1.54 (s, 9H).

d) 4-(Benzyloxy)-1-(1,1,9-trimethyl-2,3,4,9-tetrahydro-1H-pyrido[3,4-b]indol-7-yl)pyridin-2(1H)-one hydrochloride

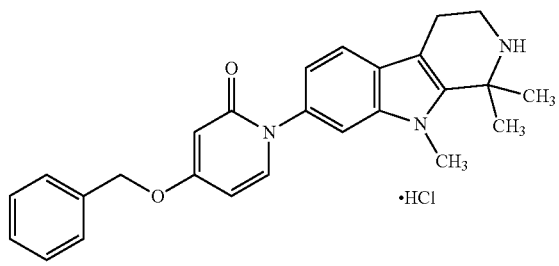

Chemical Formula: C₂₆H₂₈ClN₃O₂
Exact Mass: 449.19
Molecular Weight: 449.97

TFA (1 mL) was added to a solution of tert-butyl 7-(4-(benzyloxy)-2-oxopyridin-1(2H)-yl)-1,1,9-trimethyl-3,4-dihydro-1H-pyrido[3,4-b]indole-2(9H)-carboxylate (72 mg, 0.14 mmol) in CH₂Cl₂ (10 mL) under N₂, and the resulting solution was stirred at 25° C. for 30 min. Saturated NaHCO₃ solution and CH₂Cl₂ were added to the solution and the phases were separated. The organic phase was dried over Na₂SO₄ and concentrated under reduced pressure. Purification by semi-preparative HPLC (Phenomenex Luna C18 (2), 250.0×21.20 mm, 10 micron, H₂O with 0.05% TFA and CH₃CN with 0.05% TFA) afforded 14 mg of clear crystals. 1 M HCl in Et₂O (0.04 ml, 0.04 mmol) was added to a solution of the clear crystals in CH₂Cl₂ (10 mL) under N₂ and the resulting solution was stirred at 25° C. for 30 min. The solution was concentrated under reduced pressure to yield the title compound (15 mg, 24%) as an off-white powder: mp 296-298; ¹H NMR (500 MHz, DMSO-d₆) δ 9.59 (s, 2H), 7.58-7.51 (m, 3H), 7.49-7.41 (m, 4H), 7.40-7.35 (m, 1H), 7.01 (dd, J=8.5, 1.5 Hz, 1H), 6.10 (dd, J=7.5, 2.8 Hz, 1H), 5.97 (d, J=2.8 Hz, 1H), 5.16 (s, 2H), 3.80 (s, 3H), 3.52-3.48 (m, 2H), 2.99 (t, J=6.0 Hz, 2H), 1.81 (s, 6H); ESI MS m/z 414 [M+H]⁺.

Example 111

Preparation of (S)-4-(Benzyloxy)-1-(9-methyl-2-(pyrrolidin-2-ylmethyl)-2,3,4,9-tetrahydro-1H-pyrido[3,4-b]indol-7-yl)pyridin-2(1H)-one dihydrochloride a) (S)-tert-Butyl 2-(bromomethyl)pyrrolidine-1-carboxylate Beilstein Registry Number 6325435

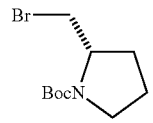

Chemical Formula: C₁₀H₁₈BrNO₂
Exact Mass: 263.05
Molecular Weight: 264.16

This compound was prepared in accordance with the procedure of Kawara et al., *Tetrahedron Lett.*, 1994, 35, 8805-8808.

b) (S)-4-(Benzyloxy)-1-(9-methyl-2-(pyrrolidin-2-ylmethyl)-2,3,4,9-tetrahydro-1H-pyrido[3,4-b]indol-7-yl)pyridin-2(1H)-one dihydrochloride

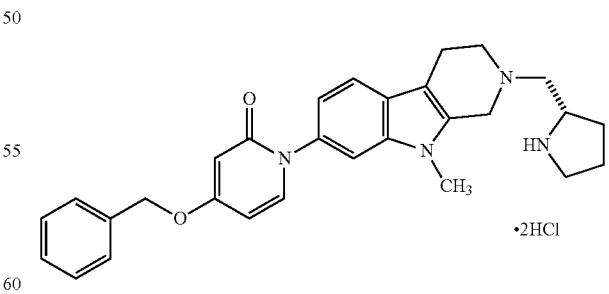

Chemical Formula: C₂₉H₃₄Cl₂N₄O₂
Exact Mass: 540.21
Molecular Weight: 541.51

A suspension of 4-(benzyloxy)-1-(9-methyl-2,3,4,9-tetrahydro-1H-pyrido[3,4-b]indol-7-yl)pyridin-2(1H)-one (250 mg, 0.646 mmol), (S)-tert-butyl 2-(bromomethyl)pyrrolidine-1-carboxylate (342 mg, 1.29 mmol) and Cs$_2$CO$_3$ (841 mg, 2.58 mmol) in DMSO (10 mL) under N$_2$ was stirred at 25° C. for 16 h. The suspension was heated at 60° C. for 1 d. The suspension was cooled, and H$_2$O was added. The suspension was filtered. The solid was washed with H$_2$O and dried under reduced pressure. Flash chromatograph (silica gel, hexanes/(9:0.9:0.1 Et$_2$O/MeOH/NH$_4$OH), 100:0 to 0:100) afforded 18 mg of a yellow solid. TFA (1 mL) was added to a solution of the yellow solid in CH$_2$Cl$_2$ (5 mL) under N$_2$ and the resulting solution was stirred at 25° C. for 3.5 h. Saturated NaHCO$_3$ solution and CH$_2$Cl$_2$ were added and the phases were separated. The organic phase was dried over Na$_2$SO$_4$ and concentrated under reduced pressure. Flash chromatograph (silica gel, (1:1 EtOAc/hexanes)/(9: 0.9:0.1 Et$_2$O/MeOH/NH$_4$OH), 100:0 to 0:100) yielded 10 mg of a yellow solid. 1 M HCl in Et$_2$O (0.04 ml, 0.04 mmol) was added to a solution of the yellow solid in CH$_2$Cl$_2$ (10 mL) under N$_2$, and the resulting solution was stirred at 25° C. for 30 min. The solution was concentrated under reduced pressure to yield the title compound (10 mg, 3%) as an off-white powder: mp 160-162° C.; $^1$H NMR (500 MHz, DMSO-d$_6$) δ 9.25 (br s, 1H), 7.56 (d, J=7.5 Hz, 1H), 7.54-7.40 (m, 6H), 7.39-7.34 (m, 1H), 7.04-6.93 (m, 1H), 6.11 (dd, J=7.5, 2.5 Hz, 1H), 5.97 (d, J=2.5 Hz, 1H), 5.16 (s, 2H), 3.98-3.45 (m, 11H), 3.39 (s, 1H), 3.30-3.21 (m, 2H), 2.25-2.10 (m, 1H), 2.05-1.74 (m, 2H), 1.73-1.60 (m, 1H); ESI MS m/z 469 [M+H]$^+$.

Example 112

Preparation of 4-(4-Chloro-2-methoxyphenyl)-1-(5-methyl-2,3,4,5-tetrahydro-1H-pyrido[4,3-b]indol-7-yl)pyridin-2(1H)-one hydrochloride a) 4-(4-Chloro-2-methoxyphenyl)pyridine 1-oxide

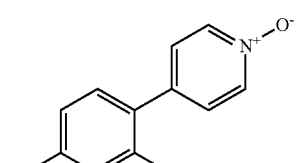

Chemical Formula: C$_{12}$H$_{10}$ClNO$_2$
Exact Mass: 235.04
Molecular Weight: 235.67

4-Chloropyridine-N-oxide (500 mg, 3.85 mmol), 2-methoxy-4-chlorophenylboronic acid (862 mg, 4.63 mmol) and K$_2$CO$_3$ (1.59 g, 11.55 mmol) were suspended in DMSO (5 mL) and PdCl$_2$(dppf) (314 mg, 0.385 mmol) was added. The reaction mixture was placed under vacuum for 20 min and flushed with N$_2$. This process was repeated, and the reaction mixture was heated at 120° C. for 3 h. The reaction mixture was cooled to 25° C. and partitioned between methylene chloride and 5% lithium chloride. The aqueous phase was removed, and the organic phase was washed with brine, dried over Na$_2$SO$_4$, filtered and concentrated to dryness under reduced pressure. Flash chromatography (ISCO 40 g column, methylene chloride/MeOH 100:0 to 90:10) provided the title compound (673 mg, 74%) as a tan solid: $^1$H NMR (300 MHz, CD$_3$OD) δ 8.21 (dd, J=5.4, 1.8 Hz, 2H), 7.47 (dd, J=5.6, 1.6 Hz, 2H), 7.26 (d, J=8.2 Hz, 1H), 7.06 (dd, J=8.3, 2.4 Hz, 1H), 7.00 (d, J=1.7 Hz, 1H), 3.87 (s, 3H); ESI MS m/z 235 [M+H]$^+$.

b) 4-(4-Chloro-2-methoxyphenyl)pyridin-2(1H)-one

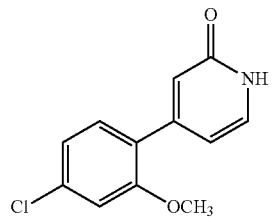

Chemical Formula: C$_{12}$H$_{10}$ClNO$_2$
Exact Mass: 235.04
Molecular Weight: 235.67

4-(4-Chloro-2-methoxyphenyl)pyridine 1-oxide (673 mg, 2.86 mmol) and acetic anhydride (10 mL) were heated at reflux for 3 h. The mixture was concentrated under reduced pressure, and a 1:1 solution of H$_2$O/MeOH (20 mL) was added. The reaction mixture was heated to reflux for 1 h, cooled to 25° C. and concentrated under reduced pressure. The resulting residue was dissolved in hot 2-propanol (3 mL), triturated with Et$_2$O, sonicated for 30 min then placed in the freezer. The solid was filtered off providing the title compound (550 mg, 91%) as a tan solid: $^1$H NMR (500 MHz, DMSO-d$_6$) δ 11.54 (s, 1H), 7.35-7.33 (m, 2H), 7.01 (s, 1H), 7.08 (d, J=6.6 Hz, 1H), 6.36 (s, 1H), 6.28 (s, 1H), 3.82 (s, 3H); ESI MS m/z 235 [M+H]$^+$.

c) tert-Butyl 7-(4-(4-chloro-2-methoxyphenyl)-2-oxopyridin-1(2H)-yl)-5-methyl-3,4-dihydro-1H-pyrido[4,3-b]indole-2(5H)-carboxylate

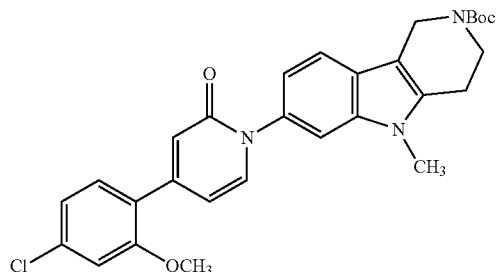

Chemical Formula: C$_{29}$H$_{30}$ClN$_3$O$_4$
Exact Mass: 519.19
Molecular Weight: 520.02

A suspension of 4-(4-chloro-2-methoxyphenyl)pyridin-2 (1H)-one (126 mg, 0.534 mmol), tert-butyl 7-bromo-5-methyl-3,4-dihydro-1H-pyrido[4,3-b]indole-2(5H)-carboxylate (234 mg, 0.641 mmol), CuI (122 mg, 0.641 mmol), 8-hydroxyquinoline (93 mg, 0.64 mmol) and Cs$_2$CO$_3$ (191 mg, 0.587 mmol) in DMSO (5 mL) was degassed under reduced pressure for 45 min. The suspension was put under Ar and heated at 135° C. with stirring overnight. The suspension was cooled, 40:9:1 CH$_2$Cl$_2$/MeOH/NH$_4$OH was added, and the resulting suspension was stirred at 25° C. for 10 min. The suspension was passed through a plug of silica gel, and the filtrate was washed with brine. The solution was dried over Na$_2$SO$_4$ and concentrate under reduced pressure. Flash chromatography (silica gel, (1:1 EtOAc/hexanes)/(9:0.9:0.1 CH$_2$Cl$_2$/MeOH/NH$_4$OH) 100:0 to 0:100) gave the title compound (123 mg, 44%) as a yellow solid: $^1$H NMR (300 MHz, CDCl$_3$) δ 7.54 (d, J=8.1 Hz, 1H), 7.42-7.35 (m, 2H), 7.31 (d, J=8.1 Hz, 1H), 7.12-7.02 (m, 2H), 6.99 (d, J=1.8 Hz, 1H), 6.81 (d, J=1.8 Hz, 1H), 6.44 (dd, J=7.2, 1.8 Hz, 1H), 4.65 (br s, 2H), 3.88 (s, 3H), 3.90-3.81 (m, 2H), 3.65 (s, 3H), 2.87-2.79 (m, 2H), 1.51 (s, 9H).

d) 4-(4-Chloro-2-methoxyphenyl)-1-(5-methyl-2,3,4,5-tetrahydro-1H-pyrido[4,3-b]indol-7-yl)pyridin-2(1H)-one hydrochloride

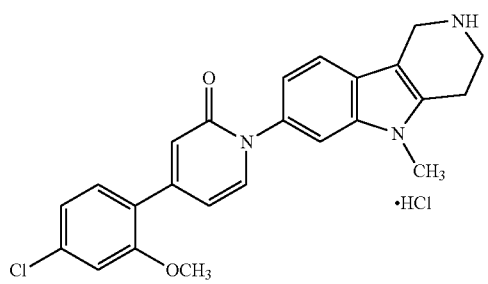

Chemical Formula: C$_{24}$H$_{23}$Cl$_2$N$_3$O$_2$
Exact Mass: 455.12
Molecular Weight: 456.36

TFA (2 mL) was added to a solution of tert-butyl 7-(4-(4-chloro-2-methoxyphenyl)-2-oxopyridin-1(2H)-yl)-5-methyl-3,4-dihydro-1H-pyrido[4,3-b]indole-2(5H)-carboxylate (124 mg, 0.238 mmol) in CH$_2$Cl$_2$ (10 mL) under N$_2$, and the resulting solution was stirred at 25° C. for 1 h. Saturated NaHCO$_3$ solution and CH$_2$Cl$_2$ were added to the solution, and the phases were separated. The organic phase was dried over Na$_2$SO$_4$ and concentrated under reduced pressure. Flash chromatography (silica gel, (1:1 EtOAc/hexanes)/(9:0.9:0.1 CH$_2$Cl$_2$/MeOH/NH$_4$OH) 100:0 to 0:100) yielded 70 mg of an off-white solid. 1 M HCl in Et$_2$O (0.03 ml, 0.03 mmol) was added to a solution of the off-white solid (10 mg) in CH$_2$Cl$_2$ (10 mL) under N$_2$ and the resulting solution was stirred at 25° C. for 30 min. The solution was concentrated under reduced pressure to yield the title compound (9 mg, 26%) as an off-white powder: mp 290-292° C.; $^1$H NMR (500 MHz, DMSO-d$_6$) δ 9.17 (br s, 2H), 7.65 (d, J=7.0 Hz, 1H), 7.62 (d, J=1.8 Hz, 1H), 7.59 (d, J=8.5 Hz, 1H), 7.44 (d, J=8.0 Hz, 1H), 7.26 (d, J=1.8 Hz, 1H), 7.14 (dd, J=8.0, 1.8 Hz, 1H), 7.09 (dd, J=8.5, 1.8 Hz, 1H), 6.57 (d, J=2.0 Hz, 1H), 6.47 (dd, J=7.0, 2.0 Hz, 1H), 4.37 (br s, 2H), 3.87 (s, 3H), 3.70 (s, 3H), 3.57-3.52 (m, 2H), 3.10 (t, J=6.0 Hz, 2H); ESI MS m/z 420 [M+H]$^+$.

Example 113

Preparation of 4-(4-Chloro-2-methoxyphenyl)-1-(2,5-dimethyl-2,3,4,5-tetrahydro-1H-pyrido[4,3-b]indol-7-yl)pyridin-2(1H)-one hydrochloride a) 4-(4-Chloro-2-methoxyphenyl)-1-(2,5-dimethyl-2,3,4,5-tetrahydro-1H-pyrido[4,3-b]indol-7-yl)pyridin-2(1H)-one hydrochloride

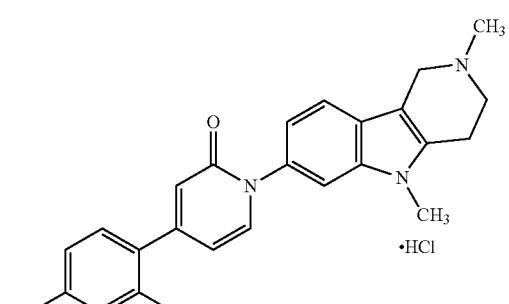

Chemical Formula: C$_{25}$H$_{25}$Cl$_2$N$_3$O$_2$
Exact Mass: 469.13
Molecular Weight: 470.39

TFA (2 mL) was added to a solution of tert-butyl 7-(4-(4-chloro-2-methoxyphenyl)-2-oxopyridin-1(2H)-yl)-5-methyl-3,4-dihydro-1H-pyrido[4,3-b]indole-2(5H)-carboxylate (124 mg, 0.238 mmol) in CH$_2$Cl$_2$ (10 mL) under N$_2$, and the resulting solution was stirred at 25° C. for 1 h. Saturated NaHCO$_3$ solution and CH$_2$Cl$_2$ were added to the solution, and the phases were separated. The organic phase was dried over Na$_2$SO$_4$ and concentrated under reduced pressure. Flash chromatography (silica gel, (1:1 EtOAc/hexanes)/(9:0.9:0.1 CH$_2$Cl$_2$/MeOH/NH$_4$OH), 100:0 to 0:100) yielded 70 mg of an off-white solid. Formaldehyde (37% in H$_2$O, 0.02 mL, 0.2 mmol) was added to a solution of the off-white solid (43 mg) in 1:1 MeOH/CH$_2$Cl$_2$ (5 mL) and the resulting solution was stirred at 25° C. for 45 min. NaBH(OAc)$_3$ (43 mg, 0.20 mmol) was added to the solution, and the resulting suspension was stirred at 25° C. for 30 min. The suspension was concentrated under reduced pressure, and the resulting residue was diluted with CH$_2$Cl$_2$ and saturated NaHCO$_3$ solution. The phases were separated. The organic phase was dried over Na$_2$SO$_4$ and concentrated under reduced pressure. Purification by semi-preparative HPLC (Phenomenex Luna C18 (2), 250.0×21.20 mm, 10 micron, H$_2$O with 0.05% TFA and CH$_3$CN with 0.05% TFA) afforded 13 mg of an off-white solid. 1 M HCl in Et$_2$O (0.03 ml, 0.03 mmol) was added to a solution of the off-white solid in CH$_2$Cl$_2$ (10 mL) under N$_2$ and the resulting solution was stirred at 25° C. for 30 min. The solution was concentrated under reduced pressure to yield the title compound (14 mg, 17%) as an off-white powder: mp 270-272° C.; $^1$H NMR (500 MHz, DMSO-d$_6$) δ 10.15 (br s, 1H), 7.66 (d, J=7.0 Hz, 1H), 7.63 (d, J=1.5 Hz, 1H), 7.55 (d, J=8.0 Hz, 1H), 7.44 (d, J=8.5 Hz, 1H), 7.26 (d, J=1.8 Hz, 1H), 7.14 (dd, J=8.5, 1.5 Hz, 1H), 7.11 (dd, J=8.0, 1.8 Hz, 1H), 6.57 (d, J=2.0 Hz, 1H), 6.47 (dd, J=7.0, 2.0 Hz, 1H), 4.67 (d, J=13.5 Hz, 1H), 4.33 (dd, J=14.3, 6.0 Hz, 1H), 3.87 (s, 3H), 3.86-3.79 (m, 1H), 3.71 (s, 3H), 3.55-3.47 (m, 1H), 3.24-3.15 (m, 2H), 3.01 (s, 3H); ESI MS m/z 434 [M+H]$^+$.

Example 114

Preparation of 1-(5-Methyl-2,3,4,5-tetrahydro-1H-pyrido[4,3-b]indol-7-yl)-4-(pyrimidin-2-ylmethoxy)pyridin-2(1H)-one dihydrochloride a) 4-(Pyrimidin-2-ylmethoxy)pyridine 1-oxide

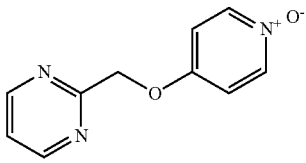

Chemical Formula: C$_{10}$H$_9$N$_3$O$_2$
Exact Mass: 203.07
Molecular Weight: 203.20

Following the procedure of Example 137 (step a), but substituting pyrimidin-2ylmethanol (3.0 g, 27 mmol) for imidazo[1,2-a]pyridine-2-ylmethanol, the title compound (0.95 g, 17%) was prepared as an orange solid: $^1$H NMR (300 MHz, CD$_3$OD) δ 8.81 (d, J=5.1 Hz, 2H), 8.23-8.21 (m, 2H), 7.45 (t, J=4.8 Hz, 1H), 7.24-7.21 (m, 2H), 5.46 (s, 2H).

b) 4-(Pyrimidin-2-ylmethoxy)pyridin 2(1H)-one

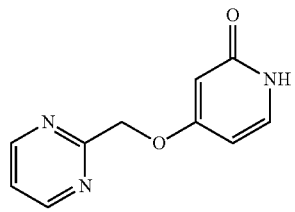

Chemical Formula: C$_{10}$H$_9$N$_3$O$_2$
Exact Mass: 203.07
Molecular Weight: 203.20

Following the procedure of Example 137 (step b), but substituting 4-(pyrimidin-2-ylmethoxy)pyridine 1-oxide (0.95 g, 4.6 mmol) for 4-(imidazo[1,2-a]pyridin-2-ylmethoxy)pyridine 1-oxide, the title compound (0.55 g, 58%) was prepared as a dark brown solid: $^1$H NMR (500 MHz, DMSO-d$_6$) δ 11.09 (br s, 1H), 8.84 (d, J=4.5 Hz, 2H), 7.48 (t, J=5.0 Hz, 1H), 7.25-7.23 (m, 1H), 5.92 (dd, J=7.0, 2.5 Hz, 1H), 5.66 (d, J=8.0, 2.5 Hz, 1H), 5.23 (s, 2H).

c) tert-Butyl 5-methyl-7-(2-oxo-4-(pyrimidin-2-ylmethoxy)pyridin-1(2H)-yl)-3,4-dihydro-1H-pyrido[4,3-b]indole-2(5H)-carboxylate

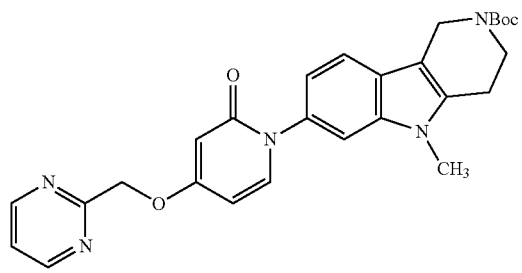

Chemical Formula: C$_{27}$H$_{29}$N$_5$O$_4$
Exact Mass: 487.22
Molecular Weight: 487.55

A suspension of 4-(pyrimidin-2-ylmethoxy)pyridin-2(1H)-one (242 mg, 1.19 mmol), tert-butyl 7-bromo-5-methyl-3,4-dihydro-1H-pyrido[4,3-b]indole-2(5H)-carboxylate (522 mg, 1.43 mmol), CuI (272 mg, 1.43 mmol), 8-hydroxyquinoline (35 mg, 0.24 mmol) and Cs$_2$CO$_3$ (426 mg, 1.31 mmol) in DMSO (10 mL) was degassed under reduced pressure for 45 min. The suspension was put under Ar and heated at 135° C. with stirring overnight. The suspension was cooled, 40:9:1 CH$_2$Cl$_2$/MeOH/NH$_4$OH (50 mL) was added, and the resulting suspension was stirred at 25° C. for 1 h. The suspension was passed through a plug of silica gel, and the filtrate was washed with brine. The solution was dried over Na$_2$SO$_4$ and concentrated under reduced pressure. Flash chromatography (silica gel, (1:1 EtOAc/hexanes)/(4:0.9:0.1 CH$_2$Cl$_2$/MeOH/NH$_4$OH), 100:0 to 0:100) yielded the title compound (256 mg, 44%) as a yellow solid: $^1$H NMR (500 MHz, CDCl$_3$) δ 8.81 (d, J=4.5 Hz, 1H), 7.50 (d, J=8.0 Hz, 1H), 7.32 (d, J=7.5 Hz, 1H), 7.31-7.27 (m, 3H), 7.01 (br d, J=8.0 Hz, 1H), 6.17 (dd, J=7.5, 2.8 Hz, 1H), 6.00 (d, J=2.8 Hz, 1H), 5.32 (s, 2H), 4.64 (br s, 2H), 3.88-3.79 (m, 2H), 3.62 (s, 3H), 2.84-2.78 (m, 2H), 1.50 (s, 9H).

d) 1-(5-Methyl-2,3,4,5-tetrahydro-1H-pyrido[4,3-b]indol-7-yl)-4-(pyrimidin-2-ylmethoxy)pyridin-2(1H)-one dihydrochloride

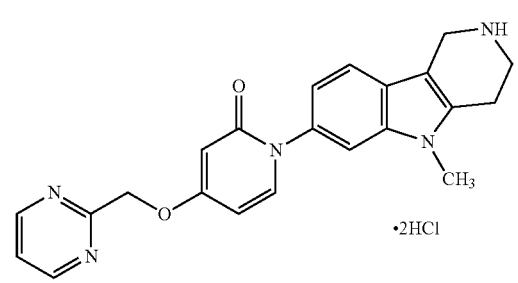

Chemical Formula: C$_{22}$H$_{23}$Cl$_2$N$_5$O$_2$
Exact Mass: 459.12
Molecular Weight: 460.36

TFA (2 mL) was added to a solution of tert-butyl 5-methyl-7-(2-oxo-4-(pyrimidin-2-ylmethoxy)pyridin-1(2H)-yl)-3,4-dihydro-1H-pyrido[4,3-b]indole-2(5H)-carboxylate (256 mg, 0.525 mmol) in CH$_2$Cl$_2$ (10 mL) under N$_2$, and the resulting solution was stirred at 25° C. for 1 h. Saturated NaHCO$_3$ solution and CH$_2$Cl$_2$ were added to the solution, and the phases were separated. The organic phase was dried over Na$_2$SO$_4$ and concentrated under reduced pressure. Flash chromatography (silica gel, (1:1 EtOAc/hexanes)/(4:0.9:0.1 CH$_2$Cl$_2$/MeOH/NH$_4$OH), 100:0 to 0:100) yielded 35 mg of a yellow foam. 1 M HCl in Et$_2$O (0.08 ml, 0.08 mmol) was added to a solution of the yellow foam (16 mg) in CH$_2$Cl$_2$ (10 mL) under N$_2$, and the resulting solution was stirred at 25° C. for 30 min. The solution was concentrated under reduced pressure to yield the title compound (16 mg, 14%) as an off-white powder: mp 234-236° C.; $^1$H NMR (500 MHz, DMSO-d$_6$) δ 9.10 (br s, 2H), 8.88 (d, J=5.0 Hz, 2H), 7.58-7.52 (m, 4H), 6.99 (dd, J=8.0, 1.8 Hz, 1H), 6.14 (dd, J=7.5, 2.5 Hz, 1H), 5.86 (d, J=2.5 Hz, 1H), 5.33 (s, 2H), 4.36 (br s, 2H), 3.68 (s, 3H), 3.57-3.52 (m, 2H), 3.11-3.05 (m, 2H); ESI MS m/z 388 [M+H]$^+$.

Example 115

Preparation of 4-(Imidazo[1,2-a]pyridin-6-ylmethoxy)-1-(5-methyl-2,3,4,5-tetrahydro-1H-pyrido[4,3-b]indol-7-yl)pyridin-2(1H)-one dihydrochloride a) tert-Butyl 7-(4-(imidazo[1,2-a]pyridin-6-ylmethoxy)-2-oxopyridin-1(2H)-yl)-5-methyl-3,4-dihydro-1H-pyrido[4,3-b]indole-2(5H)-carboxylate

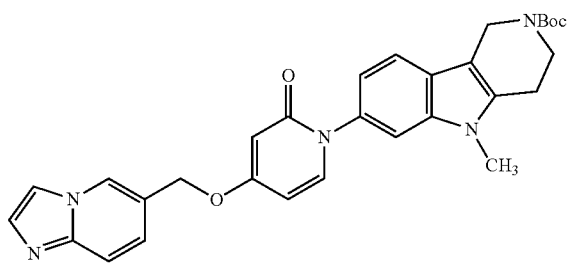

Chemical Formula: C$_{30}$H$_{31}$N$_5$O$_4$
Exact Mass: 525.24
Molecular Weight: 525.60

A suspension of 4-(imidazo[1,2-a]pyridin-6-ylmethoxy)pyridin-2(1H)-one (270 mg, 1.12 mmol), tert-butyl 7-bromo-5-methyl-3,4-dihydro-1H-pyrido[4,3-b]indole-2(5H)-carboxylate (493 mg, 1.35 mmol), CuI (257 mg, 1.35 mmol), 8-hydroxyquinoline (98 mg, 0.67 mmol) and Cs$_2$CO$_3$ (401 mg, 1.23 mmol) in DMSO (10 mL) was degassed under reduced pressure for 45 min. The suspension was put under Ar and heated at 135° C. with stirring for 4.5 h. The suspension was cooled, 40:9:1 CH$_2$Cl$_2$/MeOH/NH$_4$OH (50 mL) was added, and the resulting suspension was stirred at 25° C. for 30 min. The suspension was passed through a plug of silica gel, and the filtrate was washed with brine. The solution was dried over Na$_2$SO$_4$ and concentrate under reduced pressure. Flash chromatography (silica gel, (1:1 EtOAc/hexanes)/(4:0.9:0.1 CH$_2$Cl$_2$/MeOH/NH$_4$OH), 100:0 to 0:100) yielded the title compound (167 mg, 28%) as a yellow solid: $^1$H NMR (300 MHz, CDCl$_3$) δ 8.34-8.25 (m, 1H), 7.79-7.61 (m, 3H), 7.58-7.50 (m, 1H), 7.40-7.25 (m, 3H), 7.07-6.69 (m, 1H), 6.17-6.10 (m, 1H), 6.09-6.02 (m, 1H), 5.11 (s, 2H), 4.65 (br s, 2H), 3.92-3.80 (m, 2H), 3.65 (s, 3H), 2.89-2.80 (m, 2H), 1.52 (s, 9H); ESI MS m/z 526 [M+H]$^+$.

b) 4-(Imidazo[1,2-a]pyridin-6-ylmethoxy)-1-(5-methyl-2,3,4,5-tetrahydro-1H-pyrido[4,3-b]indol-7-yl)pyridin-2(1H)-one dihydrochloride

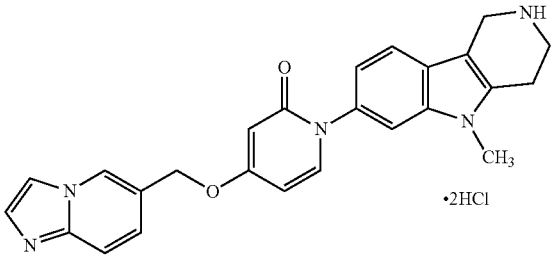

Chemical Formula: C$_{25}$H$_{25}$Cl$_2$N$_5$O$_2$
Exact Mass: 497.14
Molecular Weight: 498.40

TFA (2 mL) was added to a solution of tert-butyl 7-(4-(imidazo[1,2-a]pyridin-6-ylmethoxy)-2-oxopyridin-1(2H)-yl)-5-methyl-3,4-dihydro-1H-pyrido[4,3-b]indole-2(5H)-carboxylate (167 mg, 0.317 mmol) in CH$_2$Cl$_2$ (10 mL) under N$_2$, and the resulting solution was stirred at 25° C. for 1 h. Saturated NaHCO$_3$ solution and CH$_2$Cl$_2$ were added to the solution, and the phases were separated. The organic phase was dried over Na$_2$SO$_4$ and concentrated under reduced pressure. Flash chromatography (silica gel, (1:1 EtOAc/hexanes)/(4:0.9:0.1 CH$_2$Cl$_2$/MeOH/NH$_4$OH), 100:0 to 0:100) yielded 51 mg of a yellow solid. Purification by semi-preparative HPLC (Phenomenex Luna C18 (2), 250.0× 21.20 mm, 10 micron, H$_2$O with 0.05% TFA and CH$_3$CN with 0.05% TFA) afforded 7 mg of a white solid. 1 M HCl in Et$_2$O (0.03 ml, 0.03 mmol) was added to a solution of the white solid (7 mg) in CH$_2$Cl$_2$ (10 mL) under N$_2$, and the resulting solution was stirred at 25° C. for 30 min. The solution was concentrated under reduced pressure to yield the title compound (8 mg, 5%) as a white powder: $^1$H NMR (500 MHz, DMSO-d$_6$) δ 9.28 (br s, 2H), 9.06 (s, 1H), 8.38 (s, 1H), 8.19 (s, 1H), 8.05-7.94 (m, 2H), 7.62 (d, J=7.5 Hz, 1H), 7.56 (d, J=8.0 Hz, 1H), 7.50 (d, J=1.5 Hz, 1H), 6.99 (dd, J=8.0, 1.5 Hz, 1H), 6.13 (dd, J=7.5, 2.5 Hz, 1H), 6.09 (d, J=2.5 Hz, 1H), 5.33 (s, 2H), 4.35 (br s, 2H), 3.69 (s, 3H), 3.56-3.50 (m, 2H), 3.12-3.05 (m, 2H); ESI MS m/z 426 [M+H]$^+$.

Example 116

Preparation of 4-(Imidazo[1,2-a]pyridin-2-ylmethoxy)-1-(5-methyl-2,3,4,5-tetrahydro-1H-pyrido[4,3-b]indol-7-yl)pyridin-2(1H)-one dihydrochloride a) tert-Butyl 7-(4-(imidazo[1,2-a]pyridin-2-ylmethoxy)-2-oxopyridin-1(2H)-yl)-5-methyl-3,4-dihydro-1H-pyrido[4,3-b]indole-2(5H)-carboxylate

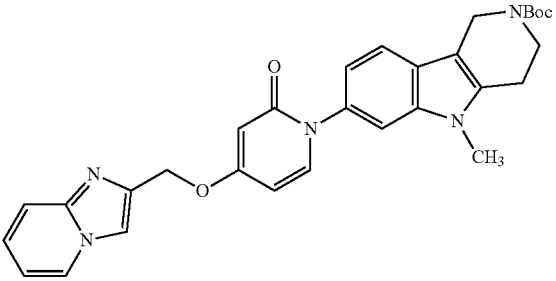

Chemical Formula: C$_{30}$H$_{31}$N$_5$O$_4$
Exact Mass: 525.24
Molecular Weight: 525.60

A suspension of 4-(imidazo[1,2-a]pyridin-2-ylmethoxy)pyridin-2(1H)-one (231 mg, 0.960 mmol), tert-butyl 7-bromo-5-methyl-3,4-dihydro-1H-pyrido[4,3-b]indole-2(5H)-carboxylate (421 mg, 1.15 mmol), CuI (219 mg, 1.15 mmol), 8-hydroxyquinoline (84 mg, 0.576 mmol) and $Cs_2CO_3$ (345 mg, 1.06 mmol) in DMSO (10 mL) was degassed under reduced pressure for 45 min. The suspension was put under Ar and heated at 135° C. with stirring overnight. The suspension was cooled, 40:9:1 $CH_2Cl_2$/MeOH/$NH_4OH$ (50 mL) was added, and the resulting suspension was stirred at 25° C. for 30 min. The suspension was passed through a plug of silica gel, and the filtrate was washed with brine and 10% $CuSO_4$ solution. The solution was dried over $Na_2SO_4$ and concentrated under reduced pressure. Flash chromatography (silica gel, (1:1 EtOAc/hexanes)/(4:0.9:0.1 $CH_2Cl_2$/MeOH/$NH_4OH$), 100:0 to 0:100) gave the title compound (132 mg, 26%) as a yellow solid: $^1$H NMR (300 MHz, $CDCl_3$) δ 8.12 (d, J=6.9 Hz, 1H), 7.70 (br s, 1H), 7.62 (d, J=8.7 Hz, 1H), 7.50 (d, J=8.4 Hz, 1H), 7.33-7.18 (m, 3H), 7.02 (d, J=7.5 Hz, 1H), 6.82 (dd, J=6.9, 6.9 Hz, 1H), 6.17 (d, J=2.1 Hz, 1H), 6.08 (dd, J=7.5, 2.1 Hz, 1H), 5.25 (s, 2H), 3.84 (br s, 2H), 3.63 (s, 3H), 2.84-2.79 (m, 2H), 1.72-1.60 (m, 2H), 1.50 (s, 9H).

b) 4-(Imidazo[1,2-α]pyridin-2-ylmethoxy)-1-(5-methyl-2,3,4,5-tetrahydro-1H-pyrido[4,3-b]indol-7-yl)pyridin-2(1H)-one dihydrochloride

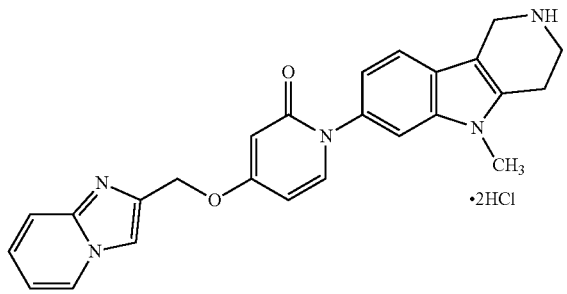

Chemical Formula: $C_{25}H_{25}Cl_2N_5O_2$
Exact Mass: 497.14
Molecular Weight: 498.40

TFA (1 mL) was added to a solution of tert-butyl 7-(4-(imidazo[1,2-α]-pyridin-2-ylmethoxy)-2-oxopyridin-1(2H)-yl)-5-methyl-3,4-dihydro-1H-pyrido[4,3-b]indole-2(5H)-carboxylate (132 mg, 0.251 mmol) in $CH_2Cl_2$ (10 mL) under $N_2$, and the resulting solution was stirred at 25° C. for 1 h. Saturated $NaHCO_3$ solution and $CH_2Cl_2$ were added to the solution, and the phases were separated. The aqueous phase was extracted with EtOAc. The combined organic phases were dried over $Na_2SO_4$ and concentrated under reduced pressure. Flash chromatography (silica gel, (1:1 EtOAc/hexanes)/(4:0.9:0.1 $CH_2Cl_2$/MeOH/$NH_4OH$), 100:0 to 0:100) yielded 42 mg of an off-white solid. 1 M HCl in $Et_2O$ (0.07 ml, 0.07 mmol) was added to a solution of the off-white solid (15 mg) in $CH_2Cl_2$ (10 mL) under $N_2$, and the resulting solution was stirred at 25° C. for 30 min. The solution was concentrated under reduced pressure to yield the title compound (15 mg, 34%) as a white powder: $^1$H NMR (500 MHz, DMSO-$d_6$) δ 9.30 (br s, 2H), 8.84 (s, 1H), 8.37 (s, 1H), 7.89-7.70 (m, 2H), 7.64-7.53 (m, 2H), 7.50 (s, 1H), 7.37-7.29 (m, 1H), 7.03-6.97 (m, 1H), 6.20-6.09 (m, 2H), 5.41 (s, 2H), 4.35 (br s, 2H), 3.69 (s, 3H), 3.58-3.50 (m, 2H), 3.13-3.07 (m, 2H); ESI MS m/z 426 [M+H]$^+$.

Example 117

Preparation of 1-(2,5-Dimethyl-2,3,4,5-tetrahydro-1H-pyrido[4,3-b]indol-7-yl)-4-(imidazo[1,2-α]pyridin-2-ylmethoxy)pyridin-2(1H)-one dihydrochloride a) 1-(2,5-Dimethyl-2,3,4,5-tetrahydro-1H-pyrido[4,3-b]indol-7-yl)-4-(imidazo[1,2-α]pyridin-2-ylmethoxy)pyridin-2(1H)-one dihydrochloride

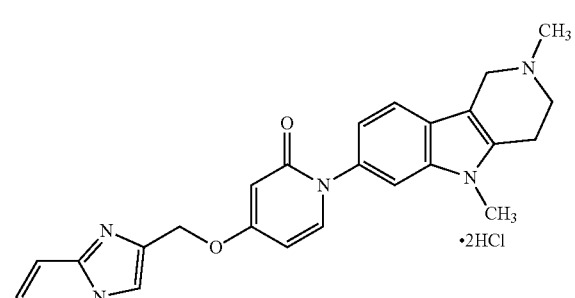

Chemical Formula: $C_{26}H_{27}Cl_2N_5O_2$
Exact Mass: 511.15
Molecular Weight: 512.43

TFA (1 mL) was added to a solution of tert-butyl 7-(4-(imidazo[1,2-α]pyridin-2-ylmethoxy)-2-oxopyridin-1(2H)-yl)-5-methyl-3,4-dihydro-1H-pyrido[4,3-b]indole-2(5H)-carboxylate (132 mg, 0.251 mmol) in $CH_2Cl_2$ (10 mL) under $N_2$, and the resulting solution was stirred at 25° C. for 1 h. Saturated $NaHCO_3$ solution and $CH_2Cl_2$ were added to the solution, and the phases were separated. The aqueous phase was extracted with EtOAc. The combined organic phases were dried over $Na_2SO_4$ and concentrated under reduced pressure. Flash chromatography (silica gel, (1:1 EtOAc/hexanes)/(4:0.9:0.1 $CH_2Cl_2$/MeOH/$NH_4OH$), 100:0 to 0:100) yielded 42 mg of an off-white solid. Formaldehyde (37% in $H_2O$, 0.01 mL, 0.12 mmol) was added to a solution of the off-white solid (27 mg) in 1:1 MeOH/$CH_2Cl_2$ (5 mL), and the resulting solution was stirred at 25° C. for 45 min. $NaBH(OAc)_3$ (27 mg, 0.13 mmol) was added to the solution, and the resulting suspension was stirred at 25° C. for 30 min. The suspension was concentrated under reduced pressure, and the residue was diluted with $CH_2Cl_2$ and saturated $NaHCO_3$ solution. The phases were separated. The organic phase was dried over $Na_2SO_4$ and concentrated under reduced pressure to afford 25 mg of a viscous oil. 1 M HCl in $Et_2O$ (0.11 ml, 0.11 mmol) was added to a solution of the off-white solid in $CH_2Cl_2$ (10 mL) under $N_2$, and the resulting solution was stirred at 25° C. for 30 min. The solution was concentrated under reduced pressure to yield the title compound (25 mg, 30%) as an off-white powder: $^1$H NMR (500 MHz, DMSO-$d_6$) 10.79 (br s, 1H), 8.87 (d, J=6.5 Hz, 1H), 8.41 (s, 1H), 7.90-7.78 (m, 2H), 7.61 (d, J=7.5 Hz, 1H), 7.53-7.49 (m, 2H), 7.42-7.35 (m, 1H), 7.00 (dd, J=8.5, 1.5 Hz, 1H), 6.15 (d, J=2.5 Hz, 1H), 6.12 (dd, J=7.5, 2.5 Hz, 1H), 5.43 (s, 2H), 4.62 (d, J=14.0 Hz, 1H), 4.29 (dd, J=14.0, 7.5 Hz, 1H), 3.80-3.75 (m, 1H), 3.69 (s, 3H), 3.55-3.46 (m, 1H), 3.23-3.16 (m, 2H), 2.97 (s, 3H); ESI MS m/z 440 [M+H]$^+$.

Example 118

Preparation of 1-(2-Acetyl-9-methyl-2,3,4,9-tetrahydro-1H-pyrido[3,4-b]indol-7-yl)-4-(benzyloxy)pyridin-2(1H)-one

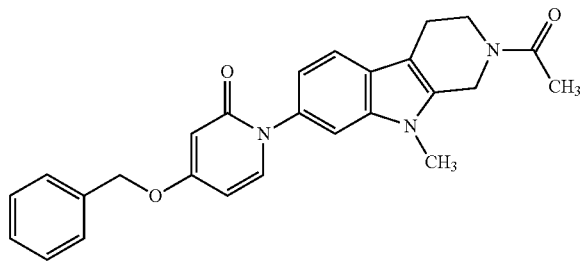

Chemical Formula: $C_{26}H_{25}N_3O_3$
Exact Mass: 427.19
Molecular Weight: 427.50

AcCl (0.023 mL, 0.32 mmol) was added to a solution of 4-(benzyloxy)-1-(9-methyl-2,3,4,9-tetrahydro-1H-pyrido[3,4-b]indol-7-yl)pyridin-2(1H)-one dihydrochloride (100 mg, 0.216 mmol), DMAP (5 mg, 0.04 mmol) and Et$_3$N (0.09 mL, 0.6 mmol) in CH$_2$Cl$_2$ (20 mL) under N$_2$, and the resulting solution was stirred at 25° C. for 4 h. H$_2$O was added to the solution, and the phases were separated. The organic phase was washed with saturated NH$_4$Cl solution, dried over Na$_2$SO$_4$ and concentrated under reduced pressure. Flash chromatography (silica gel, (1:1 EtOAc/hexanes)/(9:0.9:0.1 CH$_2$Cl$_2$/MeOH/NH$_4$OH), 100:0 to 0:100) afforded the title compound (61 mg, 66%) as a mixture of rotamers as a white powder: mp 80-82° C.; $^1$H NMR (500 MHz, DMSO-d$_6$) δ 7.56 (d, J=7.5 Hz, 1H), 7.52-7.35 (m, 7H), 6.94 (dd, J=8.0, 1.5 Hz, 1H), 6.12-6.08 (m, 1H), 5.97 (d, J=3.0 Hz, 1H), 5.15 (s, 2H), 4.77-4.72 (m, 2H), 3.82-3.72 (m, 2H), 3.69-3.65 (m, 3H), 3.82-2.78 (m, 1.3H), 2.71-2.68 (m, 0.7H), 2.16 (s, 3H); ESI MS m/z 428 [M+H]$^+$.

Example 119

Preparation of 1-(2-Acetyl-5-methyl-2,3,4,5-tetrahydro-1H-pyrido[4,3-b]indol-7-yl)-4-(5-(trifluoromethyl)pyridin-2-yl)pyridin-2(1H)-one

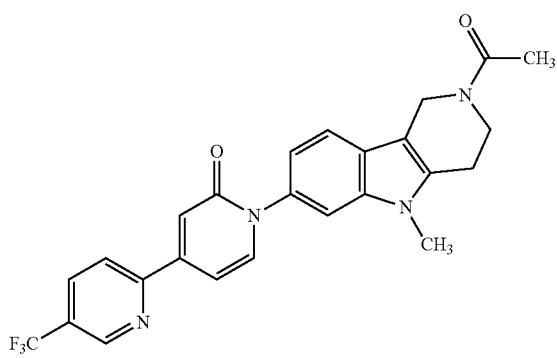

Chemical Formula: $C_{25}H_{21}F_3N_4O_2$
Exact Mass: 466.16
Molecular Weight: 466.46

AcCl (0.03 mL, 0.4 mmol) was added to a solution of 1-(5-methyl-2,3,4,5-tetrahydro-1H-pyrido[4,3-b]indol-7-yl)-4-(5-(trifluoromethyl)pyridin-2-yl)pyridin-2(1H)-one (125 mg, 0.294 mmol), DMAP (7 mg, 0.06 mmol) and Et$_3$N (0.08 mL, 0.6 mmol) in CH$_2$Cl$_2$ (10 mL) under N$_2$, and the resulting solution was stirred at 25° C. for 17 h. H$_2$O was added to the solution, and the phases were separated. The organic phase was washed with saturated NH$_4$Cl solution, dried over Na$_2$SO$_4$ and concentrated under reduced pressure. Flash chromatography (silica gel, (1:1 EtOAc/hexanes)/(9:0.9:0.1 CH$_2$Cl$_2$/MeOH/NH$_4$OH), 100:0 to 0:100) afforded the title compound (116 mg, 84%) as a mixture of rotamers as a white powder: mp 232-236° C.; $^1$H NMR (500 MHz, DMSO-d$_6$) δ 9.15 (s, 1H), 8.38 (d, J=8.3 Hz, 1H), 8.35 (d, J=8.3 Hz, 1H), 7.84 (d, J=7.5 Hz, 1H), 7.59-7.54 (m, 2H), 7.28 (d, J=1.5 Hz, 1H), 7.08-7.03 (m, 2H), 4.70 (s, 0.8H), 4.68 (s, 1.2H), 3.88 (t, J=5.5 Hz, 0.8H), 3.83 (t, J=5.5 Hz, 1.2 H), 3.67 (s, 3H), 2.97-2.91 (m, 1.2H), 2.86-2.81 (m, 0.8H), 2.15 (s, 1.8H), 2.13 (s, 1.2H); ESI MS m/z 467 [M+H]$^+$.

Example 120

Preparation of 1-(2-Ethyl-5-methyl-2,3,4,5-tetrahydro-1H-pyrido[4,3-b]indol-7-yl)-4-(5-(trifluoromethyl)pyridin-2-yl)pyridin-2(1H)-one dihydrochloride

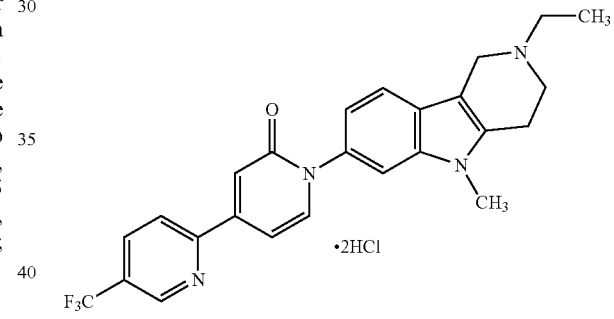

Chemical Formula: $C_{25}H_{25}Cl_2F_3N_4O$
Exact Mass: 524.14
Molecular Weight: 525.39

2-Picoline borane (63 mg, 0.59 mmol) was added to a suspension of 1-(5-methyl-2,3,4,5-tetrahydro-1H-pyrido[4,3-b]indol-7-yl)-4-(5-(trifluoromethyl)pyridin-2-yl)pyridin-2(1H)-one dihydrochloride (98 mg, 0.20 mmol) and acetylaldhyde (0.03 mL, 1 mmol) in 9:1 CH$_2$Cl$_2$/AcOH (10 mL) under N$_2$, and the resulting solution was stirred under N$_2$ for 4 h. Acetylaldehyde (0.03 mL, 1 mmol) was added to the solution under N$_2$ and the resulting solution was stirred at 25° C. for 15 min. The solution was neutralized with saturated NaHCO$_3$ solution, and the phases were separated. The organic phase was dried over Na$_2$SO$_4$ and concentrated under reduced pressure. Flash chromatography (silica gel, (1:1 EtOAc/hexanes)/(9:0.9:0.1 CH$_2$Cl$_2$/MeOH/NH$_4$OH), 100:0 to 0:100) afforded 67 mg of a yellow powder. 2 N HCl in Et$_2$O (0.15 mL, 0.330 mmol) was added to a solution of the yellow powder in 1:1 MeOH/CH$_2$Cl$_2$ (10 mL) under N$_2$, and the resulting solution was stirred at 25° C. for 15 min. Et$_2$O was added to the solution, and the resulting suspension was filtered under N$_2$ to afford the title compound (78 mg, 75%) as a yellow powder: mp 300-302° C.; $^1$H NMR (500 MHz, DMSO-d$_6$) δ 10.16 (br s, 1H), 9.15 (s, 1H), 8.42-8.35

(m, 2H), 7.85 (d, J=7.0 Hz, 1H), 7.65 (d, J=1.5 Hz, 1H), 7.61 (d, J=8.5 Hz, 1H), 7.30 (d, J=2.0 Hz, 1H), 7.13 (dd, J=8.5, 1.5 Hz, 1H), 7.08 (dd, J=7.5, 2.0 Hz, 1H), 4.70 (d, J=12.5 Hz, 1H), 4.32 (dd, J=14.5, 8.0 Hz, 1H), 3.91-3.83 (m, 1H), 3.72 (s, 3H), 3.52-3.43 (m, 1H), 3.41-3.30 (m, 2H), 3.24-3.16 (m, 2H), 1.38 (t, J=7.3 Hz, 3H); ESI MS m/z 453 [M+H]$^+$.

Example 121

Preparation of 1-(2-Isopropyl-5-methyl-2,3,4,5-tetrahydro-1H-pyrido[4,3-b]indol-7-yl)-4-(5-(trifluoromethyl)pyridin-2-yl)pyridin-2(1H)-one dihydrochloride

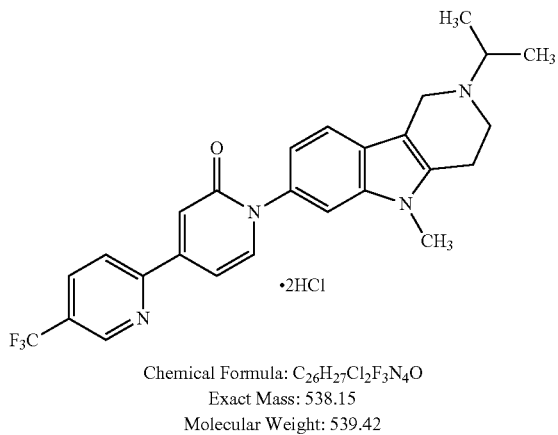 [SMILES: CC(C)N1CCc2c(c3ccc(-n4ccc(-c5ccc(C(F)(F)F)cn5)cc4=O)cc3n2C)C1]

Chemical Formula: C$_{26}$H$_{27}$Cl$_2$F$_3$N$_4$O
Exact Mass: 538.15
Molecular Weight: 539.42

2-Picoline borane (87 mg, 0.81 mmol) was added to a suspension of 1-(5-methyl-2,3,4,5-tetrahydro-1H-pyrido[4,3-b]indol-7-yl)-4-(5-(trifluoromethyl)pyridin-2-yl)pyridin-2(1H)-one dihydrochloride (134 mg, 0.27 mmol) and acetone (0.10 mL, 1.4 mmol) in 9:1 CH$_2$Cl$_2$/AcOH (10 mL) under N$_2$, and the resulting solution was stirred for 24 h. Acetone (1 mL) was added to the solution and the resulting solution was stirred at 25° C. for 24 h. Acetone (1 mL) and 2-picoline borane (87 mg, 0.81 mmol) were added to the solution, and the resulting solution was stirred at reflux for 24 h. The solution was cooled, H$_2$O was added, and the reaction mixture was neutralized with saturated NaHCO$_3$ solution. The phases were separated, and the organic phase was dried over Na$_2$SO$_4$ and concentrated under reduced pressure. Flash chromatography (silica gel, (1:1 EtOAc/hexanes)/(9:0.9:0.1 CH$_2$Cl$_2$/MeOH/NH$_4$OH), 100:0 to 0:100) afforded 88 mg of a yellow powder. 2 N HCl in Et$_2$O (0.15 mL, 0.330 mmol) was added to a solution of the yellow powder in 1:1 MeOH/CH$_2$Cl$_2$ (10 mL) under N$_2$, and the resulting solution was stirred at 25° C. for 30 min. Et$_2$O was added to the solution, and the resulting solid was collected by filtration under N$_2$. The solid was washed with Et$_2$O to afford the title compound (25 mg, 17%) as a yellow powder: $^1$H NMR (500 MHz, DMSO-d$_6$) δ 9.80 (br s, 1H), 9.15 (d, J=2.0 Hz, 1H), 8.42-8.35 (m, 2H), 7.85 (d, J=7.5 Hz, 1H), 7.66 (d, J=1.5 Hz, 1H), 7.62 (d, J=8.5 Hz, 1H), 7.30 (d, J=2.0 Hz, 1H), 7.14 (dd, J=8.5, 1.5 Hz, 1H), 7.08 (dd, J=7.5, 2.0 Hz, 1H), 4.58 (d, J=13.0 Hz, 1H), 4.48-4.40 (m, 1H), 3.90-3.82 (m, 1H), 3.78-3.70 (m, 4H), 3.51-3.42 (m, 1H), 3.38-3.15 (m, 2H), 1.45-1.36 (m, 6H); ESI MS m/z 467 [M+H]$^+$.

Example 122

Preparation of 4-(4-Methoxyphenyl)-1-(9-methyl-2,3,4,9-tetrahydro-1H-pyrido[3,4-b]indol-7-yl)pyridin-2(1H)-one hydrochloride a) 4-(4-Methoxyphenyl)pyridin-2(1H)-one

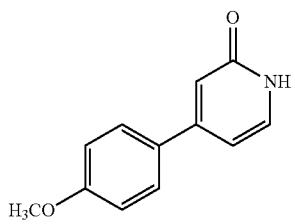

Chemical Formula: C$_{12}$H$_{11}$NO$_2$
Exact Mass: 201.08
Molecular Weight: 201.22

A suspension of 4-bromo-2-methoxypyridine (1.22 g, 6.49 mmol), 4-methoxyphenyl boronic acid (1.97 g, 13.0 mmol), PdCl$_2$(dppf) (530 mg, 0.649 mmol) and K$_2$CO$_3$ (1.79 g, 13.0 mmol) in DMSO (10 mL) was degassed under reduced pressure for 45 min. The suspension was put under Ar and stirred at 95° C. for 2 h. The suspension was cooled, H$_2$O was added, and the suspension was filtered to afford a light colored solid. Flash chromatography (silica gel, hexanes/(1:1 EtOAc/hexanes), 100:0 to 0:100) afforded 1.10 g of a white powder. The white powder was diluted with concentrated HCl solution (50 mL) and stirred at reflux for 12 h. The reaction was cooled and concentrated under reduced pressure. Flash chromatography (silica gel, (1:1 EtOAc/hexanes)/(9:0.9:0.1 CH$_2$Cl$_2$/MeOH/NH$_4$OH), 100:0 to 0:100) afforded the title compound (313 mg, 24%) as a white powder: $^1$H NMR (300 MHz, DMSO-d$_6$) δ 11.47 (s, 1H), 7.65 (d, J=8.7 Hz, 2H), 7.38 (d, J=6.8 Hz, 1H), 7.01 (d, J=8.7 Hz, 2H), 6.51 (br s, 1H), 6.47 (d, J=6.8 Hz, 1H), 3.79 (s, 3H).

b) tert-Butyl 7-(4-(4-methoxyphenyl)-2-oxopyridin-1(2H)-yl)-9-methyl-3,4-dihydro-1H-pyrido[3,4-b]indole-2(9H)-carboxylate

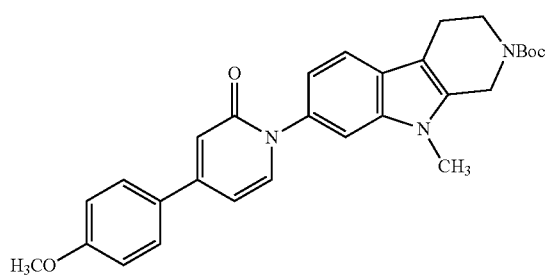

Chemical Formula: C$_{29}$H$_{31}$N$_3$O$_4$
Exact Mass: 485.23
Molecular Weight: 485.57

A suspension of 4-(4-methoxyphenyl)pyridin-2(1H)-one (103 mg, 0.510 mmol), tert-butyl 7-bromo-9-methyl-3,4-dihydro-1H-pyrido[3,4-b]indole-2(9H)-carboxylate (223 mg, 0.612 mmol), CuI (116 mg, 0.612 mmol), 8-hydroxyquinoline (15 mg, 0.10 mmol) and $Cs_2CO_3$ (183 mg, 0.561 mmol) in DMSO (10 mL) was degassed under reduced pressure for 45 min. The suspension was put under Ar and stirred at 135° C. overnight. The suspension was cooled, 9:0.9:0.1 $CH_2Cl_2$/MeOH/$NH_4OH$ was added, and the resulting suspension was stirred at 25° C. for 30 min. The suspension was passed through a plug of silica gel, and the filtrate was washed with brine. The resulting solution was dried over $Na_2SO_4$ and concentrated under reduced pressure. Flash chromatography (silica gel, (1:1 EtOAc/hexanes)/(9:0.9:0.1 $CH_2Cl_2$/MeOH/$NH_4OH$), 100:0 to 0:100) afforded the title compound (98 mg, 40%) as a yellow powder: $^1$H NMR (300 MHz, $CDCl_3$) δ 7.64-7.53 (m, 3H), 7.46 (d, J=7.2 Hz, 1H), 7.36 (br s, 1H), 7.08 (dd, J=8.1, 1.5 Hz, 1H), 7.01 (d, J=8.7 Hz, 2H), 6.87 (d, J=1.8 Hz, 1H), 6.51 (dd, J=7.2, 1.8 Hz, 1H), 4.68-4.60 (m, 2H), 3.88 (s, 3H), 3.82-3.73 (m, 2H), 3.65 (s, 3H), 2.85-2.78 (m, 2H), 1.52 (s, 9H).

c) 4-(4-Methoxyphenyl)-1-(9-methyl-2,3,4,9-tetrahydro-1H-pyrido[3,4-b]indol-7-yl)pyridin-2(1H)-one hydrochloride

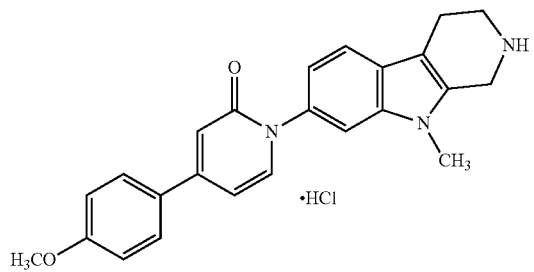

Chemical Formula: $C_{24}H_{24}ClN_3O_2$
Exact Mass: 421.16
Molecular Weight: 421.92

TFA (1 ml) was added to a solution of tert-butyl 7-(4-(4-methoxyphenyl)-2-oxopyridin-1 (2H)-yl)-9-methyl-3,4-dihydro-1H-pyrido[3,4-b]indole-2(9H)-carboxylate (98 mg, 0.20 mmol) in $CH_2Cl_2$ (10 mL) under $N_2$ and the resulting solution was stirred for 2.5 h at 25° C. Saturated $NaHCO_3$ solution was added, and the phases were separated. The organic phase was dried over $Na_2SO_4$ and concentrated under reduced pressure. Flash chromatography (silica gel, (1:1 EtOAc/hexanes)/(9:0.9:0.1 $CH_2Cl_2$/MeOH/$NH_4OH$), 100:0 to 0:100) afforded 49 mg of a white powder. 1 N HCl in $Et_2O$ (0.07 mL, 0.07 mmol) was added to a solution of the white powder in $CH_2Cl_2$ (10 mL) under $N_2$, and the resulting solution was stirred at 25° C. for 1 h. The solution was concentrated under reduced pressure to yield the title compound (47 mg, 55%) as a yellow powder: mp 306-308° C.; $^1$H NMR (500 MHz, DMSO-$d_6$) δ 9.43 (br s, 2H), 7.76 (d, J=9.0 Hz, 2H), 7.70 (d, J=7.0 Hz, 1H), 7.61-7.58 (m, 2H), 7.11-7.05 (m, 3H), 6.73 (d, J=2.0 Hz, 1H), 6.68 (dd, J=7.0, 2.0 Hz, 1H), 4.51-4.45 (m, 2H), 3.83 (s, 3H), 3.70 (s, 3H), 3.48-3.42 (m, 2H), 2.99 (t, J=6.0 Hz, 2H); ESI MS m/z 386 [M+H]$^+$.

Example 123

Preparation of 1-(5-Methyl-2,3,4,5-tetrahydro-1H-pyrido[4,3-b]indol-7-yl)-4-(4-(methylthio)phenyl)pyridin-2(1H)-one hydrochloride a) 4-(4-(Methylthio)phenyl)pyridin-2(1H)-one

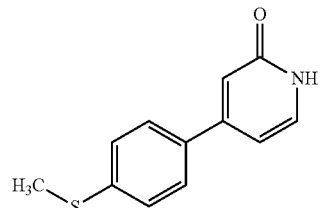

Chemical Formula: $C_{12}H_{11}NOS$
Exact Mass: 217.06
Molecular Weight: 217.29

A suspension of 4-bromo-2-methoxypyridine (1.225 g, 6.511 mmol), 4-methylthiophenyl boronic acid (2.188 g, 13.02 mmol), $PdCl_2(dppf)$ (531 mg, 0.651 mmol) and $K_2CO_3$ (1.797 g, 13.02 mmol) in DMSO (10 mL) was degassed under reduced pressure for 25 min. The suspension was put under $N_2$ and stirred at 95° C. for 16 h. The suspension was cooled, $H_2O$ was added, and the suspension was filtered to afford a light colored solid. Flash chromatography (silica gel, hexanes/(1:1 EtOAc/hexanes), 100:0 to 0:100) afforded 1.10 g of a white powder. The white powder was diluted with concentrated HCl solution (50 mL) and stirred at reflux for 24 h. The reaction was cooled and concentrated under reduced pressure. The residue was neutralized with saturated $NaHCO_3$ solution, and the solid was collected by filtration. The solid was washed with $H_2O$ to afford the title compound (1.103 g, 71%) as a tan solid: $^1$H NMR (300 MHz, DMSO-$d_6$) δ 7.65 (d, J=8.4 Hz, 2H), 7.43 (d, J=6.9 Hz, 1H), 7.34 (d, J=8.4 Hz, 2H), 6.57 (d, J=1.7 Hz, 1H), 6.50 (dd, J=6.9, 1.7 Hz, 1H), 3.34 (s, 3H).

b) 1-(5-Methyl-2,3,4,5-tetrahydro-1H-pyrido[4,3-b]indol-7-yl)-4-(4-(methylthio)phenyl)pyridine-2(1H)-one hydrochloride

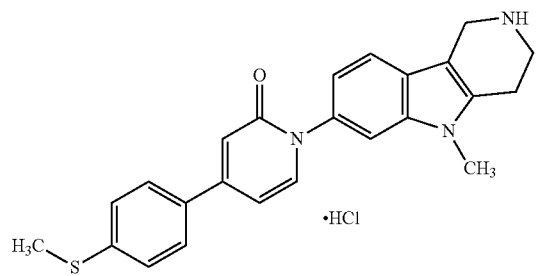

Chemical Formula: $C_{24}H_{24}ClN_3OS$
Exact Mass: 437.13
Molecular Weight: 437.98

A suspension of 4-(4-(methylthio)phenyl)pyridine-2(1H)-one (134 mg, 0.615 mmol), tert-butyl 7-bromo-5-methyl-3,4-dihydro-1H-pyrido[4,3-b]indole-2(5H)-carboxylate (247 mg, 0.676 mmol), CuI (140 mg, 0.738 mmol), 8-hydroxyquinoline (18 mg, 0.12 mmol) and $Cs_2CO_3$ (220 mg, 0.676 mmol) in DMSO (10 mL) was degassed under reduced pressure for 45 min. The suspension was put under $N_2$ and stirred at 135° C. overnight. The suspension was cooled, 9:0.9:0.1 $CH_2Cl_2$/MeOH/$NH_4OH$ was added, and the resulting suspension was stirred at 25° C. for 30 min. The suspension was passed through a plug of silica gel, and the filtrate was washed with brine. The resulting solution was dried over $Na_2SO_4$ and concentrated under reduced pressure. Flash chromatography (silica gel, (1:1 EtOAc/hexanes)/(9:0.9:0.1 $CH_2Cl_2$/MeOH/$NH_4OH$), 100:0 to 0:100) afforded 179 mg of a yellow powder. 2 N HCl in $Et_2O$ (300 mL) was added to a solution of the yellow powder in 1:1 $CH_2Cl_2$/MeOH (8 mL) under $N_2$, and the resulting suspension was stirred at 25° C. for 17 h. The suspension was filtered and the solid was washed with $CH_2Cl_2$ and 99:1 $CH_2Cl_2$/MeOH to afford the title compound (41 mg, 15%) as an off-white solid: mp 306-310° C.; $^1$H NMR (500 MHz, DMSO-$d_6$) δ 9.27 (br s, 2H), 7.77-7.71 (m, 3H), 7.61-7.58 (m, 2H), 7.39 (d, J=8.5 Hz, 2H), 7.09 (dd, J=8.5, 2.0 Hz, 1H), 6.78 (d, J=2.0 Hz, 1H), 6.69 (dd, J=7.5, 2.0 Hz, 1H), 4.36 (br s, 2H), 3.70 (s, 3H), 3.56-3.51 (m, 2H), 3.10 (t, J=5.5 Hz, 2H), 2.54 (s, 3H); ESI MS m/z 402 [M+H]$^+$.

Example 124

Preparation of 1-(9-Methyl-2,3,4,9-tetrahydro-1H-pyrido[3,4-b]indol-7-yl)-4-(4-(methylthio)phenyl)pyridine-2(1H)-one hydrochloride a) tert-Butyl 9-methyl-7-(4-(4-(methylthio)phenyl)-2-oxopyridin-1(2H)-yl)-3,4-dihydro-1H-pyrido[3,4-b]indole-2(9H)-carboxylate

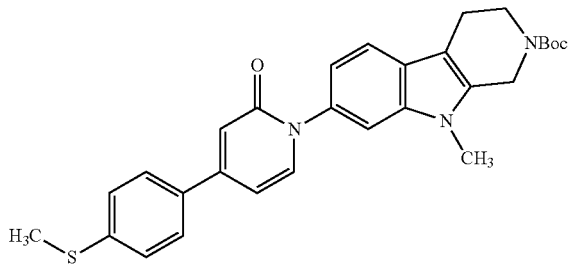

Chemical Formula: $C_{29}H_{31}N_3O_3S$
Exact Mass: 501.21
Molecular Weight: 501.64

A suspension of 4-(4-(methylthio)phenyl)pyridine-2(1H)-one (110 mg, 0.505 mmol), tert-butyl 7-bromo-9-methyl-3,4-dihydro-1H-pyrido[3,4-b]indole-2(9H)-carboxylate (203 mg, 0.555 mmol), CuI (115 mg, 0.606 mmol), 8-hydroxyquinoline (15 mg, 0.10 mmol) and $Cs_2CO_3$ (181 mg, 0.555 mmol) in DMSO (10 mL) was degassed under reduced pressure for 45 min. The suspension was put under $N_2$ and stirred at 135° C. overnight. The suspension was cooled, 9:0.9:0.1 $CH_2Cl_2$/MeOH/$NH_4OH$ was added, and the resulting suspension was stirred at 25° C. for 30 min. The suspension was passed through a plug of silica gel, and the filtrate was washed with brine. The resulting solution was dried over $Na_2SO_4$ and concentrated under reduced pressure. Flash chromatography (silica gel, (1:1 EtOAc/hexanes)/(9:0.9:0.1 $CH_2Cl_2$/MeOH/$NH_4OH$), 100:0 to 0:100) afforded the title compound (97 mg, 38%) as an off-white powder: $^1$H NMR (500 MHz, CDCl$_3$) δ 7.61-7.54 (m, 3H), 7.48 (d, J=7.5 Hz, 1H), 7.38-7.32 (m, 3H), 7.08 (dd, J=8.5, 2.0 Hz, 1H), 6.89 (d, J=2.0 Hz, 1H), 6.50 (dd, J=7.5, 2.0 Hz, 1H), 4.70-4.61 (m, 2H), 3.81-3.73 (m, 2H), 3.65 (s, 3H), 2.84-2.78 (m, 2H), 2.54 (s, 3H), 1.52 (s, 9H).

b) 1-(9-Methyl-2,3,4,9-tetrahydro-1H-pyrido[3,4-b]indol-7-yl)-4-(4-(methylthio)phenyl)pyridine-2(1H)-one hydrochloride

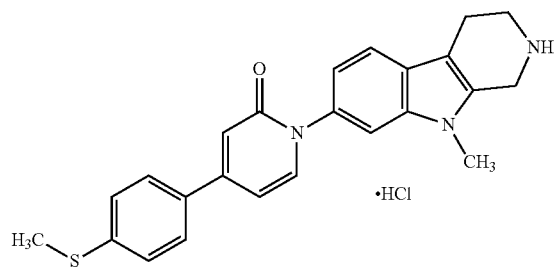

Chemical Formula: $C_{24}H_{24}ClN_3OS$
Exact Mass: 437.13
Molecular Weight: 437.98

TFA (1 ml) was added to a solution of tert-butyl 9-methyl-7-(4-(4-(methylthio)phenyl)-2-oxopyridin-1(2H)-yl)-3,4-dihydro-1H-pyrido[3,4-b]indole-2(9H)-carboxylate (97 mg, 0.19 mmol) in $CH_2Cl_2$ (10 mL) under $N_2$, and the resulting solution was stirred for 1.5 h at 25° C. Saturated $NaHCO_3$ solution was added to the reaction mixture, and the resulting suspension was filtered. Flash chromatography (silica gel, (1:1 EtOAc/hexanes)/(9:0.9:0.1 $CH_2Cl_2$/MeOH/$NH_4OH$), 100:0 to 0:100) afforded 35 mg of a yellow powder. 2 N HCl in $Et_2O$ (0.09 mL, 0.09 mmol) was added to a solution of the yellow solid in $CH_2Cl_2$ (10 mL) under $N_2$, and the resulting solution was stirred at 25° C. for 15 min. $Et_2O$ was added to the solution, and the resulting suspension was filtered under $N_2$. The solid was washed with $Et_2O$ to afford the title compound (37 mg, 17%) as a yellow powder: mp 300-304° C.; $^1$H NMR (500 MHz, DMSO-$d_6$) δ 9.32 (br s, 2H), 7.75 (d, J=8.5 Hz, 2H), 7.73 (d, J=7.3 Hz, 1H), 7.62-7.58 (m, 2H), 7.38 (d, J=8.5 Hz, 2H), 7.10 (dd, J=8.5, 2.0 Hz, 1H), 6.78 (d, J=2.0 Hz, 1H), 6.69 (dd, J=7.3, 2.0 Hz, 1H), 4.49 (br s, 2H), 3.70 (s, 3H), 3.60-3.32 (m, 2H), 2.99 (t, J=5.5 Hz, 2H), 2.54 (s, 3H); ESI MS m/z 402 [M+H]$^+$.

Example 125

Preparation of 4-(Benzyloxy)-1-(3,3,9-trimethyl-2,3,4,9-tetrahydro-1H-pyrido[3,4-b]indol-7-yl)pyridine-2(1H)-one hydrochloride a) 4-(1,3-Dioxolan-2-yl)-2-methylbutan-2-amine Beilstein Registry Number 9387059

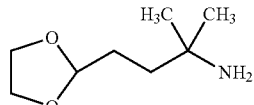

Chemical Formula: $C_8H_{17}NO_2$
Exact Mass: 159.13
Molecular Weight: 159.23

This compound was prepared in accordance with the procedure of Hinderaker, et al., *Protien Sci.* 2003, 12, 1188-1194.

b) tert-Butyl 7-bromo-3,3-dimethyl-3,4-dihydro-1H-pyrido[3,4-b]indole-2(9H)-carboxylate

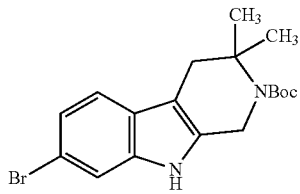

Chemical Formula: $C_{18}H_{23}BrN_2O_2$
Exact Mass: 378.09
Molecular Weight: 379.29

A mixture of 4-(1,3-dioxolan-2-yl)-2-methylbutan-2-amine (3.28 g, 20.4 mmol), 3-bromophenylhydrazine hydrochloride (4.34 g, 19.4 mmol) and $ZnCl_2$ (2.90 g, 21.3 mmol) was stirred at 180° C. for 2.5 h. The mixture was cooled to 120° C., MeOH was added, and the resulting suspension was concentrated on silica gel. Flash chromatography (silica gel, (1:1 EtOAc/hexanes)/(9:0.9:0.1 $CH_2Cl_2$/MeOH/$NH_4OH$), 100:0 to 0:100) afforded 4.20 g of a red amorphous solid. Glyoxylic acid (1.87 g, 20.4 mmol) was added to a suspension of the red amorphous solid in 4:2:1 $H_2O$/MeOH/(concentrated HCl solution) (70 mL), and the resulting solution was stirred at 25° C. for 30 min. The solution was adjusted to pH 3.5 with 6 N NaOH in $H_2O$, and the resulting solution was stirred at 25° C. overnight. The solution was adjusted to pH 5 with saturated $NaHCO_3$ solution and the suspension was filtered. The solid was diluted with 2 N HCl in $H_2O$, and the resulting suspension was stirred at reflux for 2.5 h. The solution was concentrated under reduced pressure and neutralized with saturated $NaHCO_3$ solution. The resulting suspension was filtered, and the solid was dissolved in $CH_2Cl_2$. The resulting solution was dried over $Na_2SO_4$ and concentrated under reduced pressure. Flash chromatography (silica gel, (1:1 EtOAc/hexanes)/(9:0.9:0.1 $CH_2Cl_2$/MeOH/$NH_4OH$), 100:0 to 0:100) afforded 577 mg of a white solid. $Boc_2O$ (2.71 g, 12.4 mmol) was added to a suspension of the white solid and $K_2CO_3$ (571 mg, 4.14 mmol) in 1:1 $H_2O$/i-PrOH (40 mL), and the resulting suspension was stirred at 25 C for 5.5 h. The suspension was concentrated under reduced pressure, and the residue was diluted with water. The solid was collected by filtration, and flash chromatography (silica gel, hexanes/(1:1 EtOAc/hexanes), 100:0 to 0:100) afforded the title compound (200 mg, 3%) as a white solid: $^1$H NMR (300 MHz, $CDCl_3$) δ 7.83 (br s, 1H), 7.47 (br s, 1H), 7.31 (br d, J=8.7 Hz, 1H), 7.20 (br d, J=8.7 Hz, 1H), 4.62 (br s, 2H), 2.77 (br s, 2H), 1.53 (s, 6H), 1.48 (s, 9H).

c) tert-Butyl 7-bromo-3,3,9-trimethyl-3,4-dihydro-1H-pyrido[3,4-b]indole-2(9H)-carboxylate

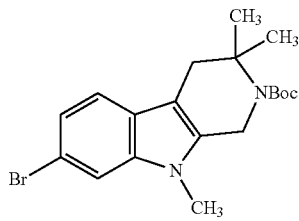

Chemical Formula: $C_{19}H_{25}BrN_2O_2$
Exact Mass: 392.11
Molecular Weight: 393.32

NaH (60% dispersion in oil, 42 mg, 1.1 mmol) was added to a solution of tert-butyl 7-bromo-3,3-dimethyl-3,4-dihydro-1H-pyrido[3,4-b]indole-2(9H)-carboxylate (200 mg, 0.528 mmol) in DMF (10 mL) under $N_2$, and the resulting suspension was stirred at 25° C. for 30 min. MeI (0.05 mL, 0.8 mmol) was added to the suspension, and the resulting suspension was stirred at 25° C. for 1 h. $H_2O$ was added, and the resulting solid was collected by filtration. Flash chromatography (silica gel, hexanes/(1:1 EtOAc/hexanes), 100:0 to 0:100) afforded the title compound (145 mg, 70%) as a white solid: $^1$H NMR (300 MHz, $CDCl_3$) δ 7.43 (d, J=1.5 Hz, 1H), 7.30 (d, J=8.3 Hz, 1H), 7.18 (dd, J=8.3, 1.5 Hz, 1H), 4.62 (s, 2H), 3.61 (s, 3H), 2.77 (s, 2H), 1.52 (s, 6H), 1.49 (s, 9H).

d) 4-(Benzyloxy)-1-(3,3,9-trimethyl-2,3,4,9-tetrahydro-1H-pyrido[3,4-b]indol-7-yl)pyridine-2(1H)-one hydrochloride

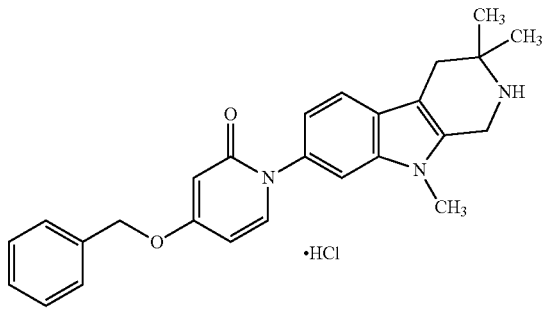

Chemical Formula: $C_{26}H_{28}ClN_3O_2$
Exact Mass: 449.19
Molecular Weight: 449.97

A suspension of 4-(benzyloxy)pyridine-2(1H)-one (67 mg, 0.34 mmol), tert-butyl 7-bromo-3,3,9-trimethyl-3,4-dihydro-1H-pyrido[3,4-b]indole-2(9H)-carboxylate (145 mg, 0.369 mmol), CuI (76 mg, 0.40 mmol), 8-hydroxyquinoline (10 mg, 0.07 mmol) and $Cs_2CO_3$ (120 mg, 0.369 mmol) in DMSO (10 mL) was degassed under reduced pressure for 45 min. The suspension was put under Ar and stirred at 135° C. overnight. The suspension was cooled, 9:0.9:0.1 $CH_2Cl_2$/MeOH/$NH_4OH$ (10 mL) was added, and the resulting suspension was stirred at 25° C. for 30 min. The suspension was passed through a plug of silica gel, and the filtrate was washed with brine. The resulting solution was dried over Na₂SO₄ and concentrated under reduced pressure. Flash chromatography (silica gel, (1:1 EtOAc/hexanes)/(9:0.9:0.1 CH₂Cl₂/MeOH/NH₄OH), 100:0 to 0:100) afforded 28 mg of a white solid. TFA (1 ml) was added to a solution of the white solid in CH₂Cl₂ (10 mL) under N₂, and the resulting solution was stirred for 1 h at 25° C. Saturated NaHCO₃ solution was added to the solution, and the phases were separated. The aqueous phase was extracted with CH₂Cl₂, and the combined organic extracts were dried over Na₂SO₄. The resulting solution was concentrated under reduced pressure. Flash chromatography (silica gel, (1:1 EtOAc/hexanes)/(9:0.9:0.1 CH₂Cl₂/MeOH/NH₄OH), 100:0 to 0:100) afforded 14 mg of a white powder. 2 N HCl in Et₂O (0.01 mL, 0.02 mmol) was added to a solution of the white solid in CH₂Cl₂ (10 mL) under N₂, and the resulting solution was stirred at 25° C. for 30 min. The solution was concentrated under reduced pressure to afford the title compound (5.2 mg, 3%) as a white powder: mp 184-186° C.; ¹H NMR (500 MHz, DMSO-d₆) δ 9.34 (br s, 2H), 7.57 (d, J=7.5 Hz, 1H), 7.53-7.50 (m, 2H), 7.49-7.41 (m, 4H), 7.40-7.35 (m, 1H), 6.99 (dd, J=8.0, 2.0 Hz, 1H), 6.11 (dd, J=8.0, 2.5 Hz, 1H), 5.98 (d, J=2.5 Hz, 1H), 5.16 (s, 2H), 4.50 (br s, 2H), 3.70 (s, 3H), 2.89 (s, 2H), 1.42 (s, 6H); ESI MS m/z 414 [M+H]⁺.

Example 126

Preparation of 4-(4-Methoxy-2-methylphenyl)-1-(9-methyl-2,3,4,9-tetrahydro-1H-pyrido[3,4-b]indol-7-yl)pyridin-2(1H)-one hydrochloride a) 4-(4-Methoxy-2-methylphenyl)pyridin-2(1H)-one

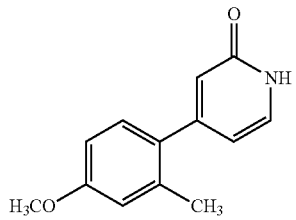

Chemical Formula: C₁₃H₁₃NO₂
Exact Mass: 215.09
Molecular Weight: 215.25

A suspension of 4-bromo-2-methoxypyridine (341 mg, 1.82 mmol), 4-methyloxy-2-methylphenyl boronic acid (452 mg, 2.72 mmol), Pd(PPh₃)₂Cl₂ (133 mg, 0.182 mmol) and K₂CO₃ (503 mg, 3.64 mmol) in DMSO (10 mL) was degassed under reduced pressure for 1 h. The suspension was put under Ar and stirred at 90° C. for 2 h. The suspension was cooled, H₂O was added, and the suspension was filtered to afford a light colored solid. Flash chromatography (silica gel, hexanes/(1:1 EtOAc/hexanes), 100:0 to 0:100) afforded 235 mg of a white powder. The white powder was diluted with concentrated HCl solution (20 mL) and stirred at reflux for 24 h. The reaction was cooled and concentrated under reduced pressure. The residue was neutralized with saturated NaHCO₃ solution, and the solid was collected by filtration. Flash chromatography (silica gel, (1:1 EtOAc/hexanes)/(9:0.9:0.1 CH₂Cl₂/MeOH/NH₄OH), 100:0 to 0:100) afforded the title compound (62 mg, 16%) as a white powder: ¹H NMR (300 MHz, DMSO-d₆) δ 11.54 (br s, 1H), 7.35 (d, J=6.9 Hz, 1H), 7.13 (d, J=8.4 Hz, 1H), 6.87-6.76 (m, 2H), 6.15-6.09 (m, 2H), 3.75 (s, 3H), 1.97 (s, 3H).

b) 4-(4-Methoxy-2-methylphenyl)-1-(9-methyl-2,3,4,9-tetrahydro-1H-pyrido[3,4-b]indol-7-yl)pyridin-2(1H)-one hydrochloride

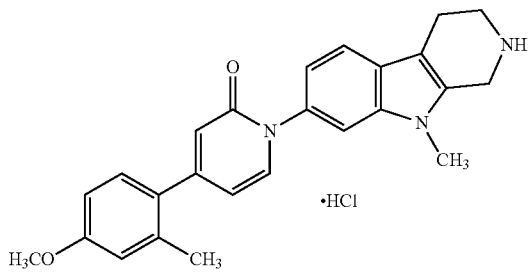

Chemical Formula: C₂₅H₂₆ClN₃O₂
Exact Mass: 435.17
Molecular Weight: 435.95

A suspension of 4-(4-methoxy-2-methylphenyl)pyridin-2(1H)-one (62 mg, 0.29 mmol), tert-butyl 7-bromo-3,3,9-trimethyl-3,4-dihydro-1H-pyrido[3,4-b]indole-2(9H)-carboxylate (126 mg, 0.344 mmol), CuI (66 mg, 0.34 mmol), 8-hydroxyquinoline (8 mg, 0.06 mmol) and Cs₂CO₃ (103 mg, 0.316 mmol) in DMSO (10 mL) was degassed under reduced pressure for 45 min. The suspension was put under Ar and stirred at 135° C. overnight. The suspension was cooled, 9:0.9:0.1 CH₂Cl₂/MeOH/NH₄OH (10 mL) was added, and the resulting suspension was stirred at 25° C. for 1 h. The suspension was passed through a plug of silica gel, and the filtrate was washed with brine. The resulting solution was dried over Na₂SO₄ and concentrated under reduced pressure. Flash chromatography (silica gel, (1:1 EtOAc/hexanes)/(9:0.9:0.1 CH₂Cl₂/MeOH/NH₄OH), 100:0 to 0:100) afforded 52 mg of a yellow amorphous solid. TFA (1 ml) was added to a solution of the yellow amorphous solid in CH₂Cl₂ (10 mL) under N₂ and the resulting solution was stirred for 1 h at 25° C. Saturated NaHCO₃ solution was added to the solution, and the phases were separated. The aqueous phase was extracted with CH₂Cl₂, and the combined organic extracts were dried over Na₂SO₄. The resulting solution was concentrated under reduced pressure. Flash chromatography (silica gel, (1:1 EtOAc/hexanes)/(9:0.9:0.1 CH₂Cl₂/MeOH/NH₄OH), 100:0 to 0:100) afforded 19 mg of a viscous oil. 1 N HCl in Et₂O (0.05 mL, 0.05 mmol) was added to a solution of the viscous oil in CH₂Cl₂ (10 mL) under N₂, and the resulting solution was stirred at 25° C. for 30 min. The solution was concentrated under reduced pressure to afford the title compound (16 mg, 13%) as a white powder: mp 308-310° C.; ¹H NMR (500 MHz, DMSO-d₆) δ 9.44 (br s, 2H), 7.67 (d, J=7.0 Hz, 1H), 7.63 (d, J=1.5 Hz, 1H), 7.60 (d, J=8.0 Hz, 1H), 7.25 (d, J=8.5 Hz, 1H), 7.11 (dd, J=8.5, 1.5 Hz, 1H), 6.92 (d, J=2.5 Hz, 1H), 6.88 (dd, J=8.5, 2.5 Hz, 1H), 6.37 (s, 1H), 6.34 (dd, J=7.5, 1.5 Hz, 1H), 4.89 (br s, 2H), 3.79 (s, 3H), 3.70 (s, 3H), 3.49-3.43 (m, 2H), 2.99 (t, J=6.0 Hz, 2H), 2.36 (s, 3H); ESI MS m/z 400 [M+H]⁺.

Example 127

Preparation of 4-(Benzyloxy)-1-(9-methyl-2-(2-(pyrrolidin-1-yl)ethyl)-2,3,4,9,-tetrahydro-1H-pyrido[3,4-b]indol-7-yl)pyridine-2(1H)-one hydrochloride a) 4-(Benzyloxy)-1-(9-methyl-2-(2-(pyrrolidin-1-yl)ethyl)-2,3,4,9,-tetrahydro-1H-pyrido[3,4-b]indol-7-yl)pyridine-2(1H)-one

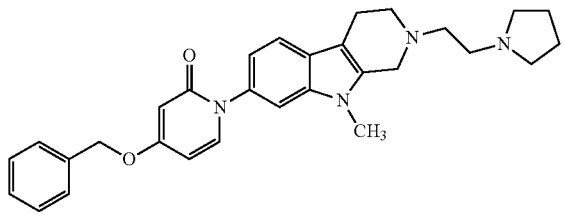

Chemical Formula: $C_{30}H_{34}N_4O_2$
Exact Mass: 482.27
Molecular Weight: 482.62

1-(2-Chloroethyl)pyrrolidine hydrochloride (50 mg, 0.29 mmol) was added to a solution of 4-(benzyloxy)-1-(9-methyl-2,3,4,9,-tetrahydro-1H-pyrido[3,4-b]indol-7-yl)pyridine-2(1H)-one (0.10 g, 0.27 mmol) and diisopropylethyl amine (0.14 mL) in EtOH (4 mL), and the resulting solution was heated at 65° C. for 2 h. The reaction mixture was concentrated to dryness under reduced pressure. Purification by flash column chromatography (40 g ISCO column, $CH_2Cl_2$/(80:18:2 $CH_2Cl_2$/MeOH/$NH_4OH$), 100:0 hold 5 column volumes increased to 0:100 over 20 column volumes) followed by preparative TLC (Analtech, 20×20 cm, 1000 microns, uV 254, 80:18:2 $CH_2Cl_2$/MeOH/$NH_4OH$) followed by preparative HPLC (Phenomenex Luna C18 (2), 250.0×21.2 mm, 10 micron, $H_2O$ with 0.05% TFA and $CH_3CN$ with 0.05% TFA) and filtration through SCX-2 column gave the title compound (10 mg, 7%) as a yellow solid: $^1H$ NMR (500 MHz, $CD_3OD$) δ 7.54 (d, J=7.5 Hz, 1H), 7.51 (d, J=8.5 Hz, 1H), 7.46-7.33 (m, 6H), 6.96 (dd, J=8.0, 1.5 Hz, 1H), 6.26 (dd, J=7.5, 2.5, Hz, 1H), 6.11 (d, J=3.0 Hz, 1H), 5.16 (s, 2H), 3.82 (s, 2H), 3.64 (s, 3H), 3.01-2.99 (m, 2H), 2.94-2.85 (m, 10H), 1.91-1.90 (m, 4H); HPLC (Method A) 95.1% (AUC), $t_R$=13.8 min.

b) 4-(Benzyloxy)-1-(9-methyl-2-(2-(pyrrolidin-1-yl)ethyl)-2,3,4,9,-tetrahydro-1H-pyrido[3,4-b]indol-7-yl)pyridine-2(1H)-one hydrochloride

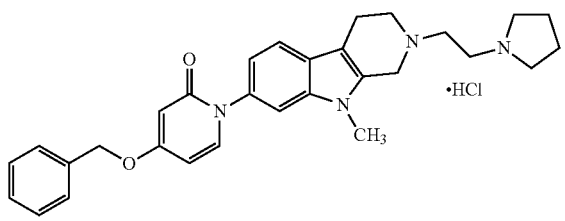

Chemical Formula: $C_{30}H_{35}ClN_4O_2$
Exact Mass: 518.24
Molecular Weight: 519.08

2 N HCl in $Et_2O$ (20 μL, 0.04 mmol) was added to a solution of 4-(benzyloxy)-1-(9-methyl-2-(2-(pyrrolidin-1-yl)ethyl)-2,3,4,9,-tetrahydro-1H-pyrido[3,4-b]indol-7-yl)pyridine-2(1H)-one (10 mg, 0.020 mmol) in $CH_2Cl_2$ mL) and the reaction was stirred at ambient temperature for 1 h under $N_2$. The reaction was concentrated to dryness under reduced pressure to provide the title compound (10 mg, quantitative) as a yellow solid: $^1H$ NMR (500 MHz, $CD_3OD$) δ 7.62-7.57 (m, 2H), 7.47-7.34 (m, 6H), 7.03 (dd, J=8.5, 1.5 Hz, 1H), 6.29 (dd, J=7.5, 2.5 Hz, 1H), 6.12 (d, J=2.5 Hz, 1H), 5.18 (s, 2H), 4.55-4.43 (m, 2H), 3.72 (s, 3H), 3.38-3.14 (m, 12H), 2.14 (m, 4H); ESI MS m/z 483 [M+H]$^+$; HPLC (Method A) 92.8% (AUC), $t_R$=13.6 min.

Example 128

Preparation of 4-(4-Chloro-2-methoxyphenyl)-1-(9-methyl-2,3,4,9-tetrahydro-1H-pyrido[3,4-b]indol-7-yl)pyridin-2(1H)-one hydrochloride a) tert-Butyl-7-(4-(4-chloro-2-methoxyphenyl)-2-oxopyridin-1(2H)-yl)-9-methyl-3,4-dihydro-1H-pyrido[3,4-b]indole-2(9H)-carboxylate

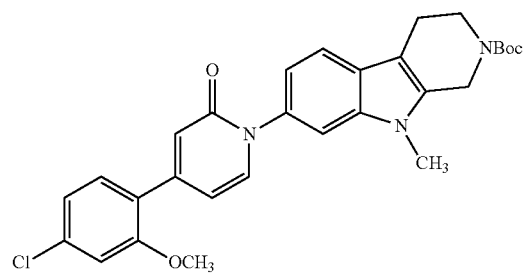

Chemical Formula: $C_{29}H_{30}ClN_3O_4$
Exact Mass: 519.19
Molecular Weight: 520.02 tert-Butyl-7-bromo-9-methyl-3,4-dihydro-1H-pyrido[3,4-b]indole-2(9H)-carboxylate (0.19 g, 0.81 mmol), 4-(4-chloro-2-methoxyphenyl)pyridin-2(1H)-one (0.30 g, 0.81 mmol), $Cs_2CO_3$ (0.29 g, 0.89 mmol) were diluted with DMSO (3.3 mL), and argon was bubbled through the suspension for 10 min. 8-Hydroxyquinoline (59 mg, 0.41 mmol) and copper iodide (0.18 g, 0.97 mmol) were added, and the resulting suspension was placed under vacuum for 15 min. The system was flushed with argon, and the degassing/argon flushing process was repeated a total of three times. The reaction mixture was heated at 130° C. for 18 h and stirred under argon. The suspension was cooled. A solution of 20% $NH_4OH$ in MeOH (40 mL) was added, and the resulting mixture was stirred for 1 h. The mixture was diluted with CH₂Cl₂ and filtered through celite. The filtrate was washed with brine (2×50 mL), dried over Na₂SO₄, and concentrated under reduced pressure. Flash chromatography (40 g ISCO (1:1 hexanes/EtOAc)/(80:18:2 CH₂Cl₂/MeOH/NH₄OH), 100:0 for 3 column volumes then increase to 50:50 over 10 column volumes and hold for 10 column volumes) gave the title compound (0.23 g, 54%) as an olive-green film: ¹H NMR (500 MHz, DMSO-d₆) δ 7.65 (d, J=7.0 Hz, 1H), 7.54 (d, J=2.0 Hz, 1H), 7.50 (d, J=8.0 Hz, 1H), 7.44 (d, J=8.0 Hz, 1H), 7.25 (d, J=1.5 Hz, 1H), 7.13 (dd, J=8.0, 1.5 Hz, 1H), 7.02 (dd, J=8.0, 1.5 Hz, 1H), 6.55 (d, J=2.0 Hz, 1H), 6.54 (dd, J=7.0, 1.5 Hz, 1H), 4.64 (s, 2H), 3.87 (s, 3H), 3.68-3.66 (m, 5H), 2.74-2.72 (m, 2H), 1.46 (s, 9H).

b) 4-(4-Chloro-2-methoxyphenyl)-1-(9-methyl-2,3,4,9-tetrahydro-1H-pyrido[3,4-b]indol-7-yl)pyridin-2(1H)-one hydrochloride

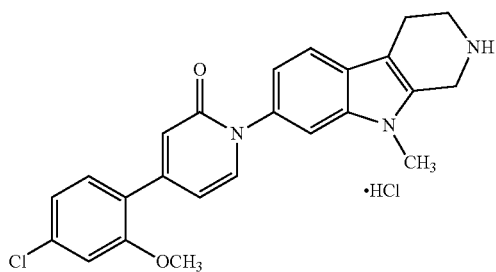

Chemical Formula: C₂₄H₂₃Cl₂N₃O₂
Exact Mass: 455.12
Molecular Weight: 456.36

Trifluoroacetic acid (1.0 mL) was added to a solution of tert-butyl-7-(4-(4-chloro-2-methoxyphenyl)-2-oxopyridin-1(2H)-yl)-9-methyl-3,4-dihydro-1H-pyrido[3,4-b]indole-2(9H)-carboxylate (0.23 g, 0.44 mmol) in CH₂Cl₂ (2 mL) under argon and stirred for 1 h. The mixture was concentrated under reduced pressure, and the residue was partitioned between CH₂Cl₂ and saturated NaHCO₃ solution. The organic phase was removed, and the aqueous phase was extracted with CH₂Cl₂ (10×25 mL). The combined organic extracts were washed with brine (25 mL), dried over Na₂SO₄, and concentrated under reduced pressure. Flash column chromatography (12 g ISCO CH₂Cl₂/(80:18:2 CH₂Cl₂/MeOH/NH₄OH), 100:0 for 2 column volumes to 0:100 over 20 column volumes and hold for 10 column volumes) provided the free base of the title compound. The free base was converted to the HCl salt using 2 N HCl in Et₂O as of Example 129 (step b), providing the title compound (0.13 g, 33%) as a yellow solid: mp 294-300° C.; ¹H NMR (500 MHz, DMSO-d₆) δ 9.43 (br s, 2H), 7.65 (d, J=7.0 Hz, 1H), 7.61 (d, J=1.5 Hz, 1H), 7.59 (d, J=8.0 Hz, 1H), 7.44 (d, J=8.5 Hz, 1H), 7.26 (d, J=2.0 Hz, 1H), 7.13 (dd, J=8.5, 2.0 Hz, 1H), 7.09 (dd, J=8.0, 2.0 Hz, 1H), 6.56 (d, J=2.0 Hz, 1H), 6.47 (dd, J=7.0, 1.5 Hz, 1H), 4.49-4.47 (m, 2H), 3.87 (m, 3H), 3.69 (s, 3H), 3.47-3.43 (m, 2H), 3.00-2.97 (m, 2H); ESI MS m/z 420 [M+H]⁺; HPLC (Method A) 96.7% (AUC), t_R=15.5 min.

Example 129

Preparation of 4-(4-Chloro-2-methoxyphenyl)-1-(2,9-dimethyl-2,3,4,9-tetrahydro-1H-pyrido[3,4-b]indol-7-yl)pyridin-2(1H)-one hydrochloride a) 4-(4-Chloro-2-methoxyphenyl)-1-(2,9-dimethyl-2,3,4,9-tetrahydro-1H-pyrido[3,4-b]indol-7-yl)pyridin-2(1H)-one

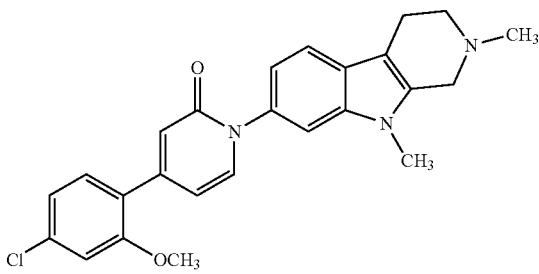

Chemical Formula: C₂₅H₂₄ClN₃O₂
Exact Mass: 433.16
Molecular Weight: 433.93

4-(4-Chloro-2-methoxyphenyl)-1-(9-methyl-2,3,4,9-tetrahydro-1H-pyrido[3,4-b]indol-7-yl)pyridin-2(1H)-one (83 mg, 0.20 mmol) and 37% aqueous formaldehyde (24 μL, 0.30 mmol) were dissolved in 1:1 MeOH/CH₂Cl₂ (1.4 mL) and stirred at room temperature for 45 min. Sodium triacetoxyborohydride (84 mg, 0.40 mmol) was added, and the reaction was stirred at ambient temperature for 30 min. The reaction mixture was neutralized with saturated NaHCO₃ solution and extracted with CH₂Cl₂ (3×25 mL). The combined organics were washed with brine (25 mL), dried over Na₂SO₄, filtered and concentrated to dryness under reduced pressure. Purification by flash column chromatography (12 g ISCO (1:1 hexanes/EtOAc)/(80:18:2 CH₂Cl₂/MeOH/NH₄OH), 95:5 to 10:90 over 20 column volumes, hold for 10 column volumes) provided the title compound (77 mg, 89%) as a yellow film: ¹H NMR (500 MHz, CDCl₃) δ 7.55 (d, J=8.0 Hz, 1H), 7.41 (d, J=7.0 Hz, 1H), 7.35-7.34 (m, 1H), 7.31 (d, J=8.0 Hz, 1H), 7.07-7.03 (m, 2H), 7.00-6.99 (m, 1H), 6.81-6.80 (m, 1H), 6.43-6.42 (m, 1H), 3.87 (s, 3H), 3.66-3.65 (m, 2H), 3.48 (s, 3H), 2.87-2.86 (m, 2H), 2.81-2.80 (m, 2H), 2.58 (s, 3H).

b) 4-(4-Chloro-2-methoxyphenyl)-1-(2,9-dimethyl-2,3,4,9-tetrahydro-1H-pyrido[3,4-b]indol-7-yl)pyridin-2(1H)-one hydrochloride

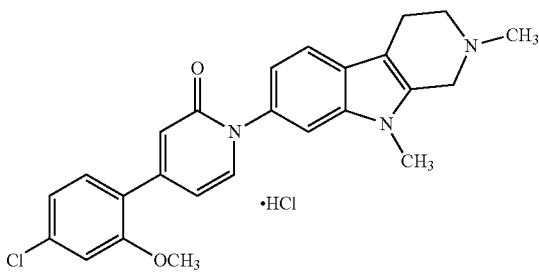

Chemical Formula: C₂₅H₂₅Cl₂N₃O₂
Exact Mass: 469.13
Molecular Weight: 470.39

2 N HCl in Et₂O (0.17 mL, 0.34 mmol) was added to a solution of 4-(4-chloro-2-methoxyphenyl)-1-(2,9-dimethyl-2,3,4,9-tetrahydro-1H-pyrido[3,4-b]indol-7-yl)pyridin-2 (1H)-one (74 mg, 0.17 mmol) in CH₂Cl₂ (2 mL) and the reaction was stirred at ambient temperature for 1.5 h under N₂. The solids were collected by filtration, washed with Et₂O and dried under reduced pressure to yield the title compound (54 mg, 68%) as a yellow powder: mp 272-280° C.; ¹H NMR (500 MHz, DMSO-d₆) δ 10.82 (br s, 1H), 7.65 (d, J=7.0 Hz, 1H), 7.62 (d, J=1.5 Hz, 1H), 7.60 (d, J=8.5 Hz, 1H), 7.44 (d, J=8.5 Hz, 1H), 7.26 (d, J=1.5 Hz, 1H), 7.14-7.09 (m, 2H), 6.56 (d, J=1.5 Hz, 1H), 6.47 (dd, J=7.0, 1.5 Hz, 1H), 4.79-4.76 (m, 1H), 4.53-4.42 (m, 1H), 3.87 (s, 3H), 3.72-3.68 (m, 4H), 3.42-3.40 (m, 1H), 3.08-3.06 (m, 2H), 3.00 (s, 3H); ESI MS m/z 434 [M+H]⁺; HPLC (Method A) 96.5% (AUC), $t_R$=15.3 min.

Example 130

Preparation of (S)-4-(Benzyloxy)-1-(5-methyl-2-pyrrolidin-2-ylmethyl)-2,3,4,5-tetrahydro-1H-pyrido[4,3-b]indol-7-yl)pyridine-2(1H)-one hydrochloride a) (S)-tert-Butyl 2-((7-(4-(benzyloxy)-2-oxopyridin-1(2H)-yl)-5-methyl-3,4-dihydro-1H-pyrido[4,3-b]indol-2(5H)-yl)methyl)pyrrolidine-1-carboxylate

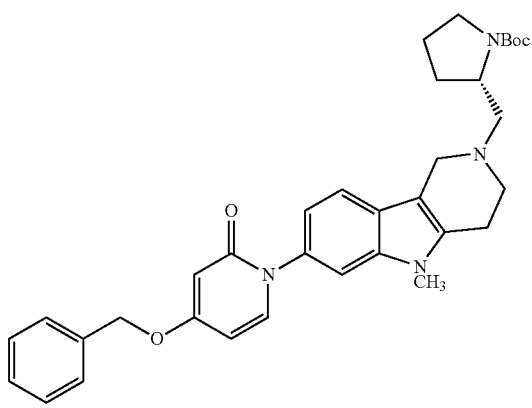

Chemical Formula: C₃₄H₄₀N₄O₄
Exact Mass: 568.30
Molecular Weight: 568.71

A solution of (S)-tert-butyl 2-(bromomethyl)pyrrolidine-1-carboxylate (0.45 g, 1.7 mmol) in DMSO (1.5 mL) was added to a solution of 4-(benzyloxy)-1-(9-methyl-2,3,4,9,-tetrahydro-1H-pyrido[3,4-b]indol-7-yl)pyridine-2(1H)-one (0.33 g, 0.85 mmol), and Cs₂CO₃ (1.10 g, 3.4 mmol) in DMSO (2.8 mL), and the resulting solution was heated at 60° C. for 18 h. The reaction mixture was diluted with H₂O and extracted with CH₂Cl₂ (3×25 mL). The combined organic extracts were washed with brine (2×25 mL), dried over Na₂SO₄ and concentrated to dryness under reduced pressure. Purification by flash column chromatography (40 g ISCO column, CH₂Cl₂/(80:18:2 CH₂Cl₂/MeOH/NH₄OH), 100:0 hold 5 column volumes, increased to 0:100:0 over 20 column volumes) provided a clear film. The film was diluted with EtOAc and washed with brine (4×10 mL), dried over Na₂SO₄, filtered and concentrated under reduced pressure to provide the title compound (19 mg, 3%) as a clear film: ESI MS m/z 569 [M+H]⁺.

b) (S)-4-(Benzyloxy)-1-(5-methyl-2-pyrrolidin-2-ylmethyl)-2,3,4,5-tetrahydro-1H-pyrido[4,3-b]indol-7yl)pyridine-2(1H)-one

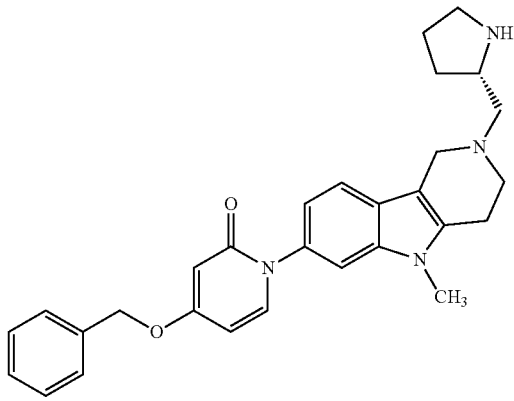

Chemical Formula: C₂₉H₃₂N₄O₂
Exact Mass: 468.25
Molecular Weight: 468.59

Trifluoroacetic acid (1.0 mL) was added to a solution of (S)-tert-butyl 2-((7-(4-(benzyloxy)-2-oxopyridin-1(2H)-yl)-5-methyl-3,4-dihydro-1H-pyrido[4,3-b]indol-2(5H)-yl)methyl)pyrrolidine-1-carboxylate (19 mg, 0.033 mmol) in 2:1 CDCl₃/MeOH (1.5 mL) under argon and stirred for 30 min. The mixture was concentrated to dryness under reduced pressure. Flash column chromatography (4 g ISCO CH₂Cl₂/(80:18:2 CH₂Cl₂/MeOH/NH₄OH), 95:5 for 20 column volumes to 0:100 over 40 column volumes and hold for 100 column volumes) yielded the title compound (10 mg, 65%) as a clear film: ESI MS m/z 469 [M+H]⁺ c) (S)-4-(Benzyloxy)-1-(5-methyl-2-pyrrolidin-2-ylmethyl)-2,3,4,5-tetrahydro-1H-pyrido[4,3-b]indol-7yl)pyridine-2(1H)-one hydrochloride

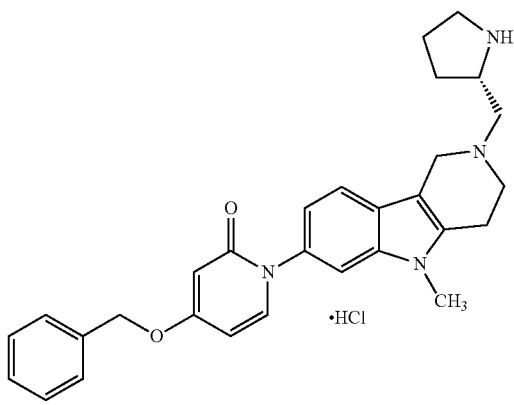

Chemical Formula: C₂₉H₃₃ClN₄O₂
Exact Mass: 504.23
Molecular Weight: 505.05

2 N HCl in Et₂O (0.12 μL, 0.024 mmol) was added to a solution of (S)-4-(benzyloxy)-1-(5-methyl-2-pyrrolidin-2-ylmethyl)-2,3,4,5-tetrahydro-1H-pyrido[4,3-b]indol-7yl)

pyridine-2(1H)-one) (10 mg, 0.021 mmol) in CH$_2$Cl$_2$ (0.6 mL), and the solution was stirred at ambient temperature for 1.5 h under N$_2$. The reaction mixture was concentrated under reduced pressure to provide the title compound (6.0 mg, 56%) as a white solid: $^1$H NMR (500 MHz, CD$_3$OD) δ 7.59-7.56 (m, 2H), 7.47-7.45 (m, 3H), 7.42-7.39 (m, 2H), 7.37-7.34 (m, 1H), 7.06 (dd, J=8.5, 2.0 Hz, 1H), 6.29 (dd, J=7.5, 2.5 Hz, 1H), 6.12 (d, J=3.0 Hz, 1H), 5.18 (s, 2H), 4.70-4.49 (br m, 2H), 4.28-4.26 (m, 1H), 3.75-3.73 (m, 7H), 3.46-3.43 (m, 2H), 3.34-3.33 (m, 2H), 2.46-2.43 (m, 1H), 2.21-2.08 (m, 2H), 1.91-1.86 (m, 1H); ESI MS m/z 469 [M+H]$^+$; HPLC (Method A) 93.8% (AUC), t$_R$=13.5 min.

Example 131

Preparation of 4-(4-Methoxyphenyl)-1-(5-methyl-2,3,4,5-tetrahydro-1H-pyrido[4,3-b]indol-7-yl)pyridin-2(1H)-one hydrochloride c) tert-Butyl 7-(4-(4-methoxyphenyl)-2-oxopyridin-1(2H)-yl)-5-methyl-3,4-dihydro-1H-pyrido[4,3-b]indole-2(5H)-carboxylate

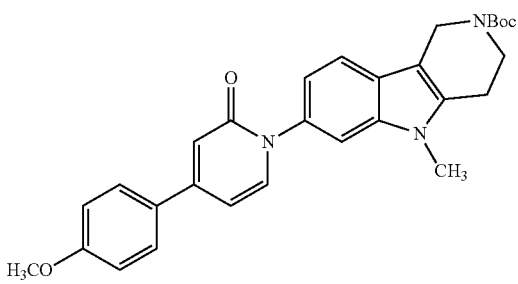

Chemical Formula: C$_{29}$H$_{31}$N$_3$O$_4$
Exact Mass: 485.23
Molecular Weight: 485.57 tert-Butyl-7-bromo-5-methyl-3,4-dihydro-1H-pyrido[4,3-b]indole-2(5H)-carboxylate (0.19 g, 0.54 mmol), 4-(4-methoxyphenyl)pyridin-2(1H)-one (90 mg, 0.45 mmol) and Cs$_2$CO$_3$ (0.16 g, 0.49 mmol) were suspense in DMSO (2.0 mL) and degassed under vacuum for 15 min. The system was then flushed with Ar and 8-hydroxyquinoline (19 mg, 0.13 mmol) and copper iodide (0.10 g, 0.54 mmol) were added. The degassing/Ar flushing process was repeated twice more, and the reaction mixture was heated at 133° C. for 18 h under N$_2$. The suspension was cooled, diluted with 20% NH$_4$OH/MeOH (25 mL) and stirred at ambient temperature for 30 min. The suspension was further diluted with CH$_2$Cl$_2$ (100 mL). The solution was filtered through silica gel and concentrated under reduced pressure. The concentrate was diluted with CH$_2$Cl$_2$ and washed with brine (3×25 mL). The organic phase was dried over Na$_2$SO$_4$, filtered and concentrated to dryness. Flash column chromatography (12 g ISCO column, (1:1 hexanes/EtOAc)/(80:18:2 CH$_2$Cl$_2$/MeOH/NH$_4$OH), 100:0 for 10 column volumes, increased to 50:50 over 20 column volumes and then hold for 5 column volumes) gave the title compound (75 mg, 34%) as a yellow solid: $^1$H NMR (500 MHz, CDCl$_3$) δ 7.60 (d, J=9.0 Hz, 2H), 7.53 (d, J=8.0 Hz, 1H), 7.46 (d, J=7.5 Hz, 1H), 7.37 (d, J=1.5 Hz, 1H), 7.08 (d, J=7.5 Hz, 1H), 7.00 (d, J=9.0 Hz, 2H), 6.86 (d, J=2.0 Hz, 1H), 6.50 (dd, J=7.0, 2.0 Hz, 1H), 4.66-4.64 (m, 2H), 3.87 (s, 3H), 3.85-3.84 (m, 2H), 3.64 (s, 3H), 2.84-2.83 (m, 2H), 1.50 (s, 9H).

b) 4-(4-Methoxyphenyl)-1-(5-methyl-2,3,4,5-tetrahydro-1H-pyrido[4,3-b]indol-7-yl)pyridin-2(1H)-one

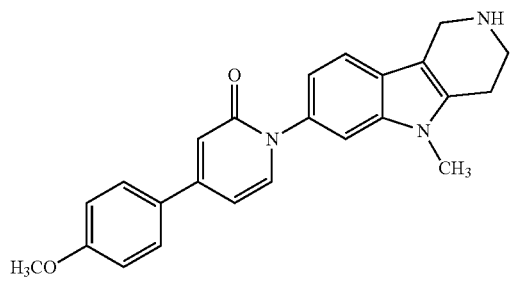

Chemical Formula: C$_{24}$H$_{23}$N$_3$O$_2$
Exact Mass: 385.18
Molecular Weight: 385.46

Trifluoroacetic acid (1.0 mL) was added to a solution of tert-butyl 7-(4-(4-methoxyphenyl)-2-oxopyridin-1(2H)-yl)-5-methyl-3,4-dihydro-1H-pyrido[4,3-b]indole-2(5H)-carboxylate (74 mg, 0.15 mmol) in CH$_2$Cl$_2$ (1 mL) under N$_2$ and stirred for 2 h at ambient temperature. The mixture was concentrated, and the residue was partitioned between CH$_2$Cl$_2$ and saturated NaHCO$_3$ solution. The organic phase was removed, and the aqueous phase was extracted with CH$_2$Cl$_2$ (4×25 mL). The combined organic extracts were washed with brine (25 mL), dried over Na$_2$SO$_4$ and concentrated under reduced pressure. Flash column chromatography (12 g ISCO CH$_2$Cl$_2$/(80:18:2 CH$_2$Cl$_2$/MeOH/NH$_4$OH), 100:0 for 5 column volumes to 0:100 over 20 column volumes and hold for 5 column volumes) yielded the title compound (46 mg, 78%) as a yellow solid: $^1$H NMR (500 MHz, CDCl$_3$) δ 7.60 (d, J=9.0 Hz, 2H), 7.50-7.46 (m, 2H), 7.36 (d, J=2.0 Hz, 1H), 7.05 (dd, J=8.5, 2.0 Hz, 1H), 7.00 (d, J=8.5 Hz, 2H), 6.86 (d, J=1.5 Hz, 1H), 6.49 (dd, J=7.0, 2.0 Hz, 1H), 4.08 (s, 2H), 3.87 (s, 3H), 3.63 (s, 3H), 3.27 (t, J=6.0 Hz, 2H), 2.77 (t, J=5.5 Hz, 2H).

c) 4-(4-Methoxyphenyl)-1-(5-methyl-2,3,4,5-tetrahydro-1H-pyrido[4,3-b]indol-7-yl)pyridin-2(1H)-one hydrochloride

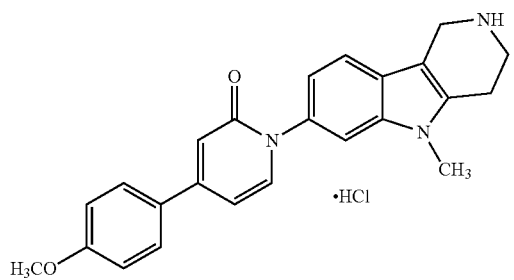

Chemical Formula: C$_{24}$H$_{24}$ClN$_3$O$_2$
Exact Mass: 421.16
Molecular Weight: 421.92

2 N HCl in Et$_2$O (0.12 mL, 0.24 mmol) was added to a solution of 4-(4-methoxyphenyl)-1-(5-methyl-2,3,4,5-tetrahydro-1H-pyrido[4,3-b]indol-7-yl)pyridin-2(1H)-one (45 mg, 0.12 mmol) in CH$_2$Cl$_2$ (2.0 mL), and the solution was stirred at ambient temperature for 2.5 h under N$_2$. The reaction mixture was concentrated, partially diluted with H$_2$O and lyophilized to provide the title compound (46 mg, 95%) as a yellow powder: $^1$H NMR (500 MHz, DMSO-d$_6$) δ 9.26 (br s, 2H), 7.76 (d, J=9.0 Hz, 2H), 7.70 (d, J=7.0 Hz, 1H), 7.60-7.57 (m, 2H), 7.09-7.06 (m, 3H), 6.73 (d, J=2.0 Hz, 1H), 6.68 (dd, J=7.5, 2.0 Hz, 1H), 4.37-4.35 (m, 2H), 3.83 (s, 3H), 3.70 (s, 3H), 3.54-3.53 (m, 2H), 3.10 (t, J=6.0 Hz, 2H); ESI MS m/z 386 [M+H]$^+$.

Example 132

Preparation of 4-(4-Methoxy-2-methylphenyl)-1-(5-methyl-2,3,4,5-tetrahydro-1H-pyrido[4,3-b]indol-7-yl)pyridin-2(1H)-one hydrochloride a) tert-Butyl 7-(4-(4-methoxy-2-methylphenyl)-2-oxopyridin-1(2H)-yl)-5-methyl-3,4-dihydro-1H-pyrido[4,3-b]indole-2(5H)-carboxylate

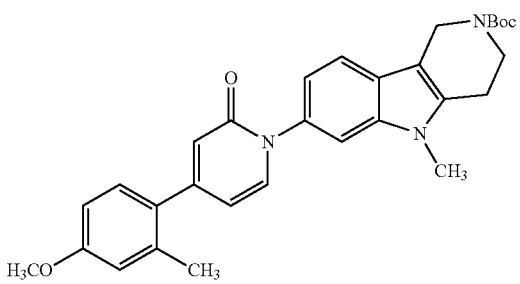

Chemical Formula: C$_{30}$H$_{33}$N$_3$O$_4$
Exact Mass: 499.25
Molecular Weight: 499.60 tert-Butyl-7-bromo-5-methyl-3,4-dihydro-1H-pyrido[4,3-b]indole-2(5H)-carboxylate (0.35 g, 0.96 mmol), 4-(4-methoxy-2-methylphenyl)pyridin-2(1H)-one (0.21 g, 0.96 mmol) and Cs$_2$CO$_3$ (0.35 g, 1.1 mmol) were suspended in DMSO (5.6 mL), and the resulting suspension was degassed under vacuum for 15 min. The system was then flushed with Ar, and 8-hydroxyquinoline (42 mg, 0.29 mmol) and copper iodide (0.22 g, 1.2 mmol) were added. The evacuation/Ar flushing process was repeated twice more, and the reaction mixture was heated at 130° C. for 18 h under N$_2$. The suspension was cooled, diluted with 20% NH$_4$OH/MeOH (10 mL) and stirred at ambient temperature for 30 min. The reaction was further diluted with CH$_2$Cl$_2$ (100 mL). The solution was filtered through silica gel and concentrated. The concentrate was diluted with CH$_2$Cl$_2$ and washed with brine (4×20 mL). The organic phase was dried over Na$_2$SO$_4$ and concentrated to dryness under reduced pressure. Flash column chromatography (12 g ISCO column, (1:1 hexanes/EtOAc)/(80:18:2 CH$_2$Cl$_2$/MeOH/NH$_4$OH), 100:0 for 5 column volumes, increased to 50:50 over 20 column volumes and then hold for 5 column volumes, increase to 0:100 over 10 column volumes and hold for 5 column volumes) gave the title compound (0.25 g, 52%) as a yellow film: $^1$H NMR (500 MHz, CDCl$_3$) δ 7.54 (d, J=8.0 Hz, 1H), 7.42 (d, J=6.5 Hz, 1H), 7.39 (d, J=1.5 Hz, 1H), 7.22 (d, J=8.0 Hz, 1H), 7.10 (d, J=7.0 Hz, 1H), 6.82-6.80 (m, 2H), 6.60 (d, J=1.5 Hz, 1H), 6.24 (dd, J=6.5, 1.5 Hz, 1H), 4.67-4.65 (m, 2H), 3.86-3.83 (m, 5H), 3.65 (s, 3H), 2.93 (m, 3H), 2.82-2.84 (m, 2H), 1.50 (s, 9H).

b) 4-(4-Methoxy-2-methylphenyl)-1-(5-methyl-2,3,4,5-tetrahydro-1H-pyrido[4,3-b]indol-7-yl)pyridin-2(1H)-one

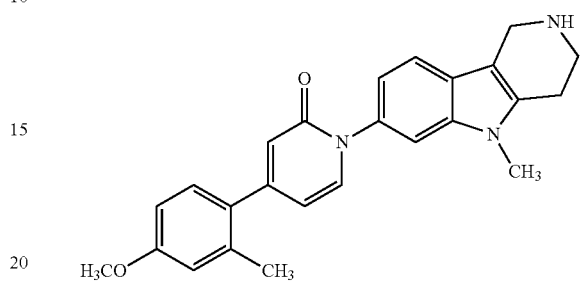

Chemical Formula: C$_{25}$H$_{25}$N$_3$O$_2$
Exact Mass: 399.19
Molecular Weight: 399.48

Trifluoroacetic acid (1.0 mL) was added to a solution of tert-butyl 7-(4-(4-methoxy-2-methylphenyl)-2-oxopyridin-1(2H)-yl)-5-methyl-3,4-dihydro-1H-pyrido[4,3-b]indole-2(5H)-carboxylate (0.25 g, 0.50 mmol) in CH$_2$Cl$_2$ (2.0 mL) under N$_2$ and stirred for 1 h. The reaction mixture was made basic with saturated NaHCO$_3$ solution and the resolution solution was extracted with CH$_2$Cl$_2$ (3×25 mL). The combined organic extracts were dried over Na$_2$SO$_4$ and concentrated under reduced pressure. Flash column chromatography (12 g ISCO CH$_2$Cl$_2$/(80:18:2 CH$_2$Cl$_2$/MeOH/NH$_4$OH), 100:0 for 5 column volumes to 0:100 over 20 column volumes and hold for 40 column volumes) yielded the title compound (0.16 g, 80%) as an off-white film: $^1$H NMR (500 MHz, CDCl$_3$) δ 7.50 (d, J=8.0 Hz, 1H), 7.42 (d, J=7.0 Hz, 1H), 7.38 (m, 1H), 7.22 (d, J=8.0 Hz, 1H), 7.07 (dd, J=8.5, 2.0 Hz, 1H), 6.82-6.80 (m, 2H), 6.60 (d, J=1.5 Hz, 1H), 6.23 (dd, J=7.0, 1.5 Hz, 1H), 4.09 (s, 2H), 3.84 (s, 3H), 3.64 (s, 3H), 2.77 (t, J=5.5 Hz, 2H), 2.27 (t, J=6.0 Hz, 2H), 2.39 (s, 3H).

c) 4-(4-Methoxy-2-methylphenyl)-1-(5-methyl-2,3,4,5-tetrahydro-1H-pyrido[4,3-b]indol-7-yl)pyridin-2(1H)-one hydrochloride

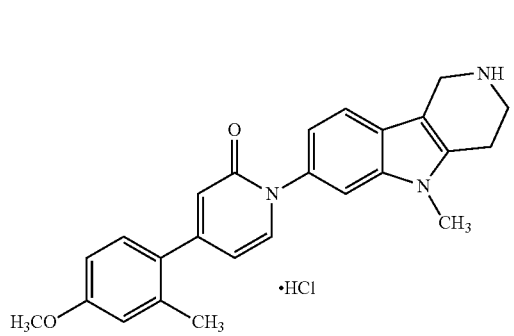

Chemical Formula: C$_{25}$H$_{26}$ClN$_3$O$_2$
Exact Mass: 435.17
Molecular Weight: 435.95

2 N HCl in Et$_2$O (0.40 mL, 0.80 mmol) was added to a solution of 4-(4-methoxy-2-methylphenyl)-1-(5-methyl-2,3,4,5-tetrahydro-1H-pyrido[4,3-b]indol-7-yl)pyridin-2(1H)-one (0.16 g, 0.40 mmol) in CH$_2$Cl$_2$ (1.5 mL), and the solution was stirred at ambient temperature for 1 h under N$_2$. The solids were collected by filtration, washed with Et$_2$O and dried to yield the title compound (0.15 g, 85%) as an off-white powder: $^1$H NMR (500 MHz, DMSO-d$_6$) δ 9.39 (br s, 2H), 7.67 (d, J=7.0 Hz, 1H), 7.59 (d, J=8.0 Hz, 1H), 7.27 (d, J=2.0 Hz, 1H), 7.25 (d, J=8.5 Hz, 1H), 7.10 (dd, J=8.5, 2.0 Hz, 1H), 6.92 (d, J=2.5 Hz, 1H), 6.88 (dd, J=8.0, 2.5 Hz, 1H), 6.37 (d, J=2.0 Hz, 1H), 6.34 (dd, J=7.0, 2.0 Hz, 1H), 4.36-4.34 (m, 2H), 3.79 (s, 3H), 3.71 (s, 3H), 3.53-3.52 (m, 2H), 3.10 (t, J=6.0 Hz, 2H), 2.35 (s, 3H); ESI MS m/z 400 [M+H]$^+$; HPLC (Method A) 95.8% (AUC), t$_R$=14.5 min.

Example 133

Preparation of (4-Benzyloxy)-1-(9-(difluoromethyl)-2,3,4,9-tetrahydro-1H-pyrido[4,3-b]indol-7-yl)pyridin-2(1H)-one hydrochloride a) tert-Butyl 7-bromo-9-(difluoromethyl)-3,4-dihydro-1H-pyrido[4,3-b]indole-2(9H)-carboxylate

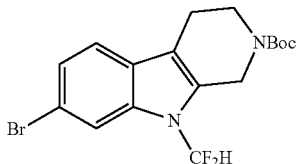

Chemical Formula: C$_{17}$H$_{19}$BrF$_2$N$_2$O$_2$
Exact Mass: 400.06
Molecular Weight: 401.25

Sodium hydride (60% in mineral oil, 0.347 g, 8.71 mmol) was added to a solution of tert-butyl 7-bromo-3,4-dihydro-1H-pyrido[3,4-b]indole-2(9H)-carboxylate (2.04 g, 5.81 mmol) in DMF (20 mL) at room temperature under N$_2$ and stirred for 30 minutes. Difluoroiodomethane (~1.5 mL), which had been condensed with a cold finger into a separate flask, was added via syringe. The reaction was sealed with a rubber septum and stirred overnight at ambient temperature. The mixture was quenched with H$_2$O. EtOAc was added and the mixture was stirred for 40 minutes. The mixture was extracted with EtOAc (3×40 mL), and the combined organic extracts were washed with brine (2×20 mL), dried over Na$_2$SO$_4$ and concentrated under reduced pressure. Flash chromatography (40+M Biotage column, hexanes/(4:1 hexanes/EtOAc), 100:0 to 0:100) provided the title compound (0.93 g, 40%) as a white solid: $^1$H NMR (300 MHz, CDCl$_3$) δ 7.62 (s, 1H), 7.17 (t, J=56.0 Hz, 1H), 7.33 (m, 2H), 4.71 (s, 2H), 3.75 (m, 2H), 2.74 (s, 2H), 1.50 (s, 9H).

b) tert-Butyl 7-(4-benzyloxy)-2-oxopyridin-1(2H)-yl)-9-(difluoromethyl)-3,4-dihydro-1H-pyrido[4,3-b]indole-2(9H)-carboxylate

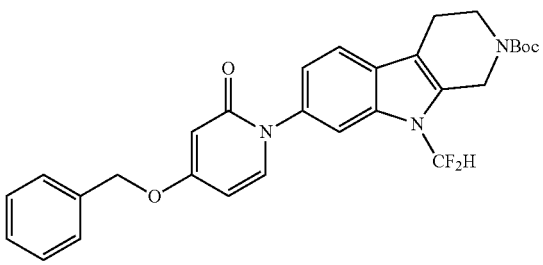

Chemical Formula: C$_{29}$H$_{29}$F$_2$N$_3$O$_4$
Exact Mass: 521.21
Molecular Weight: 521.56 tert-Butyl 7-bromo-9-(difluoromethyl)-3,4-dihydro-1H-pyrido[4,3-b]indole-2(9H)-carboxylate (0.936 g, 2.33 mmol), 4-benzyloxypyridone (0.469 g, 2.33 mmol), Cs$_2$CO$_3$ (0.834 g, 2.57 mmol) and H$_2$O (1 drop) were diluted with DMSO (10.4 mL) and argon was bubbled through the suspension for 10 minutes. 8-Hydroxyquinoline (0.101 g, 0.699 mmol) and copper iodide (133 mg, 0.699 mmol) were added, and the resulting suspension was placed under vacuum for 15 min. The system was flushed with argon. The degassing/argon flushing process was repeated a total of three times. The reaction mixture was heated to 130° C. for 18 h and stirred under argon. The suspension was cooled. A solution of 20% NH$_4$OH in MeOH (40 mL) was added, and the resulting mixture was stirred for 1 h. The mixture was diluted with CH$_2$Cl$_2$ and filtered through celite. The filtrate was washed with brine (3×25 mL), dried over Na$_2$SO$_4$ and concentrated under reduced pressure. Flash chromatography (40+M Biotage column, (20% EtOAc in hexanes)/(50% EtOAc in hexanes)/(80:18:2 CH$_2$Cl$_2$/MeOH/NH$_4$OH), 100:0:0 to 0:100:0 over 1.2 L then 0:100:0 to 0:0:100 over 1.2 L) gave the title compound (0.41 g, 33%) as a yellow foam: $^1$H NMR (500 MHz, DMSO-d$_6$) δ 8.10 (t, J=58.0 Hz, 1H), 7.74 (d, J=1.4 Hz, 1H), 7.60 (d, J=3.2 Hz, 1H), 7.58 (d, J=3.9 Hz, 1H), 7.47-7.35 (m, 5H), 7.16 (dd, J=8.3, 1.7 Hz, 1H), 6.12 (dd, J=7.6, 2.6 Hz, 1H), 5.99 (d, J=2.7 Hz, 1H), 5.15 (s, 2H), 4.72 (m, 2H), 4.03 (s, 2H), 3.70 (m, 2H), 1.44 (s, 9H).

c) (4-Benzyloxy)-1-(9-(difluoromethyl)-2,3,4,9-tetrahydro-1H-pyrido[4,3-b]indol-7-yl)pyridin-2(1H)-one hydrochloride

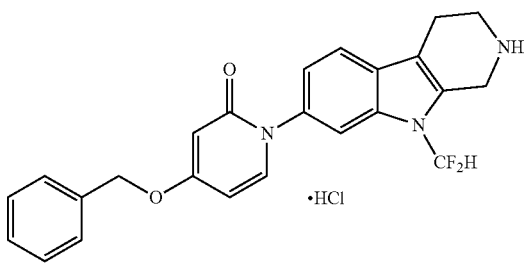

Chemical Formula: C$_{24}$H$_{22}$ClF$_2$N$_3$O$_2$
Exact Mass: 457.14
Molecular Weight: 457.90

2 N HCl in Et₂O (15.0 mL) was added to a solution of tert-butyl 7-(4-benzyloxy)-2-oxopyridin-1(2H)-yl)-9-(difluoromethyl)-3,4-dihydro-1H-pyrido[4,3-b]indole-2(9H)-carboxylate (0.39 g, 0.75 mmol) in 1:1 MeOH/CH₂Cl₂ (5 mL). The reaction was stirred at ambient temperature for 2 h under N₂. The reaction was diluted with Et₂O, and the resulting solids were collected by filtration to yield the title compound (0.31 g, 92%) as a yellow solid: mp 220-230° C.; ¹H NMR (500 MHz, DMSO-d₆) δ 9.60 (br s, 2H), 8.11 (t, J=58.0 Hz, 1H), 7.78 (d, J=1.5 Hz, 1H), 7.68 (d, J=8.0 Hz, 1H), 7.60 (d, J=7.5 Hz, 1H), 7.48-7.36 (m, 5H), 7.22 (dd, J=8.5, 1.5 Hz, 1H), 6.14 (dd, J=7.5, 2.5 Hz, 1H), 5.99 (d, J=2.5 Hz, 1H), 5.16 (s, 2H), 4.52 (m, 2H), 3.49-3.48 (m, 2H), 2.99 (m, 2H); ESI MS m/z 422 [M+H]⁺; HPLC (Method A) 96.5% (AUC), t$_R$=14.4 min Example 134

Preparation of (4-Benzyloxy)-1-(9-(difluoromethyl)-2-methyl-2,3,4,9-tetrahydro-1H-pyrido[3,4-b]indol-7-yl)pyridin-2(1H)-one hydrochloride a) (4-Benzyloxy)-1-(9-(difluoromethyl)-2-methyl-2,3,4,9-tetrahydro-1H-pyrido[3,4-b]indol-7-yl)pyridin-2(1H)-one

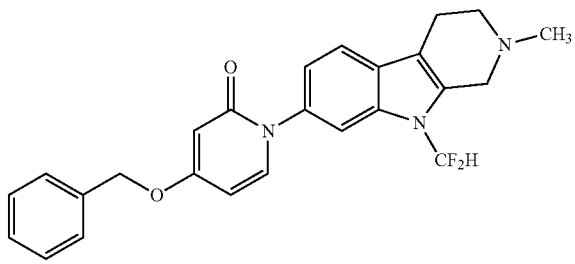

Chemical Formula: C₂₅H₂₃F₂N₃O₂
Exact Mass: 435.18
Molecular Weight: 435.47

(4-Benzyloxy)-1-(9-(difluoromethyl)-2,3,4,9-tetrahydro-1H-pyrido[4,3-b]indol-7-yl)pyridin-2(1H)-one (83 mg, 20 mmol) and 37% aqueous formaldehyde (22 μL, 0.30 mmol) were dissolved in 1:1 CH₂Cl₂/MeOH (1.0 mL) and stirred at ambient temperature for 45 min. Sodium triacetoxyborohydride (83 mg, 0.39 mmol) was added, and the resulting suspension was stirred at ambient temperature for 15 min. The suspension was concentrated, and the residue was diluted with saturated NaHCO₃ solution. The aqueous solution was extracted with CH₂Cl₂. The combined organic extracts were dried over Na₂SO₄ and concentrated under reduced pressure. Flash chromatography (10 g Biotage SNAP column, CH₂Cl₂/(80:18:2 CH₂Cl₂/MeOH/NH₄OH), 100:0 to 0:100) gave the title compound (57 mg, 67%) as a clear oil. ESI MS m/z 436 [M+H]⁺; HPLC (Method A) 98.9% (AUC), t$_R$=14.3 min.

b) (4-Benzyloxy)-1-(9-(difluoromethyl)-2-methyl-2,3,4,9-tetrahydro-1H-pyrido[3,4-b]indol-7-yl)pyridin-2(1H)-one hydrochloride

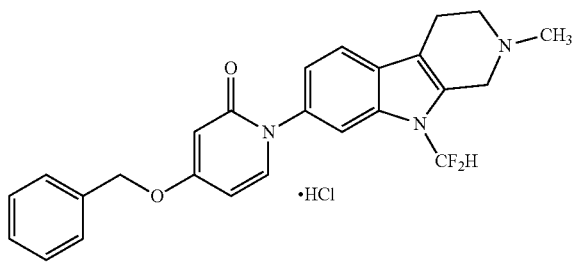

Chemical Formula: C₂₅H₂₄ClF₂N₃O₂
Exact Mass: 471.15
Molecular Weight: 471.93

A solution of (4-benzyloxy)-1-(9-(difluoromethyl)-2-methyl-2,3,4,9-tetrahydro-1H-pyrido[3,4-b]indol-7-yl)pyridin-2(1H)-one (58 mg, 0.13 mmol) in CH₂Cl₂ (1.0 mL) was treated with anhydrous 1.0 M HCl in diethyl ether (0.13 mL, 0.13 mmol). The reaction was stirred at ambient temperature for 1 h, and the solids were collected and dried to yield the title compound (53 mg, 86%) as a yellow solid: mp 250-256° C.; ¹H NMR (500 MHz, DMSO-d₆) δ 10.89 (br s, 1H), 8.15 (t, J=58.0 Hz, 1H), 7.82 (d, J=1.5 Hz, 1H), 7.69 (d, J=8.3 Hz, 1H), 7.60 (d, J=7.6 Hz, 1H), 7.47-7.36 (m, 5H), 7.23 (dd, J=8.4, 1.5 Hz, 1H), 6.14 (dd, J=7.6, 2.7 Hz, 1H), 6.00 (d, J=2.7 Hz, 1H), 5.16 (s, 2H), 4.77 (m, 1H), 4.55 (m, 1H), 3.76-3.75 (m, 1H), 3.45-3.40 (m, 1H), 3.07-3.02 (m, 5H); ESI MS m/z 436 [M+H]⁺; HPLC (Method A) 98.9% (AUC), t$_R$=14.4 min.

Example 135

Preparation of 4-(2-Fluoro-4-methoxyphenyl)-1-(9-methyl-2,3,4,9-tetrahydro-1H-pyrido[3,4-b]indol-7-yl)pyridin-2(1H)-one hydrochloride a) 4-(2-Fluoro-4-methoxyphenyl)-2-methoxypyridine

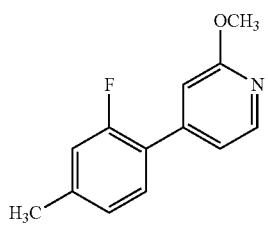

Chemical Formula: C₁₃H₁₂FNO₂
Exact Mass: 233.09
Molecular Weight: 233.24

4-Bromo-2-methoxypyridine (1.39 g, 7.42 mmol), 2-fluoro-4methoxyphenylboronic acid (2.40 g, 14.1 mmol), K₂CO₃ (2.05 g, 14.8 mmol) and bis(triphenylphosphine)palladium(II)chloride (Pd(PPh₃)₂Cl₂) (52 mg, 0.74 mmol) were stirred in DMSO (8.5 mL) under vacuum for 20 min. The flask was flushed with argon and the mixture was heated to 90° C. for 3 h. Upon cooling, the mixture was diluted with brine, and the aqueous solution was extracted with CH₂Cl₂ (3×50 mL). The combined organic extracts were washed with water (3×20 mL), dried over Na₂SO₄ and concentrated under reduced pressure. Flash chromatography (40+M Biotage column, CH₂Cl₂/(80:18:2 CH₂Cl₂/MeOH/ NH₄OH), 100:0 to 80:20) provided the title compound (0.98 g, 57%) as a yellow oil: ¹H NMR (500 MHz, CDCl₃) δ 8.20 (d, J=5.4 Hz, 1H), 7.42-7.38 (m, 1H), 7.07 (d, J=5.4 Hz, 1H), 6.93 (s, 1H), 6.80 (dd, J=8.6, 2.5 Hz, 1H), 6.74 (dd, J=12.6, 2.5 Hz, 1H), 3.99 (s, 3H), 3.85 (s, 3H).

b) 4-(2-Fluoro-4-methoxyphenyl)pyridin-2(1H)-one

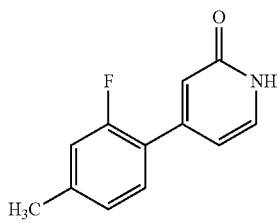

Chemical Formula: C₁₂H₁₀FNO₂
Exact Mass: 219.07
Molecular Weight: 219.21

4-(2-Fluoro-4-methoxyphenyl)-2-methoxypyridine (1.34 g, 5.72 mmol) was stirred in concentrated hydrochloric acid (25.5 mL) at reflux for 18 h. The reaction was cooled to 0° C. and neutralized with solid NaOH. The resulting solids were collected by filtration and dried under vacuum to yield the title compound (1.09 g, 87%) as a light brown solid: ¹H NMR (300 MHz, DMSO-d₆) δ 7.52-7.38 (m, 2H), 6.97-6.85 (m, 2H), 6.42-6.33 (m, 2H), 3.80 (s, 3H); ESI MS m/z 220 [M+H]⁺.

c) tert-Butyl-7(4(2-fluoro-4-methoxyphenyl)-2-oxopyridin-2(1H)-yl)-9-methyl-3,4-dihydro-1H-pyrido[3,4-b]indole-2(9H)-carboxylate

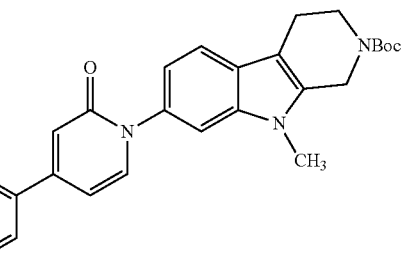

Chemical Formula: C₂₉H₃₀FN₃O₄
Exact Mass: 503.22
Molecular Weight: 503.56

Following the procedure of Example 133 (step b), but substituting 4-(2-fluoro-4-methoxyphenyl)pyridin-2(1H)-one (359 mg, 1.64 mmol) for 4-benzyloxypyridone, the title compound (288 mg, 41%) was prepared as a yellow foam: ¹H NMR (500 MHz, DMSO-d₆) δ 7.71 (d, J=7.1 Hz, 1H), 7.61 (m, 1H), 7.55 (d, J=1.6 Hz, 1H), 7.51 (d, J=8.3 Hz, 1H), 7.04-6.99 (m, 2H), 6.94 (dd, J=6.9, 2.5 Hz, 1H), 6.61 (s, 1H), 6.51-6.50 (m, 1H), 4.64 (s, 2H), 3.84 (s, 3H), 3.69-3.67 (m, 5H), 2.74-2.72 (m, 2H), 1.45 (s, 9H).

d) 4-(2-Fluoro-4-methoxyphenyl)-1-(9-methyl-2,3,4, 9-tetrahydro-1H-pyrido[3,4-b]indol-7-yl)pyridin-2 (1H)-one

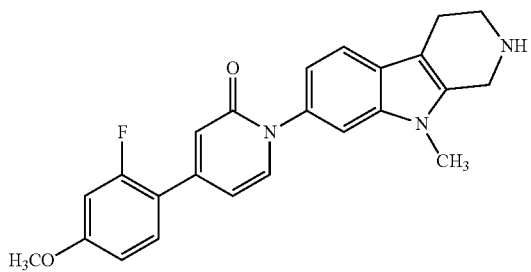

Chemical Formula: C₂₄H₂₂FN₃O₂
Exact Mass: 403.17
Molecular Weight: 403.45

Trifluoroacetic acid (1.0 mL) was added to a solution of tert-butyl-7(4(2-fluoro-4-methoxyphenyl)-2-oxopyridin-2 (1H)-yl)-9-methyl-3,4-dihydro-1H-pyrido[3,4-b]indole-2 (9H)-carboxylate (0.28 g, 0.56 mmol) in CH₂Cl₂ (5 mL) under argon and stirred for 1 h. The mixture was concentrated, and the residue was partitioned between CH₂Cl₂ and saturated NaHCO₃ solution. The organic phase was removed, and the aqueous phase was extracted with CH₂Cl₂. The combined organic extracts were dried over Na₂SO₄ and concentrated under reduced pressure. Preparative HPLC (Phenomenex Luna C18 (2), 250.0×50.0 mm, 10 micron, H₂O with 0.05% TFA and CH₃CN with 0.05% TFA) provided the title compound (87 mg, 39%) as a yellow solid: ¹H NMR (500 MHz, DMSO-d₆) δ 7.71 (d, J=7.1 Hz, 1H), 7.61 (m, 1H), 7.49-7.46 (m, 2H), 7.02-6.99 (m, 2H), 6.93 (dd, J=8.7, 2.1 Hz, 1H), 6.60 (s, 1H), 6.50 (d, J=7.1 Hz, 1H), 3.96 (m, 2H), 3.84 (s, 3H), 3.61 (s, 3H), 3.01-2.99 (m, 2H), 2.66 (m, 2H); ESI MS m/z 404 [M+H]⁺.

e) 4-(2-Fluoro-4-methoxyphenyl)-1-(9-methyl-2,3,4, 9-tetrahydro-1H-pyrido[3,4-b]indol-7-yl)pyridin-2 (1H)-one hydrochloride

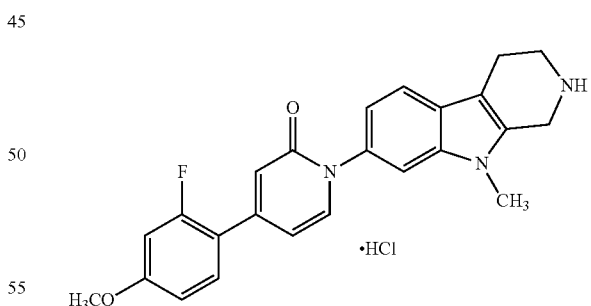

Chemical Formula: C₂₄H₂₃ClFN₃O₂
Exact Mass: 439.15
Molecular Weight: 439.91

A solution of 4-(2-fluoro-4-methoxyphenyl)-1-(9-methyl-2,3,4,9-tetrahydro-1H-pyrido[3,4-b]indol-7-yl)pyridin-2 (1H)-one (80 mg, 0.20 mmol) in CH₂Cl₂ (2.6 mL) was treated with anhydrous 1.0 M HCl in diethyl ether (0.22 mL, 0.22 mmol). The reaction was stirred at ambient temperature for 1 h, and then the solids were collected by filtration and dried to yield the title compound (68 mg, 77%) as a yellow solid: mp 290-292° C.; $^1$H NMR (500 MHz, DMSO-$d_6$) δ 9.54 (s, 2H), 7.71 (d, J=7.2 Hz, 1H), 7.62-7.58 (m, 3H), 7.10 (dd, J=8.3, 1.8 Hz, 1H), 7.01 (dd, J=13.2, 2.4 Hz, 1H), 6.94 (dd, J=8.6, 2.3 Hz, 1H), 6.62 (s, 1H), 6.53-6.52 (m, 1H), 4.48 (s, 2H), 3.95 (s, 3H), 3.69 (s, 3H), 3.45-3.44 (m, 2H), 3.00-2.97 (m, 2H); ESI MS m/z 404 [M+H]$^+$; HPLC (Method A)>99% (AUC), $t_R$=14.6 min.

Example 136

Preparation of 1-(2,9-Dimethyl-2,3,4,9-tetrahydro-1H-pyrido[3,4-b]indol-7-yl)-4-(2-fluoro-4-methoxyphenyl)pyridin-2(1H)-one hydrochloride a) 1-(2,9-Dimethyl-2,3,4,9-tetrahydro-1H-pyrido[3,4-b]indol-7-yl)-4-(2-fluoro-4-methoxyphenyl)pyridin-2(1H)-one

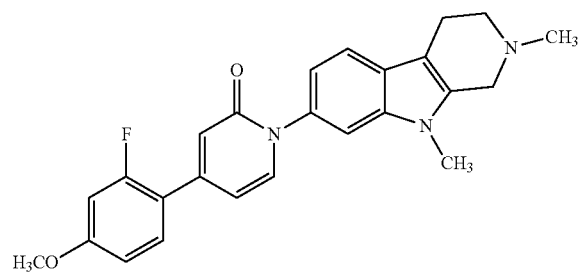

Chemical Formula: C$_{25}$H$_{24}$FN$_3$O$_2$
Exact Mass: 417.19
Molecular Weight: 417.48

Following the procedure of Example 134 (step a), but substituting 4-(2-fluoro-4-methoxyphenyl)-1-(9-methyl-2,3,4,9-tetrahydro-1H-pyrido[3,4-b]indol-7-yl)pyridin-2(1H)-one (57 mg, 0.14 mmol) for (4-benzyloxy)-1-(9-(difluoromethyl)-2,3,4,9-tetrahydro-1H-pyrido[4,3-b]indol-7-yl)pyridin-2(1H)-one, the title compound (35 mg, 59%) was provided as an off-white solid: $^1$H NMR (500 MHz, DMSO-$d_6$) δ 7.71 (d, J=7.0 Hz, 1H), 7.61 (m, 1H), 7.51 (d, J=1.8 Hz, 1H), 7.48 (d, J=8.3 Hz, 1H), 7.02-6.99 (m, 2H), 6.94 (dd, J=8.6, 2.4 Hz, 1H), 6.60 (s, 1H), 6.53-6.52 (m, 1H), 3.84 (s, 3H), 3.62 (m, 5H), 2.74-2.70 (m, 4H), 2.46 (s, 3H).

b) 1-(2,9-Dimethyl-2,3,4,9-tetrahydro-1H-pyrido[3,4-b]indol-7-yl)-4-(2-fluoro-4-ethoxyphenyl)pyridin-2(1H)-one hydrochloride

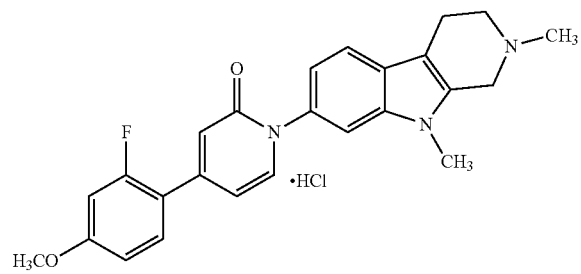

Chemical Formula: C$_{25}$H$_{25}$ClFN$_3$O$_2$
Exact Mass: 453.16
Molecular Weight: 453.94

Following the procedure of Example 134 (step b), but substituting 1-(2,9-dimethyl-2,3,4,9-tetrahydro-1H-pyrido[3,4-b]indol-7-yl)-4-(2-fluoro-4-methoxyphenyl)pyridin-2(1H)-one (35 mg, 0.84 mmol) for (4-benzyloxy)-1-(9-(difluoromethyl)-2-methyl-2,3,4,9-tetrahydro-1H-pyrido[3,4-b]indol-7-yl)pyridin-2(1H)-one, the title compound (33 mg, 87%) was provided as a yellow solid: mp 290-294° C.; $^1$H NMR (500 MHz, DMSO-$d_6$) δ 10.71 (s, 1H), 7.71 (d, J=7.2 Hz, 1H), 7.63-7.59 (m, 3H), 7.11 (dd, J=8.3, 1.6 Hz, 1H), 7.01 (dd, J=13.2, 2.4 Hz, 1H), 6.94 (dd, J=8.7, 2.4 Hz, 1H), 6.62 (s, 1H), 6.53-6.52 (m, 1H), 4.80-4.77 (m, 1H), 4.45-4.43 (m, 1H), 3.84 (s, 3H), 3.73 (br s, 1H), 3.68 (s, 3H), 3.42-3.34 (m, 1H), 3.07-3.06 (m, 2H), 3.00 (s, 3H); ESI MS m/z 418 [M+H]$^+$; HPLC (Method A) 97.0% (AUC), $t_R$=14.0 min.

Example 137

Preparation of 4-(Imidazo[1,2-α]pyridin-2-ylmethoxy)-1-(9-methyl-2,3,4,9-tetrahydro-1H-pyrido[3,4-b]indol-7-yl)pyridin-2(1H)-one hydrochloride a) 4-(Imidazo[1,2-α]pyridin-2-ylmethoxy)pyridine 1-oxide

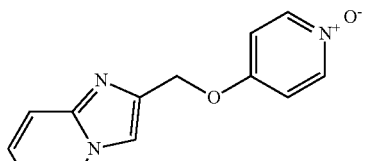

Chemical Formula: C$_{13}$H$_{11}$N$_3$O$_2$
Exact Mass: 241.09
Molecular Weight: 241.25

Imidazo[1,2-α]pyridine-2-ylmethanol (3.01 g, 20.3 mmol) was partially dissolved in 5:1 dioxane/DMF (30 mL) and the resulting slurry was added slowly to a stirring suspension of NaH (60% in mineral oil, 0.812 g, 16.9 mmol) in dioxane (29 mL). The resulting mixture was heated to 60° C. for 15 min. 4-Chloropyridine-N-oxide (1.5 g, 11.5 mmol) was added and the reaction mixture was heated for 1 h at 110° C. Upon cooling, the mixture was diluted with methylene chloride and a 20% NH$_4$OH in MeOH solution. The resulting suspension was filtered through a silica gel plug using CH$_2$Cl$_2$ (200 mL) and 20% 4:1 MeOH/NH$_4$OH in CH$_2$Cl$_2$ (500 mL). The filtrate was collected and concentrated under reduced pressure. Flash chromatography (120 g ISCO column, CH$_2$Cl$_2$/(80:18:2 CH$_2$Cl$_2$/MeOH/NH$_4$OH), 100:0 to 0:100 over 60 min) provided the title compound (1.5 g, 30%) as an orange-brown solid: $^1$H NMR (300 MHz, CD$_3$OD) δ 8.42 (m, 1H), 8.24-8.22 (m, 2H), 7.97 (d, J=0.5 Hz, 1H), 7.54 (dd, J=9.1, 0.7 Hz, 1H) 7.37-7.32 (m, 1H), 7.27-7.25 (m, 2H), 6.94 (m, 1H), 5.37 (s, 2H).

b) 4-(Imidazo[1,2-α]pyridin-2-ylmethoxy)pyridine-2(1H)-one

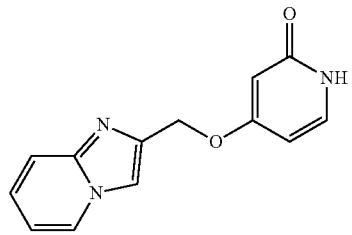

Chemical Formula: C₁₃H₁₁N₃O₂
Exact Mass: 241.09
Molecular Weight: 241.25

4-(Imidazo[1,2-α]pyridin-2-ylmethoxy)pyridine 1-oxide (1.50 g, 6.25 mmol) was heated at 140° C. in acetic anhydride (18 mL) for 2 h. The mixture was concentrated and heated at 80° C. for 2 h in 1:1 MeOH/H₂O (50 mL). The resulting black solution was concentrated. The material was then partially dissolved in iPrOH (20 mL). Et₂O (70 mL) was added, and the mixture was allowed to sit at ambient temperature for 1 h. The resulting solids were collected by filtration and washed with Et₂O to yield the title compound (951 mg, 63%) as a dark brown solid: ¹H NMR (300 MHz, DMSO-d₆) δ 11.08 (br s, 1H), 8.54 (m, 1H), 8.01 (s, 1H), 7.53 (d, J=9.0 Hz, 1H), 7.26-7.23 (m, 2H), 6.90 (m, 1H), 5.89-5.87 (m, 2H), 5.14 (s, 2H).

c) tert-Butyl-7-(4-(imidazo[1,2-α]pyridin-2-yl-methoxy)-2-oxopyridin-1(2H)-yl)-9-methyl-3,4-dihydro-1H-pyrido[3,4-b]indole-2(9H)-carboxylate

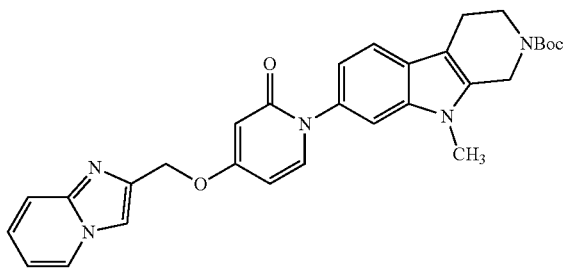

Chemical Formula: C₃₀H₃₁N₅O₄
Exact Mass: 525.24
Molecular Weight: 525.60 tert-Butyl-7-bromo-9-methyl-3,4-dihydro-1H-pyrido[3,4-b]indole-2(9H)-carboxylate (0.328 g, 0.898 mmol), 4-(imidazo[1,2-α]pyridin-2-ylmethoxy)pyridine-2(1H)-one (0.240 g, 0.998 mmol) and Cs₂CO₃ (0.358 g, 1.09 mmol) were suspended in DMSO (4.0 mL), and argon was bubbled through the system for 10 minutes. 8-Hydroxyquinoline (43.4 mg, 0.299 mmol) and copper iodide (228 mg, 1.20 mmol) were added, and resulting suspension was placed under vacuum for 15 min. The system was flushed with argon. The evacuation/argon flushing process was repeated a total of three times. The reaction mixture was heated at 130° C. for 18 h under argon. The mixture was cooled, and a solution of 20% NH₄OH in MeOH (40 mL) was added. The resulting mixture was stirred for 1 h. The mixture was diluted with CH₂Cl₂ and filtered through a silica gel plug. The filtrate was collected and concentrated. The residue was diluted with CH₂Cl₂, washed with brine (3×25 mL), dried over Na₂SO₄ and concentrated under reduced pressure. Purification by flash column chromatography (80 g ISCO column, (1:1 hexanes/EtOAc)/(80:18:2 CH₂Cl₂/MeOH/NH₄OH), 80:20 to 0:100:0 over 10 column volumes and then hold for 8 column volumes) gave the title compound (0.190 g, 40%) as a yellow foam: ¹H NMR (500 MHz, DMSO-d₆) δ 8.12 (d, J=6.8 Hz, 1H), 7.69 (s, 1H), 7.61 (d, J=9.1 Hz, 1H), 7.52 (d, J=8.3 Hz, 1H), 7.31-7.29 (m, 2H), 7.22-7.19 (m, 1H), 7.02 (dd, J=8.3, 1.7 Hz, 1H), 6.83-6.80 (m, 1H), 6.17 (d, J=2.7 Hz, 1H), 6.07 (dd, J=7.6, 2.7 Hz, 1H), 5.25 (s, 2H), 4.64 (m, 2H), 3.75 (m, 2H), 3.63 (s, 3H), 2.80 (m, 2H), 1.52 (s, 9H), ESI MS m/z 526 [M+H]⁺.

d) 4-(Imidazo[1,2-α]pyridin-2-ylmethoxy)-1-(9-methyl-2,3,4,9-tetrahydro-1H-pyrido[3,4-b]indol-7-yl)pyridin-2(1H)-one

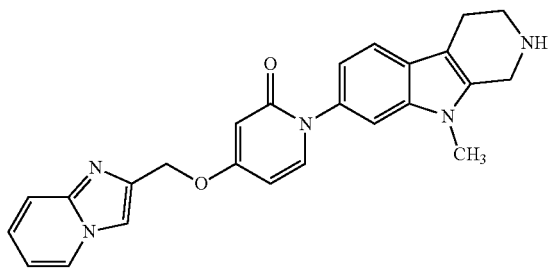

Chemical Formula: C₂₅H₂₃N₅O₂
Exact Mass: 425.19
Molecular Weight: 425.48

Following the procedure of Example 135 (step d), but substituting tert-butyl-7-(4-(imidazo[1,2-α]pyridin-2-yl-methoxy)-2-oxopyridin-1(2H)-yl)-9-methyl-3,4-dihydro-1H-pyrido[3,4-b]indole-2(9H)-carboxylate (190 mg, 362 mmol) for tert-butyl-7(4(2-fluoro-4-methoxyphenyl)-2-oxopyridin-2(1H)-yl)-9-methyl-3,4-dihydro-1H-pyrido[3,4-b]indole-2(9H)-carboxylate, the title compound (0.105 g, 68%) was prepared as a yellow film: ¹H NMR (500 MHz, CD₃OD) δ 8.45-8.43 (m, 1H), 7.98 (s, 1H), 7.59-7.54 (m, 3H), 7.41 (d, J=1.8 Hz, 1H), 7.37-7.33 (m, 1H), 7.02 (dd, J=8.3, 1.8 Hz, 1H), 6.96-6.94 (m, 1H), 6.29 (dd, J=7.6, 2.7 Hz, 1H), 6.21 (d, J=2.7 Hz, 1H), 5.31 (s, 2H), 3.96 (s, 2H), 3.68 (s, 3H), 3.42 (t, J=6.0 Hz, 2H), 3.00 (t, J=6.0 Hz, 2H); ESI MS m/z 426 [M+H]⁺.

e) 4-(Imidazo[1,2-α]pyridin-2-ylmethoxy)-1-(9-methyl-2,3,4,9-tetrahydro-1H-pyrido[3,4-b]indol-7-yl)pyridin-2(1H)-one-hydrochloride

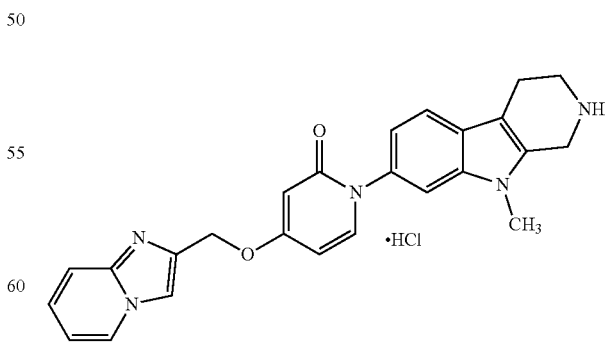

Chemical Formula: C₂₅H₂₄ClN₅O₂
Exact Mass: 461.16
Molecular Weight: 461.94

Following the procedure of Example 134 (step b), but substituting 4-(imidazo[1,2-α]pyridin-2-ylmethoxy)-1-(9-methyl-2,3,4,9-tetrahydro-1H-pyrido[3,4-b]indol-7-yl)pyridin-2(1H)-one (102 mg, 0.240 mmol) for (4-benzyloxy)-1-(9-(difluoromethyl)-2-methyl-2,3,4,9-tetrahydro-1H-pyrido[3,4-b]indol-7-yl)pyridin-2(1H)-one, the title compound (95 mg, 86%) was prepared as a yellow solid: $^1$H NMR (500 MHz, CD$_3$OD) δ 8.81 (d, J=7.0, 1.0 Hz, 1H), 8.38 (s, 1H), 8.02-7.99 (m, 1H), 7.92 (d, J=9.5 Hz, 1H), 7.66-7.62 (m, 2H), 7.52-7.49 (m, 1H), 7.46 (s, 1H), 7.05 (d, J=7.0 Hz, 1H), 6.33 (dd, J=7.5, 3.0 Hz, 1H), 6.23 (d, J=3.0 Hz, 1H), 5.50 (s, 2H), 4.55 (s, 2H), 3.72 (s, 3H), 3.60 (t, J=6.0 Hz, 2H), 3.14-3.12 (m, 2H); ESI MS m/z 426 [M+H]$^+$; HPLC (Method A) 98.5% (AUC), t$_R$=9.2 min.

Example 138

Preparation of 1-(2,9-Dimethyl-2,3,4,9-tetrahydro-1H-pyrido[3,4-b]indol-7-yl)-4-(imidazo[1,2-α]pyridin-2-ylmethoxy)pyridin-2(1H)-one hydrochloride a) 1-(2,9-Dimethyl-2,3,4,9-tetrahydro-1H-pyrido[3,4-b]indol-7-yl)-4-(imidazo[1,2-α]pyridin-2-ylmethoxy)pyridin-2(1H)-one

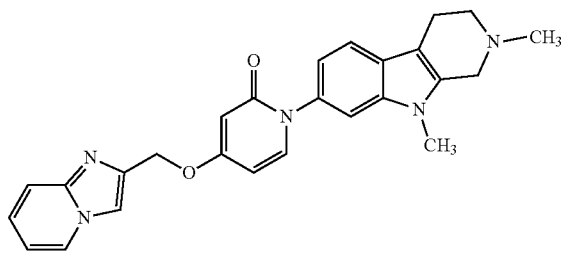

Chemical Formula: C$_{26}$H$_{25}$N$_5$O$_2$
Exact Mass: 439.20
Molecular Weight: 439.51

Following the procedure of Example 134 (step a), but substituting 4-(imidazo[1,2-α]pyridin-2-ylmethoxy)-1-(9-methyl-2,3,4,9-tetrahydro-1H-pyrido[3,4-b]indol-7-yl)pyridin-2(1H)-one (57 mg, 0.14 mmol) for (4-benzyloxy)-1-(9-(difluoromethyl)-2,3,4,9-tetrahydro-1H-pyrido[4,3-b]indol-7-yl)pyridin-2(1H)-one, the title compound (25 mg, 62%) was prepared as a yellow solid: $^1$H NMR (500 MHz, DMSO-d$_6$) δ 7.54 (d, J=7.5 Hz, 1H), 7.47-7.36 (m, 7H), 6.95 (dd, J=8.5, 1.5 Hz, 1H), 6.10 (dd, J=7.5, 2.5 Hz, 1H), 5.96 (d, J=3.0 Hz, 1H), 5.15 (s, 2H), 3.64 (m, 4H), 3.18-3.16 (m, 1H), 3.05-3.02 (m, 1H), 2.90-2.84 (m, 4H), 2.42-2.39 (m, 1H), 2.00-1.92 (m, 1H).

b) 1-(2,9-Dimethyl-2,3,4,9-tetrahydro-1H-pyrido[3,4-b]indol-7-yl)-4-(imidazo[1,2-α]pyridin-2-ylmethoxy)pyridin-2(1H)-one hydrochloride

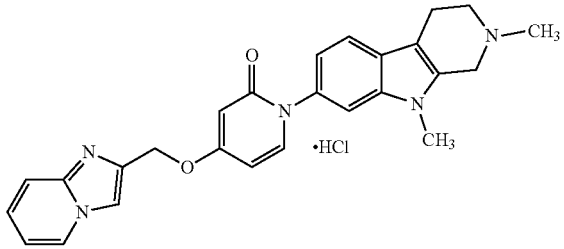

Chemical Formula: C$_{26}$H$_{26}$ClN$_5$O$_2$
Exact Mass: 475.18
Molecular Weight: 475.97

Following the procedure of Example 134 (step b), but substituting 1-(2,9-dimethyl-2,3,4,9-tetrahydro-1H-pyrido[3,4-b]indol-7-yl)-4-(imidazo[1,2-α]pyridin-2-ylmethoxy)pyridin-2(1H)-one (25 mg, 0.056 mmol) for (4-benzyloxy)-1-(9-(difluoromethyl)-2-methyl-2,3,4,9-tetrahydro-1H-pyrido[3,4-b]indol-7-yl)pyridin-2(1H)-one, the title compound (27 mg, 98%) was prepared as a yellow solid: $^1$H NMR (500 MHz, DMSO-d$_6$) δ 10.91 (br s, 1H), 8.86 (d, J=6.0 Hz, 1H), 8.39 (s, 1H), 7.87-7.79 (m, 2H), 7.61 (d, J=7.5 Hz, 1H), 7.57 (d, J=8.0 Hz, 1H), 7.51 (s, 1H), 7.37-7.35 (m, 1H), 7.01 (dd, J=8.5, 1.0 Hz, 1H), 6.15-6.11 (m, 2H), 5.42 (s, 2H), 4.77 (d, J=15.0 Hz, 1H), 4.43 (dd, J=14.0, 6.0 Hz, 1H), 3.80-3.77 (m, 1H), 3.66 (s, 3H), 3.41-3.39 (m, 1H), 3.08-3.04 (m, 2H), 2.99 (s, 3H); ESI MS m/z 440 [M+H]$^+$; HPLC (Method A) 97.1% (AUC), t$_R$=9.8 min.

Example 139

Preparation of 1-(2,9-Dimethyl-2,3,4,9-tetrahydro-1H-pyrido[3,4-b]indol-7-yl)-4-(4-(trifluoromethyl)benzyloxy)pyridin-2(1H)-one hydrochloride a) 4-(Imidazo[1,2-α]pyridin-6-ylmethoxy)pyridine 1-oxide

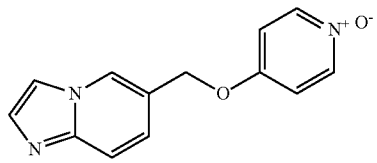

Chemical Formula: C$_{13}$H$_{11}$N$_3$O$_2$
Exact Mass: 241.09
Molecular Weight: 241.25

Following the procedure of Example 137 (step a), but substituting imidazo[1,2-α]pyridine-6-ylmethanol (2.91 g, 19.6 mmol) for imidazo[1,2-α]pyridine-2-ylmethanol, the title compound (1.69 g, 42%) was prepared as an orange solid: $^1$H NMR (300 MHz, DMSO-d$_6$) δ 8.70 (s, 1H), 8.13-8.10 (m, 2H), 7.97 (s, 1H), 7.60-7.59 (m, 2H), 7.30 (dd, J=9.3, 1.7 Hz, 1H), 7.14-7.11 (m, 2H), 5.18 (s, 2H).

b) 4-(Imidazo[1,2-α]pyridin-6-ylmethoxy)pyridine-2(1H)-one

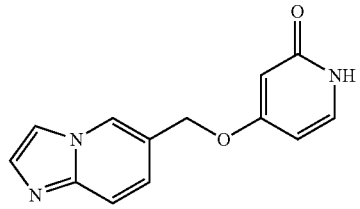

Chemical Formula: C₁₃H₁₁N₃O₂
Exact Mass: 241.09
Molecular Weight: 241.25

4-(Imidazo[1,2-α]pyridin-6-ylmethoxy)pyridine 1-oxide (1.69 g, 7.04 mmol) was heated at 140° C. in acetic anhydride (20 mL) for 4 h. The mixture was concentrated and heated at 80° C. for 3 h in a mixture of 1:1 MeOH/H₂O (50 mL). The resulting solution was concentrated. The residue was partially dissolved in iPrOH (75 mL). Et₂O (200 mL) was added, and the mixture was allowed to sit at ambient temperature for 1 h. The resulting solids were collected by filtration, washed with Et₂O and dried under reduced pressure. The solids were again subjected to iPrOH and Et₂O, and the solids were removed by filtration. The filtrate was concentrated to afford the title compound (0.47 g, 28%) as a dark brown solid: ¹H NMR (300 MHz, CD₃OD) δ 8.60 (d, J=0.7 Hz, 1H), 7.87 (d, J=0.6 Hz, 1H), 7.59 (d, J=1.4 Hz, 1H), 7.57 (s, 1H), 7.40-7.27 (m, 2H), 6.18 (dd, J=7.3, 2.5 Hz, 1H), 6.05 (d, J=2.5 Hz, 1H), 5.13 (s, 2H).

c) tert-Butyl-7-(4-(imidazo[1,2-α]pyridin-6-ylmethoxy)-2-oxopyridin-1(2H)-yl)-9-methyl-3,4-dihydro-1H-pyrido[3,4-b]indole-2(9H)-carboxylate

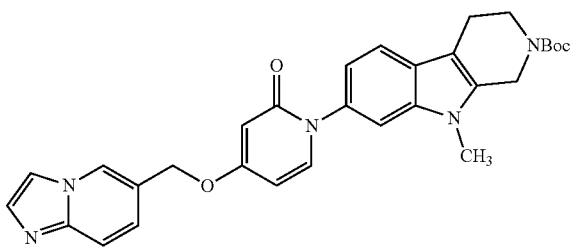

Chemical Formula: C₃₀H₃₁N₅O₄
Exact Mass: 525.24
Molecular Weight: 525.60

Following the procedure of Example 133 (step b), but substituting 4-(imidazo[1,2-α]pyridin-6-ylmethoxy)pyridine-2(1H)-one (218 mg, 0.901 mmol) for 4-benzyloxypyridone, the title compound (112 mg, 26%) was prepared as a yellow solid: ¹H NMR (500 MHz, CDCl₃) δ 8.25 (s, 1H), 7.68-7.65 (m, 2H), 7.64-7.61 (m, 1H), 7.53-7.52 (m, 1H), 7.33 (d, J=7.6 Hz, 1H), 7.28-7.26 (m, 1H), 7.22 (dd, J=9.3, 1.5 Hz, 1H), 7.01 (dd, J=8.2, 1.8 Hz, 1H), 6.11 (d, J=2.7 Hz, 1H), 6.03 (dd, J=7.5, 2.7 Hz, 1H), 5.06-5.04 (m, 2H), 4.70-4.57 (m, 2H), 3.75 (m, 2H), 3.62 (s, 3H), 2.79 (m, 2H), 1.51 (s, 9H).

d) 4-(Imidazo[1,2-α]pyridin-6-ylmethoxy)-1-(9-methyl-2,3,4,9-tetrahydro-1H-pyrido[3,4-b]indol-7-yl)pyridin-2(1H)-one hydrochloride

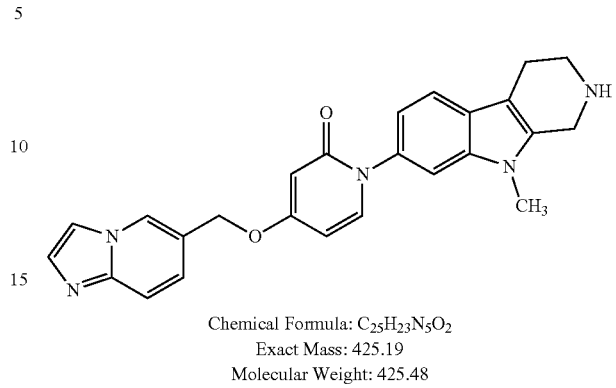

Chemical Formula: C₂₅H₂₃N₅O₂
Exact Mass: 425.19
Molecular Weight: 425.48

Following the procedure of Example 135 (step d), but substituting tert-butyl-7-(4-(imidazo[1,2-α]pyridin-6-ylmethoxy)-2-oxopyridin-1(2H)-yl)-9-methyl-3,4-dihydro-1H-pyrido[3,4-b]indole-2(9H)-carboxylate (112 mg, 0.213 mmol) for tert-butyl-7(4(2-fluoro-4-methoxyphenyl)-2-oxopyridin-2(1H)-yl)-9-methyl-3,4-dihydro-1H-pyrido[3,4-b]indole-2(9H)-carboxylate, the crude title compound was prepared. Preparative HPLC (Phenomenex Luna C18 (2), 250.0×21.2 mm, 10 micron, H₂O with 0.05% TFA and CH₃CN with 0.05% TFA) yielded the title compound (12 mg, 13%) as an off-white film: ¹H NMR (500 MHz, CDCl₃) δ 8.24 (s, 1H), 7.67-7.65 (m, 2H), 7.59 (s, 1H), 7.53 (d, J=8.3 Hz, 1H), 7.34 (d, J=7.6 Hz, 1H), 7.26 (m, 1H overlapping with solvent), 7.22 (dd, J=9.3, 1.6 Hz, 1H), 7.00 (dd, J=8.3, 1.8 Hz, 1H), 6.11 (d, J=2.7 Hz, 1H), 6.03 (dd, J=7.6, 2.7 Hz, 1H), 5.04 (s, 2H), 4.04 (s, 2H), 3.57 (s, 3H), 3.17 (t, J=5.6 Hz, 2H), 2.76 (t, J=5.6 Hz, 2H).

e) 4-(Imidazo[1,2-α]pyridin-6-ylmethoxy)-1-(9-methyl-2,3,4,9-tetrahydro-1H-pyrido[3,4-b]indol-7-yl)pyridin-2(1H)-one hydrochloride

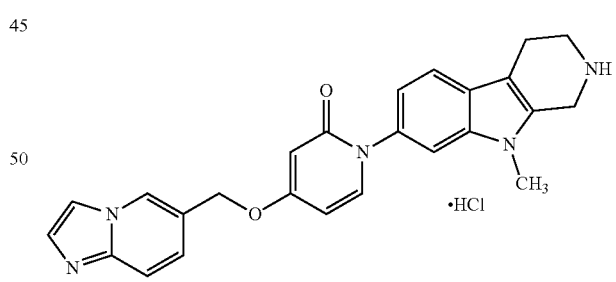

Chemical Formula: C₂₅H₂₄ClN₅O₂
Exact Mass: 461.16
Molecular Weight: 461.94

Following the procedure of Example 134 (step b), but substituting 4-(imidazo[1,2-α]pyridin-6-ylmethoxy)-1-(9-methyl-2,3,4,9-tetrahydro-1H-pyrido[3,4-b]indol-7-yl)pyridin-2(1H)-one (12 mg, 0.028 mmol) for (4-benzyloxy)-1-(9-(difluoromethyl)-2-methyl-2,3,4,9-tetrahydro-1H-pyrido[3,4-b]indol-7-yl)pyridin-2(1H)-one, the title compound (14 mg, 100%) was prepared as a light yellow solid: ¹H NMR (500 MHz, DMSO-d₆) δ 9.55 (br s, 2H), 9.01 (s, 1H), 8.33

(s, 1H), 8.11 (s, 1H), 7.97 (d, J=9.2 Hz, 1H), 7.89 (d, J=9.2 Hz, 1H), 7.61 (d, J=7.6 Hz, 1H), 7.56 (d, J=8.4 Hz, 1H), 7.50 (d, J=1.6 Hz, 1H), 7.00 (dd, J=8.4, 1.7 Hz, 1H), 6.13 (dd, J=7.6, 2.7 Hz, 1H), 6.08 (d, J=2.7 Hz, 1H), 5.31 (s, 2H), 4.46 (m, 2H), 3.67 (s, 3H), 3.44 (m, 2H), 2.97 (t, J=5.7 Hz, 2H); ESI MS m/z 426 [M+H]$^+$; HPLC (Method A)>99% (AUC), $t_R$=9.7 min.

Example 140

Preparation of 4-(Benzyloxy)-1-(8-fluoro-2,5-dimethyl-2,3,4,5-tetrahydro-1H-pyrido[4,3-b]indol-7-yl)pyridin-2(1H)-one hydrochloride a) (3-Bromo-4-fluorophenyl)hydrazine hydrochloride

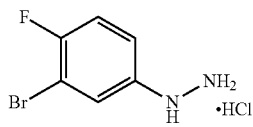

Chemical Formula: C$_6$H$_7$BrClFN$_2$
Exact Mass: 239.95
Molecular Weight: 241.49

A solution of sodium nitrite (4.2 g, 60 mmol) was added drop-wise to a mixture of 3-bromo-4-fluoroaniline (11.2 g, 58.9 mmol) and concentrated HCl (30 mL, 0.36 M) at 0° C. over 30 min. The resulting clear solution was stirred for 45 min, and a solution of SnCl$_2$.2H$_2$O (27 g, 120 mmol) in concentrated HCl (30 mL) was added drop-wise at 0° C. over 1.5 h. The mixture was stirred for 18 h at room temperature. The resulting precipitate was collected by filtration and crystallized from ethanol to provide the title compound (6.2 g, 42%) as a yellow powder: $^1$H NMR (300 MHz, DMSO-d$_6$) δ 10.24 (s, 3H), 8.42 (s, 1H), 7.36-7.30 (m, 2H), 7.03-6.98 (m, 1H).

b) 7-Bromo-8-fluoro-3,4-dihydro-1H-pyrido[4,3-b]indole-2(5H)-carboxylate

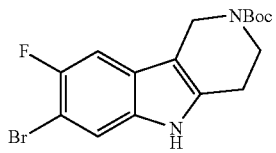

Chemical Formula: C$_{16}$H$_{18}$BrFN$_2$O$_2$
Exact Mass: 368.05
Molecular Weight: 369.23

A mixture of (3-bromo-4-fluorophenyl)hydrazine hydrochloride (3.0 g, 12 mmol), tert-butyl 4-oxopiperidine-1-carboxylate (2.48 g, 12.5 mmol) and concentrated HCl (6.0 mL, 72 mmol) in ethanol (40 mL) was stirred for 18 h at reflux. The solvent was removed under reduced pressure, the residue was suspended in dichloromethane (50 mL), and di-tert-butyl dicarbonate (3.3 g, 15 mmol) and triethylamine (2.1 mL, 30 mmol) were added. The mixture was stirred for 18 h at ambient temperature. The resulting clear solution was concentrated, and the residue was purified by flash chromatography (silica gel, hexanes/ethyl acetate, 1:0 to 1:1) to afford the title compound (0.9 g, 20%) as a yellow solid: $^1$H NMR (500 MHz, CDCl$_3$) δ 7.94 (br s, 1H), 7.45 (d, J=5.5 Hz, 1H), 7.14 (br s, 1H), 4.56 (br s 2H), 3.81 (br m 2H), 2.81 (br m 2H), 1.57 (s, 9H); ESI MS m/z 369 [M+H]$^+$.

c) tert-Butyl 7-bromo-8-fluoro-5-methyl-3,4-dihydro-1H-pyrido[4,3-b]indole-2(5H)-carboxylate

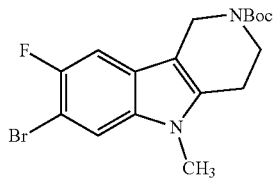

Chemical Formula: C$_{17}$H$_{20}$BrFN$_2$O$_2$
Exact Mass: 382.07
Molecular Weight: 383.26

Sodium hydride (60% weight dispersion in mineral oil, 150 mg, 3.66 mmol) was added to a solution of tert-butyl 7-bromo-8-fluoro-3,4-dihydro-1H-pyrido[4,3-b]indole-2(5H)-carboxylate (0.9 g, 2.44 mmol) in 20 ml of DMF, and the mixture was stirred for 40 min at ambient temperature. Iodomethane (0.25 mL, 3.66 mmol) was added, and the resulting suspension was stirred for 2 h. The resulting mixture was concentrated under reduced pressure to ~⅓ of initial volume and treated with water (20 mL). The resulting precipitate was collected by filtration, sequentially washed with water and diethyl ether and dried under vacuum to afford the title compound (0.75 g, 83%) as a yellow solid: $^1$H NMR (300 MHz, CDCl$_3$) δ 7.42 (d, J=5.4 Hz, 1H), 7.17 (d, J=9.3 Hz, 1H), 4.45 (br s, 2H), 3.81 (br m, 2H), 3.60 (s, 3H), 2.78 (br m, 2H), 1.52 (s, 9H); ESI MS m/z 383 [M+H]$^+$.

d) 4-(Benzyloxy)-1-(8-fluoro-5-methyl-2,3,4,5-tetrahydro-1H-pyrido[4,3-b]indol-7-yl)pyridin-2(1H)-one

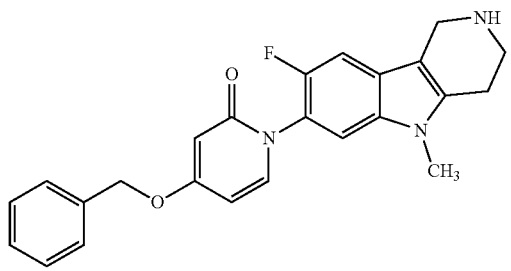

Chemical Formula: C$_{24}$H$_{22}$FN$_3$O$_2$
Exact Mass: 403.17
Molecular Weight: 403.45 tert-Butyl 7-bromo-8-fluoro-5-methyl-3,4-dihydro-1H-pyrido[4,3-b]indole-2(5H)-carboxylate (720 mg, 1.88 mmol), 4-benzyloxypyridone (380 mg, 1.9 mmol) and Cs$_2$CO$_3$ (680 mg, 2.1 mmol) were suspended in DMSO (8.0 mL) and the resulting suspension was degassed for 15 min. The system was flushed with Ar. Then 8-hydroxyquinoline (87 mg, 0.60 mmol) and copper iodide (114 mg, 0.599 mmol) were added. The degassing/Ar flushing process was repeated twice more, and the reaction mixture was heated at 133° C. for 18 h under argon. The reaction mixture was cooled, diluted with 15% solution of concentrated ammonium hydroxide in methanol (25 mL) and stirred at ambient temperature for 30 min. The reaction was further diluted with dichloromethane (75 mL). The solution was filtered through silica gel and concentrated under reduced pressure. The residue was diluted with CH$_2$Cl$_2$ and washed with H$_2$O (25 mL) and brine (3×50 mL). The combined organics were dried over Na$_2$SO$_4$ and concentrated to dryness. The crude material was purified by flash chromatography (silica gel, (1:1 hexanes/EtOAc)/(10:1:0.1 dichloromethane/methanol/concentrated ammonium hydroxide), 1:0 to 0:1) to afford crude tert-butyl 7-(4-(benzyloxy)-2-oxopyridin-1(2H)-yl)-8-fluoro-5-methyl-3,4-dihydro-1H-pyrido[4,3-b]indole-2(5H)-carboxylate (280 mg) as a yellow oil. This oil was dissolved in dichloromethane (3 mL) and TFA (1 mL) was added. The reaction mixture was stirred at ambient temperature for 1 h, concentrated and dried under vacuum overnight to provide the title compound (200 mg), which was used in the next step without further purification: ESI MS m/z 404 [M+H]$^+$.

e) 4-(Benzyloxy)-1-(8-fluoro-2,5-dimethyl-2,3,4,5-tetrahydro-1H-pyrido[4,3-b]indol-7-yl)pyridin-2(1H)-one hydrochloride

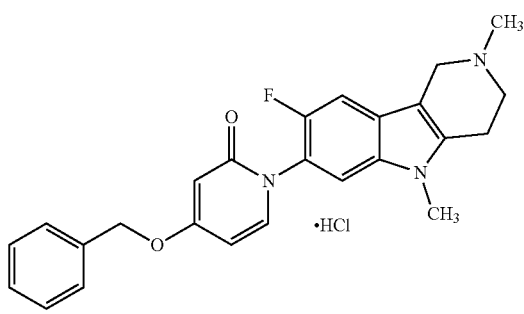

Chemical Formula: C$_{25}$H$_{25}$ClFN$_3$O$_2$
Exact Mass: 453.16
Molecular Weight: 453.94

To a solution of 4-(benzyloxy)-1-(8-fluoro-5-methyl-2,3,4,5-tetrahydro-1H-pyrido[4,3-b]indol-7-yl)pyridin-2(1H)-one (100 mg, 0.26 mmol) in dichloromethane/acetic acid (1% acetic acid, 10 mL) were sequentially added formaldehyde (37% aqueous solution, 22 µL, 0.74 mmol) and NaBH(OAc)$_3$ (316 mg, 1.49 mmol). The reaction mixture was stirred at room temperature for 2.5 h. The mixture was concentrated under reduced pressure, and the residue was dissolved in CH$_2$Cl$_2$. The organic layer was washed with H$_2$O and 5% aqueous LiCl, dried over Na$_2$SO$_4$, filtered and concentrated. Purification by flash chromatography (silica gel, CH$_2$Cl$_2$/(10:1:0.1 CH$_2$Cl$_2$/MeOH/NH$_4$OH), 0:1 to 1:1) gave 4-(benzyloxy)-1-(8-fluoro-2,5-dimethyl-2,3,4,5-tetrahydro-1H-pyrido[4,3-b]indol-7-yl)pyridin-2(1H)-one (78 mg, 38%) as a yellow solid. The free base was converted to the HCl salt using 1.25M HCl in methanol providing the title compound (75 mg, 95%) as a off-white solid: $^1$H NMR (300 MHz, CD$_3$OD) δ 7.53-7.33 (m, 7H), 7.27 (d, J=10.5 Hz, 1H), 7.28 (dd, J=7.8, 2.4 Hz, 1H), 6.10 (d, J=2.7 Hz, 1H), 5.17 (s, 2H), 3.79 (br s, 2H), 3.67 (s, 3H), 3.03-3.00 (m, 4H), 2.64 (s, 3H); ESI MS m/z 418 [M+H]$^+$; HPLC (Method A) 95.7% (AUC), $t_R$=14.5 min.

Example 141

Preparation of 4-(Benzyloxy)-1-(6-fluoro-9-methyl-2,3,4,9-tetrahydro-1H-pyrido[3,4-b]indol-7-yl)pyridin-2(1H)-one hydrochloride a) 2-(6-Bromo-5-fluoro-1H-indol-3-yl)ethanamine

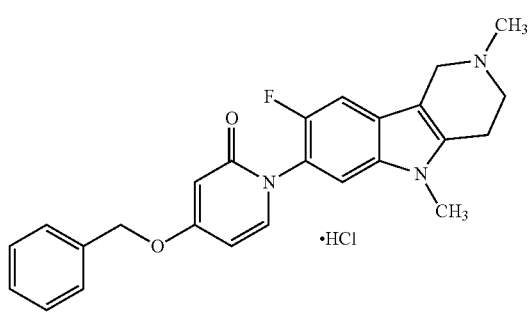

Chemical Formula: C$_{25}$H$_{25}$ClFN$_3$O$_2$
Exact Mass: 453.16
Molecular Weight: 453.94

4,4-Diethoxybutan-1-amine (4.72 g, 29.3 mmol) was added to (3-bromo-4-fluorophenyl)hydrazine hydrochloride (6.4 g, 27 mmol). The resulting mixture in an open round bottom flask was placed into a preheated oil bath at 180° C. The mixture was stirred at 180° C. for 2.5 h and then cooled to 120° C. Methanol (300 mL) was added, and the mixture was stirred at ambient temperature for 18 h. The resulting suspension was filtered through a silica gel plug, and the silica gel was then washed with methanol (5×300 mL). The combined methanol fractions were concentrated under vacuum to provide the crude title compound (8.1 g) as a yellow solid, which was used in the next step without further purification: ESI MS m/z 257 [M+H]$^+$.

b) tert-Butyl 7-bromo-6-fluoro-3,4-dihydro-1H-pyrido[3,4-b]indole-2(9H)-carboxylate

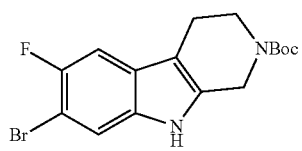

Chemical Formula: C$_{16}$H$_{18}$BrFN$_2$O$_2$
Exact Mass: 368.05
Molecular Weight: 369.23

Glyoxylic acid (8.6 g, 95 mmol) was added to a solution of 2-(6-bromo-5-fluoro-1H-indol-3-yl)ethanamine (8.1 g 31 mmol) in 2 N HCl (150 ml), and the pH of the resulting solution was adjusted to pH 3.5 with 6 N NaOH solution. The reaction mixture was stirred at ambient temperature for 18 h. The solution was adjusted to pH 5.5 with 6 N NaOH solution. The resulting precipitate was collected by filtration and dried under vacuum to afford a yellow solid. The yellow solid was suspended in 2 N HCl (100 mL), and the resulting mixture was stirred at reflux for 4.5 h. The reaction mixture was cooled to ambient temperature and was adjusted to pH 10 by addition of 2 N sodium hydroxide solution. The resulting precipitate was collected by filtration and dried under vacuum to afford a crude mixture of 7-bromo-6-fluoro-2,3,4,9-tetrahydro-1H-pyrido[3,4-b]indole and 6-bromo-7-fluoro-2,3,4,5-tetrahydro-1H-pyrido[4,3-b]indole (2.0 g, 23%) as a yellow solid. The mixture (1.9 g, 7.1 mmol) was suspended in dichloromethane (100 mL) and di-tert-butyl carbonate (1.85 g, 8.7 mmol) was added, followed by addition of DMAP (100 mg, 0.82 mmol). The reaction mixture was stirred at ambient temperature for 18 h and concentrated under vacuum. The residue was purified twice by column chromatography (silica gel, hexanes/ethyl acetate, 0:1 to 1:1) to afford the title compound (300 mg, 12%) as a pale yellow solid: $^1$H NMR (300 MHz, CDCl$_3$) δ 7.46 (d, J=5.7 Hz, 1H), 7.18 (d, J=9.0 Hz, 1H), 4.61 (s, 2H), 3.75 (br m, 2H), 2.73 (br m, 2H), 1.56 (s, 9H); ESI MS m/z 369 [M+H]$^+$.

c) tert-Butyl 7-bromo-6-fluoro-9-methyl-3,4-dihydro-1H-pyrido[3,4-b]indole-2(9H)-carboxylate

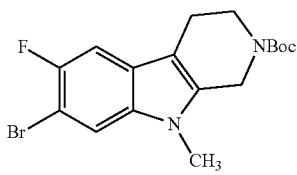

Chemical Formula: C$_{17}$H$_{20}$BrFN$_2$O$_2$
Exact Mass: 382.07
Molecular Weight: 383.26

Sodium hydride (60% weight dispersion in mineral oil, 25 mg, 0.60 mmol) was added to a solution of tert-butyl 7-bromo-6-fluoro-3,4-dihydro-1H-pyrido[3,4-b]indole-2(9H)-carboxylate (150 mg, 0.40 mmol) in DMF (10 mL) at room temperature under N$_2$ and stirred for 1 h at ambient temperature. Methyl iodide (230 mg, 0.16 mL, 0.60 mmol) was added, and the reaction mixture was stirred for 1 h. The resulting mixture was concentrated under reduced pressure to approximately ⅓ of initial volume and treated with water (20 mL). The resulting precipitate was collected by filtration, washed with water and diethyl ether and dried under vacuum to afford the title compound (140 mg, 91%) as a yellow powder: ESI MS m/z 383 [M+H]$^+$.

d) 4-(Benzyloxy)-1-(6-fluoro-9-methyl-2,3,4,9-tetrahydro-1H-pyrido[3,4-b]indol-7-yl)pyridin-2(1H)-one hydrochloride

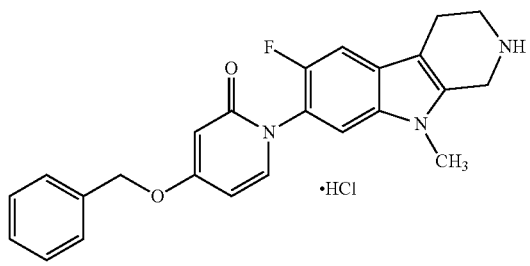

Chemical Formula: C$_{24}$H$_{23}$ClFN$_3$O$_2$
Exact Mass: 439.15
Molecular Weight: 439.91 tert-Butyl 7-bromo-6-fluoro-9-methyl-3,4-dihydro-1H-pyrido[3,4-b]indole-2(9H)-carboxylate (160 mg, 0.40 mmol), 4-benzyloxypyridone (80 mg, 0.33 mmol) and Cs$_2$CO$_3$ (390 mg, 0.38 mmol) were suspended in DMSO (8.0 mL) and degassed under vacuum for 15 min. The system was then flushed with Ar, and 8-hydroxyquinoline (30 mg, 0.18 mmol) and copper iodide (80 mg, 0.40 mmol) were added. The degassing/Ar flushing process was repeated twice, and the reaction mixture was heated at 133° C. for 18 h under argon. The mixture was cooled, diluted with 15% solution of concentrated ammonium hydroxide in methanol (25 mL) and stirred at ambient temperature for 30 min. The reaction was further diluted with CH$_2$Cl$_2$ (75 mL) and filtered through silica gel and concentrated. The concentrate was diluted with CH$_2$Cl$_2$ and washed with H$_2$O (25 mL) and brine (3×50 mL). The combined organics were dried over Na$_2$SO$_4$, filtered and concentrated under reduced pressure to dryness. The crude material was purified by flash chromatography (silica gel, (1:1 hexanes/EtOAc)/(10:1:0.1 dichloromethane/methanol/concentrated ammonium hydroxide), 1:0 to 0:1) to afford 75 mg of crude material containing the desired product. The crude mixture was dissolved in a mixture of dichloromethane and methanol (1:1, 5 mL), treated with TFA (2 mL) and stirred at ambient temperature for 30 min. The solvent was removed under reduced pressure, and the residue was neutralized by ion-exchange chromatography (SCX-2 column, 5 g). Purification by preparatory TLC (silica gel, 10:1:0.1 dichloromethane/methanol/concentrated ammonium hydroxide) provided the free base of the title compound (12 mg, 10%) as a white foam: ESI MS m/z 404 [M+H]$^+$. The free base was dissolved in methanol (25 mL) and treated with a solution of HCl (1.25 M in methanol, 0.1 mL, 0.13 mmol). The reaction mixture was sonicated for 5 min at ambient temperature. The mixture was concentrated, and the resulting residue was lyophilized from water (5 mL) to afford the title compound (14 mg, 8%) as a white powder: $^1$H NMR (500 MHz, DMSO-d$_6$) δ 9.56 (br s, 2H), 7.61 (d, J=6.0 Hz, 1H), 7.54 (d, J=7.5 Hz, 1H), 7.50-7.37 (m, 6H), 6.14-6.12 (m, 1H), 5.99 (s, 1H), 5.16 (s, 2H), 4.46 (br s, 2H), 3.67 (s, 3H), 3.43 (br m, 2H), 2.94 (m, 2H); ESI MS m/z 404 [M+H]$^+$; HPLC (Method A) 95.7% (AUC), t$_R$=14.8 min Example 142

Preparation of 4-(Benzyloxy)-1-(2-ethyl-9-methyl-2,3,4,9-tetrahydro-1H-pyrido[3,4-b]indol-7-yl)pyridin-2(1H)-one hydrochloride

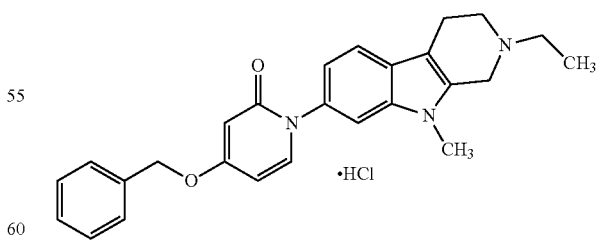

Chemical Formula: C$_{26}$H$_{28}$ClN$_3$O$_2$
Exact Mass: 449.19
Molecular Weight: 449.97

To a solution of 4-(benzyloxy)-1-(9-methyl-2,3,4,9-tetrahydro-1H-pyrido[3,4-b]indol-7-yl)pyridin-2(1H)-one hydrochloride (120 mg, 0.28 mmol) in dichloromethane/acetic acid (1% acetic acid, 10 mL) were sequentially added acetaldehyde (0.50 mL, 13 mmol) and NaBH(OAc)$_3$ (1.0 g, 4.7 mmol). The reaction mixture was stirred at ambient temperature for 1 h. The mixture was concentrated, and the residue was purified by flash chromatography (silica gel silica gel, (1:1 hexanes/EtOAc)/(10:1:0.1 dichloromethane/methanol/concentrated ammonium hydroxide), 1:0 to 0:1) to provide 4-(benzyloxy)-1-(2-ethyl-9-methyl-2,3,4,9-tetrahydro-1H-pyrido[3,4-b]indol-7-yl)pyridin-2(1H)-one (120 mg, 72%) as a white solid. The free base was converted to the HCl salt using 1.25 M HCl in methanol, providing the title compound (120 mg, 95%) as an off-white solid: $^1$H NMR (500 MHz, DMSO-d$_6$) δ 7.57 (d, J=7.5 Hz, 1H), 7.54-7.34 (m, 7H), 6.97 (d, J=8.0 Hz, 1H), 6.10 (dd, J=7.5, 2.0 Hz, 1H), 5.97 (s, 1H), 5.16 (s, 2H), 3.67 (s, 3H), 3.45-3.18 (4H, overlapping with solvent peak), 3.26 (br m, 2H), 2.96 (m, 2H), 1.33 (br m, 3H); ESI MS m/z 414 [M+H]$^+$; HPLC (Method A) 95.7% (AUC), t$_R$=14.6 min.

Example 143

Preparation of 4-(Benzyloxy)-1-(2-isopropyl-9-methyl-2,3,4,9-tetrahydro-1H-pyrido[3,4-b]indol-7-yl)pyridin-2(1H)-one hydrochloride

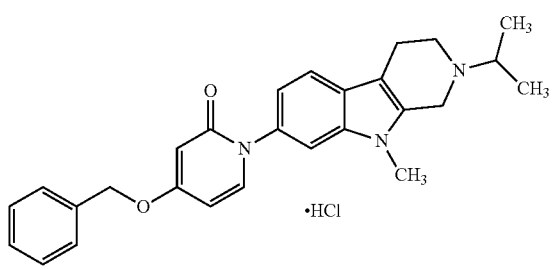

Chemical Formula: C$_{27}$H$_{30}$ClN$_3$O$_2$
Exact Mass: 463.20
Molecular Weight: 464.00

2-Bromopropane (1.5 mL, 16 mmol) was added to a mixture of 4-(benzyloxy)-1-(9-methyl-2,3,4,9-tetrahydro-1H-pyrido[3,4-b]indol-7-yl)pyridin-2(1H)-one hydrochloride (138 mg, 0.327 mmol) and Cs$_2$CO$_3$ (1.2 g, 3.7 mmol) in acetonitrile (25 mL). The mixture was stirred at 55° C. for 72 h. The resulting mixture was cooled, and the precipitate was filtered off. The mother liquor was concentrated under vacuum. The residue was purified by preparatory TLC (silica gel, 10:1:0.1 dichloromethane/methanol/concentrated ammonium hydroxide) to afford 4-(benzyloxy)-1-(2-isopropyl-9-methyl-2,3,4,9-tetrahydro-1H-pyrido[3,4-b]indol-7-yl)pyridin-2(1H)-one. The free base was converted to the HCl salt using 1.25 M HCl in methanol to provide the title compound (26 mg, 19%) as a off white solid: $^1$H NMR (500 MHz, DMSO-d$_6$) δ 10.50 (s, 1H), 7.56 (d, J=4.5 Hz, 2H), 7.52-7.38 (m, 6H), 7.01 (dd, J=4.5, 1.0 Hz, 1H), 6.11 (dd, J=4.5, 1.0 Hz, 1H), 5.97 (s, 1H), 5.16 (s, 2H), 4.60-4.53 (m, 2H), 3.78-3.70 (m, 2H), 3.70 (s, 3H), 3.40-3.28 (m, 1H), 3.18-2.98 (m, 2H), 1.44-1.39 (m, 6H); ESI MS m/z 428 [M+H]$^+$; HPLC (Method A) 95.7% (AUC), t$_R$=15.1 min.

Example 144

Preparation of Isopropyl 7-(4-(benzyloxy)-2-oxopyridin-1(2H)-yl)-9-methyl-3,4-dihydro-1H-pyrido[3,4-b]indole-2(9H)-carboxylate

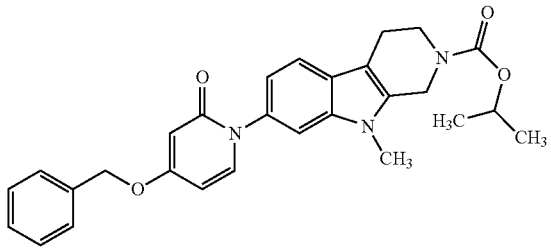

Chemical Formula: C$_{28}$H$_{29}$N$_3$O$_4$
Exact Mass: 471.22
Molecular Weight: 471.55

Following the procedure of Example 143, the title compound (12 mg, 8%) was obtained as a second product as an off-white powder after lyophilization from acetonitrile/water: $^1$H NMR (500 MHz, CDCl$_3$) δ 7.48 (d, J=8.5 Hz, 1H), 7.50-7.32 (m, 7H), 6.99 (d, J=8.5 Hz, 1H), 6.90 (s, 1H), 6.34 (d, J=6.5 Hz, 1H), 5.17 (s, 2H), 5.05-5.00 (m, 1H), 4.72-4.58 (m, 2H), 3.79 (br m, 2H), 3.76 (s, 3H), 2.82 (m, 2H), 1.42-1.32 (m, 6H); ESI MS m/z 472 [M+H]$^+$; HPLC (Method A) 95.7% (AUC), t$_R$=19.9 min.

Example 145

Preparation of 4-(Benzyloxy)-3-bromo-1-(9-methyl-2,3,4,9-tetrahydro-1H-pyrido[3,4-b]indol-7-yl)pyridine-2(1H)-one hydrochloride

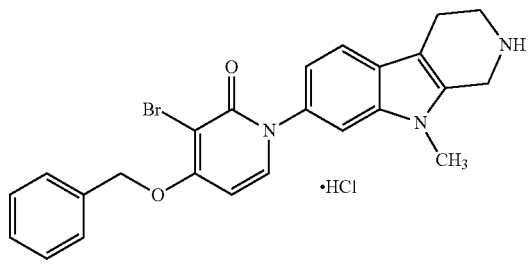

Chemical Formula: C$_{24}$H$_{23}$ClN$_3$O$_2$
Exact Mass: 499.07
Molecular Weight: 500.82

2-Bromopropane (0.25 mL, 2.7 mmol) was added to a solution of 4-(benzyloxy)-1-(9-methyl-2,3,4,9-tetrahydro-1H-pyrido[3,4-b]indol-7-yl)pyridin-2(1H)-one in DMSO (5 mL). The reaction mixture was stirred at 55° C. for 3 d. The mixture was diluted with a saturated solution of sodium bicarbonate and extracted with dichloromethane (3×50 mL). The combined organics were washed with water and brine, dried over sodium sulfate and concentrated under reduced pressure. Purification by preparatory TLC (silica gel, 10:1:0.1 dichloromethane/methanol/concentrated ammonium hydroxide) provided the free base of the title compound. The free base was converted to the HCl salt using 2.5 M HCl in methanol to afford, after lyophilization from acetonitrile/water, the title compound (15 mg, 14%) as a yellow solid: $^1$H NMR (300 MHz, CD$_3$OD) δ 7.71 (d, J=7.8 Hz, 1H), 7.63 (d, J=8.4, Hz, 1H), 7.53-7.30 (m, 6H), 7.05 (dd, J=7.8, 1.2 Hz, 1H), 6.60 (d, J=7.6 Hz, 1H), 5.40 (s, 2H), 4.54 (s, 2H), 3.71 (s, 3H), 3.62-3.55 (m, 2H), 3.22-3.02 (m, 2H); ESI MS m/z 465 [M+H]$^+$; HPLC (Method A) 95.7% (AUC), t$_R$=15.3 min.

Example 146

Preparation of 4-(Benzyloxy)-1-(2,3,4,5-tetrahydro-1H-pyrido[4,3-b]indol-7-yl)pyridin-2(1H)-one dihydrochloride a) Di-tert-butyl 7-bromo-3,4-dihydro-1H-pyrido[4,3-b]indole-2,5-dicarboxylate

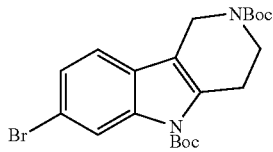

Chemical Formula: C$_{21}$H$_{27}$BrN$_2$O$_4$
Exact Mass: 450.12
Molecular Weight: 451.35

To a solution of tert-butyl 7-bromo-3,4-dihydro-1H-pyrido[4,3-b]indole-2(5H)-carboxylate (1.00 g, 2.85 mmol), Boc$_2$O (683 mg, 3.13 mol) and triethylamine (0.73 mL, 5.7 mmol) in methylene chloride (30 mL) at room temperature was added DMAP (50 mg, 0.41 mmol), and the reaction progressed for 18 h. The mixture was washed with 0.5 N HCl, and the organic phase was removed, dried over Na$_2$SO$_4$, filtered and concentrated to dryness. The crude title product (1.25 g, 98%) was recovered as an orange solid: $^1$H NMR (500 MHz, CDCl$_3$) δ 8.37 (br s, 1H), 7.34 (dd, J=8.2, 1.6 Hz, 1H), 7.24 (d, J=8.25 Hz, 1H), 4.54 (br s, 2H), 3.73 (m, 2H), 3.07 (t, J=5.6 Hz, 2H), 1.66 (s, 9H), 1.50 (s, 9H).

b) tert-Butyl 7-(4-(benzyloxy)-2-oxopyridin-1(2H)-yl)-3,4-dihydro-1H-pyrido[4,3-b]indole-2(5H)-carboxylate

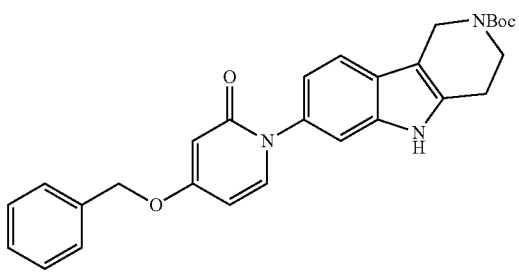

Chemical Formula: C$_{28}$H$_{29}$N$_3$O$_4$
Exact Mass: 471.22
Molecular Weight: 471.55

Prepared from di-tert-butyl 7-bromo-3,4-dihydro-1H-pyrido[4,3-b]indole-2,5-dicarboxylate (1.24 g, 2.72 mmol) and 4-benzyloxypyridone (547 mg, 2.72 mmol) according to the procedure of Example 1 (step c). Purification by flash column chromatography (silica gel, hexanes/ethyl acetate, 100:0 to 80:20 to 50:50 to 25:75 then 0:100) gave the title compound (155 mg, 10%) as a yellow solid: $^1$H NMR (500 MHz, CDCl$_3$) δ 9.40 (br s, 1H), 7.44-7.38 (m, 5H), 7.30 (d, J=7.5 Hz, 1H), 7.22 (d, J=8.2 Hz, 1H), 7.16 (s, 1H), 6.82 (dd, J=8.2, 1.4 Hz, 1H), 6.12-6.09 (m, 2H), 5.09 (s, 2H), 4.46 (br s, 2H), 3.70 (br m, 2H), 2.54 (br m, 2H), 1.50 (s, 9H).

c) 4-(Benzyloxy)-1-(2,3,4,5-tetrahydro-1H-pyrido[4,3-b]indol-7-yl)pyridin-2(1H)-one dihydrochloride

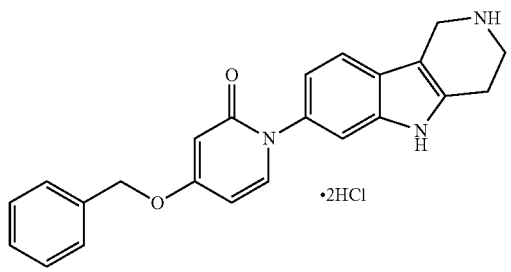

Chemical Formula: C$_{23}$H$_{23}$Cl$_2$N$_3$O$_2$
Exact Mass: 443.12
Molecular Weight: 444.35

Prepared from tert-butyl 7-(4-(benzyloxy)-2-oxopyridin-1(2H)-yl)-3,4-dihydro-1H-pyrido[4,3-b]indole-2(5H)-carboxylate (150 mg, 0.32 mmol) according to the procedure of Example 1 (step d). Purification by flash column chromatography (4 g ISCO column eluting with methylene chloride and a methanol/ammonia mixture (10:1); gradient 100% methylene chloride to 85% methylene chloride over 30 min) provided the free-base as a yellow solid. This was converted to the bis-HCl salt (2 N HCl/Et$_2$O in CH$_2$Cl$_2$) providing the title compound (36 mg, 26%) as a yellow solid: mp 240° C. dec.; $^1$H NMR (500 MHz, CD$_3$OD) δ 7.65 (d, J=7.5 Hz, 1H), 7.57 (d, J=8.2 Hz, 1H), 7.47 (d, J=7.2 Hz, 2H), 7.42-7.36 (m, 4H), 7.03 (d, J=8.5 Hz, 1H), 6.39 (dd, J=7.6, 2.5 Hz, 1H), 6.21 (d, J=2.5 Hz, 1H), 5.21 (s, 2H), 4.47 (s, 2H), 3.64 (t, J=6.0 Hz, 2H), 3.20 (t, J=6.1 Hz, 2H); ESI MS m/z 372 [M+H]$^+$; HPLC (Method A) 95.0% (AUC), t$_R$=12.2 min.

Example 147

Preparation of 4-(Benzyloxy)-1-(5-ethyl-2,3,4,5-tetrahydro-1H-pyrido[4,3-b]indol-7-yl)pyridin-2(1H)-one dihydrochloride a) tert-Butyl 7-bromo-5-ethyl-3,4-dihydro-1H-pyrido[4,3-b]indole-2(5H)-carboxylate

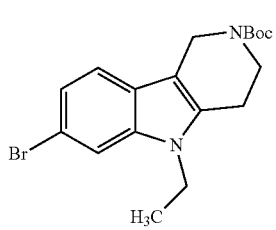

Chemical Formula: C$_{18}$H$_{23}$BrN$_2$O$_2$
Exact Mass: 378.09
Molecular Weight: 379.29

Prepared from tert-butyl 7-bromo-3,4-dihydro-1H-pyrido[4,3-b]indole-2(5H)-carboxylate (500 mg, 1.43 mmol) according to the procedure of Example 1 (step b). This provided the title compound (520 mg, 96%) as a yellow/orange solid: $^1$H NMR (500 MHz, CDCl$_3$) δ 7.36 (s, 1H), 7.23 (d, J=8.3 Hz, 1H), 7.10 (d, J=8.2 Hz, 1H), 4.54 (s, 2H), 3.96 (q, J=7.2 Hz, 2H), 3.76 (br m, 2H), 2.71 (br m, 2H), 1.43 (s, 9H), 1.25 (t, J=7.2 Hz, 3H).

b) tert-Butyl 7-(4-(benzyloxy)-2-oxopyridin-1(2H)-yl)-5-ethyl-3,4-dihydro-1H-pyrido[4,3-b]indole-2(5H)-carboxylate

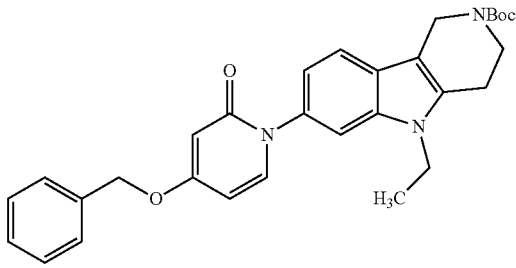

Chemical Formula: C₃₀H₃₃N₃O₄
Exact Mass: 499.25
Molecular Weight: 499.60

Prepared from tert-butyl 7-bromo-5-ethyl-3,4-dihydro-1H-pyrido[4,3-b]indole-2(5H)-carboxylate (500 mg, 1.32 mmol) and 4-benzyloxypyridone (265 mg, 1.32 mmol), according to the procedure of Example 1 (step c). Purification by flash column chromatography (silica gel, hexanes/EtOAc, 100:0 to 80:20 to 50:50 to 25:75 then 0:100) gave the title compound (317 mg, 48%) as a yellow solid: ¹H NMR (300 MHz, CDCl₃) δ 7.53 (d, J=8.2 Hz, 1H), 7.44-7.37 (m, 5H), 7.32-7.29 (m, 2H), 7.04 (d, J=8.0 Hz, 1H), 6.10-6.03 (m, 2H), 5.08 (s, 2H), 4.66 (br s, 2H), 4.10 (q, J=7.1 Hz, 2H), 3.86 (br m, 2H), 2.84 (br m, 2H), 1.53 (s, 9H), 1.25 (t, J=7.1 Hz, 3H).

c) 4-(Benzyloxy)-1-(5-ethyl-2,3,4,5-tetrahydro-1H-pyrido[4,3-b]indol-7-yl)pyridin-2(1H)-one dihydrochloride

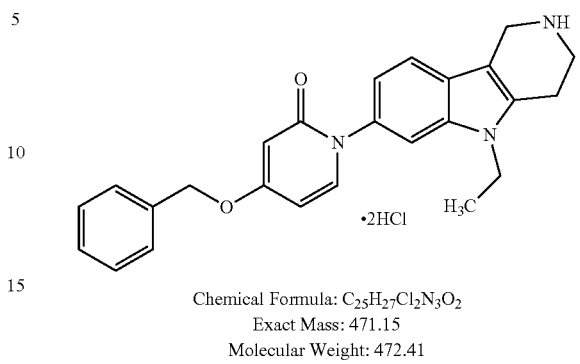

Chemical Formula: C₂₅H₂₇Cl₂N₃O₂
Exact Mass: 471.15
Molecular Weight: 472.41

Prepared from tert-butyl 7-(4-(benzyloxy)-2-oxopyridin-1(2H)-yl)-5-ethyl-3,4-dihydro-1H-pyrido[4,3-b]indole-2(5H)-carboxylate (315 mg, 0.631 mmol) according to the procedure of Example 1 (step d) providing the title compound (207 mg, 74%) as a yellow solid: mp 176-181° C.; ¹H NMR (300 MHz, CD₃OD) δ 7.83 (d, J=7.5 Hz, 1H), 7.62-7.57 (m, 2H), 7.45-7.40 (m, 5H), 7.09 (dd, J=8.4, 1.6 Hz, 1H), 6.59 (dd, J=7.5, 2.3 Hz, 1H), 6.36 (d, J=2.3 Hz, 1H), 5.28 (s, 2H), 4.49 (s, 2H), 4.23 (q, J=7.2 Hz, 2H), 3.68 (t, J=6.1 Hz, 2H), 3.22 (t, J=5.9 Hz, 2H), 1.35 (t, J=7.1 Hz, 3H); ESI MS m/z 400 [M+H]⁺; HPLC (Method A)>99% (AUC), $t_R$=13.2 min.

In accordance with further embodiments of the invention, there are provided the following compounds, which may be synthesized by analogy by the methods shown and described above:

| Name | Structure |
|---|---|
| 1-(2-Isobutyryl-5-methyl-2,3,4,5-tetrahydro-1H-pyrido[4,3-b]indol-7-yl)-4-(5-(trifluoromethyl)pyridin-2-yl)pyridin-2(1H)-one | 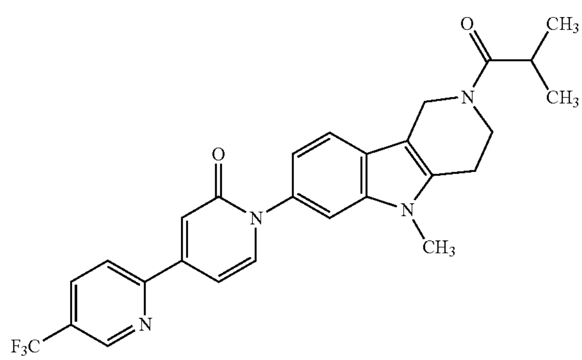 [SMILES: CC(C)C(=O)N1CCc2c(c3ccc(-n4ccc(-c5ccc(C(F)(F)F)cn5)cc4=O)cc3n2C)C1] |
| 1-(5-Methyl-2-propionyl-2,3,4,5-tetrahydro-1H-pyrido[4,3-b]indol-7-yl)-4-(5-(trifluoromethyl)pyridin-2-yl)pyridin-2(1H)-one | 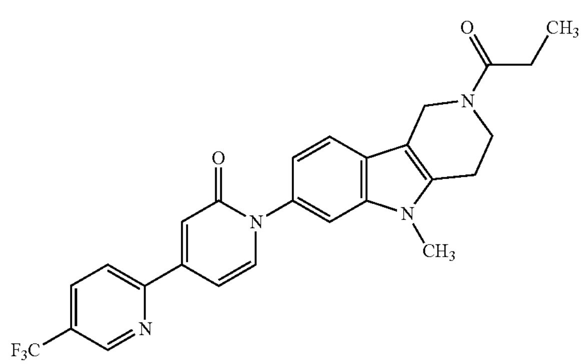 [SMILES: CCC(=O)N1CCc2c(c3ccc(-n4ccc(-c5ccc(C(F)(F)F)cn5)cc4=O)cc3n2C)C1] |

-continued

| Name | Structure |
|---|---|
| 4-(Benzyloxy)-1-(4,4,5-trimethyl-2,3,4,5-tetrahydro-1H-pyrido[4,3-b]indol-7-yl)pyridin-2(1H)-one | 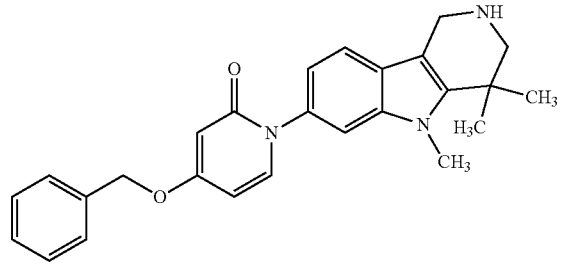 [SMILES: Cn1c2c(c3ccc(-n4ccc(OCc5ccccc5)cc4=O)cc31)CNCC2(C)C] |
| N,N,5-Trimethyl-7-(2-oxo-4-(5-(trifluoromethyl)pyridin-2-yl)pyridin-1(2H)-yl)-3,4-dihydro-1H-pyrido[4,3-b]indole-2(5H)-carboxamide | 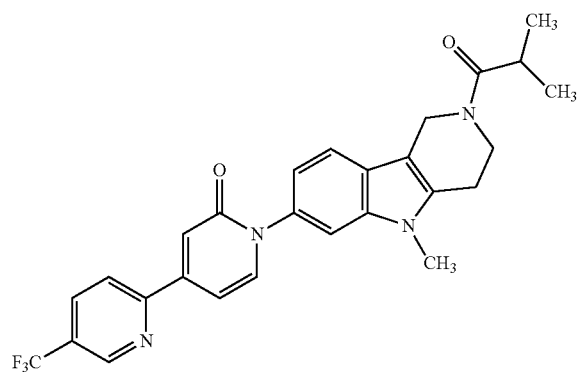 [SMILES: CC(C)C(=O)N1CCc2c(c3ccc(-n4ccc(-c5ccc(C(F)(F)F)cn5)cc4=O)cc3n2C)C1] |
| 4-((5-Fluoropyridin-2-yl)methoxy)-1-(2-isobutyryl-5-methyl-2,3,4,5-tetrahydro-1H-pyrido[4,3-b]indol-7-yl)pyridin-2(1H)-one | 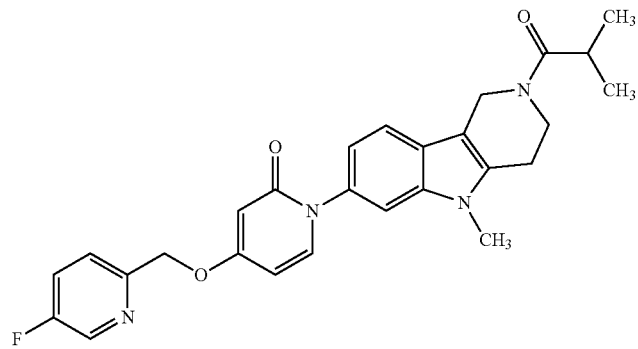 [SMILES: CC(C)C(=O)N1CCc2c(c3ccc(-n4ccc(OCc5ccc(F)cn5)cc4=O)cc3n2C)C1] |
| 1-(2-Ethyl-5-methyl-2,3,4,5-tetrahydro-1H-pyrido[4,3-b]indol-7-yl)-4-((5-fluoropyridin-2-yl)methoxy)pyridin-2(1H)-one | 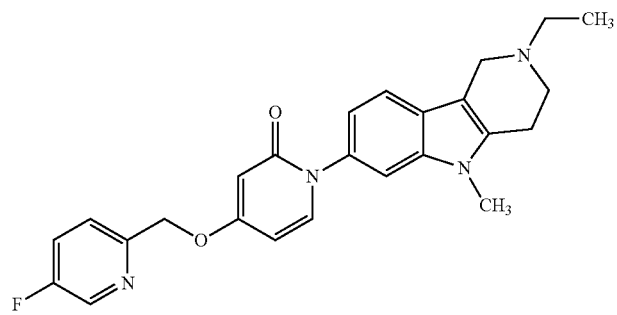 [SMILES: CCN1CCc2c(c3ccc(-n4ccc(OCc5ccc(F)cn5)cc4=O)cc3n2C)C1] |

| Name | Structure |
|---|---|
| 1-(2-(3-Hydroxy-2,2-dimethylpropanoyl)-5-methyl-2,3,4,5-tetrahydro-1H-pyrido[4,3-b]indol-7-yl)-4-(5-(trifluoromethyl)pyridin-2-yl)pyridin-2(1H)-one | 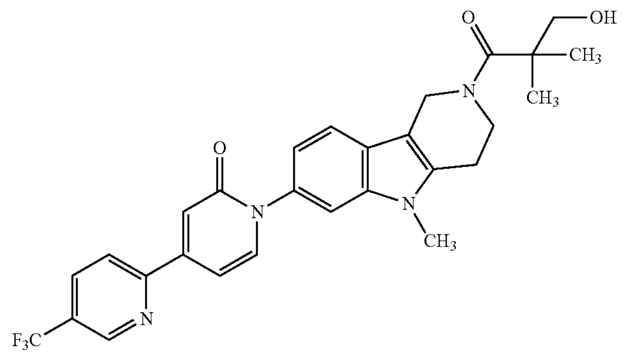 [SMILES: Cn1c2c(c3ccc(-n4ccc(-c5ccc(C(F)(F)F)cn5)cc4=O)cc31)CN(C(=O)C(C)(C)CO)CC2] |
| 1-(2-(3-Hydroxy-3-methylbutanoyl)-5-methyl-2,3,4,5-tetrahydro-1H-pyrido[4,3-b]indol-7-yl)-4-(5-(trifluoromethyl)pyridin-2-yl)pyridin-2(1H)-one | 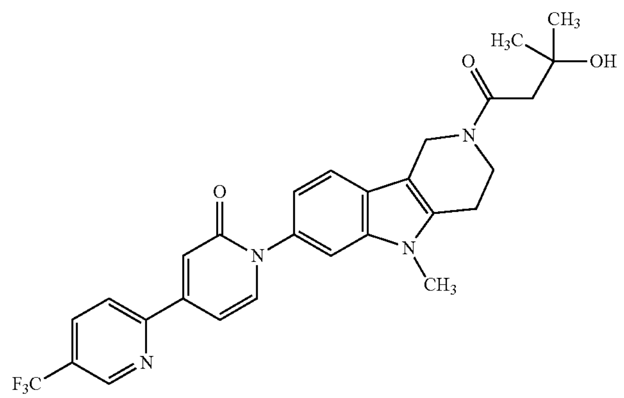 [SMILES: Cn1c2c(c3ccc(-n4ccc(-c5ccc(C(F)(F)F)cn5)cc4=O)cc31)CN(C(=O)CC(C)(C)O)CC2] |
| 1-(2-(2-Hydroxyacetyl)-5-methyl-2,3,4,5-tetrahydro-1H-pyrido[4,3-b]indol-7-yl)-4-(5-(trifluoromethyl)pyridin-2-yl)pyridin-2(1H)-one | 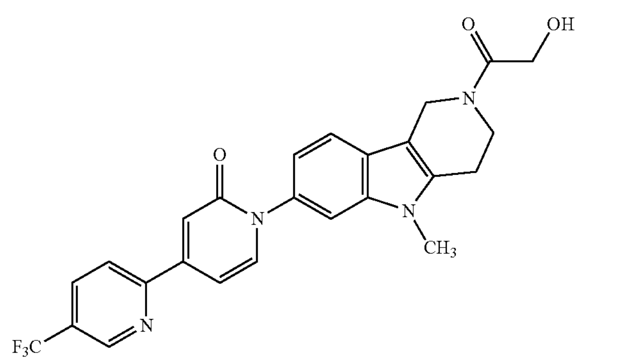 [SMILES: Cn1c2c(c3ccc(-n4ccc(-c5ccc(C(F)(F)F)cn5)cc4=O)cc31)CN(C(=O)CO)CC2] |
| 4-(Benzyloxy)-1-(2-isopropyl-9-methyl-2,3,4,9-tetrahydro-1H-pyrido[3,4-b]indol-7-yl)pyridin-2(1H)-one | 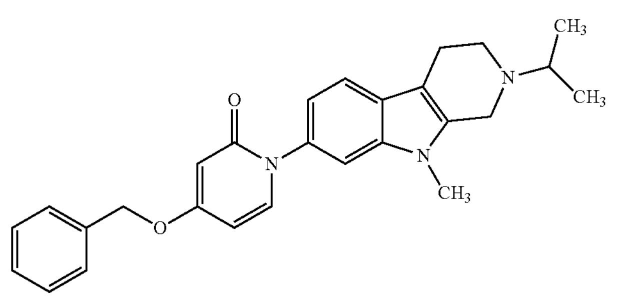 [SMILES: CC(C)N1CCc2c(n(C)c3cc(-n4ccc(OCc5ccccc5)cc4=O)ccc23)C1] |

-continued

| Name | Structure |
|---|---|
| Isopropyl 7-(4-(benzyloxy)-2-oxopyridin-1(2H)-yl)-9-methyl-3,4-dihydro-1H-pyrido[3,4-b]indole-2(9H)-carboxylate | 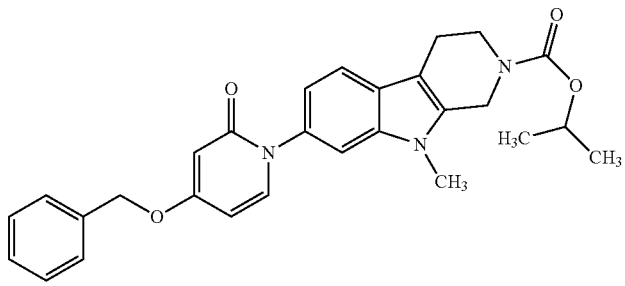 [SMILES: CC(C)OC(=O)N1CCc2c(n(C)c3cc(-n4ccc(OCc5ccccc5)cc4=O)ccc23)C1] |
| 1-(5-Methyl-2,3,4,5-tetrahydro-1H-pyrido[4,3-b]indol-7-yl)-4-(5-(trifluoromethyl)pyrazin-2-yl)pyridin-2(1H)-one | 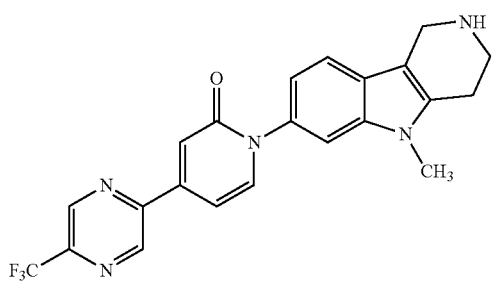 [SMILES: Cn1c2c(c3ccc(-n4ccc(-c5cnc(C(F)(F)F)cn5)cc4=O)cc31)CNCC2] |
| 1-(9-Methyl-2,3,4,9-tetrahydro-1H-pyrido[3,4-b]indol-7-yl)-4-(5-(trifluoromethyl)pyrazin-2-yl)pyridin-2(1H)-one | 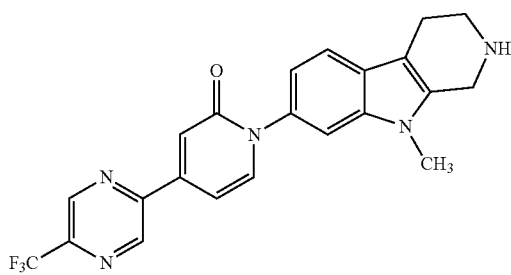 [SMILES: Cn1c2c(c3ccc(-n4ccc(-c5cnc(C(F)(F)F)cn5)cc4=O)cc31)CCNC2] |
| 2-(5-Methyl-2,3,4,5-tetrahydro-1H-pyrido[4,3-b]indol-7-yl)-5-(5-(trifluoromethyl)pyridin-2-yl)pyridazin-3(2H)-one | 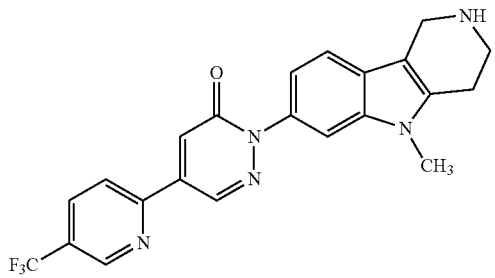 |
| 2-(9-Methyl-2,3,4,9-tetrahydro-1H-pyrido[3,4-b]indol-7-yl)-5-(5-(trifluoromethyl)pyridin-2-yl)pyridazin-3(2H)-one | 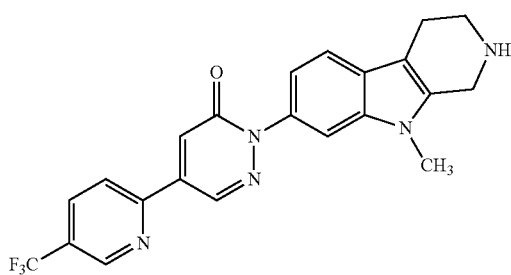 |

| Name | Structure |
|---|---|
| 2-(5-Methyl-2,3,4,5-tetrahydro-1H-pyrido[4,3-b]indol-7-yl)-5-(6-(trifluoromethyl)pyridazin-3-yl)pyridazin-3(2H)-one | 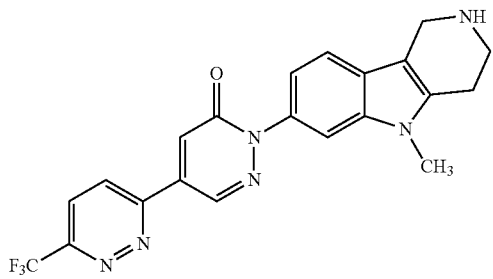 [SMILES: Cn1c2c(c3ccc(-n4ncc(-c5ccc(C(F)(F)F)nn5)cc4=O)cc31)CNCC2] |
| 2-(9-Methyl-2,3,4,9-tetrahydro-1H-pyrido[3,4-b]indol-7-yl)-5-(6-(trifluoromethyl)pyridazin-3-yl)pyridazin-3(2H)-one | 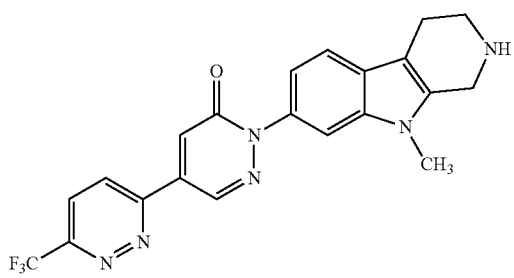 |
| 2-(5-Methyl-2,3,4,5-tetrahydro-1H-pyrido[4,3-b]indol-7-yl)-5-(4-(trifluoromethyl)phenyl)pyridazin-3(2H)-one | 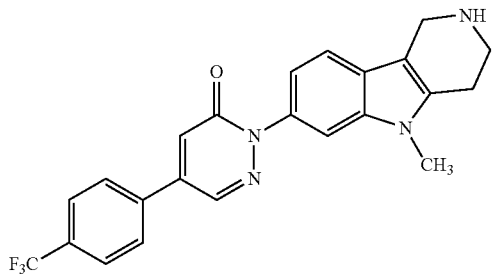 [SMILES: Cn1c2c(c3ccc(-n4ncc(-c5ccc(C(F)(F)F)cc5)cc4=O)cc31)CNCC2] |
| 2-(9-Methyl-2,3,4,9-tetrahydro-1H-pyrido[3,4-b]indol-7-yl)-5-(4-(trifluoromethyl)phenyl)pyridazin-3(2H)-one | 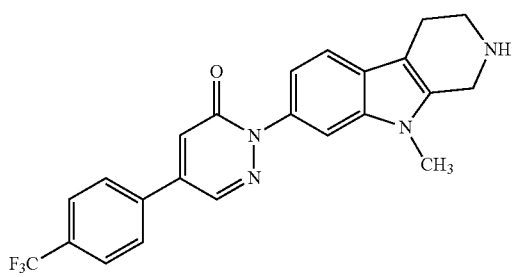 [SMILES: Cn1c2c(c3ccc(-n4ncc(-c5ccc(C(F)(F)F)cc5)cc4=O)cc31)CCNC2] |
| 4-(Benzyloxy)-1-(2-isobutyl-5-methyl-2,3,4,5-tetrahydro-1H-pyrido[4,3-b]indol-7-yl)pyridin-2(1H)-one | 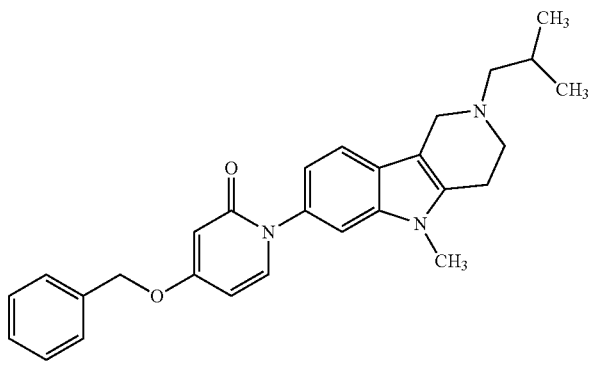 [SMILES: CC(C)CN1CCc2c(c3ccc(-n4ccc(OCc5ccccc5)cc4=O)cc3n2C)C1] |

| Name | Structure |
|---|---|
| 4-(Benzyloxy)-1-(2-isobutyl-9-methyl-2,3,4,9-tetrahydro-1H-pyrido[3,4-b]indol-7-yl)pyridin-2(1H)-one | 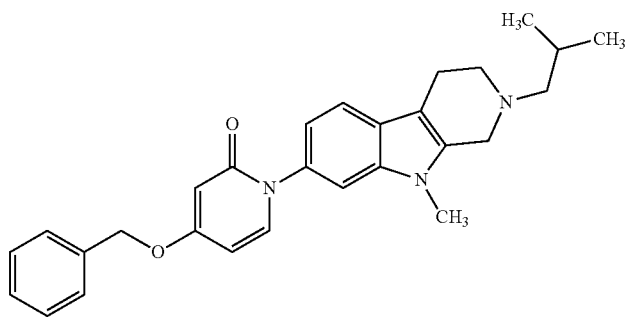 [SMILES: CC(C)CN1CCc2c(n(C)c3cc(-n4ccc(OCc5ccccc5)cc4=O)ccc23)C1] |
| 4-(Benzyloxy)-1-(2-(cyclopropylmethyl)-5-methyl-2,3,4,5-tetrahydro-1H-pyrido[4,3-b]indol-7-yl)pyridin-2(1H)-one | 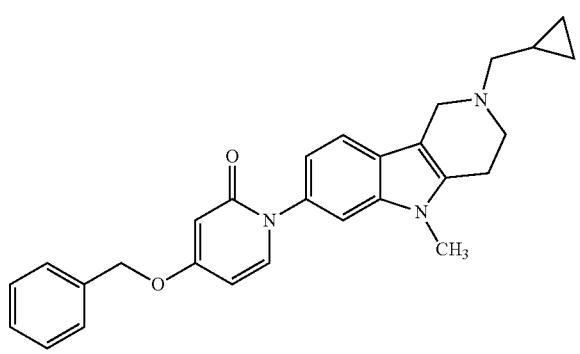 [SMILES: Cn1c2c(c3ccc(-n4ccc(OCc5ccccc5)cc4=O)cc31)CN(CC1CC1)CC2] |
| 4-(Benzyloxy)-1-(2-(cyclopropylmethyl)-9-methyl-2,3,4,9-tetrahydro-1H-pyrido[3,4-b]indol-7-yl)pyridin-2(1H)-one | 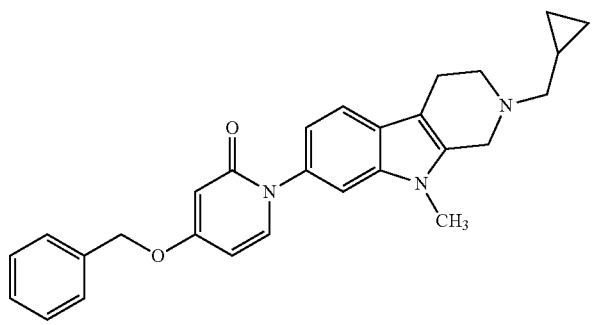 [SMILES: Cn1c2c(c3ccc(-n4ccc(OCc5ccccc5)cc4=O)cc31)CCN(CC1CC1)C2] |
| 4-(5-Methoxypyridin-2-yl)-1-(5-methyl-2,3,4,5-tetrahydro-1H-pyrido[4,3-b]indol-7-yl)pyridin-2(1H)-one | 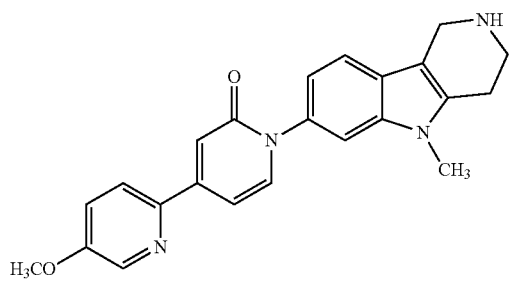 [SMILES: COc1ccc(-c2ccn(-c3ccc4c5c(n(C)c4c3)CCNC5)c(=O)c2)nc1] |
| 4-(5-Methoxypyridin-2-yl)-1-(9-methyl-2,3,4,9-tetrahydro-1H-pyrido[3,4-b]indol-7-yl)pyridin-2(1H)-one | 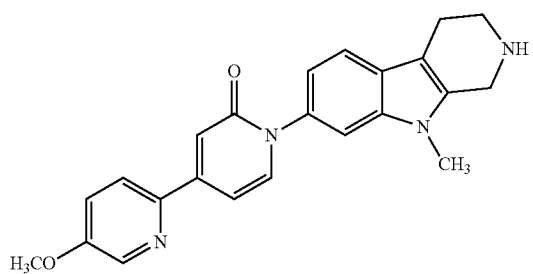 [SMILES: COc1ccc(-c2ccn(-c3ccc4c5c(n(C)c4c3)CNCC5)c(=O)c2)nc1] |

| Name | Structure |
|---|---|
| 4-(Benzyloxy)-1-(4,4,9-trimethyl-2,3,4,9-tetrahydro-1H-pyrido[3,4-b]indol-7-yl)pyridin-2(1H)-one | 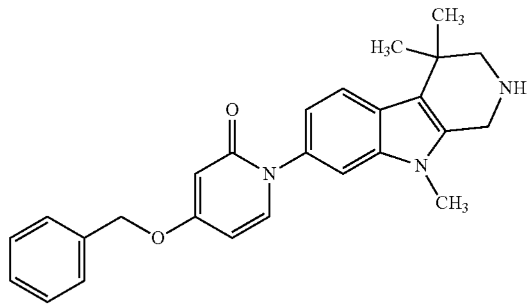 [SMILES: Cn1c2c(c3ccc(-n4ccc(OCc5ccccc5)cc4=O)cc31)C(C)(C)CNC2] |
| 4-(Benzyloxy)-1-(1,1,5-trimethyl-2,3,4,5-tetrahydro-1H-pyrido[4,3-b]indol-7-yl)pyridin-2(1H)-one | 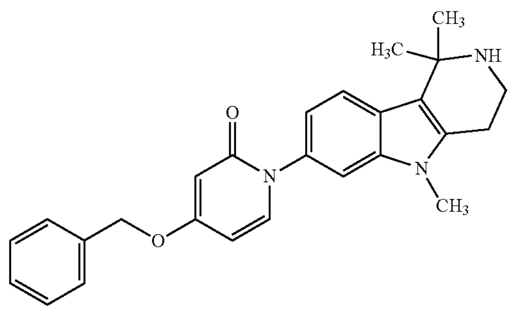 [SMILES: Cn1c2c(c3ccc(-n4ccc(OCc5ccccc5)cc4=O)cc31)C(C)(C)NCC2] |
| 4-(Benzyloxy)-1-(1,1,3,3,5-pentamethyl-2,3,4,5-tetrahydro-1H-pyrido[4,3-b]indol-7-yl)pyridin-2(1H)-one | 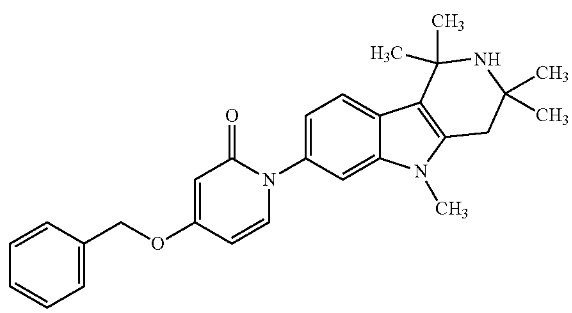 [SMILES: Cn1c2c(c3ccc(-n4ccc(OCc5ccccc5)cc4=O)cc31)C(C)(C)NC(C)(C)C2] |
| 4-(Benzyloxy)-1-(3,3,5-trimethyl-2,3,4,5-tetrahydro-1H-pyrido[4,3-b]indol-7-yl)pyridin-2(1H)-one | 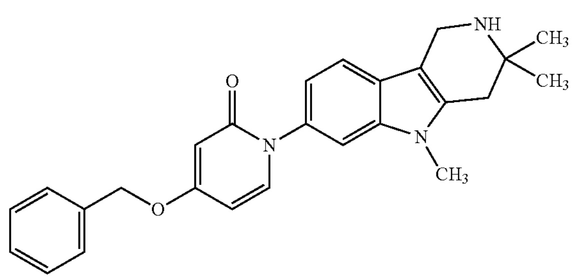 [SMILES: Cn1c2c(c3ccc(-n4ccc(OCc5ccccc5)cc4=O)cc31)CNC(C)(C)C2] |
| 1-(5-Methyl-2,3,4,5-tetrahydro-1H-pyrido[4,3-b]indol-7-yl)-4-(4-(methylsulfonyl)phenyl)pyridin-2(1H)-one | 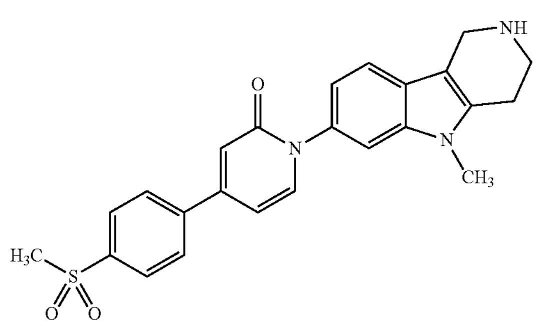 [SMILES: Cn1c2c(c3ccc(-n4ccc(-c5ccc(S(C)(=O)=O)cc5)cc4=O)cc31)CNCC2] |

-continued

| Name | Structure |
|---|---|
| 1-(9-Methyl-2,3,4,9-tetrahydro-1H-pyrido[3,4-b]indol-7-yl)-4-(4-(methylsulfonyl)phenyl)pyridin-2(1H)-one | 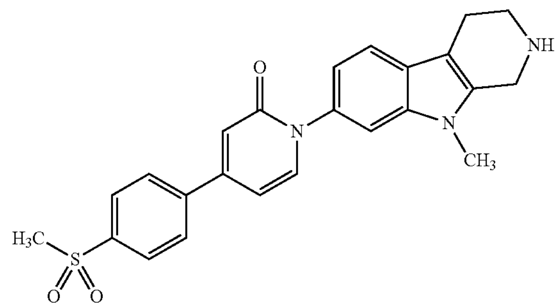 [SMILES: Cn1c2c(c3ccc(-n4ccc(-c5ccc(S(C)(=O)=O)cc5)cc4=O)cc31)CCNC2] |
| 1-(5-Methyl-2,3,4,5-tetrahydro-1H-pyrido[4,3-b]indol-7-yl)-4-(4-(methylsulfinyl)phenyl)pyridin-2(1H)-one | 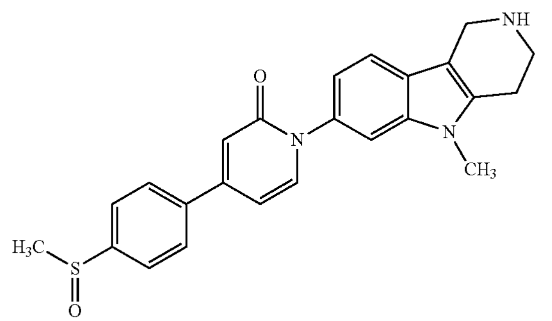 [SMILES: Cn1c2c(c3ccc(-n4ccc(-c5ccc(S(C)=O)cc5)cc4=O)cc31)CNCC2] |
| 1-(9-Methyl-2,3,4,9-tetrahydro-1H-pyrido[3,4-b]indol-7-yl)-4-(4-(methylsulfinyl)phenyl)pyridin-2(1H)-one | 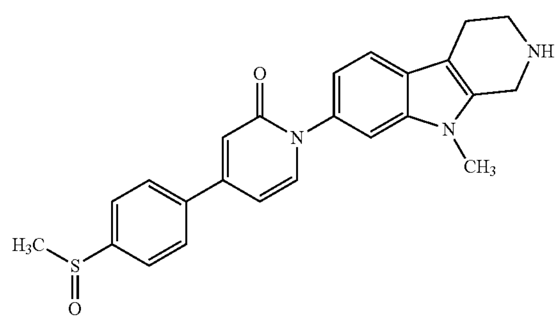 [SMILES: Cn1c2c(c3ccc(-n4ccc(-c5ccc(S(C)=O)cc5)cc4=O)cc31)CCNC2] |
| 1-(5-Methyl-2,3,4,5-tetrahydro-1H-pyrido[4,3-b]indol-7-yl)-4-(5-(methylthio)pyridin-2-yl)pyridin-2(1H)-one | 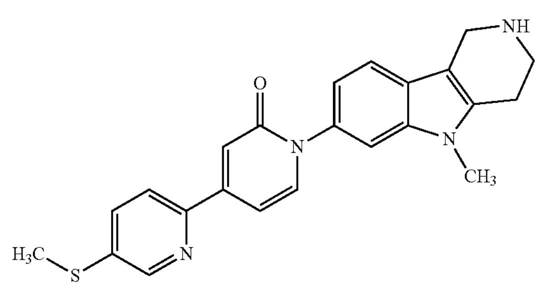 [SMILES: CSc1ccc(-c2ccn(-c3ccc4c5c(n(C)c4c3)CCNC5)c(=O)c2)nc1] |
| 1-(9-Methyl-2,3,4,9-tetrahydro-1H-pyrido[3,4-b]indol-7-yl)-4-(5-(methylthio)pyridin-2-yl)pyridin-2(1H)-one | 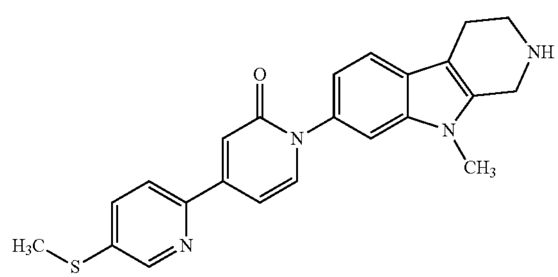 [SMILES: CSc1ccc(-c2ccn(-c3ccc4c5c(n(C)c4c3)CNCC5)c(=O)c2)nc1] |

Binding Assay I for Human Melanin-Concentrating Hormone (MCH$_1$) Receptor

Evaluation of the affinity of compounds for the human MCH$_1$ receptor was accomplished in transfected Chinese Hamster Ovary (CHO) cells determined in a radioligand binding assay, as described in MacDonald et al., "Molecular characterization of the melanin-concentrating hormone/receptor complex: identification of critical residues involved in binding and activation", Mol Pharmacol., 58:217 (2000). Cell membrane homogenates (5 μg protein) were incubated for 60 min at 22° C. with 0.1 nM [$^{125}$I][Phe$^{13}$,Tyr$^{19}$]-MCH in the absence or presence of the test compound in a buffer containing 25 mM Hepes/Tris (pH 7.4), 5 mM MgCl$_2$, 1 mM CaCl$_2$ and 0.5% bovine serum albumin (BSA). Nonspecific binding was determined in the presence of 0.1 μM MCH. Following incubation, the samples were filtered rapidly under vacuum through glass fiber filters (GF/B, Packard) and rinsed several times with an ice-cold buffer containing 25 mM Hepes/Tris (pH 7.4), 500 mM NaCl, 5 mM MgCl$_2$, 1 mM CaCl$_2$ and 0.1% BSA using a 96-sample cell harvester (Unifilter, Packard). The filters were dried, then counted for radioactivity in a scintillation counter (Topcount, Packard) using a scintillation cocktail (Microscint 0, Packard).

The results are expressed as a percent inhibition of the control radioligand specific binding. The IC$_{50}$ value (concentration causing a half-maximal inhibition of control specific binding) and Hill coefficient (n$_H$) were determined by non-linear regression analysis of the competition curve using Hill equation curve fitting. The inhibition constant (K$_i$) was calculated from the Cheng Prusoff equation: (K$_i$=IC$_{50}$/(1±(L/K$_D$)), where L=concentration of radioligand in the assay, and K$_D$=affinity of the radioligand for the receptor).

Binding Assay II for Human Melanin-Concentrating Hormone (MCH1) Receptor

Evaluation of the affinity of compounds for the human MCH$_1$ receptor was accomplished using 4-(3,4,5-tritritiumbenzyloxy)-1-(1-(2-(pyrrolidin-1-yl)ethyl)-1H-indazol-5-yl)pyridin-2(1H)-one and membranes prepared from stable CHO-K1 cells expressing the human MCH$_1$ receptor obtained from Euroscreen (Batch 1138). Cell membrane homogenates (8.92 μg protein) were incubated for 60 min at 25° C. with 1.4 nM of the [$^3$H]-labeled compound in the absence or presence of the test compound in 50 mM Tris-HCl buffer, pH 7.4. Nonspecific binding was determined in the presence of 50 μM 1-(5-(4-cyanophenyl)bicyclo[3.1.0]hexan-2-yl)-3-(4-fluoro-3-(trifluoromethyl)phenyl)-1-(3-(4-methylpiperazin-1-yl)propyl)urea. Following incubation, the samples were filtered rapidly under vacuum through Skatron 11731 filters, pre-soaked in 0.5% polyethylenimine, and washed with ice-cold 50 mM Tris-HCl buffer, pH 7.4, (wash setting 9,9,0) using a Skatron cell harvester. The filters were counted for radioactivity in a liquid scintillation counter (Tri-Carb 2100TR, Packard) using a scintillation cocktail (Ultima Gold MV, Perkin Elmer).

The results are expressed as a percent inhibition of the control radioligand specific binding. The IC$_{50}$ value (concentration causing a half-maximal inhibition of control specific binding) and Hill coefficient (n$_H$) were determined by non-linear regression analysis of the competition curve using Hill equation curve fitting. The inhibition constant (K$_i$) was calculated from the Cheng Prusoff equation: (K$_i$=IC$_{50}$/(1+(L/K$_D$)), where L=concentration of radioligand in the assay, and K$_D$=affinity of the radioligand for the receptor.

By methods as described above, the compounds listed in TABLE 1 were synthesized and tested for biological activity. All of the compounds in TABLE 1 exhibited K$_i$ of less than or equal to 3.5 μM in MCH$_1$ binding assays I or II.

TABLE 1

| Ex. No. | Structure | Mass Spec | $^1$H NMR Data |
|---|---|---|---|
| 1 | (structure) | 386 | $^1$H NMR (500 MHz, CD$_3$OD) δ 7.61-7.57 (2 × d, 2H), 7.47-7.46 (m, 3H), 7.43-7.40 (m, 2H), 7.37-7.34 (m, 1H), 7.05 (dd, J = 8.3, 1.7 Hz, 1H), 6.33 (dd, J = 7.5, 2.7 Hz, 1H), 6.16 (d, J = 2.6 Hz, 1H), 5.19 (s, 2H), 4.57 (s, 2H), 3.73 (s, 3H), 3.67 (t, J = 6.2 Hz, 2H), 3.20 (t, J = 6.1 Hz, 2H) |
| 2 | (structure) | 400 | $^1$H NMR (500 MHz, CD$_3$OD) δ 7.57 (dd, J = 7.6, 1.7 Hz, 2H), 7.47-7.46 (m, 3H) 7.43-7.34 (m, 3H), 7.06 (dd, J = 8.4, 1.9 Hz, 1H), 6.29 (dd, J = 7.6, 2.7 Hz, 1H), 6.13 (d, J = 2.6 Hz, 1H), 5.18 (s, 2H), 4.75 (d, J = 14.3 Hz, 1H), 4.38 (d, J = 14.2 Hz, 1H), 3.90 (m, 1H), 3.73 (s, 3H), 3.64-3.58 (m, 1H), 3.29-3.26 (m, 2H, partially masked by solvent), 3.13 (s, 3H) |

TABLE 1-continued

| Ex. No. | Structure | Mass Spec | ¹H NMR Data |
|---|---|---|---|
| 3 | 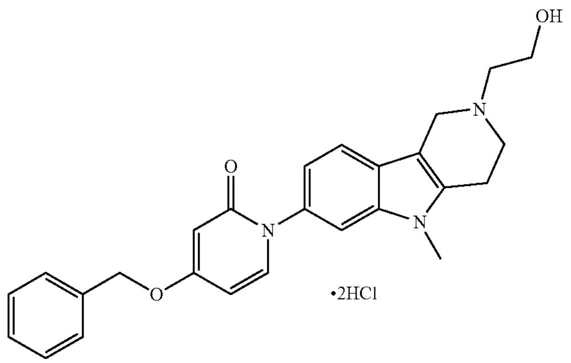 [SMILES: Cn1c2c(c3ccc(-n4ccc(OCc5ccccc5)cc4=O)cc31)CN(CCO)CC2 ; "·2HCl"] | 430 | ¹H NMR (500 MHz, CD₃OD) δ 7.63 (dd, J = 7.6, 2.0 Hz, 2H), 7.51-7.50 (m, 3H) 7.46-7.43 (m, 2H), 7.41-7.38 (m, 1H), 7.09 (dd, J = 8.3, 1.7 Hz, 1H), 6.36 (dd, J = 7.6, 2.7 Hz, 1H), 6.18 (d, J = 2.7 Hz, 1H), 5.23 (s, 2H), 4.82 (d, 1H, partially masked by solvent), 4.520 (d, J = 14.3 Hz, 1H), 4.06-4.02 (m, 3H), 3.77 (s, 3H), 3.70-3.68 (m, 1H), 3.55-3.51 (m, 2H), 3.33-3.31 (m, 2H, partially masked by solvent) |
| 4 | 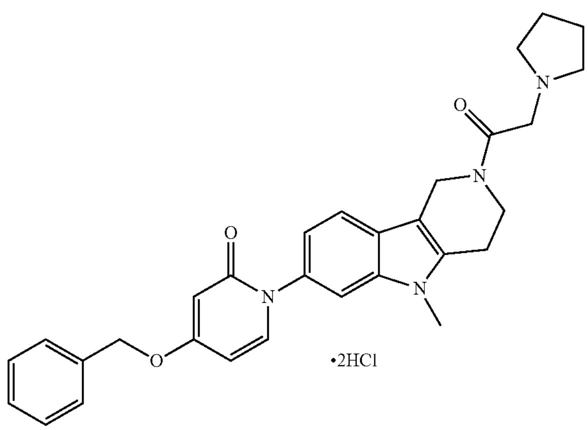 [SMILES: Cn1c2c(c3ccc(-n4ccc(OCc5ccccc5)cc4=O)cc31)CN(C(=O)CN1CCCC1)CC2 ; "·2HCl"] | 497 | ¹H NMR (500 MHz, CD₃OD) δ 7.62 (dd, J = 7.7, 1.9 Hz, 1H), 7.53 (d, J = 8.0 Hz, 1H) 7.46-7.44 (m, 2H), 7.41-7.35 (m, 4H), 7.06 (dd, J = 8.0, 1.7 Hz, 1H), 6.36 (d, J = 7.6 Hz, 1H), 6.18 (s, 1H), 5.25 (s, 2H), 4.90 (m 1H, masked by solvent), 4.82 (s, 1H), 4.53 (d, J = 14.2 Hz, 2H), 4.09 (t, J = 6.5 Hz, 1H), 3.91 (t, J = 6.4 Hz, 1H), 3.89-3.86 (m, 2H), 3.77 (s, 3H), 3.20-3.18 (m, 2H), 3.05-3.03 (m, 1H), 2.99-2.97 (m, 1H), 2.12-2.10 (m, 2H), 2.08-2.05 (m, 2H) |
| 5 | 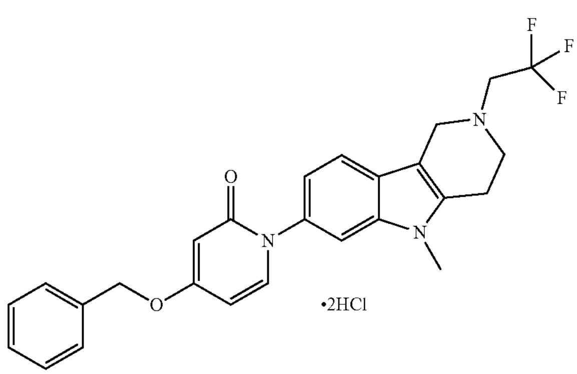 [SMILES: Cn1c2c(c3ccc(-n4ccc(OCc5ccccc5)cc4=O)cc31)CN(CC(F)(F)F)CC2 ; "·2HCl"] | 468 | ¹H NMR (300 MHz, CD₃OD) δ 7.48 (d, J = 7.5 Hz, 1H), 7.40-7.24 (m, 7H), 6.87 (dd, J = 8.3, 1.9 Hz, 1H), 6.19 (dd, J = 7.6, 2.7 Hz, 1H), 6.03 (d, J = 2.7 Hz, 1H), 5.08 (s, 2H), 3.96 (s, 2H), 3.58 (s, 3H), 3.37 (q, J = 9.7 Hz, 2H), 3.15-3.14 (m, 2H, partially masked by solvent), 2.87 (t, J = 5.5 Hz, 2H) |
| 6 | 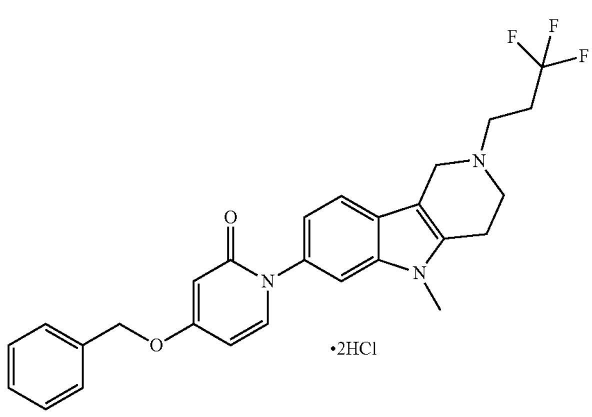 [SMILES: Cn1c2c(c3ccc(-n4ccc(OCc5ccccc5)cc4=O)cc31)CN(CCC(F)(F)F)CC2 ; "·2HCl"] | 482 | ¹H NMR (500 MHz, CD₃OD) δ 7.66 (d, J = 8.3 Hz, 1H), 7.63 (d, J = 7.6 Hz, 1H), 7.52-7.51 (m, 3H), 7.48-7.45 (m, 2H), 7.43 (d, J = 7.2 Hz, 1H), 7.11 (dd, J = 8.3, 1.7 Hz, 1H), 6.36 (dd, J = 7.6, 2.7 Hz, 1H), 6.19 (d, J = 2.7 Hz, 1H), 5.24 (s, 2H), 4.96 (m, 6H, masked by solvent), 3.79-3.74 (m, 5H), 3.03-3.02 (m, 2H) |

TABLE 1-continued

| Ex. No. | Structure | Mass Spec | ¹H NMR Data |
|---|---|---|---|
| 7 | 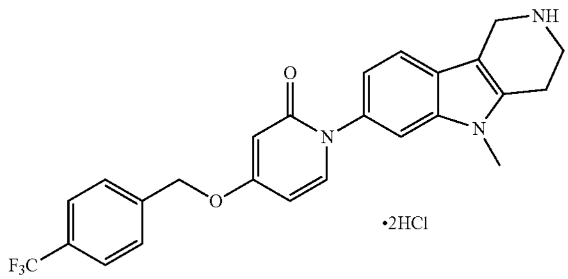 [SMILES: Cn1c2c(c3ccc(-n4ccc(OCc5ccc(C(F)(F)F)cc5)cc4=O)cc31)CNCC2 ; "·2HCl"] | 454 | ¹H NMR (500 MHz, CD₃OD) δ 7.77 (d, J = 8.3 Hz, 2H), 7.71 (d, J = 8.2 Hz, 2H), 7.65 (d, J = 7.6 Hz, 1H), 7.62 (d, J = 8.3 Hz, 1H), 7.50 (s, 1H), 7.09 (dd, J = 8.3, 1.8 Hz, 1H), 6.38 (dd, J = 7.6, 2.7 Hz, 1H), 6.17 (d, J = 2.7 Hz, 1H), 5.33 (s, 2H), 4.51 (s, 2H), 3.77 (s, 3H), 3.71 (t, J = 6.2 Hz, 2H), 3.24 (t, J = 6.1 Hz, 2H) |
| 8 | 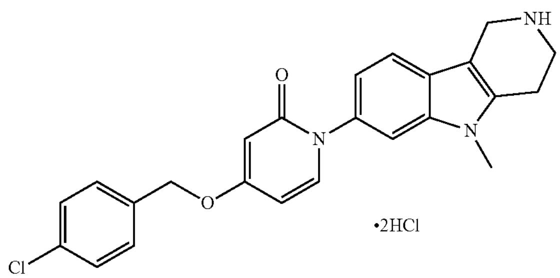 [SMILES: Cn1c2c(c3ccc(-n4ccc(OCc5ccc(Cl)cc5)cc4=O)cc31)CNCC2 ; "·2HCl"] | 420 | ¹H NMR (500 MHz, DMSO-d₆) δ 9.54 (br s, 2H), 7.57 (m, 2H), 7.51 (s, 5H), 6.99 (d, J = 7.8 Hz, 1H), 6.12 (dd, J = 7.8, 2.7 Hz, 1H), 5.99 (d, J = 2.7 Hz, 1H), 5.16 (s, 2H), 4.33 (br s, 2H), 3.68 (s, 3H), 3.52-3.48 (m, 2H), 3.12-3.08 (m, 2H) |
| 9 | 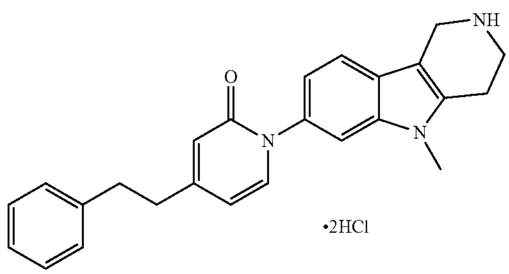 [SMILES: Cn1c2c(c3ccc(-n4ccc(CCc5ccccc5)cc4=O)cc31)CNCC2 ; "·2HCl"] | 384 | ¹H NMR (500 MHz, CD₃OD) δ 7.70 (d, J = 6.9 Hz, 1H), 7.62 (d, J = 8.3 Hz, 1H), 7.52 (s, 1H), 7.33-7.26 (m, 4H), 7.22 (t, J = 7.2 Hz, 1H), 7.09 (dd, J = 8.3, 1.6 Hz, 1H), 6.59-6.56 (m, 2H), 4.50 (s, 2H), 3.76 (s, 3H), 3.70 (t, J = 6.2 Hz, 2H), 3.24 (t, J = 6.0 Hz, 2H), 3.04-3.01 (m, 2H), 2.98-2.95 (m, 2H) |
| 10 | 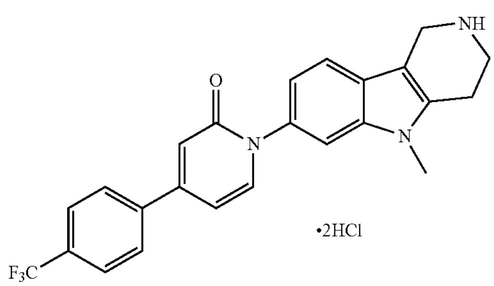 [SMILES: Cn1c2c(c3ccc(-n4ccc(-c5ccc(C(F)(F)F)cc5)cc4=O)cc31)CNCC2 ; "·2HCl"] | 424 | ¹H NMR (500 MHz, CD₃OD) δ 7.95 (d, J = 8.2 Hz, 2H), 7.84 (d, J = 8.2 Hz, 2H), 7.81 (d, J = 7.1 Hz, 1H), 7.63 (d, J = 8.3 Hz, 1H), 7.57 (s, 1H), 7.14 (dd, J = 8.3, 1.3 Hz, 1H), 6.96 (d, J = 1.6 Hz, 1H), 6.87 (dd, J = 7.1, 1.7 Hz, 1H), 4.50 (s, 2H), 3.76 (s, 3H), 3.68 (t, J = 6.1 Hz, 2H), 3.22 (t, J = 6.1 Hz, 2H) |
| 11 | 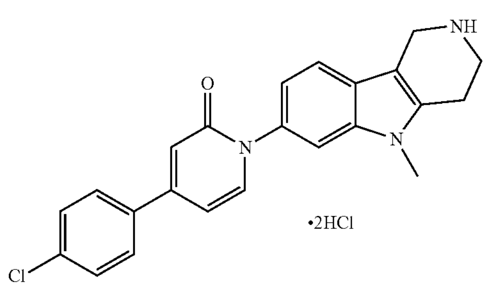 [SMILES: Cn1c2c(c3ccc(-n4ccc(-c5ccc(Cl)cc5)cc4=O)cc31)CNCC2 ; "·2HCl"] | 390 | ¹H NMR (500 MHz, CD₃OD) δ 7.80-7.78 (m, 3H), 7.66 (d, J = 8.5 Hz, 1H), 7.58-7.57 (m, 3H), 7.16 (dd, J = 8.3, 1.7 Hz, 1H), 6.94 (d, J = 1.8 Hz, 1H), 6.87 (dd, J = 7.1, 1.9 Hz, 1H), 6.17 (d, J = 2.7 Hz, 1H), 4.53 (s, 2H), 3.79 (s, 3H), 3.72 (t, J = 5.9 Hz, 2H), 3.25 (t, J = 5.9 Hz, 2H) |

TABLE 1-continued

| Ex. No. | Structure | Mass Spec | ¹H NMR Data |
|---|---|---|---|
| 12 | 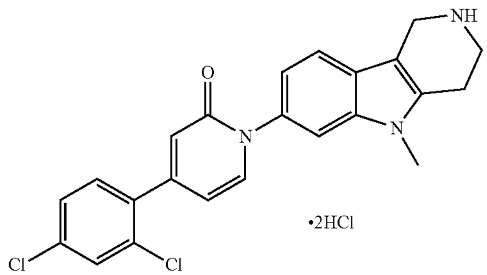 [SMILES: Cn1c2c(c3ccc(-n4ccc(-c5ccc(Cl)cc5Cl)cc4=O)cc31)CNCC2 ; "·2HCl"] | 424 | ¹H NMR (500 MHz, CD$_3$OD) δ 7.80 (d, J = 7.0 Hz, 1H), 7.70 (s, 1H), 7.68 (d, J = 7.9 Hz, 1H), 7.62 (s, 1H), 7.54 (s, 2H), 7.13 (d, J = 7.0 Hz, 1H), 6.73 (s, 1H), 6.61 (d, J = 7.2 Hz, 1H), 4.54 (s, 2H), 3.80 (s, 3H), 3.72 (t, J = 6.0 Hz, 2H), 3.26 (t, J = 5.9 Hz, 2H) |
| 13 | 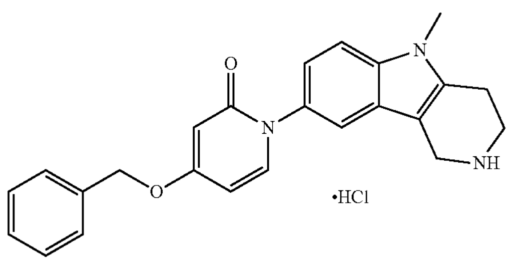 [SMILES: Cn1c2c(c3cc(-n4ccc(OCc5ccccc5)cc4=O)ccc31)CNCC2 ; Cl] | 386 | ¹H NMR (500 MHz, CD$_3$OD) δ 7.59 (d, J = 7.5 Hz, 1H), 7.54 (d, J = 9.0 Hz, 1H), 7.48-7.40 (m, 5H), 7.38-7.36 (m, 1H), 7.17 (dd, J = 8.5, 1.5 Hz, 1H), 6.33 (dd, J = 7.5, 2.5 Hz, 1H), 6.16 (d, J = 2.5 Hz, 1H), 5.20 (s, 2H), 4.45 (s, 2H), 3.77 (s, 3H), 3.67 (t, J = 6.0 Hz, 2H), 3.21 (t, J = 6.0 Hz, 2H) |
| 14 | 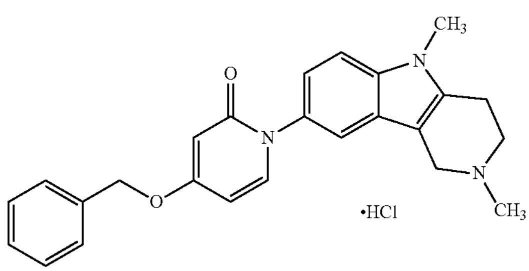 [SMILES: CN1CCc2c(c3cc(-n4ccc(OCc5ccccc5)cc4=O)ccc3n2C)C1 ; Cl] | 400 | ¹H NMR (500 MHz, DMSO-d$_6$) δ 10.26 (s, 1H), 7.56-7.36 (m, 8H), 7.10 (dd, J = 8.5, 1.5 Hz, 1H), 6.10 (dd, J = 7.5, 3.0 Hz, 1H), 5.97 (d, J = 3.0 Hz, 1H), 5.15 (s, 2H), 4.58 (m, 1H), 4.27 (m, 1H), 3.78 (m, 1H), 3.72 (s, 3H), 3.50 (m, 1H), 3.18 (m, 2H), 2.97 (s, 3H) |
| 15 | 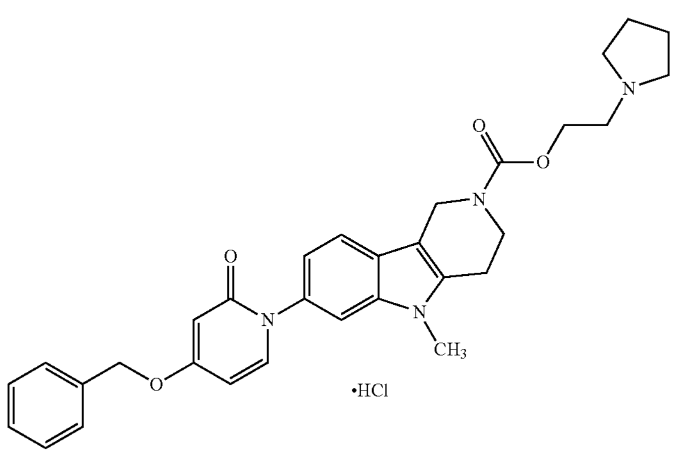 [SMILES: Cn1c2c(c3ccc(-n4ccc(OCc5ccccc5)cc4=O)cc31)CN(C(=O)OCCN1CCCC1)CC2 ; Cl] | 527 | ¹H NMR (500 MHz, CD$_3$OD) δ 7.78-7.75 (m, 1H), 7.57-7.54 (m, 1H), 7.49-7.37 (m, 6H), 7.04-7.01 (m, 1H), 6.55-6.52 (m, 1H), 6.33-6.31 (m, 1H), 5.26 (s, 2H), 4.80-4.73 (m, 2H), 4.49-4.48 (m, 2H), 3.94-3.93 (m, 2H), 3.82-3.72 (m, 2H), 3.69 (s, 3H), 3.58-3.57 (m, 2H), 3.20-3.14 (m, 2H), 2.98-2.94 (m, 2H), 2.15-1.99 (m, 4H) |

TABLE 1-continued

| Ex. No. | Structure | Mass Spec | ¹H NMR Data |
|---|---|---|---|
| 16 | [structure] | 471 | ¹H NMR (500 MHz, CD₃OD) δ 7.75-7.71 (m, 1H), 7.59-7.55 (m, 1H), 7.49-7.37 (m, 6H), 7.05-7.01 (m, 1H), 6.49-6.45 (m, 1H), 6.28-6.26 (m, 1H), 5.24 (s, 2H), 4.87 (br s, 1H), 4.69 (br s, 1H), 4.44-4.41 (m, 2H), 4.11-4.07 (m, 1H), 3.85-3.82 (m, 1H), 3.70 (2 × s, 3H), 3.06-2.92 (m, 2H), 2.97-2.94 (2 × s, 6H) |
| 17 | [structure] | 497 | ¹H NMR (500 MHz, CD₃OD) δ 7.60 (d, J = 7.5 Hz, 1H), 7.56 (d, J = 8.0 Hz, 1H), 7.49-7.35 (m, 6H), 7.06 (dd, J = 8.5, 1.5 Hz, 1H), 6.33 (dd, J = 7.5, 3.0 Hz, 1H), 6.16 (d, J = 3.0 Hz, 1H), 5.20 (s, 2H), 4.80 (d, J = 14.5 Hz, 1H), 4.54 (d, J = 14.5 Hz, 1H), 4.36 (s, 2H), 4.00-3.98 (m, 1H), 3.75 (s, 3H), 3.68-3.65 (m, 1H), 3.54 (t, J = 7.0 Hz, 2H), 3.49-3.45 (m, 2H), 3.35-3.33 (m, 2H), 2.05-1.92 (m, 4H) |
| 18 | [structure] | 511 | ¹H NMR (500 MHz, CD₃OD) δ 7.79-7.76 (m, 1H), 7.61-7.55 (m, 1H), 7.49-7.36 (m, 6H), 7.05-7.02 (m, 1H), 6.55-6.52 (m, 1H), 6.33-6.32 (m, 1H), 5.26 (s, 2H), 4.06 (t, J = 5.5 Hz, 1H), 3.94 (t, J = 5.5 Hz, 1H), 3.70-3.69 (m, 5H), 3.54-3.50 (m, 2H), 3.18-2.89 (m, 8H), 2.18-2.04 (m, 4H) |
| 19 | [structure] | 483 | ¹H NMR (500 MHz, CD₃OD) δ 7.75-7.72 (m, 1H), 7.63-7.55 (m, 1H), 7.49-7.36 (m, 6H), 7.05-7.02 (m, 1H), 6.51-6.46 (m, 1H), 6.29-6.27 (m, 1H), 5.25 (s, 2H), 4.79-4.76 (m, 2H), 4.14-3.97 (m, 2H), 3.87-3.82 (m, 1H), 3.71-3.69 (m, 4H), 3.60-3.50 (m, 1H), 3.45-3.36 (m, 3H), 3.04-3.03 (m, 1H), 2.94-2.92 (m, 1H), 2.52-2.36 (m, 1H), 2.18-2.00 (m, 1H) |

TABLE 1-continued
| Ex. No. | Structure | Mass Spec | ¹H NMR Data |
|---|---|---|---|
| 20 | 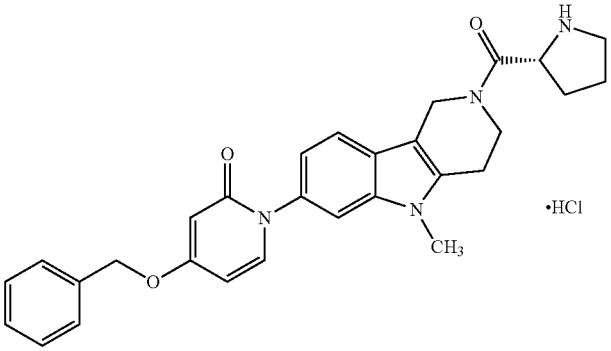 [SMILES: Cn1c2c(c3ccc(-n4ccc(OCc5ccccc5)cc4=O)cc31)CN(C(=O)[C@H]1CCCN1)CC2 ; Cl] | 483 | ¹H NMR (500 MHz, CD₃OD) δ 7.82-7.79 (m, 1H), 7.66-7.56 (m, 1H), 7.49-7.36 (m, 6H), 7.07-7.03 (m, 1H), 6.59-6.56 (m, 1H), 6.36 (dd, J = 5.0, 2.5 Hz, 1H), 5.28 (s, 2H), 4.82-4.81 (m, 2H), 4.14-4.05 (m, 1H), 3.97-3.95 (m, 1H), 3.71-3.69 (2 × s, 3H), 3.58-3.34 (m, 3H), 3.07-2.94 (m, 2H), 2.70-2.57 (m, 1H), 2.17-1.85 (m, 3H) |
| 21 | 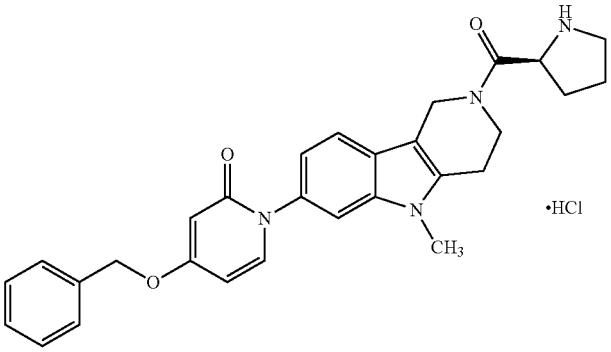 [SMILES: Cn1c2c(c3ccc(-n4ccc(OCc5ccccc5)cc4=O)cc31)CN(C(=O)[C@@H]1CCCN1)CC2 ; Cl] | 483 | ¹H NMR (500 MHz, CD₃OD) δ 7.82-7.79 (m, 1H), 7.66-7.56 (m, 1H), 7.49-7.36 (m, 6H), 7.07-7.03 (m, 1H), 6.59-6.56 (m, 1H), 6.36 (dd, J = 5.0, 2.5 Hz, 1H), 5.28 (s, 2H), 4.82-4.81 (m, 2H), 4.14-4.05 (m, 1H), 3.97-3.95 (m, 1H), 3.71-3.69 (2 × s, 3H), 3.58-3.34 (m, 3H), 3.07-2.94 (m, 2H), 2.70-2.57 (m, 1H), 2.17-1.85 (m, 3H) |
| 22 | 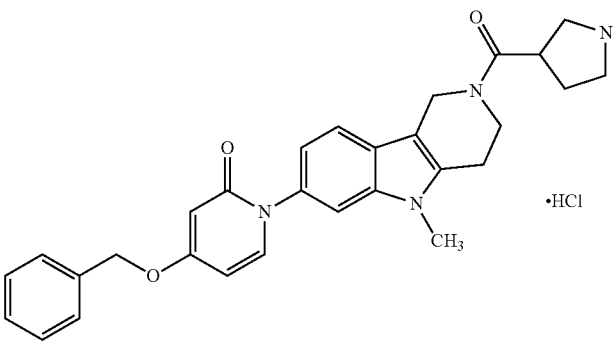 | 497 | ¹H NMR (500 MHz, CD₃OD) δ 7.61-7.33 (m, 8H), 7.02-6.98 (m, 1H), 6.29-6.27 (m, 1H), 6.12-6.11 (m, 1H), 5.17 (s, 2H), 4.79-4.76 (m, 2H), 4.09-3.97 (m, 2H), 3.81-3.79 (m, 1H), 3.69-3.67 (m, 4H), 3.49-3.42 (m, 1H), 3.22-3.16 (m, 2H), 3.00 (m, 1H), 2.92-2.91 (m, 1H), 2.81-2.78 (2 × s, 3H), 2.52-2.36 (m, 1H), 2.18-2.00 (m, 1H) |
| 23 | 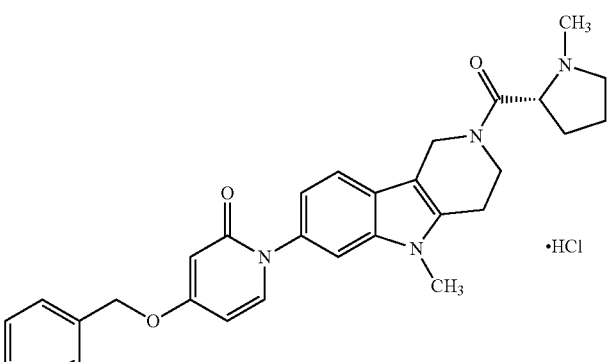 | 497 | ¹H NMR (500 MHz, CD₃OD) δ 7.61-7.33 (m, 8H), 7.03-6.99 (m, 1H), 6.30 (dd, J = 7.5, 2.5 Hz, 1H), 6.13 (d, J = 2.5 Hz, 1H), 5.18 (s, 2H), 4.80-4.70 (m, 2H), 4.12-4.09 (m, 1H), 3.92-3.90 (m, 1H), 3.78-3.72 (m, 1H), 3.69-3.68 (2 s, 3H), 3.49-3.42 (m, 1H), 3.28-3.20 (m, 1H), 3.07-3.00 (m, 2H), 2.96-2.94 (2 s, 3H), 2.79-2.65 (m, 1H), 2.21-2.09 (m, 1H), 2.09-1.86 (m, 2H) |

TABLE 1-continued

| Ex. No. | Structure | Mass Spec | ¹H NMR Data |
|---|---|---|---|
| 24 | 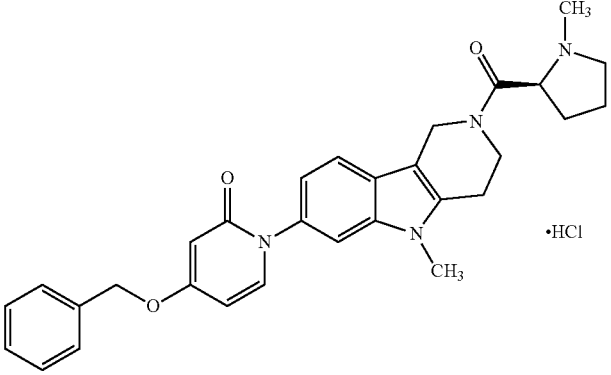 [SMILES: CN1CCC[C@H]1C(=O)N1CCc2c(c3ccc(-n4ccc(OCc5ccccc5)cc4=O)cc3n2C)C1 ; Cl] | 497 | ¹H NMR (500 MHz, CD₃OD) δ 7.61-7.33 (m, 8H), 7.03-6.99 (m, 1H), 6.30 (dd, J = 7.5, 2.5 Hz, 1H), 6.13 (d, J = 2.5 Hz, 1H), 5.18 (s, 2H), 4.80-4.70 (m, 2H), 4.12-4.09 (m, 1H), 3.92-3.90 (m, 1H), 3.78-3.72 (m, 1H), 3.69-3.68 (2 s, 3H), 3.49-3.42 (m, 1H), 3.28-3.20 (m, 1H), 3.07-3.00 (m, 2H), 2.96-2.94 (2 × s, 3H), 2.79-2.65 (m, 1H), 2.21-2.09 (m, 1H), 2.09-1.86 (m, 2H) |
| 25 | 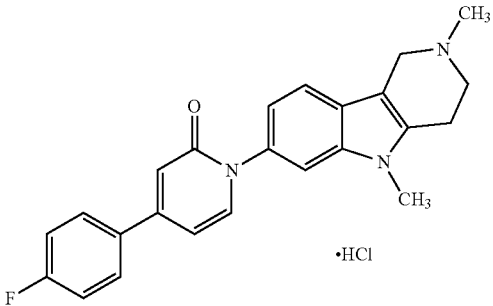 [SMILES: CN1CCc2c(c3ccc(-n4ccc(-c5ccc(F)cc5)cc4=O)cc3n2C)C1 ; Cl] | 388 | ¹H NMR (500 MHz, CD₃OD) δ 7.82-7.79 (m, 2H), 7.75 (d, J = 7.0 Hz, 1H), 7.61 (d, J = 8.5 Hz, 1H), 7.56 (d, J = 1.5 Hz, 1H), 7.29-7.25 (m, 2H), 7.14 (dd, J = 8.5, 1.5 Hz, 1H), 6.88 (d, J = 2.0 Hz, 1H), 6.82 (dd, J = 7.0, 2.0 Hz, 1H), 4.77 (d, J = 14.0 Hz, 1H), 4.41 (d, J = 14.0 Hz, 1H), 3.93-3.90 (m, 1H), 3.76 (s, 3H), 3.66-3.60 (m, 1H), 3.27 (m, 2H), 3.15 (s, 3H) |
| 26 | 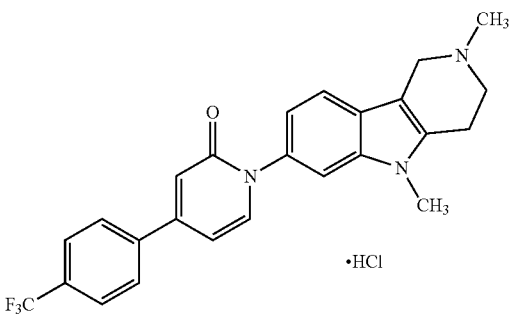 | 438 | ¹H NMR (500 MHz, CD₃OD) δ 7.95 (d, J = 8.5 Hz, 2H), 7.84 (d, J = 8.5 Hz, 2H), 7.80 (d, J = 7.5 Hz, 1H), 7.62 (d, J = 8.0 Hz, 1H), 7.57 (d, J = 1.5 Hz, 1H), 7.15 (dd, J = 8.5, 2.0 Hz, 1H), 6.96 (d, J = 1.5 Hz, 1H), 6.87 (dd, J = 7.5, 2.0 Hz, 1H), 4.78 (d, J = 14.0 Hz, 1H), 4.41 (d, J = 14.0 Hz, 1H), 3.93-3.90 (m, 1H), 3.77 (s, 3H), 3.66-3.60 (m, 1H), 3.27 (m, 2H), 3.15 (s, 3H) |
| 27 | 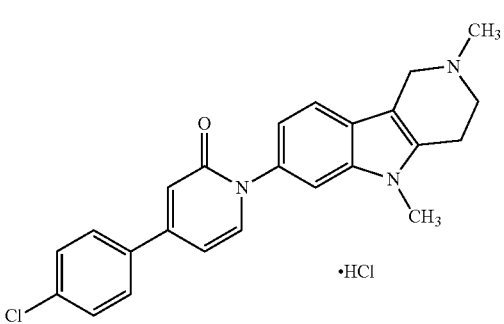 [SMILES: CN1CCc2c(c3ccc(-n4ccc(-c5ccc(Cl)cc5)cc4=O)cc3n2C)C1 ; Cl] | 404 | ¹H NMR (500 MHz, CD₃OD) δ 7.77-7.75 (m, 3H), 7.62 (d, J = 8.5 Hz, 1H), 7.57 (d, J = 2.0 Hz, 1H), 7.56-7.54 (m, 2H), 7.15 (dd, J = 8.5, 2.0 Hz, 1H), 6.91 (d, J = 2.0 Hz, 1H), 6.84 (dd, J = 7.0, 2.0 Hz, 1H), 4.78 (d, J = 14.0 Hz, 1H), 4.41 (d, J = 14.0 Hz, 1H), 3.93-3.90 (m, 1H), 3.77 (s, 3H), 3.66-3.60 (m, 1H), 3.27 (m, 2H), 3.15 (s, 3H) |

TABLE 1-continued

| Ex. No. | Structure | Mass Spec | ¹H NMR Data |
|---|---|---|---|
| 28 | 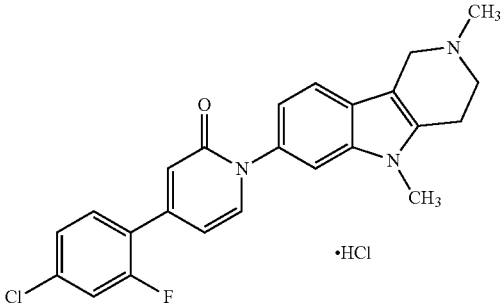 [SMILES: CN1CCc2c(c3ccc(-n4ccc(-c5ccc(Cl)cc5F)cc4=O)cc3n2C)C1 ; Cl] | 422 | ¹H NMR (500 MHz, CD₃OD) δ 7.76 (d, J = 7.0 Hz, 1H), 7.66-7.57 (m, 2H), 7.57 (d, J = 2.0 Hz, 1H), 7.42-7.39 (m, 2H), 7.15 (dd, J = 8.5, 2.0 Hz, 1H), 6.84 (s, 1H), 6.73-6.71 (m, 1H), 4.77 (d, J = 14.0 Hz, 1H), 4.41 (d, J = 14.0 Hz, 1H), 3.93-3.90 (m, 1H), 3.76(s, 3H), 3.64-3.61 (m, 1H), 3.27 (m, 2H), 3.15 (s, 3H) |
| 29 | 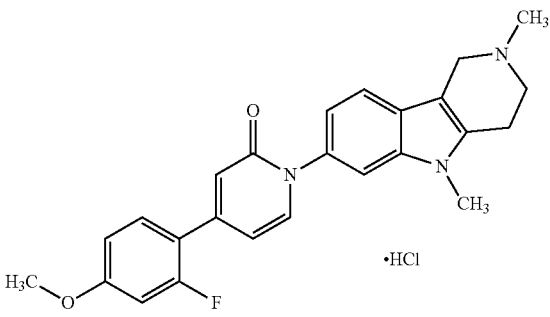 [SMILES: COc1ccc(-c2ccn(-c3ccc4c5c(n(C)c4c3)CCN(C)C5)c(=O)c2)c(F)c1 ; Cl] | 418 | ¹H NMR (500 MHz, CD₃OD) δ 7.72 (d, J = 7.0 Hz, 1H), 7.63-7.56 (m, 3H), 7.15 (dd, J = 8.5, 1.5 Hz, 1H), 6.92 (dd, J = 8.5, 2.5 Hz, 1H), 6.87 (dd, J = 13.0, 2.0 Hz, 1H), 6.83 (s, 1H), 6.76 (d, J = 7.0 Hz, 1H), 4.77 (d, J = 14.0 Hz, 1H), 4.41 (d, J = 14.0 Hz, 1H), 3.94-3.90 (m, 1H), 3.88 (s, 3H), 3.76 (s, 3H), 3.66-3.60 (m, 1H), 3.27 (m, 2H), 3.15 (s, 3H) |
| 30 | 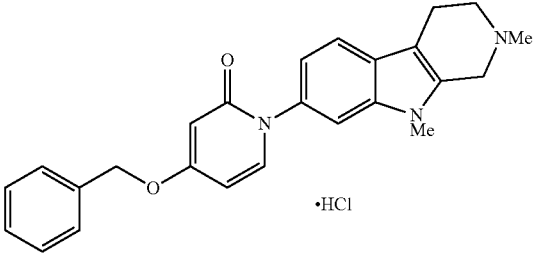 [SMILES: CN1CCc2c(n(C)c3cc(-n4ccc(OCc5ccccc5)cc4=O)ccc23)C1 ; Cl] | 400 | ¹H NMR (500 MHz, CD₃OD) δ 7.67-7.63 (m, 2H), 7.50-7.40 (m, 3H), 7.43-7.35 (m, 3H), 7.08 (dd, J = 8.3, 1.6 Hz, 1H), 6.40 (dd, J = 7.5, 2.6 Hz, 1H), 6.21 (d, J = 2.6 Hz, 1H), 5.22 (s, 2H), 4.81-4.80 (m, 1H), 4.58 (d, J = 15.3 Hz, 1H), 3.88-3.84 (m, 1H), 3.72 (s, 3H), 3.55-3.49 (m, 1H), 3.21-3.16 (m, 5H) |
| 31 | 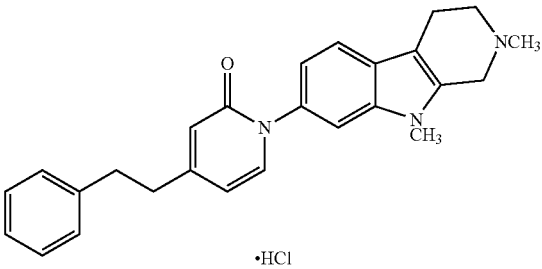 [SMILES: CN1CCc2c(n(C)c3cc(-n4ccc(CCc5ccccc5)cc4=O)ccc23)C1 ; Cl] | 398 | ¹H NMR (500 MHz, CD₃OD) δ 7.67-7.64 (m, 2H), 7.51 (d, J = 1.8 Hz, 1H), 7.30-7.24 (m, 4H), 7.20-7.17 (m, 1H), 7.08 (dd, J = 8.4, 1.9 Hz, 1H), 6.56 (dd, J = 6.9, 1.9 Hz, 1H), 6.53 (s, 1H), 4.85 (m, 1H), 4.49 (d, J = 15.3 Hz, 1H), 3.89-3.84 (m, 1H), 3.72 (s, 3H), 3.55-3.50 (m, 1H), 3.21-3.19 (m, 2H), 3.16 (s, 3H), 3.02-2.99 (m, 2H), 2.96-2.93 (m, 2H) |
| 32 | 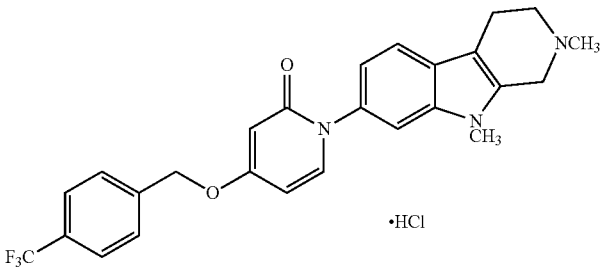 [SMILES: CN1CCc2c(n(C)c3cc(-n4ccc(OCc5ccc(C(F)(F)F)cc5)cc4=O)ccc23)C1 ; Cl] | 468 | ¹H NMR (500 MHz, CD₃OD) δ 7.78-7.73 (m, 3H), 7.69-7.64 (m, 3H), 7.52 (d, J = 1.8 Hz, 1H), 7.18-7.08 (m, 1H), 6.55-6.52 (m, 1H), 6.28 (d, J = 2.6 Hz, 1H), 5.35 (s, 2H), 4.82-4.80 (m, 1H), 4.50 (d, J = 15.4 Hz, 1H), 3.89-3.85 (m, 1H), 3.73 (s, 3H), 3.55-3.50 (m, 1H), 3.22-3.16 (m, 5H) |

TABLE 1-continued

| Ex. No. | Structure | Mass Spec | ¹H NMR Data |
|---|---|---|---|
| 33 | 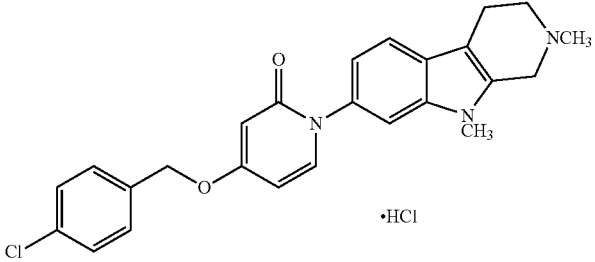 [SMILES: CN1CCc2c(n(C)c3cc(-n4ccc(OCc5ccc(Cl)cc5)cc4=O)ccc23)C1 ; Cl] | 434 | ¹H NMR (500 MHz, CD$_3$OD) δ 7.83 (d, J = 7.6 Hz, 1H), 7.68 (d, J = 8.3 Hz, 1H), 7.50-7.46 (m, 3H), 7.44-7.42 (m, 2H), 7.08 (dd, J = 8.3, 1.8 Hz, 1H), 6.41 (dd, J = 7.6, 2.6 Hz, 1H), 6.21 (d, J = 2.6 Hz, 1H), 5.21 (s, 2H), 4.86-4.84 (m, 1H), 4.49 (d, J = 15.4 Hz, 1H), 3.88-3.84 (m, 1H), 3.72 (s, 3H), 3.55-3.50 (m, 1H), 3.21-3.16 (m, 5H) |
| 34 | 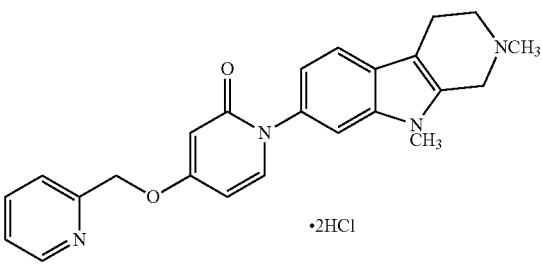 [SMILES: CN1CCc2c(n(C)c3cc(-n4ccc(OCc5ccccn5)cc4=O)ccc23)C1 ; "·2HCl"] | 401 | ¹H NMR (500 MHz, CD$_3$OD) δ 8.90 (dd, J = 5.8, 1.8 Hz, 1H), 8.65 (overlapping ddd, J = 7.9, 1.6 Hz, 1H), 8.20 (d, J = 8.0 Hz, 1H), 8.07 (overlapping dd, J = 6.4 Hz, 1H), 7.70 (d, J = 7.6 Hz, 1H), 7.65 (d, J = 6.4 Hz, 1H), 7.49 (d, J = 1.7 Hz, 1H), 7.07 (d, J = 6.8, 1.8 Hz, 1H), 6.63 (dd, J = 7.6, 2.7 Hz, 1H), 6.21 (d, J = 2.7 Hz, 1H), 5.59 (s, 2H), 4.80 (m, 1H), 4.50 (d, J = 15.3 Hz, 1H), 3.88-3.85 (m, 1H), 3.73 (s, 3H), 3.55-3.50 (m, 1H), 3.21-3.16 (m, 5H) |
| 35 | 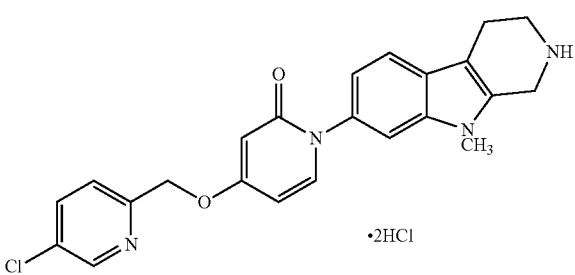 [SMILES: Cn1c2c(c3ccc(-n4ccc(OCc5ccc(Cl)cn5)cc4=O)cc31)CCNC2 ; "·2HCl"] | 421 | ¹H NMR (500 MHz, CD$_3$OD) δ 8.61 (s, 1H), 7.77 (dd, J = 8.3, 3.8 Hz, 1H), 7.64-7.62 (m, 3H), 7.47 (d, J = 1.6 Hz, 1H), 7.03 (dd, J = 8.4, 1.8 Hz, 1H), 6.37 (dd, J = 7.6, 3.8 Hz, 1H), 6.15 (d, J = 2.7 Hz, 1H), 5.28 (s, 2H), 4.54 (s, 2H), 3.71 (s, 3H), 3.60 (t, J = 6.1 Hz, 2H), 3.12 (t, J = 6.0 Hz, 2H) |
| 36 | 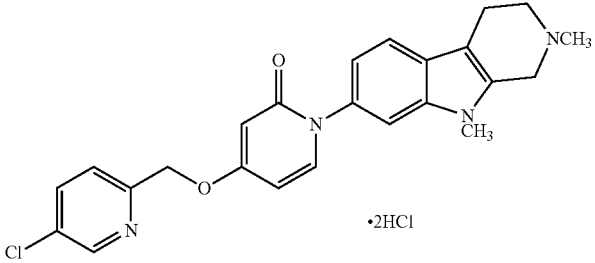 [SMILES: CN1CCc2c(n(C)c3cc(-n4ccc(OCc5ccc(Cl)cn5)cc4=O)ccc23)C1 ; "·2HCl"] | 435 | ¹H NMR (500 MHz, CD$_3$OD) δ 8.68 (br s, 1H), 8.05 (dd, J = 8.0, 2.4 Hz, 1H), 7.76 (d, J = 8.4 Hz, 1H), 7.71 (d, J = 8.4 Hz, 1H), 7.65 (d, J = 8.3 Hz, 1H), 7.51 (d, J = 1.6 Hz, 1H), 7.09 (dd, J = 8.3, 1.8 Hz, 1H), 6.53 (dd, J = 7.6, 1.7 Hz, 1H), 6.28 (d, J = 1.6 Hz, 1H), 5.36 (s, 2H), 4.85-4.80 (m, 1H), 4.49 (d, J = 15.3 Hz, 1H), 3.89-3.84 (m, 1H), 3.72 (s, 3H), 3.53-3.47 (m, 1H), 3.22-3.19 (m, 2H), 3.16 (s, 3H) |
| 37 | 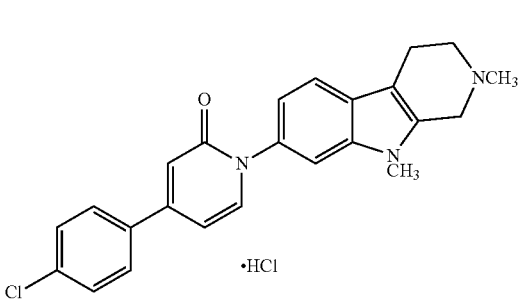 [SMILES: CN1CCc2c(n(C)c3cc(-n4ccc(-c5ccc(Cl)cc5)cc4=O)ccc23)C1 ; Cl] | 404 | ¹H NMR (500 MHz, DMSO-d$_6$) δ 11.0 (br s, 1H), 7.83 (dd, J = 6.8, 1.9 Hz, 2H), 7.76 (d, J = 7.1 Hz, 1H), 7.62-7.57 (m, 4H), 7.07 (dd, J = 8.3, 1.8 Hz, 1H), 6.81 (d, J = 2.0 Hz, 1H), 6.69 (dd, J = 7.2, 2.1 Hz, 1H), 4.79 (d, J = 15.2 Hz, 1H), 4.44 (dd, J = 15.2, 6.0 Hz, 1H), 3.74-3.68 (m, 4H), 3.48-3.38 (m, 1H), 3.10-2.99 (m, 5H) |

TABLE 1-continued

| Ex. No. | Structure | Mass Spec | ¹H NMR Data |
|---|---|---|---|
| 38 | 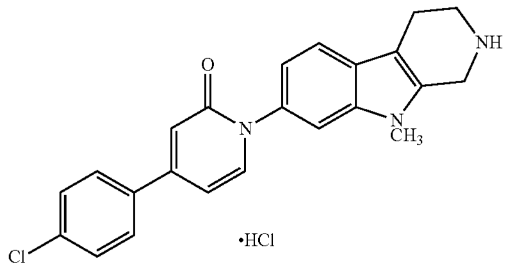 [SMILES: Cn1c2c(c3ccc(-n4ccc(-c5ccc(Cl)cc5)cc4=O)cc31)CCNC2 ; Cl] | 390 | ¹H NMR (500 MHz, CD₃OD) δ 7.78-7.75 (m, 3H), 7.67 (d, J = 8.3 Hz, 1H), 7.55-7.53 (m, 3H), 7.13 (dd, J = 8.3, 1.8 Hz, 1H), 6.91 (d, J = 1.9 Hz, 1H), 6.84 (dd, J = 7.1, 2.0 Hz, 1H), 4.56 (s, 2H), 3.74 (s, 3H), 3.61 (t, J = 6.0 Hz, 2H), 3.14 (t, J = 6.0 Hz, 2H) |
| 39 | 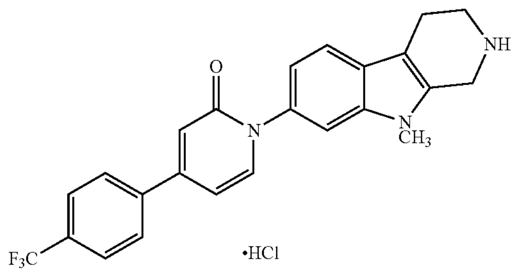 [SMILES: Cn1c2c(c3ccc(-n4ccc(-c5ccc(C(F)(F)F)cc5)cc4=O)cc31)CCNC2 ; Cl] | 424 | ¹H NMR (300 MHz, CD₃OD) δ 7.97 (d, J = 8.1 Hz, 2H), 7.87-7.80 (m, 3H), 7.68 (d, J = 8.2 Hz, 1H), 7.57 (d, J = 1.5 Hz, 1H), 7.14 (dd, J = 8.3, 1.8 Hz, 1H), 6.96 (d, J = 1.8 Hz, 1H), 6.87 (dd, J = 7.2, 1.8 Hz, 1H), 4.56 (s, 2H), 3.74 (s, 3H), 3.61 (t, J = 6.0 Hz, 2H), 3.14 (t, J = 6.0 Hz, 2H) |
| 40 | 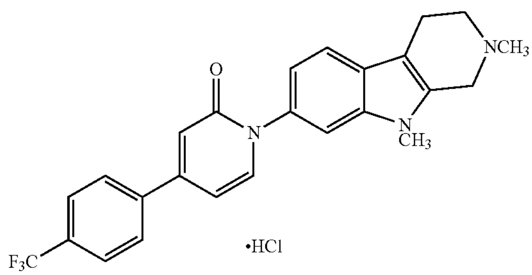 [SMILES: CN1CCc2c(n(C)c3cc(-n4ccc(-c5ccc(C(F)(F)F)cc5)cc4=O)ccc23)C1 ; Cl] | 438 | ¹H NMR (500 MHz, CD₃OD) δ 7.96 (d, J = 8.2 Hz, 2H), 7.85-7.83 (m, 3H), 7.68 (d, J = 8.3 Hz, 1H), 7.58 (d, J = 1.6 Hz, 1H), 7.16 (dd, J = 8.3, 1.7 Hz, 1H), 6.98 (d, J = 1.8 Hz, 1H), 6.90 (dd, J = 7.1, 1.9 Hz, 1H), 4.87-4.86 (m, 1H), 4.51 (d, J = 15.3 Hz, 1H), 3.90-3.86 (m, 1H), 3.74 (s, 3H), 3.57-3.51 (m, 1H), 3.23-3.20 (m, 2H), 3.17 (s, 3H) |
| 41 | 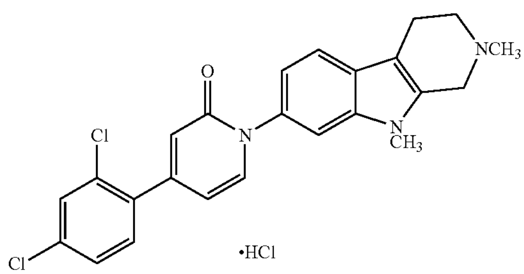 [SMILES: CN1CCc2c(n(C)c3cc(-n4ccc(-c5ccc(Cl)cc5Cl)cc4=O)ccc23)C1 ; Cl] | 438 | ¹H NMR (500 MHz, CD₃OD) δ 7.77 (d, J = 7.0 Hz, 1H), 7.68 (d, J = 8.4 Hz, 1H), 7.65 (overlapping dd, J = 1.1 Hz, 1H), 7.58 (d, J = 1.7 Hz, 1H), 7.49 (s, 2H), 7.16 (dd, J = 8.3, 1.8 Hz, 1H), 6.70 (d, J = 1.5 Hz, 1H), 6.62 (dd, J = 7.0, 1.9 Hz, 1H), 4.86 (m, 1H), 4.50 (d, J = 15.3 Hz, 1H), 3.89-3.85 (m, 1H), 3.74 (s, 3H), 3.56-3.55 (m, 1H), 3.23-3.20 (m, 2H), 3.16 (s, 3H) |
| 42 | 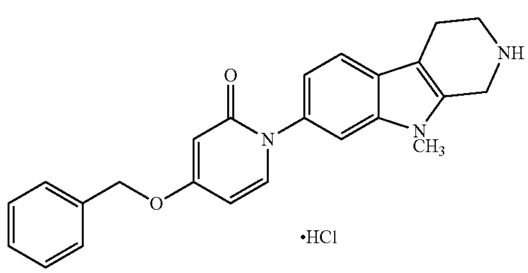 [SMILES: Cn1c2c(c3ccc(-n4ccc(OCc5ccccc5)cc4=O)cc31)CCNC2 ; Cl] | 386 | ¹H NMR (500 MHz, DMSO-d₆) δ 9.71 (br s, 2H), 7.56 (d, J = 7.6 Hz, 1H), 7.54 (d, J = 8.3 Hz, 1H), 7.50-7.47 (m, 3H), 7.44-7.41 (m, 2H), 7.38-7.37 (m, 1H), 6.99 (dd, J = 8.3, 1.8 Hz, 1H), 6.11 (dd, J = 7.6, 2.8 Hz, 1H), 5.97 (d, J = 2.6 Hz, 1H), 5.15 (s, 2H), 4.45 (s, 2H), 3.81 (s, 3H), 3.42-3.41 (m, 2H), 2.98-2.97 (m, 2H) |

TABLE 1-continued

| Ex. No. | Structure | Mass Spec | $^1$H NMR Data |
|---|---|---|---|
| 43 | 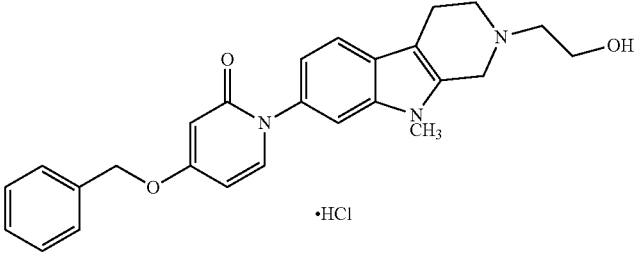 [SMILES: Cn1c2c(c3ccc(-n4ccc(OCc5ccccc5)cc4=O)cc31)CCN(CCO)C2 ; Cl] | 430 | $^1$H NMR (500 MHz, CD$_3$OD) δ 7.63 (d, J = 8.4 Hz, 1H), 7.61 (d, J = 7.5 Hz, 1H), 7.47-7.46 (m, 3H), 7.42-7.39 (m, 2H), 7.36 (d, J = 7.1 Hz, 1H), 7.06 (dd, J = 8.3, 1.8 Hz, 1H), 6.33 (dd, J = 7.6, 2.6 Hz, 1H), 6.15 (d, J = 2.6 Hz, 1H), 5.19 (s, 2H), 4.81-4.79 (m, 1H), 4.59 (d, J = 15.3 Hz, 1H), 4.01 (t, J = 5.1 Hz, 2H), 3.97-3.94 (m, 1H), 3.73 (s, 3H), 3.58-3.50 (m, 3H), 3.21-3.16 (m, 2H) |
| 44 | 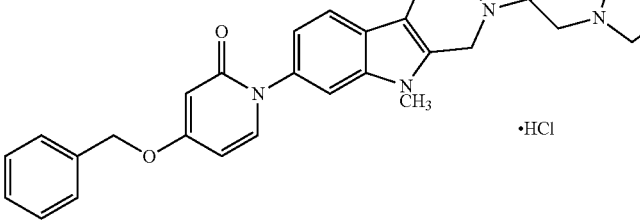 | 497 | $^1$H NMR (500 MHz, CD$_3$OD) δ 7.86 (d, J = 7.5 Hz, 1H), 7.62 (dd, J = 8.2, 2.7 Hz, 1H), 7.51-7.50 (m, 3H), 7.46-7.43 (m, 2H), 7.41-7.40 (m, 1H), 7.08-7.06 (m, 1H), 6.63 (dd, J = 7.8, 2.6 Hz, 1H), 6.40 (d, J = 1.4 Hz, 1H), 5.31 (s, 2H), 4.93 (s, 1.3H), 4.77 (s, 0.7H), 4.56-4.55 (m, 2H), 4.04-4.02 (m, 0.6H), 3.81-3.78 (m, 3.4H), 3.76 (s, 3H), 3.24-3.19 (m, 2H), 2.79-2.97 (m, 1.3H), 2.92-2.85 (m, 0.7H), 2.22-2.19 (m, 2H), 2.11-2.19 (m, 2H) |
| 45 | 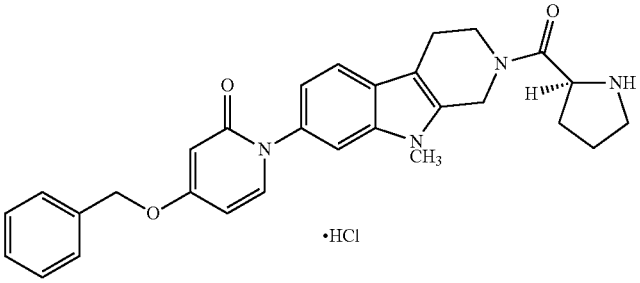 [SMILES: Cn1c2c(c3ccc(-n4ccc(OCc5ccccc5)cc4=O)cc31)CCN(C(=O)[C@@H]1CCCN1)C2 ; Cl] | 483 | $^1$H NMR (500 MHz, CD$_3$OD) δ 7.79 (dd, J = 7.5, 1.4 Hz, 1H), 7.47 (d, J = 8.3 Hz, 1H), 7.49-7.46 (m, 3H), 7.44-7.46 (m, 2H), 7.39-7.36 (m, 1H), 7.04 (dd, J = 8.3, 1.6 Hz, 1H), 6.57-6.55 (m, 1H), 6.34 (d, J = 2.5 Hz, 1H), 5.27 (s, 2H), 4.96-4.87 (m, 2H), 3.90-8.86 (m, 2H), 3.77 (s, 3H), 3.48-3.34 (m, 3H), 3.00-2.86 (m, 2H), 2.67-2.61 (m, 1H), 2.17-2.02 (m, 3H) |
| 46 | 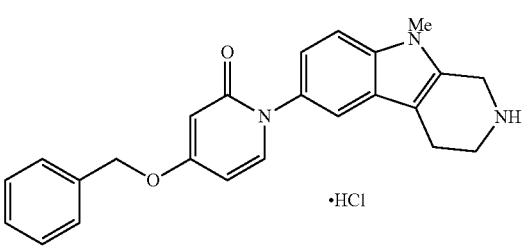 [SMILES: Cn1c2c(c3cc(-n4ccc(OCc5ccccc5)cc4=O)ccc31)CCNC2 ; Cl] | 386 | $^1$H NMR (500 MHz, CD$_3$OD) δ 7.66 (d, J = 7.5 Hz, 1H), 7.57-7.52 (m, 2H), 7.46 (d, J = 7.7 Hz, 2H), 7.41 (overlapping dd, J = 7.3 Hz, 2H), 7.36 (d, J = 7.5 Hz, 1H), 7.19 (dd, J = 8.6, 2.0 Hz, 1H), 6.42 (dd, J = 7.5, 2.7 Hz, 1H), 6.22 (d, J = 2.6 Hz, 1H), 5.22 (s, 2H), 4.55 (s, 2H), 3.75 (s, 3H), 3.58 (t, J = 6.0 Hz, 2H), 3.10 (t, J = 6.0 Hz, 2H) |
| 47 | 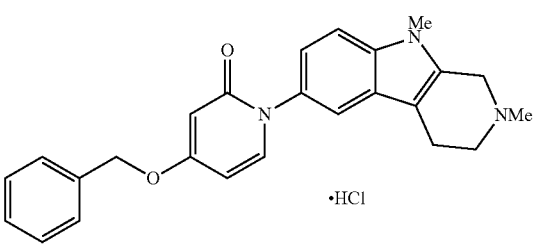 [SMILES: CN1CCc2c(n(C)c3ccc(-n4ccc(OCc5ccccc5)cc4=O)cc23)C1 ; Cl] | 400 | $^1$H NMR (500 MHz, CD$_3$OD) δ 7.56-7.53 (m, 2H), 7.51 (d, J = 1.8 Hz, 1H), 7.46 (d, J = 7.3 Hz, 2H), 7.41 (overlapping dd, J = 7.4 Hz, 2H), 7.36 (d, J = 7.2 Hz, 1H), 7.19 (dd, J = 8.6, 2.0 Hz, 1H), 6.27 (dd, J = 7.6, 2.7 Hz, 1H), 6.11 (d, J = 2.6 Hz, 1H), 5.18 (s, 2H), 4.64 (br s, 2H), 3.75 (s, 3H), 3.67 (br s, 2H), 3.18-3.13 (m, 5H) |

TABLE 1-continued

| Ex. No. | Structure | Mass Spec | ¹H NMR Data |
|---|---|---|---|
| 48 | 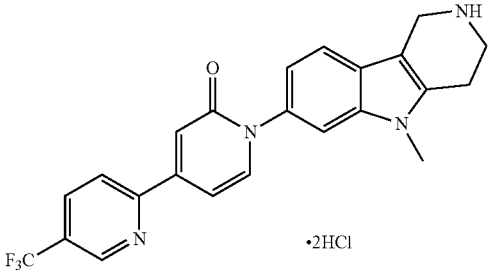 [SMILES: Cn1c2c(c3ccc(-n4ccc(-c5ccc(C(F)(F)F)cn5)cc4=O)cc31)CNCC2 ; "·2HCl"] •2HCl | 425 | ¹H NMR (500 MHz, CD$_3$OD) δ 9.06 (s, 1H), 8.28 (dd, J = 8.4, 2.1 Hz, 1H), 8.23 (d, J = 8.2 Hz, 1H), 7.87 (d, J = 7.1 Hz, 1H), 7.64 (d, J = 8.3 Hz, 1H), 7.58 (d, J = 1.6 Hz, 1H), 7.43 (d, J = 1.6 Hz, 1H), 7.29 (dd, J = Hz, 1H), 7.17 (dd, J = 8.3, 1.8 Hz, 1H), 4.50 (s, 2H), 3.76 (s, 3H), 3.69 (t, J = 6.0 Hz, 2H), 3.22 (t, J = Hz, 2H) |
| 49 | 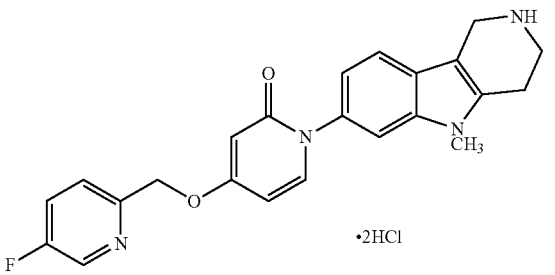 [SMILES: Cn1c2c(c3ccc(-n4ccc(OCc5ccc(F)cn5)cc4=O)cc31)CNCC2 ; "·2HCl"] •2HCl | 405 | ¹H NMR (500 MHz, CD$_3$OD) δ 8.70 (s, 1H), 8.00 (dt, J = 8.4, 2.8 Hz, 1H), 7.91-7.88 (m, 2H), 7.63 (d, J = 8.4 Hz, 1H), 7.55 (s, 1H), 7.11 (dd, J = 8.3, 1.7 Hz, 1H), 6.69 (dd, J = 7.5, 2.7 Hz, 1H), 6.45 (d, J = 2.6 Hz, 1H), 5.46 (s, 2H), 4.49 (s, 2H), 3.75 (s, 3H), 3.68 (t, J = 6.1 Hz, 2H), 3.22 (t, J = 6.1 Hz, 2H) |
| 50 | 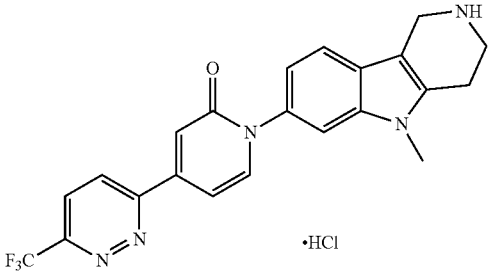 [SMILES: Cn1c2c(c3ccc(-n4ccc(-c5ccc(C(F)(F)F)nn5)cc4=O)cc31)CNCC2 ; Cl] •HCl | 426 | ¹H NMR (500 MHz, CD$_3$OD) δ 8.54 (d, J = 8.8 Hz, 1H), 8.28 (d, J = 8.9 Hz, 1H), 7.91 (d, J = 7.0 Hz, 1H), 7.64 (d, J = 8.4 Hz, 1H), 7.60 (d, J = 1.5 Hz, 1H), 7.44 (d, J = 1.5 Hz, 1H), 7.35 (dd, J = 7.2, 1.9 Hz, 1H), 7.16 (dd, J = 8.3, 1.8 Hz, 1H), 4.50 (s, 2H), 3.77 (s, 3H), 3.69 (t, J = 6.1 Hz, 2H), 3.22 (t, J = 6.0 Hz, 2H) |
| 51 | 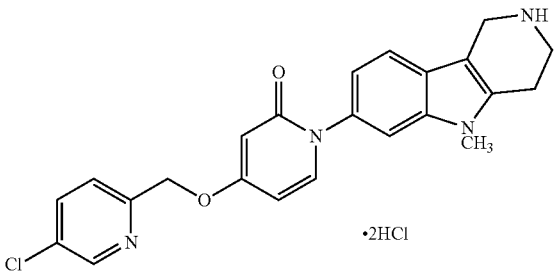 [SMILES: Cn1c2c(c3ccc(-n4ccc(OCc5ccc(Cl)cn5)cc4=O)cc31)CNCC2 ; "·2HCl"] •2HCl | 421 | ¹H NMR (300 MHz, CD$_3$OD) δ 8.61 (d, J = 2.1 Hz, 1H), 7.95 (dd, J = 8.4, 2.4 Hz, 1H), 7.62 (d, J = 7.6 Hz, 2H), 7.58 (d, J = 8.4 Hz, 1H), 7.47 (d, J = 1.6 Hz, 1H), 7.05 (dd, J = 8.3, 1.8 Hz, 1H), 6.36 (dd, J = 7.6, 2.2 Hz, 1H), 6.13 (d, J = 2.6 Hz, 1H), 5.28 (s, 2H), 4.48 (s, 2H), 3.73 (s, 3H), 3.67 (t, J = 6.2 Hz, 2H), 3.02 (t, J = 6.2 Hz, 2H) |
| 52 | 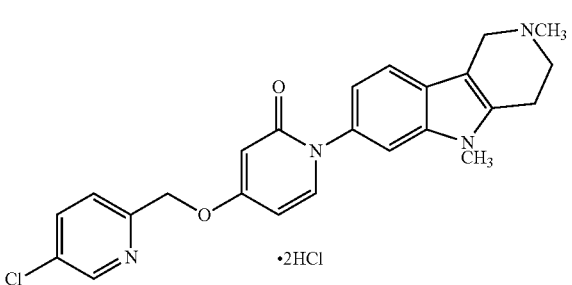 [SMILES: CN1CCc2c(c3ccc(-n4ccc(OCc5ccc(Cl)cn5)cc4=O)cc3n2C)C1 ; "·2HCl"] •2HCl | 435 | ¹H NMR (300 MHz, CD$_3$OD) δ 8.60 (d, J = 2.0 Hz, 1H), 7.96-7.92 (m, 1H), 7.61 (d, J = 7.7 Hz, 2H), 7.57 (d, J = 8.3 Hz, 1H), 7.47 (d, J = 1.4 Hz, 1H), 7.06 (dd, J = 8.4, 1.7 Hz, 1H), 6.34 (dd, J = 7.6, 2.6 Hz, 1H), 6.12 (d, J = 2.6 Hz, 1H), 5.27 (s, 2H), 4.75 (d, J = 14.2 Hz, 1H), 4.38 (d, J = 14.1 Hz, 1H), 3.95-3.85 (m, 1H), 3.73 (s, 3H), 3.63 (m, 1H), 3.31 (m overlapping with solvent, 2H), 3.13 (s, 3H) |

TABLE 1-continued

| Ex. No. | Structure | Mass Spec | ¹H NMR Data |
|---|---|---|---|
| 53 | 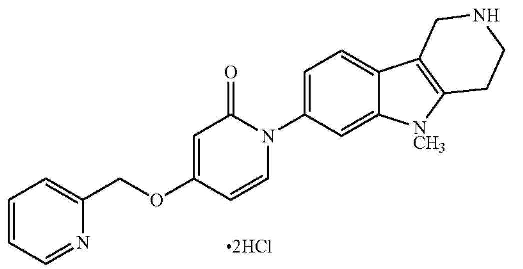 [SMILES: Cn1c2c(c3ccc(-n4ccc(OCc5ccccn5)cc4=O)cc31)CNCC2 ; "·2HCl"] | 387 | ¹H NMR (300 MHz, CDCl₃) δ 8.88 (d, J = 5.2 Hz, 1H), 8.59 (dd, J = 7.9, 1.5 Hz, 1H), 8.15 (d, J = 8.0 Hz, 1H), 8.01 (overlapping dd, J = 6.6 Hz, 1H), 7.69 (d, J = 7.6 Hz, 1H), 7.60 (d, J = 8.4 Hz, 1H), 7.48 (d, J = 1.6 Hz, 1H), 7.06 (dd, J = 8.4, 1.8 Hz, 1H), 6.44 (dd, J = 7.6, 2.7 Hz, 1H), 6.21 (d, J = 2.7 Hz, 1H), 5.57 (s, 2H), 4.48 (s, 2H), 3.74 (s, 3H), 3.68 (t, J = 6.2 Hz, 2H), 3.21 (t, J = 6.2 Hz, 2H) |
| 54 | 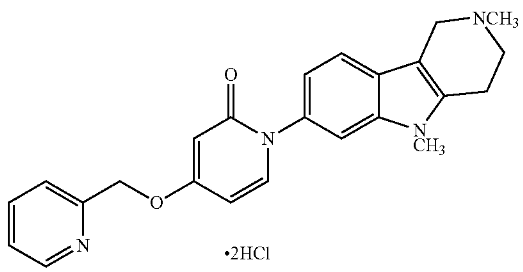 [SMILES: CN1CCc2c(c3ccc(-n4ccc(OCc5ccccn5)cc4=O)cc3n2C)C1 ; "·2HCl"] | 401 | ¹H NMR (500 MHz, CD₃OD) δ 8.87 (d, J = 5.7 Hz, 1H), 8.58 (overlapping dd, J = 8.2 Hz, 1H), 8.14 (d, J = 7.9 Hz, 1H), 8.00 (overlapping dd, J = 6.6 Hz, 1H), 7.69 (d, J = 7.6 Hz, 1H), 7.59 (d, J = 8.3 Hz, 1H), 7.49 (s, 1H), 7.07 (dd, J = 8.3, 1.7 Hz, 1H), 6.44 (dd, J = 7.5, 2.6 Hz, 1H), 6.20 (d, J = 2.0 Hz, 1H), 5.56 (s, 2H), 4.76 (d, J = 14.2 Hz, 1H), 4.40 (d, J = 14.2 Hz, 1H), 3.91 (m, 1H), 3.74 (s, 3H), 3.61 (m, 1H), 3.29-3.17 (m overlapping with solvent, 2H), 3.13 (s, 3H) |
| 55 | 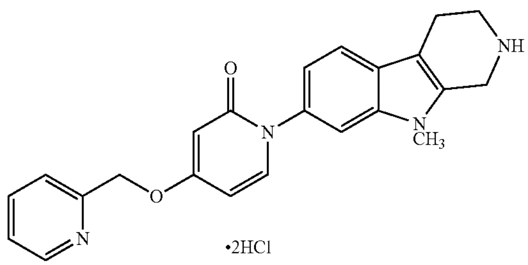 [SMILES: Cn1c2c(c3ccc(-n4ccc(OCc5ccccn5)cc4=O)cc31)CCNC2 ; "·2HCl"] | 387 | ¹H NMR (500 MHz, CD₃OD) δ 8.89 (d, J = 5.4 Hz, 1H), 8.61 (overlapping ddd, J = 8.0, 1.6 Hz, 1H), 8.16 (d, J = 8.0 Hz, 1H), 8.02 (overlapping dd, J = 6.6 Hz, 1H), 7.70 (d, J = 7.6 Hz, 1H), 7.63 (d, J = 8.4 Hz, 1H), 7.47 (d, J = 1.6 Hz, 1H), 7.06 (dd, J = 8.4, 1.8 Hz, 1H), 6.44 (dd, J = 7.6, 2.7 Hz, 1H), 6.21 (d, J = 2.6 Hz, 1H), 5.57 (s, 2H), 4.56 (s, 2H), 3.73 (s, 3H), 3.60 (t, J = 6.0 Hz, 2H), 3.13 (t, J = 6.0 Hz, 2H) |
| 56 | 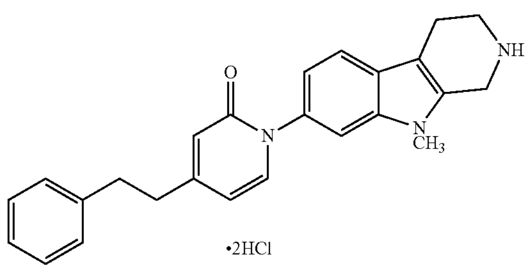 [SMILES: Cn1c2c(c3ccc(-n4ccc(CCc5ccccc5)cc4=O)cc31)CCNC2 ; "·2HCl"] | 384 | ¹H NMR (300 MHz, DMSO-d₆) δ 9.67 (s, 2H), 7.59-7.52 (m, 3H), 7.35-7.27 (m, 4H), 7.24-7.17 (m, 1H), 7.01 (dd, J = 7.4, 2.0 Hz, 1H), 6.38-6.27 (m, 2H), 4.45 (s, 2H), 3.67 (s, 3H), 3.42 (t, J = 6.4 Hz, 2H), 2.97-2.89 (m, 4H), 2.81-2.76 (m, 2H) |
| 57 | 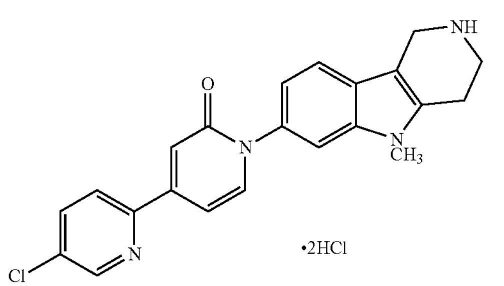 [SMILES: Cn1c2c(c3ccc(-n4ccc(-c5ccc(Cl)cn5)cc4=O)cc31)CNCC2 ; "·2HCl"] | 391 | ¹H NMR (500 MHz, CD₃OD) δ 8.74 (d, J = 2.4 Hz, 1H), 8.06 (d, J = 8.5 Hz, 1H), 8.02 (dd, J = 8.7, 2.4 Hz, 1H), 7.86 (d, J = 7.2 Hz, 1H), 7.64 (d, J = 8.3 Hz, 1H), 7.58 (d, J = 1.9 Hz, 1H), 7.37 (d, J = 1.5 Hz, 1H), 7.27 (dd, J = 8.5, 1.8 Hz, 1H), 7.15 (dd, J = 8.4, 1.8 Hz, 1H), 4.50 (s, 2H), 3.75 (s, 3H), 3.68 (t, J = 6.5 Hz, 2H), 3.22 (t, J = 6.5 Hz, 2H) |

TABLE 1-continued

| Ex. No. | Structure | Mass Spec | ¹H NMR Data |
|---|---|---|---|
| 59 | 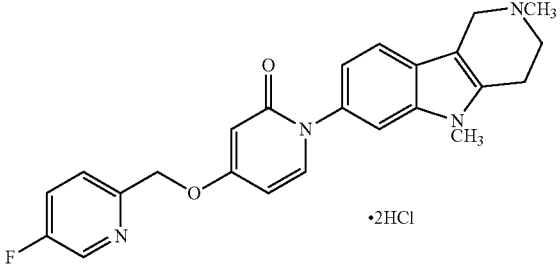 [SMILES: CN1CCc2c(c3ccc(-n4ccc(OCc5ccc(F)cn5)cc4=O)cc3n2C)C1 ; "·2HCl"] | 419 | ¹H NMR (500 MHz, CD₃OD) δ 8.65 (d, J = 2.6 Hz, 1H), 7.91 (overlapping ddd, J = 9.6, 2.1 Hz, 1H), 7.83-7.20 (m, 2H), 7.61 (d, J = 8.4 Hz, 1H), 7.53 (d, J = 1.8 Hz, 1H), 7.09 (dd, J = 8.4, 1.8 Hz, 1H), 6.59 (dd, J = 7.5, 2.6 Hz, 1H), 6.36 (d, J = 2.6 Hz, 1H), 5.41 (s, 2H), 4.76 (d, J = 14.2 Hz, 1H), 4.39 (d, J = 14.2 Hz, 1H), 3.94-3.82 (m, 2H), 3.74 (s, 3H), 3.65-3.58 (m, 2H), 3.13 (s, 3H) |
| 60 | 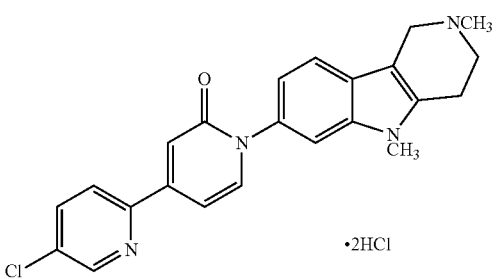 [SMILES: CN1CCc2c(c3ccc(-n4ccc(-c5ccc(Cl)cn5)cc4=O)cc3n2C)C1 ; "·2HCl"] | 405 | ¹H NMR (500 MHz, CD₃OD) δ 8.72 (d, J = 1.7 Hz, 1H), 8.03 (d, J = 7.9 Hz, 1H), 7.99 (dd, J = 8.2, 2.2 Hz, 1H), 7.79 (d, J = 7.1 Hz, 1H), 7.61 (d, J = 8.3 Hz, 1H), 7.56 (d, J = 1.3 Hz, 1H), 7.34 (d, J = 1.5 Hz, 1H), 7.19 (dd, J = 7.2, 1.8 Hz, 1H), 7.14 (dd, J = 8.3, 1.8 Hz, 1H), 4.80-4.72 (br m, 1H), 4.46-4.34 (m, 1H), 3.96-3.86 (m, 1H), 3.75 (s, 3H), 3.65-3.55 (br m, 1H), 3.28 (s, 2H), 3.14 (s, 3H) |
| 61 | 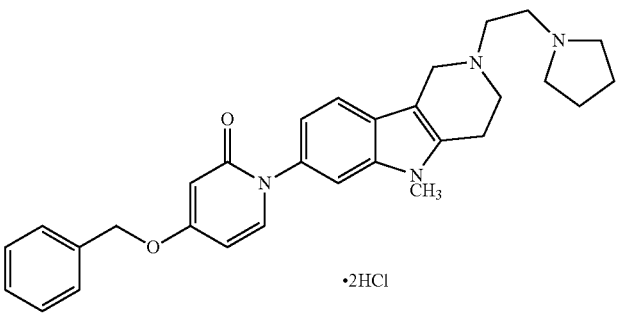 [SMILES: Cn1c2c(c3ccc(-n4ccc(OCc5ccccc5)cc4=O)cc31)CN(CCN1CCCC1)CC2 ; "·2HCl"] | 483 | ¹H NMR (300 MHz, D₂O) δ 7.50 (d, J = 8.3 Hz, 1H), 7.46 (d, J = 7.7 Hz, 1H), 7.42-7.31 (m, 6H), 6.96 (dd, J = 8.3, 1.6 Hz, 1H), 6.27 (dd, J = 7.7, 2.6 Hz, 1H), 6.10 (d, J = 2.6 Hz, 1H), 5.90 (s, 2H), 4.59 (br s, 2H), 3.81-3.59 (m, 8H), 3.55 (s, 3H), 3.20 (t, J = 5.7 Hz, 2H), 3.18-3.05 (br m, 2H), 2.15-1.90 (m, 4H) |
| 62 | 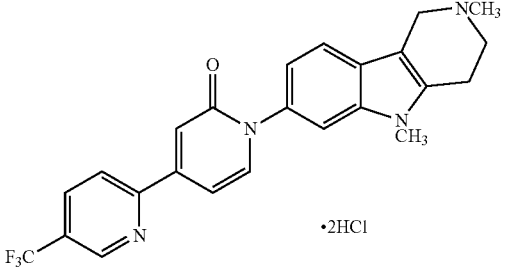 [SMILES: CN1CCc2c(c3ccc(-n4ccc(-c5ccc(C(F)(F)F)cn5)cc4=O)cc3n2C)C1 ; "·2HCl"] | 439 | ¹H NMR (500 MHz, CD₃OD) δ 9.04 (s, 1H), 8.28 (dd, J = 8.7, 1.9 Hz, 1H), 8.21 (d, J = 2.1 Hz, 1H), 7.83 (d, J = 7.1 Hz, 1H), 7.62 (d, J = 8.3 Hz, 1H), 7.58 (d, J = 1.3 Hz, 1H), 7.39 (d, J = 1.6 Hz, 1H), 7.24 (dd, J = 7.1, 1.9 Hz, 1H), 7.15 (dd, J = 8.3, 1.7 Hz, 1H), 4.80-4.71 (br m, 1H), 4.44-4.35 (br m, 1H), 3.96-3.86 (br m, 1H), 3.75 (s, 3H), 3.67-3.57 (br m, 1H), 3.28 (s, 2H), 3.14 (s, 3H) |
| 63 | 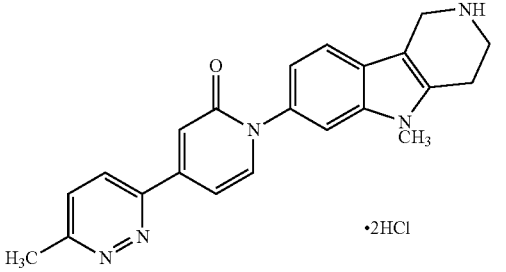 [SMILES: Cc1ccc(-c2ccn(-c3ccc4c5c(n(C)c4c3)CCNC5)c(=O)c2)nn1 ; "·2HCl"] | 372 | ¹H NMR (500 MHz, CD₃OD) δ 8.47 (d, J = 8.8 Hz, 1H), 8.03 (d, J = 8.8 Hz, 1H), 7.89 (d, J = 7.4 Hz, 1H), 7.64 (d, J = 8.4 Hz, 1H), 7.58 (d, J = 1.6 Hz, 1H), 7.35 (d, J = 1.6 Hz, 1H), 7.25 (dd, J = 7.1, 1.9 Hz, 1H), 7.15 (dd, J = 8.3, 1.9 Hz, 1H), 4.49 (s, 2H), 3.75 (s, 3H), 3.68 (t, J = 6.2 Hz, 2H), 3.24 (t, J = 6.2 Hz, 2H), 2.85 (s, 3H) |

TABLE 1-continued

| Ex. No. | Structure | Mass Spec | $^1$H NMR Data |
|---|---|---|---|
| 64 | (structure) ·2HCl | 386 | $^1$H NMR (300 MHz, DMSO-d$_6$) δ 10.9 (s, 1H), 8.32 (d, J = 8.8 Hz, 1H), 7.85 (d, J = 7.2 Hz, 1H), 7.79 (d, J = 8.8 Hz, 1H), 7.64 (d, J = 1.5 Hz, 1H), 7.56 (d, J = 8.3 Hz, 1H), 7.25 (d, J = 1.7 Hz, 1H), 7.14-7.11 (m, 2H), 4.65 (d, J = 12.1 Hz, 1H), 4.31 (dd, J = 14.2, 7.5 Hz, 1H), 3.81-3.74 (m, 1H), 3.71 (s, 3H), 3.55-3.45 (m, 1H), 3.26-3.15 (m, 2H), 2.98 (s, 3H), 2.72 (s, 3H) |
| 65 | (structure) ·HCl | 404 | $^1$H NMR (300 MHz, DMSO-d$_6$) δ 9.56 (br s, 2H), 7.64 (d, J = 7.1 Hz, 1H), 7.62-7.55 (m, 2H), 7.47 (dd, J = 8.4, 6.9 Hz, 1H), 7.12-7.06 (m, 2H), 6.90 (overlapping ddd, J = 8.4, 2.4 Hz, 1H), 6.55 (d, J = 1.6 Hz, 1H), 6.47 (dd, J = 7.1, 1.8 Hz, 1H), 4.37-4.30 (br m, 2H), 3.81 (s, 3H), 3.69 (s, 3H), 3.56-3.45 (br m, 2H), 3.10 (t, J = 5.5 Hz, 2H) |
| 66 | (structure) ·HCl | 418 | $^1$H NMR (300 MHz, DMSO-d$_6$) δ 10.83 (br s, 1H), 7.65 (d, J = 7.1 Hz, 1H), 7.61 (d, J = 1.4 Hz, 1H), 7.54 (d, J = 8.3 Hz, 1H), 7.46 (dd, J = 8.4, 6.9 Hz, 1H), 7.12-7.10 (m, 1H), 7.08 (d, J = 1.4 Hz, 1H), 6.91 (overlapping ddd, J = 8.4, 2.4 Hz, 1H), 6.55 (d, J = 1.6 Hz, 1H), 6.48 (dd, J = 7.1, 1.6 Hz, 1H), 4.62 (d, J = 12.2 Hz, 1H), 4.30 (dd, J = 14.2, 7.5 Hz, 1H), 3.86 (s, 3H), 3.80-3.76 (m, 1H), 3.75 (s, 3H), 3.52-3.42 (m, 1H), 3.24-3.15 (m, 2H), 2.79 (d, J = 4.6 Hz, 3H) |
| 67 | (structure) ·2HCl | 469 | $^1$H NMR (500 MHz, D$_2$O) δ 7.56-7.53 (m, 2H), 7.48-7.40 (m, 6H), 7.02 (dd, J = 8.4, 1.4 Hz, 1H), 6.33 (dd, J = 7.5, 2.4 Hz, 1H), 6.17 (d, J = 2.4 Hz, 1H), 5.16 (s, 2H), 4.63 (br s, 2H), 4.09-3.79 (br m, 2H), 3.69-3.53 (m, 6H), 3.26-3.23 (m, 2H), 3.14 (t, J = 12.8 Hz, 2H), 2.49 (d, J = 1.3 Hz, 2H), 2.16-2.04 (m, 2H) |

TABLE 1-continued

| Ex. No. | Structure | Mass Spec | ¹H NMR Data |
|---|---|---|---|
| 68 | ·2HCl | 483 | ¹H NMR (500 MHz, D₂O) δ 7.56-7.52 (m, 2H), 7.48-7.38 (m, 6H), 7.02 (dd, J = 8.3, 1.6 Hz, 1H), 6.33 (dd, J = 7.5, 2.6 Hz, 1H), 6.16 (d, J = 2.5 Hz, 1H), 5.16 (s, 2H), 4.63 (s, 2H), 3.85-3.83 (m, 2H), 3.74-3.71 (m, 2H), 3.62 (s, 3H), 3.26-3.14 (m, 5H), 2.89 (s, 3H), 2.55-2.50 (m, 2H), 2.19-2.12 (m, 2H) |
| 69 | ·2HCl | 425 | ¹H NMR (300 MHz, CD₃OD) δ 9.10 (d, J = 2.0 Hz, 1H), 8.41 (dd, J = 8.2, 1.7 Hz, 1H), 7.98 (d, J = 8.2 Hz, 1H), 7.85 (d, J = 7.2 Hz, 1H), 7.61 (d, J = 8.2 Hz, 1H), 7.57 (d, J = 1.6 Hz, 1H), 7.14 (dd, J = 8.3, 1.9 Hz, 1H), 7.02 (d, J = 1.6 Hz, 1H), 6.89 (dd, J = 7.1, 2.0 Hz, 1H), 4.49 (s, 2H), 3.76 (s, 3H), 3.68 (t, J = 6.2 Hz, 2H), 3.22 (t, J = 6.2 Hz, 2H) |
| 70 | ·2HCl | 439 | ¹H NMR (500 MHz, CD₃OD) δ 9.09 (d, J = 1.7 Hz, 1H), 8.42 (dd, J = 8.1, 2.0 Hz, 1H), 7.97 (d, J = 8.2 Hz, 1H), 7.85 (d, J = 7.1 Hz, 1H), 7.62 (d, J = 8.3 Hz, 1H), 7.58 (d, J = 1.5 Hz, 1H), 7.15 (dd, J = 8.3, 1.8 Hz, 1H), 7.02 (d, J = 1.8 Hz, 1H), 6.89 (dd, J = 7.1, 2.0 Hz, 1H), 4.79-4.37 (br m, 2H), 3.90-3.60 (br m, 5H), 3.30 (br m, 2H), 3.14 (s, 3H) |
| 71 | ·2HCl | 411 | ¹H NMR (500 MHz, CD₃OD) δ 9.04 (s, 1H), 8.28 (dd, J = 8.3, 2.2 Hz, 1H), 8.22 (d, J = 8.2 Hz, 1H), 7.81 (d, J = 7.0 Hz, 1H), 7.62 (d, J = 8.3 Hz, 1H), 7.46 (d, J = 1.8 Hz, 1H), 7.38 (d, J = 1.8 Hz, 1H), 7.24 (dd, J = 7.1, 2.0 Hz, 1H), 7.11 (dd, J = 8.3, 2.0 Hz, 1H), 4.49 (s, 2H), 3.65 (t, J = 6.2 Hz, 2H), 3.21 (t, J = 6.2 Hz, 2H) |
| 72 | ·HCl | 412 | ¹H NMR (300 MHz, CD₃OD) δ 8.52 (d, J = 8.9 Hz, 1H), 8.28 (d, J = 8.9 Hz, 1H), 7.89 (d, J = 7.2 Hz, 1H), 7.62 (d, J = 8.3 Hz, 1H), 7.48 (d, J = 1.5 Hz, 1H), 7.43 (d, J = 1.5 Hz, 1H), 7.33 (dd, J = 7.2, 2.0 Hz, 1H), 7.14 (dd, J = 7.4, 2.0 Hz, 1H), 4.49 (s, 2H), 3.65 (t, J = 6.2 Hz, 2H), 3.21 (t, J = 6.2 Hz, 2H) |

TABLE 1-continued

| Ex. No. | Structure | Mass Spec | 1H NMR Data |
|---|---|---|---|
| 73 | 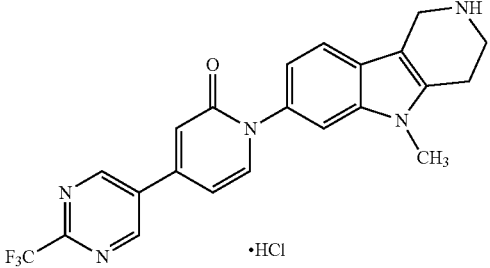 [SMILES: Cn1c2c(c3ccc(-n4ccc(-c5cnc(C(F)(F)F)nc5)cc4=O)cc31)CNCC2 ; Cl] ·HCl | 426 | 1H NMR (500 MHz, DMSO-d6) δ 9.51 (s, 2H), 9.37 (br s, 2H), 7.90 (d, J = 7.2 Hz, 1H), 7.62-7.60 (m, 2H), 7.13 (d, J = 1.9 Hz, 1H), 7.10 (dd, J = 8.3, 1.7 Hz, 1H), 6.88 (dd, J = 7.1, 2.0 Hz, 1H), 4.38-4.34 (br m, 2H), 3.70 (s, 3H), 3.56-3.50 (br m, 2H), 3.11 (t, J = 5.8 Hz, 2H) |
| 74 | 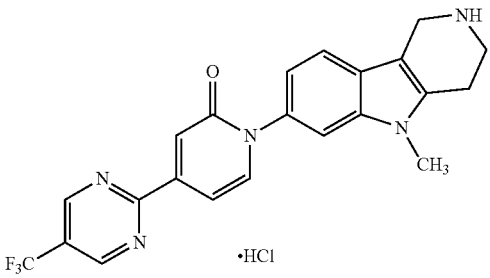 [SMILES: Cn1c2c(c3ccc(-n4ccc(-c5ncc(C(F)(F)F)cn5)cc4=O)cc31)CNCC2 ; Cl] ·HCl | 426 | 1H NMR (500 MHz, DMSO-d6) δ 9.48 (s, 2H), 9.37 (br s, 2H), 7.89 (d, J = 7.2 Hz, 1H), 7.65 (d, J = 1.6 Hz, 1H), 7.61 (d, J = 8.3 Hz, 1H), 7.50 (d, J = 1.6 Hz, 1H), 7.21 (dd, J = 7.6, 1.9 Hz, 1H), 7.12 (dd, J = 8.3, 1.8 Hz, 1H), 4.41-4.31 (br m, 2H), 3.71 (s, 3H), 3.51-3.48 (br m, 2H), 3.10 (t, J = 5.6 Hz, 2H) |
| 75 | 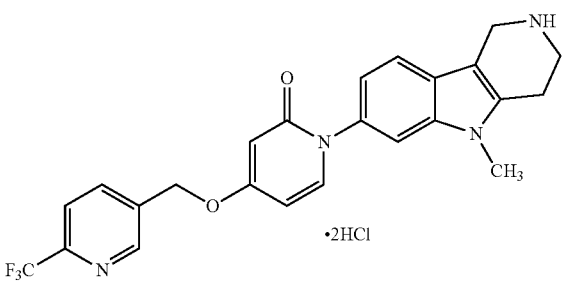 [SMILES: Cn1c2c(c3ccc(-n4ccc(OCc5ccc(C(F)(F)F)nc5)cc4=O)cc31)CNCC2 ; "·2HCl"] ·2HCl | 455 | 1H NMR (500 MHz, DMSO-d6) δ 9.54 (br s, 2H), 8.89 (s, 1H), 8.19 (dd, J = 7.9, 1.4 Hz, 1H), 8.00 (d, J = 8.0 Hz, 1H), 7.60 (d, J = 7.6 Hz, 1H), 7.55 (d, J = 8.3 Hz, 1H), 7.50 (d, J = 1.7 Hz, 1H), 6.98 (dd, J = 8.3, 1.8 Hz, 1H), 6.15 (dd, J = 7.5, 2.7 Hz, 1H), 6.02 (d, J = 2.7 Hz, 1H), 5.35 (s, 2H), 4.35-4.30 (br m, 2H), 3.67 (s, 3H), 3.53-3.47 (br m, 2H), 3.09 (t, J = 5.8 Hz, 2H) |
| 76 | 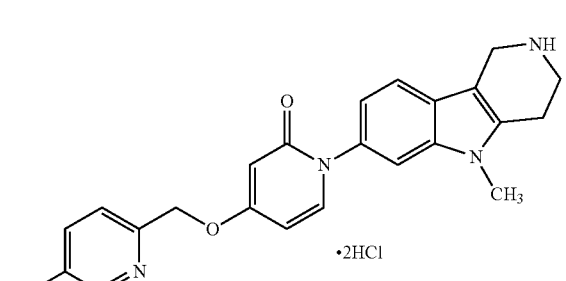 ·2HCl | 455 | 1H NMR (300 MHz, CD3OD) δ 8.93 (s, 1H), 8.23 (dd, J = 8.2, 2.1 Hz, 1H), 7.82 (d, J = 8.2 Hz, 1H), 7.70 (d, J = 7.5 Hz, 1H), 7.59 (d, J = 8.3 Hz, 1H), 7.49 (d, J = 1.7 Hz, 1H), 7.06 (dd, J = 8.3, 1.8 Hz, 1H), 6.47 (dd, J = 7.5, 2.7 Hz, 1H), 6.20 (d, J = 2.6 Hz, 1H), 5.42 (s, 2H), 4.48 (s, 2H), 3.73 (s, 3H), 3.67 (t, J = 6.1 Hz, 2H), 3.20 (t, J = 6.1 Hz, 2H) |
| 77 | 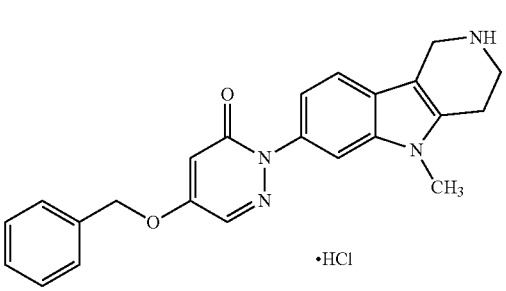 [SMILES: Cn1c2c(c3ccc(-n4ncc(OCc5ccccc5)cc4=O)cc31)CNCC2 ; Cl] ·HCl | 387 | 1H NMR (500 MHz, DMSO-d6) δ 9.23 (s, 2H), 7.96 (d, J = 2.8 Hz, 1H), 7.59 (d, J = 1.6 Hz, 1H), 7.54 (d, J = 8.4 Hz, 1H), 7.51-7.48 (m, 2H), 7.46-7.42 (m, 2H), 7.40 (d, J = 7.5 Hz, 1H), 7.13 (dd, J = 8.4, 1.7 Hz, 1H), 6.51 (d, J = 2.8 Hz, 1H), 5.22 (s, 2H), 4.34 (s, 2H), 3.69 (s, 3H), 3.52 (t, J = 5.8 Hz, 2H), 3.09 (t, J = 5.8 Hz, 2H) |

TABLE 1-continued

| Ex. No. | Structure | Mass Spec | $^1$H NMR Data |
|---|---|---|---|
| 78 | 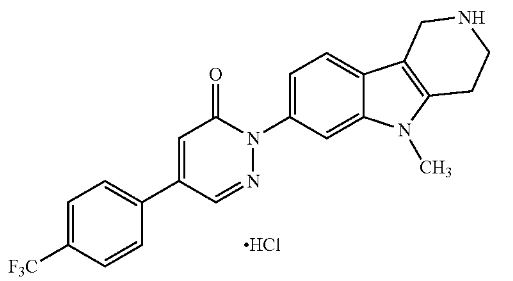 [SMILES: Cn1c2c(c3ccc(-n4ncc(-c5ccc(C(F)(F)F)cc5)cc4=O)cc31)CNCC2 ; Cl] | 425 | $^1$H NMR (300 MHz, DMSO-d$_6$) δ 9.37 (s, 2H), 8.56 (d, J = 2.2 Hz, 1H), 8.13 (d, J = Hz, 2H), 7.93 (d, J = 8.2 Hz, 2H), 7.72 (d, J = 1.6 Hz, 1H), 7.61 (d, J = 8.4 Hz, 1H), 7.48 (d, J = 2.2 Hz, 1H), 7.25 (dd, J = 8.4, 1.8 Hz, 1H), 4.36 (s, 2H), 3.70 (s, 3H), 3.58-3.48 (br m, 2H), 3.11 (t, J = 5.7 Hz, 2H) |
| 79 | 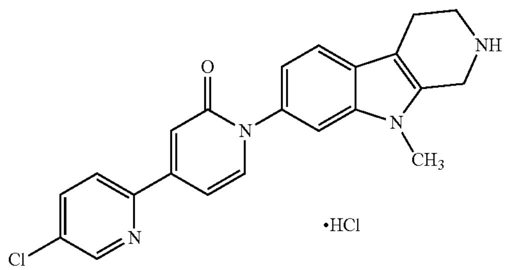 [SMILES: Cn1c2c(c3ccc(-n4ccc(-c5ccc(Cl)cn5)cc4=O)cc31)CCNC2 ; Cl] | 391 | $^1$H NMR (500 MHz, CD$_3$OD) δ 8.73 (dd, J = 2.4, 0.6 Hz, 1H), 8.03 (dd, J = 8.5, 0.5 Hz, 1H), 8.00 (dd, J = 8.5, 2.4 Hz, 1H), 7.80 (d, J = 7.1 Hz, 1H), 7.67 (d, J = 8.3 Hz, 1H), 7.56 (d, J = 1.7 Hz, 1H), 7.31 (d, J = 1.7 Hz, 1H), 7.19 (dd, J = 7.1, 2.0 Hz, 1H), 7.14 (dd, J = 8.4, 1.8 Hz, 1H), 4.56 (s, 2H), 3.74 (s, 3H), 3.61 (t, J = 6.1 Hz, 2H), 3.14 (t, J = 6.1 Hz, 2H) |
| 80 | 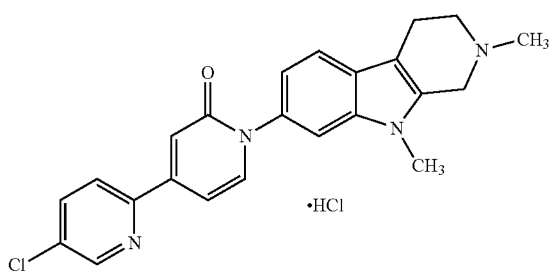 [SMILES: CN1CCc2c(n(C)c3cc(-n4ccc(-c5ccc(Cl)cn5)cc4=O)ccc23)C1 ; Cl] | 405 | $^1$H NMR (500 MHz, CD$_3$OD) δ 8.73 (d, J = 2.3 Hz, 1H), 8.03 (d, J = 8.5 Hz, 1H) 7.99 (dd, J = 8.5, 2.3 Hz, 1H), 7.79 (d, J = 7.2 Hz, 1H), 7.67 (d, J = 8.3 Hz, 1H), 7.57 (s, 1H), 7.31 (d, J = 1.6 Hz, 1H), 7.19 (dd, J = 7.1, 1.8 Hz, 1H), 7.15 (dd, J = 8.3, 1.7 Hz, 1H), 4.65 (br s, 2H), 3.74 (m, 5H), 3.21 (t, J = 5.7 Hz, 2H), 3.17 (s, 3H) |
| 81 | 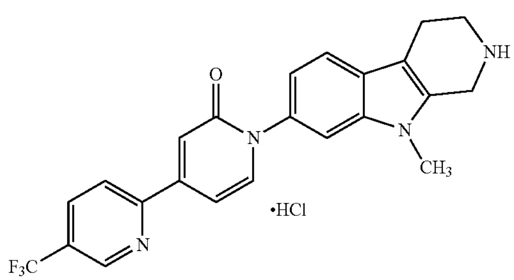 [SMILES: Cn1c2c(c3ccc(-n4ccc(-c5ccc(C(F)(F)F)cn5)cc4=O)cc31)CCNC2 ; Cl] | 425 | $^1$H NMR (500 MHz, CD$_3$OD) δ 9.05 (s, 1H), 8.28 (dd, J = 8.3, 2.2 Hz, 1H), 8.22 (d, J = 8.3, Hz, 1H), 7.84 (d, J = 7.1 Hz, 1H), 7.67 (d, J = 8.4 Hz, 1H), 7.58 (d, J = 1.8 Hz, 1H), 7.40 (d, J = 1.8 Hz, 1H), 7.25 (dd, J = 7.2, 2.0 Hz, 1H), 7.15 (dd, J = 8.4, 1.8 Hz, 1H), 4.57 (s, 2H), 3.74 (s, 3H), 3.62 (t, J = 6.1 Hz, 2H), 3.15 (t, J = 5.9 Hz, 2H) |
| 82 | 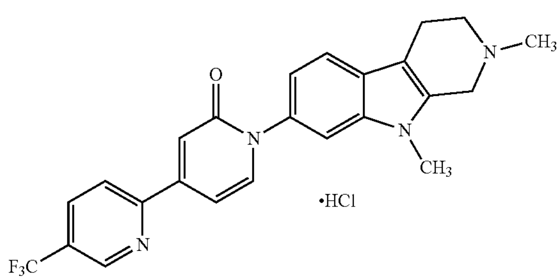 [SMILES: CN1CCc2c(n(C)c3cc(-n4ccc(-c5ccc(C(F)(F)F)cn5)cc4=O)ccc23)C1 ; Cl] | 439 | $^1$H NMR (500 MHz, CD$_3$OD) δ 9.05 (s, 1H), 8.28 (dd, J = 8.3, 2.1 Hz, 1H) 8.22 (d, J = 8.4, Hz, 1H), 7.84 (d, J = 7.1 Hz, 1H), 7.68 (d, J = 8.3 Hz, 1H), 7.59 (d, J = 1.6 Hz, 1H), 7.40 (d, J = 1.7 Hz, 1H), 7.25 (dd, J = 7.2, 1.9 Hz, 1H), 7.16 (dd, J = 8.3, 1.8 Hz, 1H), 4.87 (s, 1H), 4.51 (s, 1H), 3.87 (s, 1H), 3.75 (br s, 3H), 3.55 (br s, 1H), 3.21-3.17 (m, 5H) |

TABLE 1-continued

| Ex. No. | Structure | Mass Spec | $^1$H NMR Data |
|---|---|---|---|
| 84 | 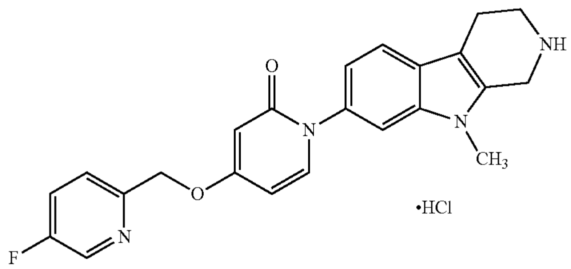 [SMILES: Cn1c2c(c3ccc(-n4ccc(OCc5ccc(F)cn5)cc4=O)cc31)CCNC2 ; Cl] | 405 | $^1$H NMR (500 MHz, CD$_3$OD) δ 8.51 (s, 1H), 7.72-7.59 (m, 4H), 7.46 (d, J = 1.0 Hz, 1H), 7.05 (dd, J = 8.3, 1.5 Hz, 1H), 6.32 (dd, J = 7.6, 2.6 Hz, 1H), 7.05 (d, J = 2.6 Hz, 1H), 5.26 (s, 2H), 4.54 (s, 2H), 3.71 (s, 3H), 3.60 (t, J = 6.0 Hz, 2H), 3.12 (t, J = 5.8 Hz, 2H) |
| 85 | 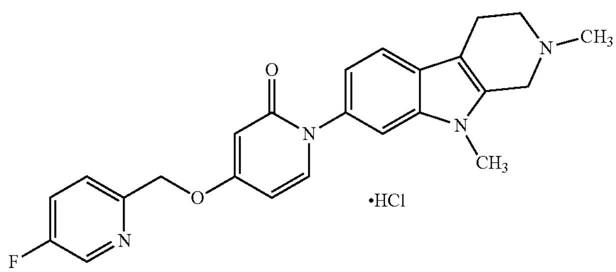 [SMILES: CN1CCc2c(n(C)c3cc(-n4ccc(OCc5ccc(F)cn5)cc4=O)ccc23)C1 ; Cl] | 419 | $^1$H NMR (500 MHz, CD$_3$OD) δ 8.51 (d, J = 2.6 Hz, 1H), 7.72-7.59 (m, 4H), 7.47 (s, 1H), 7.06 (dd, J = 8.3, 1.7 Hz, 1H), 6.32 (dd, J = 7.6, 2.6 Hz, 1H), 6.13 (d, J = 2.6 Hz, 1H), 5.26 (s, 2H), 4.68 (m, 2H), 3.71 (m, 5H), 3.18 (t, J = 5.9 Hz, 2H), 3.15 (s, 3H) |
| 86 | 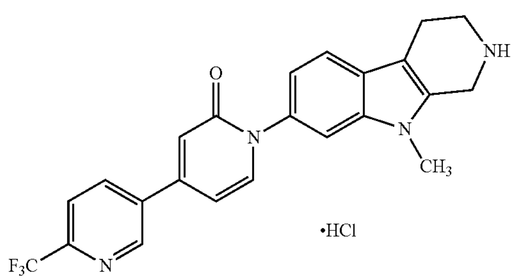 [SMILES: Cn1c2c(c3ccc(-n4ccc(-c5ccc(C(F)(F)F)nc5)cc4=O)cc31)CCNC2 ; Cl] | 425 | $^1$H NMR (500 MHz, CD$_3$OD) δ 9.10 (d, J = 1.9 Hz, 1H), 8.41 (dd, J = 8.2, 2.2 Hz, 1H), 7.97 (d, J = 8.3 Hz, 1H), 7.85 (d, J = 7.0 Hz, 1H), 7.68 (d, J = 8.3 Hz, 1H), 7.57 (d, J = 1.7 Hz, 1H), 7.15 (dd, J = 8.3, 1.8 Hz, 1H), 7.03 (d, J = 1.8 Hz, 1H), 6.89 (dd, J = 7.1, 2.0 Hz, 1H), 4.57 (br m, 2H), 3.75 (s, 3H), 3.62 (br m, 2H), 3.15 (br m, 2H) |
| 87 | 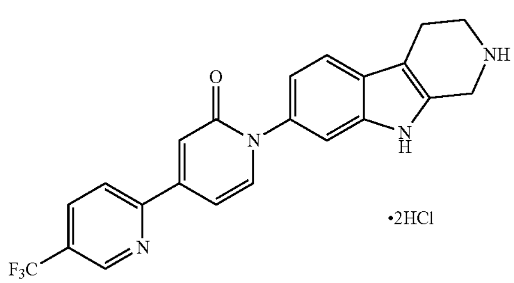 [SMILES: O=c1cc(-c2ccc(C(F)(F)F)cn2)ccn1-c1ccc2c3c([nH]c2c1)CNCC3 ; "·2HCl"] | 411 | $^1$H NMR (500 MHz, CD$_3$OD) δ 9.05 (s, 1H), 8.28 (dd, J = 8.4, 2.1 Hz, 1H), 8.22 (d, J = 8.4 Hz, 1H), 7.82 (d, J = 7.2 Hz, 1H), 7.66 (d, J = 8.4 Hz, 1H), 7.48 (d, J = 7.1 Hz, 1H), 7.39 (d, J = 1.7 Hz, 1H), 7.24 (dd, J = 7.2, 1.9 Hz, 1H), 7.13 (dd, J = 8.4, 1.8 Hz, 1H), 4.50 (s, 2H), 3.63 (t, J = 6.1 Hz, 2H), 3.14 (t, J = 6.1 Hz, 2H) |
| 88 | 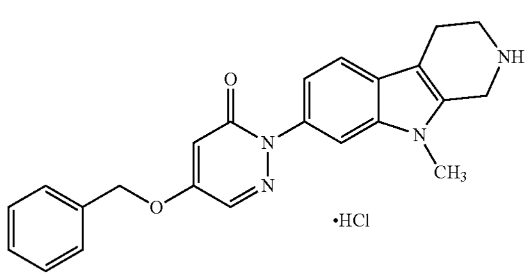 [SMILES: Cn1c2c(c3ccc(-n4ncc(OCc5ccccc5)cc4=O)cc31)CCNC2 ; Cl] | 387 | $^1$H NMR (500 MHz, CD$_3$OD) δ 7.93 (d, J = 2.7 Hz, 1H), 7.59 (d, J = 8.4 Hz, 1H), 7.56 (d, J = 1.5 Hz, 1H), 7.50-7.48 (m, 2H), 7.43 (overlapping dd, J = 7.8 Hz, 2H), 7.39 (d, J = 1.7 Hz, 1H), 7.18 (dd, J = 8.4, 1.7 Hz, 1H), 6.48 (d, J = 2.7 Hz, 1H), 5.22 (s, 2H), 4.54 (s, 2H), 3.71 (s, 3H), 3.59 (t, J = 5.6 Hz, 2H), 3.12 (t, J = 5.9 Hz, 2H) |

TABLE 1-continued

| Ex. No. | Structure | Mass Spec | ¹H NMR Data |
|---|---|---|---|
| 89 | (structure) ·HCl | 455 | ¹H NMR (500 MHz, CD$_3$OD) δ 8.75 (s, 1H), 8.08 (d, J = 7.9 Hz, 1H), 7.79 (d, J = 8.1 Hz, 1H), 7.53 (dd, J = 7.9, 2.0 Hz, 2H), 7.38 (d, J = 1.7 Hz, 1H), 6.97 (dd, J = 8.4, 1.8 Hz, 1H), 6.25 (dd, J = 7.6, 2.7 Hz, 1H), 6.08 (d, J = 2.6 Hz, 1H), 5.26 (s, 2H), 4.46 (s, 2H), 3.63 (s, 3H), 3.51 (t, J = 6.1 Hz, 2H), 3.03 (t, J = 6.1 Hz, 2H) |
| 90 | (structure) ·2HCl | 371 | ¹H NMR (500 MHz, CD$_3$OD) δ 8.59 (s, 1H), 7.95 (d, J = 8.1 Hz, 1H), 7.87 (d, J = 6.5 Hz, 1H), 7.80 (d, J = 7.0 Hz, 1H), 7.67 (d, J = 8.4 Hz, 1H), 7.56 (d, J = 1.4 Hz, 1H), 7.24 (d, J = 1.6 Hz, 1H), 7.15-7.12 (m, 2H), 4.57 (s, 2H), 3.74 (s, 3H), 3.61 (t, J = 6.0 Hz, 2H), 3.14 (t, J = 6.1 Hz, 2H), 2.46 (s, 3H) |
| 91 | (structure) ·2HCl | 371 | ¹H NMR (500 MHz, CD$_3$OD) δ 8.76 (d, J = 1.8 Hz, 1H), 8.34 (d, J = 6.9 Hz, 1H), 8.24 (d, J = 8.2 Hz, 1H), 7.94 (d, J = 7.2 Hz, 1H), 7.67 (d, J = 8.3 Hz, 1H), 7.61 (d, J = 1.7 Hz, 1H), 7.23 (d, J = 1.8 Hz, 1H), 7.17 (dd, J = 8.3, 1.8 Hz, 1H), 7.04 (dd, J = 7.1, 2.1 Hz, 1H), 4.53 (s, 2H), 3.79 (s, 3H), 3.71 (t, J = 6.2 Hz, 2H), 3.25 (t, J = 6.2 Hz, 2H), 2.61 (s, 3H) |
| 92 | (structure) ·2HCl | 371 | ¹H NMR (500 MHz, CD$_3$OD) δ 8.80 (d, J = 2.2 Hz, 1H), 8.12 (dd, J = 8.1, 2.5 Hz, 1H), 7.79 (d, J = 7.0 Hz, 1H), 7.59 (d, J = 8.3 Hz, 1H), 7.52 (d, J = 1.7 Hz, 1H), 7.47 (d, J = 8.2 Hz, 1H), 7.10 (dd, J = 8.3, 1.9 Hz, 1H), 6.93 (d, J = 1.8 Hz, 1H), 6.85 (dd, J = 7.1, 2.0 Hz, 1H), 4.34 (s, 2H), 3.73 (s, 3H), 3.52 (t, J = 6.1 Hz, 2H), 3.10 (t, J = 6.1 Hz, 2H), 2.62 (s, 3H) |
| 93 | (structure) ·2HCl | 371 | ¹H NMR (500 MHz, CD$_3$OD) δ 8.80 (d, J = 8.1 Hz, 1H), 8.11 (dd, J = 8.2, 2.5 Hz, 1H), 7.79 (d, J = 7.0 Hz, 1H), 7.64 (d, J = 8.3 Hz, 1H), 7.52 (d, J = 1.7 Hz, 1H), 7.47 (d, J = 8.2 Hz, 1H), 7.11 (dd, J = 8.3, 1.8 Hz, 1H), 6.93 (d, J = 1.9 Hz, 1H), 6.85 (dd, J = 7.1, 2.0 Hz, 1H), 4.40 (s, 2H), 3.71 (s, 3H), 3.46 (t, J = 5.9 Hz, 2H), 3.04 (t, J = 5.9 Hz, 2H), 2.62 (s, 3H) |

TABLE 1-continued

| Ex. No. | Structure | Mass Spec | ¹H NMR Data |
|---|---|---|---|
| 94 | 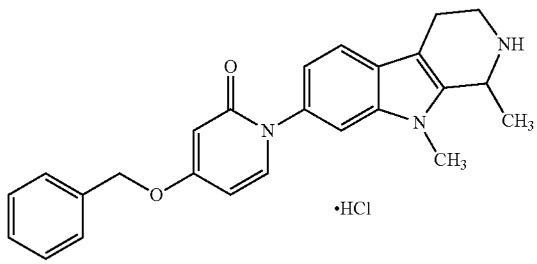 [SMILES: CC1NCCc2c1n(C)c1cc(-n3ccc(OCc4ccccc4)cc3=O)ccc21 ; Cl] | 400 | ¹H NMR (500 MHz, CD₃OD) δ 7.79 (d, J = 7.0 Hz, 1H), 7.66 (d, J = 8.0 Hz, 1H), 7.53 (s, 1H), 7.48-7.36 (m, 5H), 7.10 (d, J = 8.5 Hz, 1H), 6.55 (d, J = 6.5 Hz, 1H), 6.33 (s, 1H), 5.27 (s, 2H), 4.98 (q, J = 6.5 Hz, 1H), 3.76 (s, 3H), 3.67-3.59 (m, 2H), 3.13-3.08 (m, 2H), 1.76 (d, J = 7.0 Hz, 3H) |
| 95 | 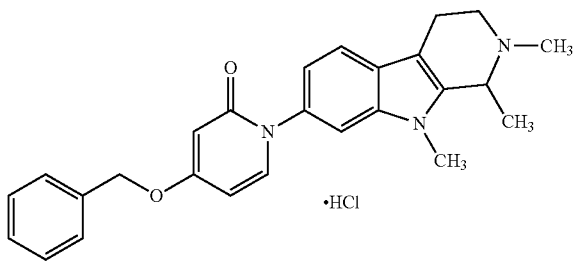 [SMILES: CC1c2c(c3ccc(-n4ccc(OCc5ccccc5)cc4=O)cc3n2C)CCN1C ; Cl] | 414 | ¹H NMR (500 MHz, CD₃OD) δ 7.58-7.55 (m, 2H), 7.47-7.34 (m, 6H), 6.99 (d, J = 8.5, 1.0 Hz, 1H), 6.28 (dd, J = 7.5, 2.5 Hz, 1H), 6.11 (d, J = 2.5 Hz, 1H), 5.18 (s, 2H), 4.27 (q, J = 6.5 Hz, 1H), 3.69 (s, 3H), 3.36-3.33 (m, 1H), 3.10-2.96 (m, 2H), 2.84-2.80 (m, 1H), 2.65 (s, 3H), 1.51 (d, J = 6.5 Hz, 3H) |
| 96 | 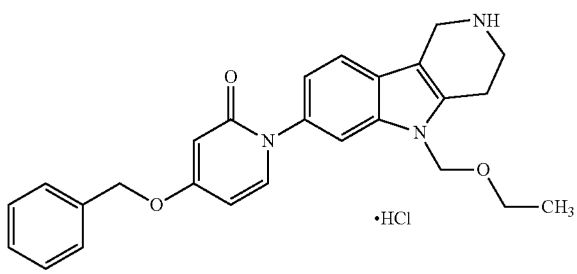 [SMILES: CCOCn1c2c(c3ccc(-n4ccc(OCc5ccccc5)cc4=O)cc31)CNCC2 ; Cl] | 430 | ¹H NMR (500 MHz, DMSO-d₆) δ 9.12 (s, 2H), 7.66 (d, J = 2.0 Hz, 1H), 7.59-7.56 (m, 2H), 7.49-7.37 (m, 5H), 7.08-7.05 (m, 1H), 6.14-6.12 (m, 1H), 5.99 (d, J = 2.5 Hz, 1H), 5.57 (s, 2H), 5.17 (s, 2H), 4.38 (m, 2H), 3.55 (m, 2H), 3.45-3.40 (m, 2H), 3.13 (m, 2H), 1.08-1.05 (m, 3H) |
| 97 | 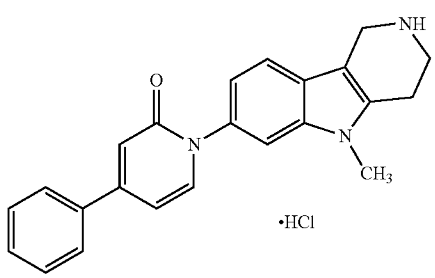 [SMILES: Cn1c2c(c3ccc(-n4ccc(-c5ccccc5)cc4=O)cc31)CNCC2 ; Cl] | 356 | ¹H NMR (500 MHz, DMSO-d₆) δ 9.26 (s, 2H), 7.79 (dd, J = 8.0, 1.5 Hz, 2H), 7.75 (d, J = 7.5 Hz, 1H), 7.62 (d, J = 1.5 Hz, 1H), 7.59 (d, J = 8.5 Hz, 1H), 7.55-7.50 (m, 3H), 7.10 (dd, J = 8.5, 2.0 Hz, 1H), 6.78 (d, J = 1.5 Hz, 1H), 6.70 (dd, J = 7.0, 2.0 Hz, 1H), 4.37 (m, 2H), 3.71 (s, 3H), 3.54-3.53 (m, 2H), 3.10 (t, J = 6.0 Hz, 2H) |
| 98 | 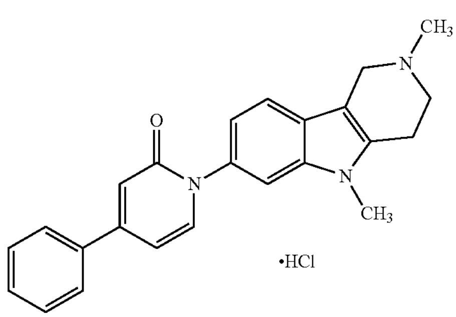 [SMILES: CN1CCc2c(c3ccc(-n4ccc(-c5ccccc5)cc4=O)cc3n2C)C1 ; Cl] | 370 | ¹H NMR (500 MHz, DMSO-d₆) δ 10.46 (s, 1H), 7.80-7.74 (m, 3H), 7.63 (s, 1H), 7.56-7.52 (m, 4H), 7.11 (d, J = 8.0 Hz, 1H), 6.78 (s, 1H), 6.70 (d, J = 7.0 Hz, 1H), 4.68-4.65 (m, 1H), 4.34-4.30 (m, 1H), 3.82-3.79 (m, 1H), 3.71 (s, 3H), 3.53-3.51 (m, 1H), 3.20 (m, 2H), 3.00 (d, J = 4.0 Hz, 3H) |

TABLE 1-continued

| Ex. No. | Structure | Mass Spec | $^1$H NMR Data |
|---|---|---|---|
| 99 | 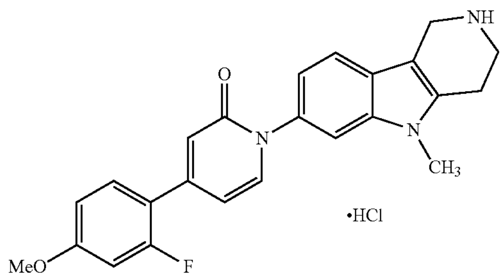 [SMILES: COc1ccc(-c2ccn(-c3ccc4c5c(n(C)c4c3)CCNC5)c(=O)c2)c(F)c1 ; Cl] | 404 | $^1$H NMR (500 MHz, CD$_3$OD) δ 7.72 (d, J = 7.0 Hz, 1H), 7.63-7.56 (m, 3H), 7.14 (dd, J = 8.5, 1.5 Hz, 1H), 6.92 (dd, J = 8.5, 2.5 Hz, 1H), 6.87 (dd, J = 13.0, 2.5 Hz, 1H), 6.84 (s, 1H), 6.77-6.75 (m, 1H), 4.50 (s, 2H), 3.88 (s, 3H), 3.76 (s, 3H), 3.68 (t, J = 6.0 Hz, 2H), 3.22 (t, J = 6.0 Hz, 2H) |
| 100 | 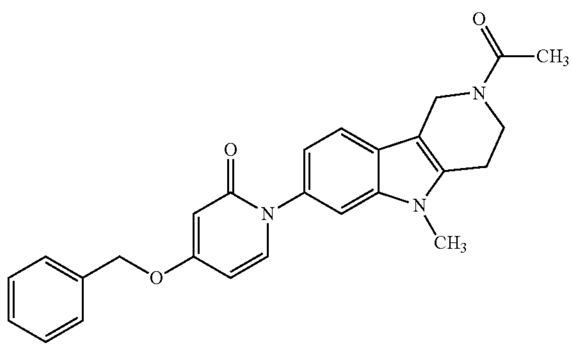 [SMILES: CC(=O)N1CCc2c(c3ccc(-n4ccc(OCc5ccccc5)cc4=O)cc3n2C)C1] | 428 | $^1$H NMR (500 MHz, CDCl$_3$) δ 7.53-7.36 (m, 6H), 7.32-7.30 (m, 2H), 7.06-7.00 (m, 1H), 6.09 (d, J = 3.0 Hz, 1H), 6.07-6.04 (m, 1H), 5.06 (s, 2H), 4.82 (s, 1H), 4.67 (s, 1H), 4.03 (t, J = 5.5 Hz, 1H), 3.84 (t, J = 5.5 Hz, 1H), 3.64 (s, 3H), 2.90 (t, J = 5.5 Hz, 1H), 2.84 (t, J = 5.5 Hz, 1H), 2.24, 2.22 (2 × s, 3H) |
| 101 | 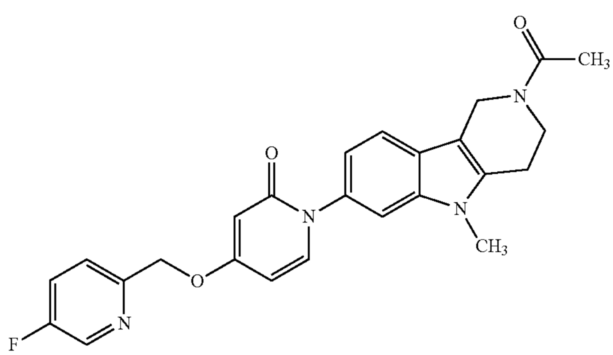 [SMILES: CC(=O)N1CCc2c(c3ccc(-n4ccc(OCc5ccc(F)cn5)cc4=O)cc3n2C)C1] | 447 | $^1$H NMR (500 MHz, CDCl$_3$) δ 8.50 (d, J = 1.5 Hz, 1H), 7.54-7.46 (m, 3H), 7.35 (d, J = 7.5 Hz, 1H), 7.32 (d, J = 2.0 Hz, 1H), 7.03 (ddd, J = 20, 8.0, 1.5 Hz, 1H), 6.15-6.08 (m, 2H), 5.18 (s, 2H), 4.83, 4.70 (2 × s, 2H), 4.04 (t, J = 5.5 Hz, 1H), 3.85 (t, J = 5.5 Hz, 1H), 3.65, 3.64 (2 × s, 3H), 2.91 (t, J = 5.5 Hz, 1H), 2.85 (t, J = 5.5 Hz, 1H), 2.23, 2.25 (2 × s, 3H) |
| 102 | 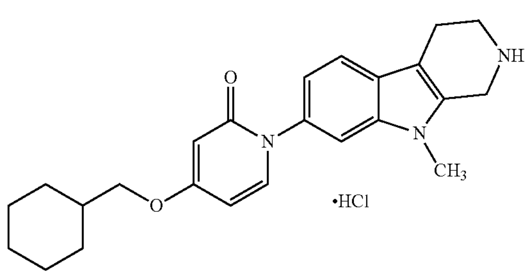 [SMILES: Cn1c2c(c3ccc(-n4ccc(OCC5CCCCC5)cc4=O)cc31)CCNC2 ; Cl] | 392 | $^1$H NMR (500 MHz, CD$_3$OD) δ 7.67-7.65 (m, 2H), 7.50 (s, 1H), 7.09 (d, J = 8.5 Hz, 1H), 6.35 (d, J = 6.0 Hz, 1H), 6.10 (s, 1H), 4.58 (s, 2H), 3.92 (d, J = 5.5 Hz, 2H), 3.75 (s, 3H), 3.63 (t, J = 6.0 Hz, 2H), 3.15 (d, J = 6.0 Hz, 2H), 1.92-1.74 (m, 6H), 1.39-1.19 (m, 5H) |
| 103 | 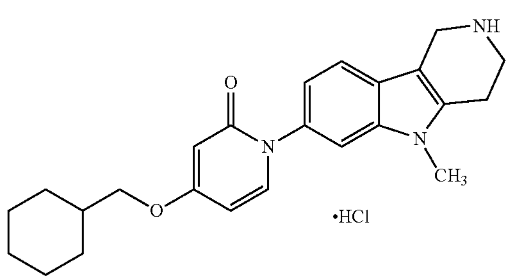 [SMILES: Cn1c2c(c3ccc(-n4ccc(OCC5CCCCC5)cc4=O)cc31)CNCC2 ; Cl] | 392 | $^1$H NMR (500 MHz, DMSO-d$_6$) δ 9.21 (s, 2H), 7.55 (d, J = 8.5 Hz, 1H), 7.52 (d, J = 7.5 Hz, 1H), 7.50 (s, 1H), 6.99 (dd, J = 8.5, 1.5 Hz, 1H), 6.04 (dd, J = 7.5, 2.5 Hz, 1H), 5.85 (d, J = 2.5 Hz, 1H), 4.35 (s, 2H), 3.82 (d, J = 6.0 Hz, 2H), 3.68 (s, 3H), 3.54-3.53 (m, 2H), 3.09 (t, J = 5.5 Hz, 2H), 1.80-1.65 (m, 6H), 1.30-1.01 (m, 5H) |

TABLE 1-continued

| Ex. No. | Structure | Mass Spec | ¹H NMR Data |
|---|---|---|---|
| 104 | 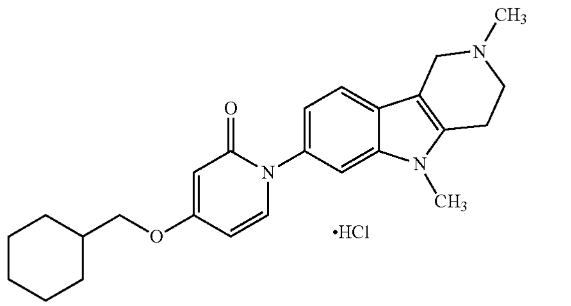 [SMILES: CN1CCc2c(c3ccc(-n4ccc(OCC5CCCCC5)cc4=O)cc3n2C)C1 ; Cl] | 406 | ¹H NMR (500 MHz, DMSO-d$_6$) δ 10.53 (s, 1H), 7.53 (d, J = 7.5 Hz, 1H), 7.51 (d, J = 8.0 Hz, 1H), 7.50 (d, J = 1.5 Hz, 1H), 7.00 (dd, J = 8.5, 1.5 Hz, 1H), 6.04 (dd, J = 7.5, 2.5 Hz, 1H), 5.85 (d, J = 3.0 Hz, 1H), 4.64 (d, J = 13 Hz, 1H), 4.30 (dd, J = 14, 7.5 Hz, 1H), 3.82 (d, J = 6.0 Hz, 2H), 3.80-3.78 (m, 1H), 3.69 (s, 3H), 3.51-3.47 (m, 1H), 3.18 (t, J = 5.5 Hz, 2H), 2.98 (d, J = 4.5 Hz, 3H), 1.80-1.65 (m, 6H), 1.30-1.01 (m, 5H) |
| 105 | 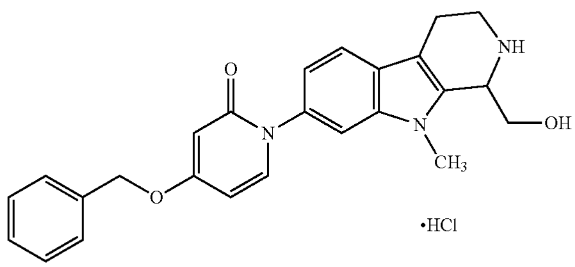 [SMILES: Cn1c2c(c3ccc(-n4ccc(OCc5ccccc5)cc4=O)cc31)CCNC2CO ; Cl] | 416 | ¹H NMR (500 MHz, DMSO-d$_6$) δ 9.48 (br s, 1H), 9.10 (br s, 1H), 7.56 (overlapping dd, J = 8.5 Hz, 2H), 7.52 (s, 1H), 7.49-7.41 (m, 4H), 7.40-7.36 (m, 1H), 7.01 (dd, J = 7.0, 1.5 Hz, 1H), 6.12 (dd, J = 7.5, 1.5 Hz, 1H), 5.98 (d, J = 1.5 Hz, 1H), 5.72 (t, J = 3.3 Hz, 1H), 5.16 (s, 2H), 4.89-4.82 (m, 1H), 4.07-4.01 (m, 1H), 3.80-3.71 (m, 1H), 3.72 (s, 3H), 3.61-3.50 (m, 1H), 3.49-3.43 (m, 1H), 3.02-2.94 (m, 2H) |
| 106 | 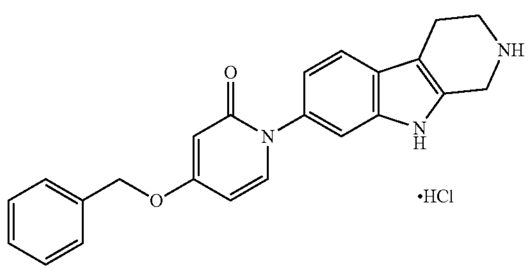 [SMILES: O=c1cc(OCc2ccccc2)ccn1-c1ccc2c3c([nH]c2c1)CNCC3 ; Cl] | 372 | ¹H NMR (500 MHz, DMSO-d$_6$) δ 11.22 (s, 1H), 9.29 (br s, 2H), 7.54 (dd, J = 12.0, 8.0 Hz, 2H), 7.50-7.41 (m, 4H), 7.40-7.33 (m, 2H), 6.96 (dd, J = 8.0, 1.5 Hz, 1H), 6.09 (dd, J = 7.5, 2.5 Hz, 1H), 5.97 (d, J = 2.5 Hz, 1H), 5.15 (s, 2H), 4.38 (s, 2H), 3.50-3.42 (m, 2H) 3.00-2.92 (m, 2H) |
| 107 | 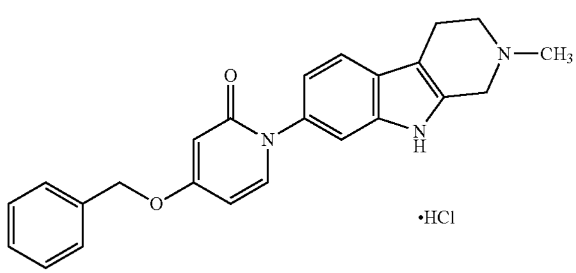 [SMILES: CN1CCc2c([nH]c3cc(-n4ccc(OCc5ccccc5)cc4=O)ccc23)C1 ; Cl] | 386 | ¹H NMR (500 MHz, DMSO-d$_6$) δ 11.30 (s, 1H), 10.50-10.41 (m, 1H), 7.58-7.52 (m, 2H), 7.49-7.40 (m, 4H), 7.39-7.35 (m, 2H), 6.96 (br d, J = 8.0 Hz, 1H), 6.09 (br d, J = 7.5 Hz, 1H), 5.97 (br s, 1H), 5.15 (s, 2H), 4.60 (br d, J = 15.0 Hz, 1H), 4.41 (dd, J = 15.0, 7.5 Hz, 1H), 3.78-3.71 (m, 1H), 3.45-3.38 (m, 1H), 3.09-2.98 (m, 5H) |
| 108 | 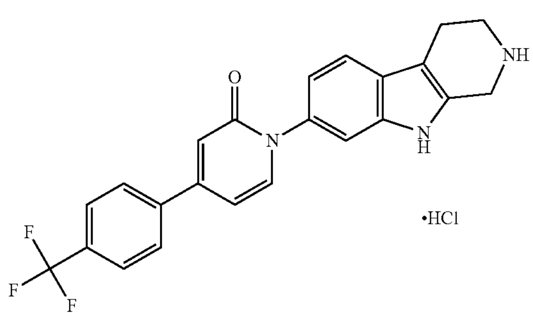 [SMILES: O=c1cc(-c2ccc(C(F)(F)F)cc2)ccn1-c1ccc2c3c([nH]c2c1)CNCC3 ; Cl] | 410 | ¹H NMR (500 MHz, DMSO-d$_6$) δ 11.28 (s, 1H), 9.21 (br s, 2H), 8.01 (d J = 8.3 Hz, 2H), 7.88 (d, J = 8.3 Hz, 2H), 7.80 (d, J = 7.0 Hz, 1H), 7.58 (d, J = 8.0 Hz, 1H), 7.49 (d, J = 1.5 Hz, 1H), 7.07 (dd, J = 8.0, 1.5 Hz, 1H), 6.87 (d, J = 2.0 Hz, 1H), 6.72 (dd, J = 7.0, 2.0 Hz, 1H), 4.40 (s, 2H), 3.52-3.48 (m, 2H), 2.99 (t, J = 6.0 Hz, 2H) |

TABLE 1-continued

| Ex. No. | Structure | Mass Spec | ¹H NMR Data |
|---|---|---|---|
| 109 | 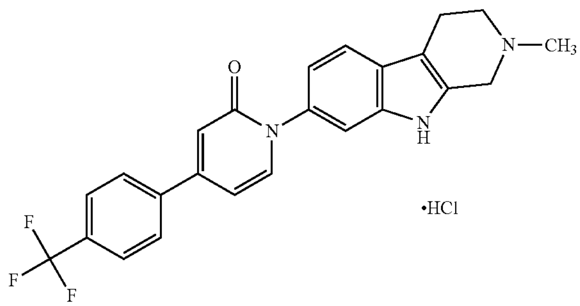 [SMILES: CN1CCc2c([nH]c3cc(-n4ccc(-c5ccc(C(F)(F)F)cc5)cc4=O)ccc23)C1 ; Cl] | 424 | ¹H NMR (500 MHz, DMSO-d$_6$) δ 11.36 (s, 1H), 10.35 (br s, 1H), 8.02 (d, J = 8.3 Hz, 2H), 7.88 (d, J = 8.3 Hz, 2H), 7.80 (d, J = 7.0 Hz, 1H), 7.59 (d, J = 8.0 Hz, 1H), 7.49 (br s, 1H), 7.07 (dd, J = 8.0, 1.5 Hz, 1H), 6.87 (d, J = 1.5 Hz, 1H), 6.72 (d, J = 7.0, 1.5 Hz, 1H), 4.62 (br d, J = 16.0 Hz, 1H), 4.49-4.40 (m, 1H), 3.81-3.73 (m, 1H), 3.49-3.39 (m, 1H), 3.12-3.00 (m, 5H) |
| 110 | 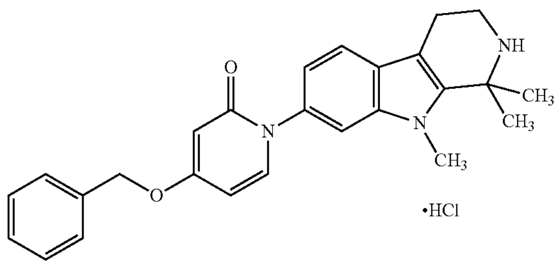 [SMILES: Cn1c2c(c3ccc(-n4ccc(OCc5ccccc5)cc4=O)cc31)CCNC2(C)C ; Cl] | 414 | ¹H NMR (500 MHz, DMSO-d$_6$) δ 9.59 (s, 2H), 7.58-7.51 (m, 3H), 7.49-7.41 (m, 4H), 7.40-7.35 (m, 1H), 7.01 (dd, J = 8.5, 1.5 Hz, 1H), 6.10 (dd, J = 7.5, 2.8 Hz, 1H), 5.97 (d, J = 2.8 Hz, 1H), 5.16 (s, 2H), 3.80 (s, 3H), 3.52-3.48 (m, 2H), 2.99 (t, J = 6.0 Hz, 2H), 1.81 (s, 6H) |
| 111 | 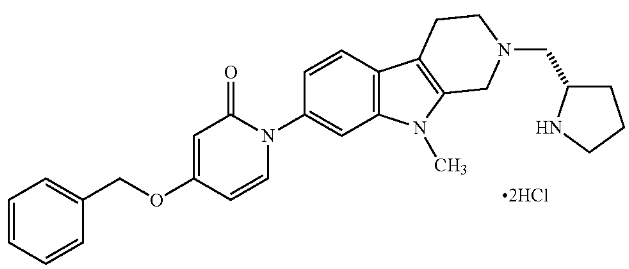 | 469 | ¹H NMR (500 MHz, DMSO-d$_6$) δ 9.25 (br s, 1H), 7.56 (d, J = 7.5 Hz, 1H), 7.54-7.40 (m, 6H), 7.39-7.34 (m, 1H), 7.04-6.93 (m, 1H), 6.11 (dd, J = 7.5, 2.5 Hz, 1H), 5.97 (d, J = 2.5 Hz, 1H), 5.16 (s, 2H), 3.98-3.45 (m, 11H), 3.39 (s, 1H), 3.30-3.21 (m, 2H), 2.25-2.10 (m, 1H), 2.05-1.74 (m, 2H), 1.73-1.60 (m, 1H) |
| 112 | 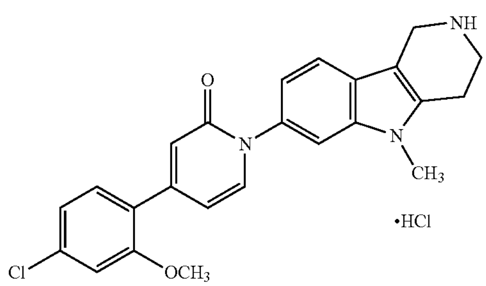 [SMILES: COc1cc(Cl)ccc1-c1ccn(-c2ccc3c4c(n(C)c3c2)CCNC4)c(=O)c1 ; Cl] | 420 | ¹H NMR (500 MHz, DMSO-d$_6$) δ 9.17 (br s, 2H), 7.65 (d, J = 7.0 Hz, 1H), 7.62 (d, J = 1.8 Hz, 1H), 7.59 (d, J = 8.5 Hz, 1H), 7.44 (d, J = 8.0 Hz, 1H), 7.26 (d, J = 1.8 Hz, 1H), 7.14 (dd, J = 8.0, 1.8 Hz, 1H), 7.09 (dd, J = 8.5, 1.8 Hz, 1H), 6.57 (d, J = 2.0 Hz, 1H), 6.47 (dd, J = 7.0, 2.0 Hz, 1H), 4.37 (br s, 2H), 3.87 (s, 3H), 3.70 (s, 3H), 3.57-3.52 (m, 2H), 3.10 (t, J = 6.0 Hz, 2H) |
| 113 | 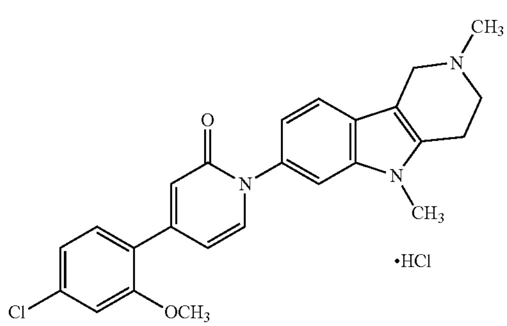 [SMILES: COc1cc(Cl)ccc1-c1ccn(-c2ccc3c4c(n(C)c3c2)CCN(C)C4)c(=O)c1 ; Cl] | 434 | ¹H NMR (500 MHz, DMSO-d$_6$) δ 10.15 (br s, 1H), 7.66 (d, J = 7.0 Hz, 1H), 7.63 (d, J = 1.5 Hz, 1H), 7.55 (d, J = 8.0 Hz, 1H), 7.44 (d, J = 8.5 Hz, 1H), 7.26 (d, J = 1.8 Hz, 1H), 7.14 (dd, J = 8.5, 1.5 Hz, 1H), 7.11 (dd, J = 8.0, 1.8 Hz, 1H), 6.57 (d, J = 2.0 Hz, 1H), 6.47 (dd, J = 7.0, 2.0 Hz, 1H), 4.67 (d, J = 13.5 Hz, 1H), 4.33 (dd, J = 14.3, 6.0 Hz, 1H), 3.87 (s, 3H), 3.86-3.79 (m, 1H), 3.71 (s, 3H), 3.55-3.47 (m, 1H), 3.24-3.15 (m, 2H), 3.01 (s, 3H) |

TABLE 1-continued

| Ex. No. | Structure | Mass Spec | ¹H NMR Data |
|---|---|---|---|
| 114 | 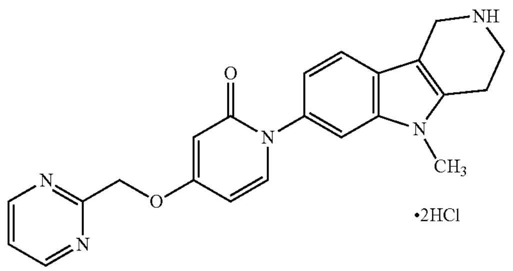 [SMILES: Cn1c2c(c3ccc(-n4ccc(OCc5ncccn5)cc4=O)cc31)CNCC2 ; "·2HCl"] | 388 | ¹H NMR (500 MHz, DMSO-$d_6$) δ 9.10 (br s, 2H), 8.88 (d, J = 5.0 Hz, 2H), 7.58-7.52 (m, 4H), 6.99 (dd, J = 8.0, 1.8 Hz, 1H), 6.14 (dd, J = 7.5, 2.5 Hz, 1H), 5.86 (d, J = 2.5 Hz, 1H), 5.33 (s, 2H), 4.36 (br s, 2H), 3.68 (s, 3H), 3.57-3.52 (m, 2H), 3.11-3.05 (m, 2H) |
| 115 | 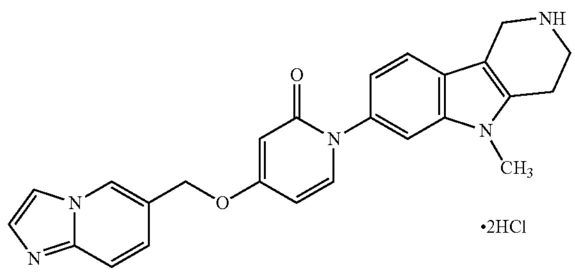 [SMILES: Cn1c2c(c3ccc(-n4ccc(OCc5ccc6nccn6c5)cc4=O)cc31)CNCC2 ; "·2HCl"] | 426 | ¹H NMR (500 MHz, DMSO-$d_6$) δ 9.28 (br s, 2H), 9.06 (s, 1H), 8.38 (s, 1H), 8.19 (s, 1H), 8.05-7.94 (m, 2H), 7.62 (d, J = 7.5 Hz, 1H), 7.56 (d, J = 8.0 Hz, 1H), 7.50 (d, J = 1.5 Hz, 1H), 6.99 (dd, J = 8.0, 1.5 Hz, 1H), 6.13 (dd, J = 7.5, 2.5 Hz, 1H), 6.09 (d, J = 2.5 Hz, 1H), 5.33 (s, 2H), 4.35 (br s, 2H), 3.69 (s, 3H), 3.56-3.50 (m, 2H), 3.12-3.05 (m, 2H) |
| 116 | 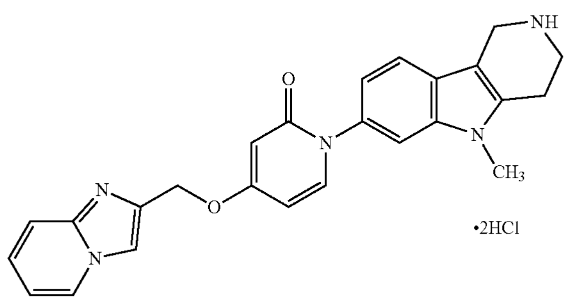 [SMILES: Cn1c2c(c3ccc(-n4ccc(OCc5cn6ccccc6n5)cc4=O)cc31)CNCC2 ; "·2HCl"] | 426 | ¹H NMR (500 MHz, DMSO-$d_6$) δ 9.30 (br s, 2H), 8.84 (s, 1H), 8.37 (s, 1H), 7.89-7.70 (m, 2H), 7.64-7.53 (m, 2H), 7.50 (s, 1H), 7.37-7.29 (m, 1H), 7.03-6.97 (m, 1H), 6.20-6.09 (m, 2H), 5.41 (s, 2H), 4.35 (br s, 2H), 3.69 (s, 3H), 3.58-3.50 (m, 2H), 3.13-3.07 (m, 2H) |
| 117 | 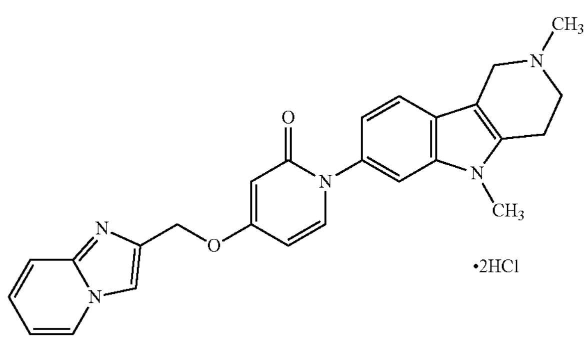 [SMILES: CN1CCc2c(c3ccc(-n4ccc(OCc5cn6ccccc6n5)cc4=O)cc3n2C)C1 ; "·2HCl"] | 440 | ¹H NMR (500 MHz, DMSO-$d_6$) 10.79 (br s, 1H), 8.87 (d, J = 6.5 Hz, 1H), 8.41 (s, 1H), 7.90-7.78 (m, 2H), 7.61 (d, J = 7.5 Hz, 1H), 7.53-7.49 (m, 2H), 7.42-7.35 (m, 1H), 7.00 (dd, J = 8.5, 1.5 Hz, 1H), 6.15 (d, J = 2.5 Hz, 1H), 6.12 (dd, J = 7.5, 2.5 Hz, 1H), 5.43 (s, 2H), 4.62 (d, J = 14.0 Hz, 1H), 4.29 (dd, J = 14.0, 7.5 Hz, 1H), 3.80-3.75 (m, 1H), 3.69 (s, 3H), 3.55-3.46 (m, 1H), 3.23-3.16 (m, 2H), 2.97 (s, 3H) |
| 118 | 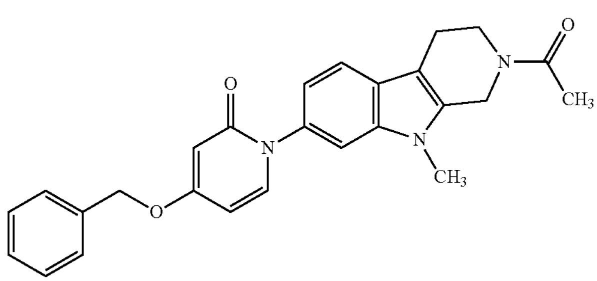 [SMILES: CC(=O)N1CCc2c(n(C)c3cc(-n4ccc(OCc5ccccc5)cc4=O)ccc23)C1] | 428 | ¹H NMR (500 MHz, DMSO-$d_6$) δ 7.56 (d, J = 7.5 Hz, 1H), 7.52-7.35 (m, 7H), 6.94 (dd, J = 8.0, 1.5 Hz, 1H), 6.12-6.08 (m, 1H), 5.97 (d, J = 3.0 Hz, 1H), 5.15 (s, 2H), 4.77-4.72 (m, 2H), 3.82-3.72 (m, 2H), 3.69-3.65 (m, 3H), 3.82-2.78 (m, 1.3H), 2.71-2.68 (m, 0.7H), 2.16 (s, 3H) |

TABLE 1-continued

| Ex. No. | Structure | Mass Spec | $^1$H NMR Data |
|---|---|---|---|
| 119 | 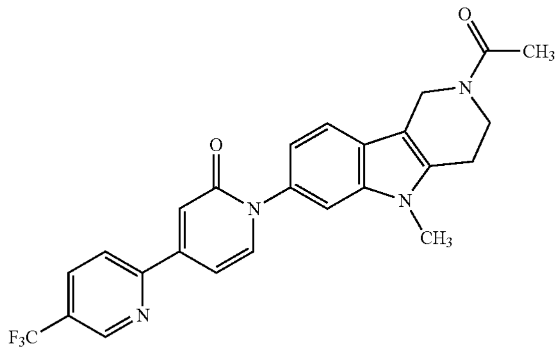 [SMILES: CC(=O)N1CCc2c(c3ccc(-n4ccc(-c5ccc(C(F)(F)F)cn5)cc4=O)cc3n2C)C1] | 467 | $^1$H NMR (500 MHz, DMSO-d$_6$) δ 9.15 (s, 1H), 8.38 (d, J = 8.3 Hz, 1H), 8.35 (d, J = 8.3 Hz, 1H), 7.84 (d, J = 7.5 Hz, 1H), 7.59-7.54 (m, 2H), 7.28 (d, J = 1.5 Hz, 1H), 7.08-7.03 (m, 2H), 4.70 (s, 0.8H), 4.68 (s, 1.2H), 3.88 (t, J = 5.5 Hz, 0.8H), 3.83 (t, J = 5.5 Hz, 1.2 H), 3.67 (s, 3H), 2.97-2.91 (m, 1.2H), 2.86-2.81 (m, 0.8H), 2.15 (s, 1.8H), 2.13 (s, 1.2H) |
| 120 | 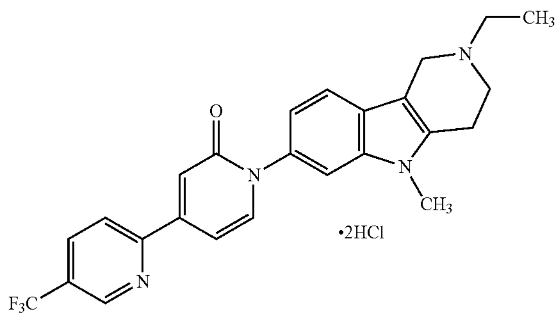 [SMILES: CCN1CCc2c(c3ccc(-n4ccc(-c5ccc(C(F)(F)F)cn5)cc4=O)cc3n2C)C1 ; "·2HCl"] | 453 | $^1$H NMR (500 MHz, DMSO-d$_6$) δ 10.16 (br s, 1H), 9.15 (s, 1H), 8.42-8.35 (m, 2H), 7.85 (d, J = 7.0 Hz, 1H), 7.65 (d, J = 1.5 Hz, 1H), 7.61 (d, J = 8.5 Hz, 1H), 7.30 (d, J = 2.0 Hz, 1H), 7.13 (dd, J = 8.5, 1.5 Hz, 1H), 7.08 (dd, J = 7.5, 2.0 Hz, 1H), 4.70 (d, J = 12.5 Hz, 1H), 4.32 (dd, J = 14.5, 8.0 Hz, 1H), 3.91-3.83 (m, 1H), 3.72 (s, 3H), 3.52-3.43 (m, 1H), 3.41-3.30 (m, 2H), 3.24-3.16 (m, 2H), 1.38 (t, J = 7.3 Hz, 3H) |
| 121 | 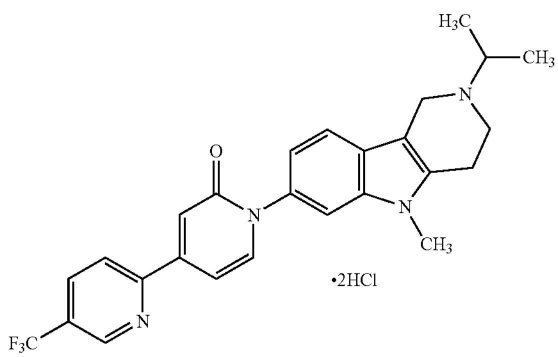 [SMILES: CC(C)N1CCc2c(c3ccc(-n4ccc(-c5ccc(C(F)(F)F)cn5)cc4=O)cc3n2C)C1 ; "·2HCl"] | 467 | $^1$H NMR (500 MHz, DMSO-d$_6$) δ 9.80 (br s, 1H), 9.15 (d, J = 2.0 Hz, 1H), 8.42-8.35 (m, 2H), 7.85 (d, J = 7.5 Hz, 1H), 7.66 (d, J = 1.5 Hz, 1H), 7.62 (d, J = 8.5 Hz, 1H), 7.30 (d, J = 2.0 Hz, 1H), 7.14 (dd, J = 8.5, 1.5 Hz, 1H), 7.08 (dd, J = 7.5, 2.0 Hz, 1H), 4.58 (d, J = 13.0 Hz, 1H), 4.48-4.40 (m, 1H), 3.90-3.82 (m, 1H), 3.78-3.70 (m, 4H), 3.51-3.42 (m, 1H), 3.38-3.15 (m, 2H), 1.45-1.36 (m, 6H) |
| 122 | 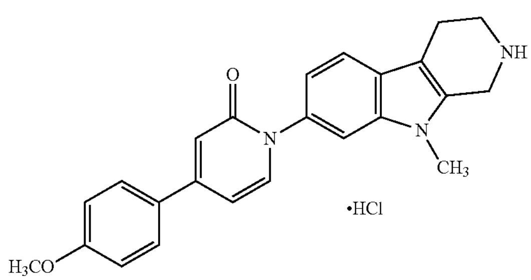 [SMILES: COc1ccc(-c2ccn(-c3ccc4c5c(n(C)c4c3)CNCC5)c(=O)c2)cc1 ; Cl] | 386 | $^1$H NMR (500 MHz, DMSO-d$_6$) δ 9.43 (br s, 2H), 7.76 (d, J = 9.0 Hz, 2H), 7.70 (d, J = 7.0 Hz, 1H), 7.61-7.58 (m, 2H), 7.11-7.05 (m, 3H), 6.73 (d, J = 2.0 Hz, 1H), 6.68 (dd, J = 7.0, 2.0 Hz, 1H), 4.51-4.45 (m, 2H), 3.83 (s, 3H), 3.70 (s, 3H), 3.48-3.42 (m, 2H), 2.99 (t, J = 6.0 Hz, 2H) |
| 123 | 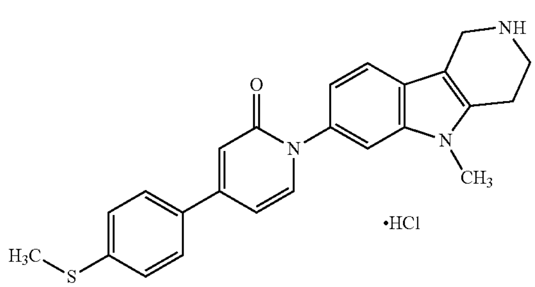 [SMILES: CSc1ccc(-c2ccn(-c3ccc4c5c(n(C)c4c3)CCNC5)c(=O)c2)cc1 ; Cl] | 402 | $^1$H NMR (500 MHz, DMSO-d$_6$) δ 9.27 (br s, 2H), 7.77-7.71 (m, 3H), 7.61-7.58 (m, 2H), 7.39 (d, J = 8.5 Hz, 2H), 7.09 (dd, J = 8.5, 2.0 Hz, 1H), 6.78 (d, J = 2.0 Hz, 1H), 6.69 (dd, J = 7.5, 2.0 Hz, 1H), 4.36 (br s, 2H), 3.70 (s, 3H), 3.56-3.51 (m, 2H), 3.10 (t, J = 5.5 Hz, 2H), 2.54 (s, 3H) |

TABLE 1-continued

| Ex. No. | Structure | Mass Spec | ¹H NMR Data |
|---|---|---|---|
| 124 | 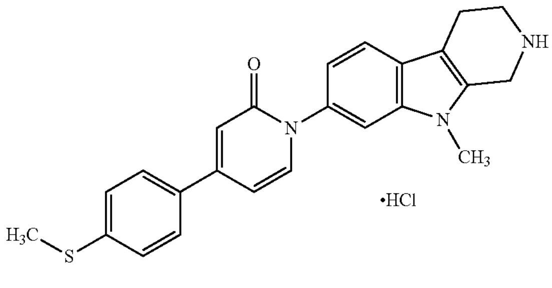 [SMILES: CSc1ccc(-c2ccn(-c3ccc4c5c(n(C)c4c3)CNCC5)c(=O)c2)cc1 ; Cl] | 402 | ¹H NMR (500 MHz, DMSO-d$_6$) δ 9.32 (br s, 2H), 7.75 (d, J = 8.5 Hz, 2H), 7.73 (d, J = 7.3 Hz, 1H), 7.62-7.58 (m, 2H), 7.38 (d, J = 8.5 Hz, 2H), 7.10 (dd, J = 8.5, 2.0 Hz, 1H), 6.78 (d, J = 2.0 Hz, 1H), 6.69 (dd, J = 7.3, 2.0 Hz, 1H), 4.49 (br s, 2H), 3.70 (s, 3H), 3.60-3.32 (m, 2H), 2.99 (t, J = 5.5 Hz, 2H), 2.54 (s, 3H) |
| 125 | 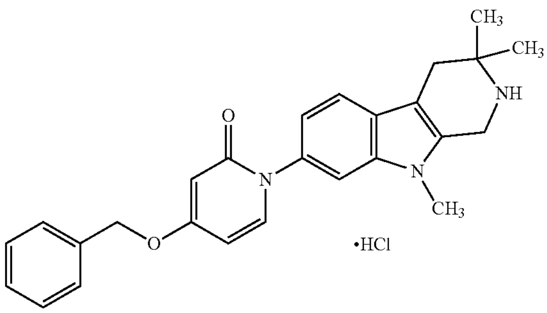 [SMILES: Cn1c2c(c3ccc(-n4ccc(OCc5ccccc5)cc4=O)cc31)CC(C)(C)NC2 ; Cl] | 414 | ¹H NMR (500 MHz, DMSO-d$_6$) δ 9.34 (br s, 2H), 7.57 (d, J = 7.5 Hz, 1H), 7.53-7.50 (m, 2H), 7.49-7.41 (m, 4H), 7.40-7.35 (m, 1H), 6.99 (dd, J = 8.0, 2.0 Hz, 1H), 6.11 (dd, J = 8.0, 2.5 Hz, 1H), 5.98 (d, J = 2.5 Hz, 1H), 5.16 (s, 2H), 4.50 (br s, 2H), 3.70 (s, 3H), 2.89 (s, 2H), 1.42 (s, 6H) |
| 126 | 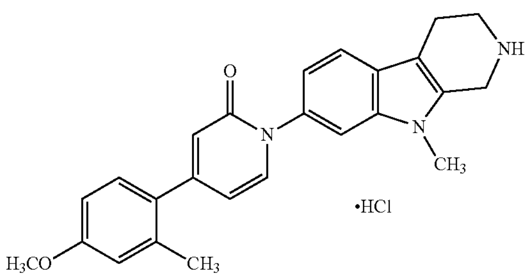 [SMILES: COc1ccc(-c2ccn(-c3ccc4c5c(n(C)c4c3)CNCC5)c(=O)c2)c(C)c1 ; Cl] | 400 | ¹H NMR (500 MHz, DMSO-d$_6$) δ 9.44 (br s, 2H), 7.67 (d, J = 7.0 Hz, 1H), 7.63 (d, J = 1.5 Hz, 1H), 7.60 (d, J = 8.0 Hz, 1H), 7.25 (d, J = 8.5 Hz, 1H), 7.11 (dd, J = 8.5, 1.5 Hz, 1H), 6.92 (d, J = 2.5 Hz, 1H), 6.88 (dd, J = 8.5, 2.5 Hz, 1H), 6.37 (s, 1H), 6.34 (dd, J = 7.5, 1.5 Hz, 1H), 4.89 (br s, 2H), 3.79 (s, 3H), 3.70 (s, 3H), 3.49-3.43 (m, 2H), 2.99 (t, J = 6.0 Hz, 2H), 2.36 (s, 3H) |
| 127 | 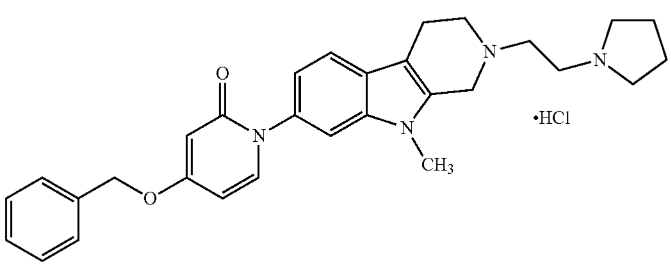 [SMILES: Cn1c2c(c3ccc(-n4ccc(OCc5ccccc5)cc4=O)cc31)CCN(CCN1CCCC1)C2 ; Cl] | 483 | ¹H NMR (500 MHz, CD$_3$OD) δ 7.62-7.57 (m, 2H), 7.47-7.34 (m, 6H), 7.03 (dd, J = 8.5, 1.5 Hz, 1H), 6.29 (dd, J = 7.5, 2.5 Hz, 1H), 6.12 (d, J = 2.5 Hz, 1H), 5.18 (s, 2H), 4.55-4.43 (m, 2H), 3.72 (s, 3H), 3.38-3.14 (m, 12H), 2.14 (m, 4H) |
| 128 | 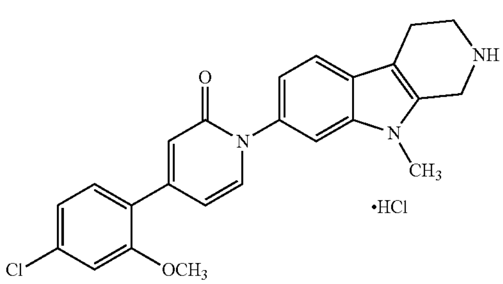 [SMILES: COc1cc(Cl)ccc1-c1ccn(-c2ccc3c4c(n(C)c3c2)CNCC4)c(=O)c1 ; Cl] | 420 | ¹H NMR (500 MHz, DMSO-d$_6$) δ 9.43 (br s, 2H), 7.65 (d, J = 7.0 Hz, 1H), 7.61 (d, J = 1.5 Hz, 1H), 7.59 (d, J = 8.0 Hz, 1H), 7.44 (d, J = 8.5 Hz, 1H), 7.26 (d, J = 2.0 Hz, 1H), 7.13 (dd, J = 8.5, 2.0 Hz, 1H), 7.09 (dd, J = 8.0, 2.0 Hz, 1H), 6.56 (d, J = 2.0 Hz, 1H), 6.47 (dd, J = 7.0, 1.5 Hz, 1H), 4.49-4.47 (m, 2H), 3.87 (m, 3H), 3.69 (s, 3H), 3.47-3.43 (m, 2H), 3.00-2.97 (m, 2H) |

TABLE 1-continued

| Ex. No. | Structure | Mass Spec | ¹H NMR Data |
|---|---|---|---|
| 129 | 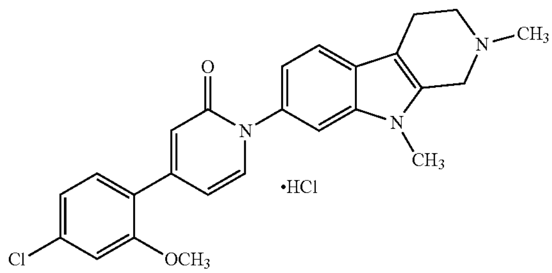 [SMILES: COc1cc(Cl)ccc1-c1ccn(-c2ccc3c4c(n(C)c3c2)CN(C)CC4)c(=O)c1 ; Cl] | 434 | ¹H NMR (500 MHz, DMSO-d$_6$) δ 10.82 (br s, 1H), 7.65 (d, J = 7.0 Hz, 1H), 7.62 (d, J = 1.5 Hz, 1H), 7.60 (d, J = 8.5 Hz, 1H), 7.44 (d, J = 8.5 Hz, 1H), 7.26 (d, J = 1.5 Hz, 1H), 7.14-7.09 (m, 2H), 6.56 (d, J = 1.5 Hz, 1H), 6.47 (dd, J = 7.0, 1.5 Hz, 1H), 4.79-4.76 (m, 1H), 4.53-4.42 (m, 1H), 3.87 (s, 3H), 3.72-3.68 (m, 4H), 3.42-3.40 (m, 1H), 3.08-3.06 (m, 2H), 3.00 (s, 3H) |
| 130 | 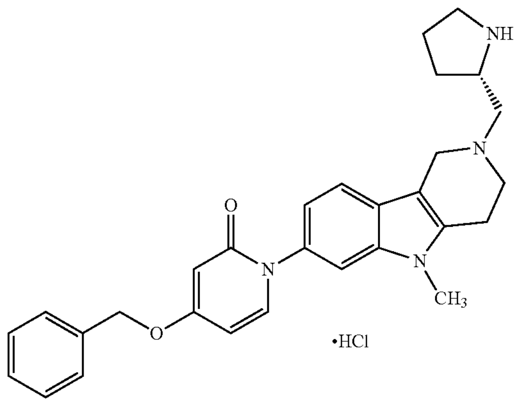 [SMILES: Cn1c2c(c3ccc(-n4ccc(OCc5ccccc5)cc4=O)cc31)CN(C[C@@H]1CCCN1)CC2 ; Cl] | 469 | ¹H NMR (500 MHz, CD$_3$OD) δ 7.59-7.56 (m, 2H), 7.47-7.45 (m, 3H), 7.42-7.39 (m, 2H), 7.37-7.34 (m, 1H), 7.06 (dd, J = 8.5, 2.0 Hz, 1H), 6.29 (dd, J = 7.5, 2.5 Hz, 1H), 6.12 (d, J = 3.0 Hz, 1H), 5.18 (s, 2H), 4.70-4.49 (br m, 2H), 4.28-4.26 (m, 1H), 3.75-3.73 (m, 7H), 3.46-3.43 (m, 2H), 3.34-3.33 (m, 2H), 2.46-2.43 (m, 1H), 2.21-2.08 (m, 2H), 1.91-1.86 (m, 1H) |
| 131 | 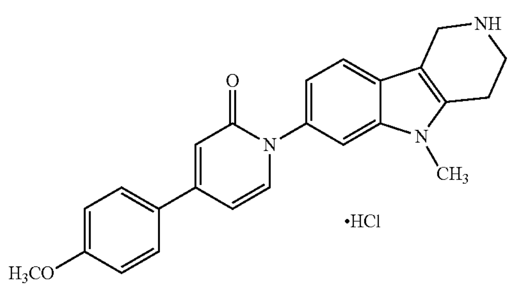 [SMILES: COc1ccc(-c2ccn(-c3ccc4c5c(n(C)c4c3)CCNC5)c(=O)c2)cc1 ; Cl] | 386 | ¹H NMR (500 MHz, DMSO-d$_6$) δ 9.26 (br s, 2H), 7.76 (d, J = 9.0 Hz, 2H), 7.70 (d, J = 7.0 Hz, 1H), 7.60-7.57 (m, 2H), 7.09-7.06 (m, 3H), 6.73 (d, J = 2.0 Hz, 1H), 6.68 (dd, J = 7.5, 2.0 Hz, 1H), 4.37-4.35 (m, 2H), 3.83 (s, 3H), 3.70 (s, 3H), 3.54-3.53 (m, 2H), 3.10 (t, J = 6.0 Hz, 2H) |
| 132 | 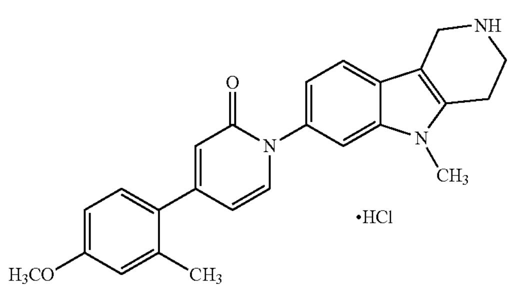 [SMILES: COc1ccc(-c2ccn(-c3ccc4c5c(n(C)c4c3)CCNC5)c(=O)c2)c(C)c1 ; Cl] | 400 | ¹H NMR (500 MHz, DMSO-d$_6$) δ 9.39 (br s, 2H), 7.67 (d, J = 7.0 Hz, 1H), 7.59 (d, J = 8.0 Hz, 1H), 7.27 (d, J = 2.0 Hz, 1H), 7.25 (d, J = 8.5 Hz, 1H), 7.10 (dd, J = 8.5, 2.0 Hz, 1H), 6.92 (d, J = 2.5 Hz, 1H), 6.88 (dd, J = 8.0, 2.5 Hz, 1H), 6.37 (d, J = 2.0 Hz, 1H), 6.34 (dd, J = 7.0, 2.0 Hz, 1H), 4.36-4.34 (m, 2H), 3.79 (s, 3H), 3.71 (s, 3H), 3.53-3.52 (m, 2H), 3.10 (t, J = 6.0 Hz, 2H), 2.35 (s, 3H) |
| 133 | 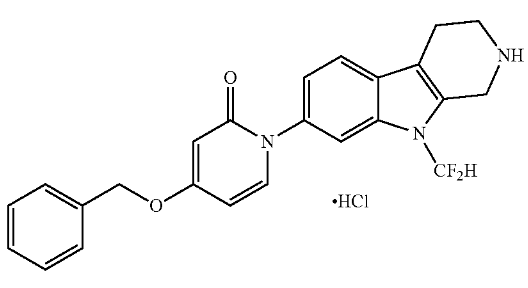 [SMILES: O=c1cc(OCc2ccccc2)ccn1-c1ccc2c3c(n(C(F)F)c2c1)CNCC3 ; Cl] | 422 | ¹H NMR (500 MHz, DMSO-d$_6$) δ 9.60 (br s, 2H), 8.11 (t, J = 58.0 Hz, 1H), 7.78 (d, J = 1.5 Hz, 1H), 7.68 (d, J = 8.0 Hz, 1H), 7.60 (d, J = 7.5 Hz, 1H), 7.48-7.36 (m, 5H), 7.22 (dd, J = 8.5, 1.5 Hz, 1H), 6.14 (dd, J = 7.5, 2.5 Hz, 1H), 5.99 (d, J = 2.5 Hz, 1H), 5.16 (s, 2H), 4.52 (m, 2H), 3.49-3.48 (m, 2H), 2.99 (m, 2H) |

TABLE 1-continued

| Ex. No. | Structure | Mass Spec | ¹H NMR Data |
|---|---|---|---|
| 134 | (structure) ·HCl | 436 | ¹H NMR (500 MHz, DMSO-d₆) δ 10.89 (br s, 1H), 8.15 (t, J = 58.0 Hz, 1H), 7.82 (d, J = 1.5 Hz, 1H), 7.69 (d, J = 8.3 Hz, 1H), 7.60 (d, J = 7.6 Hz, 1H), 7.47-7.36 (m, 5H), 7.23 (dd, J = 8.4, 1.5 Hz, 1H), 6.14 (dd, J = 7.6, 2.7 Hz, 1H), 6.00 (d, J = 2.7 Hz, 1H), 5.16 (s, 2H), 4.77 (m, 1H), 4.55 (m, 1H), 3.76-3.75 (m, 1H), 3.45-3.40 (m, 1H), 3.07-3.02 (m, 5H) |
| 135 | (structure) ·HCl | 404 | ¹H NMR (500 MHz, DMSO-d₆) δ 9.54 (s, 2H), 7.71 (d, J = 7.2 Hz, 1H), 7.62-7.58 (m, 3H), 7.10 (dd, J = 8.3, 1.8 Hz, 1H), 7.01 (dd, J = 13.2, 2.4 Hz, 1H), 6.94 (dd, J = 8.6, 2.3 Hz, 1H), 6.62 (s, 1H), 6.53-6.52 (m, 1H), 4.48 (s, 2H), 3.95 (s, 3H), 3.69 (s, 3H), 3.45-3.44 (m, 2H), 3.00-2.97 (m, 2H) |
| 136 | (structure) ·HCl | 418 | ¹H NMR (500 MHz, DMSO-d₆) δ 10.71 (s, 1H), 7.71 (d, J = 7.2 Hz, 1H), 7.63-7.59 (m, 3H), 7.11 (dd, J = 8.3, 1.6 Hz, 1H), 7.01 (dd, J = 13.2, 2.4 Hz, 1H), 6.94 (dd, J = 8.7, 2.4 Hz, 1H), 6.62 (s, 1H), 6.53-6.52 (m, 1H), 4.80-4.77 (m, 1H), 4.45-4.43 (m, 1H), 3.84 (s, 3H), 3.73 (br s, 1H), 3.68 (s, 3H), 3.42-3.34 (m, 1H), 3.07-3.06 (m, 2H), 3.00 (s, 3H) |
| 137 | (structure) ·HCl | 426 | ¹H NMR (500 MHz, CD₃OD) δ 8.81 (d, J = 7.0, 1.0 Hz, 1H), 8.38 (s, 1H), 8.02-7.99 (m, 1H), 7.92 (d, J = 9.5 Hz, 1H), 7.66-7.62 (m, 2H), 7.52-7.49 (m, 1H), 7.46 (s, 1H), 7.05 (d, J = 7.0 Hz, 1H), 6.33 (dd, J = 7.5, 3.0 Hz, 1H), 6.23 (d, J = 3.0 Hz, 1H), 5.50 (s, 2H), 4.55 (s, 2H), 3.72 (s, 3H), 3.60 (t, J = 6.0 Hz, 2H), 3.14-3.12 (m, 2H) |
| 138 | (structure) ·HCl | 440 | ¹H NMR (500 MHz, DMSO-d₆) δ 10.91 (br s, 1H), 8.86 (d, J = 6.0 Hz, 1H), 8.39 (s, 1H), 7.87-7.79 (m, 2H), 7.61 (d, J = 7.5 Hz, 1H), 7.57 (d, J = 8.0 Hz, 1H), 7.51 (s, 1H), 7.37-7.35 (m, 1H), 7.01 (dd, J = 8.5, 1.0 Hz, 1H), 6.15-6.11 (m, 2H), 5.42 (s, 2H), 4.77 (d, J = 15.0 Hz, 1H), 4.43 (dd, J = 14.0, 6.0 Hz, 1H), 3.80-3.77 (m, 1H), 3.66 (s, 3H), 3.41-3.39 (m, 1H), 3.08-3.04 (m, 2H), 2.99 (s, 3H) |

TABLE 1-continued

| Ex. No. | Structure | Mass Spec | ¹H NMR Data |
|---|---|---|---|
| 139 | 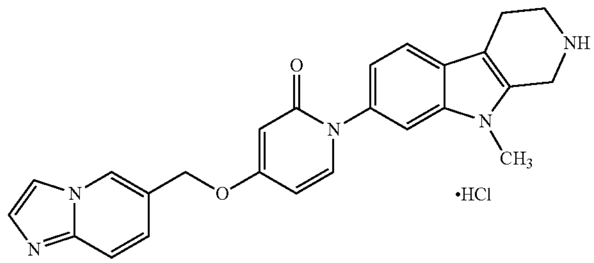 [SMILES: Cn1c2c(c3ccc(-n4ccc(OCc5ccc6nccn6c5)cc4=O)cc31)CCNC2 ; Cl] | 426 | ¹H NMR (500 MHz, DMSO-$d_6$) δ 9.55 (br s, 2H), 9.01 (s, 1H), 8.33 (s, 1H), 8.11 (s, 1H), 7.97 (d, J = 9.2 Hz, 1H), 7.89 (d, J = 9.2 Hz, 1H), 7.61 (d, J = 7.6 Hz, 1H), 7.56 (d, J = 8.4 Hz, 1H), 7.50 (d, J = 1.6 Hz, 1H), 7.00 (dd, J = 8.4, 1.7 Hz, 1H), 6.13 (dd, J = 7.6, 2.7 Hz, 1H), 6.08 (d, J = 2.7 Hz, 1H), 5.31 (s, 2H), 4.46 (m, 2H), 3.67 (s, 3H), 3.44 (m, 2H), 2.97 (t, J = 5.7 Hz, 2H) |
| 140 | 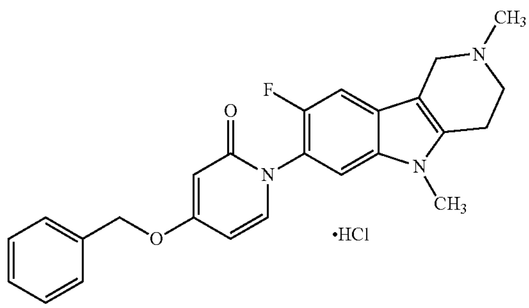 [SMILES: CN1CCc2c(c3cc(F)c(-n4ccc(OCc5ccccc5)cc4=O)cc3n2C)C1 ; Cl] | 418 | ¹H NMR (300 MHz, CD$_3$OD) δ 7.53-7.33 (m, 7H), 7.27 (d, J = 10.5 Hz, 1H), 7.28 (dd, J = 7.8, 2.4 Hz, 1H), 6.10 (d, J = 2.7 Hz, 1H), 5.17 (s, 2H), 3.79 (br s, 2H), 3.67 (s, 3H), 3.03-3.00 (m, 4H), 2.64 (s, 3H) |
| 141 | 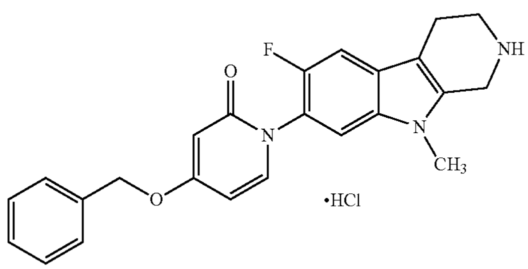 [SMILES: Cn1c2c(c3cc(F)c(-n4ccc(OCc5ccccc5)cc4=O)cc31)CCNC2 ; Cl] | 404 | ¹H NMR (500 MHz, DMSO-$d_6$) δ 9.56 (br s, 2H), 7.61 (d, J = 6.0 Hz, 1H), 7.54 (d, J = 7.5 Hz, 1H), 7.50-7.37 (m, 6H), 6.14-6.12 (m, 1H), 5.99 (s, 1H), 5.16 (s, 2H), 4.46 (br s, 2H), 3.67 (s, 3H), 3.43 (br m, 2H), 2.94 (m, 2H) |
| 142 | 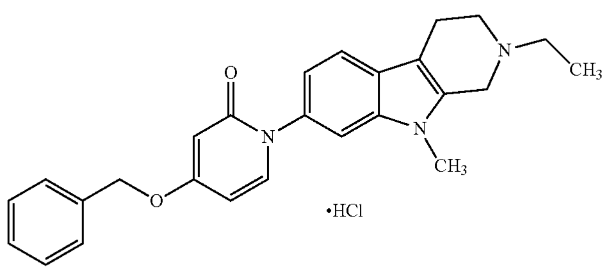 [SMILES: CCN1CCc2c(n(C)c3cc(-n4ccc(OCc5ccccc5)cc4=O)ccc23)C1 ; Cl] | 414 | ¹H NMR (500 MHz, DMSO-$d_6$) δ 7.57 (d, J = 7.5 Hz, 1H), 7.54-7.34 (m, 7H), 6.97 (d, J = 8.0 Hz, 1H), 6.10 (dd, J = 7.5, 2.0 Hz, 1H), 5.97 (s, 1H), 5.16 (s, 2H), 3.67 (s, 3H), 3.45-3.18 (4H, overlapping with solvent peak), 3.26 (br m, 2H), 2.96 (m, 2H), 1.33 (br m, 3H) |
| 143 | 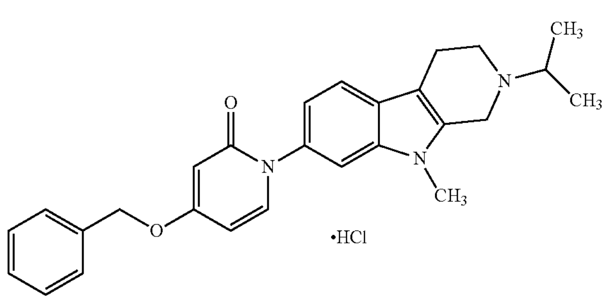 [SMILES: CC(C)N1CCc2c(n(C)c3cc(-n4ccc(OCc5ccccc5)cc4=O)ccc23)C1 ; Cl] | 428 | ¹H NMR (500 MHz, DMSO-$d_6$) δ 10.50 (s, 1H), 7.56 (d, J = 4.5 Hz, 2H), 7.52-7.38 (m, 6H), 7.01 (dd, J = 4.5, 1.0 Hz, 1H), 6.11 (dd, J = 4.5, 1.0 Hz, 1H), 5.97 (s, 1H), 5.16 (s, 2H), 4.60-4.53 (m, 2H), 3.78-3.70 (m, 2H), 3.70 (s, 3H), 3.40-3.28 (m, 1H), 3.18-2.98 (m, 2H), 1.44-1.39 (m, 6H) |

TABLE 1-continued

| Ex. No. | Structure | Mass Spec | $^1$H NMR Data |
|---|---|---|---|
| 144 | 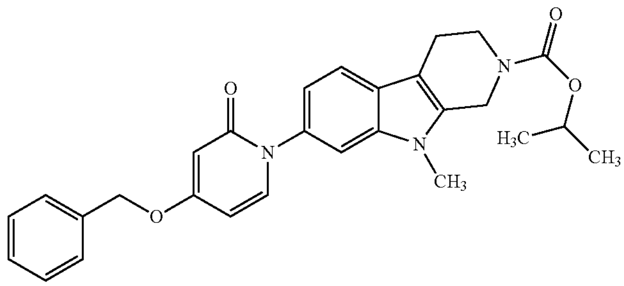 [SMILES: CC(C)OC(=O)N1CCc2c(n(C)c3cc(-n4ccc(OCc5ccccc5)cc4=O)ccc23)C1] | 472 | $^1$H NMR (500 MHz, CDCl$_3$) δ 7.48 (d, J = 8.5 Hz, 1H), 7.50-7.32 (m, 7H), 6.99 (d, J = 8.5 Hz, 1H), 6.90 (s, 1H), 6.34 (d, J = 6.5 Hz, 1H), 5.17 (s, 2H), 5.05-5.00 (m, 1H), 4.72-4.58 (m, 2H), 3.79 (br m, 2H), 3.76 (s, 3H), 2.82 (m, 2H), 1.42-1.32 (m, 6H) |
| 145 | 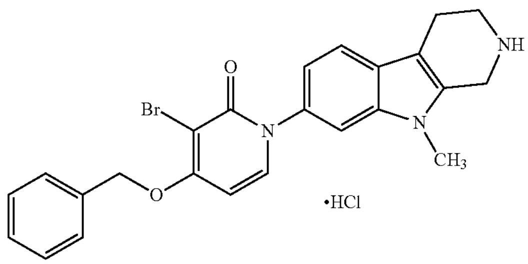 [SMILES: Cn1c2c(c3ccc(-n4ccc(OCc5ccccc5)c(Br)c4=O)cc31)CCNC2 ; Cl] | 465 | $^1$H NMR (300 MHz, CD$_3$OD) δ 7.71 (d, J = 7.8 Hz, 1H), 7.63 (d, J = 8.4, Hz, 1H), 7.53-7.30 (m, 6H), 7.05 (dd, J = 7.8, 1.2 Hz, 1H), 6.60 (d, J = 7.6 Hz, 1H), 5.40 (s, 2H), 4.54 (s, 2H), 3.71 (s, 3H), 3.62-3.55 (m, 2H), 3.22-3.02 (m, 2H) |
| 146 | 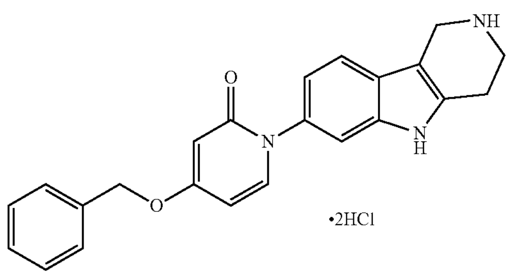 [SMILES: O=c1cc(OCc2ccccc2)ccn1-c1ccc2c3c([nH]c2c1)CCNC3 ; "·2HCl"] | 372 | $^1$H NMR (500 MHz, CD$_3$OD) δ 7.65 (d, J = 7.5 Hz, 1H), 7.57 (d, J = 8.2 Hz, 1H), 7.47 (d, J = 7.2 Hz, 2H), 7.42-7.36 (m, 4H), 7.03 (d, J = 8.5 Hz, 1H), 6.39 (dd, J = 7.6, 2.5 Hz, 1H), 6.21 (d, J = 2.5 Hz, 1H), 5.21 (s, 2H), 4.47 (s, 2H), 3.64 (t, J = 6.0 Hz, 2H), 3.20 (t, J = 6.1 Hz, 2H) |
| 147 | 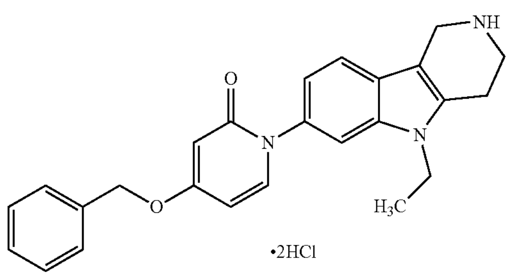 [SMILES: CCn1c2c(c3ccc(-n4ccc(OCc5ccccc5)cc4=O)cc31)CNCC2 ; "·2HCl"] | 400 | $^1$H NMR (300 MHz, CD$_3$OD) δ 7.83 (d, J = 7.5 Hz, 1H), 7.62-7.57 (m, 2H), 7.45-7.40 (m, 5H), 7.09 (dd, J = 8.4, 1.6 Hz, 1H), 6.59 (dd, J = 7.5, 2.3 Hz, 1H), 6.36 (d, J = 2.3 Hz, 1H), 5.28 (s, 2H), 4.49 (s, 2H), 4.23 (q, J = 7.2 Hz, 2H), 3.68 (t, J = 6.1 Hz, 2H), 3.22 (t, J = 5.9 Hz, 2H), 1.35 (t, J = 7.1 Hz, 3H) |

As compounds that bind strongly to MCH$_1$, compounds of formula I are expected to be effective in reducing obesity.

The present invention is not limited to the compounds found in the above examples, and many other compounds falling within the scope of the invention may also be prepared using the procedures set forth in the above synthetic schemes. The preparation of additional compounds of formula (I) using these methods will be apparent to one of ordinary skill in the chemical arts.

The invention has been described in detail with particular reference to some embodiments thereof, but it will be understood by those skilled in the art that variations and modifications can be effected within the spirit and scope of the invention.

The invention claimed is:

1. A compound of formula I:

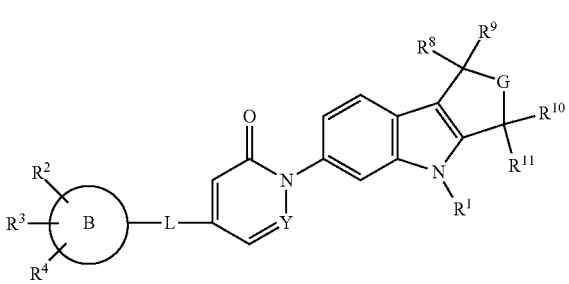

(I)

wherein

R¹ is H or optionally substituted alkyl;

R², R³, R⁴ are each independently selected from H, —O-alkyl, —S-alkyl, alkyl, halo, —CF₃, and —CN;

G is —CR¹²R¹³—NR⁵— or —NR⁵—CR¹²R¹³;

R⁵ is H, optionally substituted alkyl;

R⁸, R⁹, R¹⁰, R¹¹, R¹², and R¹³ are each independently selected from H or optionally substituted alkyl;

Y is CH;

L is —CH₂—O—; and

B is heteroaryl.

2. A compound according to claim 1 wherein G is —CH₂—NR⁵—.

3. A compound according to claim 1 wherein G is —NR⁵—CH₂—.

4. A compound according to claim 1 wherein R⁵ is H.

5. A compound according to claim 1 wherein R⁵ is optionally substituted alkyl.

6. A compound according to claim 5 wherein R⁵ is selected from methyl, ethyl, 2-propyl, 2-hydroxyethyl, 2,2,2-trifluoroethyl, 3,3,3-trifluoropropyl and 2-oxo-2-(pyrrolidin-1-yl)ethyl, 2-(pyrrolidin-1-yl)ethyl and (S)-pyrrolidin-2-ylmethyl.

7. A compound according to claim 1 wherein R¹ is H.

8. A compound according to claim 1 wherein R¹ is alkyl.

9. A compound according to claim 8 wherein R¹ is selected from methyl and ethyl.

10. A compound according to claim 1 wherein L is —CH₂—O—.

11. A compound according to claim 1 wherein B is heteroaryl.

12. A compound according to claim 11 wherein B is pyridinyl.

13. A compound according to claim 12 wherein B is pyridin-2-yl.

14. A compound according to claim 12 wherein B is pyridin-3-yl.

15. A compound according to claim 11 wherein B is pyridazinyl.

16. A compound according to claim 15 wherein B is pyridazin-3-yl.

17. A compound according to claim 11 wherein B is pyrimidinyl.

18. A compound according to claim 17 wherein B is pyrimidin-5-yl.

19. A compound according to claim 17 wherein B is pyrimidin-2-yl.

20. A compound according to claim 1 wherein B, together with R², R³ and R⁴, is selected from pyridin-2-yl, 5-chloropyridin-2-yl, 5-(trifluoromethyl)pyridin-2-yl, 5-fluoropyridin-2-yl, 6-(trifluoromethyl)pyridazin-3-yl, 6-methylpyridazin-3-yl, 6-(trifluoromethyl)pyridin-3-yl, 2-(trifluoromethyl)pyrimidin-5-yl, 5-(trifluoromethyl)pyrimidin-2-yl, 5-methylpyridin-2-yl, 6-methylpyridin-3-yl, pyrimidin-2-yl, imidazo[1,2-α]pyridin-6-yl, imidazo[1,2-α]pyridin-2-yl.

21. A compound according to claim 1 wherein the compound is selected from,

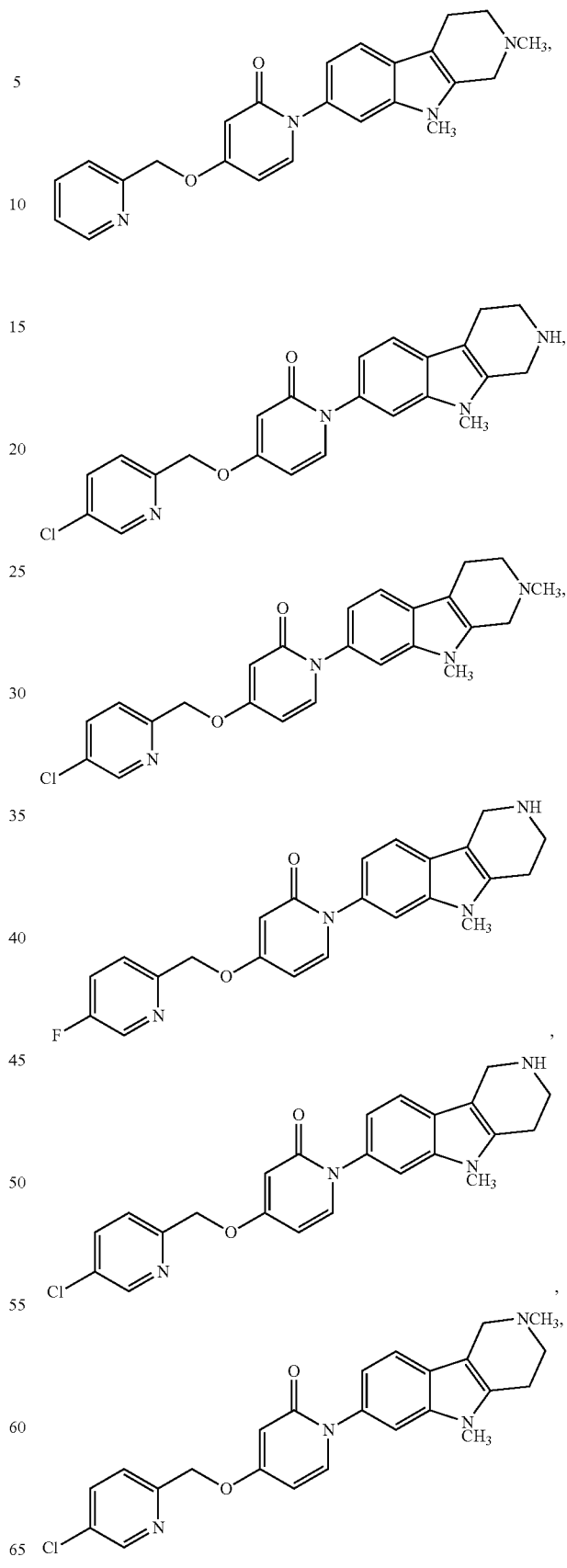

317
-continued
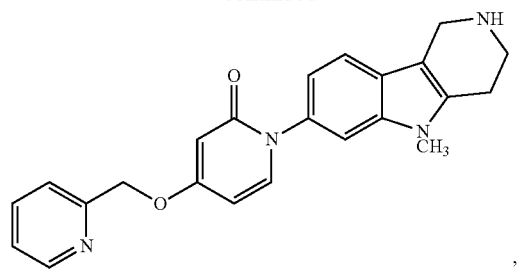
,
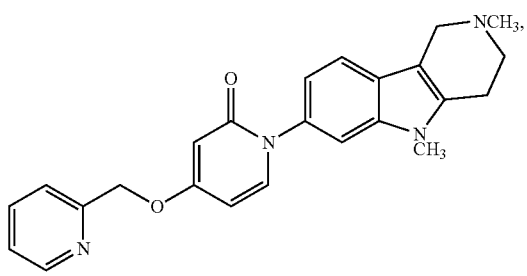
,
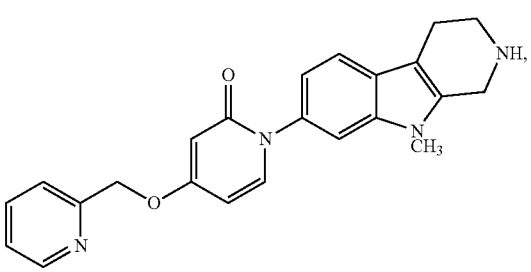
,
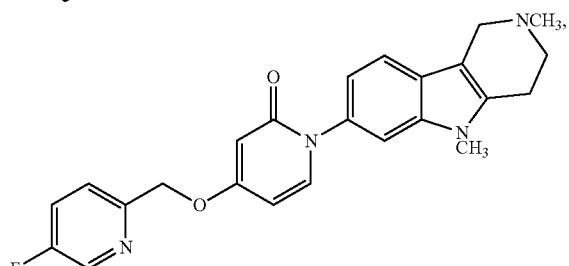
,
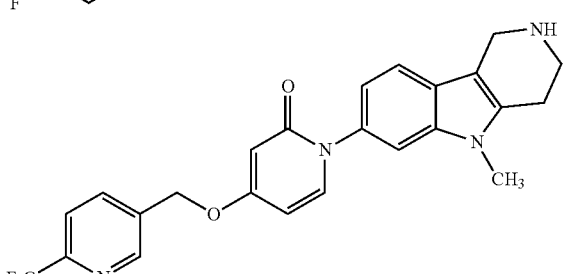
,
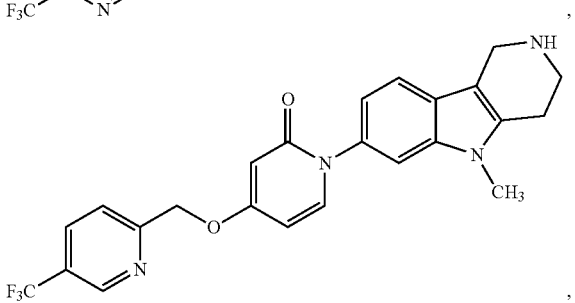
,
318
-continued
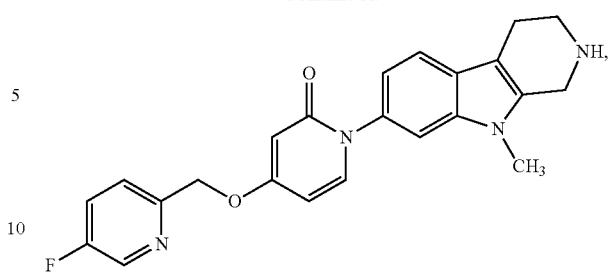
,
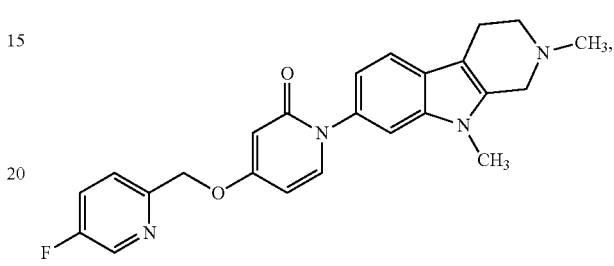
,
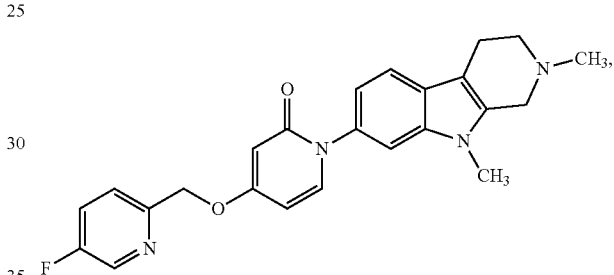
,
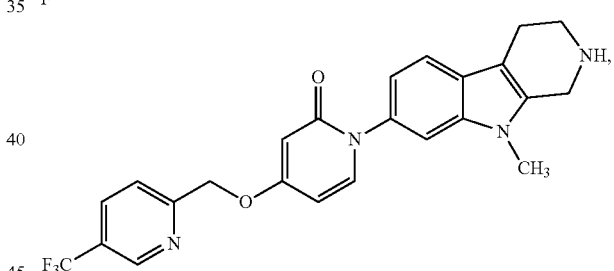
,
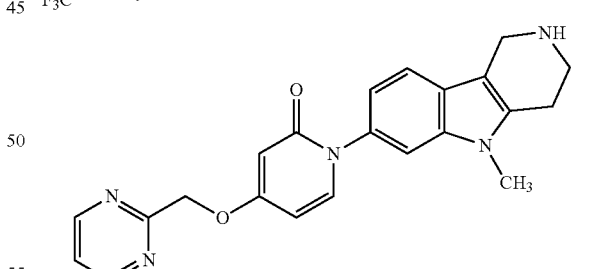
,
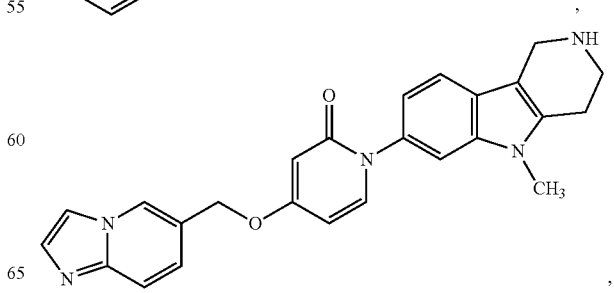
,

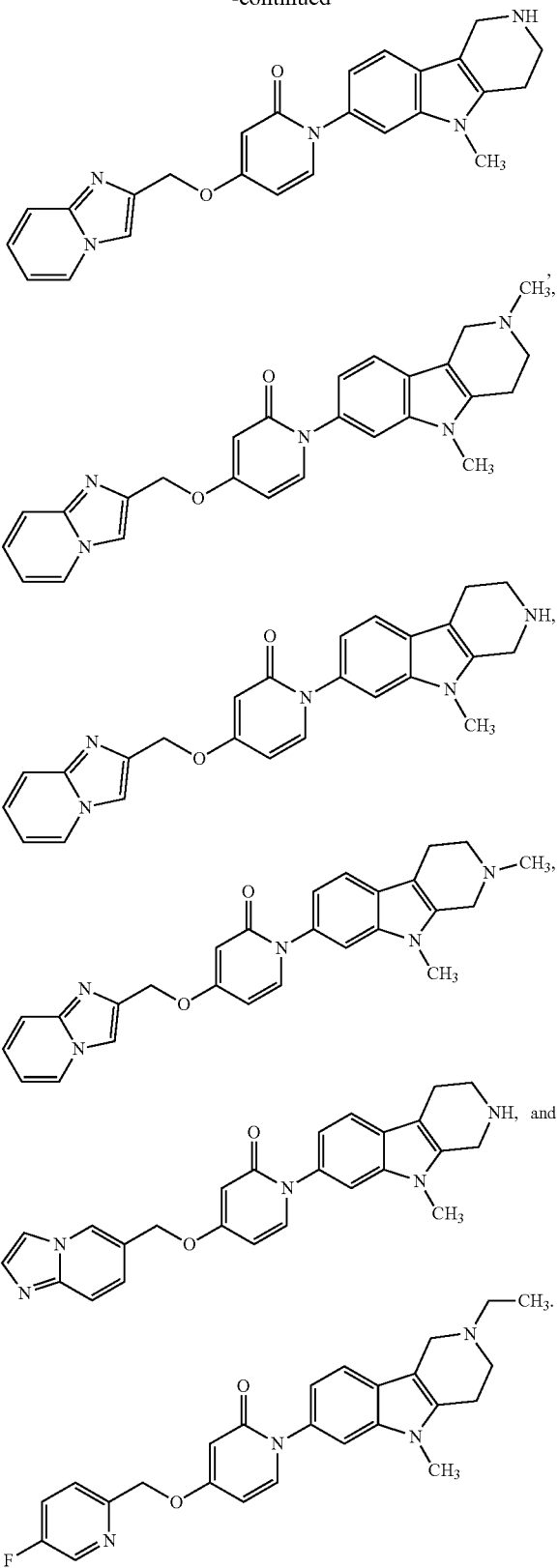

22. A compound according to claim 1 wherein at least one of $R^8$ and $R^9$ is H.

23. A compound according to claim 1 wherein at least one of $R^8$ and $R^9$ is alkyl.

24. A compound according to claim 23 wherein at least one of $R^8$ and $R^9$ is methyl.

25. A compound according to claim 1 wherein $R^{10}$ is alkyl.

26. A compound according to claim 25 wherein $R^{10}$ is methyl.

27. A compound according to claim 1 wherein $R^{11}$ is alkyl.

28. A compound according to claim 27 wherein $R^{11}$ is methyl.

29. A compound according to claim 1 wherein $R^{12}$ is alkyl.

30. A compound according to claim 29 wherein $R^{12}$ is methyl.

31. A compound according to claim 1 wherein $R^{13}$ is alkyl.

32. A compound according to claim 31 wherein $R^{13}$ is methyl.

33. A compound according to claim 1 wherein $R^{10}$, $R^{11}$, $R^{12}$ and $R^{13}$ are each methyl.

34. A compound according to claim 1 wherein

G is —$CH_2$—$NR^5$— or —$NR^5$—$CH_2$—;

$R^1$ and $R^5$ are each independently H or methyl;

B is heteroaryl; and when L is —$CH_2$—O—; then $R^2$, $R^3$, $R^4$ are each independently selected from H, —O-alkyl, —S-alkyl, alkyl, halo, —$CF_3$, and —CN.

35. A compound according to claim 1 wherein the compound is in a pharmaceutically acceptable salt form.

36. A compound according to claim 35 wherein the salt is an HCl salt.

37. A pharmaceutical composition comprising a compound according to claim 1 and a pharmaceutically acceptable carrier, excipient or diluent therefore.

38. A method of treating obesity, comprising administering to a patient in need of obesity reduction an obesity-reducing effective amount of a compound according to claim 1.

39. A method of treating anxiety, comprising administering to a patient in need of such treatment a therapeutically effective amount of a compound according to claim 1.

40. A method of treating depression, comprising administering to a patient in need of such treatment a therapeutically effective amount of a compound according to claim 1.

41. A method of treating non-alcoholic fatty liver disease, comprising administering to a patient in need of such treatment a therapeutically effective amount of a compound according to claim 1.

* * * * *

UNITED STATES PATENT AND TRADEMARK OFFICE
CERTIFICATE OF CORRECTION

PATENT NO. : 9,650,378 B2
APPLICATION NO. : 15/045652
DATED : May 16, 2017
INVENTOR(S) : Guzzo et al.

It is certified that error appears in the above-identified patent and that said Letters Patent is hereby corrected as shown below:

In the Claims

At Claim 21, Column 318, Lines 27–35, please delete the following compound:

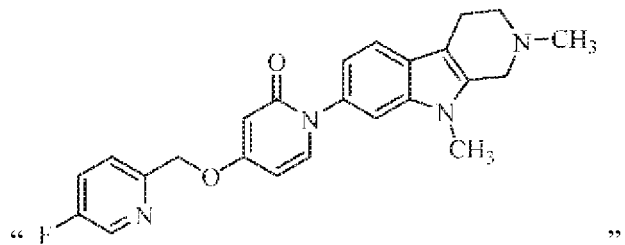

At Claim 21, Column 318, Lines 35–45, please delete the following compound:

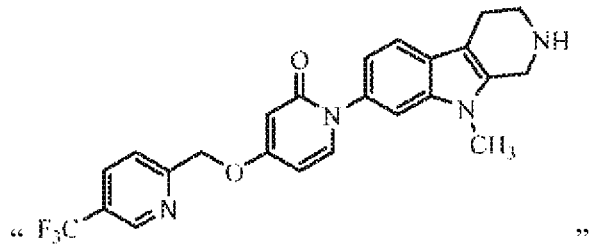

and insert in its place the following compound:

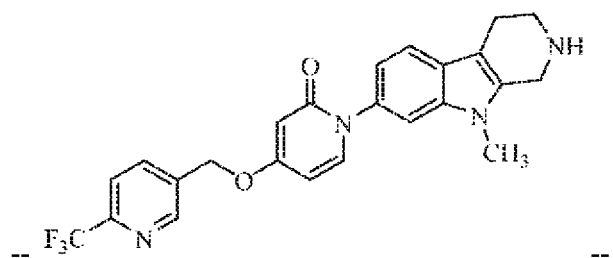

Signed and Sealed this
Eighteenth Day of July, 2017

Joseph Matal
*Performing the Functions and Duties of the
Under Secretary of Commerce for Intellectual Property and
Director of the United States Patent and Trademark Office*